US012528814B2

(12) United States Patent
Palmer et al.

(10) Patent No.: US 12,528,814 B2
(45) Date of Patent: Jan. 20, 2026

(54) BIFUNCTIONAL DEGRADERS OF INTERLEUKIN-1 RECEPTOR-ASSOCIATED KINASES AND THERAPEUTIC USE THEREOF

(71) Applicants: NURIX THERAPEUTICS, INC., San Francisco, CA (US); GILEAD SCIENCES, INC., Foster City, CA (US)

(72) Inventors: Wylie Solang Palmer, San Francisco, CA (US); Jeffrey Wu, San Francisco, CA (US); Sheila Zipfel, Foster City, CA (US); Kerem Ozboya, San Francisco, CA (US); Dahlia Weiss, San Francisco, CA (US)

(73) Assignees: Nurix Therapeutics, Inc., San Francisco, CA (US); Gilead Sciences, Inc., Foster City, CA (US)

( * ) Notice: Subject to any disclaimer, the term of this patent is extended or adjusted under 35 U.S.C. 154(b) by 736 days.

(21) Appl. No.: 17/904,592

(22) PCT Filed: Feb. 19, 2021

(86) PCT No.: PCT/US2021/018710
§ 371 (c)(1),
(2) Date: Aug. 18, 2022

(87) PCT Pub. No.: WO2021/168197
PCT Pub. Date: Aug. 26, 2021

(65) Prior Publication Data
US 2023/0142629 A1 May 11, 2023

Related U.S. Application Data

(60) Provisional application No. 62/978,635, filed on Feb. 19, 2020.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ C07D 487/04; C07D 519/00
USPC ..................................................... 514/210.16
See application file for complete search history.

(56) References Cited

U.S. PATENT DOCUMENTS

| | | | |
|---|---|---|---|
| 6,306,663 | B1 | 10/2001 | Kenten et al. |
| 7,041,298 | B2 | 5/2006 | Deshaies et al. |
| 7,208,157 | B2 | 4/2007 | Dashaies et al. |
| 9,464,326 | B2 | 10/2016 | Davila |
| 10,202,390 | B2 | 2/2019 | Duncia et al. |
| 10,336,762 | B2 | 7/2019 | Bacon et al. |
| 10,849,982 | B2 | 12/2020 | Phillips et al. |
| 10,875,866 | B2 | 12/2020 | Ammann et al. |
| 11,046,686 | B2 | 6/2021 | Ammann et al. |
| 11,976,071 | B2 | 5/2024 | Palmer |
| 2018/0215731 | A1 | 8/2018 | Crew et al. |
| 2019/0192668 | A1 | 6/2019 | Mainolfi et al. |
| 2020/0048261 | A1 | 2/2020 | Ammann et al. |
| 2020/0079769 | A1 | 3/2020 | Ammann et al. |
| 2020/0358513 | A1 | 11/2020 | Ku et al. |
| 2023/0120619 | A1 | 4/2023 | Palmer et al. |
| 2024/0417402 | A1 | 12/2024 | Palmer |

FOREIGN PATENT DOCUMENTS

| | | | |
|---|---|---|---|
| WO | 2005030144 | A2 | 4/2005 |
| WO | 2008030579 | A2 | 3/2008 |
| WO | 2015103453 | A1 | 7/2015 |
| WO | 2015160845 | A2 | 10/2015 |
| WO | 2016105518 | A1 | 6/2016 |
| WO | 2016210034 | A1 | 12/2016 |
| WO | 2016210037 | A1 | 12/2016 |
| WO | 2017075054 | A1 | 5/2017 |
| WO | 2017197046 | A1 | 11/2017 |
| WO | 2018071606 | A1 | 4/2018 |
| WO | 2018081738 | A1 | 5/2018 |
| WO | 2018232288 | A1 | 12/2018 |
| WO | 2019099926 | A1 | 5/2019 |
| WO | 2019160915 | A1 | 8/2019 |
| WO | 2021011868 | A1 | 1/2021 |
| WO | 2021067606 | A1 | 4/2021 |
| WO | 2021113557 | | 6/2021 |
| WO | 2021180103 | A1 | 9/2021 |
| WO | 2021255212 | A1 | 12/2021 |
| WO | 2021257914 | A1 | 12/2021 |
| WO | 2022235698 | A1 | 11/2022 |
| WO | 2023023255 | A1 | 2/2023 |

OTHER PUBLICATIONS

Cancer [online], [retrieved on Jul. 6, 2007] Retrieved from the Internet, URL: http://www.nim.nih.gov/medlineplus/cancer.html (Year: 2007).*

Lala et al., Role of nitric oxide in tumor progression: Lessons from experimental tumors, Cancer and Metastasis Reviews (1998), 17 , 91-106 (Year: 1998).*

Golub et al., Molecular Classification of Cancer: Class Discovery and Class Prediction by Gene Expression Monitoring, Science (1999), vol. 286, 531-537 (Year: 1999).*

International Search Report & Written Opinion for PCT/US2021/018710, mailed Mar. 31, 2021, 12 pages.

(Continued)

*Primary Examiner* — Kristin A Vajda

(74) *Attorney, Agent, or Firm* — Mintz, Levin, Cohn, Ferris, Glovsky and Popeo, P.C.

(57) ABSTRACT

The present disclosure provides bifunctional compounds as IRAK4 degraders via ubiquitin proteasome pathway, and method for treating diseases modulated by IRAK4.

57 Claims, No Drawings

(56) References Cited

OTHER PUBLICATIONS

International Search Report & Written Opinion for PCT/US2022/040765, mailed Nov. 11, 2022, 10 pages.
Office Action for China Appl. No. 202180015953.3, mailed Apr. 28, 2023, 17 pages, translation.
Li et al. (2002) "IRAK-4: A Novel Member of the IRAK Family with the Properties of an IRAK-kinase", PNAS, 6 Pages.
Lu et al. (2015) "Hijacking the E3 Ubiquitin Ligase Cereblon to Efficiently Target BRD4", Chemistry & Biology, 10 Pages.
Wang et al. (2006) "Crystal Structures of IRAK-4 Kinase in Complex with Inhibitors: A Serine/threonine Kinase with Tyrosine as a Gatekeeper", Structure, 10 Pages.
Wietek et al. (2002) "Irak-4: A New Drug Target in Inflammation, Sepsis, and Autoimmunity", Molecular Interventions, 4 Pages.
Winter et al. (2015) "Phthalimide Conjugation as a Strategy for In Vivo Target Protein Degradation", Science, 7 Pages.
Chamberlain et al., "Evolution of Cereblon-Mediated Protein Degradation as a Therapeutic Modality" ACS Med Chem Lett 10(12)1592-1602, 2019.
Canada Appl. No. 3,165,009, Office Action, dated Oct. 10, 2023, 6 pages.
JP Application No. 2022-549454, Office Action dated Jan. 29, 2025.
Nunes, "Targeting IRAK4 for Degradation with PROTACs" ACS Medicinal Chemistry Letters 10(7):1081-1085, 2019.
Jordan "Tamoxifen: A most unlikely pioneering medicine" Nature Reviews, Drug Discovery 2(3):205-213, 2003.
Hackman, Translation of Research Evidence from Animals to Humans, JAMA 296(14) 1731-1732, 2006.
Japanese Patent Application No. 2022-549454, Office Action, dated Jul. 10, 2025.
Taiwan Appl. No. 110105770, Office Action, dated May 22, 2025.
Steinebach, "A MedChem toolbox for cereblon-directed PROTACs" Med Chem Comm 10(6):1037-1041, Jun. 2019.
Troup, "Current Strategies for the Design of PROTAC Linkers: a Critical Review" Exploration of Targeted Anti-tumor Therapy 1(5):273-312, Oct. 2020.

* cited by examiner

BIFUNCTIONAL DEGRADERS OF INTERLEUKIN-1 RECEPTOR-ASSOCIATED KINASES AND THERAPEUTIC USE THEREOF

CROSS-REFERENCE TO RELATED APPLICATIONS

This application claims the benefit of priority to U.S. Provisional Application No. 62/978,635, filed Feb. 19, 2020, which application is hereby incorporated by reference in its entirety.

BACKGROUND

Technical Field

The present invention provides novel bifunctional compounds for proteolytically degrading Interleukin-1 Receptor-Associated Kinase 4 (IRAK4) and methods for treating diseases modulated by IRAK4.

Description of the Related Art

Interleukin-1 receptor-associated kinase-4 (IRAK4) is a serine/threonine kinase that plays a key role in mediating toll-like receptor (TLR) and interleukin-1 receptor (IL1R) signaling in immune cells resulting in the production of pro-inflammatory cytokines. IRAK4 functions as part of the Myddosome, a large multi-protein complex that assembles at the plasma membrane upon ligand binding to TLR and IL1R receptors. The first step in Myddosome assembly is the recruitment of the scaffolding protein MyD88, followed by IRAK4 binding to Myd88 through homotypic death domain (DD) interactions. IRAK4 then undergoes auto-activation followed by phosphorylating downstream kinases IRAK1 and IRAK2. IRAK4 is considered the "master regulator" of Myddosome signaling due to it being the most upstream kinase in this complex. The importance of IRAK4 kinase function has been demonstrated in IRAK-4 kinase dead mice which are resistant to TLR-induced septic shock due to their inability to produce pro-inflammatory cytokines.

IRAK4 is also reportedly to have kinase-independent scaffolding functions. For instance, macrophages from IRAK4 kinase-dead mice are still capable of activating NF-Kb signaling through IL1, TLR2, TLR4 & TLR7 stimulation. Similar scaffolding functions have been shown in human fibroblast cells in which kinase-dead IRAK4 is capable of restoring IL-1 induced NF-Kb signaling to comparable levels as WT IRAK4.

Thus, IRAK4 may be targeted for degradation, thereby providing therapeutic opportunities in treating autoimmune, inflammatory, and oncological diseases. Specific degradation of IRAK4 could be accomplished by using heterobifunctional small molecules to recruit IRAK4 to a ubiquitin ligase and thus promoting ubiquitylation and proteasomal degradation of IRAK4. For instance, thalidomide derivatives, such as lenalidomide or pomalidomide, have been reported to recruit potential protein substrates to cereblon (CRBN), a component of a ubiquitin ligase complex. See, e.g., WO 2019/099926, WO 2020/023851, and U.S. Published Application No. 2019/0192668.

There is a need to further develop therapeutic agents that target IRAK4.

BRIEF SUMMARY

Provided herein are bifunctional compound represented by Formula (I)

Formula (I)

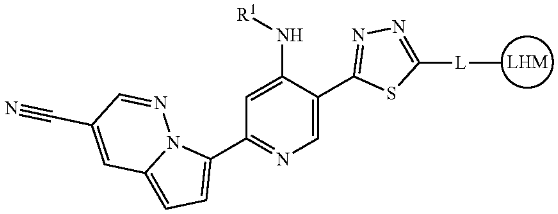

or a pharmaceutically acceptable salt, isotopic form, isolated stereoisomer, or a mixture of stereoisomers thereof, wherein:

$R^1$ is $C_{1-10}$ alkyl optionally substituted with 1-3 $R^a$; $C_{3-10}$ cycloalkyl optionally substituted with 1-3 $R^a$; or 3-12 membered heterocyclyl optionally substituted with 1-3 $R^a$;

L is $-L_1-L_2-L_3-L_4-L_5-$, each $L_1$, $L_2$, $L_3$, $L_4$ and $L_5$ being independently:

a) $C_{3-12}$ cycloalkyl optionally substituted with 1-3 $R^b$;
b) $C_{6-12}$ aryl optionally substituted with 1-3 $R^b$;
c) 3-12 membered heterocyclyl optionally substituted with 1-3 $R^b$;
d) 5-12 membered heteroaryl optionally substituted with 1-3 $R^b$;
e) direct bond;
f) $C_{1-12}$ alkylene chain optionally substituted with 1-3 $R^d$;
g) $C_{2-12}$ alkenylene chain optionally substituted with 1-3 $R^d$;
h) $C_{2-12}$ alkynylene chain optionally substituted with 1 to 3 $R^d$;
i) 1-6 ethylene glycol units;
j) 1-6 propylene glycol units; or
k) —C(O)—, —C(O)O—, —O—, —N($R^c$)—, —S—, —C(S)—, —C(S)—O—, —S(O)$_2$—, —S(O)=N—, —S(O)$_2$NH—, —C(O)—N($R^c$)—, —C=N—, —O—C(O)—N($R^c$)—, or —O—C(O)—O—;

LHM is a ligase harness moiety;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —O$R^c$;

each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—$R^c$, —N($R^c$)C(O)O—$R^c$, —N($R^c$)C(O)N($R^c$)($R^c$), —N($R^c$)S(O)$_2$($R^c$), —N$R^c$S(O)$_2$N($R^c$)($R^c$), —N($R^c$)S(O)$_2$O($R^c$), —OC(O)$R^c$, —OC(O)—N($R^c$)($R^c$), —Si($R^c$)$_3$, —S—$R^c$, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^d$;

each $R^c$ is independently hydrogen or $C_{1-6}$ alkyl; and each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

In various further embodiments, the LHM targets VHL, CRBN or IAP of E3 ligases, which are harnessed by the bifunctional compound to induce ubiquitination and subsequent proteasomal degradation of IRAK4.

In more specific embodiments, the LHM is represented by Formula (IIA), (IIB), (IIIA), (IIIB), (IIIC), (IIID), (IIIE), (IVA), (IVB), (IVC) or (IVD) or their respective substructures.

In more specific embodiments, the bifunctional compounds are Examples 1-192 described in the Examples.

A further embodiment provides a pharmaceutical composition comprising a compound of Formula (I) or any one of its substructures and a pharmaceutically acceptable carrier.

In some embodiment, the compounds of Formula (I) or pharmaceutical compositions thereof are useful as therapeutic agents for treating cancer, such as lymphomas, leukemia, acute myeloid leukemia (AML) and myelodysplastic syndrome (MDS).

In other embodiments, the compounds of Formula (I) or pharmaceutical compositions thereof are useful as therapeutic agents for treating metabolic disorders, such as diabetes (type I and type II diabetes), metabolic syndrome, dyslipidemia, obesity, glucose intolerance, hypertension, elevated serum cholesterol, and elevated triglycerides.

In other embodiments, the compounds of Formula (I) or pharmaceutical compositions thereof are useful as therapeutic agents for treating inflammatory disorders such as rheumatoid arthritis (RA), inflammatory bowel disease (IBD), Crohn's disease, ulcerative colitis, necrotizing enterocolitis, gout, Lyme disease, arthritis, psoriasis, pelvic inflammatory disease, systemic lupus erythematosus (SLE), Sjogren's syndrome, inflammation associated with gastrointestinal infections, including *C. difficile*, viral myocarditis, acute and chronic tissue injury, non-alcoholic steatohepatitis (NASH), alcoholic hepatitis and kidney disease, including chronic kidney disease and diabetic kidney disease.

DETAILED DESCRIPTION

Disclosed are bifunctional compounds capable of recruiting IRAK4 to E3 Ubiquitin Ligase for degradation, and methods of preparation and uses thereof. In particular, a bifunctional compound typically comprises an IRAK4 binder, which is covalently conjugated, via a linker, to a ligase harness moiety for targeting Ubiquitin Ligase. Advantageously, the targeted degradation of IRAK4 provides effective treatment or amelioration of disease conditions involving IRAK4 function.

One embodiment provides a bifunctional compound of Formula (I)

Formula (I)

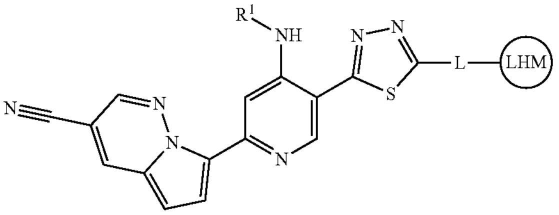

or a pharmaceutically acceptable salt, isotopic form, isolated stereoisomer, or a mixture of stereoisomers thereof, wherein:

$R^1$ is $C_{1-10}$ alkyl optionally substituted with 1-3 $R^a$; $C_{3-10}$ cycloalkyl optionally substituted with 1-3 $R^a$; or 3-12 membered heterocyclyl optionally substituted with 1-3 $R^a$;

L is $-L_1-L_2-L_3-L_4-L_5-$, each $L_1$, $L_2$, $L_3$, $L_4$ and $L_5$ being independently:

a) $C_{3-12}$ cycloalkyl optionally substituted with 1-3 $R^b$;
b) $C_{6-12}$ aryl optionally substituted with 1-3 $R^b$;
c) 3-12 membered heterocyclyl optionally substituted with 1-3 $R^b$;
d) 5-12 membered heteroaryl optionally substituted with 1-3 $R^b$;
e) direct bond;
f) $C_{1-12}$ alkylene chain optionally substituted with 1-3 $R^d$;
g) $C_{2-12}$ alkenylene chain optionally substituted with 1-3 $R^d$;
h) $C_{2-12}$ alkynylene chain optionally substituted with 1 to 3 $R^d$;
i) 1-6 ethylene glycol units;
j) 1-6 propylene glycol units;
k) —C(O)—, —C(O)O—, —O—, —N($R^c$)—, —S—, —C(S)—, —C(S)—O—, —$S(O)_2$—, —S(O)=N—, —$S(O)_2$NH—, —C(O)—N($R^c$)—, —C=N—, —O—C(O)—N($R^c$)—, or —O—C(O)—O—;

LHM is a ligase harness moiety;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —O$R^c$;

each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—R, —C(O)—$R^c$, —C(O)O—$R^c$, —C(O)—N($R^c$)($R^c$), —N($R^c$)($R^c$), —N($R^c$)C(O)—$R^c$, —N($R^c$)C(O)O—$R^c$, —N($R^c$)C(O)N($R^c$)($R^c$), —N($R^c$)$S(O)_2$($R^c$), —N$R^c$$S(O)_2$N($R^c$)($R^c$), —N($R^c$)$S(O)_2$O($R^c$), —OC(O)$R^c$, —OC(O)—N($R^c$)($R^c$), —Si$(R^c)_3$, —S—$R^c$, —S(O)$R^c$, —S(O)(NH)$R^c$, —$S(O)_2R^c$ or —$S(O)_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^d$;

each $R^c$ is independently hydrogen or $C_{1-6}$ alkyl; and each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

IRAK4 Binders

The IRAK4 Binder moiety of the bifunctional compounds of Formula (I) has the following structure, in which the wavy line shows the bond attached to the remainder of the compound of Formula (I).

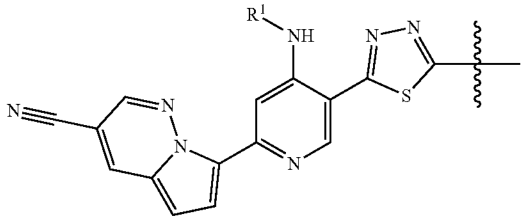

wherein $R^1$ is $C_{1-10}$ alkyl optionally substituted with 1-3 $R^a$; $C_{3-10}$ cycloalkyl optionally substituted with 1-3 $R^a$; or 3-12 membered heterocyclyl optionally substituted with 1-3 $R^a$;

In more specific embodiments, $R^1$ is:

a) $C_{1-5}$ alkyl optionally substituted with halo, —OH, or —CN;

b) 4-8 membered heterocyclyl optionally substituted with halo, $C_{1-5}$ alkyl, —OH, or —CN; or c) $C_{3-10}$ cycloalkyl optionally substituted with halo, $C_{1-5}$ alkyl, —OH, or —CN.

In more specific embodiments, $R^1$ is oxetane, tetrahydrofuran or tetrahydropyran, each may be optionally substituted with F, $C_{1-3}$ alkyl, —OH, or —CN.

In other more specific embodiments, the

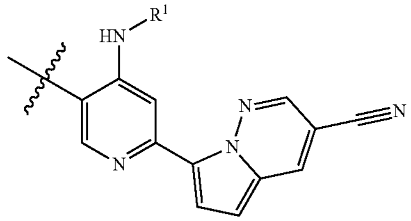

moiety has one of the following structures (the wavy line shows the bond attached to the thiadiazol moiety):

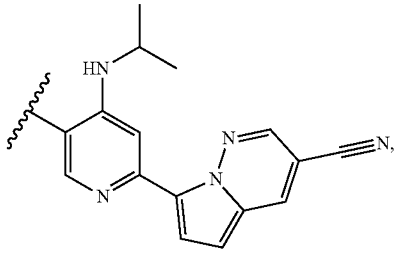
,
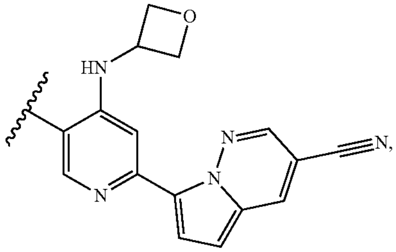
,
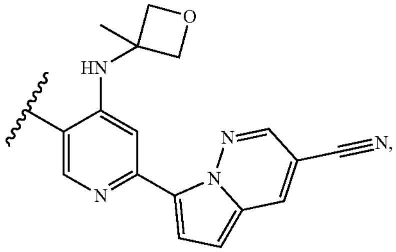
,
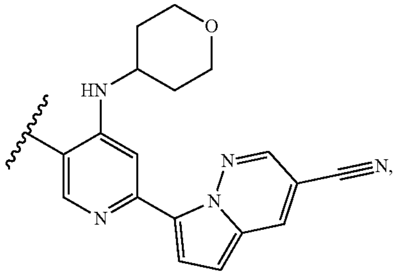
,

-continued

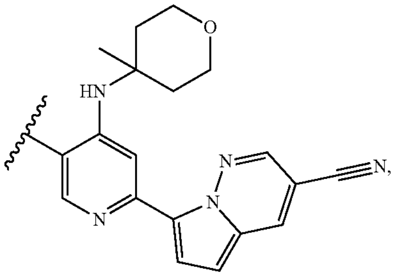
,
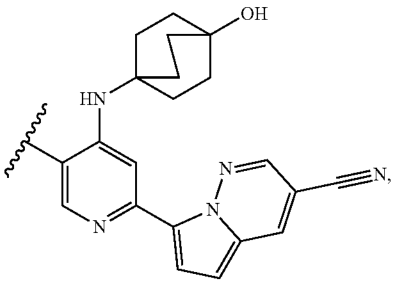
,
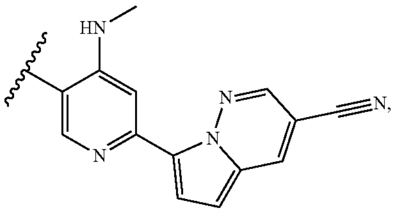
,
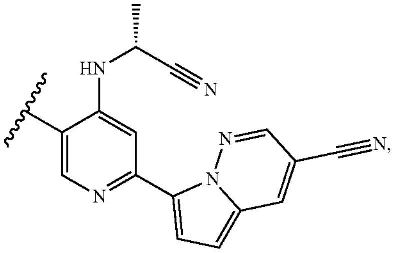
,
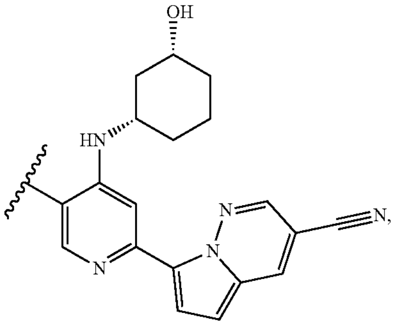
,
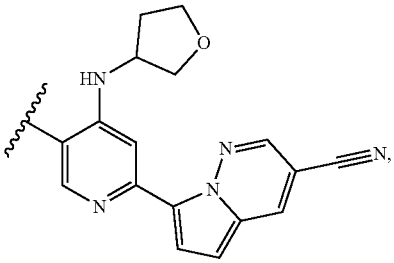
, or

-continued

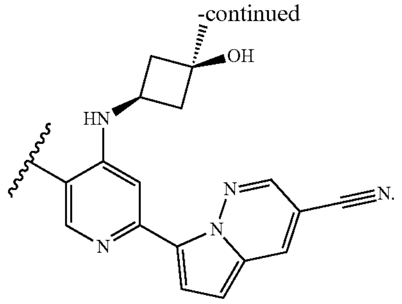

Ligase Harness Moieties (LHM)

The von Hippel-Lindau (VHL) and cereblon (CRBN) proteins are substrate recognition subunits of two ubiquitously expressed and biologically important Cullin RING E3 ubiquitin ligase complexes. In addition, Inhibitors of Apotosis Proteins (IAPs) are a protein family involved in suppressing apoptosis. The human IAP family includes 8 members, and numerous other organisms contain IAP homologs. IAPs contain an E3 ligase specific domain and baculoviral IAP repeat (BIR) domains that recognize substrates, and promote their ubiquitination.

The LHMs of compounds of Formula (I) targets VHL, CRBN or IAP of E3 ligases, which are harnessed by the bifunctional compound to induce ubiquitination and subsequent proteasomal degradation of IRAK4.

A. LHM Targeting CRBN

Thalidomide derivatives, such as lenalidomide or pomalidomide, can be used to recruit potential substrates to CRBN, a component of a ubiquitin ligase complex.

One embodiment provides a CRBN-targeting LHM having the following structure (the wavy line shows the bond attached to the remainder of the compound of Formula (I)):

Formula (IIA)

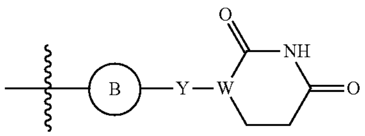

wherein,

W is —C($R^g$)— or —N—,

Y is direct bond, $C_{1-4}$ alkylene chain, —C(O)—, —C(O)O—, —O—, —N($R^g$)—, —S— —C(S)—, —C(S)—O—, —O—C(O)O—, —C(O)—N($R^g$)—, —O—C(O)—N($R^g$)—;

B ring is $C_{6-12}$ aryl, 5-12 membered heteroaryl, or 3-12 membered heterocyclyl, each being optionally substituted with 1 to 3 $R^j$;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—$R^g$, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O)$R^g$, —S(O)(NH)$R^g$, —S(O)$_2R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$;

$R^g$ is hydrogen or $C_{1-6}$ alkyl; and each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

In certain specific embodiments, Y is direct bond and Formula (IIA) has the following structure:

Formula (IIA1)

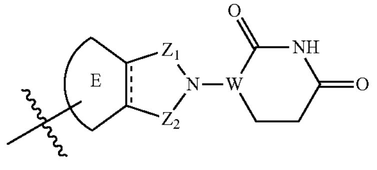

wherein,

W is —C($R^g$)— or —N—;

$Z_1$ is —C(O)—, —C(S)—, —C(N$R^g$)—, —C($R^g$)$_2$—, —N═, —N($R^g$)—, —C($R^g$)$_2$—C(O)—, —C(O)—N($R^g$)—, —C$R^g$═C$R^g$—, —C($R^g$)$_2$—C(S)—, —C($R^g$)═N—, or —C($R^g$)$_2$—C($R^g$)$_2$—;

$Z_2$ is —C(O)—, —C(S)—, —C(N$R^g$)—, —N($R^g$)—, —N═, or —C($R^g$)$_2$—;

$R^g$ is hydrogen or $C_{1-6}$ alkyl; and

E ring is phenyl, 5-6 membered heteroaryl or 5-6 membered heterocyclyl, each being optionally substituted with 1 to 3 $R^j$.

In more specific embodiments, $Z_2$ is —C(O)— and Formula (IIA1) has the following structure:

(Formula IIA1')

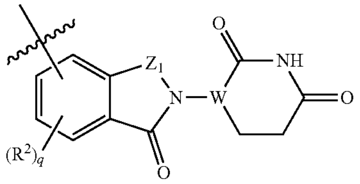

wherein,

W is —C($R^g$)— or —N—;

$Z_1$ is —C(O)—, —C(S)—, —C(N$R^g$)—, —C($R^g$)$_2$—, —C($R^g$)$_2$—C(O)—, —C(O)—N($R^g$)—, —C$R^g$═C$R^g$—, —C($R^g$)═N—, —C($R^g$)$_2$—C(S)—, or —C($R^g$)$_2$—C($R^g$)$_2$—;

q is 0, 1 or 2;

$R^g$ is hydrogen or $C_{1-6}$ alkyl; and $R^2$ is $C_{1-6}$alkyl, halo, halo $C_{1-6}$alkyl, —N($R^g$)$_2$, CN, nitro, hydroxyl, or —O—$C_{1-4}$alkyl.

In more specific embodiments of Formula (IIA1'), W is —CH—; and $Z_1$ is —C(O)—, —CH$_2$—, —CH$_2$—C(O)—, or —CH═CH—.

In specific embodiments, Formula (IIA1') has one of the following structures:

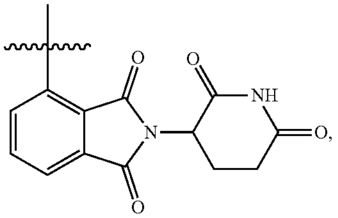
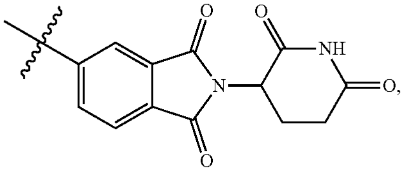
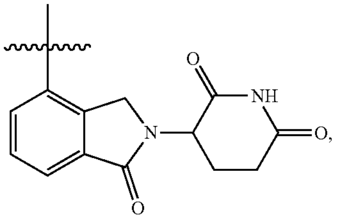
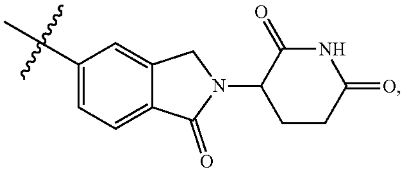
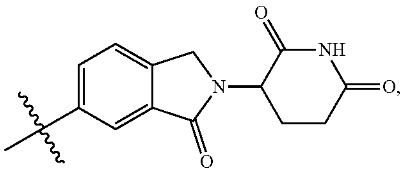
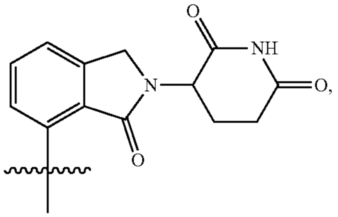
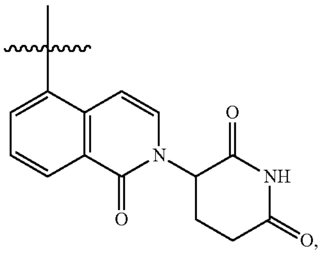
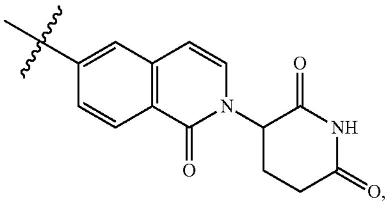
-continued
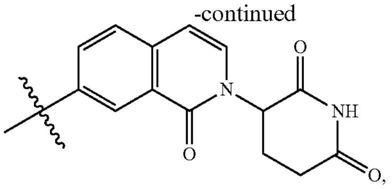
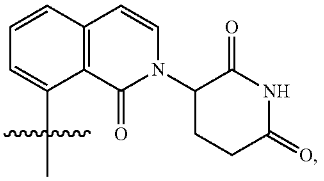
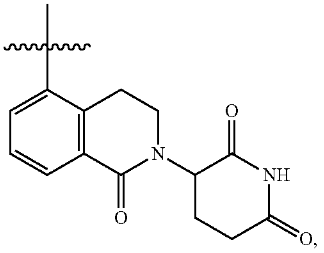
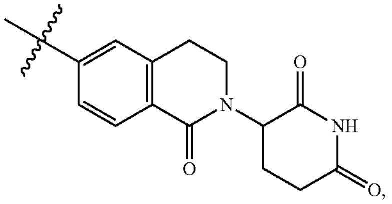
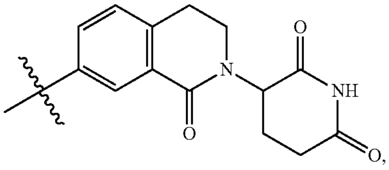
or
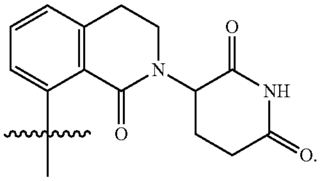
In other embodiments, Formula (IIA) has the following structure:
(Formula IIA2)
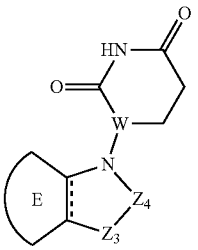
wherein,
W is —C($R^g$)— or —N—;
$Z_3$ is —C(O)—, —C(S)—, —C(N$R^g$)—, —C($R^g$)$_2$—, —N═, —N($R^g$)—, —C($R^g$)$_2$—C(O)—, —C(O)—N($R^g$)—, —C$R^g$═C$R^g$—, —C($R^g$)$_2$—C(S)—, —C($R^g$)

$=N—$, $—C(R^g)_2—C(R^g)_2—$, $—C(R^g)_2—O—$, $—C(R^g)_2—S—$, —O—, or —S—;

$Z_4$ is —C(O)—, —C(S)—, $—C(NR^g)—$, $—N(R^g)—$, —N═, —O—, —S—, or $—C(R^g)_2—$;

$R^g$ is hydrogen or $C_{1-6}$ alkyl; and

E ring is phenyl, 5-6 membered heteroaryl or 5-6 membered heterocyclyl, each being optionally substituted with 1 to 3 $R^j$.

In more specific embodiments of Formula (IIA2), W is —CtH—; $Z_3$ is $—C(R^g)_2—$, $—N(R^g)—$, $—C(R^g)_2—C(O)—$, $—C(O)—N(R^g)—$, $—CR^g═CR^g—$, $—C(R^g)_2—C(S)—$, $—C(R^g)═N—$, $—C(R^g)_2—C(R^g)_2—$, $—C(R^g)_2—O—$, or $—C(R^g)_2—S—$; and $Z_4$ is —C(O)—, —C(S)—, $—C(NR^g)—$, or $—C(R^g)_2—$.

In yet other more specific embodiments, Formula (IIA2) has the following structure:

Formula (IIA2')

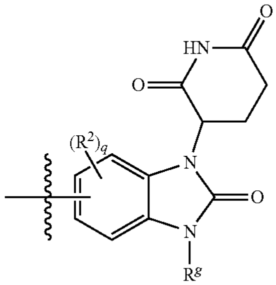

wherein, q is 0, 1 or 2; $R^g$ is hydrogen or $C_{1-6}$ alkyl; and $R^2$ is $C_{1-6}$alkyl, halo, halo $C_{1-6}$alkyl, $—N(R^g)_2$, CN, nitro, hydroxyl, or $—O—C_{1-4}$alkyl.

In more specific embodiments, Formula (IIA2') has the following structures:

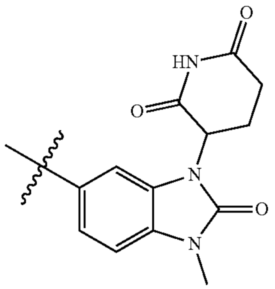

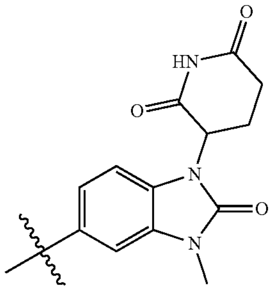

-continued

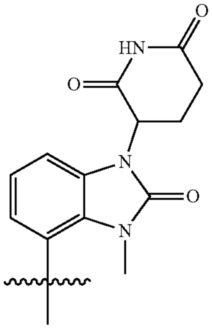

, or

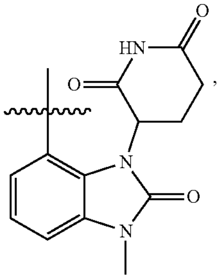

,

In more specific embodiments of Formula (IIA), W is —CH—; Y is direct bond, $C_{1-4}$ alkylene chain, —C(O)—, —C(O)O—, —O—, $—N(R^g)—$, —S—, —C(S)—, —C(S)—O—, —O—C(O)O—, $—C(O)—N(R^g)—$, $—O—C(O)—N(R^g)—$; B ring is phenyl, 5-6 membered heteroaryl, or 5-6 membered heterocyclyl, each being optionally substituted with 1-3 $R^j$.

In specific embodiments, Formula (IIA) has one of the following structures:

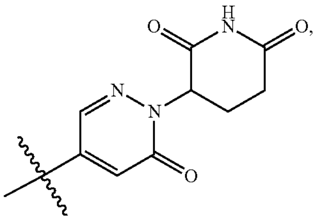

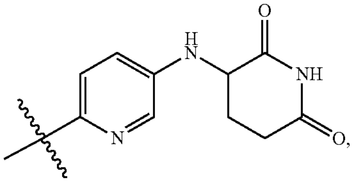

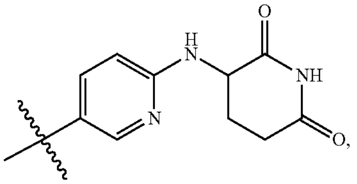

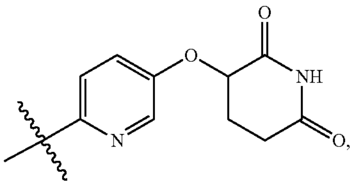

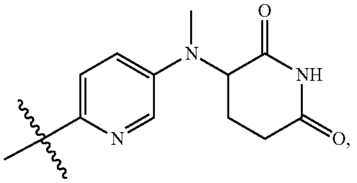

-continued

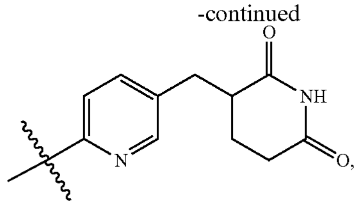

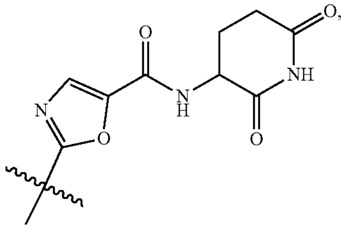

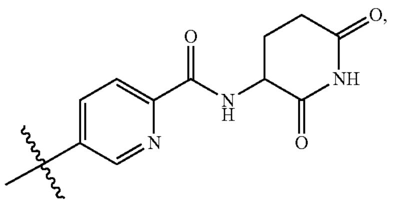

or

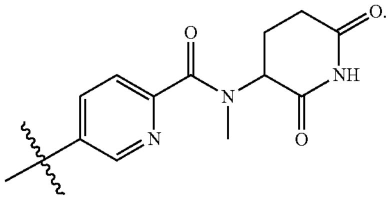

In another embodiment, the CRBN-targeting LHM has the following structure:

Formula (IIB)

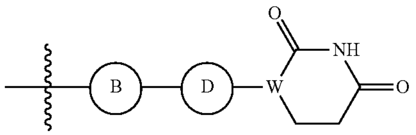

wherein,

W is —C($R^g$)— or —N—;

D ring is phenyl, 5-6 membered heteroaryl, or 5-6 membered heterocyclyl, each being optionally substituted with 1 to 3 $R^j$;

B ring is $C_{6-12}$ aryl, 5-12 membered heteroaryl, or 3-12 membered heterocyclyl, each being optionally substituted with 1 to 3 $R^j$;

$R^g$ is hydrogen or $C_{1-6}$ alkyl;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^g$, —C(O)—$R^g$, —C(O)O—R, —C(O)—N($R^g$)($R^g$), —N($R^g$)($R^g$), —N($R^g$)C(O)—$R^g$, —N($R^g$)C(O)O—R, —N($R^g$)C(O)N($R^g$)($R^g$), —N($R^g$)S$(O)_2$($R^g$), —N$R^g$S$(O)_2$N($R^g$)($R^g$), —N($R^g$)S$(O)_2$O($R^g$), —OC(O)$R^g$, —OC(O)—N($R^g$)($R^g$), —Si$(R^g)_3$, —S—$R^g$, —S(O)$R^g$, —S(O)(NH)$R^g$, —S$(O)_2R^g$ or —S$(O)_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$; and each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

In more specific embodiments, Formula (IIB) has the following structure:

Formula (IIB1)

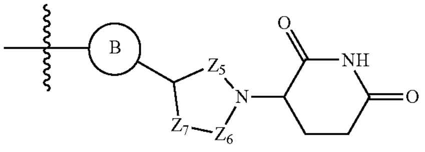

wherein, $Z_5$ is —C(O)—, —C(S)—, —C(N$R^g$)—, —N($R^g$)—, —N═, or —C$(R^g)_2$—;

$Z_6$ is —C(O)—, —C(S)—, —C(N$R^g$)—, —C$(R^g)_2$—, —N═, —N($R^g$)—, —C$(R^g)_2$—C(O)—, —C(O)—N($R^g$)—, —C$R^g$═C$R^g$—, —C$(R^g)_2$—C(S)—, —C($R^g$)═N—, or —C$(R^g)_2$—C$(R^g)_2$—;

$Z_7$ is —C(O)—, —C(S)—, —C(N$R^g$)—, —N($R^g$)—, —O—, —S—, —N═, or —C$(R^g)_2$—; and $R^g$ is hydrogen or $C_{1-6}$ alkyl.

In yet more specific embodiments, Formula (IIB1) has the following structure:

Formula (IB1')

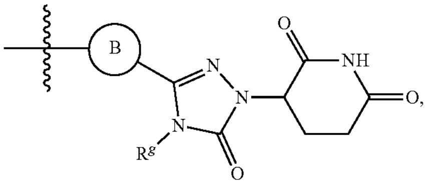

or

Formula (IIB")

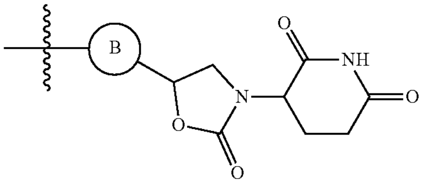

More specifically, Formula (IB1') has the following structure:

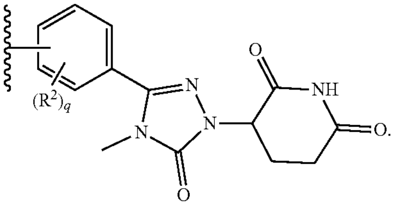

wherein, q is 0, 1 or 2; and $R^2$ is $C_{1-6}$alkyl, halo, halo $C_{1-6}$alkyl, —N$(R^g)_2$, CN, nitro, hydroxyl, or —O—$C_{1-4}$ alkyl.

In a more specific embodiment, Formula (IB1') has the following structure:

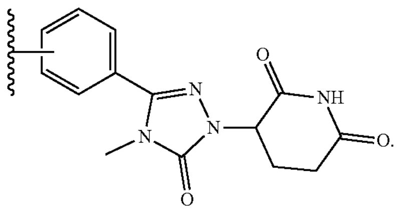

B. LHM Targeting VHL

In various embodiments, LHM that targets Von Hippel-Lindau (VHL) ligase has one of the following structures (the wavy line shows the bond attached to the remainder of the compound of Formula (I)):

Formula (IIIA)

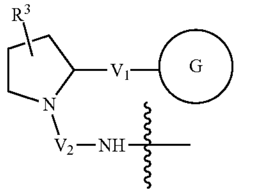

Formula (IIIB)

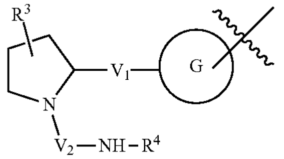

Formula (IIIC)

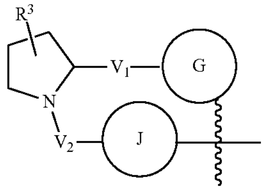

Formula (IIID)

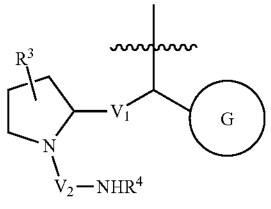

Formula (IIIE)

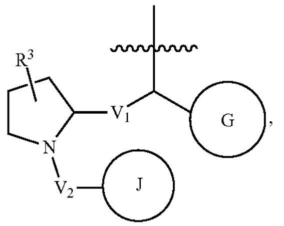

wherein, $V_1$ is —C(O)—, —C(O)O—, —C(O)O—C($R^e$)$_2$—, —C(O)—N($R^e$)—, —C(O)—C($R^e$)$_2$—, or —C(O)—N(R')—C($R^e$)$_2$—;

$V_2$ is —C(O)—C($R^e$)$_2$—;

G ring is phenyl, 5-6 membered heteroaryl or 5-6 membered heterocyclyl, each being optionally substituted with 1-3 $R^j$;

J ring is 5-12 membered heteroaryl or 5-12 membered heterocyclyl, each being optionally substituted with 1-3 $R^j$;

each $R^e$ is independently hydrogen, $C_{1-6}$ alkyl or $C_{3-8}$ cycloalkyl;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^g$, —C(O)—$R^g$, —C(O)O—R, —C(O)—N($R^g$)($R^g$), —N($R^g$)($R^g$), —N($R^g$)C(O)—$R^g$, —N($R^g$)C(O)O—R, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O)$R^g$, —S(O)(NH)$R^g$, —S(O)$_2R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$;

each $R^g$ is independently hydrogen or $C_{1-6}$ alkyl;

each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro;

$R^3$ is hydrogen or hydroxyl;

$R^4$ is —C(O)$R^f$, wherein R is $C_{1-6}$ alkyl or $C_{3-8}$ cycloalkyl, each being optionally substituted with halo or —CN.

In more specific embodiments, Formulae (IIIA), (IIIB), (IIIC), (IIID), (IIIE) have the structures of Formulae (IIIA1), (IIIB1), (IIIC1), (IIID1), (IIIE1), respectively:

Formula (IIIA1)

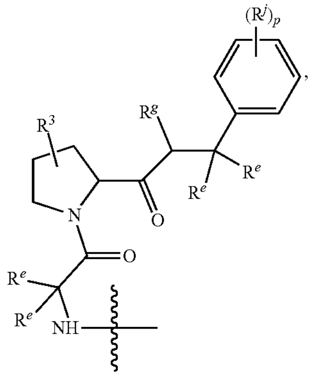

Formula (IIB1)

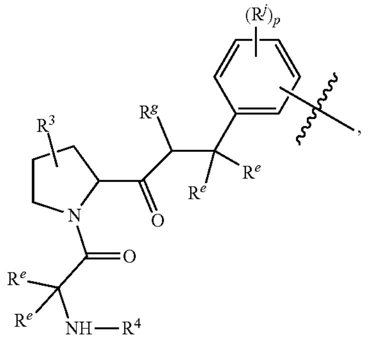

-continued

Formula (IIICI)

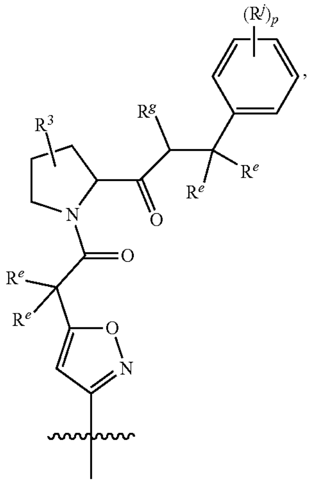

, or

Formula (IIID1)

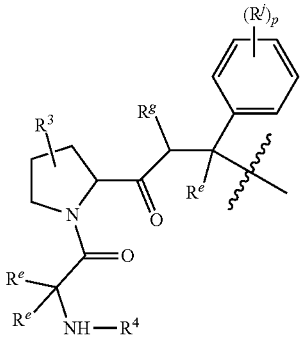

Formula (IIIE1)

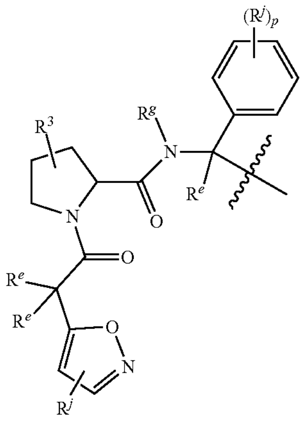

wherein, p is 0 or 1;

$R^j$ is 5-6 member heteroaryl optionally substituted with 1 to 3 $R^k$, each $R^k$ is independently halo, oxo, —CN, —OH, $C_{1-6}$ alkyl, $C_{3-8}$ cycloalkyl, or —O—$C_{1-6}$ alkyl.

each $R^e$ is independently hydrogen, $C_{1-6}$ alkyl or $C_{3-8}$ cycloalkyl;

each $R^g$ is independently hydrogen or $C_{1-6}$ alkyl;

$R^3$ is hydrogen or hydroxyl;

$R^4$ is —C(O)$R^f$, wherein $R^f$ is $C_{1-6}$ alkyl or $C_{3-8}$ cycloalkyl, each being optionally substituted with halo or —CN.

In certain more specific embodiments of any one of Formulae (IIIA1), (IIIB1) (IIIC1), (IIID1), or (IIIE1), p is 1 and $R^j$ is thiazolyl, oxazolyl, isoxazolyl, pyrazolyl, imidazolyl, 1,2,4-oxadiazolyl, 1,3,4-oxadiazolyl, each being optionally substituted with $C_{1-6}$ alkyl, $C_{3-8}$ cycloalkyl, halo, CN, haloalkyl, or hydroxyalkyl.

In preferred embodiments, $R^j$ is thiazolyl, optionally substituted with alkyl (e.g., methyl).

Thus, a more specific embodiment of Formula (IIIA) has the following structures:

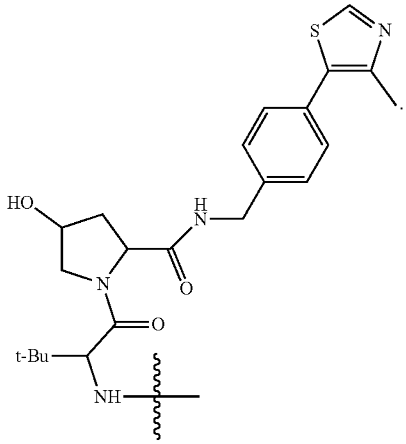 [SMILES: *NC(C(=O)N1CC(O)CC1C(=O)NCc1ccc(-c2scnc2C)cc1)C(C)(C)C]

.

A more specific embodiments of Formula (IIIB) or (IIIB1) has one of the following structures:

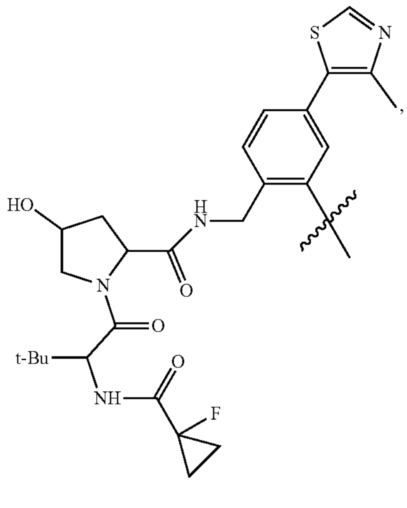

,

-continued
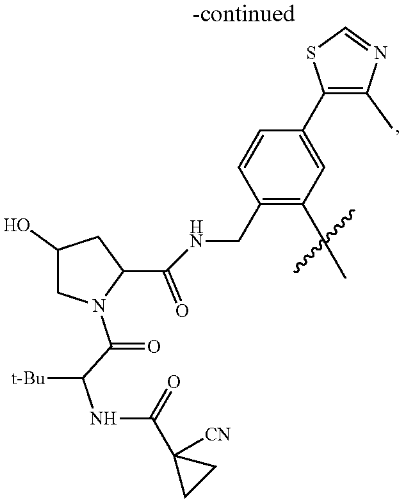
,
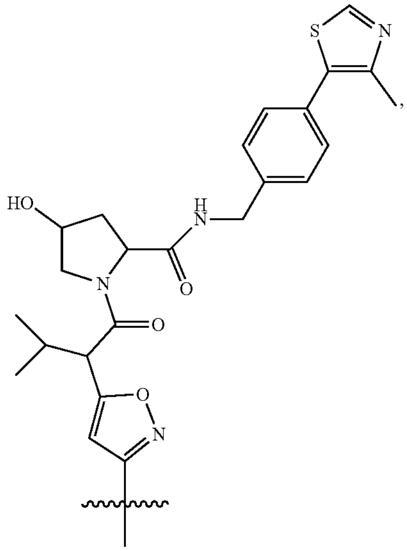
,
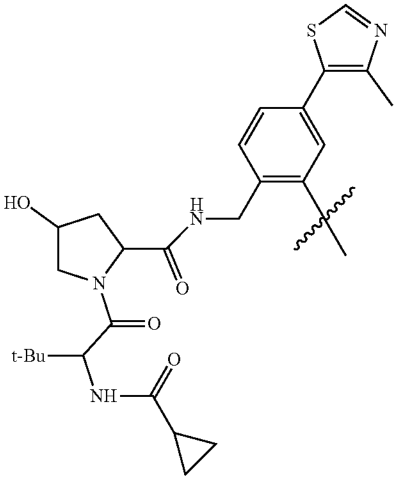
or
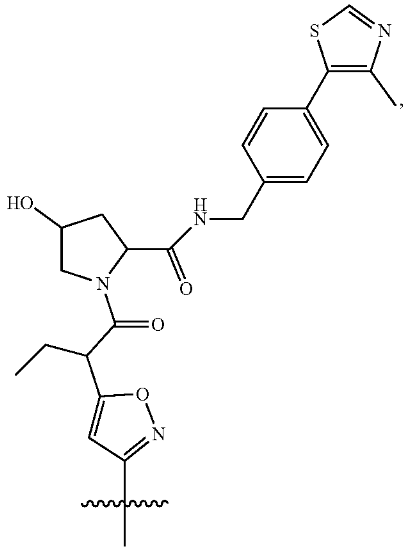
,
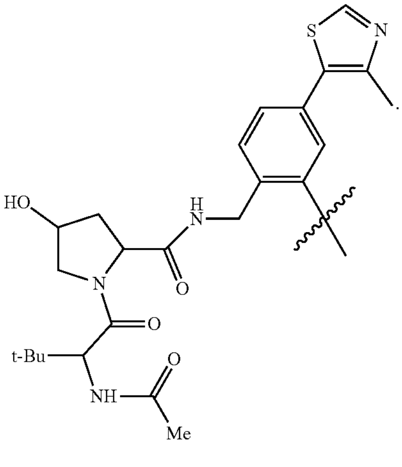 [SMILES: *c1cc(-c2scnc2C)ccc1CNC(=O)C1CC(O)CN1C(=O)C(NC(C)=O)C(C)(C)C]
.
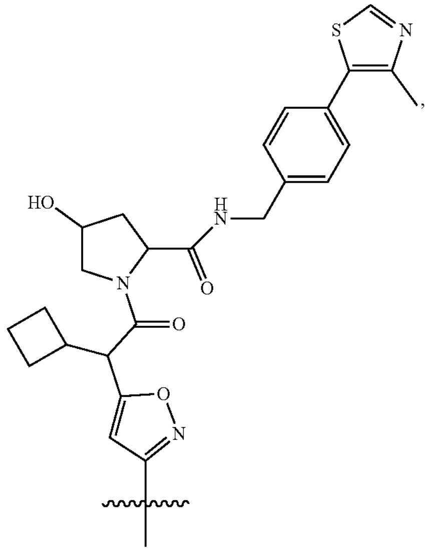
, or
A more specific embodiments of Formula (IIIC) or (IIIC1) has one the following structures:

-continued

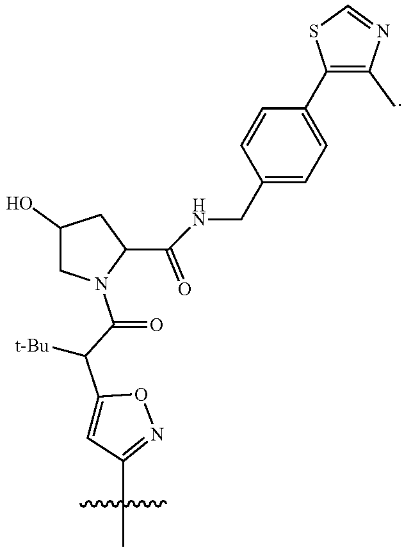 [SMILES: *c1cc(C(C(=O)N2CC(O)CC2C(=O)NCc2ccc(-c3scnc3C)cc2)C(C)(C)C)on1]

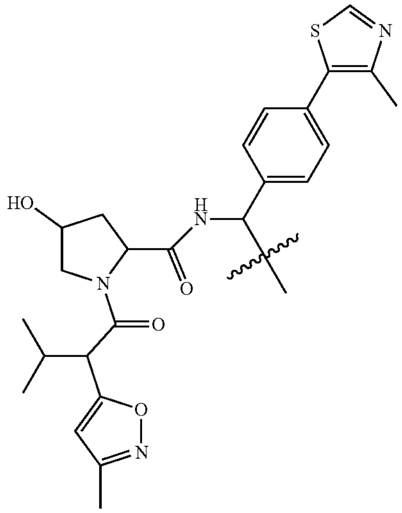

or

A more specific embodiments of Formula (IIID) or Formula (IIID1) has one the following structures:

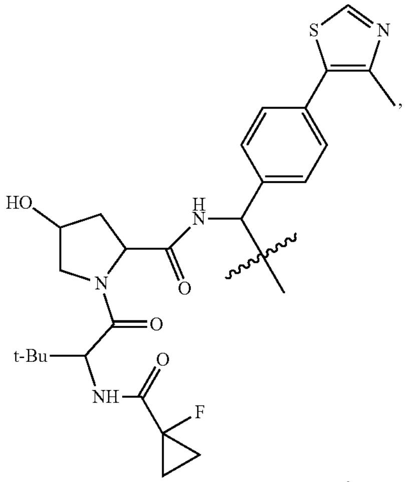

, or

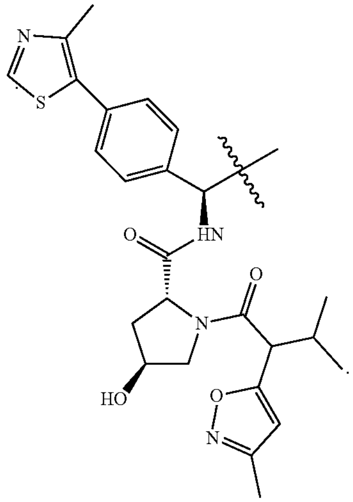

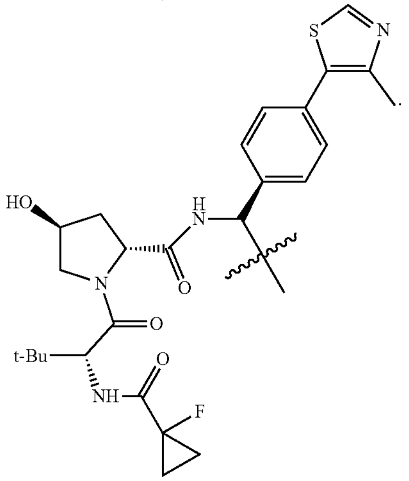

A more specific embodiments of Formula (IIIE) or (IIIE1) has one the following structures:

In other embodiments, the thiazolyl may be absent (i.e., p is 0). These des-thiazolyl LHM may still bind VHL sufficiently to induce degradation. More specifically, Formula (IIIA), (IIIB), (IIIC) or (IIID) has one of the following structures:

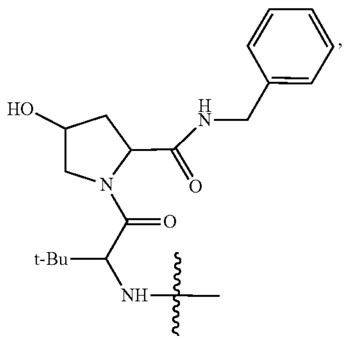

,

-continued
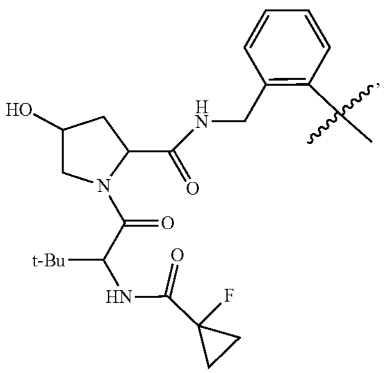
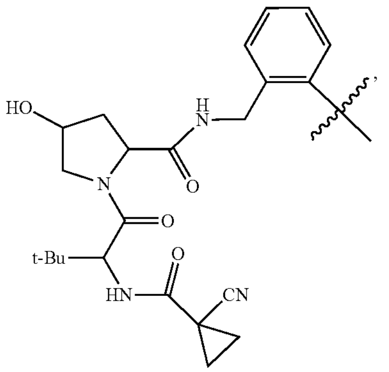
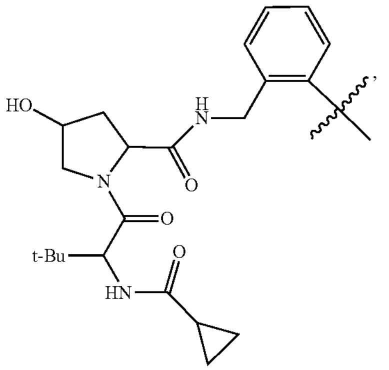
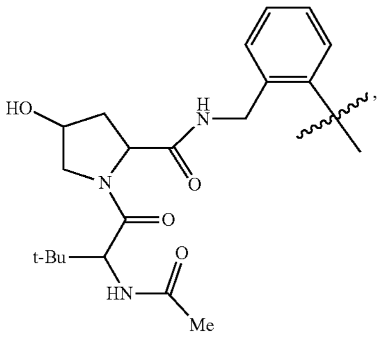
-continued
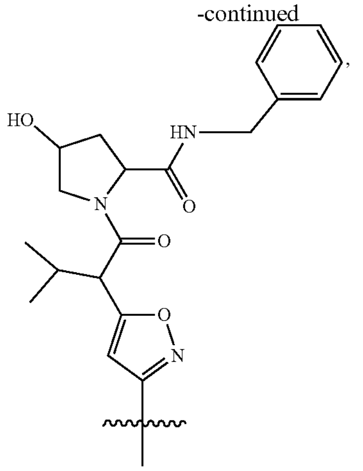
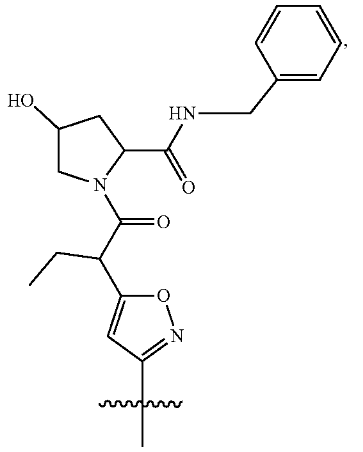
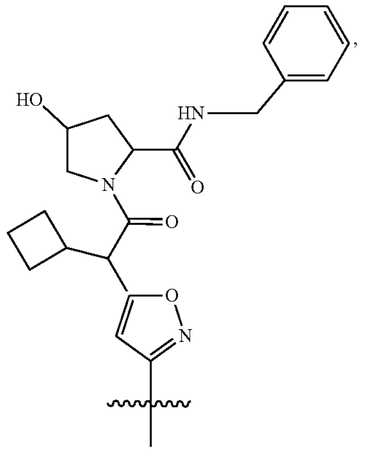

-continued

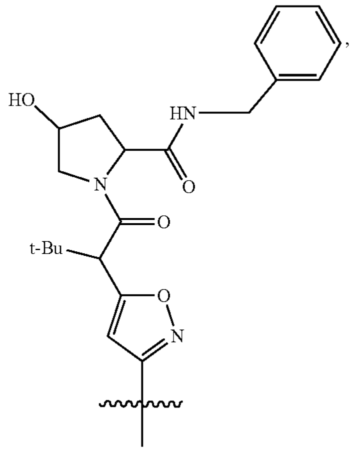

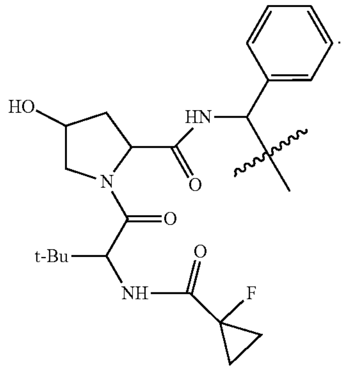

C. LHM Targeting IAP

In various embodiments, LHM that targets Von Hippel-Lindau (VHL) ligase has one of the following structures (the wavy line shows the bond attached to the remainder of the compound of Formula (I)):

Formula (IVA)

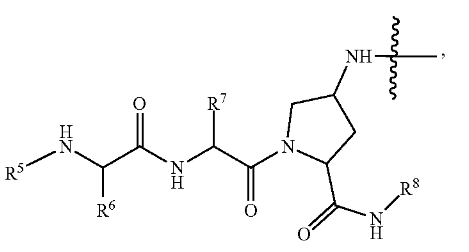

-continued

Formula (IVB)

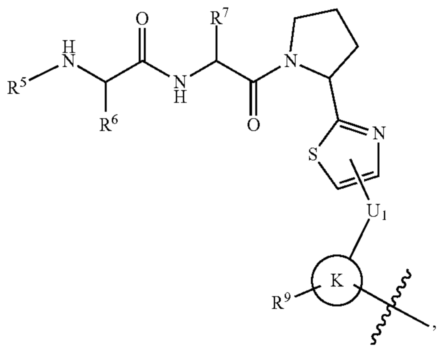

Formula (IVC)

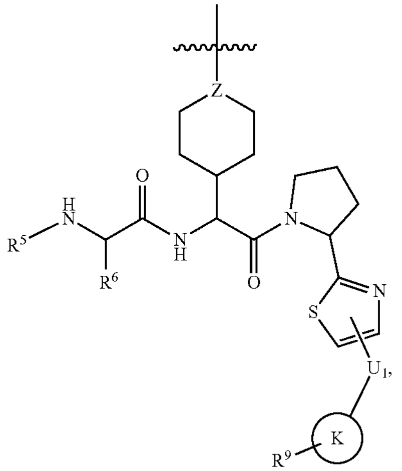

Formula (IVD)

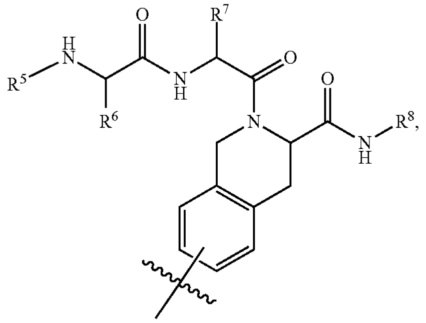

wherein, each $R^5$ is independently hydrogen or $C_{1-6}$ alkyl;

each $R^6$ is independently hydrogen, or $C_{1-6}$ alkyl;

each $R^7$ is independently hydrogen, $C_{1-6}$ alkyl, or $C_{3-8}$ cycloalkyl;

each $R^8$ is independently aryl, 5-12 membered cycloalkyl, 5-12 membered heteroaryl or 5-12 membered heterocyclyl, each being optionally substituted with 1-3 $R^j$;

each $R^g$ is independently hydrogen, halo, or $C_{1-6}$ alkyl;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^g$, —C(O)—$R^g$, —C(O)O—R, —C(O)—N($R^g$)($R^g$), —N($R^g$)($R^g$), —N($R^g$)C(O)—$R^g$, —N($R^g$)C(O)O—R, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O)$R^g$, —S(O)(NH)$R^g$, —S(O)$_2R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$;

each $R^g$ is independently hydrogen or $C_{1-6}$ alkyl;

each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro;

$U_1$ is direct bond or —C(O)—;

Z is —CH— or N; and

K ring is phenyl or naphthyl.

More specific embodiments of Formulae (IVA), (IVB), (IVC) and (IVD) have the following structure, respectively:

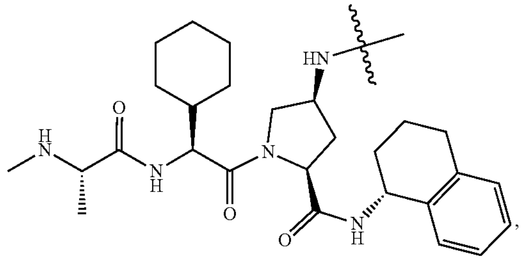

,

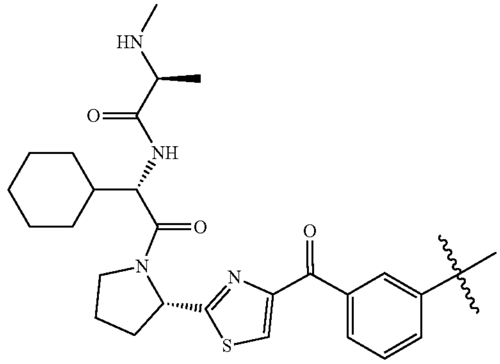

,

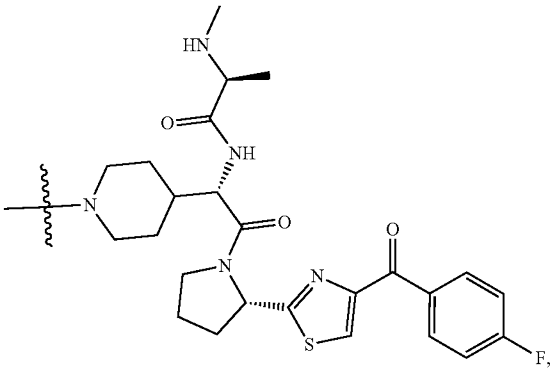

, or

-continued

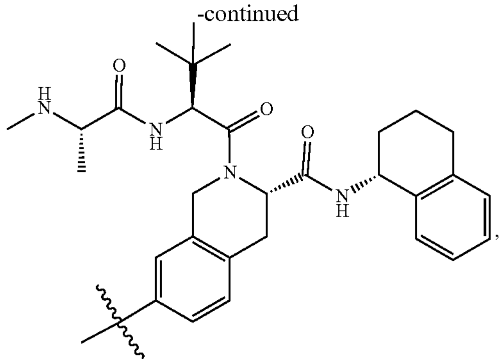

,

Linker

The bifunctional compounds of Formula (I) comprises a linker moiety that couples the IRAK4 Binder to the LHM. The structure (e.g., length or rigidity) of the linker moiety may impact the efficiency or selectivity of the degradation process. Typically, the linker moiety comprises multiple segments, which contribute to the overall length and rigidity of the linker, in addition to providing the respective attachment points to the IRAK4 binder and the LHM.

In certain embodiments, the linker moiety (L) of Formula (I) has up to 5 linker segments ($L_s$, s is 1-5) and the compound of Formula (I) has the following structure:

Formula (I')

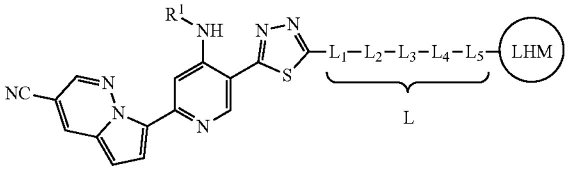

wherein each $L_1$, $L_2$, $L_3$, $L_4$ and $L_5$ is independently a bivalent moiety selected from:

a) $C_{3-10}$ cycloalkyl optionally substituted with 1-3 $R^b$;

b) aryl optionally substituted with 1-3 $R^b$;

c) 3-12 membered heterocyclyl optionally substituted with 1-3 $R^b$;

d) 5-12 membered heteroaryl optionally substituted with 1-3 $R^b$;

e) direct bond;

f) $C_{1-12}$ alkylene chain optionally substituted with 1-3 $R^d$;

g) $C_{2-12}$ alkenylene chain optionally substituted with 1-3 $R^d$;

h) $C_{2-12}$ alkynylene chain optionally substituted 1 to 3 with $R^d$;

i) 1-6 ethylene glycol units;

j) 1-6 propylene glycol units; and k) —C(O)—, —C(O)O—, —O—, —N($R^c$)—, —S—, —C(S)—, —C(S)—O—, —S(O)$_2$—, —S(O)=N—, —S(O)$_2$NH—, —C(O)—N($R^c$)—, —C=N—, —O—C(O)—N($R^c$)—, or —O—C(O)—O—;

wherein each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—$R^c$, —N($R^c$)C(O)O—$R^c$, —N($R^c$)C(O)N($R^c$)($R^c$), —N($R^c$)S(O)$_2$($R^c$), —N$R^c$S(O)$_2$N($R^c$)($R^c$), —N($R^c$)S(O)$_2$O($R^c$), —OC(O)R, —OC(O)—N($R^c$)($R^c$), —Si($R^c$)$_3$, —S—$R^c$, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^d$;

each $R^c$ is independently hydrogen or $C_{1-6}$ alkyl; and each $R^d$ is independently halo, oxo, —CN, —OH, $C_{1-6}$ alkyl optionally substituted with 1 to 3 fluoro, or $C_{3-8}$ cycloalkyl optionally substituted with 1 to 3 fluoro.

It is to be understood that, unless otherwise specified and provided that the valence is satisfied, the bivalent moieties described herein (e.g., L or $L_s$) are not limited to the direction in which they are expressed. For instance, for a given linker segment, e.g., —C(O)—NH—, the manner in which it is connected to the remainder of the molecule may be either direction: i.e., —C(O)—NH— or —NH—C(O)—, provided that the connection does not violate valence rules.

On the other hand, when L is expressed by a series of $L_s$, directionality may be established by the location of the specific $L_s$ in a manner consistent with the structure of Formula (I'). For instance, a linker segment $L_1$ is to be understood to couple directly to the IRAK4 Binder moiety; whereas a linker segment $L_5$ is to be understood to couple directly to the LHM.

One or more linker segments may be direct bonds. For instance, in -$L_2$-$L_3$-$L_4$-, when $L_3$ is a direct bond, it is effectively absent because $L_2$ and $L_4$ are attached directly to each other.

In various specific embodiments, $L_1$ is a ring selected from $C_{3-15}$ cycloalkyl; 6-15 membered aryl, 3-15 membered heterocyclyl, and 5-15 membered heteroaryl, each of which may be further substituted with up to 3 $R^d$ (as defined herein). In more specific embodiments, $L_1$ is a ring selected from $C_{3-12}$ cycloalkyl; 6-12 membered aryl, 3-12 membered heterocyclyl, and 5-12 membered heteroaryl, each of which may be further substituted with up to 3 $R^d$ (as defined herein).

In various specific embodiments, $L_1$ may be one of the following ring moieties:

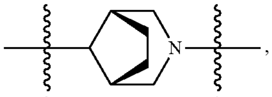,

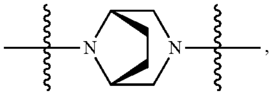,

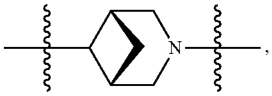,

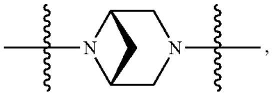,

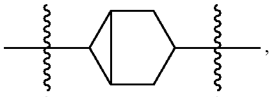,

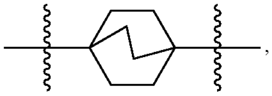,

-continued

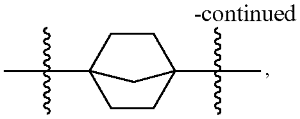,

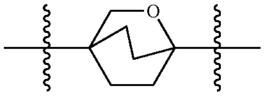, 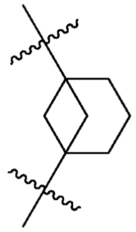,

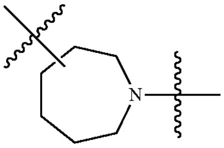, 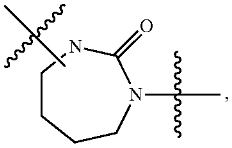,

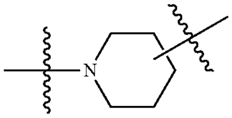,

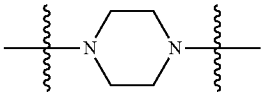, 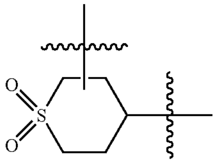,

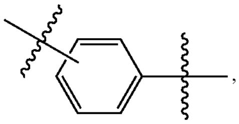, 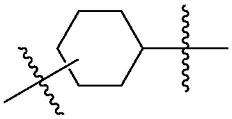,

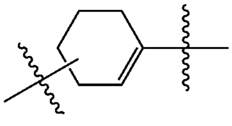, 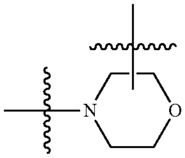,

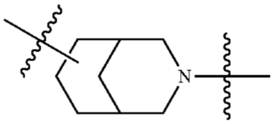,

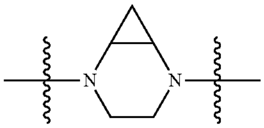,

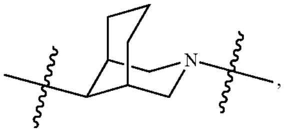,

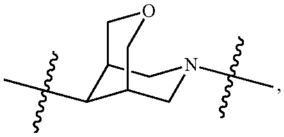,

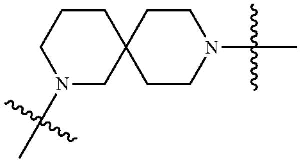,

-continued

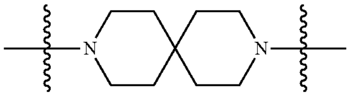,

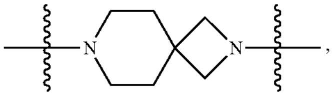,

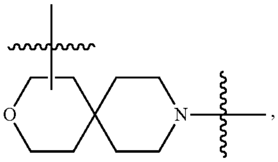,

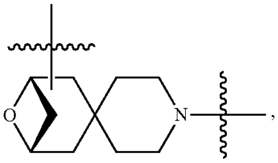, 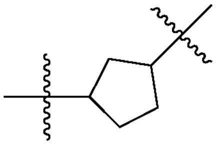,

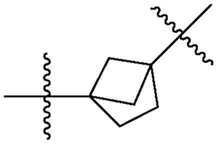, 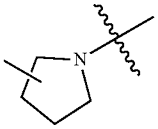,

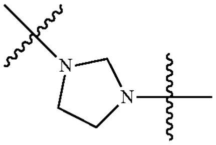, 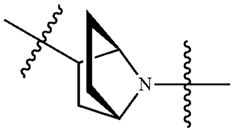,

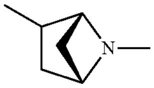, 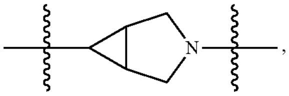,

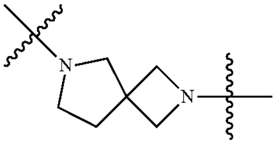,

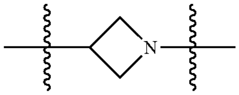, 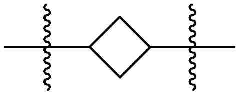,

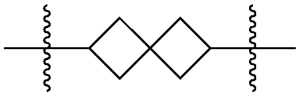,

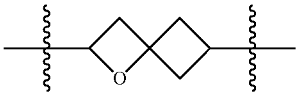,

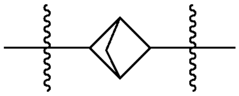, 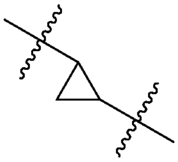,

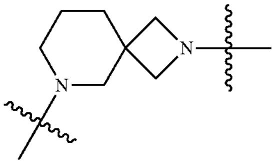, or

-continued

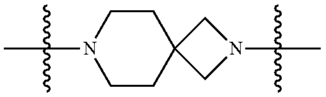.

wherein each ring may be optionally substituted by 1 to 3 $R^d$, $R^d$ is independently halo, oxo, —CN, —OH, $C_{1-6}$ alkyl, $C_{3-8}$ cycloalkyl optionally substituted with 1 to 3 fluoro, or —O—$C_{1-6}$ alkyl optionally substituted with 1 to 3 fluoro.

In more specific embodiments, $L_1$ has one of the following structures:

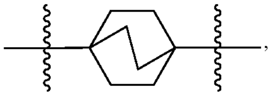,

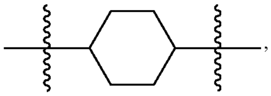,

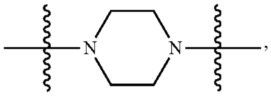,

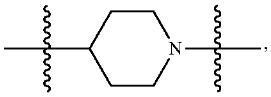 [SMILES: *C1CCC(*)CC1],

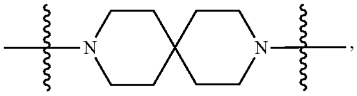,

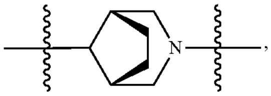,

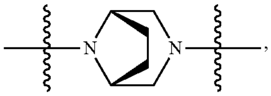,

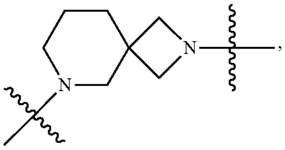,

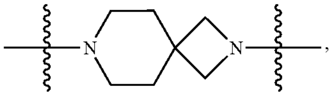,

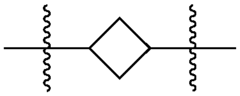 or

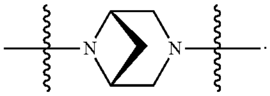.

In preferred embodiments, $L_1$ has one of the following structures:

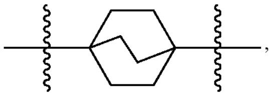,

-continued

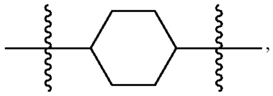,

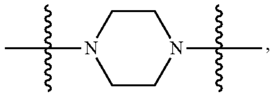,

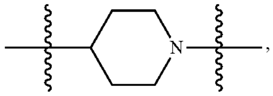,

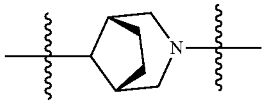,

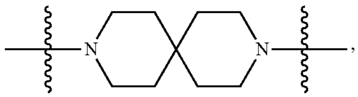,

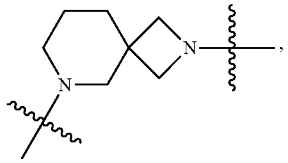,

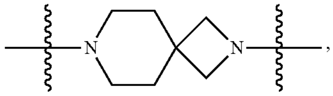, or

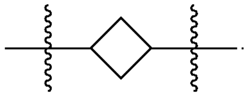.

In further embodiments, $-L_2-L_3-L_4-L_5-$ has a generally linear construction (i.e., no ring). More specifically, $-L_2-L_3-L_4-L_5-$ may be —C(O)—, —NH—C(O)—, —C(O)—$(CH_2)_n$—, —C(O)—$(CH_2)_n$—C(O)—, —C(O)—$(CH_2)_n$—O—, —$(CH_2)_n$—, —C(O)—$(CH_2)_n$—NH—, —C(O)—$(CH_2CH_2O)_m$—, —C(O)—$(CH_2CH_2O)_m$—$(CH_2)_n$—C(O)—, —C(O)—$(CH_2CH_2O)_m$—$(CH_2)_n$—NH—, —C(O)—$(CH_2CH_2O)_m$—$(CH_2)_n$—, —NH—C(O)—$(CH_2CH_2O)_m$—$(CH_2)_n$—C(O)—, —NH—C(O)—$(CH_2CH_2O)_m$—$(CH_2)_n$—NH—, —NH—C(O)—$(CH_2)_n$—C(O)—, —NH—C(O)—$(CH_2)_n$—, —NH—C(O)—$(CH_2CH_2O)_m$—, —NH—C(O)—$(CH_2)_n$—O—, —NH—C(O)—$(CH_2)_n$—NH—, or —NH—C(O)—$(CH_2CH_2O)_m$—$(CH_2)_n$—, wherein m and n is independently an integer of 1-12 and wherein one or two hydrogens of each of the above linker moieties may be replaced by $C_{1-3}$ alkyl (e.g., methyl, ethyl, n-propyl, or isopropyl).

In preferred embodiments, m is an integer of 1 to 10; and n is an integer of 1-10. In other embodiments, m is 1, 2, 3, 4, 5, or 6 and n is 1, 2 or 3. In various preferred embodiments, m is 1, 2, 3, 4, 5, or 6. In various preferred embodiments, n is 3, 4, 5, 6, 7, 8, 9, 10.

In certain embodiments, $L_1$ is

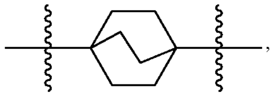, and L has the following structure:

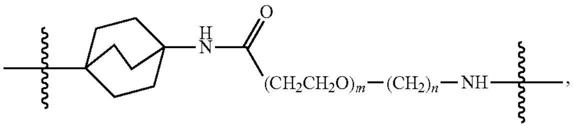,

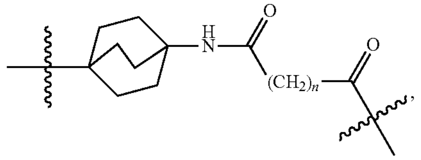,

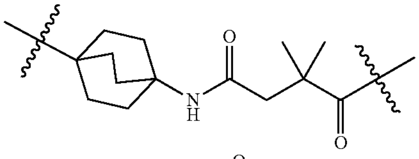 or

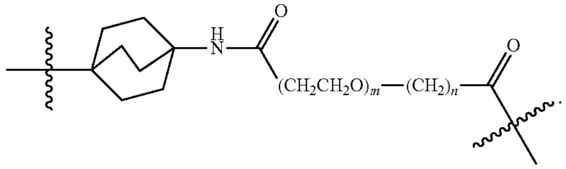.

In preferred embodiments, m is 1, 2, 3, 4, 5 or 6 and n is 1, 2, 3, 4, 5, or 6. In more preferred embodiments, m is 1, 2 or 3, and n is 1 or 2.

In other embodiments, $L_1$ is

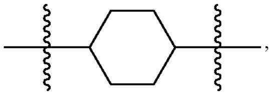, and L has the following structure:

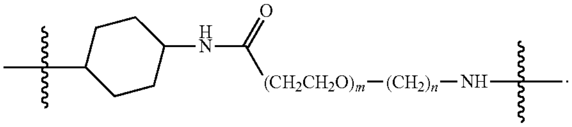.

In preferred embodiments, m is 1, 2, 3, 4, 5 or 6 and n is 2, 4, or 6. In even more preferred embodiments, m is 1, 2 or 3, and n is 2.

In other embodiments, $L_1$ is

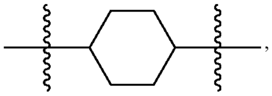 [SMILES: *C1CCC(*)CC1], and L has the following structure:

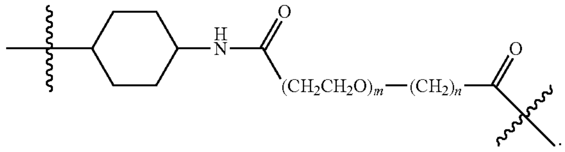.

In preferred embodiments, m is 1, 2, 3, 4, 5 or 6 and n is 2, 4, or 6. In even more preferred embodiments, m is 1, 2 or 3, and n is 2.

In other embodiments, $L_1$ is

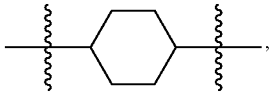 [SMILES: *C1CCC(*)CC1]

and L has the following structure:

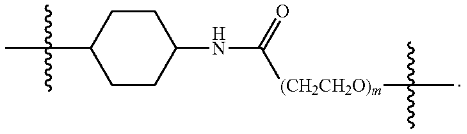

In preferred embodiments, m is 1, 2, 3, 4, 5 or 6. In even more preferred embodiments, m is 1, 2 or 3.

In other embodiments, $L_1$ is

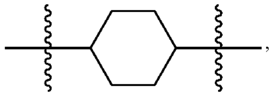

and L has the following structure:

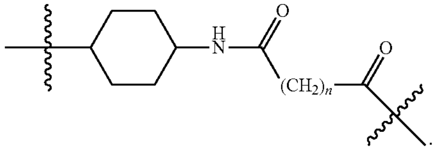

In preferred embodiments, n is 1, 2, 3, 4, 5, 6, 7 or 8. In even more preferred embodiments, n is 2, 3, 4 or 5.

In other embodiments, $L_1$ is

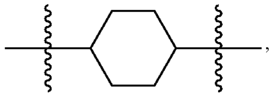

and L has the following structure:

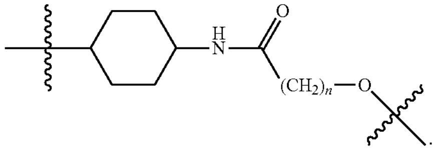

In preferred embodiments, n is 1, 2, 3, 4, 5 or 6. In even more preferred embodiments, n is 1, 3 or 5.

In other embodiments, $L_1$ is

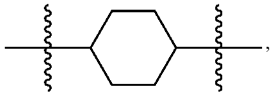

and L has the following structure:

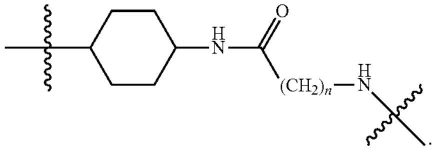

In preferred embodiments, n is 4, 5, 6, 7 or 8. In even more preferred embodiments, n is 5 or 7.

In other embodiments, $L_1$ is

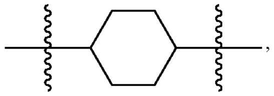

and L has the one of following structures:

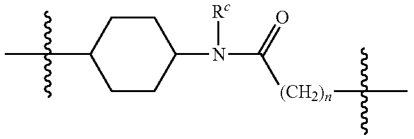

or

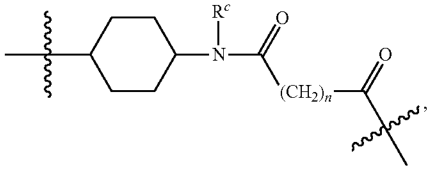

wherein $R^c$ is hydrogen or $C_{1-3}$alkyl. In preferred embodiments, n is 1, 2, 3, or 4. In even more preferred embodiments, n is 1 or 2.

In other embodiments, $L_1$ is

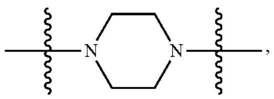

and L has the following structure:

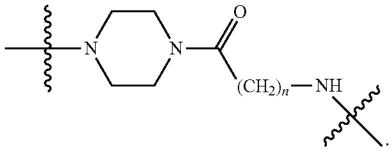

In preferred embodiments, n is 1, 2, 3, 4, 5, 6, 7 or 8. In even more preferred embodiments, n is 1, 5 or 7.

In other embodiments, $L_1$ is

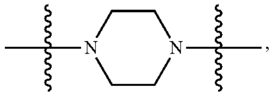

and L has the following structure:

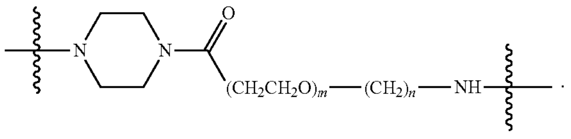

In preferred embodiments, m is 1, 2, 3, 4, 5 or 6 and n is 2, 4, or 6. In even more preferred embodiments, m is 1, 2 or 3, and n is 2.

In other embodiments, $L_1$ is

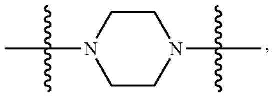 [SMILES: *N1CCN(*)CC1]

and L has the following structure:

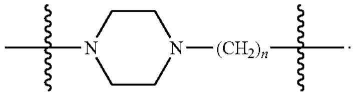

In preferred embodiments, n is 1, 2, 3, 4, 5, or 6. In even more preferred embodiments, n is 3 or 4.

In other embodiments, $L_1$ is

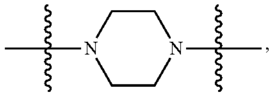

and L has the following structure:

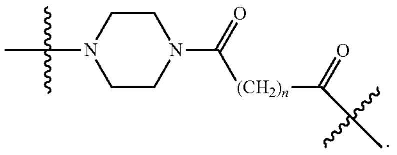

In preferred embodiments, n is 1, 2, 3, 4, 5, 6, 7, 8, 9 or 10. In even more preferred embodiments, n is 2, 3, 4, 5, 7, 7, 9 or 10.

In other embodiments $L_1$ is

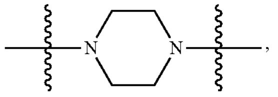

and L has the following structure:

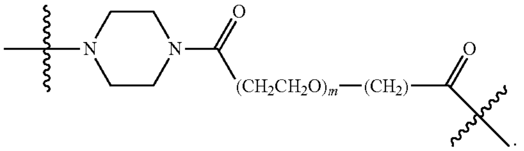

In preferred embodiments, m is 1, 2, 3, 4, 5 or 6 and n is 2, 4, or 6. In even more preferred embodiments, m is 1, 3, or 5, and n is 2.

In other embodiments $L_1$ is

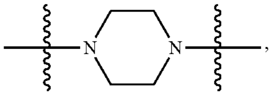

and L has the following structure:

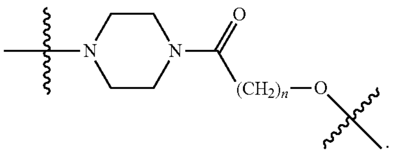

In preferred embodiments, n is 1, 2, 3, 4, 5, 6, 7, 8 or 9. In even more preferred embodiments, n is 1, 3, 5, 7 or 9.

In other embodiments, $L_1$ is

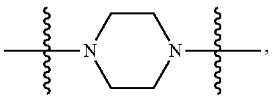

and L has the following structure:

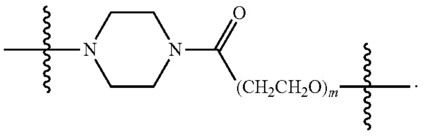

In preferred embodiments, m is 1, 2, 3, 4, 5, 6, 7 or 8. In even more preferred embodiments, m is 2, 4 or 6.

In other embodiments, $L_1$ is

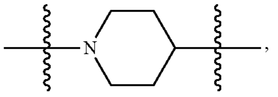

and L has one of the following structures:

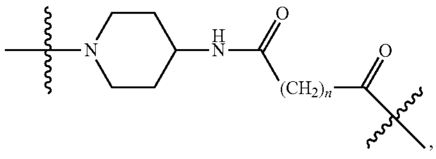

,

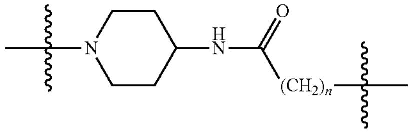

or

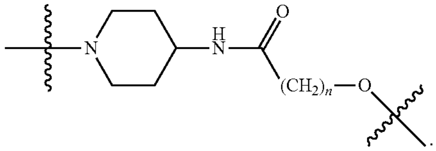

.

In preferred embodiments, n is 1, 2, 3, 4, 5, 6, 7 or 8. In even more preferred embodiments, n is 2, 3, 4 or 5.

In additional embodiments, $L_1$ is

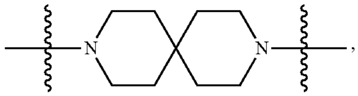 [SMILES: *N1CCC2(CC1)CCN(*)CC2]

, and L has one of the following structures:

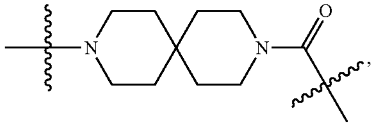

,

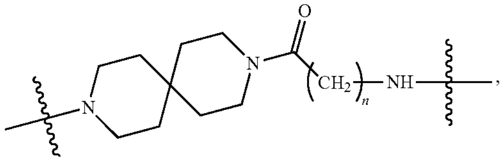

,

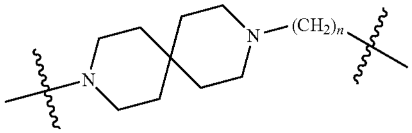

or

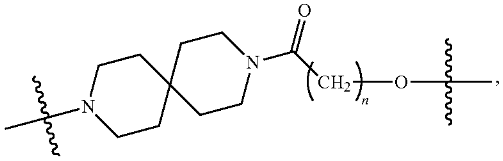

, wherein n is 1, 2 or 3. In preferred embodiments, n is 1.

In additional embodiments, $L_1$ is

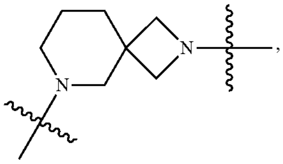

, and L has one of the following structures:

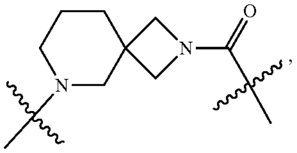

,

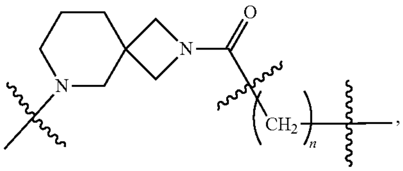

, or

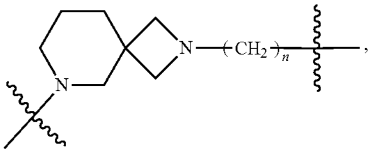

, wherein n is 1, 2, 3, 4, 5, 6, 7, 8, or 9. In preferred embodiments, n is 1, 2 or 3. In more preferred embodiments n is 1.

In additional embodiments, $L_1$ is

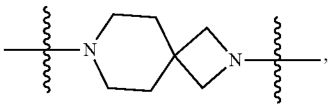 [SMILES: *N1CCC2(CC1)CN(*)C2]

, and L has one of the following structures:

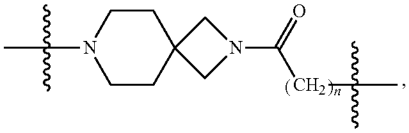

,

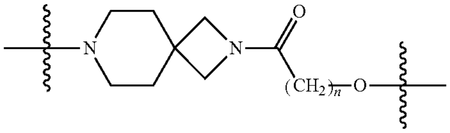

or

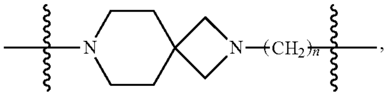

, wherein n is 1, 2, 3, 4, 5, 6, 7, 8, or 9. In preferred embodiments, n is 1, 2 or 3. In more preferred embodiments, n is 1.

In additional embodiments, $L_1$ is

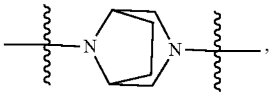 [SMILES: *N1CC2CCC(C1)N2*]

and L has the following structure:

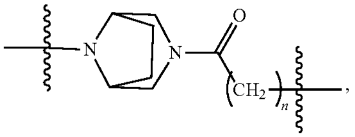

wherein n is 1, 2, or 3. In more preferred embodiments, n is 1.

In other embodiments, $L_1$ is

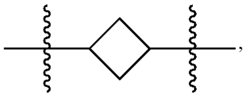 [SMILES: *C1CC(*)C1]

and L has the following structure:

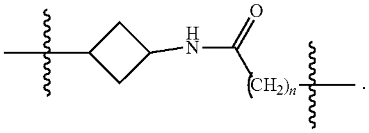

In preferred embodiments, n is 1, 2, or 3. In even more preferred embodiments, n is 1.

In further embodiments, $L_1$ is a ring, and $-L_2-L_3-L_4-L_5-$ contains at least one ring. The additional ring typically imparts more rigidity to the linker moiety. In specific embodiments, $L_1$ is one of

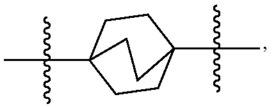

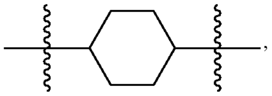

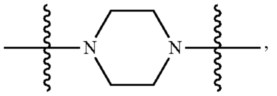

or

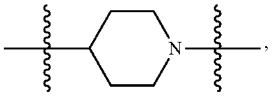

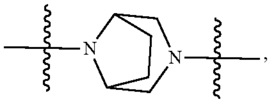

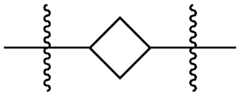

or

-continued

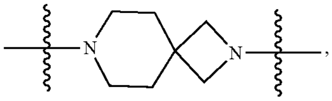

and $-L_2-L_3-L_4-L_5-$ has one of the following structures:

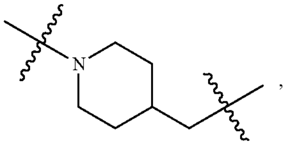

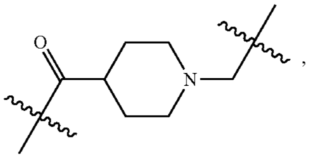

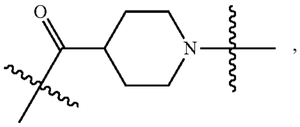

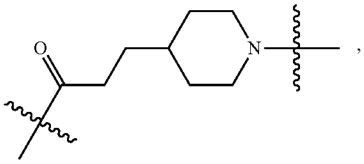

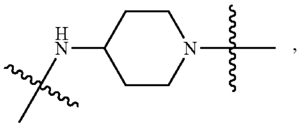

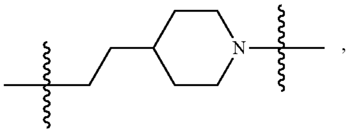

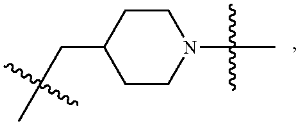

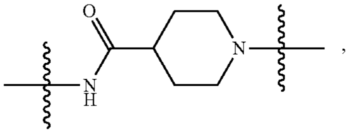

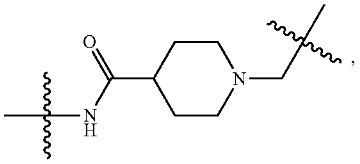

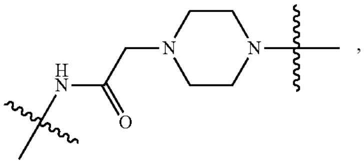

-continued
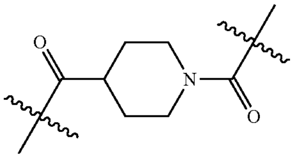
,
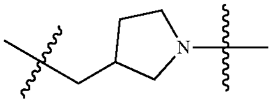
,
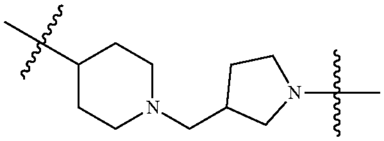
,
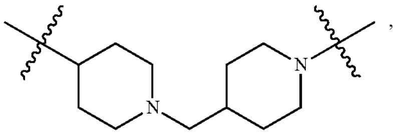
,
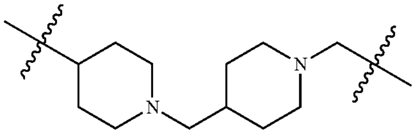
,
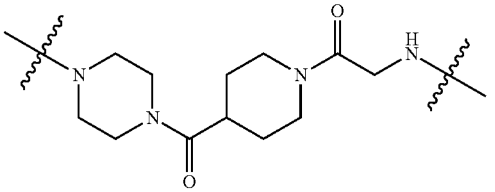
,
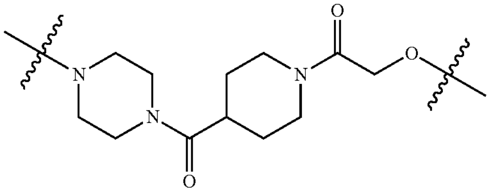
,
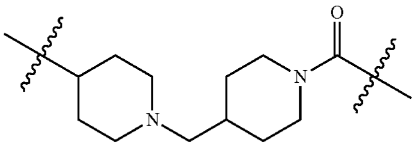
,
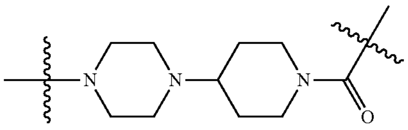
,
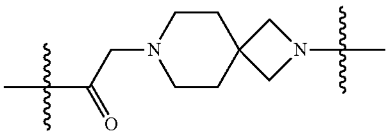
,
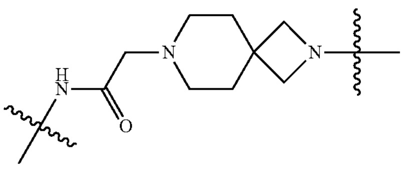
,
-continued
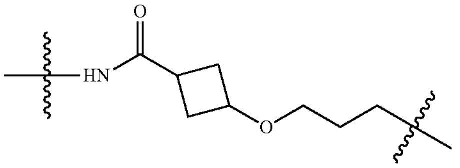
,
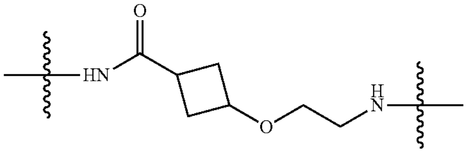
,
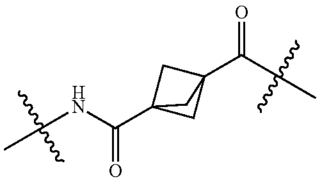
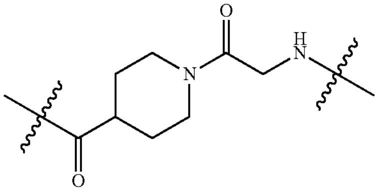
,
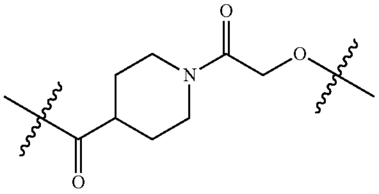
,
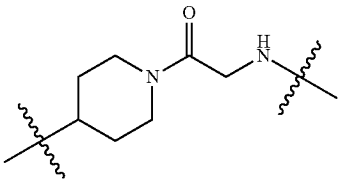
,
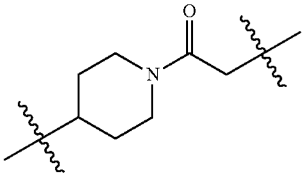
,
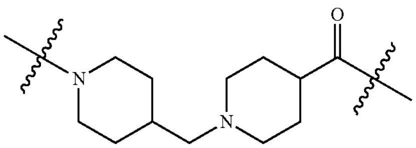
,
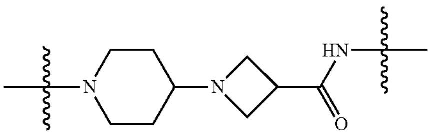
,
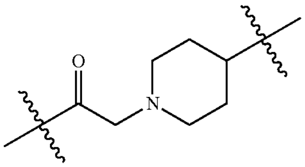
, -continued
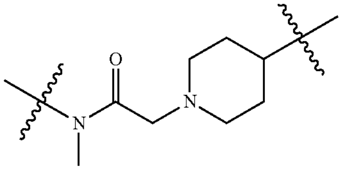,
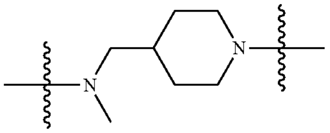,
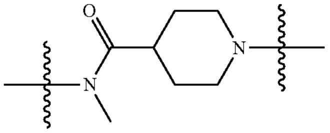,
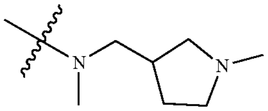,
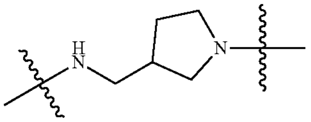,
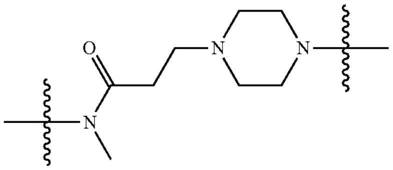,
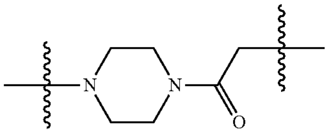,
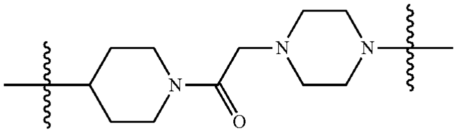,
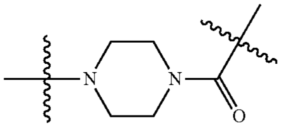,
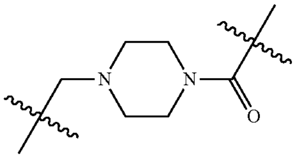,
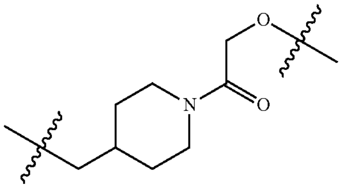,
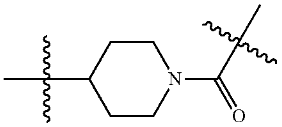,
-continued
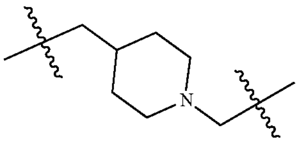,
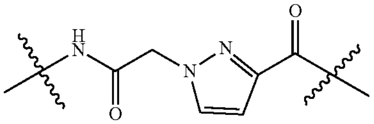,
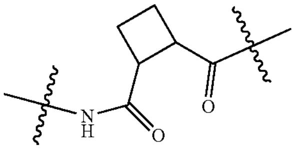,
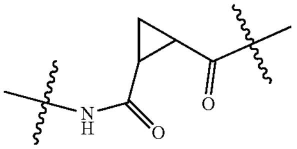,
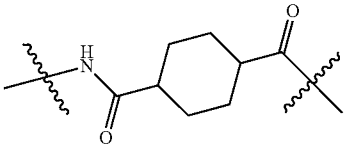,
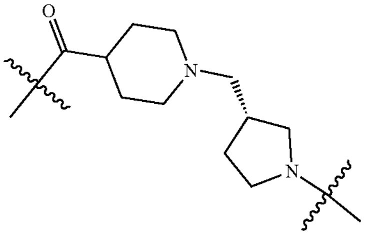,
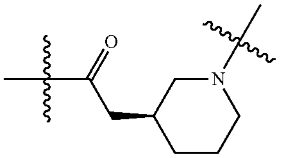,
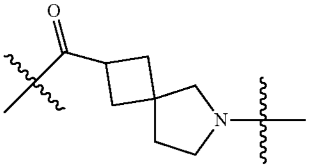, or
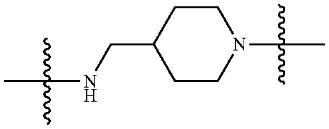.
In more specific embodiments, $L_1$ is
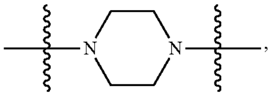, and the linker (L) has one of the following structures:
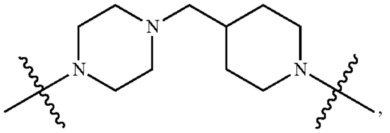
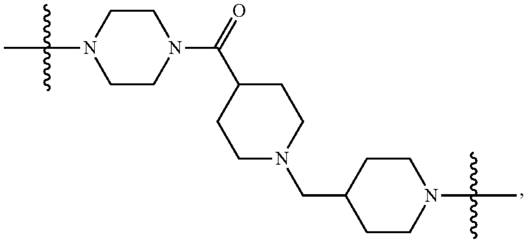
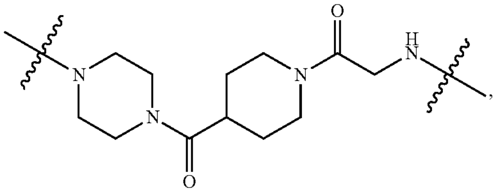
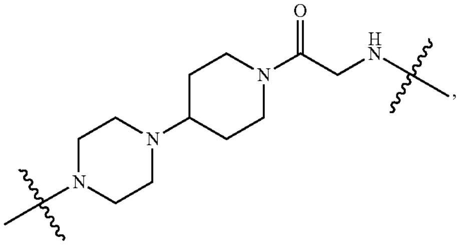
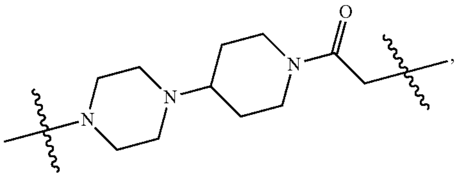
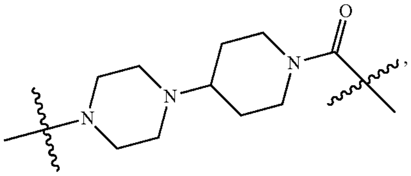
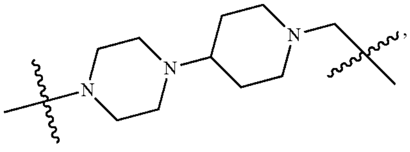
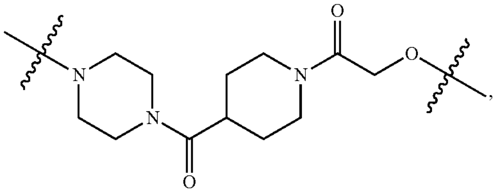
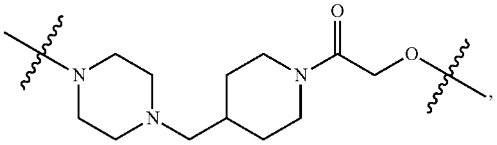
-continued
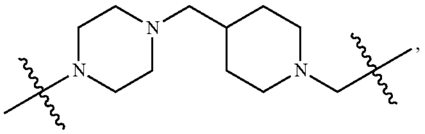
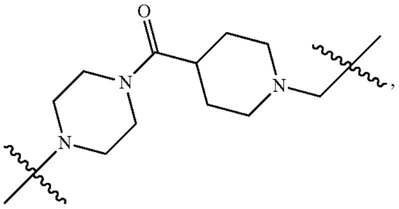
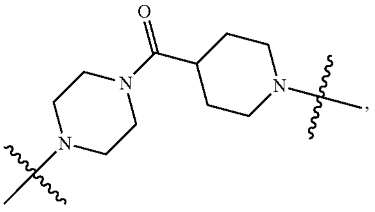
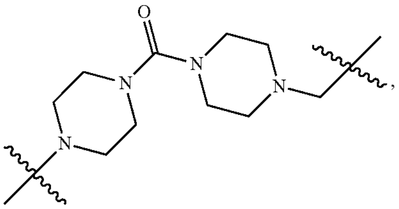
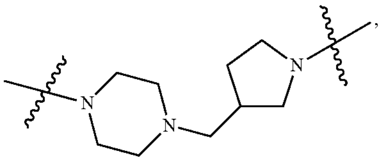
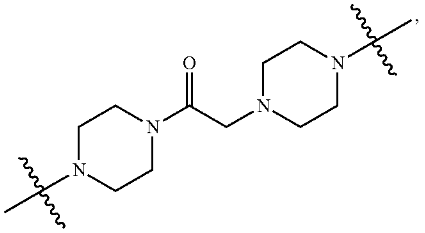
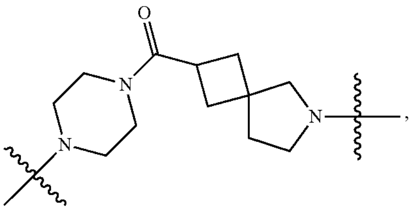
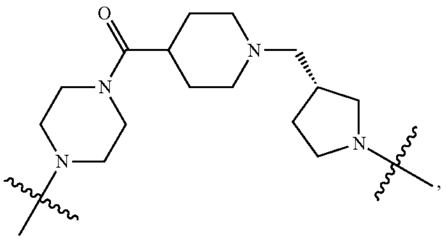

-continued
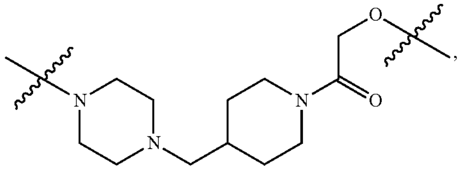
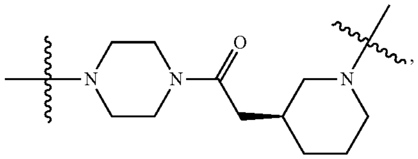
or
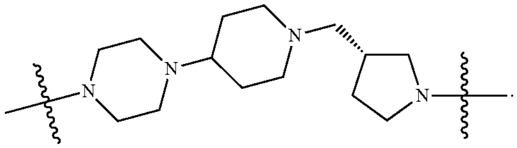
In more specific embodiments, $L_1$ is
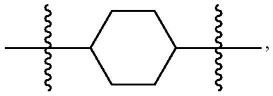 [SMILES: *C1CCC(*)CC1]
and the linker (L) has one of the following structures:
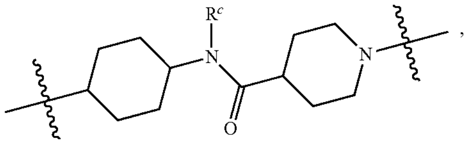
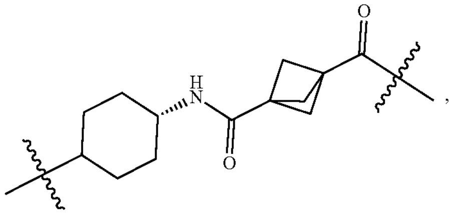
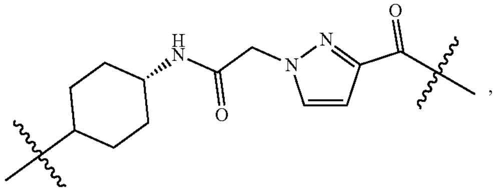
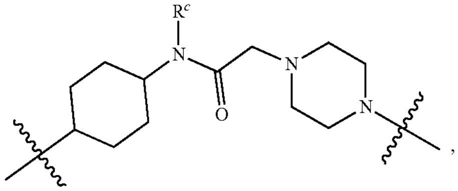
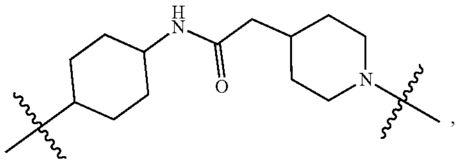
-continued
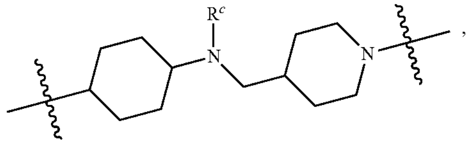
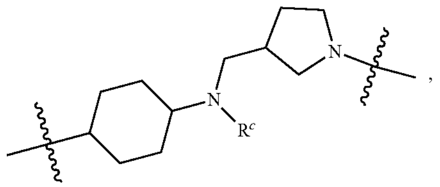
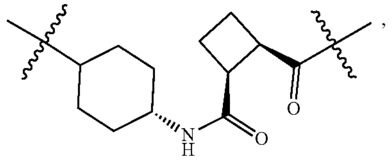
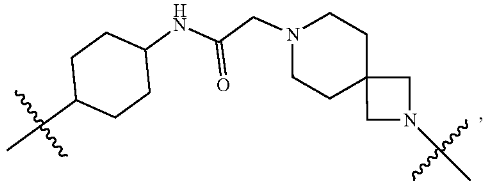
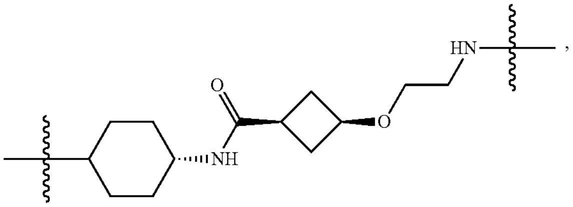
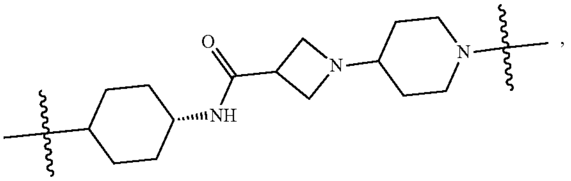
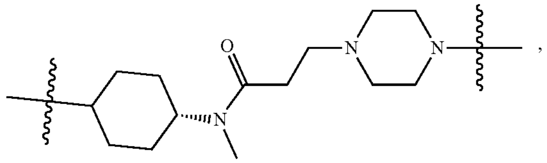
wherein $R^c$ is H or $C_{1-3}$alkyl.
In more specific embodiments, $L_1$ is
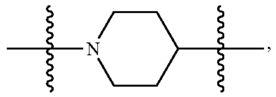
and the linker (L) has one of the following structures:
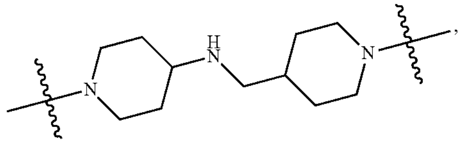

-continued
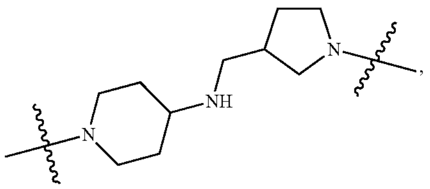
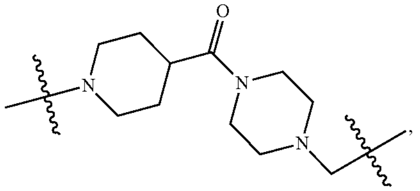
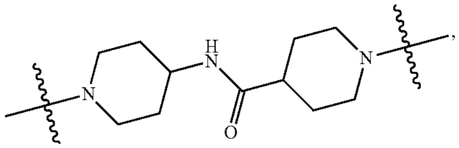
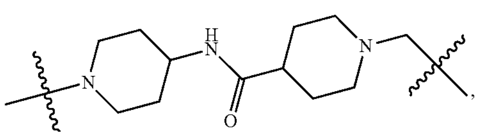
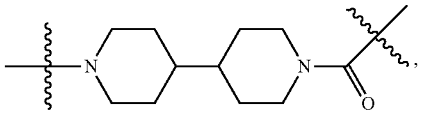
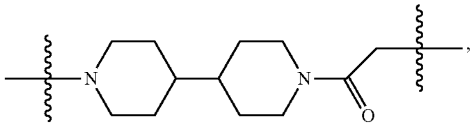
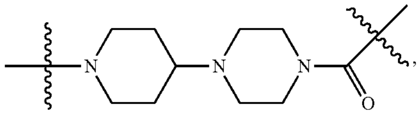
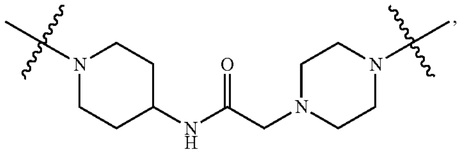
or
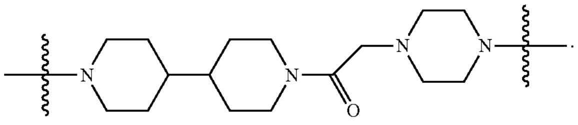
In more specific embodiments, $L_1$ is
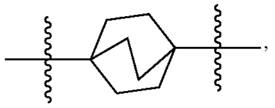 [SMILES: *C12CCC(*)(CC1)CC2]
and the linker (L) has one of the following structures:
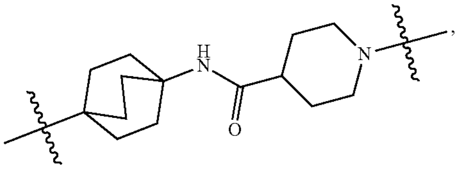
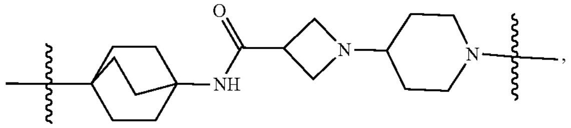
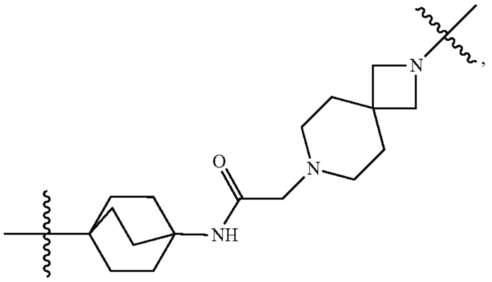
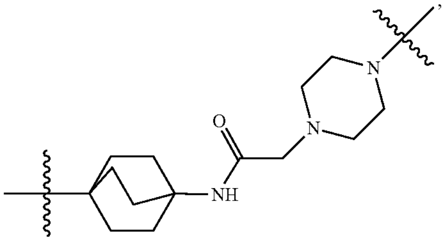
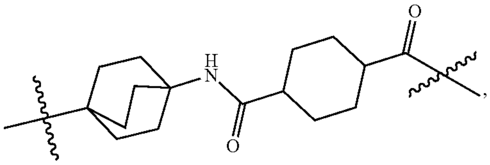
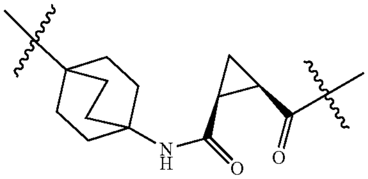
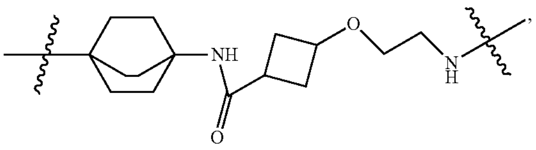
or
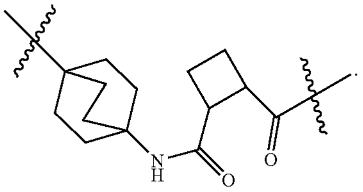

In more specific embodiments, $L_1$ is

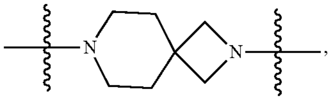 [SMILES: *N1CCC2(CC1)CN(*)C2]

and the linker (L) has one of the following structures:

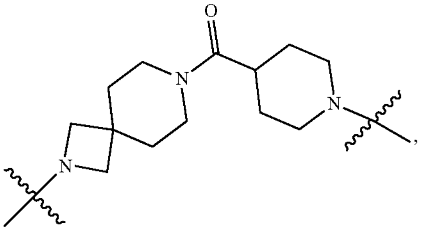

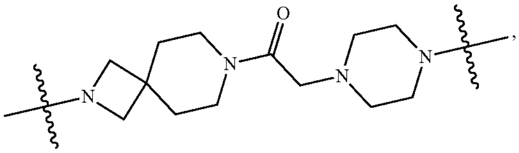

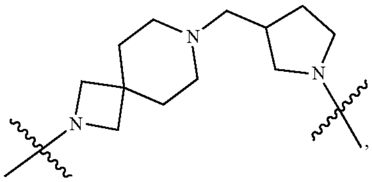

or

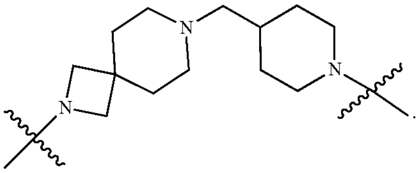

In more specific embodiments $L_1$ is

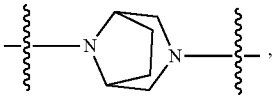

and the linker (L) has one of the following structures:

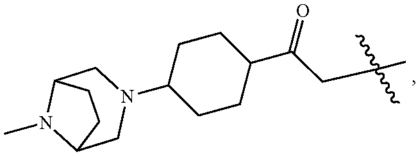

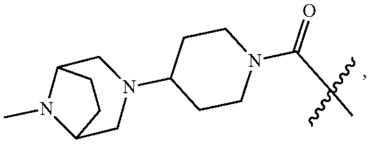

or

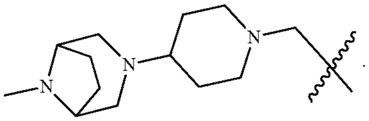

In more specific embodiments, $L_1$ is

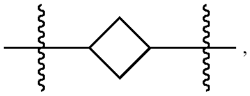

and the linker (L) has the following structure:

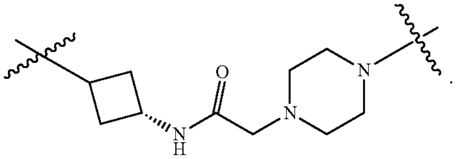

In other embodiments, $L_1$ is not a ring.

In other embodiments, a linker (L) or partial linker moiety ($-L_1-L_s-$) has one of the following structures

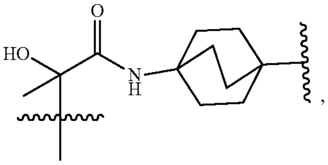

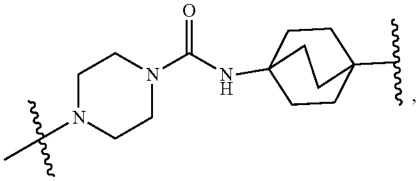

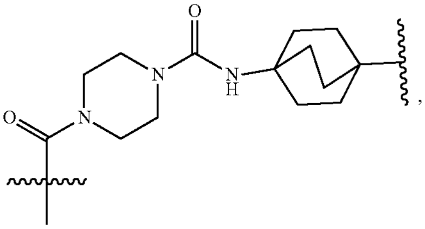

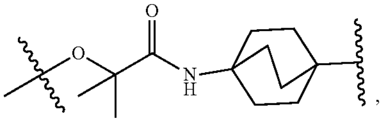

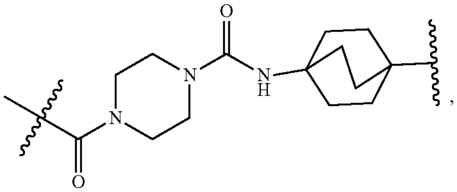

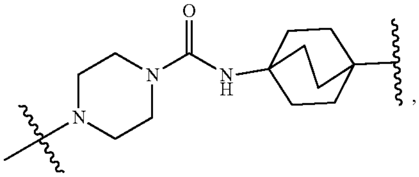

-continued
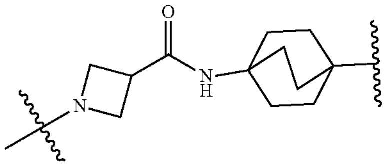,
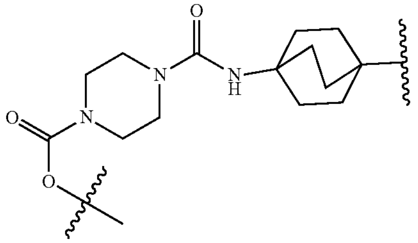,
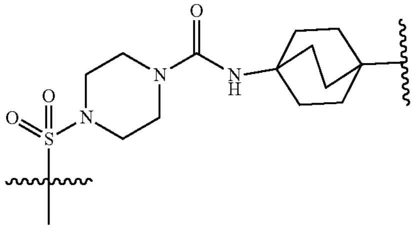,
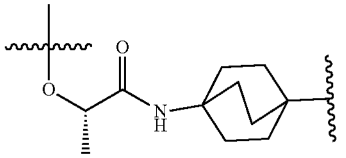,
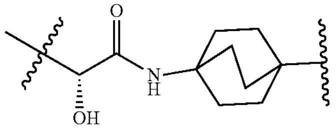,
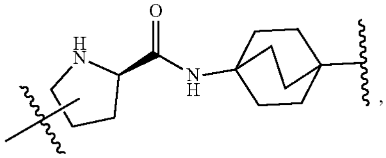,
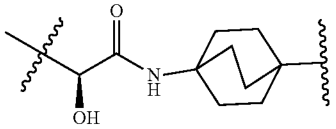, 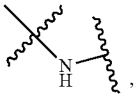,
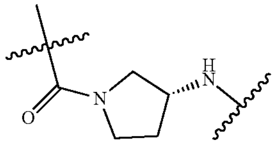,
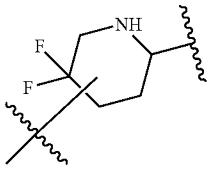,
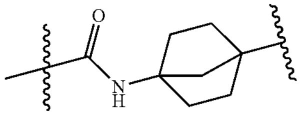,
-continued
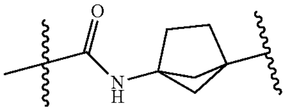,
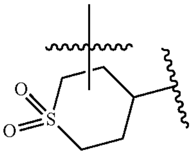, 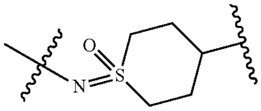,
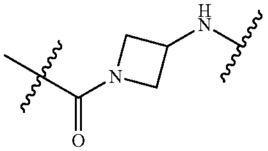, 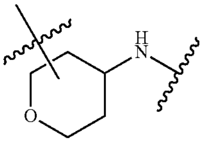,
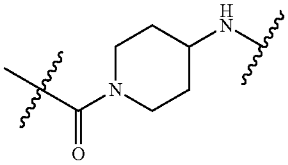,
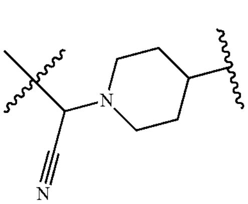, 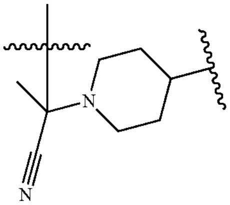,
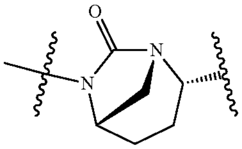,
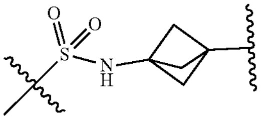,
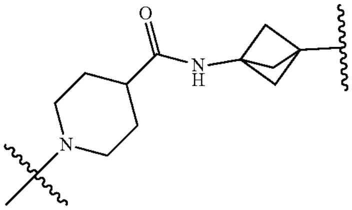,
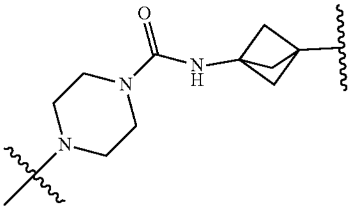,
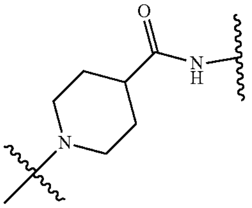, -continued
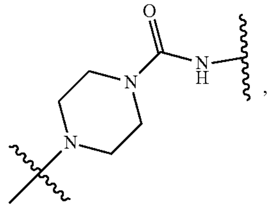,
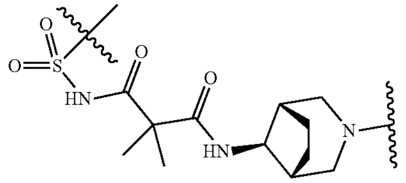,
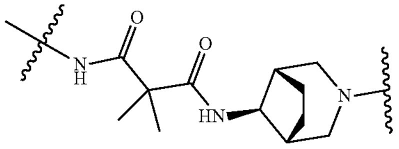,
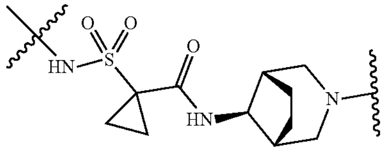,
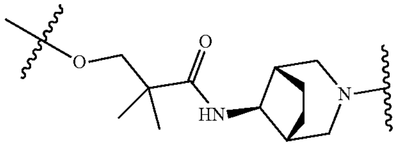,
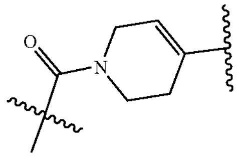, 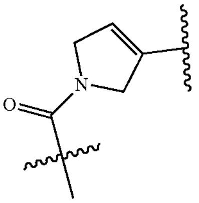,
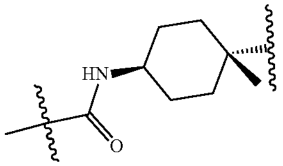,
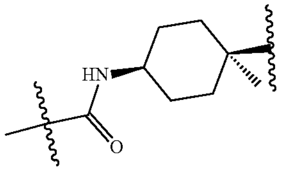,
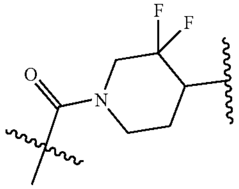, 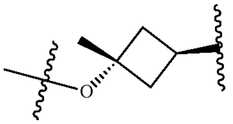,
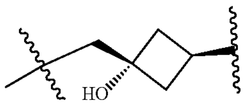, 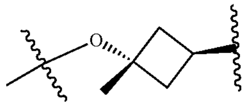,
-continued
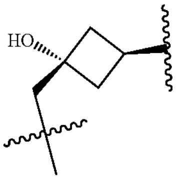, 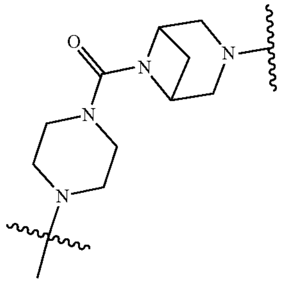,
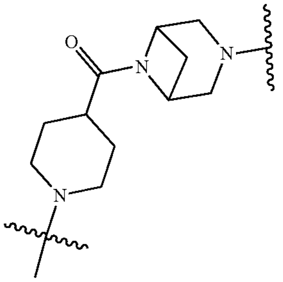,
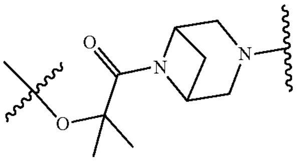,
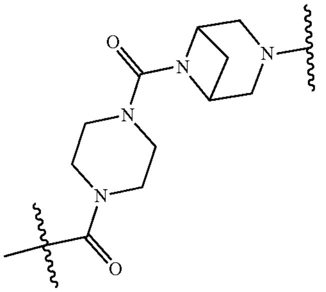,
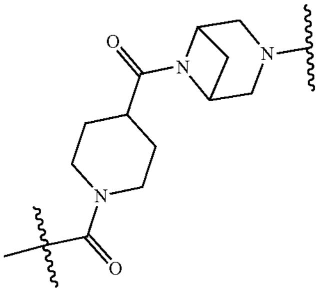,
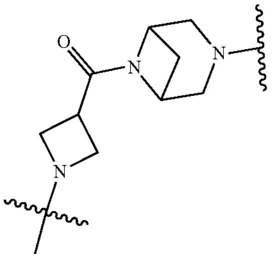, -continued
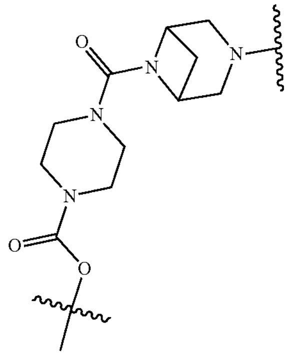
,
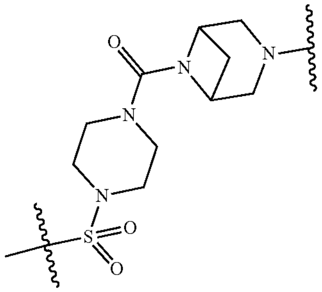
,
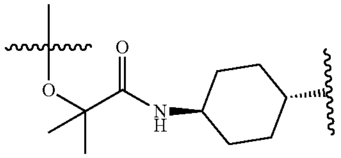
,
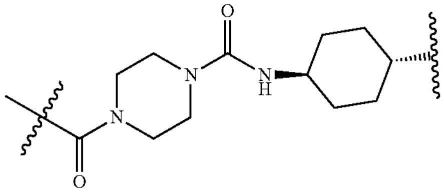
,
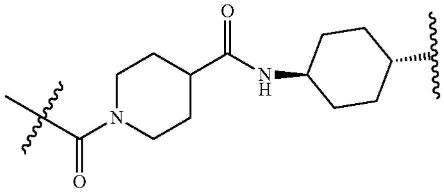
,
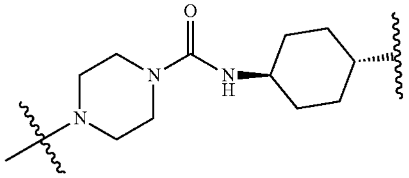
,
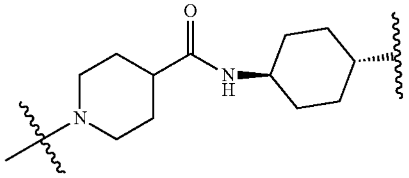
,
-continued
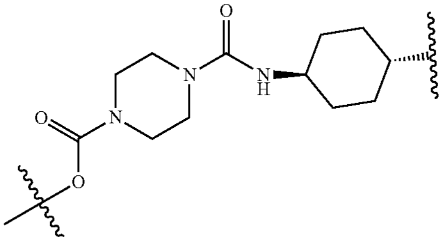
,
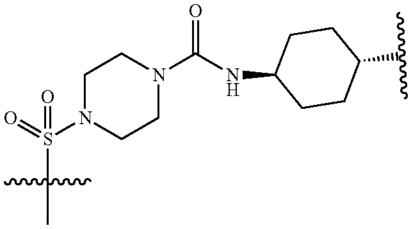
,
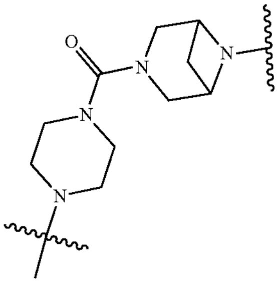
,
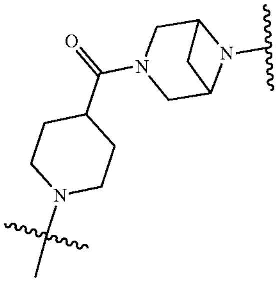
,
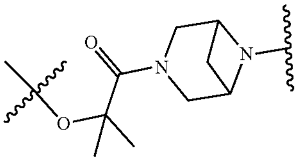
,
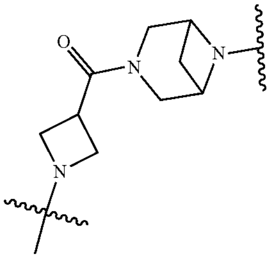
, -continued
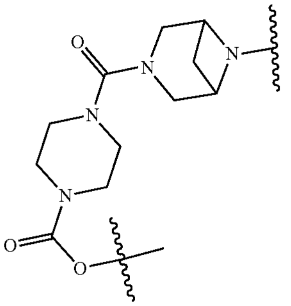,
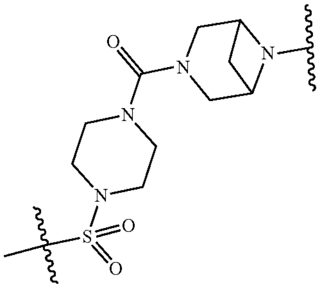,
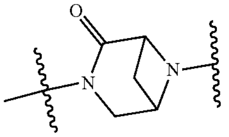, 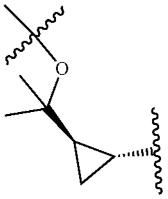,
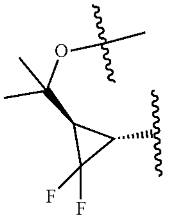, 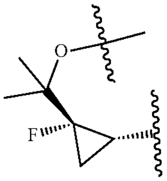,
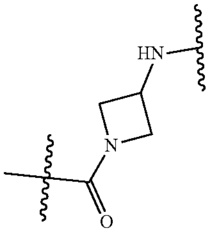, 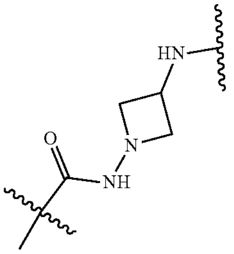,
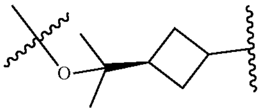,
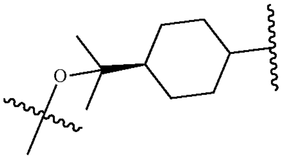,
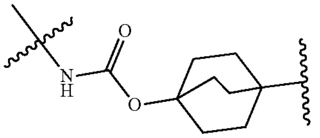,
-continued
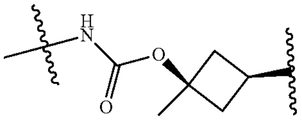,
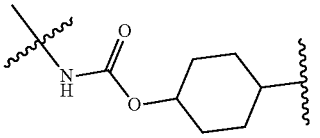,
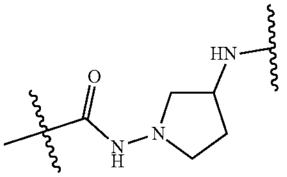,
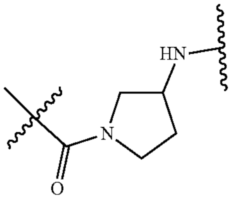,
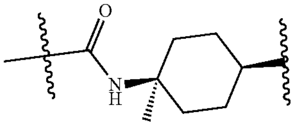,
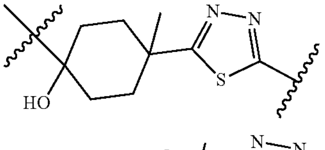,
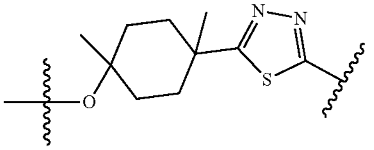,
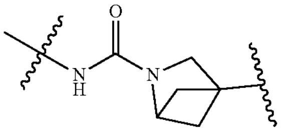,
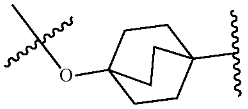,
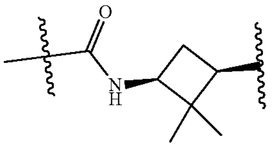,
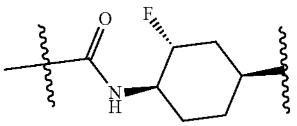,
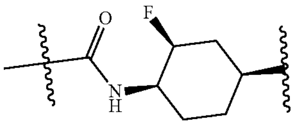, -continued

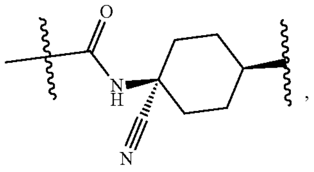

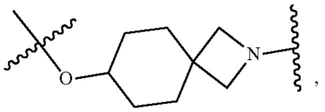

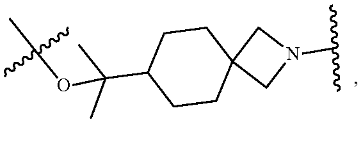

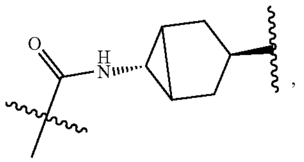

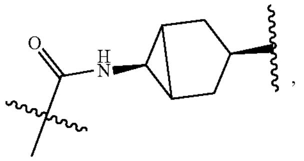

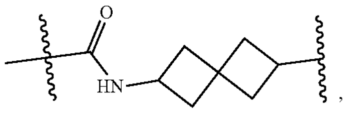

or

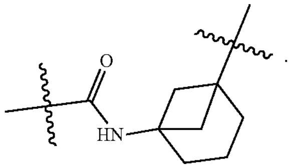

.

Construction of Compounds of Formula (I)

The synthesis or construction of the compounds of Formula (I) can be carried out in multiple steps, typically involving separately preparing building blocks of the IRAK4 binder and the LHM moiety, followed by joining the respective building blocks through covalent bond formation. Generally speaking, either or both building blocks may be prepared with one or more linker precursors ($L_x$). A linker precursor comprises one or more linker segments ($L_s$) and has a terminal reactive group for further coupling. The two building blocks can be finally coupled (via formation of an $L_s$ segment) to afford a compound of Formula (I).

The following schemes demonstrate the general approaches of preparing building blocks. Examples 1-192 are specific examples of Formula (I) that were synthesized and characterized by their respective physiochemical properties.

A. General Schemes for Preparing IRAK4 Binder Building Blocks

SCHEME A1

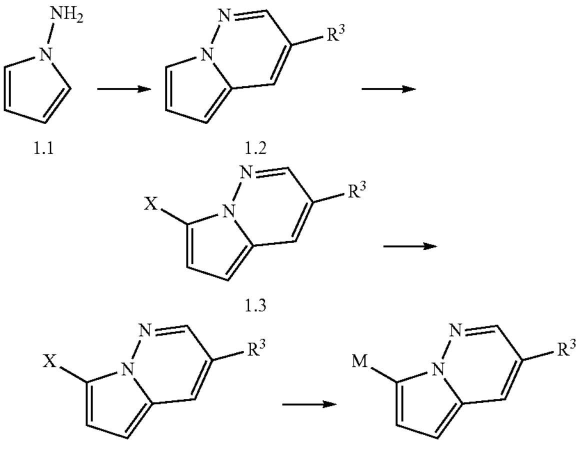

1.1 1.2 1.3 1.4 1.5

The compounds of formula 1.5 may be accessed according to the method outlined in Scheme 1. 1-aminopyrrole 1.1 may be condensed with a suitable coupling partner to produce substituted pyrrolo[1,2-b]pyridazine 1.2 using a suitable catalyst (e.g., HCl, etc.) and suitable solvent (e.g., EtOH, etc.). Halogenation at the position shown using a known halogenating reagent (e.g., NBS, etc.) can form the intermediate 1.3, which can be further substituted either via C—H activation or electrophilic aromatic substitution with a suitable reagent (e.g., selectfluor, etc.) to produce intermediate 1.4. Halogen metal exchange of —X to -M can then be achieved using a suitable reagent (e.g., n-BuLi, etc.) or transition metal coupling using a palladium catalyst and metal source (e.g., $B_2Pin_2$, $Me_6Sn_2$, etc.) to give intermediate 1.5.

SCHEME A2

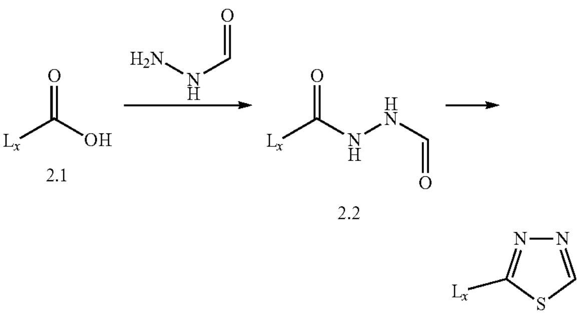

2.1 2.2 2.3

The compounds of the formula 2.3 may be accessed according to the method outlined in Scheme 2. The acid 2.1 can be converted to the corresponding acyl hydrazine using a coupling reagent (e.g., HATU, etc.) in the presence of a base (e.g., DIPEA, etc.). Cyclization of compound 2.2 can be accomplished by heating in the presence of a thionating reagent (e.g., Lawesson's reagent, etc.) to provide compound 2.3.

SCHEME A3

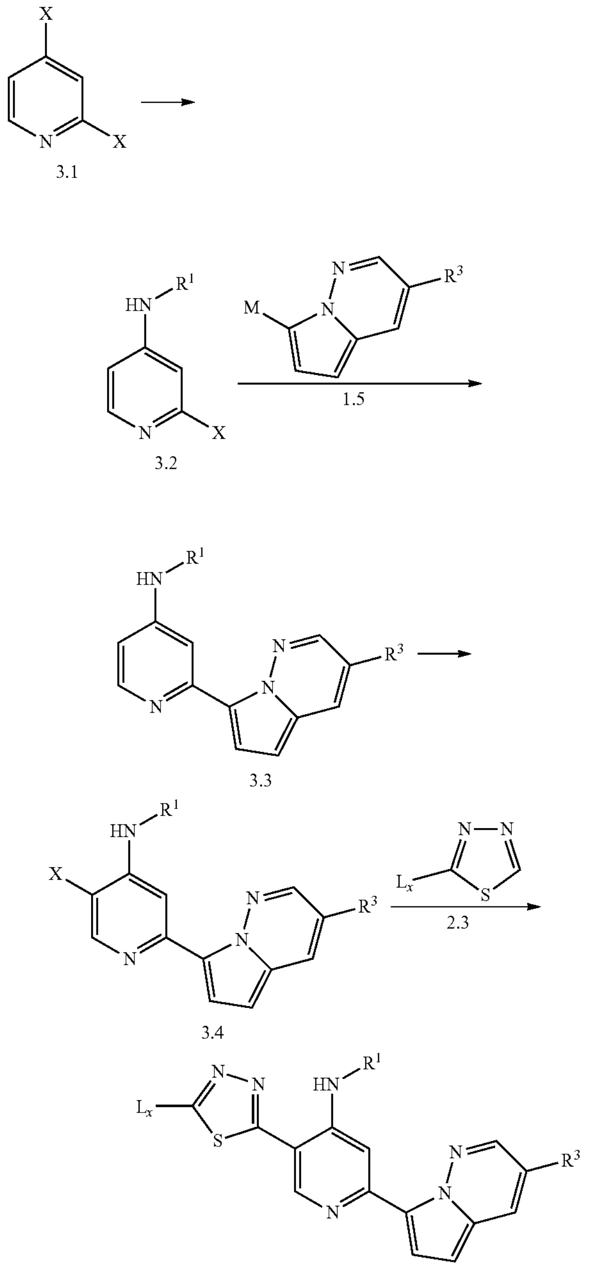

3.1 3.2 1.5 3.3 3.4 2.3 3.5

The compounds of formula 3.6 may be accessed according to the method outlined in Scheme 3. Dihalopyridine 3.1 may be converted to compound 3.2 via displacement of one of the halogen groups (e.g., nucleophilic aromatic substitution, etc.). Further functionalization of compound 3.2 using a metal-containing heterocyclic species (e.g., compound 1.5) with a suitable catalyst, such as a palladium catalyst, can afford compound 3.3. Halogenation at the position shown using a known halogenating reagent (e.g., NBS, etc.) can form the intermediate 3.4 which can be further substituted through a cross-coupling reaction using a suitable catalyst, such as a palladium catalyst, to provide compound 3.5.

SCHEME A4

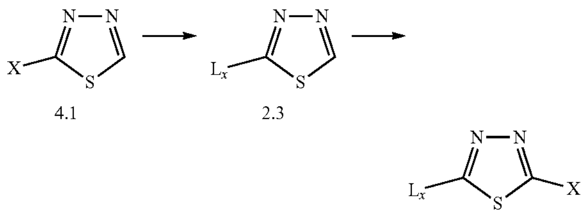

4.1 2.3 4.2

Compounds of formula 4.2 may be assembled following Scheme A4. Displacement of the halogen group (e.g., nucleophilic aromatic substitution, etc.) of a halothiadiazole 4.1 with a nucleophile (e.g., an amine, etc.) can provide compound 2.3. Halogenation at the position shown using a known halogenating reagent (e.g., NBS, etc.) can form the intermediate 4.2.

SCHEME A5

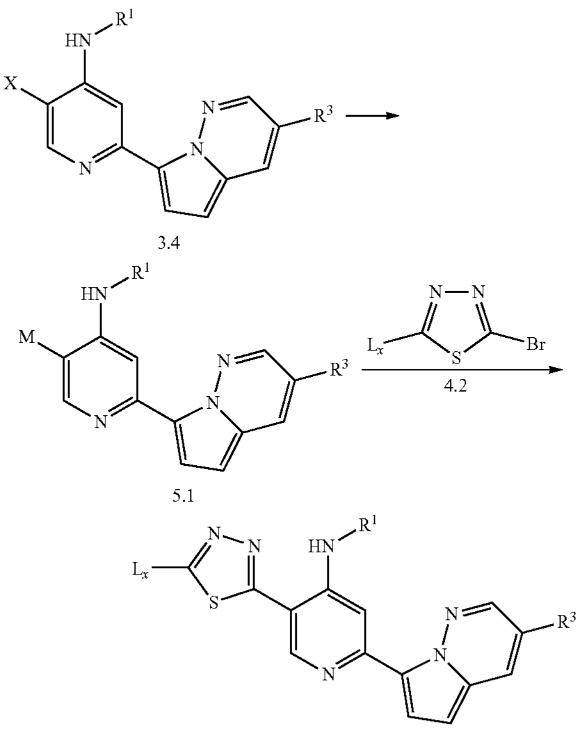

3.4 5.1 4.2 3.5

Compounds of formula 3.5 may also be assembled following Scheme A5. Halogen metal exchange of —X to -M can then be achieved using a suitable reagent (e.g., n-BuLi, etc.) or transition metal coupling using a palladium catalyst and metal source (e.g., $B_2Pin_2$, $Me_6Sn_2$, etc.) to give intermediate 5.1. Functionalization of compound 5.1 can be done utilizing a cross-coupling reaction with compound 4.2 using a suitable catalyst, such as a palladium catalyst, to provide compound 3.5.

Under Scheme A5, $L_x$ may be a ring having a reactive moiety, which could in turn be coupled to another linker segment. For instance, a BOC-protected $L_x$ may be:

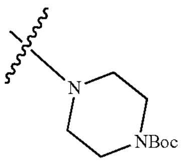

;

and compound 4.2 is

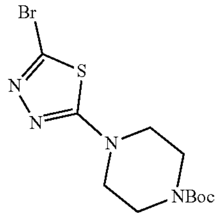

.

The resulting compound 3.5 is an IRAK4 Binder building block having an $L_1$ precursor, i.e., a piperazine ring, which can be further coupled to another linker segment via the reactive secondary amine of piperazine.

SCHEME A6

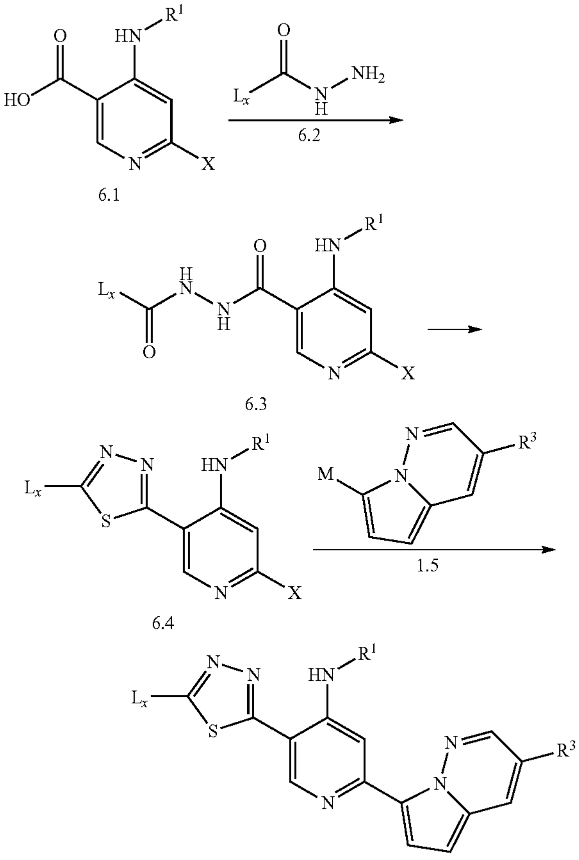

6.1 6.2 6.3 6.4 1.5 3.5

An alternative method of access compound 3.5 is shown in Scheme A6. Starting from the nicotinic acid 6.1, the corresponding acyl hydrazine can be prepared using a coupling reagent (e.g., HATU, etc.) in the presence of a base (e.g., DIPEA, etc.). Cyclization of compound 6.3 can be accomplished by heating in the presence of a thionating reagent (e.g., Lawesson's reagent, etc.) to provide compound 6.4. Further functionalization of compound 6.4 using a metal-containing heterocyclic species (e.g., compound 1.5) with a suitable catalyst, such as a palladium catalyst, can afford compound 3.5.

Under Scheme A6, $L_x$ may be a ring having a reactive moiety, which could in turn be coupled to another linker segment. For instance, $L_x$ may be:

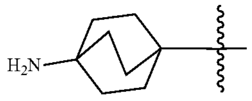 [SMILES: *C12CCC(N)(CC1)CC2]

(optionally in a BOC-protected form during synthesis) and the resulting compound 3.5 is another IRAK4 Binder building block having an $L_1$ precursor, i.e., a bicyclo[2.2.2]octane ring, which can be further coupled to another linker segment via the reactive primary amine.

Specific examples of preparing IRAK4 Binder building blocks are described in further detail below.

BB1: 7-(5-(5-(4-aminobicyclo[2.2.2]octan-1-yl)-1,3,4-thiadiazol-2-yl)-4-((tetrahydro-2H-pyran-4-yl)amino)pyridin-2-yl)pyrrolo[1,2-b]pyridazine-3-carbonitrile, hydrochloride

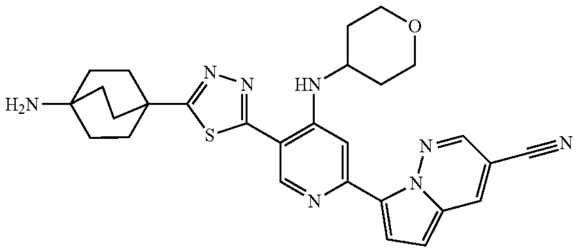

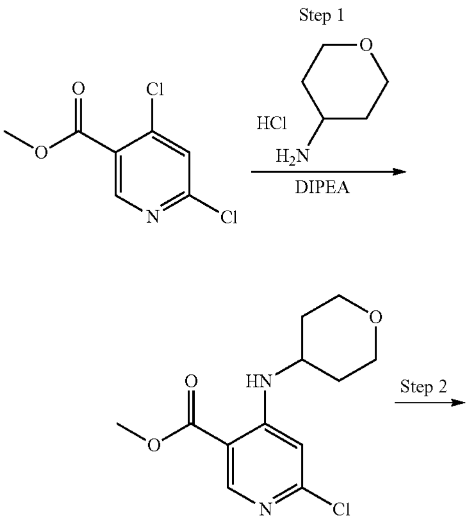

-continued

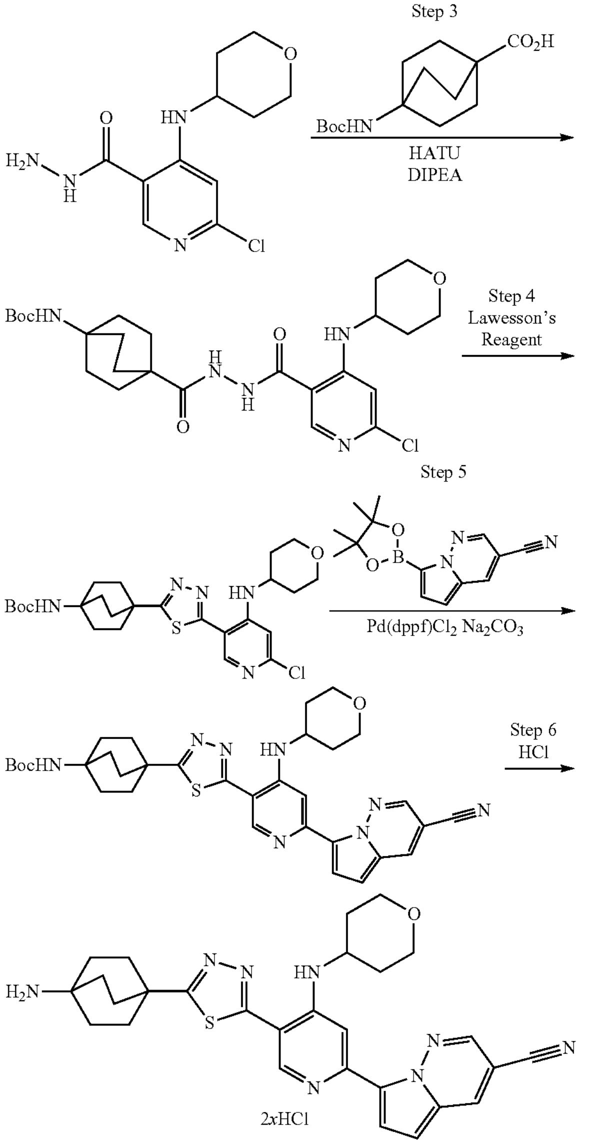

BB1

Step 1: Methyl 6-chloro-4-((tetrahydro-2H-pyran-4-yl)amino)nicotinate. To a solution methyl 4,6-dichloropyridine-3-carboxylate (4.00 g, 19.4 mmol) and tetrahydropyran-4-amine hydrochloride (4.01 g, 29.1 mmol) in THF (20.0 mL) was added DIPEA (10.1 mL, 58.2 mmol). The solution was stirred at 120° C. for 12 h and concentrated. The crude material was purified by $SiO_2$ chromatography (eluent: 20-100% EtOAc/Hexane) to provide methyl 6-chloro-4-((tetrahydro-2H-pyran-4-yl)amino)nicotinate. ES/MS: 271.238 ($M+H^+$).

Step 2: 6-chloro-4-((tetrahydro-2H-pyran-4-yl)amino)nicotinohydrazide. A solution methyl 6-chloro-4-((tetrahydro-2H-pyran-4-yl)amino)nicotinate (3.03 g, 11.2 mmol) and hydrazine hydrate (4.55 g, 90.9 mmol) in ethanol (18.0 mL) was stirred at 80° C. for 3 h and concentrated. The crude material was carried forward without further purification to provide 6-chloro-4-((tetrahydro-2H-pyran-4-yl)amino)nicotinohydrazide. ES/MS: 271.201 ($M+H^+$).

Step 3: Tert-butyl (4-(2-(6-chloro-4-((tetrahydro-2H-pyran-4-yl)amino)nicotinoyl)hydrazine-1-carbonyl)bicyclo[2.2.2]octan-1-yl)carbamate. To a solution of 6-chloro-4-((tetrahydro-2H-pyran-4-yl)amino)nicotinohydrazide (2.70 g, 9.97 mmol), 4-(tert-butoxycarbonylamino)bicyclo[2.2.2]octane-1-carboxylic acid (2.82 g, 10.5 mmol), and HATU (4.55 g, 12.0 mmol) in DMF (49.9 mL) was added DIPEA (5.70 mL, 31.9 mmol). The solution was stirred at room temperature for 30 minutes and concentrated to dryness. The crude material was purified by $SiO_2$ chromatography (eluent: 5-15% MeOH/$CH_2Cl_2$) to provide the tert-butyl (4-(2-(6-chloro-4-((tetrahydro-2H-pyran-4-yl)amino)nicotinoyl)hydrazine-1-carbonyl)bicyclo[2.2.2]octan-1-yl)carbamate. ES/MS: 522.894 ($M+H^+$).

Step 4: Tert-butyl (4-(5-(6-chloro-4-((tetrahydro-2H-pyran-4-yl)amino)pyridin-3-yl)-1,3,4-thiadiazol-2-yl)bicyclo[2.2.2]octan-1-yl)carbamate. A solution of tert-butyl (4-(2-(6-chloro-4-((tetrahydro-2H-pyran-4-yl)amino)nicotinoyl)hydrazine-1-carbonyl)bicyclo[2.2.2]octan-1-yl)carbamate (5.00 g, 9.58 mmol) in 2-MeTHF (47.9 mL) was heated to 65° C. (external temperature). Lawesson's Reagent (4.26 g, 10.5 mmol) was then added and the reaction was stirred at 65° C. for 12 h. The solution was concentrated to dryness and purified by $SiO_2$ chromatography (eluent: 50-100% EtOAc/Hex). The product fractions were combined and stirred over 10% Palladium on carbon (5 g) for 1 h. The slurry was filtered through celite, washed with $CH_2Cl_2$, and the filtrate was concentrated to dryness. The residue was purified by $SiO_2$ chromatography (eluent: 1-5% MeOH/DCM) to provide the tert-butyl (4-(5-(6-chloro-4-((tetrahydro-2H-pyran-4-yl)amino)pyridin-3-yl)-1,3,4-thiadiazol-2-yl)bicyclo[2.2.2]octan-1-yl)carbamate. ES/MS: 520.288 ($M+H^+$).

Step 5: Tert-butyl (4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)carbamate. To a solution of tert-butyl (4-(5-(6-chloro-4-((tetrahydro-2H-pyran-4-yl)amino)pyridin-3-yl)-1,3,4-thiadiazol-2-yl)bicyclo[2.2.2]octan-1-yl)carbamate (65.0 mg, 0.103 mmol), 7-(4,4,5,5-tetramethyl-1,3,2-dioxaborolan-2-yl)pyrrolo[1,2-b]pyridazine-3-carbonitrile (41.1 mg, 0.154 mmol), and [1,1'-Bis(diphenylphosphino)ferrocene]dichloropalladium(II) (15.2 mg, 0.0205 mmol) in DME (2 mL) was added sodium carbonate (2.00 M, 0.205 mL, 0.410 mmol). The solution was degassed with argon for 2 min and heated to 120° C. (microwave) for 30 min. The resulting solution was diluted with THF, filtered, and concentrated to dryness. The crude solution was purified by preparative HPLC (Gemini C18, eluent: 10-65% acetonitrile/$H_2O$/0.1% TFA) and lyophilized to tert-butyl (4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)carbamate. ES/MS: 627.547 ($M+H^+$).

Step 6: 7-(5-(5-(4-aminobicyclo[2.2.2]octan-1-yl)-1,3,4-thiadiazol-2-yl)-4-((tetrahydro-2H-pyran-4-yl)amino)pyridin-2-yl)pyrrolo[1,2-b]pyridazine-3-carbonitrile bis-hydrochloride. To a solution of tert-butyl (4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)carbamate (28 mg, 0.0378 mmol) in 1,2-dichloroethane (0.189 mL) was added 4 M HCl in dioxane (4.00 M, 0.09 mL, 0.0378 mmol). The solution was stirred at rt for 1 h and concentrated to dryness to provide 7-(5-(5-(4-aminobicyclo[2.2.2]octan-1-yl)-1,3,4-thiadiazol-2-yl)-4-((tetrahydro-2H-pyran-4-yl)amino)pyridin-2-yl)pyrrolo[1,2-b]pyridazine-3-carbonitrile bis-hydrochloride. ES/MS: 527.366 ($M+H^+$).

BB2: 7-(5-(5-((trans)-4-aminocyclohexyl)-1,3,4-thiadiazol-2-yl)-4-(isopropylamino)pyridin-2-yl) pyrrolo[1,2-b]pyridazine-3-carbonitrile, hydrochloride

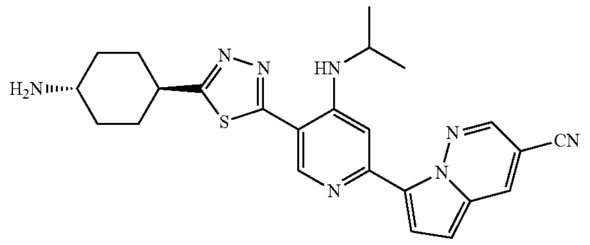

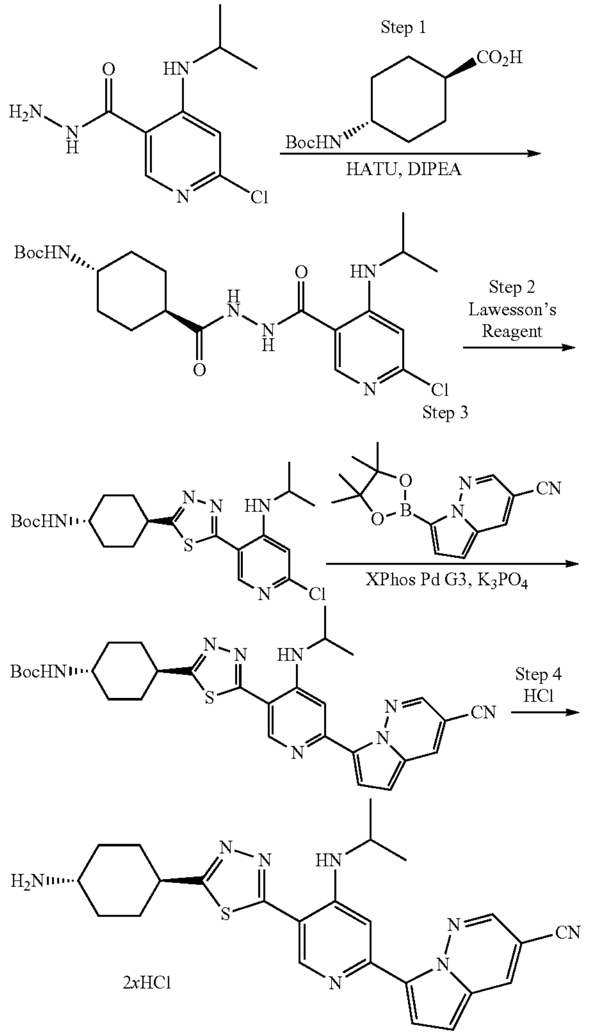

BB2

Step 1: Tert-butyl ((trans)-4-(2-(6-chloro-4-(isopropylamino)nicotinoyl)hydrazine-1-carbonyl)cyclohexyl)carbamate. To a solution of 6-chloro-4-(isopropylamino)pyridine-3-carbohydrazide (500 mg, 2.19 mmol), 4-(tert-butoxycarbonylamino)cyclohexanecarboxylic acid (612 mg, 2.52 mmol), and HATU (915 mg, 2.41 mmol) in DMF (9 mL) was added DIPEA (0.750 mL, 4.31 mmol). The solution was stirred at room temperature for 2 h and diluted with EtOAc. The solution was then washed with 1:1 mix of $H_2O$:saturated aqueous $NH_4Cl$, saturated aqueous $NH_4Cl$, and brine. The organic layer was dried over $MgSO_4$ and concentrated to dryness. The crude material was purified by $SiO_2$ chromatography (eluent: 2-5% MeOH/$CH_2Cl_2$) to provide the tert-butyl ((trans)-4-(2-(6-chloro-4-(isopropylamino)nicotinoyl)hydrazine-1-carbonyl)cyclohexyl)carbamate. ES/MS: 454.944 (M+H$^+$).

Step 2: Tert-butyl ((trans)-4-(5-(6-chloro-4-(isopropylamino)pyridin-3-yl)-1,3,4-thiadiazol-2-yl)cyclohexyl)carbamate. A solution of tert-butyl ((trans)-4-(2-(6-chloro-4-(isopropylamino)nicotinoyl)hydrazine-1-carbonyl) cyclohexyl)carbamate (739 mg, 1.63 mmol) in THF (15 mL) was heated to 65° C. (external temperature). Lawesson's Reagent (978 mg, 2.42 mmol) was then added and the reaction was stirred at 65° C. for 1 h. The solution was concentrated to dryness and purified by $SiO_2$ chromatography (eluent: 5-35% EtOAc (5% MeOH)/Hex) The product fractions were combined and stirred over 10% Palladium on carbon (1 g) for 1 h. The slurry was filtered through celite, washed with $CH_2Cl_2$, and the filtrate was concentrated to dryness. The residue was purified by $SiO_2$ chromatography (eluent: 10-40% Acetone/Hex) to provide tert-butyl ((trans)-4-(5-(6-chloro-4-(isopropylamino)pyridin-3-yl)-1,3,4-thiadiazol-2-yl)cyclohexyl)carbamate. ES/MS: 452.725 (M+H$^+$).

Step 3: Tert-butyl ((trans)-4-(5-(6-(3-cyanopyrrolo[1,2-b] pyridazin-7-yl)-4-(isopropylamino)pyridin-3-yl)-1,3,4-thiadiazol-2-yl)cyclohexyl)carbamate. To a solution of tert-butyl ((trans)-4-(5-(6-chloro-4-(isopropylamino)pyridin-3-yl)-1,3,4-thiadiazol-2-yl)cyclohexyl)carbamate (200 mg, 0.442 mmol), 7-(4,4,5,5-tetramethyl-1,3,2-dioxaborolan-2-yl)pyrrolo[1,2-b]pyridazine-3-carbonitrile (190 mg, 0.706 mmol), and XPhos Pd G3 (28.0 mg, 0.0331 mmol) in a mixture of DMF (2.25 mL) and DME (2 mL) was added potassium phosphate tribasic (2.00 M, 0.450 mL, 0.900 mmol). The solution was degassed with argon for 2 min and heated to 120° C. (microwave) for 20 min. Additional 7-(4,4,5,5-tetramethyl-1,3,2-dioxaborolan-2-yl)pyrrolo[1,2-b]pyridazine-3-carbonitrile (92.0 mg, 0.342 mmol) and XPhos Pd G3 (11.0 mg, 0.0130 mmol) were added and the solution was heated to 120° C. (microwave) for 20 min. The resulting solution was diluted with MeOH and concentrated to dryness. The residue was purified by $SiO_2$ chromatography (eluent: 2-5% MeOH/$CH_2Cl_2$) to provide tert-butyl ((trans)-4-(5-(6-(3-cyanopyrrolo[1,2-b]pyridazin-7-yl)-4-(isopropylamino)pyridin-3-yl)-1,3,4-thiadiazol-2-yl)cyclohexyl)carbamate. ES/MS: 559.658 (M+H$^+$).

Step 4: 7-(5-(5-((Trans)-4-aminocyclohexyl)-1,3,4-thiadiazol-2-yl)-4-(isopropylamino)pyridin-2-yl)pyrrolo[1,2-b] pyridazine-3-carbonitrile, bis-hydrochloride. To a solution of tert-butyl ((trans)-4-(5-(6-(3-cyanopyrrolo[1,2-b] pyridazin-7-yl)-4-(isopropylamino)pyridin-3-yl)-1,3,4-thiadiazol-2-yl)cyclohexyl)carbamate (228 mg, 0.408 mmol) in a mixture of $CH_2Cl_2$ (4 mL) and MeOH (4 mL) was added 4 M HCl in dioxane (4.00 M, 2.00 mL, 8.00 mmol). The solution was stirred at 45° C. for 18 h and concentrated to dryness to provide 7-(5-(5-((trans)-4-aminocyclohexyl)-1,3,4-thiadiazol-2-yl)-4-(isopropylamino)pyridin-2-yl)pyrrolo [1,2-b]pyridazine-3-carbonitrile, bis-hydrochloride. ES/MS: 459.629 (M+H$^+$).

BB3: 7-(5-(5-((1r,4r)-4-aminocyclohexyl)-1,3,4-thiadiazol-2-yl)-4-(methylamino)pyridin-2-yl)pyrrolo[1,2-b]pyridazine-3-carbonitrile

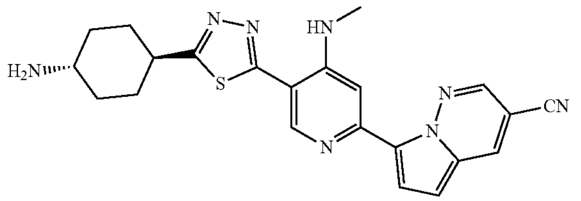 [SMILES: CNc1cc(-c2ccc3cc(C#N)cnn23)ncc1-c1nnc([C@H]2CC[C@H](N)CC2)s1]

Step 1: methyl 6-chloro-4-(methylamino)nicotinate. To a solution of methyl 4,6-dichloronicotinate (95.0 g, 461 mmol, 1.00 eq) in acetonitrile (1000 mL) was added methanamine (288 g, 2.32 mol, 25% purity, 5.03 eq) slowly at 0° C., the mixture was stirred at 0° C. for 0.5 hr and then at 25° C. for 2 hrs. TLC (Petroleum ether:Ethyl acetate=5:1) showed 4,6-dichloronicotinate (Rf=0.40) was consumed, and a new spot (Rf=0.30) was formed. The reaction mixture was concentrated under reduced pressure and extracted with ethyl acetate (3×500 mL), the combined organic layer was washed with brine (2×500 mL), dried over $Na_2SO_4$, filtered and the filtrate was concentrated under reduced pressure to give the crude product. The crude product was purified by a column chromatography ($SiO_2$, petroleum ether:Ethyl acetate=20:1-10:1, Rf=30). Methyl 6-chloro-4-(methylamino)nicotinate (39.0 g, 184 mmol, 40.0% yield, 95.0% purity) was obtained as a white solid. LCMS: $C_8H_9ClN_2O_2$ requires: 200.04, found m/z=201.1 (M+H)+. $^1$H NMR: (400 MHz $CDCl_3$) δ 8.65 (s, 1H), 8.08 (s, 1H), 6.54 (s, 1H), 3.88 (s, 3H), 2.92 (d, J=5.2 Hz, 3H). BB3 was thereafter synthesized using the same reaction sequence as BB2 starting from 6-chloro-4-(methylamino)pyridine-3-carbohydrazide. LCMS: $C_{22}H_{22}N_8S$ requires: 430.17. found: m/z=431.39 $[M+H]^+$.

BB4: 7-(4-(isopropylamino)-5-(5-(piperazin-1-yl)-1,3,4-thiadiazol-2-yl)pyridin-2-yl)pyrrolo[1,2-b]pyridazine-3-carbonitrile

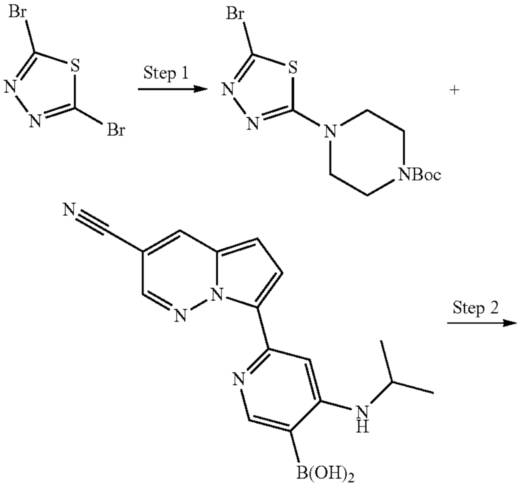

-continued

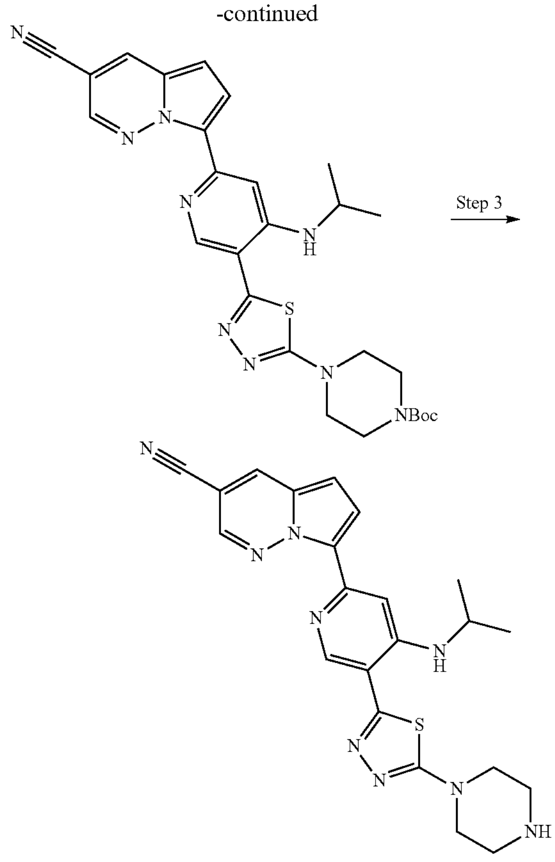

BB4

Step 1: tert-butyl 4-(5-bromo-1,3,4-thiadiazol-2-yl)piperazine-1-carboxylate. Tert-butyl piperazine-1-carboxylate (1.6 g, 8.6 mmol, 1.05 eq), dibromo-1,3,4-thiadiazole (2.0 g, 8.2 mmol) were combined in dioxane (0.15M), followed by addition of N,N-diisopropylethylamine (2.5 mL, 14.4 mmol). The vial was capped, and then heated to 110° C. for 90 minutes. The reaction was then cooled to rt, concentrated onto silica gel and purified by column chromatography (0-5% methanol in DCM) to give tert-butyl 4-(5-bromo-1,3,4-thiadiazol-2-yl)piperazine-1-carboxylate (2.0 g, 70%). LCMS: $C_{11}H_{17}BrN_4O_2S$ requires: 348.0. found: m/z=351.1 $[M+H]^+$.

Step 2: tert-butyl 4-(5-(6-(3-cyanopyrrolo[1,2-b]pyridazin-7-yl)-4-(isopropylamino)pyridin-3-yl)-1,3,4-thiadiazol-2-yl)piperazine-1-carboxylate. 6-{3-cyanopyrrolo[1,2-b]pyridazin-7-yl}-4-(isopropylamino)pyridin-3-ylboronic acid (1.5 g, 4.7 mmol), cesium carbonate (3.5 g, 10.7 mmol), xantphos (0.54 g, 0.93 mmol), palladium acetate (105 mg, 0.47 mmol), and tert-butyl 4-(5-bromo-1,3,4-thiadiazol-2-yl)piperazine-1-carboxylate (1.6 g, 4.7 mmol) were combined in dioxane (0.15 M) in a microwave vial. Nitrogen was bubbled through the reaction mixture for 1 minute before capping. Irradiation at 145 C for 35 min was performed, followed by cooling to rt and filtration with celite. The celite pad was washed with ethyl acetate, and the combined organics were concentrated onto silica gel. Chromatography (0-10% methanol in DCM) provided tert-butyl 4-(5-(6-(3-cyanopyrrolo[1,2-b]pyridazin-7-yl)-4-(isopropylamino)pyridin-3-yl)-1,3,4-thiadiazol-2-yl)piperazine-1-carboxylate which was used as-is in the next step.

Step 3: 7-[4-(isopropylamino)-5-[5-(piperazin-1-yl)-1,3,4-thiadiazol-2-yl]pyridin-2-yl]pyrrolo[1,2-b]pyridazine-3-carbonitrile. Tert-butyl 4-(5-(6-(3-cyanopyrrolo[1,2-b]pyridazin-7-yl)-4-(isopropylamino)pyridin-3-yl)-1,3,4-thiadiazol-2-yl)piperazine-1-carboxylate was stirred in minimal dioxane, followed by addition of 4N dioxane (5 mL), and stirred for 5 h. The reaction was then concentrated by rotovap onto silica, and chromatographed (0-20% methanol in DCM) to provide 7-[4-(isopropylamino)-5-[5-(piperazin-1-yl)-1,3,4-thiadiazol-2-yl]pyridin-2-yl]pyrrolo[1,2-b]pyridazine-3-carbonitrile (0.5 g, 24% yield over 2 steps). LCMS: $C_{22}H_{23}N_9S$ requires: 445.6. found: m/z=446.4 $[M+H]^+$.

BB5: 7-[4-(isopropylamino)-5-{5-[4-(piperidine-4-carbonyl)piperazin-1-yl]-1,3,4-thiadiazol-2-yl}pyridin-2-yl]pyrrolo[1,2-b]pyridazine-3-carbonitrile

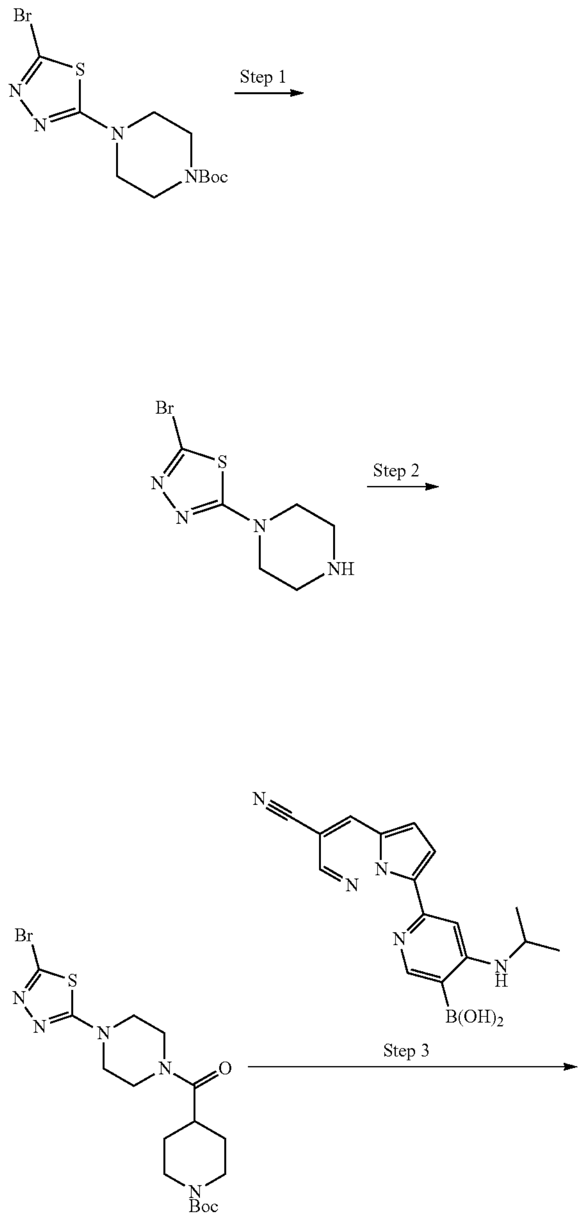

-continued

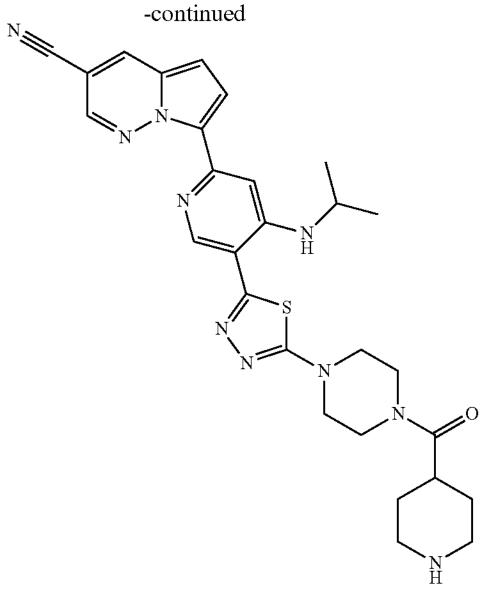

BB5

Step 1: 1-(5-bromo-1,3,4-thiadiazol-2-yl)-piperazine. Tert-butyl 4-(5-bromo-1,3,4-thiadiazol-2-yl)piperazine-1-carboxylate (1 g, 2.9 mmol) was dissolved in DCM (0.15M), followed by addition of trifluoroacetic acid (0.05M volume) and stirred at room temperature for 3 h. The reaction was then concentrated, re-taken up in ether, concentrated and dried on vacuum (0.6 g, 84%). The crude 1-(5-bromo-1,3,4-thiadiazol-2-yl)-piperazine was used as-is in the next reaction. LCMS: $C_6H_9BrN_4S$ requires: 248.0. found: m/z=249.1 $[M+H]^+$.

Step 2: tert-butyl 4-[4-(5-bromo-1,3,4-thiadiazol-2-yl)piperazine-1-carbonyl]piperidine-1-carboxylate. 1-(5-bromo-1,3,4-thiadiazol-2-yl)piperazine (300 mg, 1.2 mmol) was added to a solution of 1-(tert-butoxycarbonyl)piperidine-4-carboxylic acid (276 mg, 1.2 mmol) and HATU (570 mg, 1.5 mmol) in DMF (5 mL) and triethylamine (0.6 mL, 4.2 mmol). The reaction was stirred at room temperature for 18 h. The reaction was then partitioned between ethyl acetate and water. The water layer was re-extracted with ethyl acetate. The combined organics were washed with brine, then dried over magnesium sulfate, and concentrated onto silica gel. Silica gel chromatography (0-10% methanol in DCM) provided tert-butyl 4-[4-(5-bromo-1,3,4-thiadiazol-2-yl)piperazine-1-carbonyl]piperidine-1-carboxylate (0.2 g, 36%). LCMS: $C_{17}H_{26}BrN_5O_3S$ requires: 460.4. found: m/z=484.3 $[M+Na]^+$.

Step 3: 7-[4-(isopropylamino)-5-{5-[4-(piperidine-4-carbonyl)piperazin-1-yl]-1,3,4-thiadiazol-2-yl}pyridin-2-yl]pyrrolo[1,2-b]pyridazine-3-carbonitrile. 6-{3-cyanopyrrolo[1,2-b]pyridazin-7-yl}-4-(isopropylamino)pyridin-3-ylboronic acid (150 mg, 0.47 mmol), cesium carbonate (0.42 g, 1.3 mmol), xantphos (0.11 g, 0.19 mmol), palladium acetate (21 mg, 0.09 mmol), and tert-butyl 4-[4-(5-bromo-1,3,4-thiadiazol-2-yl)piperazine-1-carbonyl]piperidine-1-carboxylate were combined in a microwave vial followed by addition of dioxane (0.1 M), and bubbling with $N_2$. Irradiation in the microwave reactor at 145° C. for 30 minutes was performed, followed by cooling and filtration with Celite. The solution was concentrated onto silica gel, and then chromatographed (0-10% methanol in DCM). This material was then subjected to 4N HCl in dioxane (0.15M), followed by stirring for 2 h. The reaction was then concentrated to provide 7-[4-(isopropylamino)-5-{5-[4-(piperidine-4-carbonyl)piperazin-1-yl]-1,3,4-thiadiazol-2-yl}pyridin-2-yl]pyrrolo[1,2-b]pyridazine-3-carbonitrile (0.1 g, 39% over two steps). LCMS: $C_{28}H_{32}N_{10}OS$ requires: 556.7. found: m/z=557.4 $[M+H]^+$.

BB6: 7-[4-(isopropylamino)-5-{5-[4-(piperidin-4-yl)piperazin-1-yl]-1,3,4-thiadiazol-2-yl}pyridin-2-yl]pyrrolo[1,2-b]pyridazine-3-carbonitrile

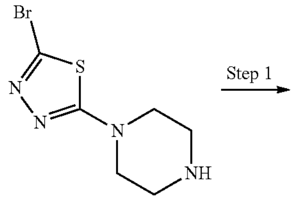

-continued

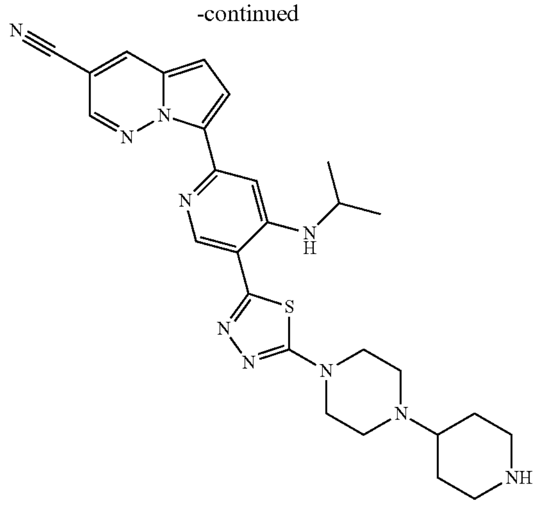

BB6

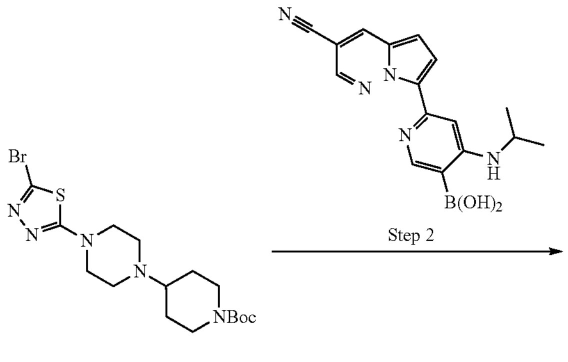

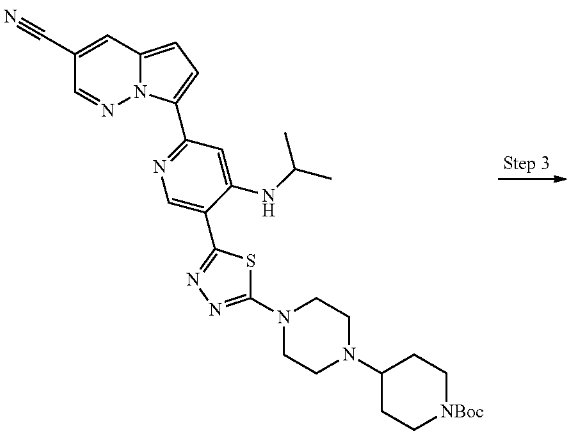

Step 1: tert-butyl 4-[4-(5-bromo-1,3,4-thiadiazol-2-yl)piperazin-1-yl]piperidine-1-carboxylate. 1-(5-bromo-1,3,4-thiadiazol-2-yl)piperazine (300 mg, 1.2 mmol), tert-butyl 4-oxopiperidine-1-carboxylate, were combined in DCE (0.2 M) and TEA (0.5 mL, 3.6 mmol). After stirring for 5 minutes, sodium triacetoxyborohydride (0.45 g, 2.1 mmol) was added in one portion. The reaction was stirred at room temperature for 3 h, followed by filtration with celite, and concentration onto silica gel. Chromatography (0-10% methanol in DCM) provided desired tert-butyl 4-[4-(5-bromo-1,3,4-thiadiazol-2-yl)piperazin-1-yl]piperidine-1-carboxylate (0.2 g, 39%). LCMS: $C_{16}H_{26}N_5O_2SBr$ requires: 432.4. found: m/z=456.3$[M+Na]^+$.

Step 2: tert-butyl 4-{4-[5-(6-{3-cyanopyrrolo[1,2-b]pyridazin-7-yl}-4-(isopropylamino)pyridin-3-yl)-1,3,4-thiadiazol-2-yl]piperazin-1-yl}piperidine-1-carboxylate. 6-{3-cyanopyrrolo[1,2-b]pyridazin-7-yl}-4-(isopropylamino)pyridin-3-ylboronic acid (150 mg, 0.47 mmol), xantphos (110 mg, 0.19 mmol), cesium carbonate (0.42 g, 1.28 mmol), palladium acetate (21 mg, 0.09 mmol) and tert-butyl 4-[4-(5-bromo-1,3,4-thiadiazol-2-yl)piperazin-1-yl]piperidine-1-carboxylate (200 mg, 0.47 mmol) were combined in a microwave vial followed by addition of dioxane (0.15 M).

Nitrogen was bubbled through the reaction mixture for 30 seconds before capping, and irradiation at 145 C for 30 minutes in the microwave reactor. The reaction was then cooled, filtered with Celite, and concentrated onto silica gel. Chromatography (0-10% methanol in DCM) provided tert-butyl 4-{4-[5-(6-{3-cyanopyrrolo[1,2-b]pyridazin-7-yl}-4-(isopropylamino)pyridin-3-yl)-1,3,4-thiadiazol-2-yl]piperazin-1-yl}piperidine-1-carboxylate (100 mg, 34%). LCMS: $C_{32}H_{40}N_{10}O_2S$ requires: 626.8. found: m/z=629.7 $[M+H]^+$.

Step 3: 7-[4-(isopropylamino)-5-{5-[4-(piperidin-4-yl)piperazin-1-yl]-1,3,4-thiadiazol-2-yl}pyridin-2-yl]pyrrolo[1,2-b]pyridazine-3-carbonitrile. tert-butyl 4-{4-[5-(6-{3-cyanopyrrolo[1,2-b]pyridazin-7-yl}-4-(isopropylamino)pyridin-3-yl)-1,3,4-thiadiazol-2-yl]piperazin-1-yl}piperidine-1-carboxylate (100 mg) was dissolved in dioxane (1 mL) followed by addition of 4N HCl in dioxane (1 mL). The reaction was stirred for 2 h, then concentrated to provide the hydrochloride salt of 7-[4-(isopropylamino)-5-{5-[4-(piperidin-4-yl)piperazin-1-yl]-1,3,4-thiadiazol-2-yl}pyridin-2-yl]pyrrolo[1,2-b]pyridazine-3-carbonitrile (0.08 g, 95%) which was used without further purification. LCMS: $C_{27}H_{32}N_{10}S$ requires: 528.7. found: m/z=529.7 $[M+H]^+$.

BB7: 7-(5-(5-(4-aminopiperidin-1-yl)-1,3,4-thiadiazol-2-yl)-4-(isopropylamino)pyridin-2-yl)pyrrolo[1,2-b]pyridazine-3-carbonitrile hydrochloride

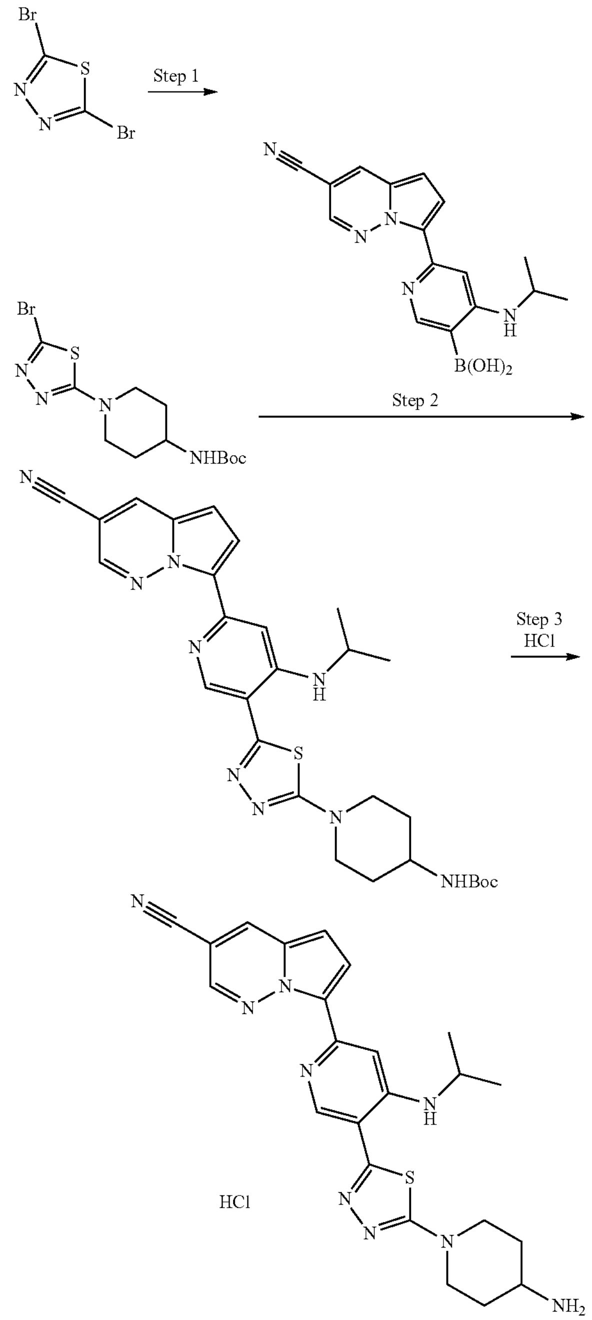

BB7

Step 1: tert-butyl N-[1-(5-bromo-1,3,4-thiadiazol-2-yl)piperidin-4-yl]carbamate. Dibromo-1,3,4-thiadiazole (1.0 g, 4.1 mmol), tert-butyl N-(piperidin-4-yl)carbamate (840 mg, 4.2 mmol) were dissolved in dioxane (0.15 M), followed by addition of N,N-diisopropylethylamine (1.25 mL, 7.2 mmol). The reaction was heated to 110 C in a sealed vial and stirred for 90 minutes. The reaction was then cooled and concentrated onto silica gel. Column chromatography (0-5% methanol in DCM) provided tert-butyl N-[1-(5-bromo-1,3,4-thiadiazol-2-yl)piperidin-4-yl]carbamate (1.0 g, 67%). LCMS: $C_{12}H_{19}BrN_4O_2S$ requires: 363.3. found: m/z=365.3 $[M+H]^+$.

Step 2: tert-butyl N-{1-[5-(6-{3-cyanopyrrolo[1,2-b]pyridazin-7-yl}-4-(isopropylamino)pyridin-3-yl)-1,3,4-thiadiazol-2-yl]piperidin-4-yl}carbamate. 6-{3-cyanopyrrolo[1,2-b]pyridazin-7-yl}-4-(isopropylamino)pyridin-3-ylboronic acid (90 mg, 0.28 mmol), cesium carbonate (0.25 g, 0.77 mmol), xantphos (0.06 g, 0.11 mmol), palladium acetate (13 mg, 0.06 mmol), and tert-butyl N-[1-(5-bromo-1,3,4-thiadiazol-2-yl)piperidin-4-yl]carbamate (102 mg, 0.28 mmol) were combined in a microwave vial followed by addition of dioxane (0.15 M) and bubbling with nitrogen. The reaction was stirred at room temperature for 3 minutes before irradiation at 145 C for 30 minutes in the microwave reactor. The reaction was cooled, filtered with Celite, and concentrated onto silica gel. Column chromatography (0-5% methanol in DCM) provided tert-butyl N-{1-[5-(6-{3-cyanopyrrolo[1,2-b]pyridazin-7-yl}-4-(isopropylamino)pyridin-3-yl)-1,3,4-thiadiazol-2-yl]piperidin-4-yl}carbamate (0.1 g, 64%).

Step 3: 7-(5-(5-(4-aminopiperidin-1-yl)-1,3,4-thiadiazol-2-yl)-4-(isopropylamino)pyridin-2-yl)pyrrolo[1,2-b]pyridazine-3-carbonitrile hydrochloride. To a solution of tert-butyl N-{1-[5-(6-{3-cyanopyrrolo[1,2-b]pyridazin-7-yl}-4-(isopropylamino)pyridin-3-yl)-1,3,4-thiadiazol-2-yl]piperidin-4-yl}carbamate was added excess 4N HCl to give the title compound. LCMS: $C_{23}H_{25}N_9S$ requires: 459.2. found: m/z=460.5 $[M+H]^+$.

BB8: 7-(5-(5-(3,9-diazaspiro[5.5]undecan-3-yl)-1,3,4-thiadiazol-2-yl)-4-(isopropylamino)pyridin-2-yl)pyrrolo[1,2-b]pyridazine-3-carbonitrile

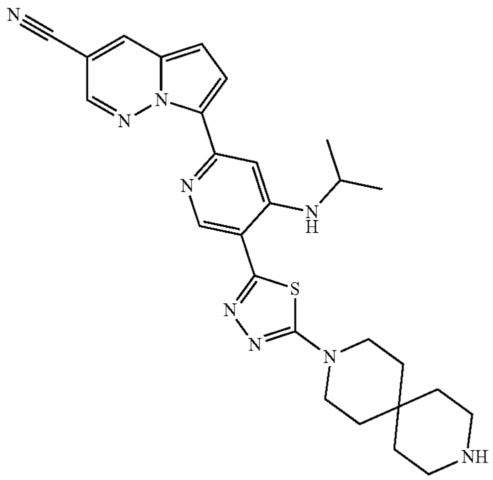 [SMILES: CC(C)Nc1cc(-c2ccc3cc(C#N)cnn23)ncc1-c1nnc(N2CCC3(CCNCC3)CC2)s1]

BB8 was synthesized following the same route as BB4 except with tert-butyl 3,9-diazaspiro[5.5]undecane-3-carboxylate as the amine in step 1. LCMS: $C_{27}H_{31}N_9S$ requires: 513.2. found: m/z=514.6 $[M+H]^+$.

BB9: 7-(4-(methylamino)-5-(5-(4-(piperidine-4-carbonyl)piperazin-1-yl)-1,3,4-thiadiazol-2-yl)pyridin-2-yl)pyrrolo[1,2-b]pyridazine-3-carbonitrile

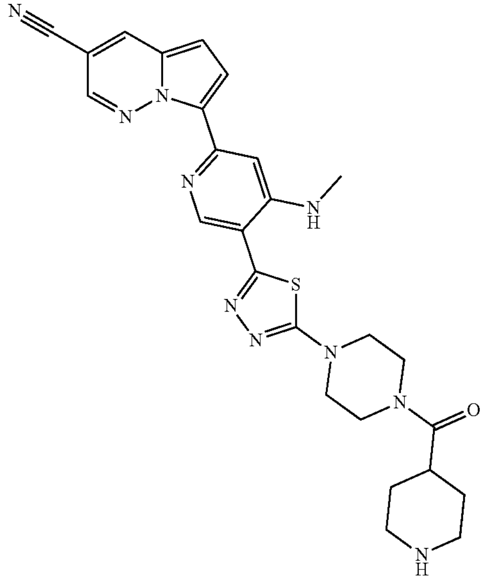 [SMILES: CNc1cc(-c2ccc3cc(C#N)cnn23)ncc1-c1nnc(N2CCN(C(=O)C3CCNCC3)CC2)s1]

BB9 was synthesized following the same route as BB5 except with (6-(3-cyanopyrrolo[1,2-b]pyridazin-7-yl)-4-(methylamino)pyridin-2-yl)boronic acid in step 3. LCMS: $C_{26}H_{28}N_{10}OS$ requires: 528.2. found: m/z=529.4 $[M+H]^+$.

BB10: 7-[4-(methylamino)-5-[5-(piperazin-1-yl)-1,3,4-thiadiazol-2-yl]pyridin-2-yl]pyrrolo[1,2-b]pyridazine-3-carbonitrile

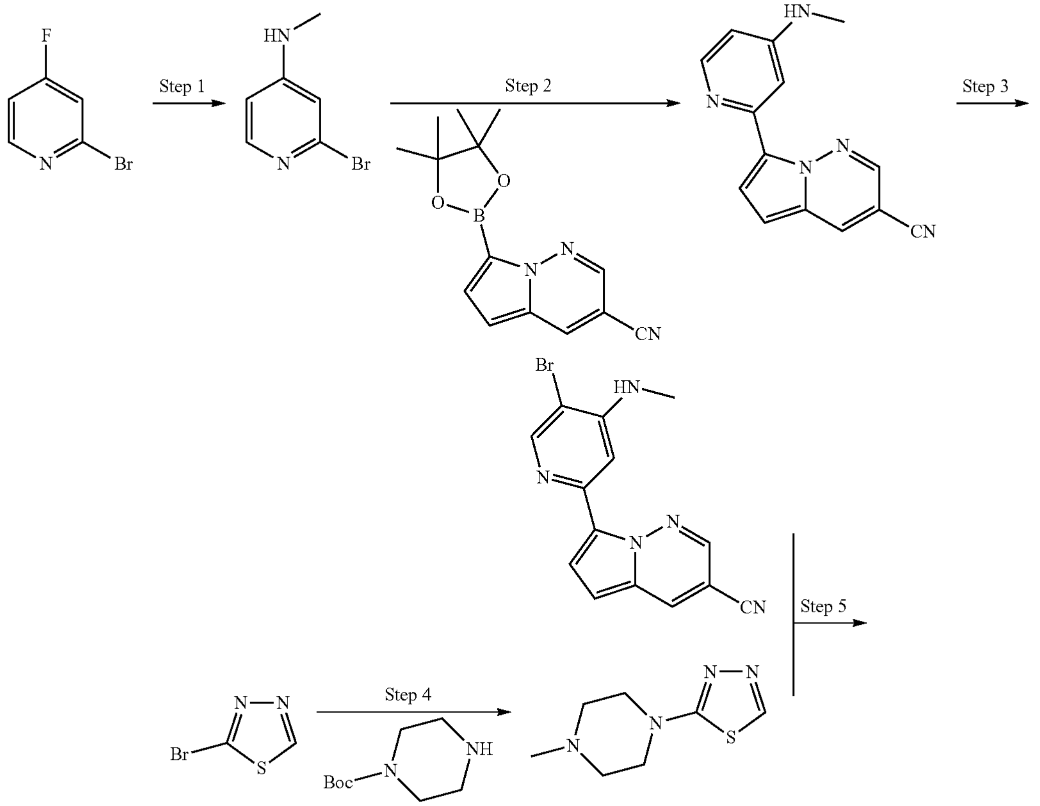

-continued

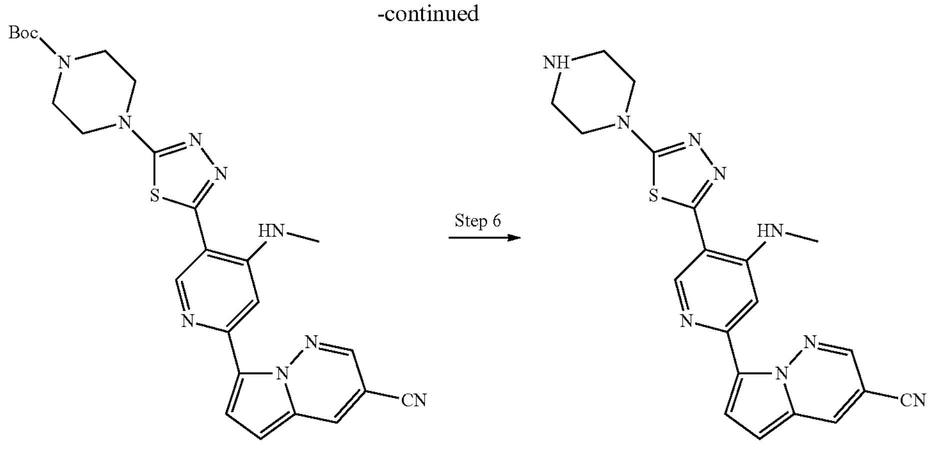

BB10

Step 1: 2-bromo-N-methylpyridin-4-amine. To a mixture of 2-bromo-4-fluoro-pyridine (25.0 g, 0.142 mol, 1.0 eq) the methylamine in methanol (9.8 M) (142 ml, 1.42 mol, 10 eq) was added and resulting mixture was heated at 80° C. overnight. After completion, the reaction mixture was cooled, evaporated all volatiles in vacuo, solubilized in EtOAc and washed with water. The organic layer was dried over sodium sulfate, filtered and concentrated to give the desired product. (25 g, 89% yield): ESI(+)$[M+H]^+$=188.94; $^1$H NMR (300 MHz, DMSO-$d_6$), δ: 7.77 (d, J=5.8 Hz, 1H), 6.98-6.78 (m, 1H), 6.59 (m, 1H), 6.48 (m, 1H), 2.69 (d, J=4.9 Hz, 3H).

Step 2: 7-[4-(methylamino)pyridin-2-yl]pyrrolo[1,2-b]pyridazine-3-carbonitrile. To a solution of 2-bromo-N-methylpyridin-4-amine (6.0 g, 32.08 mmol, 1.0 eq), 7-(4,4,5,5-tetramethyl-1,3,2-dioxaborolan-2-yl)pyrrolo[1,2-b]pyridazine-3-carbonitrile (12.09 g, 44.91 mmol, 1.4 eq) and Xphos G3 (2.17 g, 2.57 mmol, 0.08 eq) in anhydrous dimethoxyethane (80 ml, 0.4 M), 2M aq sol $K_3PO_4$ (32.1 ml, 64.16 mmol, 2.0 eq) was added. The solution was degassed with argon for 15 min and then heated at 120° C. with vigorous stirred overnight. The reaction mixture was filtrated through Celite and evaporated under reduced pressure to dryness. The crude residue obtained was purified by chromatography using methanol in dichloromethane (0-10%) to give a desired product as a yellow solid (6.1 g, 76% yield); $^1$H NMR (300 MHz, DMSO-$d_6$), δ: 8.79 (d, J=2.2 Hz, 1H), 8.64 (d, J=2.2 Hz, 1H), 8.19 (d, J=5.6, 1H), 7.87 (d, J=2.3, 1H), 7.76 (d, J=4.7 Hz, 1H), 7.08 (d, J=4.7, 1H), 6.80 (d, J=5.0, 1H), 6.45 (m, 1H), 2.77 (d, J=4.8 Hz, 3H); ESI(+)$[M+H]^+$=250.36.

Step 3: 7-[5-bromo-4-(methylamino)pyridin-2-yl]pyrrolo[1,2-b]pyridazine-3-carbonitrile, 7-[4-(methylamino)-2-pyridyl]pyrrolo[1,2-b]pyridazine-3-carbonitrile (5.3 g, 20.05 mmol, 1.0 eq) was dissolved in acetonitrile (65 ml, 0.3 M) and dichloromethane (20 ml, 0.7 M) and N-bromosuccinimide (3.57 g, 20.05 mmol, 1.0 eq) was added by one portion at r. t. The reaction was stirred at the ambient conditions for 30 min. After completion, the mixture was evaporated under reduced pressure and the resulting residue purified with chromatography using 0-5% ethyl acetate in dichloromethane to give the product as a yellow solid (5.95 g, 88% yield); $^1$H NMR (300 MHz, DMSO-$d_6$), δ: 8.80 (d, J=2.2 Hz, 1H), 8.67 (d, J=2.2 Hz, 1H), 8.36 (s, 1H), 7.94 (s, 1H), 7.76 (d, J=4.8 Hz, 1H), 7.08 (d, J=4.8 Hz, 1H), 6.45 (q, J=4.3 Hz, 1H), 2.90 (d, J=4.7 Hz, 3H); ESI(+)$[M+H]^+$=330.16.

Step 4: tert-butyl 4-(1,3,4-thiadiazol-2-yl)piperazine-1-carboxylate. To a solution of 2-bromo-1,3,4-thiadiazole (7.292 g, 42.424 mmol, 1.0 eq) and t-butyl piperazine-1-carboxylate hydrochloride (19.75 g, 106.05 mmol, 2.5 eq) in n-butanol (83.18 ml, 0.51 M) the N,N-diisopropylethylamine (29.57 ml, 169.68 mmol, 4.0 eq) was added. The reaction mixture was heated thermally at 120° C. for 1 hour. After completion, the resulting mixture was cooled, concentrated in vacuo to provide the crude product. After chromatography purification (0 to 70% ethyl acetate in hexane) the desired compound was given as a pink crystalline solid (9.93 g, 86% yield); $^1$H NMR (300 MHz, DMSO-$d_6$), δ: 8.84 (s, 1H), 3.46 (s, 8H), 1.42 (s, 9H); ESI(+)$[M+H]^+$=272.16.

Step 5: tert-butyl 4-[5-(6-{3-cyanopyrrolo[1,2-b]pyridazin-7-yl}-4-(methylamino)pyridin-3-yl)-1,3,4-thiadiazol-2-yl]piperazine-1-carboxylate. 7-[5-bromo-4-(methylamino)pyridin-2-yl]pyrrolo[1,2-b]pyridazine-3-carbonitrile (0.5 g, 1.524 mmol, 1.0 eq), palladium (II) acetate (0.051 g, 0.227 mmol, 0.15 eq), 4,5-bis(diphenylphosphino)-9,9-dimethylxanthene (0.26 g, 0.45 mmol, 0.3 eq), cesium carbonate (0.1 g, 3.05 mmol, 2.0 eq) and cuprous iodide (0.087 g, 0.457 mmol, 0.3 eq) were taken in an oven-dried screw-cap vial and tert-butyl 4-(1,3,4-thiadiazol-2-yl)piperazine-1-carboxylate 4-(1,3,4-thiadiazol-2-yl)piperazine-1-carboxylate (0.434 g, 1.53 mmol, 1 eq), dioxane (25.39 ml, 0.06 M) were added to it. The reaction tube was evacuated-backfilled with argon for 20 minutes, sealed and subsequently heated at 105° C. overnight. After completion of the reaction (confirmed by UPLC), all volatiles were evaporated in vacuo and the resulting residue was purified with chromatography (0 to 31% ethyl acetate in dichloromethane) to give the desired product as a yellow crystalline solid (0.57 g, 61% yield); $^1$H NMR (300 MHz, DMSO-$d_6$), δ: 8.83 (s, 1H), 8.73 (s, 1H), 8.48 (m, 2H), 8.14 (s, 1H), 7.86 (s, 1H), 7.12 (d, J=4.8 Hz, 1H), 3.54 (s, 8H), 3.06 (d, J=4.9 Hz, 3H), 1.44 (s, 9H); ESI(+)$[M+H]^+$=518.64.

Step 6: 7-[4-(methylamino)-5-[5-(piperazin-1-yl)-1,3,4-thiadiazol-2-yl]pyridin-2-yl]pyrrolo[1,2-b]pyridazine-3-carbonitrile. The solution of tert-butyl 4-[5-(6-{3-cyanopyrrolo[1,2-b]pyridazin-7-yl}-4-(methylamino)-pyridin-3-yl)-1,3,4-thiadiazol-2-yl]piperazine-1-carboxylate (0.25 g, 0.48 mmol, 1 eq) in 1,1,1,3,3,3-hexafluoro-2-propanol (0.769 ml, 7.25 mmol, 15 eq) was heated at 140° C. with MW for 3 h. All volatiles were evaporated under reduced pressure and the remaining residue was purified via chromatography (0 to 7% methanol in dichloromethane) to give the target product as a yellow solid (0.15 g, 73% yield): LCMS: ESI(+)[M+H]$^+$=418.06; $^1$H NMR (300 MHz, DMSO-$d_6$), δ: 8.83 (d, J=2.2 Hz, 1H), 8.72 (s, 1H), 8.54-8.42 (m, 2H), 8.13 (s, 1H), 7.85 (d, J=4.8 Hz, 1H), 7.11 (d, J=4.8 Hz, 1H), 3.46 (s, 4H), 3.06 (d, J=4.9 Hz, 3H), 2.84 (s, 4H), 2.61 (br m, 1H).

BB11: 7-(5-(5-(4-aminopiperidin-1-yl)-1,3,4-thiadiazol-2-yl)-4-(methylamino)pyridin-2-yl)pyrrolo[1,2-b]pyridazine-3-carbonitrile

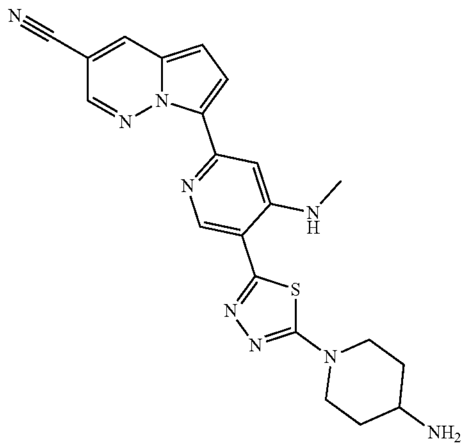 [SMILES: CNc1cc(-c2ccc3cc(C#N)cnn23)ncc1-c1nnc(N2CCC(N)CC2)s1]

BB11 was synthesized following the same route as BB7 except with (6-(3-cyanopyrrolo[1,2-b]pyridazin-7-yl)-4-(methylamino)pyridin-2-yl)boronic acid in step 2. LCMS: $C_{21}H_{21}N_9S$ requires: 431.2. found: m/z=432.4 [M+H]$^+$.

BB12: 7-(4-(methylamino)-5-(5-(4-(piperidin-4-yl)piperazin-1-yl)-1,3,4-thiadiazol-2-yl)pyridin-2-yl)pyrrolo[1,2-b]pyridazine-3-carbonitrile

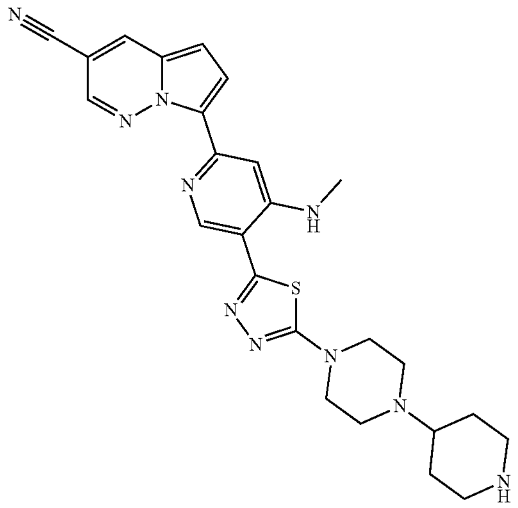 [SMILES: CNc1cc(-c2ccc3cc(C#N)cnn23)ncc1-c1nnc(N2CCN(C3CCNCC3)CC2)s1]

BB12 was synthesized following the same route as BB6 except with (6-(3-cyanopyrrolo[1,2-b]pyridazin-7-yl)-4-(methylamino)pyridin-2-yl)boronic acid in step 2. LCMS: $C_{25}H_{28}N_{10}S$ requires: 500.2. found: m/z=501.5 [M+H]$^+$.

BB13: 7-(5-(5-(4-aminobicyclo[2.2.2]octan-1-yl)-1,3,4-thiadiazol-2-yl)-4-(methylamino)pyridin-2-yl)pyrrolo[1,2-b]pyridazine-3-carbonitrile

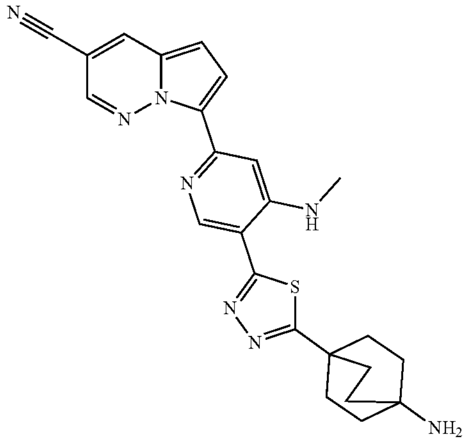 [SMILES: CNc1cc(-c2ccc3cc(C#N)cnn23)ncc1-c1nnc(C23CCC(N)(CC2)CC3)s1]

BB13 was synthesized following the same route as BB3 except with 4-((tert-butoxycarbonyl)amino)bicyclo[2.2.2]octane-1-carboxylic acid in step 1. LCMS: $C_{24}H_{24}N_8S$ requires: 456.2. found: m/z=457.1 [M+H]$^+$.

BB14: 7-(5-(5-((1s,4s)-4-aminocyclohexyl)-1,3,4-thiadiazol-2-yl)-4-(methylamino)pyridin-2-yl)pyrrolo[1,2-b]pyridazine-3-carbonitrile

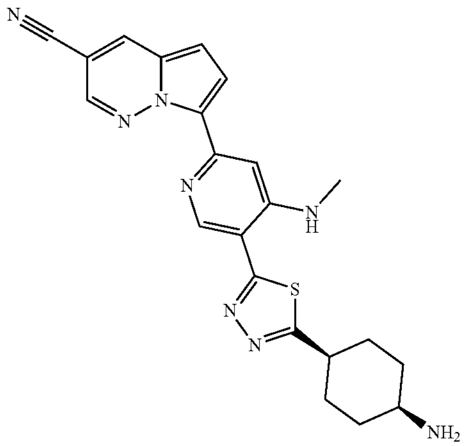 [SMILES: CNc1cc(-c2ccc3cc(C#N)cnn23)ncc1-c1nnc([C@H]2CC[C@@H](N)CC2)s1]

BB14 was synthesized following the same route as BB3 except with cis-4-(tert-butoxycarbonylamino)cyclohexanecarboxylic acid in step 1. LCMS: $C_{22}H_{22}N_8S$ requires: 430.2. found: m/z=431.3 [M+H]$^+$.

BB15: 7-(5-(5-(2,6-diazaspiro[3.5]nonan-6-yl)-1,3,4-thiadiazol-2-yl)-4-(methylamino)pyridin-2-yl)pyrrolo[1,2-b]pyridazine-3-carbonitrile

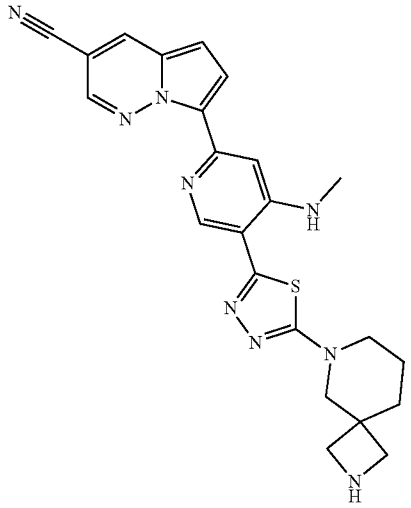 [SMILES: CNc1cc(-c2ccc3cc(C#N)cnn23)ncc1-c1nnc(N2CCCC3(CNC3)C2)s1]

BB15 was synthesized following the same route as BB10 except with tert-butyl 2,6-diazaspiro[3.5]nonane-2-carboxylate as the amine in step 1. LCMS: $C_{23}H_{23}N_9S$ requires: 457.2. found: m/z=458.3 $[M+H]^+$.

BB16: 7-(4-(methylamino)-5-(5-(4-(piperazine-1-carbonyl)piperazin-1-yl)-1,3,4-thiadiazol-2-yl)pyridin-2-yl)pyrrolo[1,2-b]pyridazine-3-carbonitrile

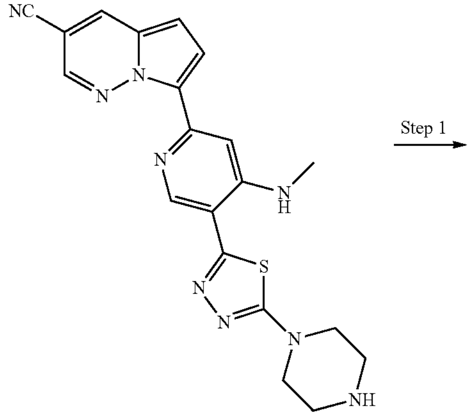

BB10

-continued

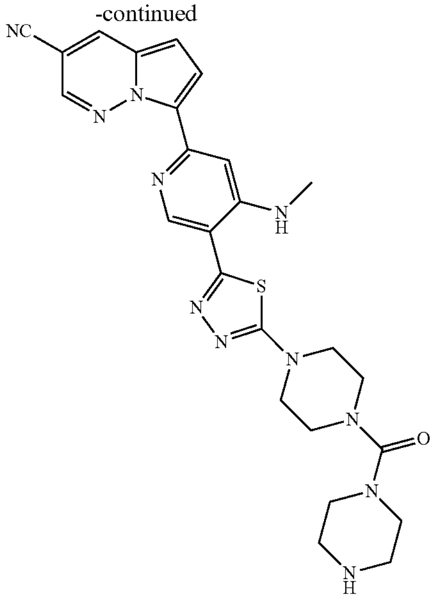

BB16

BB10 (55 mg, 0.22 mmol) was stirred with tert-butyl 4-(carboxy)piperazine-1-carboxylate (1 eq) in DIEA (2.2 eq) and DMF (0.2M) at rt for 5 h. Then the reaction was partitioned between ethyl acetate and water. The organic layer was separated, dried over magnesium sulfate, and concentrated. This crude material was directly dissolved in DCM:TFA (4:1 ratio, 0.1M) and stirred for 18 h. The reaction was then concentrated to dryness and triturated with diethyl ether to provide desired product (30 mg, 26% yield). LCMS: $C_{25}H_{27}N_{11}OS$ requires: 529.6. found: m/z=530.5 $[M+H]^+$.

BB17: 7-(4-(methylamino)-5-(5-(4-(piperazine-1-carbonyl)piperidin-1-yl)-1,3,4-thiadiazol-2-yl)pyridin-2-yl)pyrrolo[1,2-b]pyridazine-3-carbonitrile

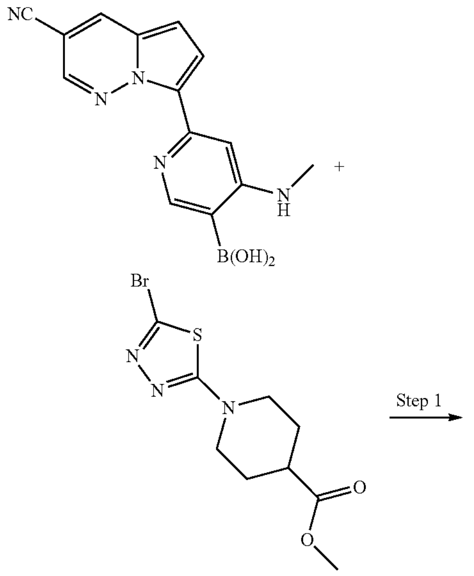

-continued

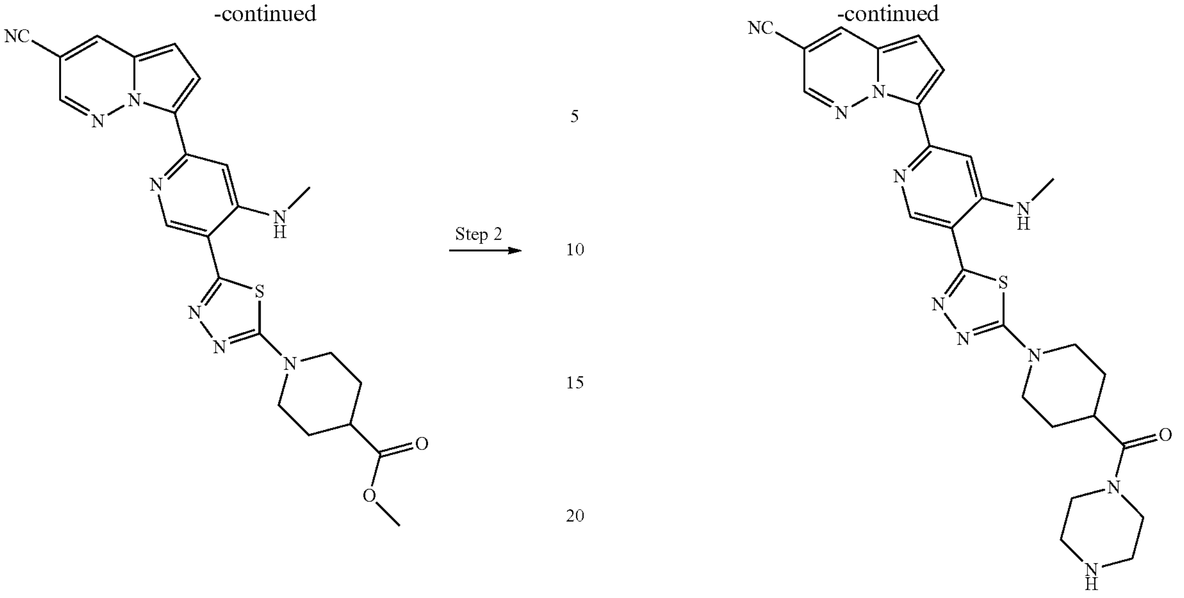

BB17

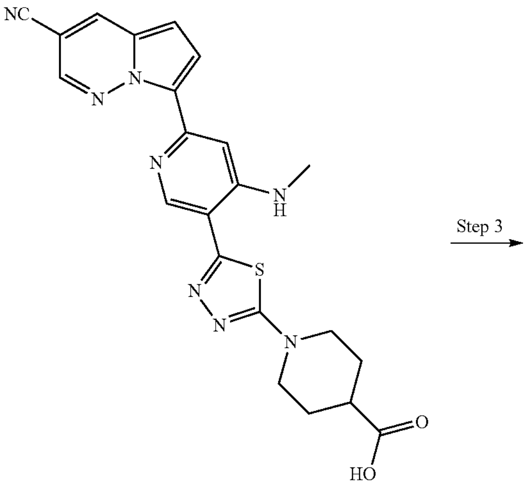

Step 1: ethyl 1-(5-(6-(3-cyanopyrrolo[1,2-b]pyridazin-7-yl)-4-(methylamino)pyridin-3-yl)-1,3,4-thiadiazol-2-yl)piperidine-4-carboxylate. 6-{3-cyanopyrrolo[1,2-b]pyridazin-7-yl}-4-(methylamino)pyridin-3-ylboronic acid (200 mg, 0.68 mmol) was combined with cesium carbonate (2.75 eq), Xantphos (0.4 eq), (acetyloxy)palladio acetate (0.2 eq), and ethyl 1-(5-bromo-1,3,4-thiadiazol-2-yl)piperidine-4-carboxylate (1 eq, see step 1 of BB4) in a microwave vial, followed by addition of dioxane (8 mL). The reaction was then purged with $N_2$ for 1 min, and stirred for 3 minutes before irradiation at 145° C. for 30 min in the microwave reactor. The reaction was then filtered with celite, and concentrated onto silica gel. Chromatography (0-10% methanol in DCM) provided desired product.

Step 2: 1-(5-(6-(3-cyanopyrrolo[1,2-b]pyridazin-7-yl)-4-(methylamino)pyridin-3-yl)-1,3,4-thiadiazol-2-yl)piperidine-4-carboxylic acid. Hydrolysis of the ester was performed with THF/ethanol (10:1) and 2 mL of 2M LiOH (aq). The reaction was stirred for 3 h, then dried onto silica gel and chromatographed (C18 column, 0-100% acetonitrile in water) to provide desired acid (100 mg, 32% over 2 steps).

Step 3: 7-(4-(methylamino)-5-(5-(4-(piperazine-1-carbonyl)piperidin-1-yl)-1,3,4-thiadiazol-2-yl)pyridin-2-yl)pyrrolo[1,2-b]pyridazine-3-carbonitrile. The carboxylic acid (100 mg) was combined with HATU (1.25 eq) DIEA (5 eq) in DMF (0.1M), and stirred for 10 minutes before addition of tert-butyl piperazine-1-carboxylate (1.2 eq). The reaction was stirred for 24 h, then partitioned between ethyl acetate and water. The organic layer was separated, and then re-dissolved in DCM/TFA (4:1, 0.1M) and stirred overnight. After concentration, crude material was obtained and used as-is (50 mg, 44% yield): LCMS: $C_{26}H_{28}N_{10}OS$ requires: 528.64. found: m/z=529.6 $[M+H]^+$.

BB18: 7-[4-(methylamino)-5-{5-[(1r,4r)-4-(methylamino)cyclohexyl]-1,3,4-thiadiazol-2-yl}pyridin-2-yl]pyrrolo[1,2-b]pyridazine-3-carbonitrile

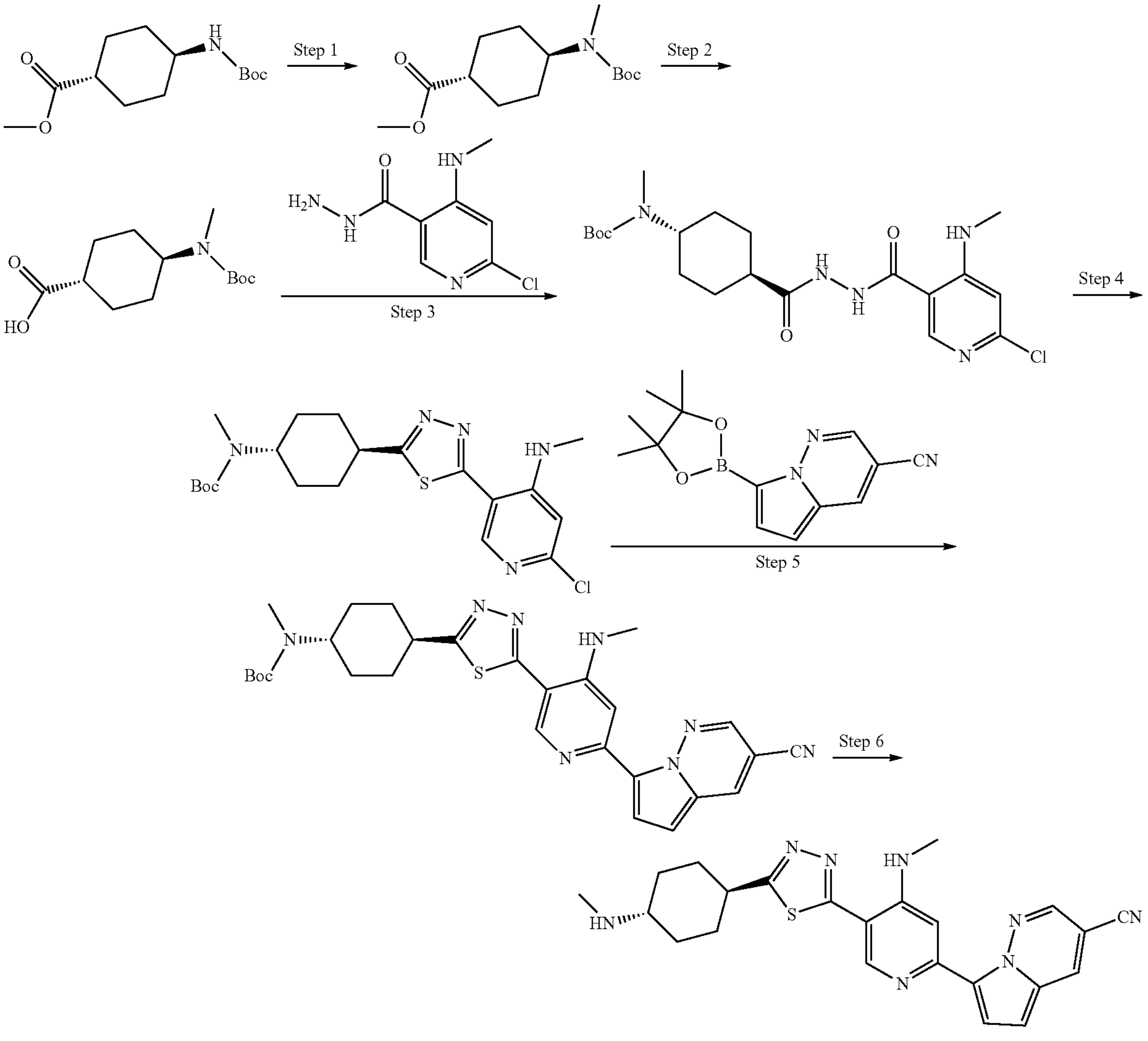

BB18

Step 1: methyl (1r,4r)-4-{[(tert-butoxy)carbonyl](methyl)amino}cyclohexane-1-carboxylate. Methyl trans-4-(tert-butoxycarbonylamino)cyclohexanecarboxylate (3.0 g, 11.658 mmol, 1.0 eq) was dissolved in DMF (20 ml, 0.6M) and cooled down to 0° C. Then NaH (0.536 g, 13.99 mmol, 1.2 eq) was added and the reaction mixture was stirred at 0° C. for 30 min. After that methyl iodide (1.09 ml, 17.49 mmol, 1.5 eq) was added, cooling bath was removed and the reaction mixture was stirred at RT for 18 h. The mixture was poured into a saturated aqueous ammonium chloride and extracted with ethyl acetate. The crude was purified by Hexane:EtOAc to acquire 1.4 g (44% yield) of desired product; $^1$H NMR (300 MHz, DMSO-$d_6$) δ 3.58 (s, 3H), 2.64 (s, 3H), 2.25 (tt, J=11.7, 3.6 Hz, 1H), 1.94 (dt, J=12.3, 2.6 Hz, 2H), 1.60-1.41 (m, 4H), 1.38 (d, J=1.6 Hz, 12H).

Step 2: (1r,4r)-4-{[(tert-butoxy)carbonyl]amino}cyclohexane-1-carboxylic acid. Methyl (1r,4r)-4-{[(tert-butoxy)carbonyl](methyl)amino}cyclohexane-1-carboxylate (1.3 g, 4.79 mmol, 1.0 eq) was dissolved in THF (18 ml, 0.27 M) followed by addition of solution of LiOH (4.8 ml, 4.79 mmol, 2.0 eq) and stirred at RT for 5 h. TLC showed remains of the starting material, another portion of LiOH (2.4 ml, 2.39 mmol, 1.0 eq) was added and the reaction mixture was stirred overnight. The TLC showed full conversion, mixture was quenched with saturated solution of $KHSO_4$ till pH<5 and extracted with DCM to acquire 1.18 g (96% yield) of desired product as a free acid; $^1$H NMR (300 MHz, DMSO-$d_6$) δ 3.90-3.52 (m, 1H) 2.65 (s, 3H), 2.13 (tt, J=11.7, 3.6 Hz, 1H), 2.02-1.91 (m, 2H), 1.66-1.45 (m, 4H), 1.39 (d, J=1.2 Hz, 11H).

Step 3: tert-butyl N-methyl-N-[(1r,4r)-4-{N'-[6-chloro-4-(methylamino)pyridine-3-carbonyl]hydrazinecarbonyl}cyclohexyl]carbamate. To a solution of 6-chloro-4-(methylamino)pyridine-3-carbohydrazide (0.84 g, 0.7975 mmol, 1.0 eq) and (1r,4r)-4-{[(tert-butoxy)carbonyl]amino}cyclohexane-1-carboxylic acid (1.19 g, 4.61 mmol, 1.1 eq) in DMF (10 mL) were added DIPEA (2.2 ml, 12.56 mmol, 3.0 eq) and HATU (1.91 g, 5.024 mmol, 1.2 eq). The mixture was stirred at 25° C. for 1 hour. The UPLC showed mass of desired product. The reaction mixture was quenched with water and extracted with ethyl acetate. The combined organic layers were washed with water, brine, dried over $Na_2SO_4$ and concentrated to get a crude product. The crude product was purified by chromatography eluted by DCM:MeOH (0-10%) to acquire 1.18 g (64% yield) of desired product: ESI(+)$[M+H]^+$=440.6; $^1$H NMR (300 MHz, DMSO-$d_6$) δ 10.30 (s, 1H), 9.78 (s, 1H), 8.33 (s, 1H), 8.11 (s, 1H), 6.66 (s, 1H), 2.82 (d, 3H), 2.65 (s, 3H), 2.13 (tt, J=11.7, 3.6 Hz, 1H), 2.02-1.91 (m, 2H), 1.66-1.45 (m, 4H), 1.39 (d, J=1.2 Hz, 12H).

Step 4: tert-butyl N-methyl-N-[(1r,4r)-4-{5-[6-chloro-4-(methylamino)pyridin-3-yl]-1,3,4-thiadiazol-2-yl}cyclohexyl]carbamate. To a suspension of tert-butyl N-methyl-N-[(1r,4r)-4-{N'-[6-chloro-4-(methylamino)pyridine-3-carbonyl]hydrazinecarbonyl}cyclohexyl]carbamate (1.18 g, 2.68 mmol, 1.0 eq.) in dry toluene (50 mL, 0.05 M) was added Lawesson's reagent (1.20 g, 2.95 mmol, 1.1 eq.). The reaction mixture was then stirred under reflux for 1.5 h. After that the reaction mixture was quenched with water, washed with sat. solution of $NaHCO_3$, extracted with DCM and concentrated under reduced pressure. The crude was purified by flash column chromatography (DCM/MeOH) to give 0.7 g (60% yield) of the desired product as a white solid: ESI(+)$[M+H]^+$=438.6; $^1$H NMR (300 MHz, DMSO-$d_6$) δ 8.66 (d, J=5.0 Hz, 1H), 8.40 (s, 1H), 6.83 (s, 1H), 3.25-3.09 (m, 1H), 2.98 (d, J=4.9 Hz, 3H), 2.71 (s, 3H), 2.21 (d, J=10.3 Hz, 2H), 1.69 (d, J=7.4 Hz, 6H), 1.41 (s, 9H).

Step 5: tert-butyl N-methyl-N-[(1r,4r)-4-[5-(6-{3-cyanopyrrolo[1,2-b]pyridazin-7-yl}-4-(methylamino)pyridin-3-yl)-1,3,4-thiadiazol-2-yl]cyclohexyl]carbamate. To a solution of tert-butyl N-methyl-N-[(1r,4r)-4-{5-[6-chloro-4-(methylamino)pyridin-3-yl]-1,3,4-thiadiazol-2-yl}cyclohexyl]carbamate (0.7 g, 1.6 mmol, 1.0 eq), 7-(4,4,5,5-tetramethyl-1,3,2-dioxaborolan-2-yl)pyrrolo[1,2-b]pyridazine-3-carbonitrile (0.6 g, 2.23 mmol, 1.4 eq) and $Pd(dppf)Cl_2 \cdot CH_2Cl_2$ (0.328 g, 0.4 mmol, 0.25 eq) in dioxane (30 ml), was added 2M $K_2CO_3$ (1.6 ml, 3.2 mmol, 2.0 eq). The solution was degassed with argon for 2-3 min and then heated to 120° C. and stirred overnight. UPLC showed full conversion of the starting material. The resulting solution was diluted with MeOH, filtrated through Celite and concentrated to dryness.

The crude was purified by chromatography eluted by DCM:MeOH (0-10%) to acquire 0.7 g (80% yield) of desired product: ESI(+)$[M+H]^+$=546.1; $^1$H NMR (300 MHz, DMSO-$d_6$) δ 8.85 (d, J=2.2 Hz, 1H), 8.74 (d, J=2.2 Hz, 1H), 8.71-8.58 (m, 2H), 8.19 (s, 1H), 7.88 (d, J=4.8 Hz, 1H), 7.13 (d, J=4.8 Hz, 1H), 3.24-3.15 (m, 1H), 3.09 (d, J=4.9 Hz, 3H), 2.71 (s, 3H), 2.30-2.12 (m, 2H), 1.76-1.53 (m, 6H), 1.42 (s, 9H).

Step 6: 7-[4-(methylamino)-5-{5-[(1r,4r)-4-(methylamino)cyclohexyl]-1,3,4-thiadiazol-2-yl}pyridin-2-yl]pyrrolo[1,2-b]pyridazine-3-carbonitrile. Tert-butyl N-methyl-N-[(1r,4r)-4-[5-(6-{3-cyanopyrrolo[1,2-b]pyridazin-7-yl}-4-(methylamino)pyridin-3-yl)-1,3,4-thiadiazol-2-yl]cyclohexyl]carbamate (0.67 g, 1.23 mmol, 1.0 eq.) was dissolved in Hexafluro-2-propanol (4.0 ml, 30.0 eq) in sealed vial and irradiated by microwave for 2 h at 150° C. The UPLC showed full deprotection of the starting material. The solvent was evaporated to dryness to acquire desired product 0.54 g (99% yield) as yellow solid: LCMS: ESI(+) $[M+H]^+$=444.97; $^1$H NMR (300 MHz, DMSO-$d_6$) δ 8.84 (d, J=2.3 Hz, 1H), 8.73 (d, J=2.2 Hz, 1H), 8.68-8.47 (m, 2H), 8.18 (s, 1H), 7.88 (d, J=4.8 Hz, 1H), 7.13 (d, J=4.8 Hz, 1H), 3.20-3.10 (m, 1H), 3.09 (d, J=4.8 Hz, 3H), 2.36-2.26 (m, 4H), 2.20-2.08 (m, 2H), 2.07-1.96 (m, 2H), 1.70-1.49 (m, 3H), 1.33-1.11 (m, 2H).

BB19: 7-[5-(5-{3,8-diazabicyclo[3.2.1]octan-3-yl}-1,3,4-thiadiazol-2-yl)-4-(methylamino)pyridin-2-yl]pyrrolo[1,2-b]pyridazine-3-carbonitrile

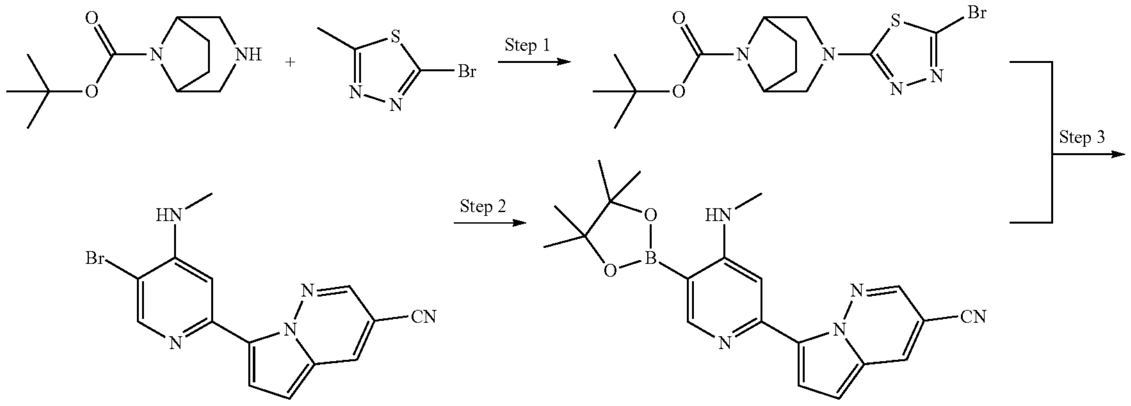

-continued

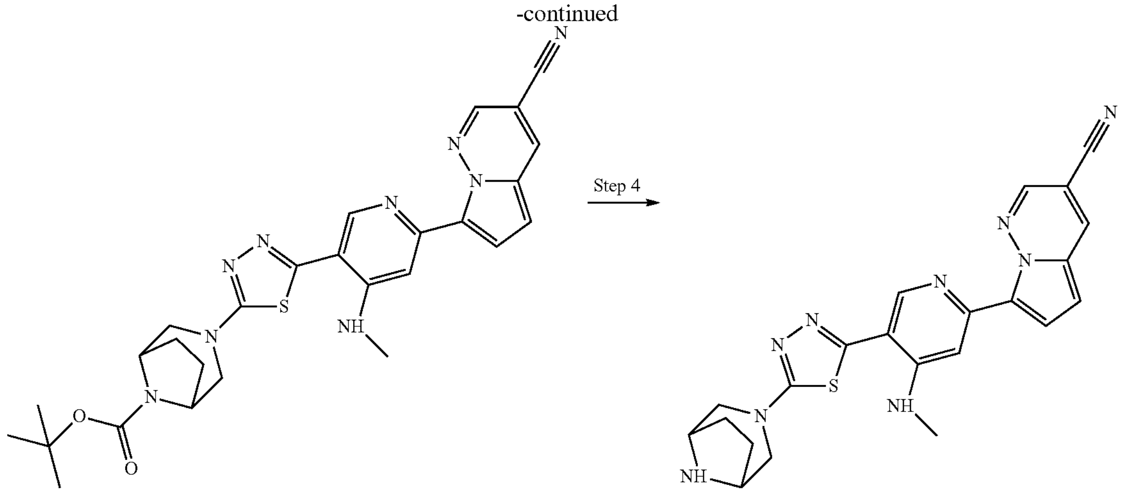

V BB19

Step 1: tert-butyl 3-(5-bromo-1,3,4-thiadiazol-2-yl)-3,8-diazabicyclo[3.2.1]octane-8-carboxylate. A stirred suspension of 2,5-dibromo-1,3,4-thiadiazole (1.05 g, 4.305 mmol, 1.0 eq), 8-Boc-3,8-diaza-bicyclo[3.2.1]octane (1.005 g, 4.734 mmol, 1.1 eq) and N,N-Diisopropylethylamine (1.125 ml, 6.459 mmol, 1.5 eq) in dioxane (21.53 ml, 0.2 M) was heated at 120° C. for 1 hour. The reaction mixture was diluted with water, extracted with DCM, and the organic phase was concentrated onto silica gel. The crude material was purified by flash chromatography using an EtOAc/hexane gradient to afford the title compound as a yellow oil (0.819 g, 2.182 mmol, 71%): ESI(+)$[M+H]^+$=337.3; $^1H$ NMR (300 MHz, Chloroform-d) δ 4.37 (s, 2H), 3.72-3.26 (m, 4H), 2.03 (m, 2H), 1.82 (m, 2H), 1.50 (d, J=0.8 Hz, 9H).

Step 2: 7-[4-(methylamino)-5-(4,4,5,5-tetramethyl-1,3,2-dioxaborolan-2-yl)pyridin-2-yl]pyrrolo[1,2-b]pyridazine-3-carbonitrile. 7-[5-bromo-4-(methylamino)pyridin-2-yl]pyrrolo[1,2-b]pyridazine-3-carbonitrile (1.5 g, 4.57 mmol, 1.0 eq) was dissolved in dioxane (25 ml, 0.18 M) in sealed reactor followed by addition of bis(pinacolato)diboron (1.39 g, 5.49 mmol, 1.2 eq) and KOAc (1.39 g, 14.17 mmol, 3.1 eq). Solution was bubbled for few minutes with argon and $Pd(dppf)Cl_2$*DCM (0.373 g, 0.46 mmol, 0.1 eq) was added followed by repeated bubbling. The reaction mixture was then moved to pre heated oil bath and stirred at 90° C. overnight. The reaction mixture was filtrated through Celite and evaporated to dryness. Crude was used in next step without further purification.

Step 3: tert-butyl 3-[5-(6-{3-cyanopyrrolo[1,2-b]pyridazin-7-yl}-4-(methylamino)pyridin-3-yl)-1,3,4-thiadiazol-2-yl]-3,8-diazabicyclo[3.2.1]octane-8-carboxylate. To a solution of 7-[4-(methylamino)-5-(4,4,5,5-tetramethyl-1,3,2-dioxaborolan-2-yl)pyridin-2-yl]pyrrolo[1,2-b]pyridazine-3-carbonitrile (0.58 g, 1.55 mmol, 1.0 eq), tert-butyl 3-(5-bromo-1,3,4-thiadiazol-2-yl)-3,8-diazabicyclo[3.2.1]octane-8-carboxylate (0.638 g, 1.70 mmol, 1.1 eq) in dioxane (40 ml, 0.04M) were added $Cs_2CO_3$ (1.26 g, 3.86 mmol, 2.5 eq) and $Pd(OAc)_2$ (0.069 g, 0.309 mmol, 0.2 eq). The reaction was bubbled with argon for few mins followed by addition of Xantphos (0.358 g, 0.618 mmol, 0.4 eq). The solution was degassed with argon for 2-3 min and then heated to 120° C. and stirred overnight. The reaction mixture was filtrated through Celite and evaporated to dryness. The crude was purified thrice by chromatography eluted by DCM:MeOH (0-10%). Main fraction repurified by pTLC DCM:MeOH (0-10%) and triturated with $Et_2O$ to acquire 0.190 g (23% yield) of desired product: ESI(+)$[M+H]^+$=544.77; $^1H$ NMR (300 MHz, DMSO-$d_6$) δ: 8.83 (1H, d, J 2.2), 8.72 (1H, d, J 2.3), 8.51-8.43 (2H, m), 8.14 (1H, s), 7.85 (1H, d, J 4.8), 7.12 (1H, d, J 4.8), 4.28 (2H, s), 3.67 (2H, d, J 11.8), 3.37 (2H, d), 3.06 (3H, d, J 4.9), 1.91 (2H, d, J 6.3), 1.75 (2H, d, J 7.4), 1.44 (9H, s).

Step 4: 7-[5-(5-{3,8-diazabicyclo[3.2.1]octan-3-yl}-1,3,4-thiadiazol-2-yl)-4-(methylamino)pyridin-2-yl]pyrrolo[1,2-b]pyridazine-3-carbonitrile. To tert-butyl 3-[5-(6-{3-cyanopyrrolo[1,2-b]pyridazin-7-yl}-4-(methylamino)pyridin-3-yl)-1,3,4-thiadiazol-2-yl]-3,8-diazabicyclo[3.2.1]octane-8-carboxylate (0.120 g, 0.22 mmol, 1.0 eq.) was added in hexafluoro-2-propanol (0.7 ml) in pressure vessel and irradiated in microwave for 2.5 h at 150° C. The solvent was evaporated to dryness and triturated with $Et_2O$ to acquired 0.080 g (82% yield) of desired product: ESI(+)$[M+H]^+$=444.05; $^1H$ NMR (300 MHz, DMSO-$d_6$) δ: 8.83 (1H, d, J 2.3), 8.72 (1H, d, J 2.2), 8.52-8.44 (2H, m), 8.13 (1H, s), 7.85 (1H, d, J 4.8), 7.12 (1H, d, J 4.8), 3.61-3.46 (4H, m), 3.29 (3H, s), 3.06 (3H, m), 1.70 (4H, dd, J 9.8, 6.7).

BB20: 7-(4-(methylamino)-5-(5-(8-(piperidin-4-yl)-3,8-diazabicyclo[3.2.1]octan-3-yl)-1,3,4-thiadiazol-2-yl)pyridin-2-yl)pyrrolo[1,2-b]pyridazine-3-carbonitrile

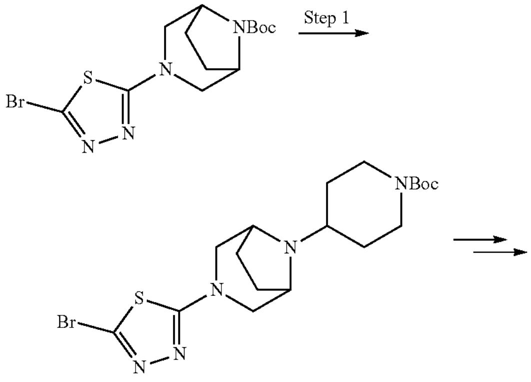

-continued

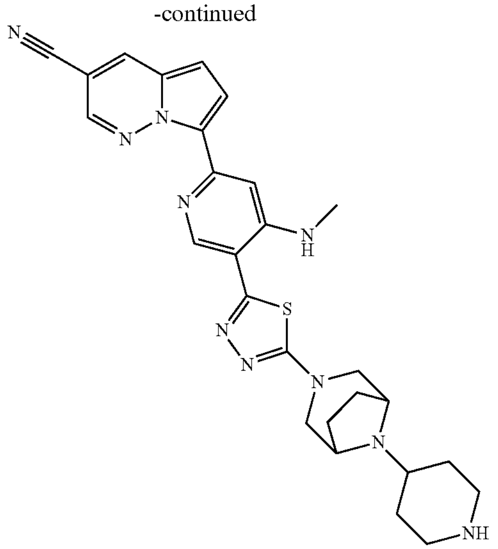

BB20

Step 1: tert-butyl 4-(3-(5-bromo-1,3,4-thiadiazol-2-yl)-3,8-diazabicyclo[3.2.1]octan-8-yl)piperidine-1-carboxylate. tert-butyl 3-(5-bromo-1,3,4-thiadiazol-2-yl)-3,8-diazabicyclo[3.2.1]octane-8-carboxylate (600 mg, 1.6 mmol) (see, Step 1 of BB19) was subjected to 1:4 TFA/DC (0.1M) for 2 h, then it was concentrated.

The crude material was dissolved in DCE and TEA, followed by addition of tert-butyl 4-oxopiperidine-1-carboxylate (1 eq). After 10 minutes, STAB (2.2 eq) was added and the reaction was stirred overnight. The reaction mixture was partitioned between DCM and water. The organic layer was separated and dried over mag sulfate, then concentrated. Chromatography (0-10% methanol in DCM) provided desired product (500 mg, 68%). Completion of this synthetic route was done as previously described as Step 2 and 3 of BB6. LCMS: $C_{27}H_{30}N_{10}S$ requires: 526.2. found: m/z=527.6 $[M+H]^+$.

BB21:7-[5-(5-{2,7-diazaspiro[3.5]nonan-2-yl}-1,3,4-thiadiazol-2-yl)-4-(methylamino)pyridin-2-yl]pyrrolo[1,2-b]pyridazine-3-carbonitrile

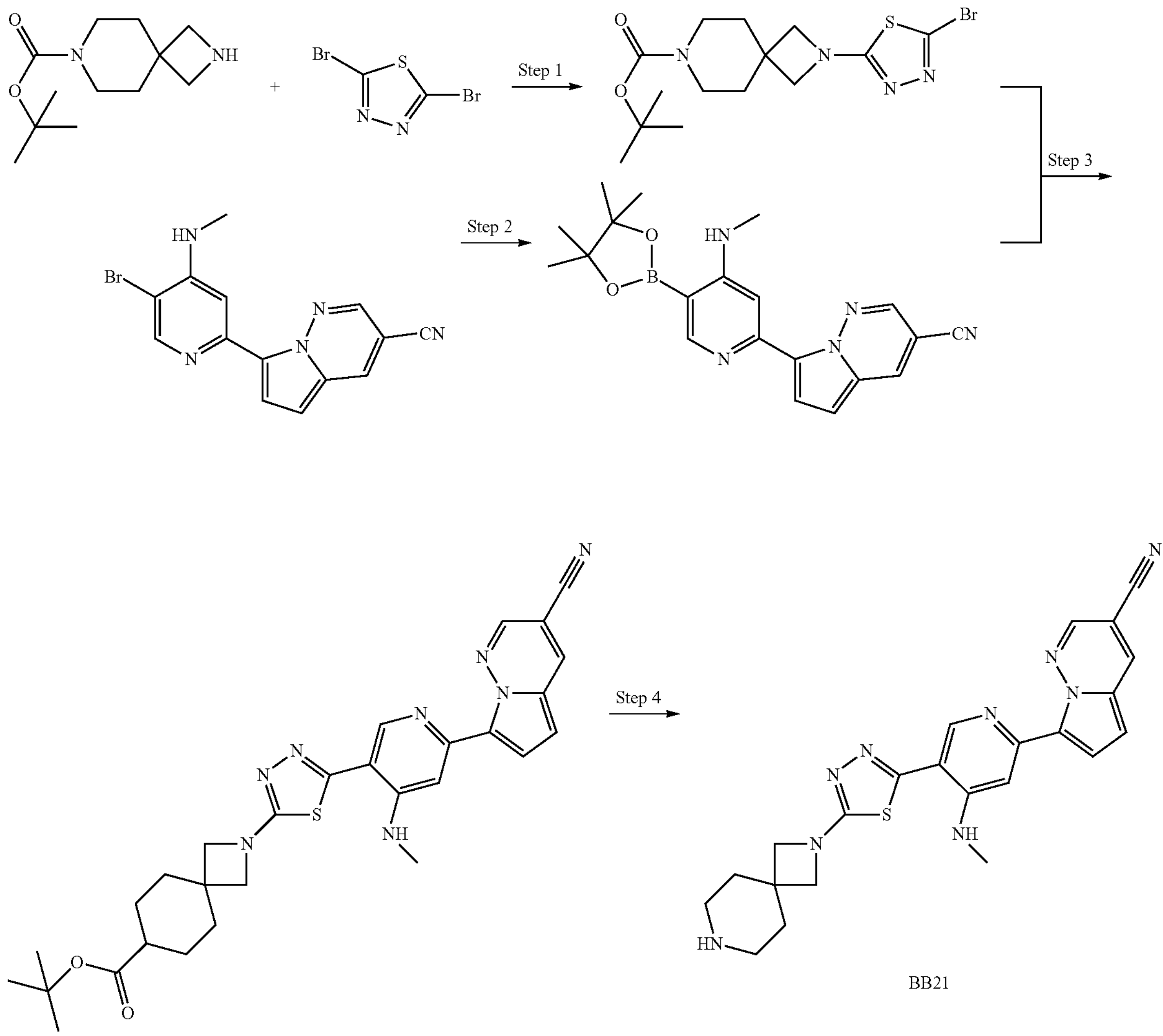

BB21

Step 1: tert-butyl 2-(5-bromo-1,3,4-thiadiazol-2-yl)-2,7-diazaspiro[3.5]nonane-7-carboxylate. A stirred suspension of 2,5-dibromo-1,3,4-thiadiazole (970 mg, 3.98 mmol, 1.0 eq.), tert-butyl 2,7-diazaspiro[3.5]nonane-7-carboxylate (990 mg, 4.37 mmol, 1.1 eq) and DIPEA (1.038 ml, 4.61 mmol, 1.5 eq) in dioxane (15 mL, 0.21 M) was heated at 120° C. for 1 hour. The reaction mixture was diluted with water (10 mL) and extracted with DCM (20 mL). The crude material was purified by flash chromatography eluted by Hexane: EtOAc to acquire 1.54 g of yellow oil (96% yield): ESI(+) $[M+H]^+$=391.31 $^1H$ NMR (300 MHz, DMSO-$d_6$) δ 3.83 (s, 4H), 3.31-3.21 (m, 4H), 1.75-1.62 (m, 4H), 1.39 (s, 9H).

Step 2: 7-[4-(methylamino)-5-(4,4,5,5-tetramethyl-1,3,2-dioxaborolan-2-yl)pyridin-2-yl]pyrrolo[1,2-b]pyridazine-3-carbonitrile. 7-[5-bromo-4-(methylamino)pyridin-2-yl]pyrrolo[1,2-b]pyridazine-3-carbonitrile (1.5 g, 4.57 mmol 1.0 eq) was dissolved in Dioxane (25 ml) in pressure vessel followed by addition of Bis(pinacolato)diboron (1.39 g, 5.49 mmol, 1.2 eq) and KOAc (0.89 g, 9.14 mmol, 2.0 eq). Solution was bubbled for 7 mins with argon and Pd(dppf)$Cl_2$*DCM (0.375 g, 0.457 mmol, 0.1 eq) was added followed by repeated bubbling. The reaction mixture was then moved to pre heated oil bath and stirred at 90° C. overnight. The UPLC showed formation of product. The reaction mixture was filtrated through Celite cake and evaporated to dryness. The crude was used in next step without further purification. ESI(+)$[M+H]^+$=294.2

Step 3: tert-butyl 2-[5-(6-{3-cyanopyrrolo[1,2-b]pyridazin-7-yl}-4-(methylamino)pyridin-3-yl)-1,3,4-thiadiazol-2-yl]-2,7-diazaspiro[3.5]nonane-7-carboxylate. To a solution of tert-butyl 2-(5-bromo-1,3,4-thiadiazol-2-yl)-2,7-diazaspiro[3.5]nonane-7-carboxylate (1.377 g, 2.57 mmol, 1.0 eq) and 7-[4-(methylamino)-5-(4,4,5,5-tetramethyl-1,3,2-dioxaborolan-2-yl)pyridin-2-yl]pyrrolo[1,2-b]pyridazine-3-carbonitrile (1.0 g, 2. mmol, 1.0 eq) in dioxane (13 ml, 0.2 M) in pressure vessel were added cesium carbonate (2.09 g, 6.42 mmol, 2.5 eq) and palladium acetate (0.115 g, 0.51 mmol, 0.2 eq). The reaction was bubbled with argon for 7 mins followed by addition of Xantphos (0.59 g, 1.03 mmol, 0.4 eq). The solution was degassed with argon for 2-3 min and then heated to 120° C. and stirred overnight. UPLC showed formation of product. The reaction mixture was filtrated through Celite cake and evaporated to dryness. The crude was purified by chromatography eluted by DCM: MeOH (0-10%) to acquire 0.415 g (29% yield) of desired product. ESI(+)$[M+H]^+$=558.8; $^1H$ NMR (300 MHz, DMSO-$d_6$) δ 8.83 (d, J=2.2 Hz, 1H), 8.73 (d, J=2.2 Hz, 1H), 8.48 (s, 2H), 8.14 (s, 1H), 7.85 (d, J=4.8 Hz, 1H), 7.12 (d, J=4.8 Hz, 1H), 3.91 (s, 4H), 3.06 (d, J=4.8 Hz, 3H), 1.75 (t, J=5.6 Hz, 4H), 1.40 (s, 9H).

Step 4: 7-[5-(5-{2,7-diazaspiro[3.5]nonan-2-yl}-1,3,4-thiadiazol-2-yl)-4-(methylamino)pyridin-2-yl]pyrrolo[1,2-b]pyridazine-3-carbonitrile. Tert-butyl 2-[5-(6-{3-cyanopyrrolo[1,2-b]pyridazin-7-yl}-4-(methylamino)pyridin-3-yl)-1,3,4-thiadiazol-2-yl]-2,7-diazaspiro[3.5]nonane-7-carboxylate (0.2 g, 0.359 mmol, 1.0 eq.) was dissolved in hexafluoro-2-propanol (1.13 mL, 30.0 eq) in sealed reactor and heated in microwave for 2 h at 150° C. The UPLC showed full deprotection of the starting material. The solvent was evaporated to dryness and solid was triturated with $Et_2O$ to get desired product 146 mg (87% yield) as a yellow solid. LCMS: ESI(+)$[M+H]^+$=458.08; $^1H$ NMR (300 MHz, DMSO-$d_6$) δ 8.83 (d, J=2.2 Hz, 1H), 8.72 (d, J=2.2 Hz, 1H), 8.47 (s, 2H), 8.13 (s, 1H), 7.85 (d, J=4.8 Hz, 1H), 7.12 (d, J=4.8 Hz, 1H), 3.86 (s, 4H), 3.06 (d, J=4.8 Hz, 3H), 2.63 (t, J=5.4 Hz, 4H), 1.87-1.60 (m, 4H).

BB22: 7-(5-(5-([4,4'-bipiperidin]-1-yl)-1,3,4-thiadiazol-2-yl)-4-(methylamino)pyridin-2-yl)pyrrolo[1,2-b]pyridazine-3-carbonitrile

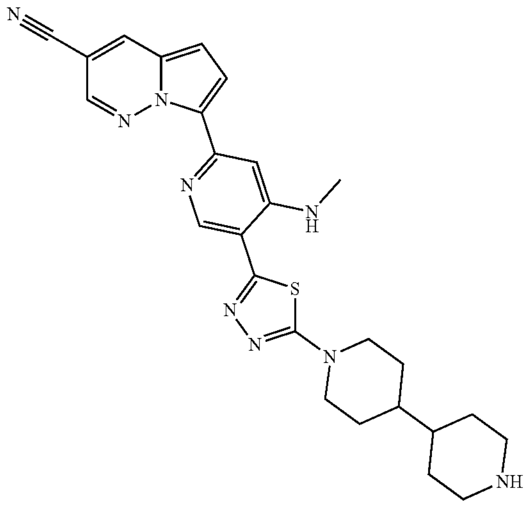 [SMILES: CNc1cc(-c2ccc3cc(C#N)cnn23)ncc1-c1nnc(N2CCC(C3CCNCC3)CC2)s1]

BB22 was synthesized following the same route as BB10 except with tert-butyl [4,4'-bipiperidine]-1-carboxylate as the amine in step 1. LCMS: $C_{26}H_{29}N_9S$ requires: 499.2. found: m/z=500.4 $[M+H]^+$.

BB23: 7-(4-(methylamino)-5-(5-(4-(piperazin-1-yl)piperidin-1-yl)-1,3,4-thiadiazol-2-yl)pyridin-2-yl)pyrrolo[1,2-b]pyridazine-3-carbonitrile

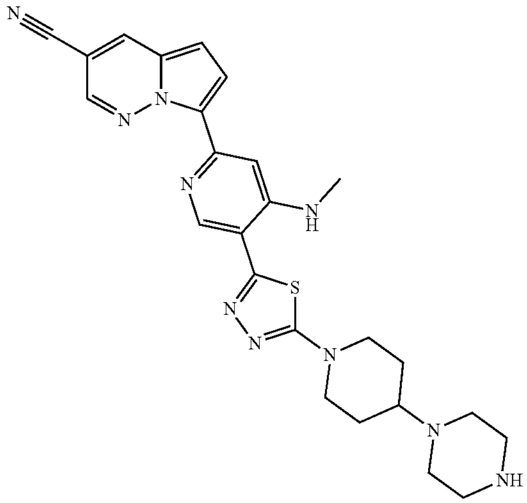 [SMILES: CNc1cc(-c2ccc3cc(C#N)cnn23)ncc1-c1nnc(N2CCC(N3CCNCC3)CC2)s1]

BB23 was synthesized following the same route as BB10 except with tert-butyl 4-(piperidin-4-yl)piperazine-1-carboxylate as the amine in step 1. LCMS: $C_{25}H_{28}N_{10}S$ requires: 500.2. found: m/z=501.4 $[M+H]^+$.

BB24: 7-[4-(methylamino)-5-{5-[(1r,3r)-3-aminocyclobutyl]-1,3,4-thiadiazol-2-yl}pyridin-2-yl]pyrrolo[1,2-b]pyridazine-3-carbonitrile

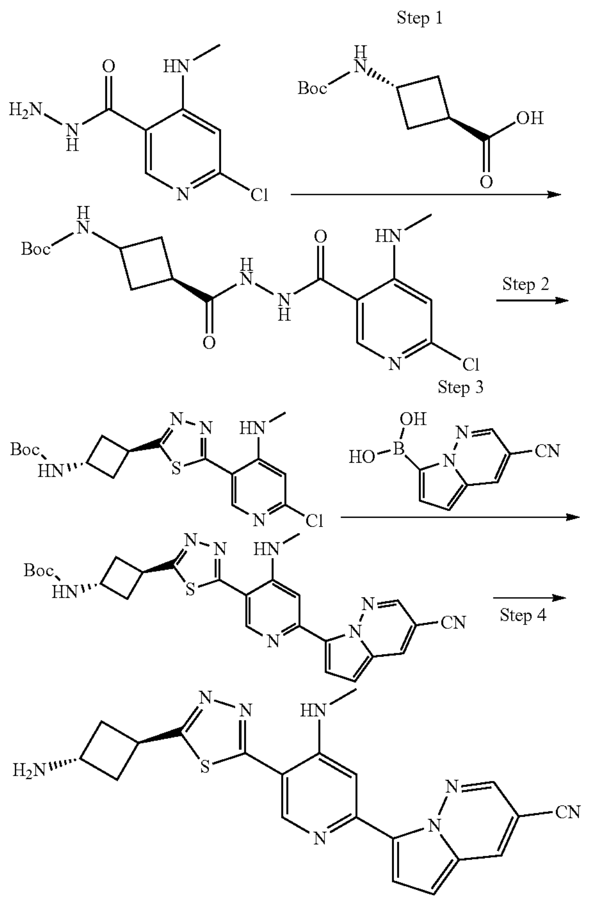

BB24

Step 1: tert-butyl N-[3-({[6-chloro-4-(methylamino)pyridin-3-yl]formohydrazido}carbonyl)cyclobutyl]carbamate. To a solution of 6-chloro-4-(methylamino)pyridine-3-carbohydrazide (3.0 g, 19.93 mmol, 1.0 eq) and trans-3-((tert-Butoxycarbonyl)amino)cyclobutanecarboxylic acid (3.54 g, 16.48 mmol, 1.1 eq) in DMF (38 mL) were added DIPEA (7.81 ml, 44.86 mmol, 3.0 eq) and HATU (6.82 g, 17.94 mmol, 1.2 eq), and the mixture was stirred at 25° C. for 1 hour. TLC (Dichloromethane:Methanol=10:1) showed consumption of the starting material and a new spot was formed. The reaction mixture was quenched with water and extracted with ethyl acetate. The combined organic layers were washed with water, brine, dried over $Na_2SO_4$ and concentrated to get a crude product. The crude product was purified by chromatography eluted by DCM; MeOH (0-10%) to acquire 4.73 g (80% yield) of desired product. ESI(+)[M+H]$^+$=400.5; $^1$H NMR (300 MHz, DMSO-$d_6$) δ 10.32 (s, 1H), 9.78 (s, 1H), 8.34 (s, 1H), 8.10 (d, J=5.1 Hz, 1H), 7.20 (d, J=8.0 Hz, 1H), 6.67 (s, 1H), 4.13 (q, J=7.9 Hz, 1H), 2.96-2.88 (m, 1H), 2.83 (d, J=4.9 Hz, 3H), 2.40-2.28 (m, 2H), 2.20-2.08 (m, 2H), 1.37 (s, 9H).

Step 2: tert-butyl N-[(1r,3r)-3-{5-[6-chloro-4-(methylamino)pyridin-3-yl]-1,3,4-thiadiazol-2-yl}cyclobutyl]carbamate. To a solution of tert-butyl N-[3-({[6-chloro-4-(methylamino)pyridin-3-yl]formohydrazido}carbonyl)cyclobutyl]carbamate (4.73 g, 1 mmol, 1.0 eq) in Toluene (94.0 mL, 0.13 M) was added Lawesson's Reagent (5.28 g, 13.08 mmol, 1.1 eq), the mixture was stirred at 90° C. for 2 h. The reaction mixture was washed with $NaHCO_3$, extracted with DCM, concentrated and purified by chromatography eluted by DCM:MeOH (0-10%) to acquire 3.9 g (50% yield) of desired product with 60% purity. ESI(+)[M+H]$^+$=298.5; $^1$H NMR (300 MHz, DMSO-$d_6$) δ 8.68-8.60 (m, 1H), 8.39 (s, 1H), 7.39 (d, J=8.0 Hz, 1H), 6.83 (s, 1H), 4.36-4.16 (m, 1H), 2.99 (d, 3H), 2.59-2.51 (m, 4H), 1.38 (s, 9H).

Step 3: tert-butyl N-[(1r,3r)-3-[5-(6-{3-cyanopyrrolo[1,2-b]pyridazin-7-yl}-4-(methylamino)pyridin-3-yl)-1,3,4-thiadiazol-2-yl]cyclobutyl]carbamate, To a solution of tert-butyl N-[(1r,3r)-3-{5-[6-chloro-4-(methylamino)pyridin-3-yl]-1,3,4-thiadiazol-2-yl}cyclobutyl]carbamate (1.0 g, 1.51 mmol, 1.0 eq), {3-cyanopyrrolo[1,2-b]pyridazin-7-yl}boronic acid (0.496 g, 2.12 mmol, 1.4 eq) and Pd(dppf)$Cl_2 \cdot CH_2Cl_2$ (0.310 g, 0.379 mmol, 0.25 eq) in pressure vessel in anhydrous dioxane (19 ml, 0.08 M), was added 2M $K_2CO_3$ (1.51 ml, 3.03 mmol, 2.0 eq). The solution was degassed with argon for 2-3 min and then put in oil bath heated to 120° C. and stirred overnight. LCMS showed full conversion of the starting material. The resulting solution was diluted with MeOH, washed through Celite cake and concentrated to dryness. The crude was purified by chromatography eluted by DCM:MeOH (0-10%) and then by pPTLC DCM:MeOH 4% to acquire 190 mg (25% yield) of desired product. ESI(+)[M+H]$^+$=503.8; $^1$H NMR (300 MHz, DMSO-$d_6$) δ 8.85 (d, J=2.2 Hz, 1H), 8.75 (d, J=2.3 Hz, 1H), 8.73-8.52 (m, 1H), 8.21 (s, 1H), 7.89 (d, J=4.8 Hz, 1H), 7.40 (d, J=8.0 Hz, 1H), 7.13 (d, J=4.8 Hz, 1H), 4.35-4.23 (m, 1H), 4.00-3.87 (m, 1H), 3.10 (d, J=4.9 Hz, 3H), 2.63-2.52 (m, 4H), 1.39 (s, 9H).

Step 4: 7-[4-(methylamino)-5-{5-[(1r,3r)-3-aminocyclobutyl]-1,3,4-thiadiazol-2-yl}pyridin-2-yl]pyrrolo[1,2-b]pyridazine-3-carbonitrile. Tert-butyl N-[(1r,3r)-3-[5-(6-{3-cyanopyrrolo[1,2-b]pyridazin-7-yl}-4-(methylamino)pyridin-3-yl)-1,3,4-thiadiazol-2-yl]cyclobutyl]carbamate (0.17 g, 0.338 mmol, 1.0 eq.) was dissolved in Hexafluoro-2-propanol (1.1 ml, 30.0 eq) in sealed reactor and put in microwave for 2 h at 150° C. The LCMS showed full deprotection of the starting material. The solvent was evaporated to dryness and solid was triturated with $Et_2O$ to get desired product 101 mg (70% yield). LCMS: ESI(+)[M+H]$^+$=403.03; 1H NMR (300 MHz, DMSO-$d_6$) δ 8.83 (d, J=2.3 Hz, 1H), 8.73 (d, J=2.2 Hz, 1H), 8.67-8.56 (m, 2H), 8.18 (s, 1H), 7.87 (d, J=4.8 Hz, 1H), 7.12 (d, J=4.8 Hz, 1H), 3.89 (dq, J=8.8, 4.3, 3.9 Hz, 1H), 3.64 (q, J=7.4 Hz, 1H), 3.09 (d, J=4.8 Hz, 3H), 2.59-2.52 (m, 2H), 2.34-2.18 (m, 2H).

BB25: 7-[4-(isopropylamino)-5-{5-[4-(piperidin-4-ylmethyl)piperazin-1-yl]-1,3,4-thiadiazol-2-yl}pyridin-2-yl]pyrrolo[1,2-b]pyridazine-3-carbonitrile

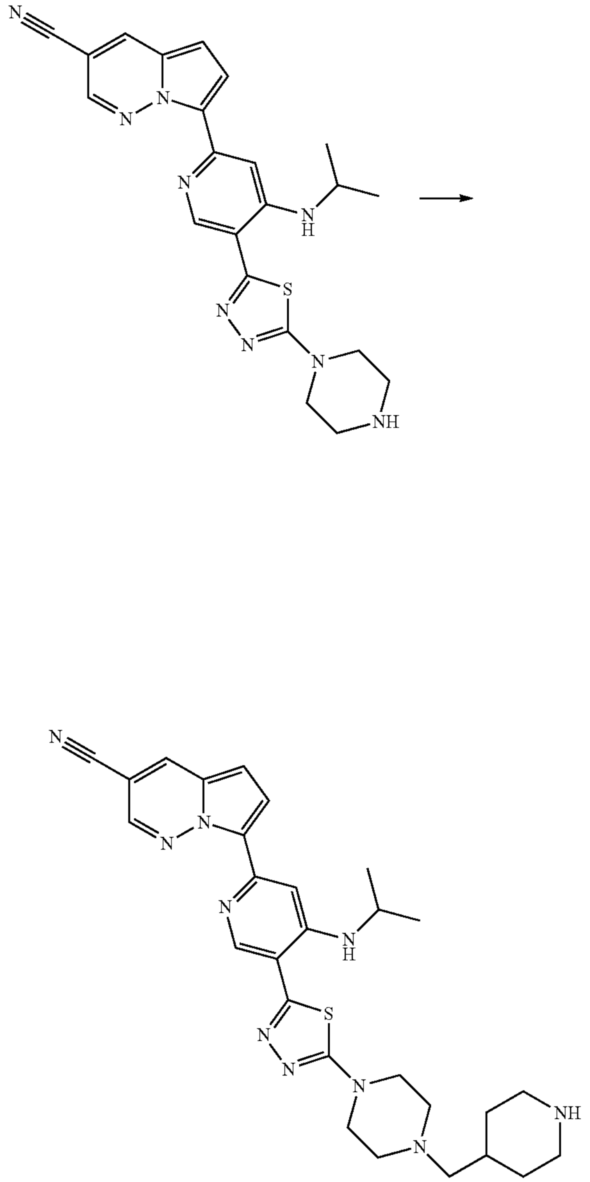

BB25

BB4 (105 mg, 0.23 mmol) and tert-butyl 4-formylpiperidine-1-carboxylate (50 mg, 0.23 mmol) were combined in DCE (0.1M), and then TEA (5 eq) was added. After 5 minutes, the STAB (124 mg, 2.5 eq) was added in one portion. After overnight stirring, the reaction mixture was partitioned between DCM and water. The organic layer was separated, dried over magnesium sulfate, and concentrated. The crude material was subjected to 4 M dioxane for 3 h, followed by concentration by rotary evaporator. Reverse phase ISCO (C18 column, 0-100% acetonitrile in water) provided a yellow solid (50 mg, 39%). LCMS: $C_{28}H_{34}N_{10}S$ requires: 542.3. found: m/z=543.5 [M+H]$^+$.

BB26: 7-(5-(5-((1r,4r)-4-(ethylamino)cyclohexyl)-1,3,4-thiadiazol-2-yl)-4-(methylamino)pyridin-2-yl)pyrrolo[1,2-b]pyridazine-3-carbonitrile

BB26

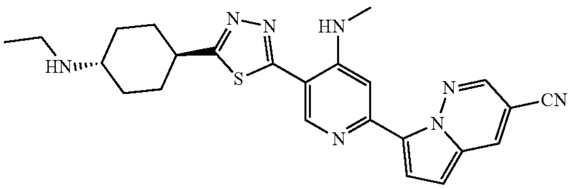

BB26 was synthesized in a similar manner as BB18 substituting ethyl iodide for methyl iodide in Step 1 to give the title compound. LCMS: $C_{24}H_{26}N_8S$ requires: 458.2. found: m/z=459.0 [M+H]$^+$ B. General Schemes for Preparing LHM Building Blocks CRBN-targeting LHM can be generally prepared according to Scheme B1:

SCHEME B1

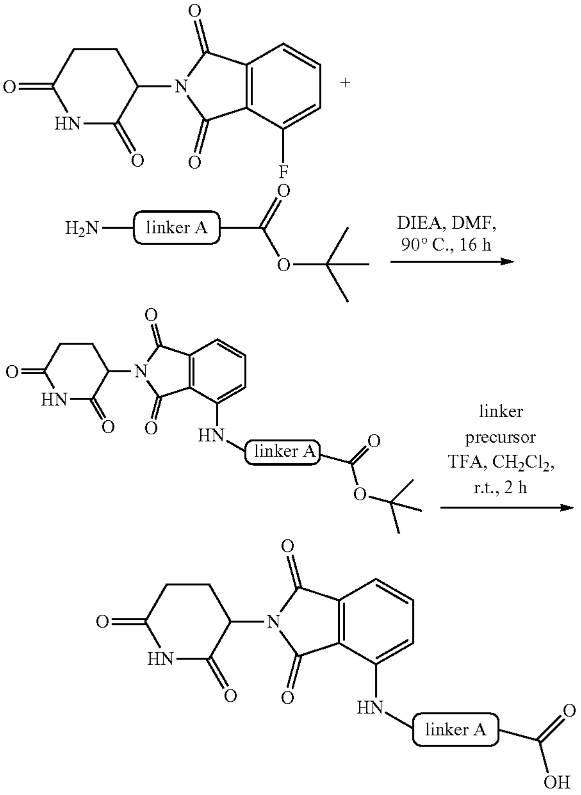

In Scheme B1, a functionalized thalidomide (e.g., at the 4- or 5-location of the phthalimide ring) is first coupled to a linker precursor. The linker precursor (an amino ester) comprises "linker A" (representing one or more linker segments, including $L_5$) and two terminal reactive groups, amine and a protected carboxylic acid in an ester form. Step 1 describes in more detail of the initial coupling step using an exemplary aminoester linker precursor.

Step 1: A mixture of 2-(2,6-dioxopiperidin-3-yl)-4-fluoro-2,3-dihydro-1H-isoindole-1,3-dione (0.26 mmol), aminoester (0.26 mmol), ethylbis(propan-2-yl)amine (0.52 mmol) and DMF (1 mL) was allowed to stir at 90° C. overnight. The mixture was cooled and purified by HPLC (5-95% MeCN in $H_2O$ with 0.1% TFA) to afford the tert-butylester intermediate.

The tert-butylester intermediate thereafter undergoes hydrolysis (see Step 2) to provide a CRBN-targeting LHM building block having "linker A" terminated in a carboxylic acid group, which may be further reactively coupled to another moiety.

Step 2: A mixture of tert-butyl 4-{[2-(2,6-dioxopiperidin-3-yl)-1,3-dioxo-2,3-dihydro-1H-isoindol-4-yl]amino}butanoate (0.10 mmol), $CH_2Cl_2$ (1 mL), and TFA (1 mL) was allowed to stir at r.t. for 2 h. The mixture was concentrated to afford the carboxylic acid product.

Described below are additional examples of CRBN-targeting LHM building blocks that may be prepared according to Scheme B1.

HCB1: 3-(2-((2-(2,6-dioxopiperidin-3-yl)-1,3-dioxoisoindolin-4-yl)amino)ethoxy)propanoic acid

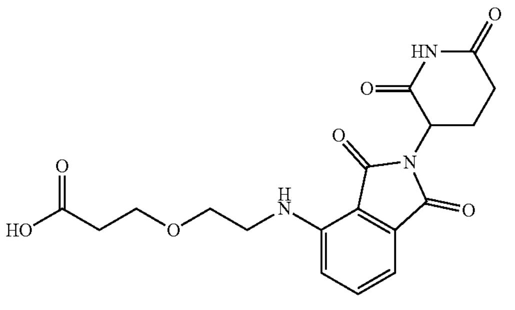 [SMILES: O=C(O)CCOCCNc1cccc2c1C(=O)N(C1CCC(=O)NC1=O)C2=O]

Step 1 product: tert-butyl 3-[2-[[2-(2,6-dioxo-3-piperidyl)-1,3-dioxo-isoindolin-4-yl]amino]ethoxy]propanoate (1.8 g, 51.9%). LCMS; $C_{22}H_{27}N_3O_7$ requires: 445. found: m/z=468 $[M+Na]^+$.

Step 2 product: 3-[2-[[2-(2,6-dioxo-3-piperidyl)-1,3-dioxo-isoindolin-4-yl]amino]ethoxy]propanoic acid (526 mg, 32%). LCMS; $C_{18}H_{19}N_3O_7$ requires: 389. found: m/z=390 $[M+H]^+$.

HCB2: 3-(2-(2-(2-((2-(2,6-dioxopiperidin-3-yl)-1,3-dioxoisoindolin-4-yl)amino)ethoxy)ethoxy)ethoxy)propanoic acid

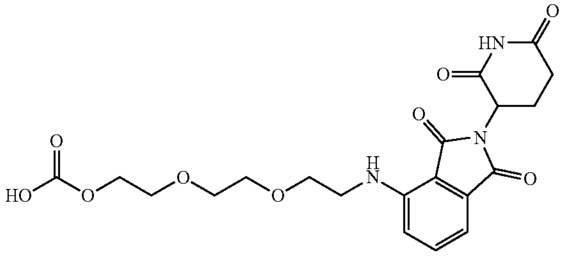 [SMILES: O=C1CCC(N2C(=O)c3cccc(NCCOCCOCCOC(=O)O)c3C2=O)C(=O)N1]

Step 1 product: tert-butyl 3-[2-[2-[2-[[2-(2,6-dioxo-3-piperidyl)-1,3-dioxoisoindolin-4-yl]amino]ethoxy]ethoxy]ethoxy]propanoate (1.6 g, 41%). LCMS; $C_{26}H_{35}N_3O_9$ requires: 533. found: m/z=534 $[M+H]^+$.

Step 2 product: 3-[2-[2-[2-[[2-(2,6-dioxo-3-piperidyl)-1,3-dioxo-isoindolin-4-yl]amino]ethoxy]ethoxy]ethoxy]propanoic acid (1.2 g, 73.62%). LCMS; $C_{22}H_{27}N_3O_9$ requires: 477. found: m/z=478 $[M+H]^+$.

HCB3: 6-((2-(2,6-dioxopiperidin-3-yl)-1,3-dioxoisoindolin-5-yl)amino)hexanoic acid

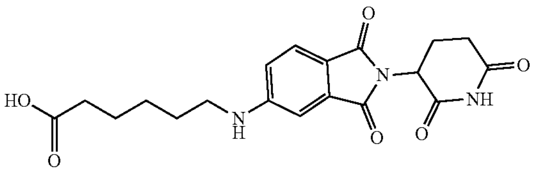 [SMILES: O=C(O)CCCCCNc1ccc2c(c1)C(=O)N(C1CCC(=O)NC1=O)C2=O]

Step 1: tert-butyl 6-{[2-(2,6-dioxopiperidin-3-yl)-1,3-dioxoisoindol-5-yl]amino}hexanoate To a mixture of 2-(2,6-dioxopiperidin-3-yl)-5-fluoroisoindole-1,3-dione (250 mg, 0.91 mmol), tert-butyl 6-aminohexanoate hydrochloride (203 mg, 0.91 mmol) in 3 ml of NMP, was added N,N-diisopropylethylamine (0.6 mL) at heating to 85° C. overnight. The crude reaction mixture was purified by silica gel chromatography using EtOAc/Hexane (0-100%), to give tert-butyl 6-{[2-(2,6-dioxopiperidin-3-yl)-1,3-dioxoisoindol-5-yl]amino}hexanoate (111 mg, 28%). LCMS: $C_{23}H_{29}N_3O_6$, requires: 443.5. found: m/z=444.4 $[M+H]^+$.

Step 2: 6-((2-(2,6-dioxopiperidin-3-yl)-1,3-dioxoisoindolin-5-yl)amino)hexanoic acid To a solution of tert-butyl 6-{[2-(2,6-dioxopiperidin-3-yl)-1,3-dioxoisoindol-5-yl]amino}hexanoate (111 mg, 0.25 mmol) in DCM was added TFA (0.5 mL). The reaction mixture was stirred at room temperature for 30 min, then the reaction mixture was concentrated to give 6-((2-(2,6-dioxopiperidin-3-yl)-1,3-dioxoisoindolin-5-yl)amino)hexanoic acid (78 mg, 78%). $^1$H NMR (500 MHz, DMSO-$d_6$) δ 12.00 (s, 1H), 11.06 (s, 1H), 7.57 (d, J=8.3 Hz, 1H), 7.11 (s, 1H), 6.95 (d, J=2.1 Hz, 1H), 6.85 (dd, J=8.4, 2.1 Hz, 1H), 5.04 (dd, J=12.7, 5.4 Hz, 1H), 3.16 (q, J=6.4 Hz, 2H), 2.23 (t, J=7.4 Hz, 2H), 2.03-1.97 (m, 1H), 1.56 (dq, J=14.8, 7.2 Hz, 4H), 1.39 (q, J=7.9 Hz, 2H). LCMS: $C_{19}H_{21}N_3O_6$, requires: 387.4. found: m/z=388.4 $[M+H]^+$.

HCB4: (1s,3s)-3-(2-((2-(2,6-dioxopiperidin-3-yl)-1,3-dioxoisoindolin-4-yl)amino)ethoxy)cyclobutane-1-carboxylic acid

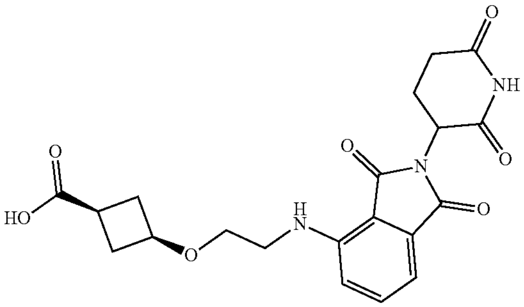 [SMILES: O=C1CCC(N2C(=O)c3cccc(NCCO[C@H]4C[C@@H](C(=O)O)C4)c3C2=O)C(=O)N1]

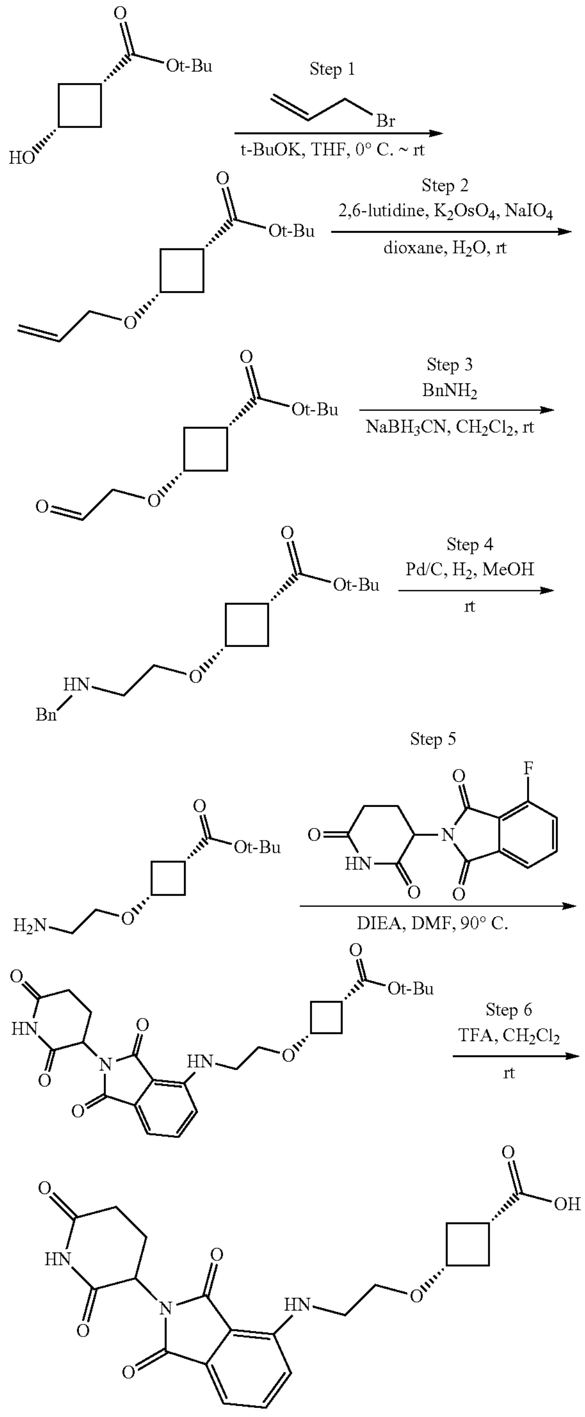

Step-1: Synthesis of cis-tert-butyl-3-(prop-2-en-1-yloxy)cyclobutane-1-carboxylate: To a solution of cis-tert-butyl-3-hydroxycyclobutane-1-carboxylate (10.0 g, 58.06 mmol) in tetrahydrofuran (100 mL) was added t-BuOK (64 mL, 1 M in THF) dropwise at 0° C. under nitrogen and stirred for 10 min. To the above solution was added 3-bromoprop-1-ene (7.02 g, 58.03 mmol) dropwise at 0° C. The resulting mixture was stirred at room temperature for 16 h. After the reaction was completed, the resulting solution was quenched by the addition of saturated $NH_4Cl$ aqueous solution. The aqueous phase was extracted with ethyl acetate. The combined organic layer was washed with brine, dried over anhydrous sodium sulfate, filtered and concentrated under vacuum. The residue was purified by flash column chromatography with 0~20% ethyl acetate in petroleum ether to afford cis-tert-butyl-3-(prop-2-en-1-yloxy)cyclobutane-1-carboxylate (11.3 g, 92%) as a colorless oil. $^1H$ NMR (300 MHz, Chloroform-d) δ 6.10-5.85 (m, 1H), 5.33-5.10 (m, 2H), 3.95-3.75 (m, 3H), 2.60-2.36 (m, 3H), 2.29-2.07 (m, 2H), 1.44 (s, 9H).

Step-2: Synthesis of cis-tert-butyl-3-(2-oxoethoxy)cyclobutane-1-carboxylate: To a solution of cis-tert-butyl-3-(prop-2-en-1-yloxy)cyclobutane-1-carboxylate (1.0 g, 4.71 mmol) in dioxane (30 mL) and $H_2O$ (15 mL) were added $K_2OsO_4 \cdot 2H_2O$ (86.28 mg, 0.24 mmol), 2,6-dimethylpyridine (1.01 g, 9.43 mmol) and $NaIO_4$ (2.02 g, 9.42 mmol). The resulting mixture was stirred at room temperature for 2 h. After the reaction was completed, the mixture was diluted with water and extracted with ethyl acetate. The combined organic layer was washed with brine, dried over anhydrous sodium sulfate, filtered and concentrated under vacuum. The residue was purified by flash column chromatography with 0~50% ethyl acetate in petroleum ether to afford cis-tert-butyl-3-(2-oxoethoxy)cyclobutane-1-carboxylate (505 mg, 50%) as a colorless oil. $^1H$ NMR (300 MHz, Chloroform-d) δ 9.72 (s, 1H), 6.97 (d, J=7.8 Hz, 1H), 5.31 (s, 1H), 4.05-3.94 (m, 2H), 2.64-2.41 (m, 2H), 2.36-2.12 (m, 2H), 1.47 (s, 9H).

Step-3: Synthesis of cis-tert-butyl-3-[2-(benzylamino)ethoxy]cyclobutane-1-carboxylate: To a solution of cis-tert-butyl-3-(2-oxoethoxy)cyclobutane-1-carboxylate (2.0 g, 9.33 mmol) in methanol (20 mL) were added 1-phenylmethanamine (3.0 g, 28.00 mmol) and $NaBH_3CN$ (1.76 g, 28.00 mmol). The resulting solution was stirred at room temperature for 16 h before concentrated under vacuum. The residue was purified by flash column chromatography with 0~100% ethyl acetate in petroleum ether to afford cis-tert-butyl-3-[2-(benzylamino)ethoxy]cyclobutane-1-carboxylate (1.1 g, 39%) as a colorless oil. MS (ESI) calculated for ($C_{18}H_{27}NO_3$) $[M+H]^+$, 306.2; found, 306.1.

Step-4: Synthesis of cis-tert-butyl-3-(2-aminoethoxy)cyclobutane-1-carboxylate: To a solution of cis-tert-butyl-3-[2-(benzylamino)ethoxy]cyclobutane-1-carboxylate (2.0 g, 6.55 mmol) in methanol (20 mL) was added Pd/C (10%, 0.5 g). The resulting solution was stirred at room temperature for 72 h under hydrogen (40 atm). After the reaction was completed, the solids were filtered out and the filtrate was concentrated under vacuum to afford cis-tert-butyl-3-(2-aminoethoxy)cyclobutane-1-carboxylate (1.0 g, crude) as a colorless oil, which was used in the next step without further purification. MS (ESI) calculated for ($C_{11}H_{21}NO_3$) $[M+H]^+$, 216.2; found, 216.1.

Step-5: Synthesis of cis-tert-butyl-3-(2-[[2-(2,6-dioxopiperidin-3-yl)-1,3-dioxo-2,3-dihydro-1H-isoindol-4-yl]amino]ethoxy)cyclobutane-1-carboxylate: To a solution of cis-tert-butyl-3-(2-aminoethoxy)cyclobutane-1-carboxylate (1.0 g, 4.64 mmol) in N,N-dimethylformamide (10 mL) were added DIEA (6.0 g, 46.43 mmol) and 2-(2,6-dioxopiperidin-3-yl)-4-fluoro-2,3-dihydro-1H-isoindole-1,3-dione (6.72 g, 24.33 mmol). The resulting solution was stirred at 90° C. for 4 h. After the reaction was completed, the resulting solution was diluted with water and extracted with ethyl acetate. The combined organic layer was washed with brine, dried over anhydrous sodium sulfate and concentrated under vacuum. The residue was purified by reverse phase flash column chromatography with 0-100% acetonitrile in water to afford cis-tert-butyl-3-(2-[[2-(2,6-dioxopiperidin-3-yl)-1,3-dioxo-2,3-dihydro-1H-isoindol-4-yl]amino]ethoxy)

cyclobutane-1-carboxylate (250 mg, 11%) as a red solid. MS (ESI) calculated for ($C_{24}H_{29}N_3O_7$) $[M+H]^+$, 472.2; found, 472.1.

Step 6: Synthesis of cis-3-(2-[[2-(2,6-dioxopiperidin-3-yl)-1,3-dioxo-2,3-dihydro-1H-isoindol-4-yl]amino]ethoxy) cyclobutane-1-carboxylic acid: To a solution of cis-tert-butyl-3-(2-[[2-(2,6-dioxopiperidin-3-yl)-1,3-dioxo-2,3-dihydro-1H-isoindol-4-yl]amino]ethoxy)cyclobutane-1-carboxylate (850 mg, 1.8 mmol) in dichloromethane (10 mL) was added trifluoroacetic acid (10 mL). The resulting solution was stirred at room temperature for 3 h before concentrated under vacuum. The residue was purified by reverse phase flash column chromatography with 0-100% acetonitrile in water to afford crude product, which was further purified by non-chiral prep-SFC with the following conditions [Column: Ultimate XB-$NH_2$, 21.2*250 mm; Sum; Mobile Phase A: CO2: 50, Mobile Phase B: MeOH—Preparative: 50; Flow rate: 40 mL/min; 220 nm] to afford cis-3-(2-[[2-(2,6-dioxopiperidin-3-yl)-1,3-dioxo-2,3-dihydro-1H-isoindol-4-yl]amino]ethoxy)cyclobutane-1-carboxylic acid (359.1 mg, 37) as a yellow solid. MS (ESI) calculated for ($C_{20}H_{21}N_3O_7$) $[M+H]^+$, 416.4; found, 416.2. $^1H$ NMR (400 MHz, DMSO-$d_6$) δ 12.16 (s, 1H), 11.11 (s, 1H), 7.63-7.55 (m, 1H), 7.15 (d, J=8.0 Hz, 1H), 7.05 (d, J=8.0 Hz, 1H), 6.59 (t, J=5.6 Hz, 1H), 5.12-5.03 (m, 1H), 3.96-3.84 (m, 1H), 3.59-3.40 (m, 4H), 2.98-2.82 (m, 1H), 2.64-2.52 (m, 3H), 2.48-2.37 (m, 2H), 2.08-1.91 (m, 3H).

Scheme B2 shows an alternative approach for preparing a CRBN-targeting LHM building block.

SCHEME B2

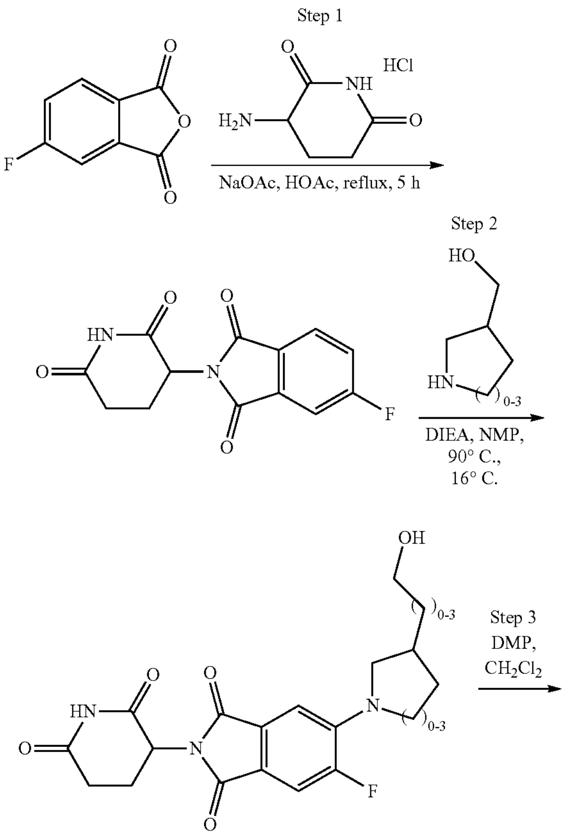

-continued

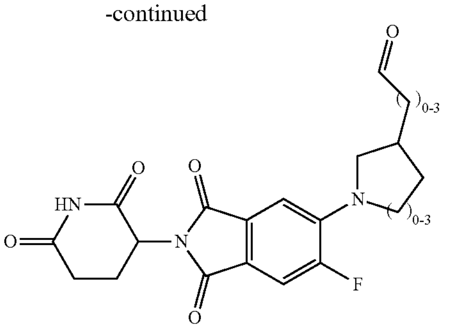

Step 1: 2-(2,6-dioxopiperidin-3-yl)-5-fluoroisoindoline-1,3-dione. A mixture of 5-fluoro-1,3-dihydro-2-benzofuran-1,3-dione (5.0 g, 30.10 mmol), 3-aminopiperidine-2,6-dione hydrochloride (6.9 g, 42.14 mmol) and NaOAc (4.2 g, 51.17 mmol) in HOAc (50 mL) was stirred at 120° C. for 5 h before concentrated under vacuum. The residue was washed with water and the solid was collected by filtration. The crude product was washed with water twice and ethyl acetate twice and dried under oven to afford 2-(2,6-dioxopiperidin-3-yl)-5-fluoroisoindoline-1,3-dione (7.7 g, 92%) as a light brown solid. $^1H$ NMR (300 MHz, DMSO-$d_6$) δ 11.16 (s, 1H), 8.03-8.00 (m, 1H), 7.87-7.85 (m, 1H), 7.75-7.70 (m, 1H), 5.19-5.15 (m, 1H), 2.94-2.86 (m, 1H), 2.63-2.48 (m, 2H), 2.12-2.06 (m, 1H). F NMR (300 MHz, DMSO-$d_6$) δ −102.078.

Step 2: Amine displacement of aryl fluoride. To a solution of 2-(2,6-dioxopiperidin-3-yl)-5-fluoro-2,3-dihydro-1H-isoindole-1,3-dione (1.0 g, 3.62 mmol) in N-Methyl pyrrolidone (10 mL) were added the amine (3.60 mmol) and DIEA (1.4 g, 10.83 mmol). The resulting solution was stirred at 80° C. for 16 h. The reaction mixture was cooled down to room temperature and purified by reverse phase flash chromatography to afford the corresponding final product.

Step 3: Alcohol oxidation to the aldehyde. To a mixture of the alcohol (1.06 mmol) in $CH_2Cl_2$ (10 mL) was added Dess-Martin periodinane (2.12 mmol). The mixture was allowed to stir at room temperature for 1 h. The mixture was purified by column chromatography to afford the desired aldehyde.

Described below are additional examples of CRBN-targeting LHM building blocks that may be prepared according to Scheme B2.

HCB5: (3S)-1-(2-(2,6-dioxopiperidin-3-yl)-1,3-dioxoisoindolin-5-yl)pyrrolidine-3-carbaldehyde

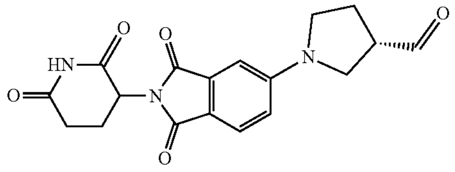 [SMILES: O=C[C@H]1CCN(c2ccc3c(c2)C(=O)N(C2CCC(=O)NC2=O)C3=O)C1]

Step 1: 2-(2,6-dioxopiperidin-3-yl)-5-fluoroisoindoline-1,3-dione. Same as Step 1 of Scheme B2.

Step 2: 2-(2,6-dioxopiperidin-3-yl)-5-((S)-3-(hydroxymethyl)pyrrolidin-1-yl)isoindoline-1,3-dione. 2-(2,6-dioxopiperidin-3-yl)-5-fluoroisoindoline-1,3-dione was reacted with (S)-pyrrolidin-3-ylmethanol to afford 2-(2,6-dioxopiperidin-3-yl)-5-((S)-3-(hydroxymethyl)pyrrolidin-1-yl)isoindoline-1,3-dione (643.1 mg, 33%) as a yellow solid. $^1$H NMR (300 MHz, DMSO-$d_6$) δ 11.08 (s, 1H), 7.64 (d, J 8.4 Hz, 1H), 6.89 (d, J 2.1 Hz, 1H), 6.80 (dd, J 8.4, 2.1 Hz, 1H), 5.06 (dd, J 12.9, 5.4 Hz, 1H), 4.78 (t, J 5.4 Hz, 1H), 3.59-3.41 (m, 5H), 3.22-3.17 (m, 1H), 2.95-2.83 (m, 1H), 2.67-2.44 (m, 3H), 2.12-1.88 (m, 2H), 1.87-1.76 (m, 1H). MS (ESI) calc'd for ($C_{18}H_{19}N_3O_5$) $[M+H]^+$, 358.1. found 358.1.

Step 3: (3S)-1-(2-(2,6-dioxopiperidin-3-yl)-1,3-dioxoisoindolin-5-yl)pyrrolidine-3-carbaldehyde. To a mixture of 2-(2,6-dioxopiperidin-3-yl)-5-[(3S)-3-(hydroxymethyl)pyrrolidin-1-yl]isoindole-1,3-dione (258 mg, 0.72 mmol) in DCM (5 mL) was added 1,1-bis(acetyloxy)-3-oxo-1λ$^5$,2-benziodaoxol-1-yl acetate (0.61 g, 1.44 mmol). After 90 minutes, silica gel was added and the mixture was concentrated to dryness. The resulting powder was transferred to a loading cartridge and the mixture was purified by flash chromatography on a 24 g column eluted with 0 to 100% ethyl acetate/hexanes to provide (3S)-1-[2-(2,6-dioxopiperidin-3-yl)-1,3-dioxoisoindol-5-yl]pyrrolidine-3-carbaldehyde (198 mg, 77%). LCMS $C_{18}H_{17}N_3O_5$ requires: 355. found: m/z=356 $[M+H]^+$.

HCB6: 3-{4-[2-(2,6-dioxopiperidin-3-yl)-1,3-dioxoisoindol-5-yl]piperazin-1-yl}propanoic acid

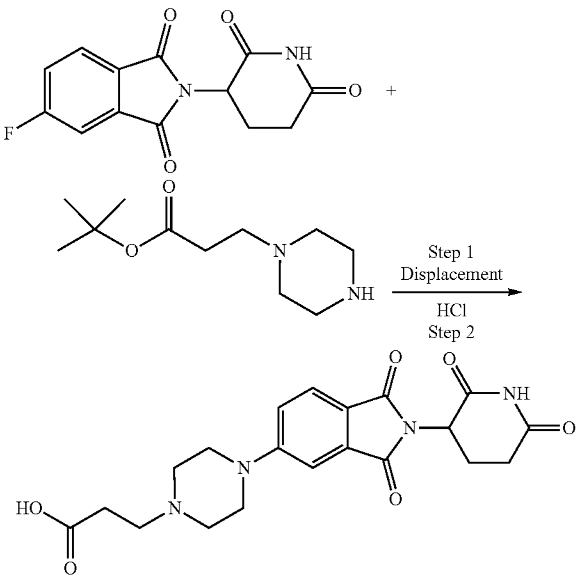

Step 1: tert-butyl 3-(4-(2-(2,6-dioxopiperidin-3-yl)-1,3-dioxoisoindolin-5-yl)piperazin-1-yl)propanoate. Tert-butyl 3-(piperazin-1-yl)propanoate (400.00 mg, 1.87 mmol) and 2-(2,6-dioxopiperidin-3-yl)-5-fluoroisoindole-1,3-dione (515.56 mg, 1.87 mmol) in 10 ml NMP, N,N-diisopropylethylamine (0.65 mL, 0.48 g, 3.73 mmol) added, heating at 85-90° C. for 16 hr. Partition between EtOAc/water×2, then organic layer was washed with brine, dried, concentrated. Silica gel column purification using 10-100% EtOAc/Hexanes, obtained 823 mg desired product. LCMS: $C_{24}H_{30}N_4O_6$, requires: 470.5. found: m/z=471.8 $[M+H]^+$.

Step 2: 3-{4-[2-(2,6-dioxopiperidin-3-yl)-1,3-dioxoisoindol-5-yl]piperazin-1-yl}propanoic acid. Tert-butyl 3-{4-[2-(2,6-dioxopiperidin-3-yl)-1,3-dioxoisoindol-5-yl]piperazin-1-yl}propanoate (820.00 mg, 1.74 mmol) was dissolved in trifluoroacetic acid (9.94 g, 87.14 mmol), after 1 hr, evaporated TFA. Lyophilized product to dryness, obtained 3-{4-[2-(2,6-dioxopiperidin-3-yl)-1,3-dioxoisoindol-5-yl]piperazin-1-yl}propanoic acid (722 mg, 100% yield). LCMS: $C_{20}H_{22}N_4O_6$, requires: 414.4. found: m/z=415.4 $[M+H]^+$.

HCB7: 2-(2-(2-(2,6-dioxopiperidin-3-yl)-1,3-dioxoisoindolin-5-yl)-2,7-diazaspiro[3.5]nonan-7-yl)acetic acid

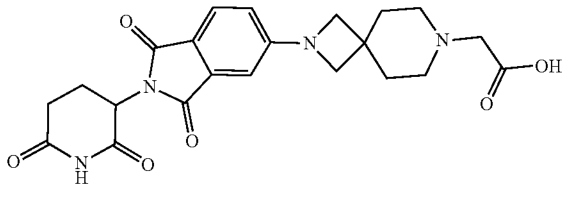 [SMILES: O=C(O)CN1CCC2(CC1)CN(c1ccc3c(c1)C(=O)N(C1CCC(=O)NC1=O)C3=O)C2]

Step 1: benzyl 2-{2-[2-(2,6-dioxopiperidin-3-yl)-1,3-dioxoisoindol-5-yl]-2,7-diazaspiro[3.5]nonan-7-yl}acetate. To a mixture of 2-(2,6-dioxopiperidin-3-yl)-5-fluoroisoindole-1,3-dione (70.00 mg, 0.25 mmol) and benzyl 2-{2,7-diazaspiro[3.5]nonan-7-yl}acetate (69.53 mg, 0.25 mmol) in 2 ml of NMP, was added N,N-diisopropylethylamine (0.13 mL), heated to 85° C. overnight. The crude mixture was purified by column chromatography eluting with EtOAc/Hexane (10-100%) to give benzyl 2-{2-[2-(2,6-dioxopiperidin-3-yl)-1,3-dioxoisoindol-5-yl]-2,7-diazaspiro[3.5]nonan-7-yl}acetate (68 mg, 51%). LCMS $C_{29}H_{30}N_4O_6$ requires: 530. found: m/z=532 $[M+H]^+$.

Step 2: 2-(2-(2-(2,6-dioxopiperidin-3-yl)-1,3-dioxoisoindolin-5-yl)-2,7-diazaspiro[3.5]nonan-7-yl)acetic acid. To a solution of benzyl 2-{2-[2-(2,6-dioxopiperidin-3-yl)-1,3-dioxoisoindol-5-yl]-2,7-diazaspiro[3.5]nonan-7-yl}acetate (68.00 mg, 0.13 mmol) in EtOH (5 mL) and DCM (2 mL), was added Palladium on carbon (6 mg, 0.06 mmol). The reaction mixture was sparged with hydrogen and kept under one atmosphere of hydrogen using a balloon, stirred at room temp for 48 hrs. The reaction mixture was filtered through a pad of Celite and concentrated to give benzyl 2-{2-[2-(2,6-dioxopiperidin-3-yl)-1,3-dioxoisoindol-5-yl]-2,7-diazaspiro[3.5]nonan-7-yl}acetate (56 mg, 99%). LCMS $C_{22}H_{24}N_4O_6$ requires: 440. found: m/z=441 $[M+H]^+$.

HCB8: 2-(1-(2-(2,6-dioxopiperidin-3-yl)-1,3-dioxoisoindolin-5-yl)piperidin-4-yl)acetaldehyde

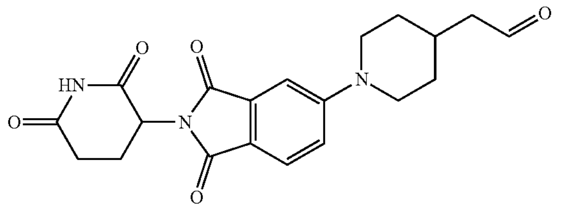 [SMILES: O=CCC1CCN(c2ccc3c(c2)C(=O)N(C2CCC(=O)NC2=O)C3=O)CC1]

Step 1: 2-(2,6-dioxopiperidin-3-yl)-5-fluoroisoindoline-1,3-dione. Same as Step 1 of Scheme B2.

Step 2: 2-(2,6-dioxopiperidin-3-yl)-5-(4-(2-hydroxyethyl)piperidin-1-yl)isoindoline-1,3-dione. 2-(2,6-dioxopiperidin-3-yl)-5-fluoroisoindoline-1,3-dione was reacted with 2-(piperidin-4-yl)ethan-1-ol to afford 2-(2,6-dioxopiperidin-3-yl)-5-(4-(2-hydroxyethyl)piperidin-1-yl)isoindoline-1,3-dione (823 mg, 59%) as a yellow solid. $^1$H NMR (300 MHz, DMSO-$d_6$) δ11.09 (s, 1H), 7.65 (d, J 8.4 Hz, 1H), 7.30 (d, J 2.4 Hz, 1H), 7.23 (dd, J 8.4, 2.4 Hz, 1H), 5.07 (dd, J 12.6, 5.4 Hz, 1H), 4.40 (t, J 5.1 Hz, 1H), 4.04 (d, J=13.2 Hz, 2H), 3.64-3.40 (m, 2H), 3.09-2.79 (m, 3H), 2.70-2.51 (m, 2H), 2.07-1.94 (m, 1H), 1.77-1.66 (m, 3H), 1.41-1.34 (m, 2H), 1.24-1.12 (m, 2H). MS (ESI) calc'd for ($C_{20}H_{23}N_3O_5$) $[M+H]^+$, 386.2. found 386.1.

Step 3: 2-(1-(2-(2,6-dioxopiperidin-3-yl)-1,3-dioxoisoindolin-5-yl)piperidin-4-yl)acetaldehyde. According to Scheme B2, 2-(2,6-dioxopiperidin-3-yl)-5-(4-(2-hydroxyethyl)piperidin-1-yl)isoindoline-1,3-dione was oxidized to afford the title compound. LCMS $C_{20}H_{21}N_3O_5$ requires: 383. found: m/z=384 $[M+H]^+$.

HCB9: 1-(2-(2,6-dioxopiperidin-3-yl)-1,3-dioxoisoindolin-5-yl)piperidine-4-carbaldehyde

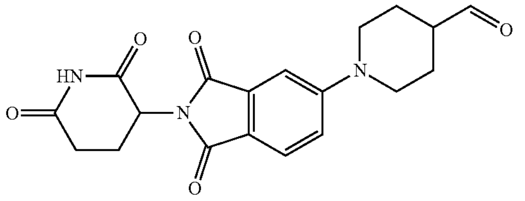 [SMILES: O=CC1CCN(c2ccc3c(c2)C(=O)N(C2CCC(=O)NC2=O)C3=O)CC1]

Step 1: 2-(2,6-dioxopiperidin-3-yl)-5-fluoroisoindoline-1,3-dione. Same as Step 1 of Scheme B2.

Step 2: 2-(2,6-dioxopiperidin-3-yl)-5-(4-(hydroxymethyl)piperidin-1-yl)isoindoline-1,3-dione. 2-(2,6-dioxopiperidin-3-yl)-5-fluoroisoindoline-1,3-dione was reacted with piperidin-4-ylmethanol to afford 2-(2,6-dioxopiperidin-3-yl)-5-(4-(hydroxymethyl)piperidin-1-yl)isoindoline-1,3-dione (939 mg, 70%) as a yellow solid. $^1$H NMR (300 MHz, DMSO-$d_6$) δ 11.09 (s, 1H), 7.65 (d, J 8.4 Hz, 1H), 7.30 (d, J 2.4 Hz, 1H), 7.23 (dd, J 8.4, 2.4 Hz, 1H), 5.07 (dd, J 12.6, 5.4 Hz, 1H), 4.51 (t, J 5.1 Hz, 1H), 4.07 (d, J 13.2 Hz, 2H), 3.27 (t, J 5.7 Hz, 2H), 2.99-2.80 (m, 3H), 2.62-2.55 (m, 2H), 2.17-1.95 (m, 1H), 1.76-1.67 (m, 3H), 1.24-1.12 (m, 2H). MS (ESI) calc'd for ($C_{19}H_{21}N_3O_5$) $[M+H]^+$, 372.1. found 372.2.

Step 3: 1-(2-(2,6-dioxopiperidin-3-yl)-1,3-dioxoisoindolin-5-yl)piperidine-4-carbaldehyde. According to Scheme B2, 2-(2,6-dioxopiperidin-3-yl)-5-(4-(hydroxymethyl)piperidin-1-yl)isoindoline-1,3-dione was oxidized to afford 1-(2-(2,6-dioxopiperidin-3-yl)-1,3-dioxoisoindolin-5-yl)piperidine-4-carbaldehyde. LCMS $C_{19}H_{19}N_3O_5$ requires: 369. found: m/z=370 $[M+H]^+$.

HCB10: 1-[2-(2,6-dioxopiperidin-3-yl)-1-oxoisoquinolin-6-yl]piperidine-4-carbaldehyde

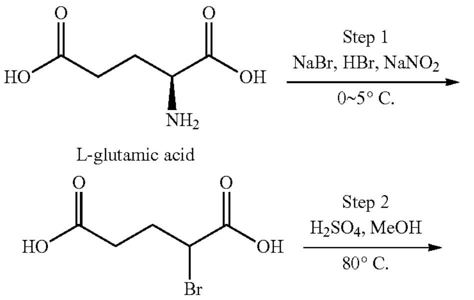

-continued

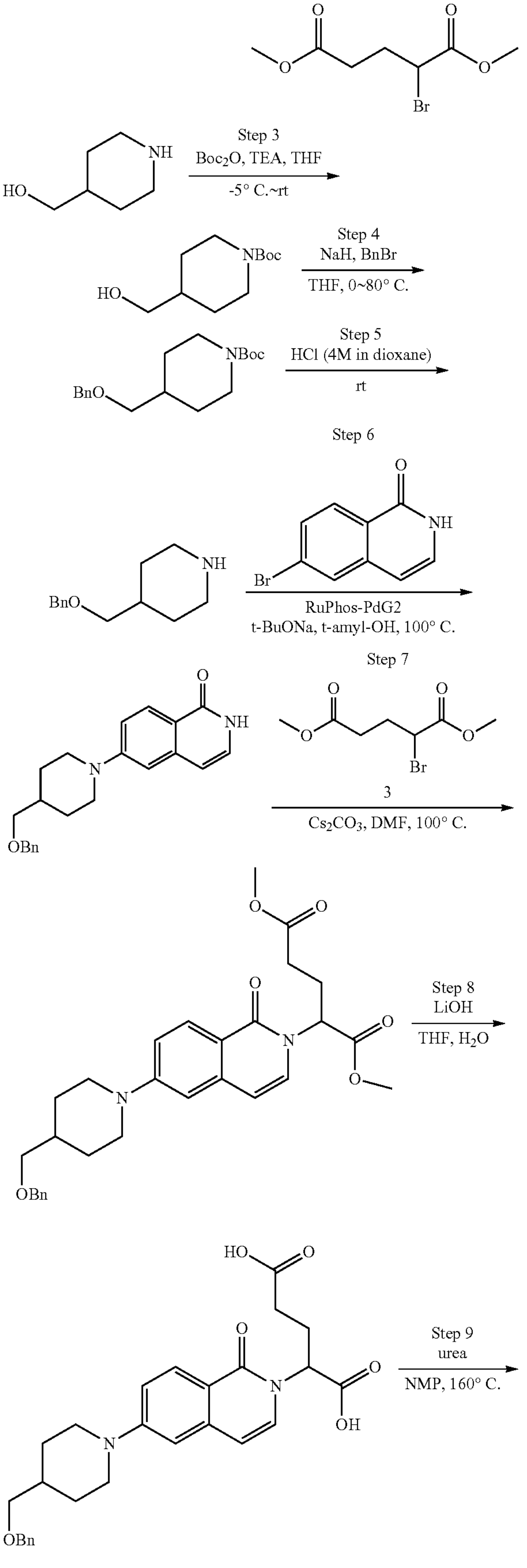

-continued

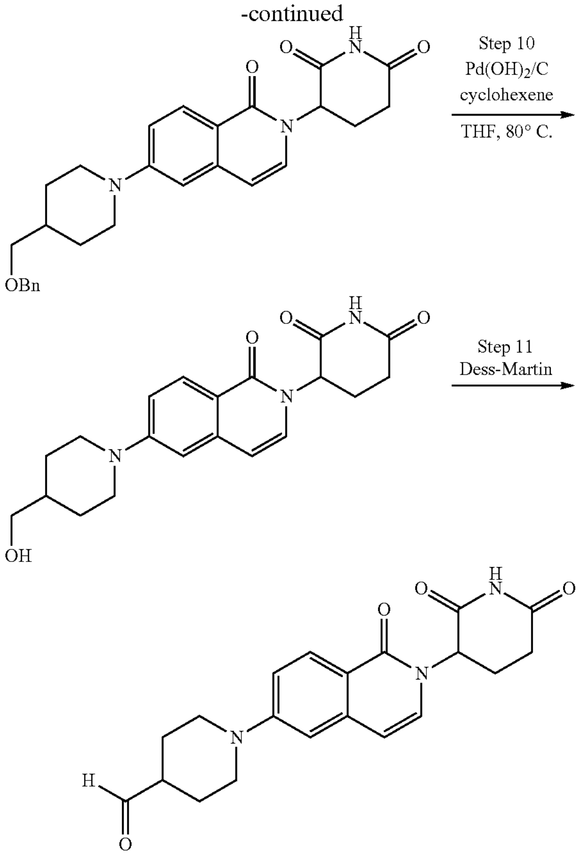

HCB10

Step 1: Synthesis of 2-bromopentanedioic acid. To a solution of L-glutamic acid (100.0 g, 0.7 mol) and NaBr (244.7 g, 2.4 mol) in HBr (1 L, 40% in water) was added a solution of $NaNO_2$ (84.4 g, 1.2 mol, in 200 mL water) dropwise at 0° C. under nitrogen atmosphere. The resulting solution was stirred at 0-5° C. for 2 h. The reaction was quenched by the addition of 30 mL concentrated $H_2SO_4$ at 0° C. and stirred for 10 min. The resulting mixture was extracted with ethyl acetate. The combined organic layers were washed with brine, dried over anhydrous $Na_2SO_4$ and filtered. The filtrate was concentrated under vacuum to afford 2-bromopentanedioic acid (51 g, crude) as light brown oil, which was used in the next step without further purification.

Step 2: Synthesis of dimethyl 2-bromopentanedioate. To a solution of 2-bromopentanedioic acid (51.0 g, 241.69 mmol) in MeOH (500 mL) was added concentrated $H_2SO_4$ (10 mL, 187.60 mmol). The mixture was stirred at 80° C. for 3 h before concentrated under vacuum. The residue was diluted with water and extracted with ethyl acetate. The combined organic layers were washed with brine, dried over anhydrous $Na_2SO_4$ and filtered. The filtrate was concentrated under vacuum. The residue was purified by flash column chromatography with 0~30% ethyl acetate in petroleum ether to afford dimethyl 2-bromopentanedioate (36 g, 62%) as a light yellow oil. 1H NMR (300 MHz, Chloroform-d) δ 4.38 (dd, J=8.4, 5.7 Hz, 1H), 3.79 (s, 3H), 3.69 (s, 3H), 2.55-2.51 (m, 2H), 2.47-2.20 (m, 2H).

Step 3: Synthesis of tert-butyl 4-(hydroxymethyl)piperidine-1-carboxylate. To a mixture of piperidin-4-ylmethanol (5.0 g, 43.41 mmol) and $Et_3N$ (5.3 g, 52.37 mmol) in THF (50 mL) was added a solution of Boc2O (10.4 g, 47.65 mmol, in 10 mL THF) dropwise at −5° C. The resulting mixture was warmed to room temperature and stirred for 16 h. The solvent was removed under vacuum and the residue was partitioned between ethyl acetate and water. The collected organic layers were washed with 5% HCl aqueous solution, water and brine, dried over anhydrous $Na_2SO_4$ and filtered. The filtrate was concentrated under vacuum. The crude product was triturated with hexane to afford tert-butyl 4-(hydroxymethyl)piperidine-1-carboxylate (7.7 g, 82%) as a white solid. MS (ESI) calculated for (C11H21NO3) $[M+H]^+$, 216.2. found 216.0.

Step 4: Synthesis of tert-butyl 4-(benzyloxymethyl)piperidine-1-carboxylate. To a mixture of NaH (42.0 g, 1021.86 mmol, 60%) in THF (500 mL) was added a solution of tert-butyl 4-(hydroxymethyl)piperidine-1-carboxylate (100.0 g, 464.483 mmol, in 500 mL THF) dropwise at 0° C. and stirred for 30 min at room temperature under nitrogen atmosphere. And then Benzyl bromide (174.8 g, 1021.88 mmol) was added to the above mixture dropwise at room temperature. The resulting solution was stirred at 80° C. for 2 h under nitrogen atmosphere. The reaction mixture was quenched by the addition of saturated $NH_4Cl$ aqueous solution cautiously. The aqueous layer was extracted with ethyl acetate. The combined organic layers were washed with brine, dried over anhydrous $Na_2SO_4$ and filtered. The filtrate was concentrated under vacuum. The residue was purified by flash column chromatography with 0~10% ethyl acetate in petroleum ether to afford tert-butyl 4-(benzyloxymethyl)piperidine-1-carboxylate (115.6 g, 81%) as a light yellow oil. MS (ESI) calculated for (C18H27NO3) $[M+H]^+$, 306.2. found 306.0.

Step 5: Synthesis of 4-((benzyloxy)methyl)piperidine. A solution of tert-butyl 4-(benzyloxymethyl)piperidine-1-carboxylate (94.0 g, 307.2 mmol) in HCl (4M in dioxane) (1000 mL) was stirred at room temperature for 2 h. The solvent was removed under vacuum. The residue was partitioned between ethyl acetate and 10% potassium carbonate aqueous solution. The collected organic layers were dried over anhydrous $Na_2SO_4$ and filtered. The filtrate was concentrated under vacuum to afford 4-[(benzyloxy)methyl]piperidine (54.0 g, 85%) as a yellow oil. MS (ESI) calculated for (C13H19NO) $[M+H]^+$, 206.2. found 206.2.

Step 6: Synthesis of 6-(4-(benzyloxymethyl)piperidin-1-yl)isoquinolin-1(2H)-one. To a degassed solution of 6-bromo-2H-isoquinolin-1-one (4.0 g, 17.85 mmol) in t-amyl alcohol (50 mL) were added 4-[(benzyloxy)methyl]piperidine (4.4 g, 21.42 mmol), t-BuONa (5.2 g, 53.91 mmol) and RuPhos-PdCl-2nd G (1.39 g, 1.78 mmol). The mixture was stirred at 100° C. for 3 h under nitrogen atmosphere. The reaction mixture was quenched by the addition of saturated citric acid aqueous solution and extracted with ethyl acetate. The combined organic layers were washed with brine, dried over anhydrous $Na_2SO_4$ and filtered. The filtrate was concentrated under vacuum. The residue was purified by flash column chromatography with 0-10% methanol in dichloromethane to afford 6-(4-(benzyloxymethyl)piperidin-1-yl)isoquinolin-1(2H)-one (5.5 g, 88%) as a brown solid. MS (ESI) calculated for (C22H24N2O2) $[M+H]^+$, 349.2; found 349.2.

Step 7: Synthesis of dimethyl 2-(6-(4-(benzyloxymethyl)piperidin-1-yl)-1-oxoisoquinolin-2(1H)-yl)pentanedioate. To a solution of 6-(4-(benzyloxymethyl)piperidin-1-yl)isoquinolin-1(2H)-one (6.2 g, 17.79 mmol) in DMF (60 mL) were added dimethyl 2-bromopentanedioate (5.0 g, 20.91 mmol) and $Cs_2CO_3$ (17.4 g, 53.40 mmol). The resulting mixture was stirred at 100° C. for 16 h under nitrogen atmosphere. The mixture was diluted with saturated citric acid aqeuous solution and extracted with ethyl acetate. The combined organic layers were washed with brine, dried over anhydrous $Na_2SO_4$ and filtered. The filtrate was concentrated under vacuum to afford dimethyl 2-(6-(4-(benzyloxymethyl)piperidin-1-yl)-1-oxoisoquinolin-2(1H)-yl)pentanedioate (6 g, crude) as a a brown oil, which was used in the next step without further purification. MS (ESI) calculated for (C29H34N2O6) $[M+H]^+$, 507.2; found 507.2.

Step 8: Synthesis of 2-(6-(4-(benzyloxymethyl)piperidin-1-yl)-1-oxoisoquinolin-2(1H)-yl)pentanedioic acid: To a solution of 1,5-dimethyl 2-(6-[4-[(benzyloxy)methyl]piperidin-1-yl]-1-oxoisoquinolin-2-yl)pentanedioate (20.0 g, 39.48 mmol) in MeOH (80 mL), THF (80 mL) and $H_2O$ (80 mL) was added LiOH (5.67 g, 236.87 mmol). The mixture was stirred at room temperature for 16 h. The organic solvents were removed under vacuum and the residue was diluted with water, extracted with ethyl acetate. The collected aqueous layer was acidified to pH 5-6 by citric acid and extracted with ethyl acetate. The combined organic layers were washed with brine, dried over anhydrous $Na_2SO_4$ and filtered. The filtrate was concentrated under vacuum to afford 2-(6-(4-(benzyloxymethyl)piperidin-1-yl)-1-oxoisoquinolin-2(1H)-yl)pentanedioic acid (15 g, crude) as a brown oil, which was used in the next step without further purification. MS (ESI) calculated for (C27H30N2O6) $[M+H]^+$, 479.2; found 479.0.

Step 9: Synthesis of 3-(6-(4-(benzyloxymethyl)piperidin-1-yl)-1-oxoisoquinolin-2(1H)-yl)piperidine-2,6-dione. To a solution of 2-(6-(4-(benzyloxymethyl)piperidin-1-yl)-1-oxoisoquinolin-2(1H)-yl)pentanedioic acid (1.60 g, 3.34 mmol) in NMP (15 mL) was added urea (2.0 g, 33.30 mmol). The mixture was stirred at 180° C. for 4 h under nitrogen atmosphere. The resulting mixture was cooled down to room temperature and diluted with water. The mixture was extracted with ethyl acetate. The combined organic layers were washed with brine, dried over anhydrous $Na_2SO_4$ and filtered. The filtrate was concentrated under vacuum. The residue was purified by reverse phase flash column chromatography with 5-65% acetonitrile in water to afford 3-(6-(4-(benzyloxymethyl)piperidin-1-yl)-1-oxoisoquinolin-2(1H)-yl)piperidine-2,6-dione (350 mg, 22%) as an off-white solid. MS (ESI) calculated for (C27H29N3O4) $[M+H]^+$, 460.2. found 460.2.

Step 10: Synthesis of 3-(6-(4-(hydroxymethyl)piperidin-1-yl)-1-oxoisoquinolin-2(1H)-yl)piperidine-2,6-dione. To a solution of 3-(6-(4-(benzyloxymethyl)piperidin-1-yl)-1-oxoisoquinolin-2(1H)-yl)piperidine-2,6-dione (1.8 g, 3.91 mmol) in THF (60 mL) were added $Pd(OH)_2/C$ (10%, 1.8 g) and cyclohexene (3.2 g, 38.96 mmol). The mixture was stirred at 80° C. for 24 h under nitrogen atmosphere. When the reaction was completed, the solids were filtered out and the filtrate was concentrated under vacuum. The residue was purified by high-pressure flash column chromatography with the following conditions: [column, C18 silica gel; mobile phase, MeCN in water (0.1% $NH_4HCO_3$), 15% to 40% gradient in 30 min; detector, UV 254 nm] to afford 3-(6-(4-(hydroxymethyl)piperidin-1-yl)-1-oxoisoquinolin-2(1H)-yl) piperidine-2,6-dione (800 mg, 55%) as an off-white solid. $^1H$ NMR (300 MHz, DMSO-$d_6$) δ 10.72 (s, 1H), 7.94 (d, J=9.0 Hz, 1H), 7.23 (d, J=7.5 Hz, 1H), 7.14 (dd, J=9.0, 2.4 Hz, 1H), 6.92 (d, J=2.4 Hz, 1H), 6.44 (d, J=7.5 Hz, 1H), 5.40 (s, 1H), 4.47 (t, J=5.1 Hz, 1H), 3.97-3.94 (m, 2H), 3.27-3.24 (m, 2H), 2.85-2.78 (m, 3H), 2.58-2.52 (m, 2H), 1.98-1.94 (m, 1H), 1.81-1.67 (m, 2H), 1.65-1.59 (m, 1H), 1.26-1.12 (m, 2H). MS (ESI) calculated for (C20H23N3O4) $[M+H]^+$, 370.2; found, 370.3.

Step 11: 1-[2-(2,6-dioxopiperidin-3-yl)-1-oxoisoquinolin-6-yl]piperidine-4-carbaldehyde. 3-{6-[4-(hydroxymethyl) piperidin-1-yl]-1-oxoisoquinolin-2-yl}piperidine-2,6-dione (150.00 mg, 0.41 mmol) was dissolved in $CH_2Cl_2$ (2 mL) and 1,1-bis(acetyloxy)-3-oxo-1$\lambda^5$,2-benziodaoxol-1-yl acetate (172 mg, 0.41 mmol) was added in one portion at rt. After 5 h the reaction mixture was diluted with $NaHCO_3$ (2 mL sat. aq.) and $Na_2S_2O_3$ (sat. aq.) was added and the mixture was stirred for 30 min. The organic phase was removed. The aqueous layer was extracted (2×20 mL $CH_2Cl_2$) and the combined organic phases were dried ($Na_2SO_4$), filtered, and concentrated. Purification by silica gel column chromatography (2-6% $MeOH/CH_2Cl_2$) afforded 1-[2-(2,6-dioxopiperidin-3-yl)-1-oxoisoquinolin-6-yl]piperidine-4-carbaldehyde (120 mg, 80%). LCMS $C_{20}H_{21}N_3O_4$ requires: 367.2. found: m/z=368.4 $[M+H]^+$.

HCB11: rac-(R)-1-(4-(1-(2,6-dioxopiperidin-3-yl)-4-methyl-5-oxo-4,5-dihydro-1H-1,2,4-triazol-3-yl) phenyl)piperidine-4-carbaldehyde

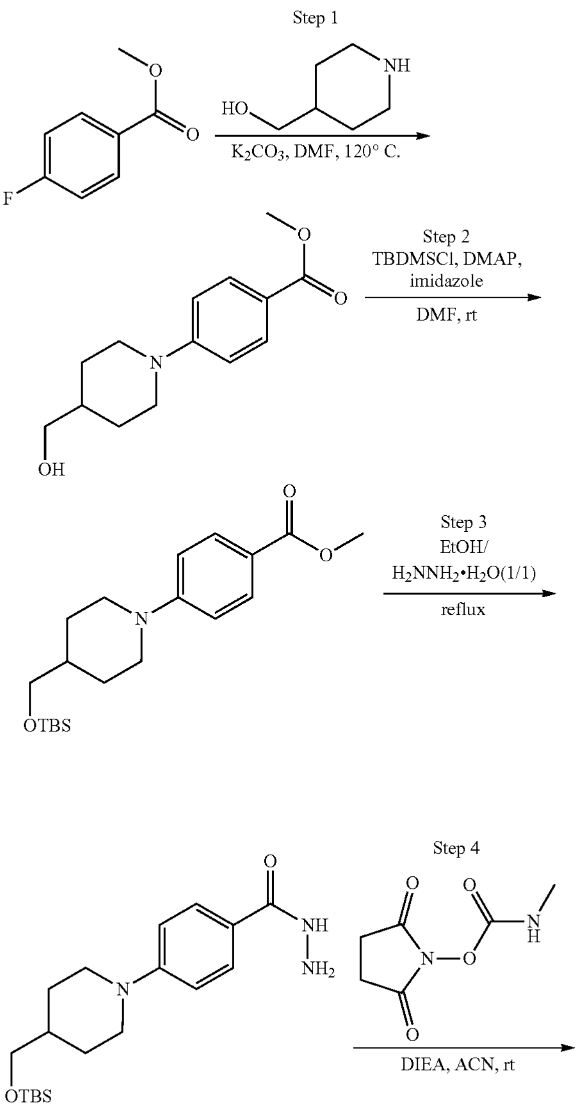

-continued

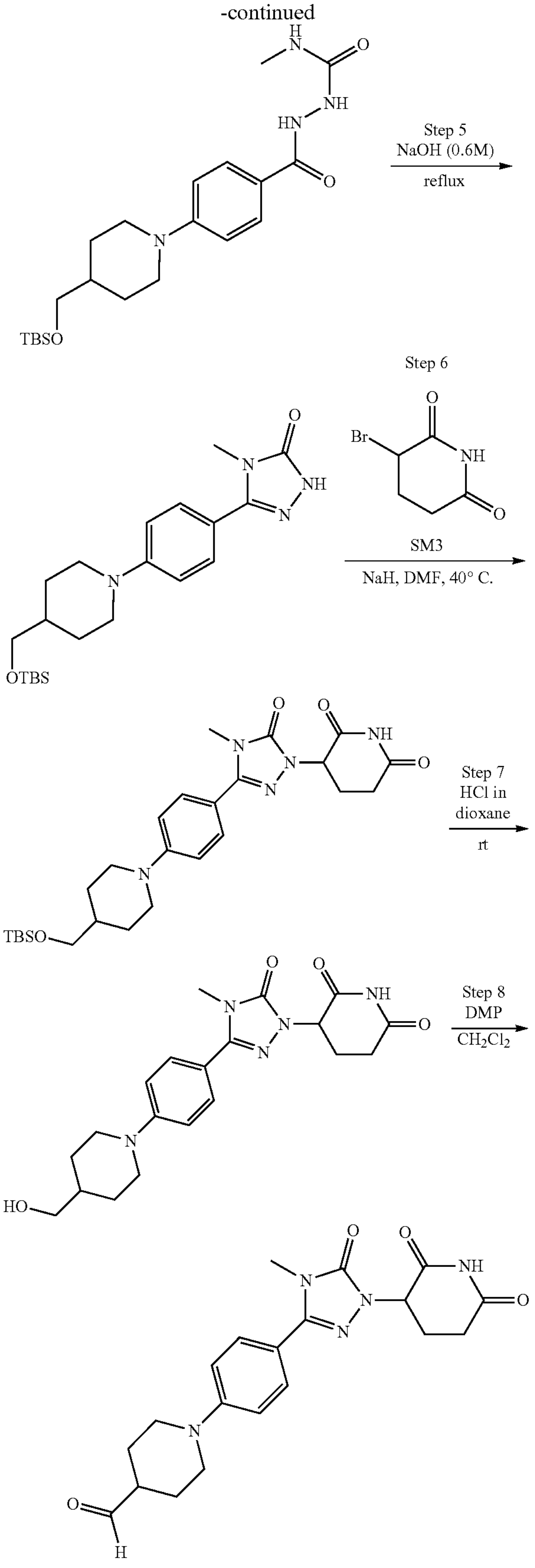

HCB11

Step 1: Synthesis of methyl 4-(4-(hydroxymethyl)piperidin-1-yl)benzoate. To a solution of methyl 4-fluorobenzoate (25.0 g, 162.190 mmol) in DMF (250 mL) were added piperidin-4-ylmethanol (18.6 g, 162.18 mmol) and $K_2CO_3$ (44.8 g, 324.38 mmol). The resulting solution was stirred at 120° C. for 16 h. When the reaction was completed, the reaction mixture was cooled down to room temperature and quenched by the addition of water. The resulting mixture was extracted with ethyl acetate. The combined organic layers were washed with brine, dried over anhydrous $Na_2SO_4$ and filtered. The filtrate was concentrated under vacuum. The residue was purified by silica gel column chromatography with 0~50% ethyl acetate in petroleum ether to afford methyl 4-(4-(hydroxymethyl)piperidin-1-yl)benzoate (14 g, 34%) as a white solid. MS (ESI) calculated for ($C_{14}H_{19}NO_3$) $[M+H]^+$, 250.1. found 250.0.

Step 2: Synthesis of methyl 4-(4-((tert-butyldimethylsilyloxy)methyl)piperidin-1-yl)benzoate. To a solution of methyl 4-(4-(hydroxymethyl)piperidin-1-yl)benzoate (40.0 g, 160.44 mmol) in DMF (400 mL) were added imidazole (21.8 g, 320.88 mmol), DMAP (1.9 g, 16.04 mmol) and t-butyldimethylchlorosilane (29.0 g, 192.53 mmol). The resulting mixture was stirred at room temperature for 3 h under nitrogen atmosphere. The reaction mixture was quenched by the addition of water and extracted with ethyl acetate. The combined organic layers were washed with water and brine, dried over anhydrous $Na_2SO_4$ and filtered. The filtrate was concentrated under vacuum. The residue was purified by silica gel column chromatography with 0~20% ethyl acetate in petroleum ether to afford methyl 4-(4-((tert-butyldimethylsilyloxy)methyl)piperidin-1-yl)benzoate (35.0 g, 60%) as a white solid. MS (ESI) calculated for ($C_{20}H_{33}NO_3Si$) $[M+H]^+$, 364.2. found 364.2.

Step 3: Synthesis of 4-(4-((tert-butyldimethylsilyloxy)methyl)piperidin-1-yl)benzohydrazide. To a solution of methyl 4-(4-((tert-butyldimethylsilyloxy)methyl)piperidin-1-yl)benzoate (35.0 g, 96.26 mmol) in EtOH (150 mL) was added hydrazine (150 mL, 80%). The mixture was stirred at 90° C. for 6 h before concentrated under vacuum. The crude residue was diluted with water and extracted with ethyl acetate. The combined organic layers were washed with brine, dried over anhydrous $Na_2SO_4$ and filtered. The filtrate was concentrated under vacuum to afford 4-(4-((tert-butyldimethylsilyloxy)methyl)piperidin-1-yl)benzohydrazide (29.0 g, crude) as a white solid, which was used in the next step without further purification. MS (ESI) calculated for ($C_{19}H_{33}N_3O_2Si$) $[M+H]^+$, 364.2. found 364.0.

Step 4: Synthesis of 2-(4-(4-((tert-butyldimethylsilyloxy)methyl)piperidin-1-yl)benzoyl)-N-methylhydrazinecarboxamide. To a solution of 4-(4-((tert-butyldimethylsilyloxy)methyl)piperidin-1-yl)benzohydrazide (29.0 g, 79.76 mmol) in MeCN (300 mL) were added 2,5-dioxopyrrolidin-1-yl N-methylcarbamate (20.6 g, 119.64 mmol) and DIEA (30.9 g, 239.28 mmol). The mixture was stirred at room temperature for 16 h under nitrogen atmosphere. The reaction mixture was quenched by the addition of water and extracted with ethyl acetate. The combined organic layers were washed with brine, dried over anhydrous $Na_2SO_4$ and filtered. The filtrate was concentrated under vacuum to afford 2-(4-(4-((tert-butyldimethylsilyloxy)methyl)piperidin-1-yl)benzoyl)-N-methylhydrazinecarboxamide (38.0 g, crude) as an off-white solid, which was used in the next step without further purification. MS (ESI) calculated for ($C_{21}H_{36}N_4O_3Si$) $[M+H]^+$, 421.3. found 421.0.

Step 5: Synthesis of 5-(4-(4-((tert-butyldimethylsilyloxy)methyl)piperidin-1-yl)phenyl)-4-methyl-2H-1,2,4-triazol-3(4H)-one. To a solution of NaOH (7.2 g, 180.68 mmol) in water (300 mL) was added 2-(4-(4-((tert-butyldimethylsilyloxy)methyl)piperidin-1-yl)benzoyl)-N-methylhydrazinecarboxamide (38.0 g, 90.34 mmol). The mixture was stirred at 100° C. for 3 h under nitrogen atmosphere. After cooled down to room temperature, the resulting mixture was extracted with ethyl acetate. The combined organic layers were washed with brine, dried over anhydrous $Na_2SO_4$ and concentrated under vacuum. The residue was purified by silica gel column chromatography with 0-10% methanol in dichloromethane to afford 5-(4-(4-((tert-butyldimethylsilyloxy)methyl)piperidin-1-yl)phenyl)-4-methyl-2H-1,2,4-triazol-3(4H)-one (12 g, 33%) as an off-white solid. MS (ESI) calculated for ($C_{21}H_{34}N_4O_2Si$) $[M+H]^+$, 403.2. found 403.2.

Step 6: Synthesis of 3-(3-(4-(4-((tert-butyldimethylsilyloxy)methyl)piperidin-1-yl)phenyl)-4-methyl-5-oxo-4,5-dihydro-1,2,4-triazol-1-yl)piperidine-2,6-dione. To a solution of 5-(4-(4-((tert-butyldimethylsilyloxy)methyl)piperidin-1-yl)phenyl)-4-methyl-2H-1,2,4-triazol-3(4H)-one (9.6 g, 23.84 mmol) in DMF (100 mL) was added NaH (60%, 2.6 g, 65.0 mmol) in portions at 0° C. The mixture was stirred at room temperature for 30 min under nitrogen atmosphere. 3-bromopiperidine-2,6-dione (7.7 g, 40.10 mmol) was added to the above mixture at 0° C. The resulting mixture was stirred at 40° C. for 4 h under nitrogen atmosphere. The reaction mixture was poured into saturated $NH_4Cl$ aqueous solution cautiously, and then extracted with ethyl acetate. The combined organic layers were washed with brine, dried over anhydrous sodium sulfate and filtered. The filtrate was concentrated under vacuum. The residue was purified by flash column chromatography with 0~8% methanol in dichloromethane to afford 3-(3-(4-(4-((tert-butyldimethylsilyloxy)methyl)piperidin-1-yl)phenyl)-4-methyl-5-oxo-4,5-dihydro-1,2,4-triazol-1-yl)piperidine-2,6-dione (8.2 g, 66%) as a brown oil. MS (ESI) calculated for ($C_{26}H_{39}N_5O_4Si$) $[M+H]^+$, 514.3. found 514.3.

Step 7: Synthesis of 3-(3-(4-(4-(hydroxymethyl)piperidin-1-yl)phenyl)-4-methyl-5-oxo-4,5-dihydro-1,2,4-triazol-1-yl)piperidine-2,6-dione. A mixture of 3-(3-(4-(4-((tert-butyldimethylsilyloxy)methyl)piperidin-1-yl)phenyl)-4-methyl-5-oxo-4,5-dihydro-1,2,4-triazol-1-yl)piperidine-2,6-dione (350 mg, 0.68 mmol) in HCl (4 M in 1,4-dioxane, 5 mL) was stirred at room temperature for 2 h. The solvent was removed under vacuum. The crude residue was diluted with DMF and basified to pH 8-9 with triethyl amine. The resulting mixture was purified by reverse flash chromatography with the following conditions: [column, C18 silica gel; mobile phase, ACN in water (0.05% $NH_4HCO_3$), 10% to 35% gradient in 30 min; detector, UV 254 nm] to afford 3-(3-(4-(4-(hydroxymethyl)piperidin-1-yl)phenyl)-4-methyl-5-oxo-4,5-dihydro-1,2,4-triazol-1-yl)piperidine-2,6-dione (90 mg, 22%) as a white solid. $^1H$ NMR (300 MHz, DMSO-$d_6$+D2O) δ 7.55-7.41 (m, 2H), 7.12-6.88 (m, 2H), 5.15-5.05 (m, 1H), 3.85-3.76 (m, 2H), 3.34-3.20 (m, 5H), 2.91-2.58 (m, 4H), 2.48-2.34 (m, 1H), 2.21-2.05 (m, 1H), 1.78-1.66 (m, 2H), 1.63-1.48 (m, 1H), 1.24-1.08 (m, 2H). MS (ESI) calculated for ($C_{20}H_{25}N_5O_4$) $[M+H]^+$, 400.2; found, 400.1.

Step 8: rac-(R)-1-(4-(1-(2,6-dioxopiperidin-3-yl)-4-methyl-5-oxo-4,5-dihydro-1H-1,2,4-triazol-3-yl)phenyl)piperidine-4-carbaldehyde. To a solution of 3-(3-(4-(4-(hydroxymethyl)piperidin-1-yl)phenyl)-4-methyl-5-oxo-4,5-dihydro-1,2,4-triazol-1-yl)piperidine-2,6-dione (0.30 g, 0.75 mmol) in DCM (5 mL) was added Dess-Martin periodinane (0.38 g, 0.90 mmol). The reaction mixture was stirred at rt for 2 h, filtered through a pad of celite, concentrated onto silica gel, then purified by column chromatography (0-100% EtOAc/hexanes) to give the title compound. LCMS $C_{20}H_{23}N_5O_4$ requires: 397.2. found: m/z=398.4 $[M+H]^+$ minor, 416.4 $[M+H_2O]^+$ major.

HCB12: 3-(2-((2-(2,6-dioxopiperidin-3-yl)-1,3-dioxoisoindolin-5-yl)amino)ethoxy)propanoic acid

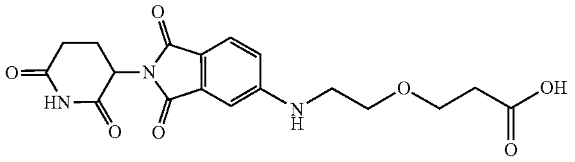 [SMILES: O=C(O)CCOCCNc1ccc2c(c1)C(=O)N(C1CCC(=O)NC1=O)C2=O]

Prepared in a similar manner as HCB1 substituting 2-(2,6-dioxopiperidin-3-yl)-5-fluoroisoindoline-1,3-dione for 2-(2,6-dioxopiperidin-3-yl)-4-fluoroisoindoline-1,3-dione to give the title compound. LCMS $C_{18}H_{19}N_3O_7$ requires: 389.1. found: m/z=387.8 $[M-H]^-$ HCB13: 1-(1-(2-(2,6-dioxopiperidin-3-yl)-1,3-dioxoisoindolin-5-yl)piperidin-4-yl)azetidine-3-carboxylic acid

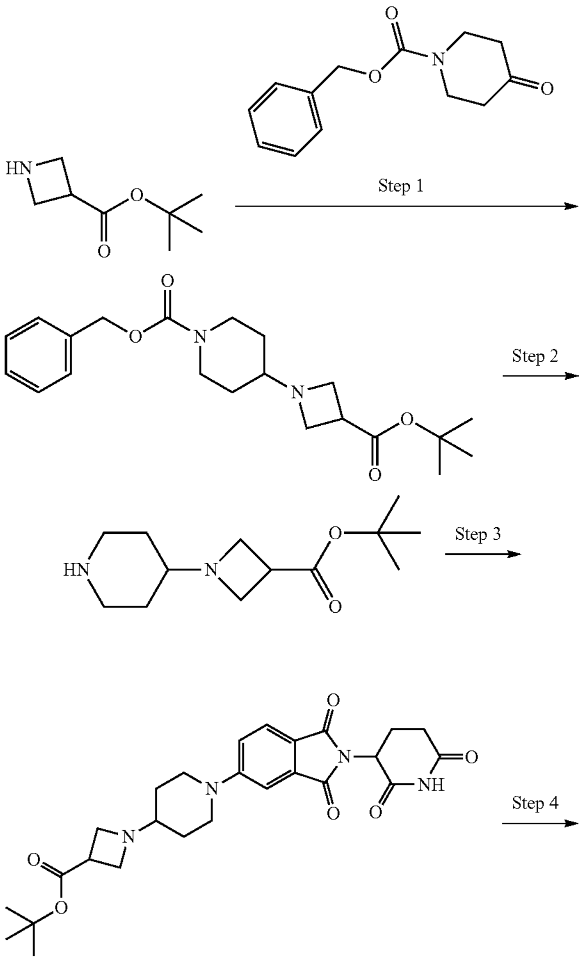

-continued

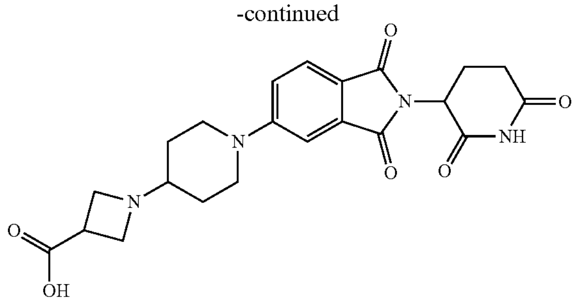

HCB13

Step 1: benzyl 4-{3-[(tert-butoxy)carbonyl]azetidin-1-yl}piperidine-1-carboxylate. To a solution of tert-butyl azetidine-3-carboxylate (4.5 g, 28.62 mmol, 1.0 eq) and 1-(benzyloxycarbonyl)-4-piperidinone (7.35 g, 31.49 mmol, 1.10 eq) in DCE (136 mL, 0.2 M) was added acetic acid (2.46 ml, 42.94 mmol, 1.5 eq) and the reaction was stirred at RT for 1 h. After that $NaBH(OAc)_3$ (9.71 g, 45.8 mmol, 1.6 eq) was added and the reaction was stirred at RT overnight. The reaction mixture was quenched with aqueous $NaHCO_3$, extracted with DCM (3×), washed with brine, dried over $Na_2SO_4$ an concentrated to dryness. The colorless oil was purified by flash column chromatography eluted by DCM: MeOH (0-10%) to give 9.39 g (88% yield) of the desired product as a white solid. ESI[M+H]=375.6

Step 2: tert-butyl 1-(piperidin-4-yl)azetidine-3-carboxylate. A solution of benzyl 4-{3-[(tert-butoxy)carbonyl]azetidin-1-yl}piperidine-1-carboxylate (9.39 g, 25.07 mmol, 1.0 eq) in MeOH (250 ml, 0.1 M) was degassed and filled with argon 3 times. Then $Pd(OH)_2$ (0.7 g, 5.0 mmol, 0.2 eq) was added and the mixture was again degassed and field with argon 3 times. After that, the RM was degassed and charged with $H_2$ balloon and stirred at RT overnight. The UPLC confirmed Cbz cleavage. The reaction mixture was filtrated through a celite pad and filtrate was concentrated to afford 5.81 g (96% yield) of the desired product.

Step 3: tert-butyl 1-{1-[2-(2,6-dioxopiperidin-3-yl)-1,3-dioxo-2,3-dihydro-1H-isoindol-5-yl]piperidin-4-yl}azetidine-3-carboxylate. To a solution of 2-(2,6-dioxopiperidin-3-yl)-5-fluoro-2,3-dihydro-1H-isoindole-1,3-dione (6.05 g, 21.9 mmol, 1.0 eq) in DMSO (43.8 mL, 0.5 M) were added tert-butyl 1-(piperidin-4-yl)azetidine-3-carboxylate (5.79 g, 24.09 mmol, 1.1 eq) and DIPEA (7.63 mL, 43.8 mmol, 2.0 eq). The reaction mixture was then moved to pre-heated bath to 90° C., and stirred overnight under Ar atmosphere. The UPLC showed the formation of the desired product. The RM was quenched with water, extracted with DCM (3×) and the organic phase was washed with ice-cold water. The crude was purified by FC eluted by DCM: Acetone (0-10%) to acquire 6.95 g (64% yield) of the product as a yellow solid. $ESI[M+H]^+$=497.4.

Step 4: 1-{1-[2-(2,6-dioxopiperidin-3-yl)-1,3-dioxo-2,3-dihydro-1H-isoindol-5-yl]piperidin-4-yl}azetidine-3-carboxylic acid hydrochloride. To a solution of tert-butyl 1-{1-[2-(2,6-dioxopiperidin-3-yl)-1,3-dioxo-2,3-dihydro-1H-isoindol-5-yl]piperidin-4-yl}azetidine-3-carboxylate (4.95 g, 9.97 mmol, 1.0 eq) in an DCM (100 mL, 0.1 M) was added 2M HCl in $Et_2O$ (50 ml, 99.69 mmol, 10.0 eq). The reaction mixture was then stirred at room temperature for 2 h. and UPLC showed remaining SM. Another portion of HCl in $Et_2O$ (50 ml, 99.69 mmol, 10.0 eq) was added and the RM was left stirring for another 3 h. The UPLC showed 10% of the SM. The precipitate was filtrated out and again dissolved in DCM, followed by the addition of 2M HCl in $Et_2O$ (50 ml, 99.69 mmol, 10.0 eq) and the RM was sonicated for 45 min. The precipitated solid was filtrated off, washed with $Et_{20}$, and dried under vacuum resulting in 4.83 g (quant yield) of the desired product as an HCl salt. LCMS (254 nm): RT=2.83 min, 94.5%, $ESI[M+H]^+$=441.07; $^1H$ NMR (300 MHz, $D_2O$) δ 7.68 (d, J=8.5 Hz, 1H), 7.37 (s, 1H), 7.22 (dd, J=8.6, 2.3 Hz, 1H), 5.14 (dd, J=12.8, 5.6 Hz, 1H), 4.49-4.28 (m, 4H), 4.08 (d, J=13.6 Hz, 2H), 3.80 (t, J=9.0 Hz, 1H), 3.69-3.56 (m, 1H), 3.03 (t, J=12.8 Hz, 2H), 2.92-2.73 (m, 2H), 2.61 (qd, J=12.8, 5.6 Hz, 1H), 2.24-2.09 (m, 2H), 1.59-1.42 (m, 2H).

HCB14: 2-(4-(2-(2,6-dioxopiperidin-3-yl)-1,3-dioxoisoindolin-5-yl)piperazin-1-yl)acetic acid

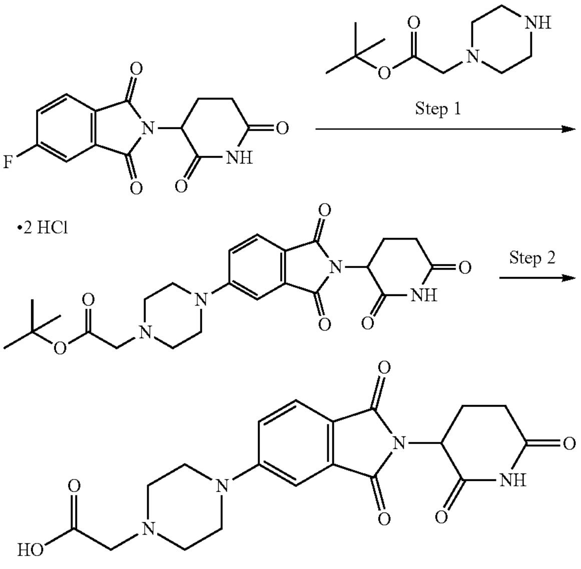

HCB14

Step 1: tert-Butyl 2-{4-[2-(2,6-dioxopiperidin-3-yl)-1,3-dioxo-2,3-dihydro-1H-isoindol-5-yl]piperazin-1-yl}acetate. To a solution of tert-butyl piperazin-1-yl-acetate dihydrochloride (4.46 g, 0.0163 mmol, 1.1 eq) in DMSO (29.7 mL, 0.5 M) were added DIPEA (3.93 mL, 0.0297 mmol, 2 eq) and 2-(2,6-dioxopiperidin-3-yl)-5-fluoroisoindoline-1,3-dione (4.1 g, 0.0148 mmol, 1 eq). The reaction mixture was heated at 90° C. under argon for 40 h. The reaction mixture was cooled down to rt and 5 mL of water was added dropwise. A bright-yellow precipitate was formed and it was filtered off, washed 2 times with water on the filter. The filtrate was extracted 2 times with DCM. The combined DCM layers were concentrated in vacuo and combined with the precipitate. The crude was purified by flash column chromatography to give tert-butyl 2-{4-[2-(2,6-dioxopiperidin-3-yl)-1,3-dioxo-2,3-dihydro-1H-isoindol-5-yl]piperazin-1-yl}acetate as a yellow solid (5.49 g, 81% yield). ESI[M+H]=457.7; $^1H$ NMR (300 MHz, Chloroform-d) δ 8.07 (s, 1H), 7.72 (d, J=8.5 Hz, 1H), 7.31 (d, J=2.3 Hz, 1H), 7.08 (dd, J=8.6, 2.4 Hz, 1H), 4.96 (dd, J=12.2, 5.2 Hz, 1H), 3.55-3.45 (m, 4H), 3.21 (s, 2H), 2.98-2.81 (m, 2H), 2.81-2.72 (m, 5H), 2.24-2.09 (m, 1H), 1.50 (s, 9H).

Step 2: 2-{4-[2-(2,6-dioxopiperidin-3-yl)-1,3-dioxo-2,3-dihydro-1H-isoindol-5-yl]piperazin-1-yl}acetic acid trifluoroacetate. To a solution of tert-butyl 2-{4-[2-(2,6-dioxopiperidin-3-yl)-1,3-dioxo-2,3-dihydro-1H-isoindol-5-yl]piperazin-1-yl}acetate (5.49 g, 12.03 mmol, 1 eq) in DCM (100 mL, 0.12 M) TFA (50.6 mL, 661 mmol, 55 eq) was added. The reaction mixture was stirred 16 h at rt and then concentrated under reduced pressure. The resulting bright-yellow sticky solid was sonicated with 200 mL of anhydrous diethyl ether and additionally stirred for 1 hour. The resulting precipitate was filtered, washed twice with anhydrous $Et_{2}O$, and dried under reduced pressure to give a bright-yellow solid (6.55 g, quant). LCMS (254 nm): RT=2.69 min, 98.59%, ESI$[M+H]^+$=401.14; $^1H$ NMR (400 MHz, DMSO-$d_6$) δ 11.11 (s, 1H), 10.87 (br. s, 1H), 7.77 (d, J=8.4 Hz, 1H), 7.48 (d, J=2.3 Hz, 1H), 7.34 (dd, J=8.6, 2.3 Hz, 1H), 6.27 (br. s, 2H), 5.10 (dd, J=12.9, 5.4 Hz, 1H), 4.22 (s, 2H), 4.11 (br. s, 2H), 3.45 (br. s, 6H), 3.38 (dd, J=139.7, 7.0 Hz, 8H), 2.90 (ddd, J=17.4, 14.1, 5.5 Hz, 1H), 2.65-2.52 (m, 2H), 2.10-1.97 (m, 1H).

HCB15: 6-((2-(2,6-dioxopiperidin-3-yl)-1,3-dioxoisoindolin-4-yl)amino)hexanoic acid

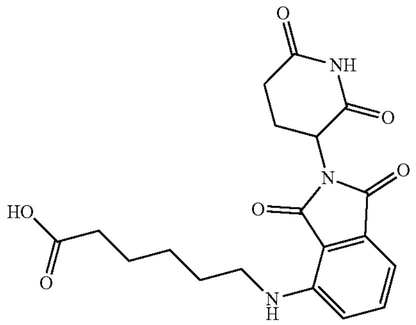 [SMILES: O=C(O)CCCCCNc1cccc2c1C(=O)N(C1CCC(=O)NC1=O)C2=O]

Prepared in a similar manner as HCB3 substituting 2-(2,6-dioxopiperidin-3-yl)-4-fluoroisoindoline-1,3-dione for 2-(2,6-dioxopiperidin-3-yl)-5-fluoroisoindoline-1,3-dione to give the title compound. LCMS $C_{19}H_{21}N_3O_6$ requires: 387.1. found: m/z=385.9$[M-H]^-$ HCB16: 8-((2-(2,6-dioxopiperidin-3-yl)-1,3-dioxoisoindolin-5-yl)amino)octanoic acid

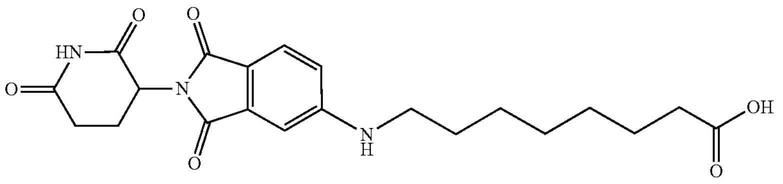 [SMILES: O=C(O)CCCCCCCNc1ccc2c(c1)C(=O)N(C1CCC(=O)NC1=O)C2=O]

Prepared in a similar manner as HCB3 substituting tert-butyl 6-aminohexanoate hydrochloride for tert-butyl 8-aminooctanoate to give the title compound. LCMS $C_{21}H_{25}N_3O_6$ requires: 415.2. found: m/z=414.2$[M-H]^-$ HCB17: 2-(4-(2-(1-methyl-2,6-dioxopiperidin-3-yl)-1,3-dioxoisoindolin-5-yl)piperazin-1-yl)acetic acid

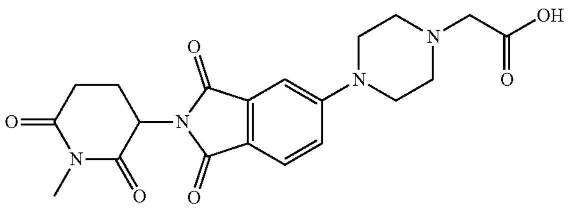 [SMILES: CN1C(=O)CCC(N2C(=O)c3ccc(N4CCN(CC(=O)O)CC4)cc3C2=O)C1=O]

The title compound was synthesized in a similar manner as HCB14 substituting 2-(2,6-dioxopiperidin-3-yl)-5-fluoroisoindoline-1,3-dione with 5-fluoro-2-(1-methyl-2,6-dioxopiperidin-3-yl)isoindoline-1,3-dione. LCMS $C_{20}H_{22}N_4O_6$ requires: 414.2. found: m/z=415.4$[M+H]^+$ HCB18: N-(2,6-dioxopiperidin-3-yl)-5-(4-formylpiperidin-1-yl)pyridine-2-carboxamide

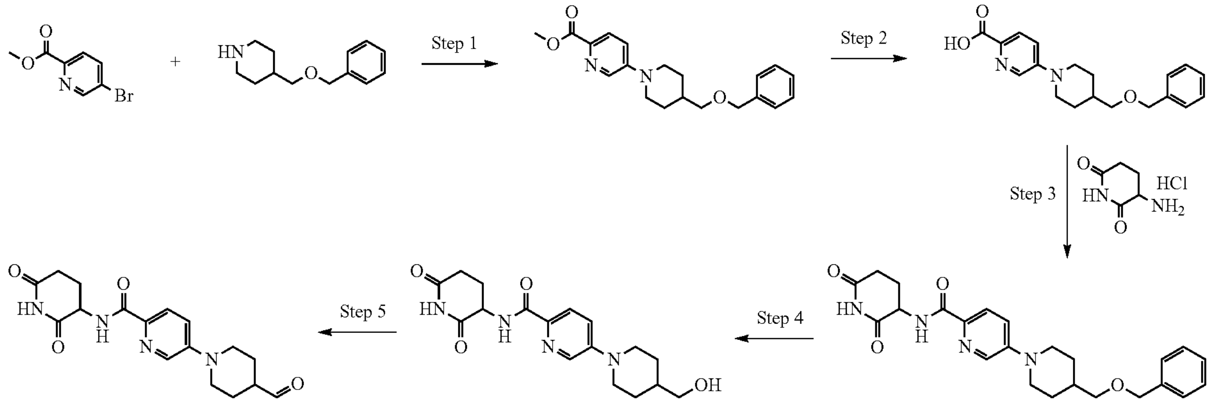

HCB18

Step 1: methyl 5-{4-[(benzyloxy)methyl]piperidin-1-yl}pyridine-2-carboxylate. A mixture of methyl 5-bromopyridine-2-carboxylate (1.0 g, 4.63 mmol, 1.0 equiv), 4-[(benzyloxy)methyl]piperidine (950 mg, 4.63 mmol, 1.0 equiv), rac-BINAP (288 mg, 463 μmol, 0.1 equiv), $Pd_2(dba)_3$ (432 mg, 463 μmol, 0.1 equiv), $Cs_2CO_3$ (4.52 g, 13.9 mmol, 3.0 equiv) was suspended in toluene (30 mL) and the mixture was heated to 100° C. for 12 h. The reaction mixture was cooled to rt and diluted with EtOAc (100 mL) before being filtered and purified ($SiO_2$, 10→100% EtOAc/Hexanes, elutes at 70%) afforded methyl 5-{4-[(benzyloxy)methyl]piperidin-1-yl}pyridine-2-carboxylate (1.1 g, 67%). LCMS: $C_{20}H_{24}N_2O_3$ requires: 340. found: m/z=341 $[M+H]^+$.

Step 2: afford 5-{4-[(benzyloxy)methyl]piperidin-1-yl}pyridine-2-carboxylic acid. Methyl 5-{4-[(benzyloxy)methyl]piperidin-1-yl}pyridine-2-carboxylate (510 mg, 1.50 mmol, 1.0 equiv) was suspended in MeOH/$H_2O$ (1:4) and NaOH (90 mg, 2.25 mmol, 1.5 equiv) was added in one portion at rt. After 16 h, HCl (1 M, aq) was added to result in a pH=5 solution. The solids were collected by filtration to afford 5-{4-[(benzyloxy)methyl]piperidin-1-yl}pyridine-2-carboxylic acid (800 mg, 83%). LCMS: $C_{19}H_{22}N_2O_3$ requires: 326. found: m/z=327 $[M+H]^+$.

Step 3: 5-{4-[(benzyloxy)methyl]piperidin-1-yl}-N-(2,6-dioxopiperidin-3-yl)pyridine-2-carboxamide. 5-{4-[(benzyloxy)methyl]piperidin-1-yl}pyridine-2-carboxylic acid (510 mg, 1.56 mmol, 1.0 equiv) was DMF (1 mL) and HATU (594 mg, 1.56 mmol, 1.0 equiv) was added at rt. After 5 min 3-aminopiperidine-2,6-dione hydrochloride (257 mg, 1.56 mmol, 1.0 equiv) and DIPEA (1.09 mL, 6.25 mmol, 4.0 equiv) were added. The mixture was stirred for 16 h and partitioned between EtOAc/$H_2O$ (20 mL ea). The organic phase was washed (2×5 mL $H_2O$, 1×5 mL brine) and the organic phase was dried ($Na_2SO_4$), filtered, and concentrated.

Purification ($SiO_2$, 0→4% MeOH/$CH_2Cl_2$) afforded 5-{4-[(benzyloxy)methyl]piperidin-1-yl}-N-(2,6-dioxopiperidin-3-yl)pyridine-2-carboxamide (625 mg, 92%) as a white solid. LCMS: $C_{24}H_{28}N_4O_4$ requires: 436. found: m/z=437 $[M+H]^+$.

Step 4: N-(2,6-dioxopiperidin-3-yl)-5-[4-(hydroxymethyl)piperidin-1-yl]pyridine-2-carboxamide. 5-{4-[(benzyloxy)methyl]piperidin-1-yl}-N-(2,6-dioxopiperidin-3-yl)pyridine-2-carboxamide (500 mg, 1.15 mmol, 1.0 equiv), acetic acid (196 μL, 3.44 mmol, 3.0 equiv), $Pd(OH)_2$ (50 mg) and Pd/C (50 mg) were suspended in EtOH (100 mL) under an atmosphere of $H_2$ (balloon). The mixture was heated to 40° C. for 18 h before being cooled, filtered and concentrated. Purification ($SiO_2$, 0→8% MeOH/$CH_2Cl_2$) afforded N-(2,6-dioxopiperidin-3-yl)-5-[4-(hydroxymethyl)piperidin-1-yl]pyridine-2-carboxamide (233 mg, 58%) as a white solid. $^1H$ NMR (500 MHz, DMSO-$d_6$) δ 10.84 (s, 1H), 8.69 (d, J=8.3 Hz, 1H), 8.30 (d, J=3.0 Hz, 1H), 7.83 (d, J=8.8 Hz, 1H), 7.40 (dd, J=9.0, 3.0 Hz, 1H), 4.74 (dq, J=13.3, 6.4, 5.8 Hz, 1H), 3.95 (d, J=12.7 Hz, 2H), 3.28 (d, J=6.1 Hz, 2H), 2.88-2.73 (m, 3H), 2.53 (s, 2H), 2.23-2.11 (m, 1H), 2.01 (d, J=13.1 Hz, 1H), 1.78-1.71 (m, 2H), 1.61 (s, 1H), 1.21 (h, J=11.0, 10.6 Hz, 2H). LCMS: $C_{17}H_{22}N_4O_4$ requires: 346. found: m/z=347 $[M+H]^+$.

Step 5: N-(2,6-dioxopiperidin-3-yl)-5-(4-formylpiperidin-1-yl)pyridine-2-carboxamide. A mixture of N-(2,6-dioxopiperidin-3-yl)-5-[4-(hydroxymethyl)piperidin-1-yl]pyridine-2-carboxamide (200 mg, 580 μmol, 1.0 equiv) and $Et_3N$ (321 μL, 2.31 mmol, 4.0 equiv) was dissolved in DMSO (500 μL) and $CH_2C_{12}$ (500 μL). The reaction mixture was cooled to 0° C. and $SO_3$.pyridine (184 mg, 1.15 equiv, 2.0 equiv, solution in 300 μL DMSO) was added dropwise. The reaction mixture was warmed to rt and stirred for 30 min before $NaHCO_3$ (5 mL, sat. aq.) was added. After 1 min the suspension was diluted with $CH_2C_{12}$ (10 mL) and the aqueous phase was extracted (3×10 mL $CH_2Cl_2$). The combined organics were washed (2×5 mL $H_2O$, 1×5 mL brine), dried ($Na_2SO_4$), filtered, and concentrated. Purification ($SiO_2$, 0→10% MeOH/$CH_2Cl_2$, elutes at 5%) afforded N-(2,6-dioxopiperidin-3-yl)-5-(4-formylpiperidin-1-yl)pyridine-2-carboxamide as a white foam (190 mg, 95%). LCMS: $C_{17}H_{20}N_4O_4$ requires: 344. found: m/z=345 $[M+H]^+$.

HCB19: N-(2,6-dioxopiperidin-3-yl)-4-formylbenzamide

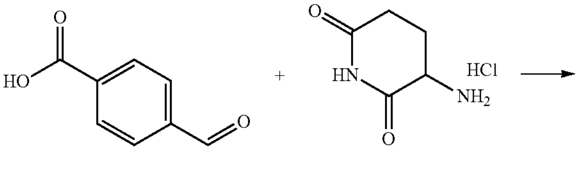

-continued

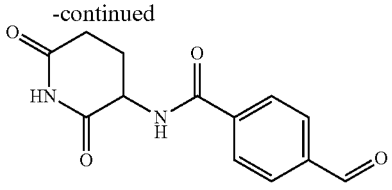

HCB19

4-Formylbenzoic acid (500 mg, 3.33 mmol) and HATU were combined in DMF, followed by addition of DIPEA (4 eq, 13.3 mmol), and stirring for 5 minutes. 3-aminopiperidine-2,6-dione hydrochloride was then added and the reaction stirred for 18 hr before direct purification with reverse phase chromatography C18 column, 0-100% acetonitrile in water) to provide desired product (0.6 g, 69% yield).

LCMS: $C_{13}H_{12}N_2O_4$ requires: 260.1. found: m/z=261.2 $[M+H]^+$.

HCB20: (3R)-1-(1-(2,6-dioxopiperidin-3-yl)-3-methyl-2-oxo-2,3-dihydro-1H-benzo[d]imidazol-5-yl)pyrrolidine-3-carbaldehyde

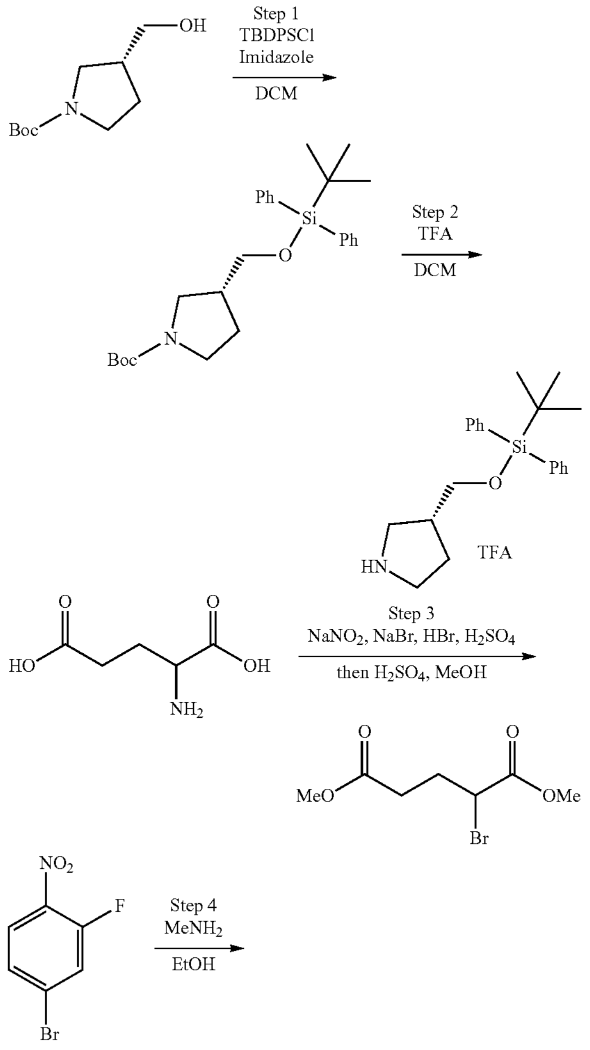

-continued

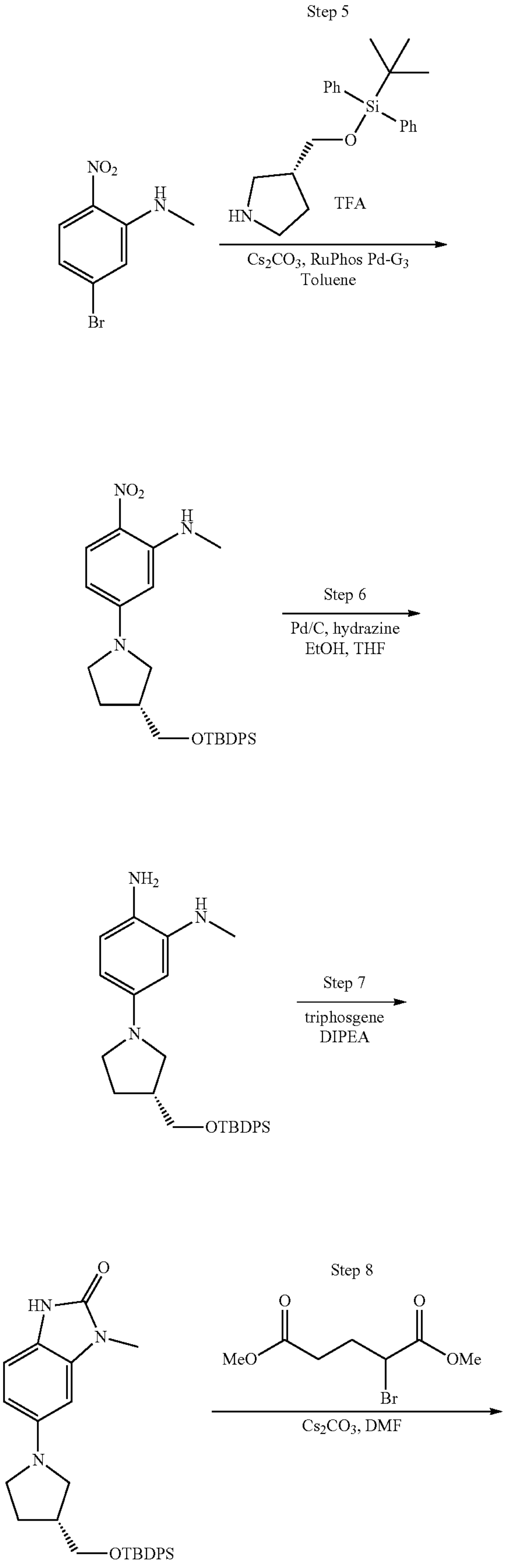

-continued

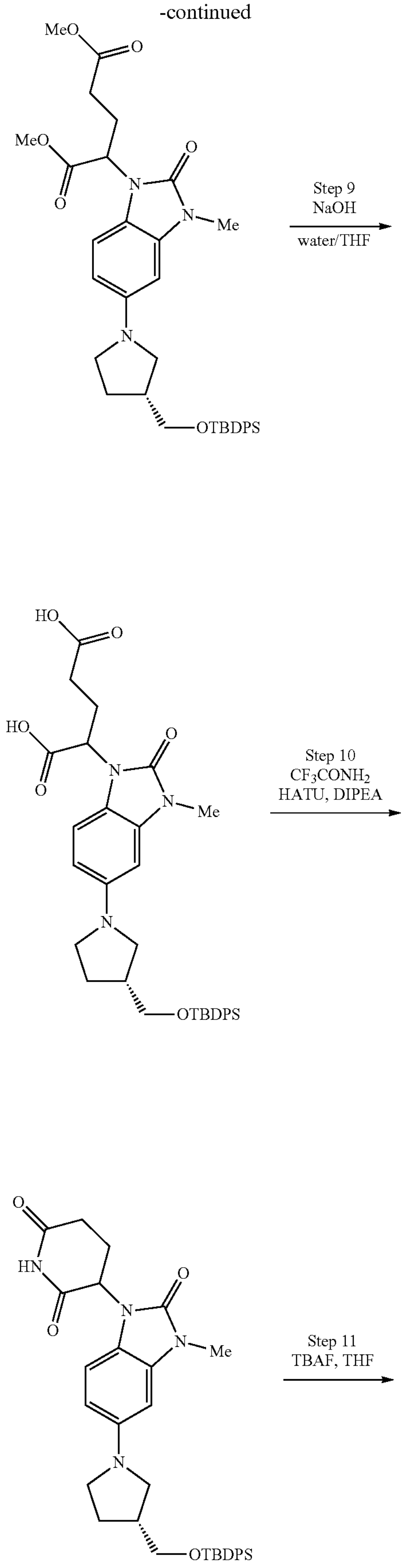

-continued

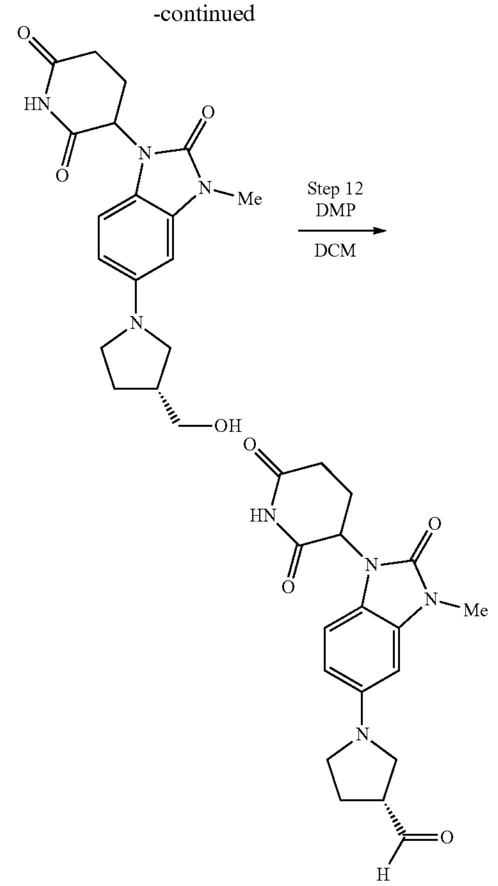

HCB20

Step 1: tert-butyl (3R)-3-[[tert-butyl(diphenyl)silyl]oxymethyl]pyrrolidine-1-carboxylate. TBDPSCl (32.3 mL, 124 mmol) was added to a mixture of tert-butyl (3R)-3-(hydroxymethyl)pyrrolidine-1-carboxylate (25.0 g, 124 mmol) and imidazole (10.1 g, 149 mmol) in DCM (500 mL) at 0° C. under nitrogen. The mixture was stirred at 23° C. for 16 h and diluted with water (300 mL). The organic phase was washed with water (100 mL), brine (3×100 mL), dried ($Na_2SO_4$), filtrated, and concentrated to provide the title compound as an oil (54.0 g, 99%). m/z: $ES^+$ $[M-C_6H_5-tBu+H]^+$=306.2, LCMS (A05); $t_R$=2.47 min.; $^1H$ NMR (500 MHz, $CDCl_3$) δ 7.67-7.60 (m, 4H), 7.46-7.34 (m, 6H), 3.64-3.55 (m, 2H), 3.45-3.37 (m, 1H), 3.37-3.22 (m, 1H), 3.17-3.07 (m, 1H), 2.42 (m, 1H), 1.97-1.86 (m, 1H), 1.74-1.62 (m, 1H), 1.60 (s, 1H), 1.46 (s, 9H), 1.08-1.02 (m, 9H);

Step 2: tert-butyl-diphenyl-[[(3R)-pyrrolidin-3-yl]methoxy]silane 2,2,2-trifluoroacetic acid. TFA (50 mL) was added to a mixture of tert-butyl (3R)-3-[[tert-butyl(diphenyl)silyl]oxymethyl]pyrrolidine-1-carboxylate, (54.0 g, 123 mmol) in DCM (200 mL) at 23° C. under nitrogen. The mixture was stirred at 23° C. for 1.5 h and concentrated. The residue was diluted with PhMe (150 mL) and concentrated (process repeated twice) to provide the title compound as an oil (55.7 g, quant.). m/z: $ES+[M+H-TFA]^+$=340.3, LCMS (A05); $t_R$=2.32 min. $^1H$ NMR (500 MHz, $CDCl_3$) δ 8.82 (s, 2H), 7.65-7.57 (m, 4H), 7.52-7.40 (m, 6H), 3.65 (d, J=6.4 Hz, 2H), 3.35-3.27 (m, 1H), 3.24-3.10 (m, 2H), 3.01-2.91 (m, 1H), 2.58-2.52 (m, 1H), 2.04-1.93 (m, 1H), 1.74-1.63 (m, 1H), 1.01 (s, 9H);

Step 3: dimethyl 2-bromopentanedioate. A solution of $NaNO_2$ (25.5 g, 370 mmol) in water (50 mL) was added to a mixture of (2S)-2-aminopentanedioic acid (30 g, 204 mmol), NaBr (73.2 g, 711 mol) and HBr (50 mL, 48% in water), in water (100 mL) at 0° C. (keeping the internal temperature below 10° C.) under nitrogen. The mixture was stirred at 23° C. for 6 h and $H_2SO_4$ (25.0 mL) was added at 23° C. The mixture was extracted with $Et_2O$ (4×70.0 mL) and the combined organic phases were washed with brine (2×50.0 mL), dried ($Na_2SO_4$), filtered and concentrated. $H_2SO_4$ (10.0 mL) was added to the mixture of the residue in MeOH (80.0 mL) at 23° C. under nitrogen. The mixture was refluxed for 16 h, cooled to 23° C. and concentrated. The residue was diluted with $Et_2O$ (100 mL) and water (100 mL). The aq. phase was extracted with $Et_{20}$ (4×50.0 mL). The combined organic layers were washed with water (60.0 mL), $NaHCO_3$ (2×60.0 mL), brine (2×50.0 mL), dried ($Na_2SO_4$), filtered, and concentrated to provide the title compound as an oil (19 g, 39%). $^1$H NMR (400 MHz, $CDCl_3$) δ 4.34 (dd, J=8.5, 5.8 Hz, 1H), 3.75 (s, 3H), 3.65 (s, 3H), 2.52-2.45 (m, 2H), 2.40-2.30 (m, 1H), 2.26 (m, 1H).

Step 4: 5-bromo-N-methyl-2-nitro-aniline. Methylamine (56.6 mL, 455 mmol, 33% wt in EtOH) was added to a mixture of 4-bromo-2-fluoro-1-nitro-benzene (50.0 g, 227 mmol) in EtOH (455 mL) at 23° C. under nitrogen. The mixture was stirred at 23° C. for 30 min, filtered and washed with cold EtOH (200 mL) to provide the title compound as a solid (48.2 g, 92%). m/z (ES+) $[M+H]^+$=231.0, LCMS (A05); $t_R$=2.51 min. $^1$H NMR (400 MHz, DMSO-$d_6$) δ 8.23 (d, J=4.3 Hz, 1H), 7.98 (d, J=9.1 Hz, 1H), 7.17 (d, J=2.0 Hz, 1H), 6.82 (dd, J=9.1, 2.1 Hz, 1H), 2.95 (d, J=5.0 Hz, 3H)

Step 5: [(3R)-1-[3-(methylamino)-4-nitro-phenyl]pyrrolidin-3-yl]methanol. RuPhos-Pd-G3 (2.71 g, 3.25 mmol) was added to a mixture of 5-bromo-N-methyl-2-nitro-aniline, (25 g, 108 mmol), tert-butyl-diphenyl-[[(3R)-pyrrolidin-3-yl]methoxy]silane 2,2,2-trifluoroacetic acid_(60.0 g, 119 mmol, 90% purity) and $Cs_2CO_3$ (106 g, 325 mmol) in PhMe (600 mL) at 23° C. under nitrogen. The mixture was degassed by bubbling nitrogen for 15 min at 23° C., stirred at 100° C. for 19 h, cooled to 23° C., filtered, and concentrated. The product was purified by silica gel chromatography (2×330 g cartridges in series) with hexanes and EtOAc (0-50%) to provide the title compound as a solid (41.0 g, 77%). m/z: $ES^+$ $[M+H]^+$=490.4; $^1$H NMR (400 MHz, DMSO-$d_6$) δ 8.36 (d, J=4.9 Hz, 1H), 7.91 (d, J=9.6 Hz, 1H), 7.64-7.57 (m, 4H), 7.50-7.37 (m, 6H), 6.07 (dd, J=9.6, 2.5 Hz, 1H), 5.50 (d, J=2.4 Hz, 1H), 3.68 (d, J=6.6 Hz, 2H), 3.54-3.46 (m, 1H), 3.46-3.37 (m, 2H), 3.27-3.21 (m, 1H), 2.90 (d, J=5.0 Hz, 3H), 2.64-2.55 (m, 1H), 2.16-2.04 (m, 1H), 1.90-1.79 (m, 1H), 1.01 (s, 9H)

Step 6: 4-[(3R)-3-ethylpyrrolidin-1-yl]-$N_2$-methyl-benzene-1,2-diamine. A solution of [(3R)-1-[3-(methylamino)-4-nitro-phenyl]pyrrolidin-3-yl]methanol, (20.0 g, 40.8 mmol) in THF (100 mL) and EtOH (100 mL) was added to 10% Pd/C (4.4 g, 4.1 mmol, 50% wet.) at 23° C. under nitrogen. The mixture was refluxed, and hydrazine hydrate (16 mL, 163 mmol) was added (over 30 min). The mixture was refluxed for 2 h, cooled to 23° C., filtered (Celite), washed with EtOAc (200 mL) and EtOH (200 mL), and concentrated to provide the title compound as an oil (18.0 g, 96%). m/z $ESI^+$ $[M-Ph-tBu+H]^+$=328.16; $^1$H NMR (400 MHz, DMSO-$d_6$) δ 7.65-7.59 (m, 4H), 7.48-7.38 (m, 6H), 6.45-6.40 (m, 1H), 5.71 (d, J=2.5 Hz, 1H), 5.66 (dd, J=8.1, 2.5 Hz, 1H), 4.50 (d, J=4.9 Hz, 1H), 3.65 (d, J=6.8 Hz, 2H), 3.33 (br. s, 2H), 3.21 (dd, J=9.1, 7.6 Hz, 1H), 3.14-3.07 (m, 2H), 2.97 (dd, J=9.2, 5.9 Hz, 1H), 2.68 (d, J=4.2 Hz, 3H), 2.56-2.51 (m, 1H), 2.05-1.95 (m, 1H), 1.76-1.67 (m, 1H), 1.01 (s, 9H);

Step 7: 5-[(3R)-3-ethylpyrrolidin-1-yl]-3-methyl-1H-benzimidazol-2-one. A mixture of triphosgene (8.09 g, 27.3 mmol) in DCM (30 mL) was added to a mixture of ISN-4-[(3R)-3-ethylpyrrolidin-1-yl]-$N_2$-methyl-benzene-1,2-diamine, (38.0 g, 82.7 mmol) and DIPEA (115 mL, 661 mmol) in DCM (300 mL) at to 0° C. under nitrogen.

The mixture was stirred at 0° C. for 30 min and diluted with water (300 mL). The aq. phase was extracted with DCM (2×100 mL), and the combined organic phases were washed with brine (50.0 mL), dried ($MgSO_4$), filtered, and concentrated. The product was purified by silica gel chromatography (2×330 g cartridge) with DCM and MeOH (0-10%) to provide the title compound as a solid (21 g, 52%). m/z: $ES^+$ $[M+H]^+$=486.4, Step 8: Dimethyl 2-[5-[(3R)-3-ethylpyrrolidin-1-yl]-3-methyl-2-oxo-benzimidazol-1-yl]pentanedioate. Dimethyl 2-bromopentanedioate (10.9 g, 30.9 mmol, 68% purity) was added to a mixture of 5-[(3R)-3-ethylpyrrolidin-1-yl]-3-methyl-1H-benzimidazol-2-one, (10.0 g, 20.6 mmol) and $Cs_2CO_3$ (20.3 g, 62.3 mmol) in DMF (100 mL) at 23° C. under nitrogen. The mixture was stirred at 100° C. for 18 h, cooled to 23° C. and diluted with EtOAc (200 mL) and water (100 mL). The aq. phase was extracted with EtOAc (2×100 mL), and the combined organic phases were washed with brine (2×50 mL), dried ($MgSO_4$), filtered, and concentrated. The product was purified by silica gel chromatography (220 g cartridge) with hexanes and EtOAc (0-50%) to provide the title compound as a solid (9.00 g, 68%). m/z: $ES^+$ $[M+H]^+$ =644.4, LCMS (A05); $t_R$=2.33 min.

Step 9: 2-[5-[(3R)-3-ethylpyrrolidin-1-yl]-3-methyl-2-oxo-benzimidazol-1-yl]pentanedioic acid. Aq. NaOH (5 M, 14.0 mL, 70.0 mmol) was added to a mixture of Dimethyl 2-[5-[(3R)-3-ethylpyrrolidin-1-yl]-3-methyl-2-oxo-benzimidazol-1-yl]pentanedioate, (9.00 g, 14.0 mmol) in a mixture of THF and water (200 mL, 1:1 v/v) at 23° C. under nitrogen. The mixture was stirred at 23° C. for 1 h and diluted with EtOAc (100 mL) and aq. HCl (1 M, 80.0 mL). The aq. phase was extracted with EtOAc (3×50.0 mL) and the combined organic phases were washed with brine (2×50.0 mL), dried ($Na_2SO_4$), filtered, and concentrated to provide the title compound as a solid (8.6 g, quant.). $^1$H NMR (500 MHz, DMSO-$d_6$) δ 7.67-7.58 (m, 4H), 7.51-7.36 (m, 6H), 6.93-6.81 (m, 1H), 6.41-6.30 (m, 1H), 6.27-6.17 (m, 1H), 4.95 (dd, J=10.8, 5.0 Hz, 1H), 3.69 (d, J=6.6 Hz, 2H), 3.38-3.31 (m, 1H), 3.29 (s, 3H), 3.27-3.19 (m, 2H), 3.12-3.03 (m, 1H), 2.65-2.55 (m, 1H), 2.41-2.21 (m, 2H), 2.21-2.02 (m, 3H), 1.86-1.79 (m, 1H), 1.02 (s, 9H).

Step 10: 3-[5-[(3R)-3-ethylpyrrolidin-1-yl]-3-methyl-2-oxo-benzimidazol-1-yl]piperidine-2,6-dione. HATU (6.792 g, 17.9 mmol) was added to a mixture of 2-[5-[(3R)-3-ethylpyrrolidin-1-yl]-3-methyl-2-oxo-benzimidazol-1-yl] pentanedioic acid, (5.0 g, 8.12 mmol), trifluoroacetamide (1.01 g, 8.93 mmol) and DIPEA (5.66 mL, 32.5 mmol) in DMF (50.0 mL) at 23° C. under nitrogen. The mixture was stirred at 23° C. for 18 h and concentrated. The product was purified by silica gel chromatography (120 g cartridge) with DCM and MeOH (0-5%) to provide the title compound as a solid (3.30 g, 68%). $^1$H NMR (500 MHz, DMSO-$d_6$) δ 11.04 (s, 1H), 7.65-7.60 (m, 4H), 7.50-7.39 (m, 6H), 6.93-6.87 (m, 1H), 6.35 (d, J=2.1 Hz, 1H), 6.20 (dd, J=8.6, 2.2 Hz, 1H), 5.26 (dd, J=12.8, 5.4 Hz, 1H), 3.69 (d, J=6.6 Hz, 2H), 3.29 (s, 3H), 3.26-3.20 (m, 2H), 3.08-3.02 (m, 1H), 2.93-2.85 (m, 1H), 2.70 (s, 2H), 2.67-2.55 (m, 2H), 2.13-2.04 (m, 1H), 1.98-1.95 (m, 1H), 1.86-1.76 (m, 1H), 1.02 (s, 9H).

Step 11: 3-[5-[(3R)-3-(hydroxymethyl)pyrrolidin-1-yl]-3-methyl-2-oxo-benzimidazol-1-yl]piperidine-2,6-dione.

TBAF (8.00 mL, 8.00 mmol, 1M in THF) was added to a mixture of 3-[5-[(3R)-3-ethylpyrrolidin-1-yl]-3-methyl-2-oxo-benzimidazol-1-yl]piperidine-2,6-dione, (3.20 g, 5.36 mmol) in THF (20 mL) at 23° C. under nitrogen. The mixture was stirred at 23° C. for 3 h and concentrated. The product was purified by silica gel chromatography (220 g cartridge) with DCM and MeOH (0-12%) to provide the title compound as a solid (1.30 g, 67%). m/z: $ES^+$ $[M]^+$=358.2; $^1H$ NMR (400 MHz, DMSO-$d_6$) δ 11.03 (s, 1H), 6.89 (d, J=8.5 Hz, 1H), 6.37 (d, J=2.2 Hz, 1H), 6.21 (dd, J=8.6, 2.2 Hz, 1H), 5.25 (dd, J=12.9, 5.4 Hz, 1H), 4.69 (t, J=5.2 Hz, 1H), 3.48-3.36 (m, 2H), 3.37-3.32 (m, 1H), 3.29 (s, 3H), 3.27-3.15 (m, 2H), 3.05-2.97 (m, 1H), 2.95-2.83 (m, 1H), 2.73-2.55 (m, 2H), 2.48-2.37 (m, 1H), 2.08-1.92 (m, 2H), 1.79-1.68 (m, 1H);

Step 12: (3R)-1-(1-(2,6-dioxopiperidin-3-yl)-3-methyl-2-oxo-2,3-dihydro-1H-benzo[d]imidazol-5-yl)pyrrolidine-3-carbaldehyde. To a mixture of (3RS)-3-{5-[(3R)-3-(hydroxymethyl)pyrrolidin-1-yl]-3-methyl-2-oxo-1,3-benzodiazol-1-yl}piperidine-2,6-dione (33.50 mg, 0.09 mmol) in DMSO (1.00 mL) was added triethylamine (0.26 mL, 0.19 g, 1.87 mmol) followed by sulfur trioxide pyridine complex (148.77 mg, 0.93 mmol). After 25 minutes, water was added, and the mixture was extracted with DCM twice. The combined organic layers were concentrated to give the title compound without further purification. m/z: $ES^+$ $[M]^+$=357.2. VHL-targeting LHM building block can be generally prepared according to Scheme B3, in which a LHM is first coupled to a linker precursor comprising "linker A" (representing one or more linker segments) and two terminal reactive groups. One of the reactive groups is carboxylic acid or reactive equivalent thereof, the other reactive group X may be, for example, carboxylic acid, hydroxyl or aldehyde group. The resulting LHM building block has a reactive moiety (X), which can be further coupled to another moiety.

HCB21: N-(2,6-dioxopiperidin-3-yl)-4-(4-formylpiperidin-1-yl)-N-methylbenzamide

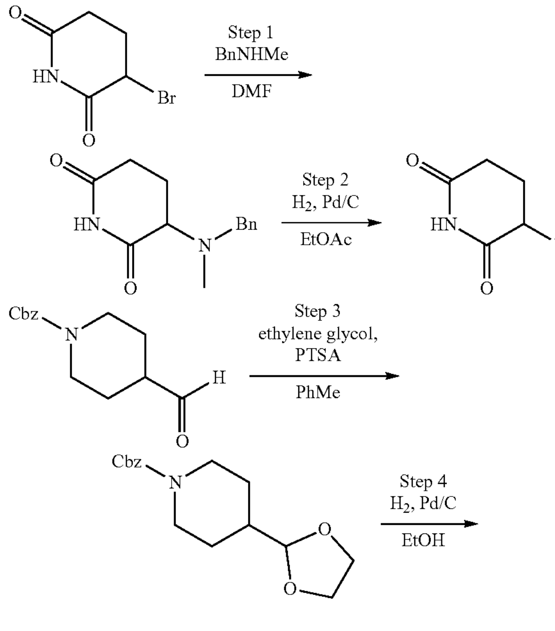

-continued

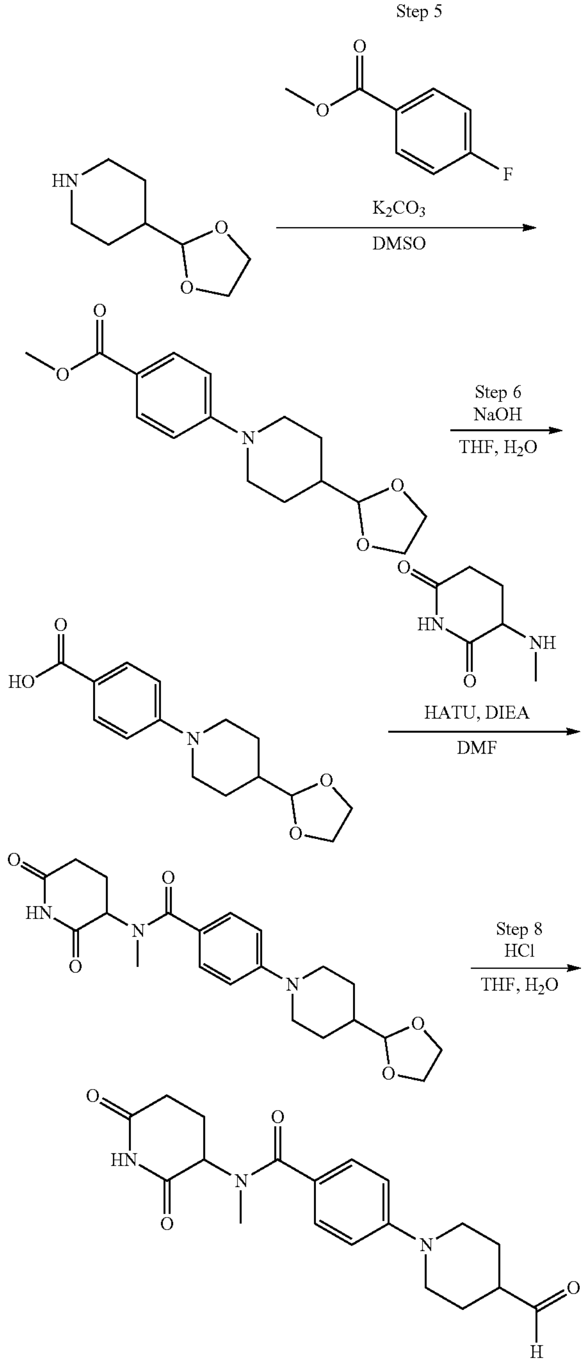

HCB21

Step 1: 3-[benzyl(methyl)amino]piperidine-2,6-dione. A mixture of 3-bromopiperidine-2,6-dione (6.00 g, 31.2 mmol), N-methyl-1-phenyl-methanamine (10.0 g, 82.5 mmol) in DMF (30.0 mL) was stirred at 23° C. for 16 h. The mixture was concentrated. The residue was diluted with toluene (100 mL) and DCM (20.0 mL). The solid was filtered off. The filtrate was further diluted with water (200 mL), ether (100 mL) and EtOAc (200 mL). The organic phase was separated, and the aq. phase was extracted with EtOAc (3×100 mL). The combined organic phases were washed with brine (3×50.0 mL), dried ($Na_2SO_4$), filtered, and concentrated. The residue was suspended in hexanes/ ether (10:1 ratio by volume; 200 mL) and stirred for 10 minutes. The solid was collected by filtration and dried under high vacuum to provide the title compound as an off white solid (5.65 g, 78%). $^1$H NMR (500 MHz, DMSO-$d_6$) δ 10.63 (s, 1H), 7.36-7.29 (m, 4H), 7.27-7.21 (m, 1H), 3.78 (s, 2H), 3.61 (dd, J=12.1, 4.7 Hz, 1H), 2.66-2.57 (m, 1H), 2.51 (s, 1H), 2.25 (s, 3H), 2.15-2.05 (m, 1H), 1.98-1.90 (m, 1H).

Step 2: 3-(methylamino)piperidine-2,6-dione. Into a Parr shaker vessel, a solution of 3-[benzyl(methyl)amino]piperidine-2,6-dione (5.65 g, 24.3 mmol) in EtOAc (60.0 mL) was added to 10% Pd/C (1.58 g, 1.49 mmol) under nitrogen. The mixture was purged with hydrogen and stirred at 23° C. for 18 h at 50 psi. The mixture was filtered through celite, washing with EtOAc (100 mL) and DCM (100 mL). The filtrate was concentrated to provide the title compound as a light blue solid (3.10 g, 90%). $^1$H NMR (400 MHz, DMSO-$d_6$) δ 10.63 (s, 1H), 3.16 (dd, J=10.3, 4.8 Hz, 1H), 2.52-2.41 (m, 2H), 2.27 (s, 3H), 2.26-2.22 (m, 1H), 2.02-1.93 (m, 1H), 1.71-1.57 (m, 1H). m/z (ES$^+$), [M+H]$^+$ 143.1

Step 3: Benzyl 4-(1,3-dioxolan-2-yl)piperidine-1-carboxylate. A solution of benzyl 4-formylpiperidine-1-carboxylate (25.0 g, 101 mmol), PTSA (515 mg, 2.71 mmol) and ethylene glycol (35.0 mL, 142 mmol) in toluene (120 mL) was refluxed with Dean-Stark apparatus for 7 h. After cooling to 23° C., the mixture was concentrated. The residue was diluted with sat. $NaHCO_3$ (100 mL) and EtOAc (200 mL). The organic phase was separated, washed with sat. $NaHCO_3$ (2×50.0 mL), brine (2×100 mL), dried ($Na_2SO_4$), filtered, and concentrated to provide the title compound as a light yellow oil (29.5 g 100%). $^1$H NMR (400 MHz, $CDCl_3$) δ 7.36-7.24 (m, 5H), 5.09 (s, 2H), 4.61 (d, J=4.6 Hz, 1H), 4.30-4.08 (m, 2H), 3.94-3.86 (m, 2H), 3.86-3.78 (m, 2H), 2.83-2.63 (m, 2H), 1.77-1.64 (m, 3H), 1.40-1.21 (m, 2H).

Step 4: 4-(1,3-dioxolan-2-yl)piperidine. A solution of Benzyl 4-(1,3-dioxolan-2-yl)piperidine-1-carboxylate_ (29.5 g, 422 mmol) in EtOH (120 mL) was added to 10% Pd/C (7.20 g, 6.76 mmol) under nitrogen. The suspension was purged with hydrogen and stirred at 23° C. for 4 h. The mixture was filtered through Celite and washing with DCM (200 mL). The filtrated was concentrated to provide the title compound as a colorless oil (15.1 g, 95%). $^1$H NMR (500 MHz, $CDCl_3$) δ 4.60 (dd, J=5.1, 2.3 Hz, 1H), 3.96-3.89 (m, 2H), 3.84 (dd, J=4.2, 2.2 Hz, 2H), 3.08 (d, J=2.0 Hz, 2H), 2.58 (tt, J=12.3, 2.3 Hz, 2H), 1.70 (s, 2H), 1.68-1.61 (m, 1H), 1.34-1.24 (m, 2H), 1.21 (d, J=3.3 Hz, 1H).

Step 5: Methyl 4-[4-(1,3-dioxolan-2-yl)-1-piperidyl]benzoate. A mixture of 4-(1,3-dioxolan-2-yl)piperidine (8.00 g, 50.9 mmol), methyl 5-fluoropyridine-2-carboxylate (7.85 g, 50.9 mmol) and $K_2CO_3$ (7.04 g, 50.9 mmol) in anhydrous DMSO (20.0 mL) was heated at 80° C. for 4 h. After cooling to 23° C., water (200 mL) was added. The solid was collected by filtration and dried under high vacuum to provide the title compound as an off white solid (13.8 g, 93%). m/z (ES$^+$), [M+H]$^+$ 292.2

Step 6: 4-[4-(1,3-dioxolan-2-yl)-1-piperidyl]benzoic acid. Aq. NaOH (5 M, 35.0 mL, 175 mmol) was added to a mixture of Methyl 4-[4-(1,3-dioxolan-2-yl)-1-piperidyl] benzoate (10.0 g, 34.3 mmol) in a water/THF mixture (1:1 v/v, 200 mL). The solution was stirred at 23° C. for 2 h. The reaction mixture was diluted with EtOAc (100 mL) and pH was adjusted to 4 by adding aq. HCl (1 M). The organic phase was separated, and the aq. phase was extracted with EtOAc (4×100 mL). The combined organic phases were washed with brine (100 mL), dried ($Na_2SO_4$), filtered, and concentrated to provide the title compound as light brown solid (7.10 g, 75%). m/z (ES$^+$), [M+H]$^+$ 278.2

Step 7: 4-[4-(1,3-dioxolan-2-yl)-1-piperidyl]-N-(2,6-dioxo-3-piperidyl)-N-methyl-benzamide. DIPEA (3.58 mL, 20.6 mmol) was added to a mixture of 4-[4-(1,3-dioxolan-2-yl)-1-piperidyl]benzoic acid (2.50 g, 9.01 mmol), HATU (6.86 g, 18.0 mmol) and 3-(methylamino)piperidine-2,6-dione (1.54 g, 10.8 mmol) in anhydrous DMF (20.0 mL) at 23° C. The mixture was stirred at 23° C. for 2 h and diluted with water (200 mL). The aq. phase was extracted with a mixture of iPrOH/$CHCl_3$ (1/9 v/v, 4×100 mL). The combined organic phases were washed with brine (100 mL), dried ($Na_2SO_4$), filtered, and concentrated. The residue was suspended in $Et_2O$ (200 mL) and sonicated for 5 minutes. The solid was collected by filtration and dried under high vacuum to provide the title compound as a colorless solid (1.70 g, 45%). m/z (ES$^+$), [M+H]$^+$ 402.3

Step 8: N-(2,6-dioxo-3-piperidyl)-4-(4-formyl-1-piperidyl)-N-methyl-benzamide. Aq. HCl (3 M, 10.0 mL, 30 mmol) was added to a mixture of 4-[4-(1,3-dioxolan-2-yl)-1-piperidyl]-N-(2,6-dioxo-3-piperidyl)-N-methyl-benzamide (1.60 g, 3.99 mmol) in THF (16.0 mL) and water (60.0 mL) at 23° C. The solution was heated at 55° C. for 5 h. After cooling to 0° C., a solution of $NaHCO_3$ (1.20 g, 13.9 mmol) in water (100 mL) was slowly added. The aq. phase was extracted with a mixture of iPrOH/$CHCl_3$ (1:9 v/v, 8×100 mL). The combined organic phases were washed with brine (100 mL), dried ($Na_2SO_4$), filtered, and concentrated. The residue was suspended in $Et_2O$ (200 mL) and sonicated for 5 min. The solid was collected by filtration and dried under high vacuum to provide the title compound as a colorless solid (1.10 g, 77%). $^1$H NMR (500 MHz, DMSO-$d_6$) δ 10.86 (s, 1H), 9.64 (s, 1H), 7.39-7.21 (m, 2H), 7.00-6.92 (m, 2H), 5.14-4.52 (m, 1H), 3.72 (d, J=12.8 Hz, 2H), 3.04-2.86 (m, 4H), 2.87-2.63 (m, 2H), 2.61-2.51 (m, 2H), 2.44-2.30 (m, 1H), 2.03-1.84 (m, 3H), 1.66-1.46 (m, 2H). m/z (ES$^+$), [M+H]$^+$ 358.2.

SCHEME B3

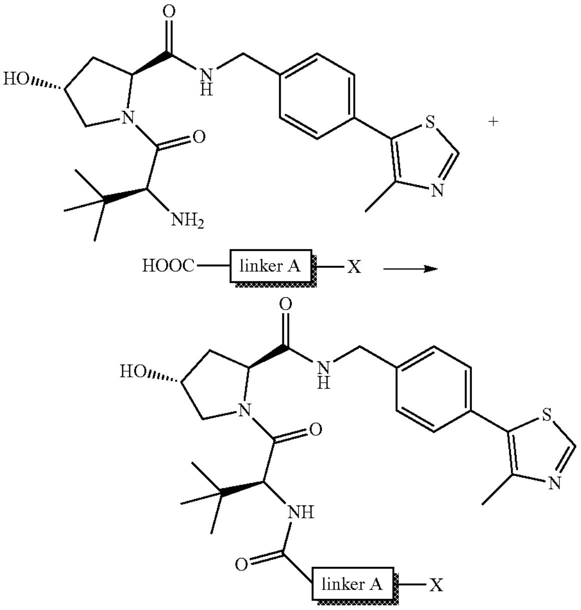

X is a reactive group such as —COOH, OH, CHO

Described below are additional examples of VHL-targeting LHM building blocks that may be prepared according to Scheme B3.

HVB1: 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid

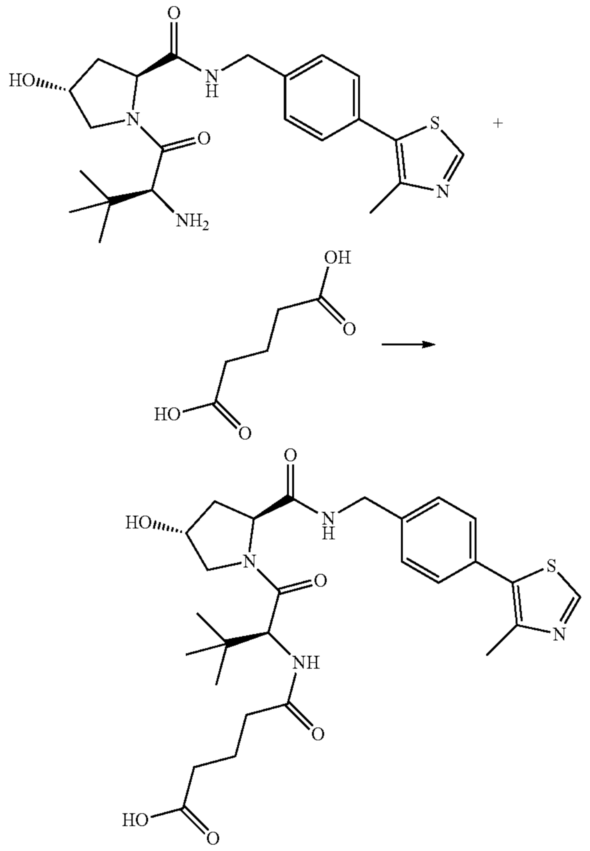

HVB1

To a solution of glutaric acid (135 mg, 1.0 mmol) in THF (10 mL) and methanol (5 mL) were added HATU (0.39 g, 1.0 mmol) and N,N-diisopropylethylamine (0.33 mL, 1.9 mmol) and the reaction mixture was stirred for 5 minutes, then (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide (0.40 g, 0.93 mmol) was added. The reaction mixture was stirred for 16 h, followed by quenching with 4N dioxanes (0.25 mL), then the crude mixture was concentrated onto silica gel and purified by reverse phase chromatography. LCMS $C_{27}H_{36}N_4O_6S$ requires: 544. found: m/z=567.5 $[M+Na]^+$.

$^1H$ NMR (500 MHz, DMSO-$d_6$) δ 12.01 (s, 1H), 9.00 (s, 1H), 8.58 (d, J=6.4 Hz, 1H), 7.91 (d, J=9.3 Hz, 1H), 7.43 (p, J=7.8, 6.7 Hz, 4H), 5.14 (d, J=3.7 Hz, 1H), 4.55 (d, J=9.2 Hz, 1H), 4.53-4.43 (m, 2H), 4.37 (s, 1H), 4.23 (dd, J=16.0, 5.2 Hz, 1H), 3.78-3.52 (m, 2H), 2.46 (s, 3H), 2.28 (dt, J=15.7, 7.7 Hz, 1H), 2.25-2.15 (m, 3H), 2.05 (t, J=10.6 Hz, 1H), 1.98-1.83 (m, 1H), 1.72 (h, J=6.4 Hz, 2H), 0.95 (s, 9H).

HVB2: (1r,4r)-4-{[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}cyclohexane-1-carboxylic acid

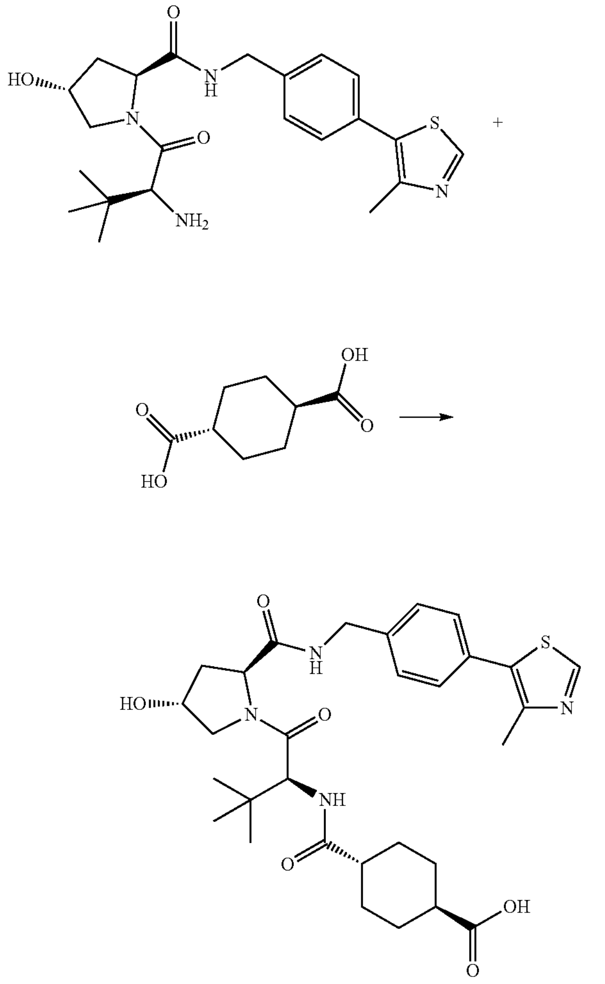

HVB2

(2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide (350 mg, 0.81 mmol) was added to a solution of [(dimethylamino)({[1,2,3]triazolo[4,5-b]pyridin-3-yloxy})methylidene]dimethylazanium; hexafluoro-lambda5-phosphanuide (0.34 g, 0.89 mmol) and (1r,4r)-cyclohexane-1,4-dicarboxylic acid (154 mg, 0.89 mmol) stirred in THF:DCM (1:2 ratio) and N,N-diisopropylethylamine (0.26 g, 2.0 mmol) and stirred for 16 h. The reaction was then quenched with excess 4N HCl in dioxane, followed by concentration onto silica gel. Reverse phase column chromatography (0-100% acetonitrile in water) provided (1r,4r)-4-{[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}cyclohexane-1-carboxylic acid (0.17 g, 36%). LCMS: $C_{30}H_{40}N_4O_6S$ requires: 584.73. found: m/z=607.6 $[M+Na]^+$.

HVB3: (2S,4R)-1-[(2S)-3,3-dimethyl-2-{1[(1r,4r)-4-formylcyclohexyl]formamido}butanoyl]-4-hydroxy-N-{[4-(4-methyl-1,3-thiazol-5-yl)phenyl]methyl}pyrrolidine-2-carboxamide

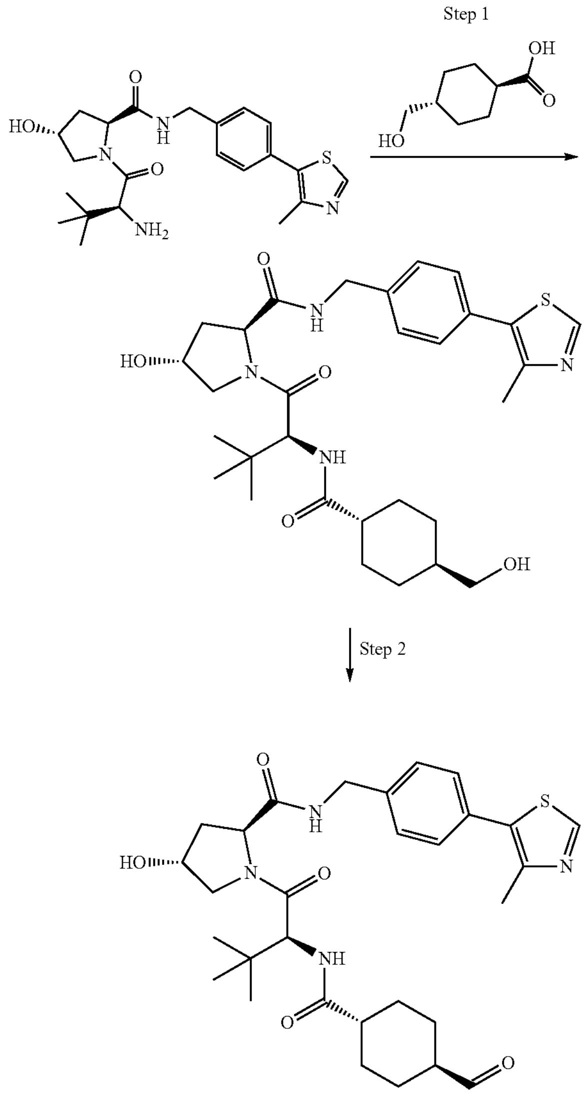

HVB3

Step 1: (2S,4R)-1-[(2S)-3,3-dimethyl-2-{[(1r,4r)-4-(hydroxymethyl)cyclohexyl]formamido}butanoyl]-4-hydroxy-N-{[4-(4-methyl-1,3-thiazol-5-yl)phenyl]methyl}pyrrolidine-2-carboxamide. (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide (350 mg, 0.81 mmol) was added to a solution of [(dimethylamino)({[1,2,3]triazolo[4,5-b]pyridin-3-yloxy})methylidene]dimethylazanium; hexafluoro-lambda5-phosphanuide (0.34 g, 0.89 mmol) and (1r,4r)-4-(hydroxymethyl)cyclohexane-1-carboxylic acid (141 mg, 0.89 mmol) stirred in THF:DCM (1:2 ratio) and N,N-diisopropylethylamine (0.26 g, 2.0 mmol) and stirred for 16 h. The reaction was then quenched with two drops of 4N HCl in dioxane, followed by concentration onto silica gel. Reverse phase chromatography (0-100% acetonitrile in water) provided (2S,4R)-1-[(2S)-3,3-dimethyl-2-{[(1r,4r)-4-(hydroxymethyl)cyclohexyl]formamido}butanoyl]-4-hydroxy-N-{[4-(4-methyl-1,3-thiazol-5-yl)phenyl]methyl}pyrrolidine-2-carboxamide (0.33 g, 71%). LCMS: $C_{30}H_{42}N_4O_5S$ requires: 570.8. found: m/z=571.6 $[M+H]^+$.

Step 2: (2S,4R)-1-[(2S)-3,3-dimethyl-2-{[(1r,4r)-4-formylcyclohexyl]formamido}butanoyl]-4-hydroxy-N-{[4-(4-methyl-1,3-thiazol-5-yl)phenyl]methyl}pyrrolidine-2-carboxamide. (2S,4R)-1-[(2S)-3,3-dimethyl-2-{[(1r,4r)-4-(hydroxymethyl)cyclohexyl]formamido}butanoyl]-4-hydroxy-N-{[4-(4-methyl-1,3-thiazol-5-yl)phenyl]methyl}pyrrolidine-2-carboxamide (330 mg, 0.58 mmol) was dissolved in DCM (0.1M) followed by addition of 1,1-bis(acetyloxy)-3-oxo-1lambda5,2-benziodaoxol-1-yl acetate (0.3 g, 0.7 mmol). The reaction was stirred for 2 h, followed by filtration with Celite, and concentration onto silica gel. Chromatography (0-10% methanol in DCM) provided (2S,4R)-1-[(2S)-3,3-dimethyl-2-{[(1r,4r)-4-formylcyclohexyl]formamido}butanoyl]-4-hydroxy-N-{[4-(4-methyl-1,3-thiazol-5-yl)phenyl]methyl}pyrrolidine-2-carboxamide (0.2 g, 61%) as a white solid. LCMS: $C_{30}H_{40}N_4O_5S$ requires: 568.7. found: m/z=569.6 $[M+H]^+$.

Scheme B4 shows another approach to generating VHL-targeting LHM building block via a different attachment point to the LHM:

SCHEME B4

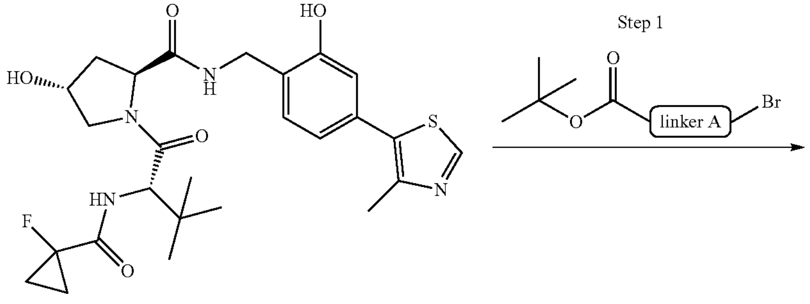

-continued
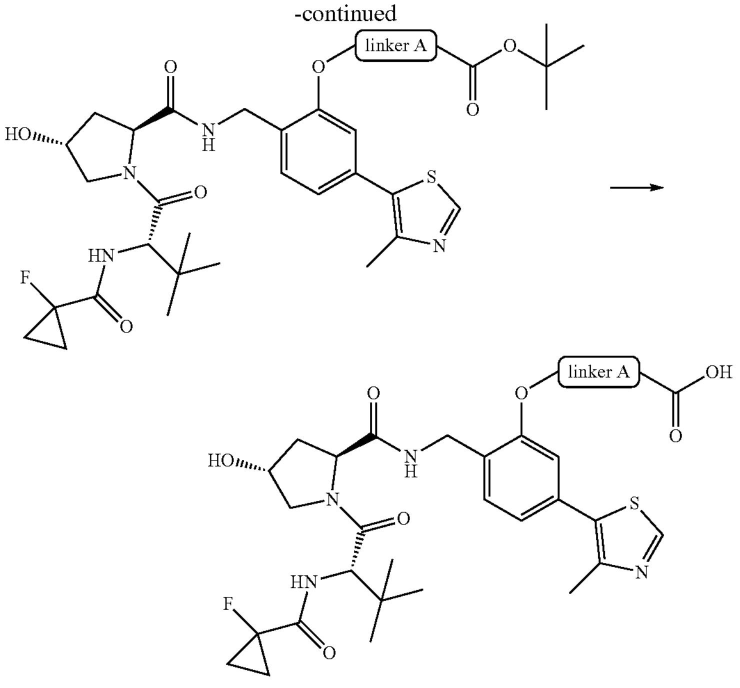
Scheme B4 begins with coupling a linker precursor to a VHL-targeting LHM, namely, (2S,4R)-1-[(2S)-2-[(1-Fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide. The VHL-targeting LHM is prepared according to the following steps.
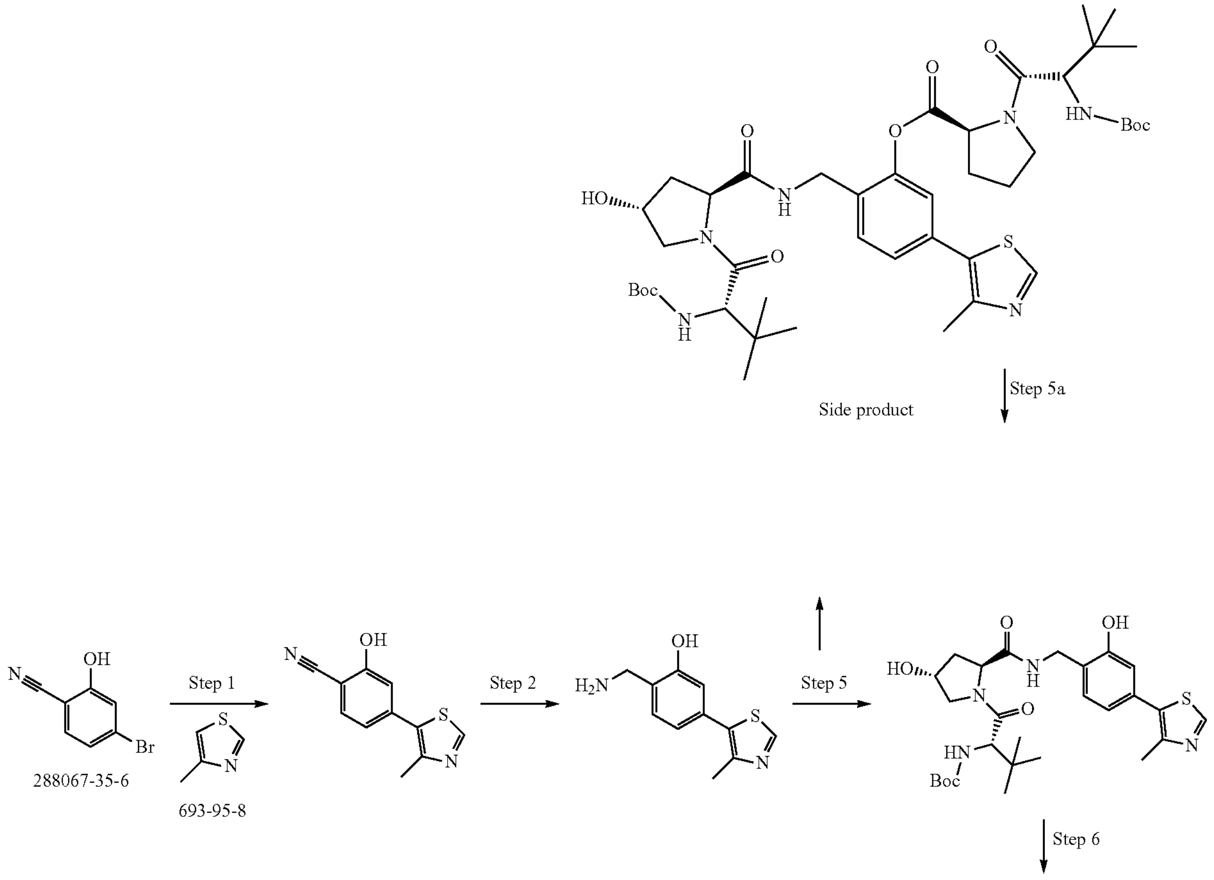

-continued

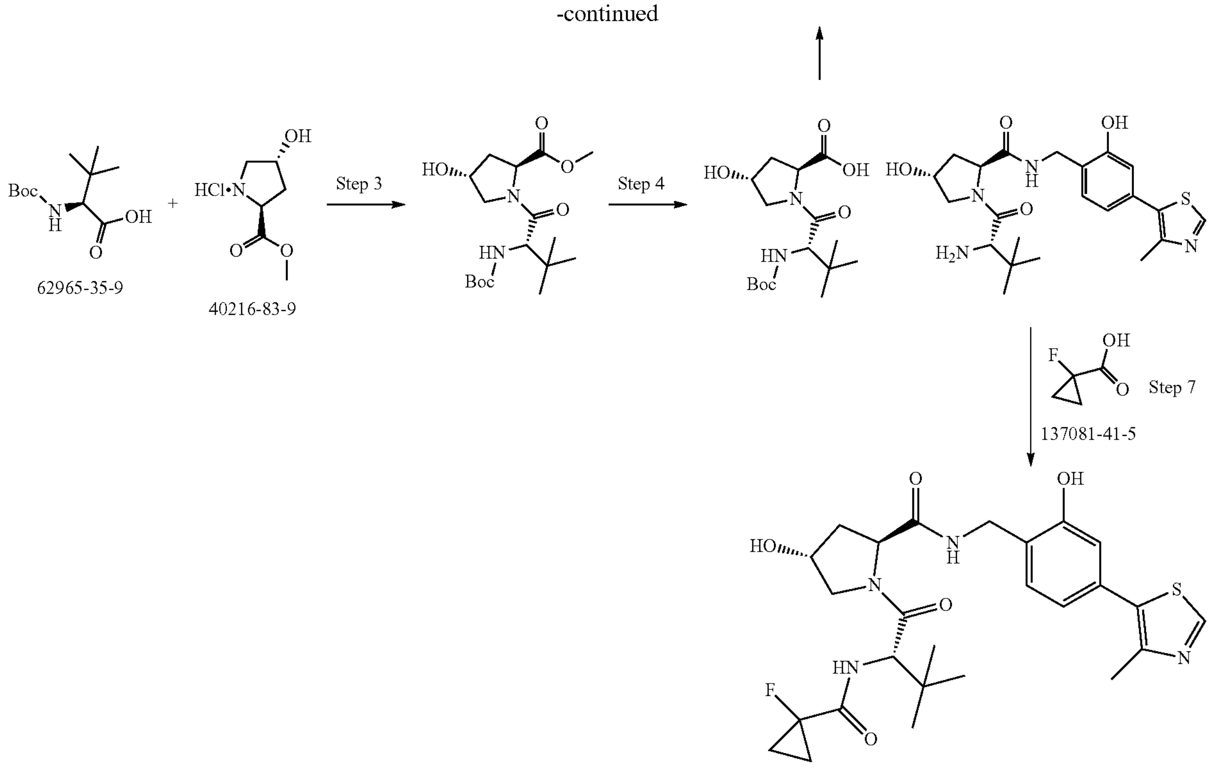

Step 1: 2-Hydroxy-4-(4-methyl-1,3-thiazol-5-yl)benzonitrile. A solution of 4-bromo-2-hydroxybenzonitrile (25 g, 126.25 mmol), 4-methylthiazole (25.035 g, 252.5 mmol, 2.0 eq) and anhydrous KOAc (24.78 g, 252.5 mmol) in DMF (210.42 mL, 0.6 M) was barbotated with argon on ultrasonic bath for 10 min. Then, $Pd(OAc)_2$ (0.567 g, 2.52 mmol) was added. The resulting mixture was stirred at 110° C. for 5 h under argon, while adding three times an additional amount of $Pd(OAc)_2$ (0.283 g, 1.26 mmol) each hour to the total amount of $Pd(OAc)_2$ (1.417 g, 6.31 mmol). The reaction mixture was cooled down to rt, filtered through Celite, diluted with water and extracted with ethyl acetate. The combined organic layers were washed with brine, dried over anhydrous sodium sulfate and concentrated under reduced pressure. The residue was purified by silica gel column chromatography (DCM/MeOH) to provide 2-hydroxy-4-(4-methyl-1,3-thiazol-5-yl)benzonitrile (17.64 g, 64.6%) as a yellow solid. LCMS: $C_{11}H_8N_2OS$ requires: 216.3. found: m/z=217.49 $[M+H]^+$; $^1H$ NMR (300 MHz, DMSO-$d_6$) δ 11.36 (s, 1H), 9.08 (s, 1H), 7.71 (d, J=8.1 Hz, 1H), 7.14 (d, J=1.6 Hz, 1H), 7.08 (dd, J=8.0, 1.7 Hz, 1H), 2.50 (s, 3H).

Step 2: 2-(Aminomethyl)-5-(4-methyl-1,3-thiazol-5-yl)phenol. To a solution of LAH 1M in THF (203.9 mL, 203.92 mmol) a solution of 2-hydroxy-4-(4-methyl-1,3-thiazol-5-yl)benzonitrile (17.64 g, 81.57 mmol) in THF (203.92 mL, 0.4 M) was added slowly under argon at −10° C. After the complete addition the reaction mixture was allowed slowly to the rt during 5 hours. The reaction was quenched by addition of $Na_2SO_4.10H_2O$ and concentrated under reduced pressure. The residue was purified by silica gel column chromatography (DCM/MeOH) to provide 2-(aminomethyl)-5-(4-methyl-1,3-thiazol-5-yl)phenol (9.18 g, 52%) as an amber oil. LCMS: $C_{11}H_{12}N_2OS$ requires: 220.3. found: m/z=221.5 $[M+H]^+$; $^1H$ NMR (300 MHz, DMSO-$d_6$) δ 8.96 (s, 1H), 7.23-7.15 (m, 1H), 6.87-6.81 (m, 2H), 3.88 (s, 2H), 2.45 (s, 3H).

Step 3: Methyl (2S,4R)-1-[(2S)-2-{[(tert-butoxy)carbonyl]amino}-3,3-dimethylbutanoyl]-4-hydroxypyrrolidine-2-carboxylate. To the solution of methyl (2S)-2-{[(tert-butoxy)carbonyl]amino}-3,3-dimethylbutanoic acid (41.0 g, 0.177 mol) and DIPEA (46.3 mL, 0.266 mol) in an THF (1770 mL, 0.1 M) HATU (70.8 g, 0.186 mol) was added as a solid in portions at 10° C. to form activated ester within 30 min. In the separate reactor the solution of (2S,4R)-4-hydroxypyrrolidine-2-carboxylate hydrochloride (48.0 g, 1.266 mol) and DIPEA (46.3 mL, 0.266 mol, 1.5 eq) was prepared and cooled down to −45° C. under inert atmosphere. The solution of activated ester was added dropwise at −45 to −40° C. over 0.5 h and RM was left to slowly warm up to RT overnight. Water (~500 mL) was added in single portion to quench the reaction and volatiles were concentrated under vacuum. Oily residue was extracted with EtOAc (3×400 mL), washed with sat. aqueous $NaHCO_3$ (250 mL), 10% aqueous $KHSO_4$ (250 mL), brine (300 mL), dried over $MgSO_4$, filtered and evaporated to give a crude which was purified by FC. Concentration of corresponding fractions gave methyl (2S,4R)-1-[(2S)-2-{[(tert-butoxy)carbonyl]amino}-3,3-dimethylbutanoyl]-4-hydroxypyrrolidine-2-carboxylate as a pale yellow oil (64 g, 99%). LCMS: $C_{17}H_{30}N_2O_6$ requires: 358.44. found: m/z=359.3 $[M+H]^+$; $^1H$ NMR (300 MHz, DMSO-$d_6$) δ 6.54 (d, J=9.3 Hz, 1H), 5.23 (d, J=3.8 Hz, 1H), 4.42-4.29 (m, 2H), 4.16 (d, J=9.4 Hz, 1H), 3.71-3.61 (m, 2H), 2.11 (dd, J=12.2, 9.2 Hz, 1H), 1.95-1.85 (m, 1H), 1.38 (s, 10H), 0.94 (s, 9H).

Step 4: (2S,4R)-1-[(2S)-2-{[(Tert-butoxy)carbonyl]amino}-3,3-dimethylbutanoyl]-4-hydroxypyrrolidine-2-carboxylic acid. To the solution of methyl (2S,4R)-1-[(2S)-2-{[(tert-butoxy)carbonyl]amino}-3,3-dimethylbutanoyl]-4-hydroxypyrrolidine-2-carboxylate (63.54 g, 0.177 mol) in THF (220 mL, 0.8 M) the LiOH $H_2O$ (14.88 g, 0.355 mol) was added as an aqueous solution (86 mL, 0.2 M) at once at RT. The RM was left to stir at Rt for 3 h and monitored by TLC/UPLC. Once reaction was completed, 10% aqueous $KHSO_4$ was added until pH ~3. The THF was concentrated by rotovap and residue was extracted with EtOAc (3×400 mL). Combined organic fractions were washed with 10% aqueous $KHSO_4$ (200 mL), brine (300 mL), dried over $MgSO_4$, filtered and evaporated to dryness. Viscous pale yellow oily residue was sonicated with an. THF (300 ml) to give off-white precipitate, which was filtered and dried in vacuum at 50° C. yielding 69.6 g of (2S,4R)-1-[(2S)-2-{[(tert-butoxy)carbonyl]amino}-3,3-dimethylbutanoyl]-4-hydroxypyrrolidine-2-carboxylic acid (69.6 g, including THF ~15% by weight). LCMS: $C_{16}H_{28}N_2O_6$ requires: 344.4. found: m/z=345.2 $[M+H]^+$; $^1H$ NMR (300 MHz, DMSO-$d_6$) δ 12.43 (s, 1H), 6.49 (d, J=9.4 Hz, 1H), 5.18 (d, J=3.7 Hz, 1H), 4.33 (bs, 1H), 4.26 (t, J=8.4 Hz, 1H), 4.16 (d, J=9.4 Hz, 1H), 3.69-3.52 (m, 2H), 2.18-2.02 (m, 1H), 1.89 (ddd, J=13.2, 9.1, 4.6 Hz, 1H), 1.38 (s, 9H), 0.94 (s, 9H).

Step 5: tert-Butyl N-[(2S)-1-[(2S,4R)-4-hydroxy-2-({[2-hydroxy-4-(4-methyl-1,3-thiazol-5-yl)phenyl]methyl}carbamoyl)pyrrolidin-1-yl]-3,3-dimethyl-1-oxobutan-2-yl]carbamate. To a solution of (2S,4R)-1-[(2S)-2-{[(tert-butoxy)carbonyl]amino}-3,3-dimethylbutanoyl]-4-hydroxypyrrolidine-2-carboxylic acid (14.352 g, 41.67 mmol) in DMF (138.9 mL, 0.3 M) cooled with ice-water bath under argon were added DIPEA (10.89 mL, 62.51 mmol) and HATU (16.644 g, 43.76 mmol). The resulting mixture was allowed to the room temperature during 0.5 h and slowly added dropwise to a solution of 2-(aminomethyl)-5-(4-methyl-1,3-thiazol-5-yl)phenol (9.180 g, 41.67 mmol) and DIPEA (7.26 mL, 42.67 mmol) in DMF (83.34 mL, 0.5 M) at −40° C. under argon. After addition the reaction mixture was left in cooling bath to slowly allow to the room temperature for 5 hours. The reaction was quenching by addition of 5 mL of water and concentrated under reduced pressure. The residue was purified by silica gel flash chromatography (DCM/MeOH) to provide (2S,4R)-1-[(2S)-2-{[(tert-butoxy)carbonyl]amino}-3,3-dimethylbutanoyl]-4-hydroxypyrrolidine-2-carboxylic acid (13.36 g, 58.64%) as a yellowish solid. LCMS: $C_{27}H_{38}N_4O_6S$ requires: 546.7. found: m/z=547.9 $[M+H]^+$. After purification by flash chromatography was obtained also the double-acylated side product—2-({[(2S,4R)-1-[(2S)-2-{[(tert-butoxy)carbonyl]amino}-3,3-dimethylbutanoyl]-4-hydroxypyrrolidin-2-yl]formamido}methyl)-5-(4-methyl-1,3-thiazol-5-yl)phenyl (2S)-1-(2-{[(tert-butoxy)carbonyl]amino}-3,3-dimethylbutanoyl)pyrrolidine-2-carboxylate. The acyl group can be cleaved according to Step 5a. $^1H$ NMR (300 MHz, Chloroform-d) δ 9.28 (br s, 1H), 8.70 (s, 1H), 8.11 (t, J=6.6 Hz, 1H), 7.13 (d, J=7.8 Hz, 1H), 6.98 (d, J=1.8 Hz, 1H), 6.88 (dd, J=7.7, 1.8 Hz, 1H), 5.19 (d, J=8.9 Hz, 1H), 4.77 (t, J=7.9 Hz, 1H), 4.51 (dd, J=15.0, 6.9 Hz, 2H), 4.12 (td, J=20.4, 8.4 Hz, 3H), 3.57 (dd, J=11.4, 3.6 Hz, 1H), 2.85 (br s, 2H), 2.53 (m, 4H), 2.11 (dd, J=13.5, 8.1 Hz, 1H), 1.56-1.43 (m, 2H), 1.41 (s, 9H), 0.84 (s, 9H).

Step 5a: tert-Butyl N-[(2S)-1-[(2S,4R)-4-hydroxy-2-({[2-hydroxy-4-(4-methyl-1,3-thiazol-5-yl)phenyl]methyl}carbamoyl)pyrrolidin-1-yl]-3,3-dimethyl-1-oxobutan-2-yl]carbamate. To a solution of the 2-({[(2S,4R)-1-[(2S)-2-{[(tert-butoxy)carbonyl]amino}-3,3-dimethylbutanoyl]-4-hydroxypyrrolidin-2-yl]formamido}methyl)-5-(4-methyl-1,3-thiazol-5-yl)phenyl (2S)-1-(2-{[(tert-butoxy)carbonyl]amino}-3,3-dimethylbutanoyl)pyrrolidine-2-carboxylate (3 g, 3.5 mmol) in MeOH (70 mL, 0.05 M) was added $K_2CO_3$ (0.484 g, 3.5 mmol). The reaction mixture was left to stir at rt for 12 h. The reaction mixture was concentrated, the residue diluted with water, neutralized with $KHSO_4$ and extracted with DCM (×3 times), obtained organic layer were dried under $Na_2SO_4$, concentrated under reduced pressure. The obtained residue was purified by silica gel flash chromatography (5% DCM/MeOH) to provide tert-butyl N-[(2S)-1-[(2S,4R)-4-hydroxy-2-({[2-hydroxy-4-(4-methyl-1,3-thiazol-5-yl)phenyl]methyl}carbamoyl)pyrrolidin-1-yl]-3,3-dimethyl-1-oxobutan-2-yl]carbamate (2.14 g, 99%) as a yellowish solid. LCMS: $C_{27}H_{38}N_4O_6S$ requires: 546.7. found: m/z=547.2 $[M+H]^+$; $^1H$ NMR (300 MHz, Chloroform-d) δ 9.29 (s, 1H), 8.80 (s, 1H), 8.19 (s, 1H), 7.14 (d, J=7.8 Hz, 1H), 6.98 (d, J=1.8 Hz, 1H), 6.87 (dd, J=7.7, 1.8 Hz, 1H), 5.14 (d, J=8.9 Hz, 1H), 4.81 (t, J=7.9 Hz, 1H), 4.56 (q, J=7.8 Hz, 2H), 4.12 (td, J=13.6, 12.6, 4.7 Hz, 3H), 3.56 (dd, J=11.4, 3.5 Hz, 1H), 2.56 (s, 4H), 2.19-2.05 (m, 1H), 0.83 (s, 10H).

Step 6: (2S,4R)-1-[(2S)-2-Amino-3,3-dimethylbutanoyl]-4-hydroxy-N-{[2-hydroxy-4-(4-methyl-1,3-thiazol-5-yl)phenyl]methyl}pyrrolidine-2-carboxamide. To a solution of tert-butyl N-[(2S)-1-[(2S,4R)-4-hydroxy-2-({[2-hydroxy-4-(4-methyl-1,3-thiazol-5-yl)phenyl]methyl}carbamoyl)pyrrolidin-1-yl]-3,3-dimethyl-1-oxobutan-2-yl]carbamate (2.14 g) (5.27 g, 9.64 mmol) in DCM (48.2 mL, 0.2 M) cooled with ice-water bath was added HCl 2M in $Et_2O$ (38.56 mL, 77.12 mmol). The reaction mixture was stirred at room temperature for 2 hours. The solid was triturated on ultrasonic bath, filtered off, washed on the filter with DCM and dried under vacuum to provide (2S,4R)-1-[(2S)-2-amino-3,3-dimethylbutanoyl]-4-hydroxy-N-{[2-hydroxy-4-(4-methyl-1,3-thiazol-5-yl)phenyl]methyl}pyrrolidine-2-carboxamide (5.05 g, 99%) as a white solid. LCMS: $C_{22}H_{30}N_4O_4S$ requires: 446.6. found: m/z=447.7 $[M+H]^+$; $^1H$ NMR (300 MHz, D2O) δ 9.50 (d, J=1.0 Hz, 1H), 7.30 (d, J=7.8 Hz, 1H), 7.04-6.89 (m, 2H), 4.58 (dd, J=9.9, 7.6 Hz, 1H), 4.52 (s, 1H), 4.44-4.23 (m, 2H), 4.08 (s, 1H), 3.80 (d, J=11.9 Hz, 1H), 3.68 (dd, J=11.9, 3.4 Hz, 1H), 3.46 (q, J=7.1 Hz, 1H), 2.45 (s, 3H), 2.28 (dd, J=13.9, 7.7 Hz, 1H), 2.01 (ddd, J=14.0, 9.9, 4.2 Hz, 1H), 1.08 (t, J=7.1 Hz, 2H), 0.98 (s, 9H).

Step 7: (2S,4R)-1-[(2S)-2-[(1-Fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide. To a solution of 1-fluorocyclopropane-1-carboxylic acid (1.337 g, 12.85 mmol) in DMF (128 mL, 0.1 M) cooled with ice-water bath were added HATU (5.129 g, 13.49 mmol) and DIPEA (3.36 mL, 19.27 mmol). The resulting mixture was allowed to the room temperature during 0.5 h and then added dropwise to the solution of (2S,4R)-1-[(2S)-2-amino-3,3-dimethylbutanoyl]-4-hydroxy-N-{[2-hydroxy-4-(4-methyl-1,3-thiazol-5-yl)phenyl]methyl}pyrrolidine-2-carboxamide (5.05 g, quant. yield) (6.674 g, 12.85 mmol) and DIPEA (7.83 mL, 44.97 mmol) in DMF (42 mL, 0.3 M) at −40° C. After addition the reaction mixture was left in cooling bath to slowly allow to the room temperature over 16 hours. The reaction was then diluted with water and extracted with ethyl acetate. The combined organic layers were washed with brine, dried over anhydrous sodium sulfate and concentrated under reduced pressure. The residue was purified by silica gel column chromatography (DCM/MeOH) to provide (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (5.05 g, 74%) as a yellow solid. LCMS: $C_{26}H_{33}N_4O_5SF$ requires: 532.6. found: m/z=533.8 $[M+H]^+$; $^1H$ NMR (300 MHz, Chloroform-d) δ 9.29 (s, 1H), 8.70 (s, 1H), 8.09 (dd, J=7.5, 5.5 Hz, 1H), 7.13 (d, J=7.8 Hz, 1H), 7.01 (dd, J=8.5, 3.7 Hz, 1H), 6.98 (d, J=1.8 Hz, 1H), 6.88 (dd, J=7.7, 1.8 Hz, 1H), 4.73 (t, J=7.9 Hz, 1H), 4.53 (br s, 1H), 4.51-4.40 (m, 2H), 4.18 (dd, J=14.6, 5.4 Hz, 1H), 3.99 (d, J=11.3 Hz, 1H), 3.63 (dd, J=11.2, 3.7 Hz, 1H), 2.53 (s, 3H), 2.47 (ddd, J=12.9, 7.9, 4.6 Hz, 1H), 2.15-2.01 (m, 1H), 1.36-1.22 (m, 4H), 0.91 (s, 9H).

Described below are additional examples of VHL-targeting LHM building blocks that may be prepared according to Scheme B4.

HVB4: 6-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)hexanoic acid tert-butyl 6-bromohexanoate (CAS 65868-63-5, 0.85 g, 3.4 mmol, 1.4 eq). The reaction mixture was purged with argon, sealed and stirred at 25° C. for 16 hours. The solids were filtered, washed with EtOAc (5 mL) and discarded. Obtained filtrate was diluted with water (60 mL) and extracted with ethyl acetate (3x20 mL). The combined organic layers were washed with brine (20 mL), dried over $Na_2SO_4$, filtered and concentrated under reduced pressure to give crude which was by flash chromatography (hexane/ethyl acetate) to give 1.38 g of desired product as a white solid (81.1% yield). ESI(+)$[M+H]^+$=703.8

Step 2: 6-[2-({[(2S,4R)-1-[(2S)-2-[(1-fluorocyclopropyl)formamido]-3,3-dimethylbutanoyl]-4-hydroxypyrrolidin-2-

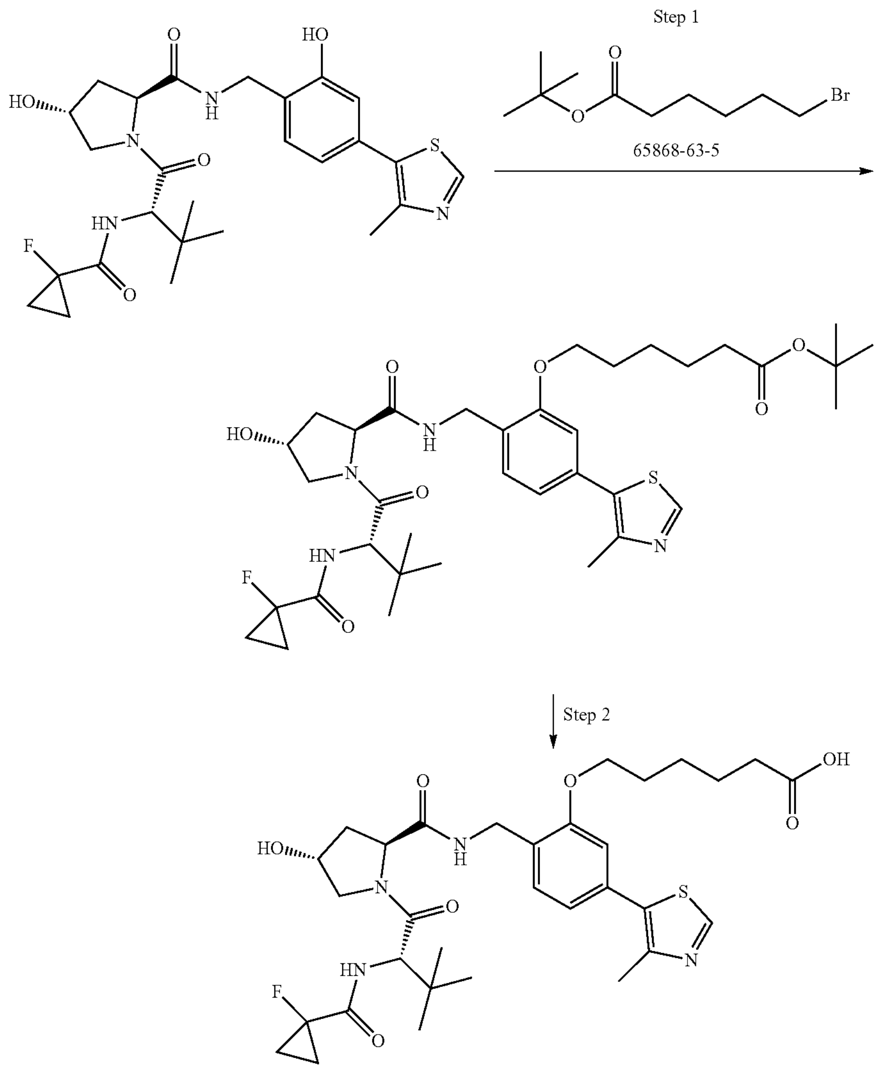

HVB4

Step 1: tert-butyl 6-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]hexanoate. To a solution of (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (1.29 g, 2.42 mmol, 1.0 eq) in an. DMF (16 mL, 0.15 M) were added $Cs_2CO_3$ (1.184 g, 3.63 mmol, 1.5 eq) and yl]formamido}methyl)-5-(4-methyl-1,3-thiazol-5-yl)phenoxy]hexanoic acid. To a solution of tert-butyl 6-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]hexanoate (1.38 g, 1.96 mmol, 1.0 eq) in anhydrous DCM (147.3 mL, 0.4 M) was added HCl in diethyl ether (2M, 30 mL). Reaction mixture was stirred overnight at room temperature. Solvent was evaporated under reduced pressure to give a residue, which was dissolved in THF (10 mL) and triturated with aq ammonia (3 M, 5 mL) for 10 min and concentrated again. Obtained crude was purified by reverse phase flash chromatography to give 6-(2-(((2S,4R)-1-((S)-2-(1-fluorocyclopropane-1-carboxamido)-3,3-dimethylbutanoyl)-4-hydroxypyrrolidine-2-carboxamido) methyl)-5-(4-methylthiazol-5-yl)phenoxy)hexanoic acid (614 mg, 48%) as an off-white amorphous solid. LCMS 254 nm, RT=2.59 min, 95.62% purity, ESI(+)=647.13[M+H]$^+$; $^1$H NMR (300 MHz, Methanol-d4) δ 8.86 (s, 1H), 7.50 (dd, J=19.7, 9.1 Hz, 2H), 7.07-6.92 (m, 2H), 4.80-4.66 (m, 1H), 4.63 (t, J=8.3 Hz, 1H), 4.50 (d, J=3.2 Hz, 1H), 4.42 (d, J=9.6 Hz, 1H), 4.07 (t, J=6.2 Hz, 2H), 3.91-3.62 (m, 2H), 2.48 (s, 3H), 2.34 (t, J=7.2 Hz, 2H), 2.27-2.02 (m, 2H), 1.87 (p, J=6.6 Hz, 2H), 1.65 (dp, J=33.1, 8.5, 7.8 Hz, 4H), 1.47-1.18 (m, 5H), 1.03 (s, 10H).

HVB5: 8-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)octanoic acid HVB5 was prepared according to the same method as HVB4, except that the hexanoic acid was replaced with octanoic acid to give the title compound. LCMS: $C_{34}H_{47}FN_4O_7S$ requires: 674.3. found: m/z=672.7 [M−H]$^-$ HVB6: 10-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)decanoic acid

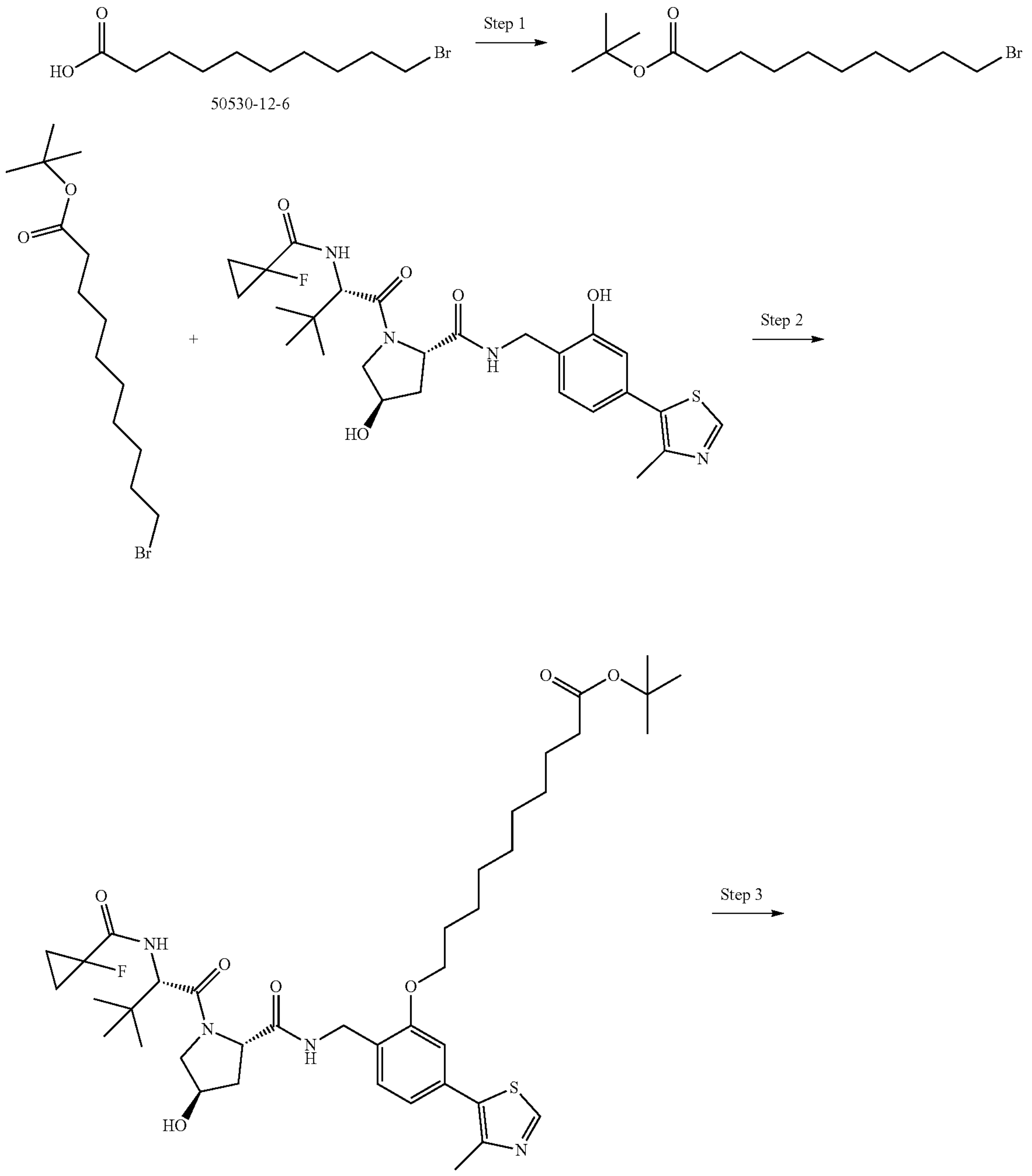

-continued

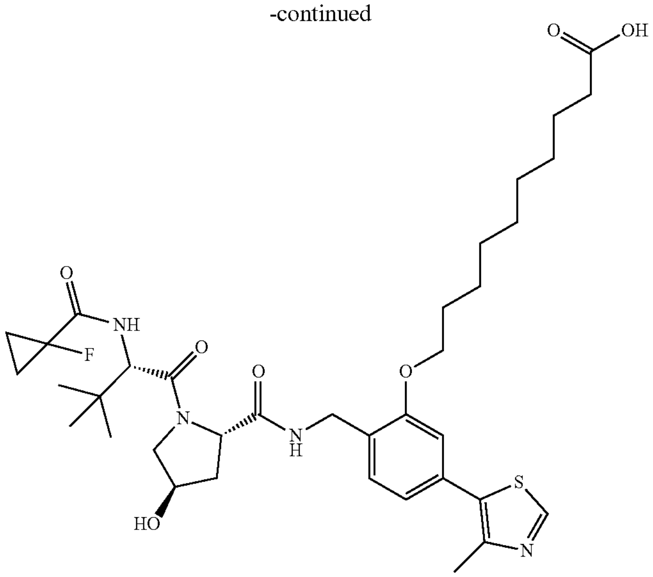

HVB6

Step 1: tert-butyl 10-bromodecanoate. To solution of 10-bromodecanoic acid (CAS: 50530-12-6, 10.0 g, 39.8 mmol, 1.0 eq) in an. dichloromethane (0.25 M) was added tert-butyl alcohol (18.9 mL, 199 mmol, 5.0 eq) followed by DMAP (0.96 g, 4.0 mmol, 0.1 equiv) at 0° C. under nitrogen. After 5 min, dicyclohexylcarbodiimide (9.04 g, 44 mmol, 1.1 equiv) was added to this solution at 0° C. The reaction mixture was allowed to warm to room temperature and stirred for 20 h. The volatiles were concentrated and then crude was directly loaded onto silica (5-10% EtOAc in hexane). The desired product has been isolated (9.0 g) contaminated with DCC as an impurity (according to the $^1$H NMR analysis). The additional purification was performed by FC (eluent: 10-50% DCM in hexane) to give 5.8 g of tert-butyl 10-bromodecanoate as an colorless oil (47% yield). $^1$H NMR (300 MHz, Chloroform-d) δ 3.42 (t, J=6.9 Hz, 2H), 2.22 (t, J=7.5 Hz, 2H), 1.87 (p, J=6.9 Hz, 2H), 1.68-1.51 (m, 2H), 1.46 (s, 9H), 1.45-1.37 (m, 2H), 1.31 (s, 8H).

Step 2: tert-butyl 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoate. To a solution of (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (0.8 g, 1.5 mmol, 1.0 eq) in an. DMF (15 mL, 0.1 M) were added $Cs_2CO_3$ (0.734 g, 2.25 mmol, 1.5 eq) and tert-butyl 10-bromodecanoate (0.646 g, 2.10 mmol, 1.4 eq). The reaction mixture was purged with argon, sealed and stirred at 25° C. for 16 hours. The solids were filtered, washed with EtOAc (5 mL) and discarded. Obtained filtrate was diluted with water (60 mL) and extracted with ethyl acetate (3×20 mL). The combined organic layers were washed with brine (20 mL), dried over $Na_2SO_4$, filtered and concentrated under reduced pressure to give crude which was by flash chromatography (hexane/ethyl acetate) to give 0.99 g of desired product as a white solid (87.1% yield). ESI(+)[M+H]$^+$=782.4; $^1$H NMR (300 MHz, Chloroform-d) δ 8.70 (s, 1H), 7.34 (d, J=7.7 Hz, 1H), 7.25 (t, J=5.9 Hz, 1H), 7.05 (dd, J=8.7, 3.6 Hz, 1H), 6.96 (dd, J=7.6, 1.6 Hz, 1H), 6.89 (d, J=1.6 Hz, 1H), 4.76 (t, J=7.7 Hz, 1H), 4.61-4.49 (m, 3H), 4.44 (dd, J=14.8, 5.4 Hz, 1H), 4.09-3.97 (m, 3H), 3.64 (dd, J=11.3, 3.9 Hz, 1H), 2.65-2.56 (m, 1H), 2.55 (s, 3H), 2.22 (t, J=7.5 Hz, 2H), 2.15 (d, J=2.6 Hz, 1H), 1.87 (p, J=6.6 Hz, 2H), 1.59 (t, J=7.1 Hz, 2H), 1.52 (m, 2H), 1.46 (s, 9H), 1.43-1.32 (m, 10H), 0.96 (s, 9H).

Step 3: 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoic acid. To a solution of tert-butyl 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoate (0.993 g, 1.31 mmol, 1.0 eq) in an. DCM (6.5 mL, 0.2 M) was added TFA (2.00 mL, 26.17 mmol, 20 eq). The reaction was stirred at 25° C. for 3 hours. The reaction was evaporated in vacuo and the resulting oil was treated with aq ammonia (20%, 5 mL). Agitation for 1 hour resulted in formation of an oil. The supernatant was decantated. The oil was dried in vacuo and purified using reverse-phase flash chromatography (20% to 60% acetonitrile/0.1% aqueous solution of formic acid) to give 0.703 g of title compound as a white solid (76.5% yield). LCMS (254 nm): RT=3.037 min, 100.00% purity, ESI(+)[M+H]$^+$=703.18; $^1$H NMR (300 MHz, DMSO-$d_6$) δ 12.00 (s, 1H), 8.99 (s, 1H), 8.51 (t, J=5.9 Hz, 1H), 7.41 (d, J=7.8 Hz, 1H), 7.31 (dd, J=9.3, 2.9 Hz, 1H), 7.01 (d, J=1.7 Hz, 1H), 6.96 (dd, J=7.7, 1.6 Hz, 1H), 5.19 (s, 1H), 4.66-4.57 (m, 1H), 4.53 (t, J=8.2 Hz, 1H), 4.36 (s, 1H), 4.25 (qd, J=16.7, 5.9 Hz, 2H), 4.05 (t, J=6.3 Hz, 2H), 3.73-3.56 (m, 2H), 2.47 (s, 3H), 2.19 (t, J=7.3 Hz, 2H), 2.15-2.09 (m, 1H), 1.93 (ddd, J=13.0, 8.9, 4.5 Hz, 1H), 1.76 (p, J=6.4 Hz, 2H), 1.57-1.38 (m, 6H), 1.38-1.15 (m, 12H), 0.97 (s, 9H).

HVB7: 3-{2-[2-({[(2S,4R)-1-[(2S)-2-[(1-fluorocyclopropyl)formamido]-3-methylbutanoyl]-4-hydroxypyrrolidin-2-yl]formamido}methyl)-5-(4-methyl-1,3-thiazol-5-yl)phenoxy]ethoxy}propanoic acid

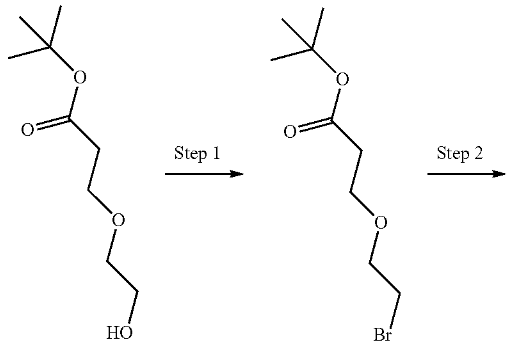

671802-00-9

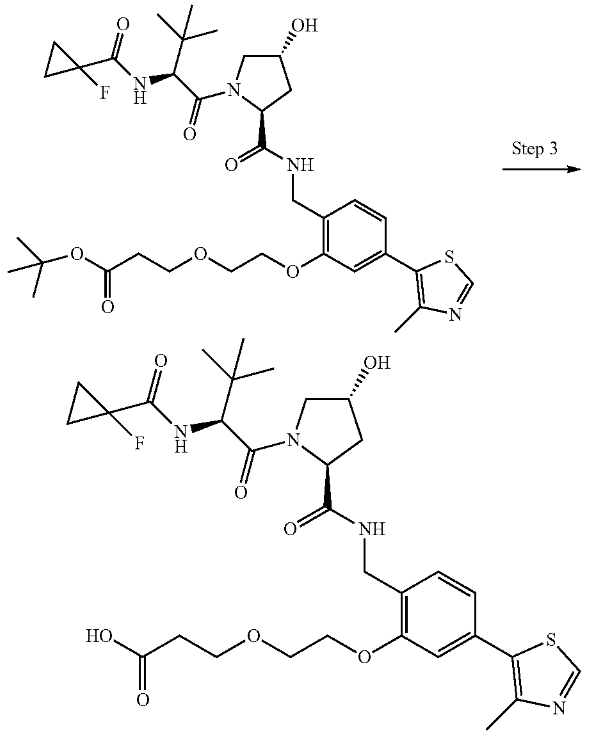

HVB7

Step 1: tert-butyl 3-(2-bromoethoxy)propanoate. A solution of tert-butyl 3-(2-hydroxyethoxy)propanoate (3.0 g, 15.7 mmol, 1 eq) and carbon tetrabromide (3.9 g, 11.87 mmol, 1.5 eq) in dichloromethane (15 mL, 0.5 mL) was prepared in a 50 mL flask and cooled to 0° C. Triphenyl phosphine (3.1 g, 11.87 mmol, 1.5 eq) was added via powder funnel in portions over 30 min with vigorous stirring. Upon addition of the phosphine, the colorless solution turned a pale brown color and was stirred for an additional 2 h at room temperature. The mixture was concentrated and quickly added to stirring hexane (50 mL). The white precipitate was filtered, the remaining solution was concentrated, obtained residue was purified by FC (eluted DCM/MeOH—9/1 to give 4.1 g of the DP as a white solid (yield 62.8%).

Step 2: tert-butyl 3-{2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]ethoxy}propanoate. To a solution (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (1.5 g, 2.82 mmol, 1.0 eq) in DMF (18.77 mL, 0.15 M) were added $Cs_2CO_3$ (1.376 g, 4.22 mmol, 1.5 eq) and tert-butyl 3-(2-bromoethoxy)propanoate (2.18 g, 3.94 mmol, 1.4 eq). The resulting mixture was stirred at room temperature for overnight. The reaction mixture was diluted with water and extracted with EtOAc (3 times), organic layer were dried under $Na_2SO_4$, concentrated, the residue was purified by FC, eluted with DCM/MeOH—9/1 to give 1.8 g of the DP as a pale yellow oil (quantitative yield). UPLC (12 min, 254 nm): RT=6.25 min, 100% purity, ESI[$M+H^+$]$^+$=705.55

Step 3: 3-{2-[2-({[(2S,4R)-1-[(2S)-2-[(1-fluorocyclopropyl)formamido]-3-methylbutanoyl]-4-hydroxypyrrolidin-2-yl]formamido}methyl)-5-(4-methyl-1,3-thiazol-5-yl)phenoxy]ethoxy}propanoic acid. To a solution of tert-butyl 3-{2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]ethoxy}propanoate (1.8 g, 2.64 mmol, 1 eq) in DCM (17.6 mL, 0.15 M) at 0° C. was added dropwise TFA (13.2 mL, 0.2 M). The reaction mixture was left to stir at RT for 1 h. The reaction mixture was concentrated, the residue was diluted with 50 mL of aq $NH_4OH$ (till pH=11), left in ultrasonic bath for 0.5 h and then for 1 h just by stirring. The resulting slurry was concentrated and purified by RF twice: First, eluted with ACN/$H_2O$ to give 0.3 g of the desired product; second time, eluted with ACN/$H_2O$ (0.1% formic acid) to give 1 g of the desired product. After neutralization with $NH_4OH$ the product has been got in form ammonium salt, which was released with formic acid during the second purification. All amount was combined to give 1.3 g of the desired product (yield 76%). LCMS (254 nm): RT=2.29 min, 99% purity: ESI(+) [M+H]$^+$=649.10; $^1$H NMR (300 MHz, Chloroform-d) δ 8.70 (s, 1H), 7.37 (d, J=7.8 Hz, 2H), 7.09-7.03 (m, 1H), 6.99 (dd, J=7.7, 1.6 Hz, 1H), 6.91 (d, J=1.6 Hz, 1H), 4.76 (t, J=8.1 Hz, 1H), 4.64-4.51 (m, 3H), 4.41 (dd, J=14.3, 5.2 Hz, 1H), 4.20 (t, J=4.2 Hz, 2H), 4.03 (d, J=11.3 Hz, 1H), 3.89 (td, J=8.6, 7.8, 4.4 Hz, 4H), 3.77 (dd, J=11.3, 3.7 Hz, 1H), 2.66 (ddd, J=19.7, 14.9, 5.1 Hz, 2H), 2.54 (s, 3H), 2.33-2.14 (m, 2H), 1.41-1.23 (m, 4H), 1.03 (s, 9H).

HVB8: 1-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)-3,6,9,12,15-pentaoxaoctadecan-18-oic acid HVB8 was prepared in an analogous manner as HVB7 by substituting tert-butyl 3-(2-hydroxyethoxy)propanoate for tert-butyl 3-{2-[2-(2-bromoethoxy)ethoxy]ethoxy}propanoate in Step 1 to obtain the title compound as a white solid. LCMS (254 nm): RT=2.27 min, 96.35% purity, ESI[M+H]$^+$=736.88.

$^1$H NMR (300 MHz, DMSO-$d_6$) δ 8.98 (s, 1H), 8.51 (t, J=6.0 Hz, 1H), 7.41 (d, J=7.8 Hz, 1H), 7.31 (dd, J=9.2, 2.9 Hz, 1H), 7.04 (d, J=1.7 Hz, 1H), 6.97 (dd, J=7.7, 1.6 Hz, 1H), 5.19 (s, 1H), 4.60 (d, J=9.1 Hz, 1H), 4.51 (t, J=8.2 Hz, 1H), 4.35 (s, 1H), 4.28 (d, J=6.1 Hz, 1H), 4.25-4.14 (m, 3H), 3.79 (dd, J=5.8, 3.4 Hz, 2H), 3.66-3.46 (m, 12H), 2.46 (s, 3H), 2.42 (t, J=6.3 Hz, 2H), 2.10 (dd, J=13.0, 8.0 Hz, 1H), 1.92 (ddd, J=13.1, 9.0, 4.4 Hz, 1H), 1.49-1.28 (m, 2H), 1.21 (tq, J=8.4, 4.6, 3.8 Hz, 2H), 0.96 (s, 9H).

HVB9: tert-butyl 1-(2-(((2S,4R)-1-((S)-2-(1-fluoro-cyclopropane-1-carboxamido)-3,3-dimethylbutanoyl)-4-hydroxypyrrolidine-2-carboxamido)methyl)-5-(4-methylthiazol-5-yl)phenoxy)-3,6,9,12,15-pentaoxaoctadecan-18-oate HVB9 was prepared in an analogous manner as HVB7 by substituting tert-butyl 3-(2-hydroxyethoxy)propanoate for tert-butyl 1-bromo-3,6,9,12,15-pentaoxaoctadecan-18-oate in Step 1 to obtain the title compound as a white solid. LCMS (254 nm): RT=2.27 min, 99.8% purity, ESI(+)[M+H]$^+$=825.21

$^1$H NMR (300 MHz, DMSO-$d_6$) δ 8.98 (s, 1H), 8.50 (t, J=6.0 Hz, 1H), 7.41 (d, J=7.8 Hz, 1H), 7.29 (dd, J=9.4, 2.9 Hz, 1H), 7.04 (d, J=1.7 Hz, 1H), 6.96 (dd, J=7.8, 1.6 Hz, 1H), 4.60 (d, J=9.2 Hz, 1H), 4.51 (t, J=8.2 Hz, 1H), 4.35 (s, 1H), 4.28 (d, J=6.0 Hz, 1H), 4.24-4.11 (m, 3H), 3.79 (dd, J=5.5, 3.7 Hz, 2H), 3.67-3.42 (m, 22H), 2.46 (s, 3H), 2.42 (t, J=6.4 Hz, 2H), 2.13-2.03 (m, 1H), 1.96-1.86 (m, 1H), 1.46-1.27 (m, 2H), 1.23 (dq, J=8.6, 4.1 Hz, 2H), 0.96 (s, 9H).

HVB10: 3-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}propanoic acid

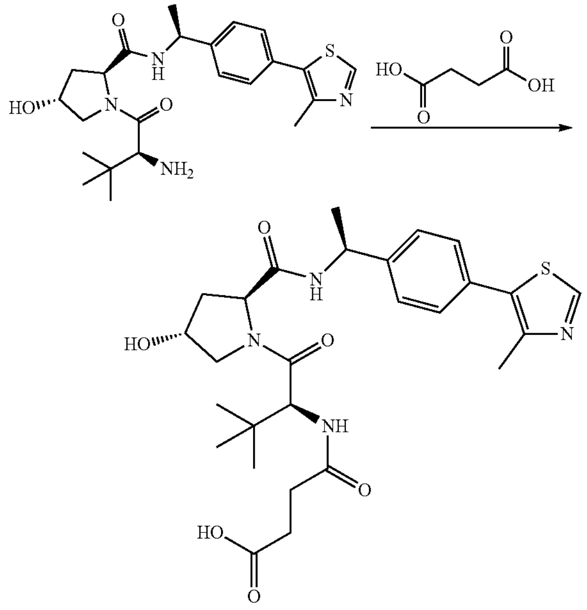

HVB10

(2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide (1.5 g, 3.37 mmol) was added to a solution of [(dimethylamino)({[1,2,3]triazolo[4,5-b]pyridin-3-yloxy})methylidene]dimethylazanium; hexafluoro-lambda5-phosphanuide (1.41 g, 3.71 mmol) and succinic acid (398 mg, 3.37 mmol) stirred in THF:DCM (1:2 ratio). N,N-diisopropylethylamine (0.72 mL, 8.43 mmol) was added and the reaction was stirred for 16 h. The reaction was then quenched with excess 4N HCl in dioxane, followed by concentration onto silica gel. Reverse phase column chromatography (0-100% acetonitrile in water) provided title compound. LCMS: $C_{27}H_6N_4O_6S$ requires: 544.24. found: m/z=545.6 [M+H]$^+$.

HVB11: 3-[3-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-3-oxo-propoxy]propanoic acid

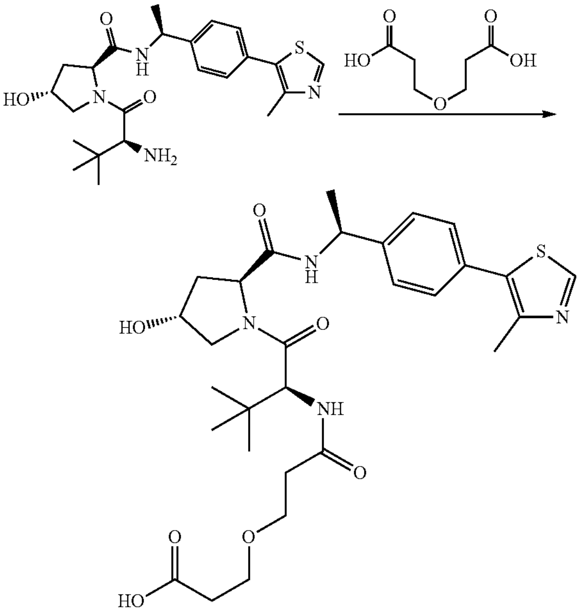

HVB11

To a solution of 3-(2-carboxyethoxy)propanoic acid (1.5 g, 9.4 mmol) and HATU (2.6 g, 6.9 mmol) in DCM (30 mL) was slowly added DIPEA (5.3 mL, 31 mmol) and the solution was stirred for 5 min at rt. To the mixture was added (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide; hydrochloride 2 (3.0 g, 6.2 mmol) and the reaction mixture was stirred for 30 min. The mixture was diluted with 1M NaOH (5.0 mL) and stirred for 5 min. The mixture was then acidified to pH 5 using 5% citric acid.

The layers were separated, and the aqueous layer was extracted with EtOAc (7×50 mL) and DCM (3×50 mL). The combined organic layers were dried (sodium sulfate), filtered and concentrated under reduced pressure. The material was purified by reverse phase chromatography on C18 using a 10-30% gradient of MeCN and water (contains 0.1% ammonium formate/formic acid) to afford the title compound as a solid (1.28 g, 35%). MS (ESI) [M+H]$^+$=589.3.

$^1$H NMR (500 MHz, DMSO) δ 8.99 (s, 1H), 8.39 (d, J=7.8 Hz, 1H), 7.87 (d, J=9.3 Hz, 1H), 7.47-7.41 (m, 2H), 7.39 (s, 2H), 4.92 (p, J=7.0 Hz, 1H), 4.53 (d, J=9.4 Hz, 1H), 4.44 (t, J=8.0 Hz, 1H), 4.28 (s, 1H), 3.65-3.49 (m, 6H), 2.46 (s, 3H), 2.37 (t, J=6.7 Hz, 2H), 2.39-2.31 (m, 1H), 2.05-1.99 (m, 1H), 1.80 (ddd, J=12.9, 8.4, 4.7 Hz, 1H), 1.37 (t, J=8.2 Hz, 3H), 0.94 (s, 9H).

HVB12: 4-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]butanoic acid

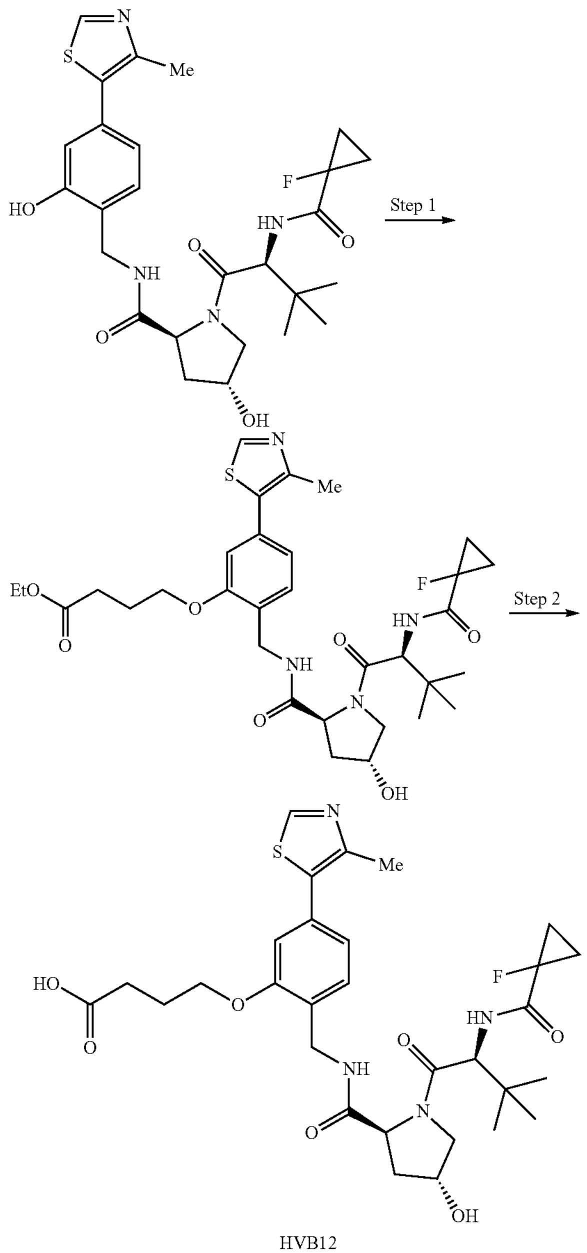

HVB12

Step 1. Ethyl 4-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]butanoate. Combined (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (50.00 mg, 0.09 mmol) and potassium carbonate (20.73 mg, 0.15 mmol) and suspended in N,N-Dimethylformamide (2.00 mL). Added ethyl 4-bromobutanoate (0.02 mL, 21.97 mg, 0.11 mmol) and stirred over 3 days at room temperature. Quenched with water and extracted with ethyl acetate. Washed with water two more times, then once with brine. Dried over sodium sulfate, filtered, and concentrated. Reaction taken crude to next step. $^1$H NMR (500 MHz, Chloroform-d) δ 7.35 (d, J=7.7 Hz, 1H), 6.99 (dd, J=7.7, 1.6 Hz, 2H), 4.78 (t, J=7.7 Hz, 2H), 4.63-4.47 (m, 3H), 4.47-4.38 (m, 1H), 4.10 (d, J=5.7 Hz, 7H), 4.07 (s, 4H), 3.69-3.58 (m, 1H), 3.50 (t, J=6.5 Hz, 5H), 2.20 (p, J=6.8 Hz, 7H), 2.12 (s, 2H), 1.59 (s, 4H), 1.29 (t, J=7.2 Hz, 13H), 0.96 (s, 8H).

Step 2. 4-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]butanoic acid. Dissolved ethyl 4-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]butanoate (50.00 mg, 0.08 mmol) in Tetrahydrofuran (2.00 mL) and Water (0.50 mL) and added lithium hydroxide hydrate (32.44 mg, 0.77 mmol). Stirred at room temperature for 2 days. Quenched with saturated ammonium chloride and extracted with ethyl acetate. Washed with brine, then dried over sodium sulfate. Filtered and concentrated to a white solid to provide 4-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]butanoic acid (0.0400 g, 83.6%). ESI Requires 618.25. Found 641.7 (M+Na$^+$)

HVB13: 6-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}hexanoic acid

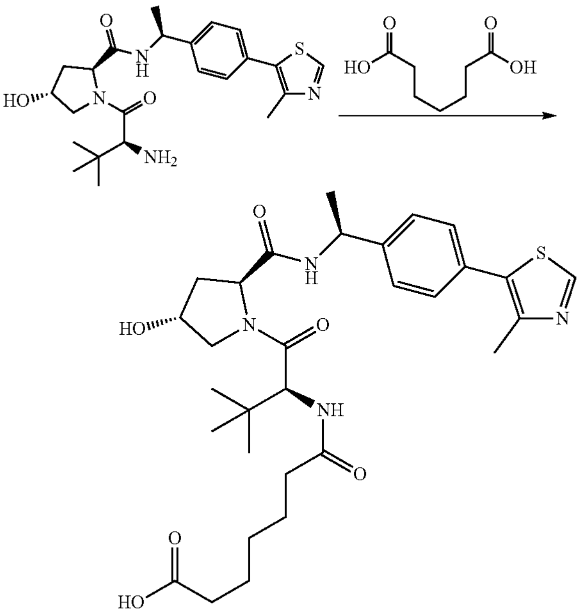

HVB13

To a solution of (2S,4R)-1-[(2S)-2-amino-3,3-dimethylbutanoyl]-4-hydroxy-N-[(1S)-1-[4-(4-methylthiazol-5-yl)phenyl]ethyl]pyrrolidine-2-carboxamide; hydrochloride 2 (1.75 g, 3.64 mmol), heptanedioic acid (874 mg, 5.46 mmol) and HATU (1.94 g, 5.09 mmol) in DCM (70.0 mL) at 0° C., was added DIPEA (3.11 mL, 18.2 mmol) and the reaction mixture was stirred for 2 h. The mixture was diluted with 1M NaOH (50 mL) and stirred for 1 h. The layers were separated, and the organic layer was extracted with 1M NaOH (2×30 mL). The combined aqueous layers were acidified to pH 5-6 and extracted with EtOAc (5×50 mL). The combined organic layers were dried (sodium sulfate), filtered and concentrated under reduced pressure. The material was further purified by reverse phase chromatography on C18 using a 10-60% gradient of MeCN and water (contains 0.1% ammonium formate/formic acid) to afford the title compound as a solid (0.924 g, 43%). LCMS: $C_{30}H_{42}N_4O_6S$ requires: 586.75. found: m/z=587.3 $[M+H]^+$.

$^1H$ NMR (500 MHz, DMSO) δ 8.99 (s, 1H), 8.37 (d, J=7.8 Hz, 1H), 7.79 (d, J=9.3 Hz, 1H), 7.46-7.41 (m, 2H), 7.40-7.36 (m, 2H), 4.92 (p, J=7.0 Hz, 1H), 4.52 (d, J=9.4 Hz, 1H), 4.43 (t, J=8.1 Hz, 1H), 4.30-4.26 (m, 1H), 3.65-3.57 (m, 2H), 3.46-3.33 (m, 1H), 2.46 (s, 3H), 2.28-2.20 (m, 1H), 2.18 (t, J=7.4 Hz, 2H), 2.15-2.06 (m, 1H), 2.04-1.97 (m, 1H), 1.80 (ddd, J=12.9, 8.5, 4.7 Hz, 1H), 1.54-1.42 (m, 4H), 1.38 (d, J=7.0 Hz, 3H), 1.28-1.20 (m, 2H), 0.94 (s, 9H).

HVB14: (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid

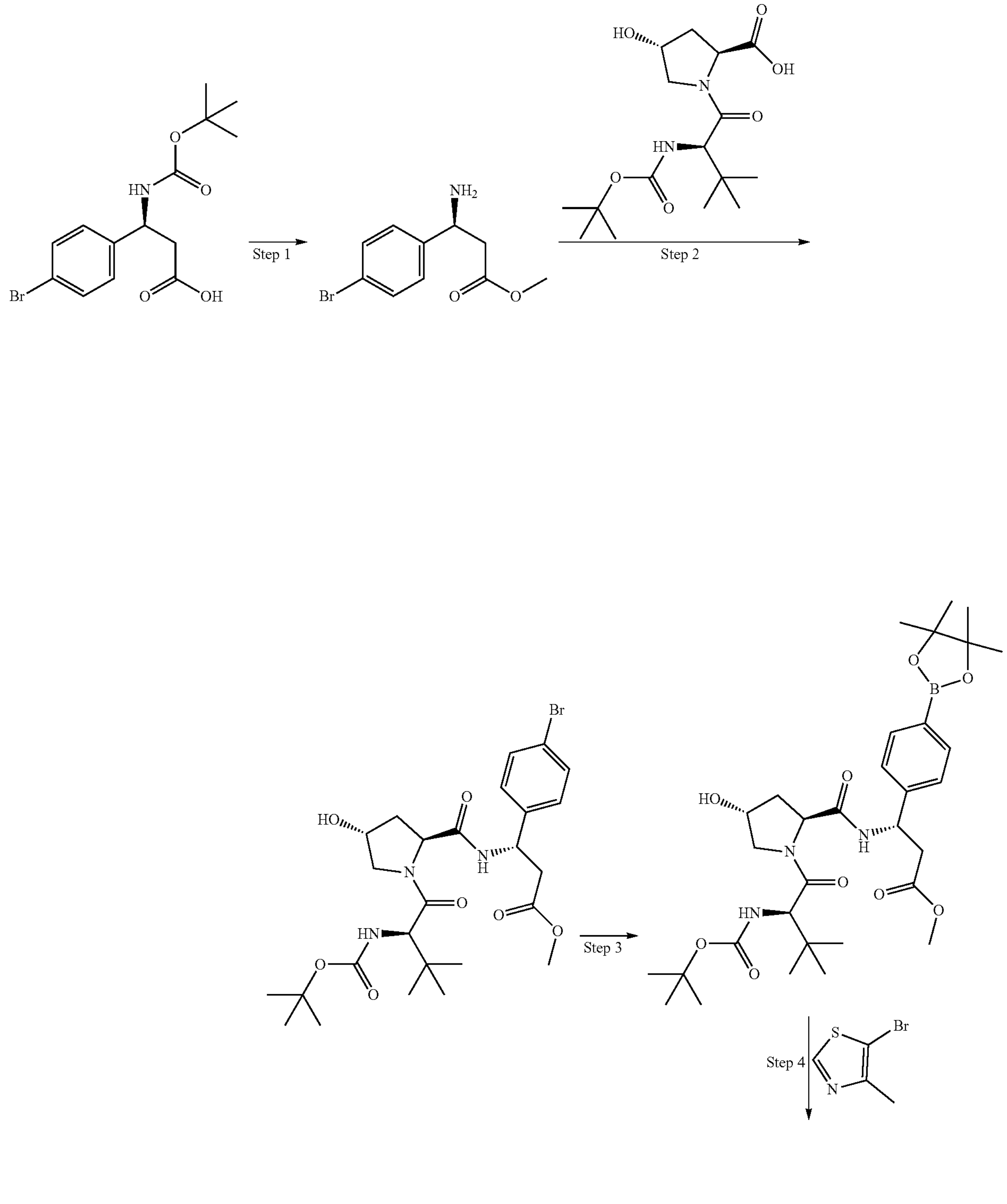

-continued

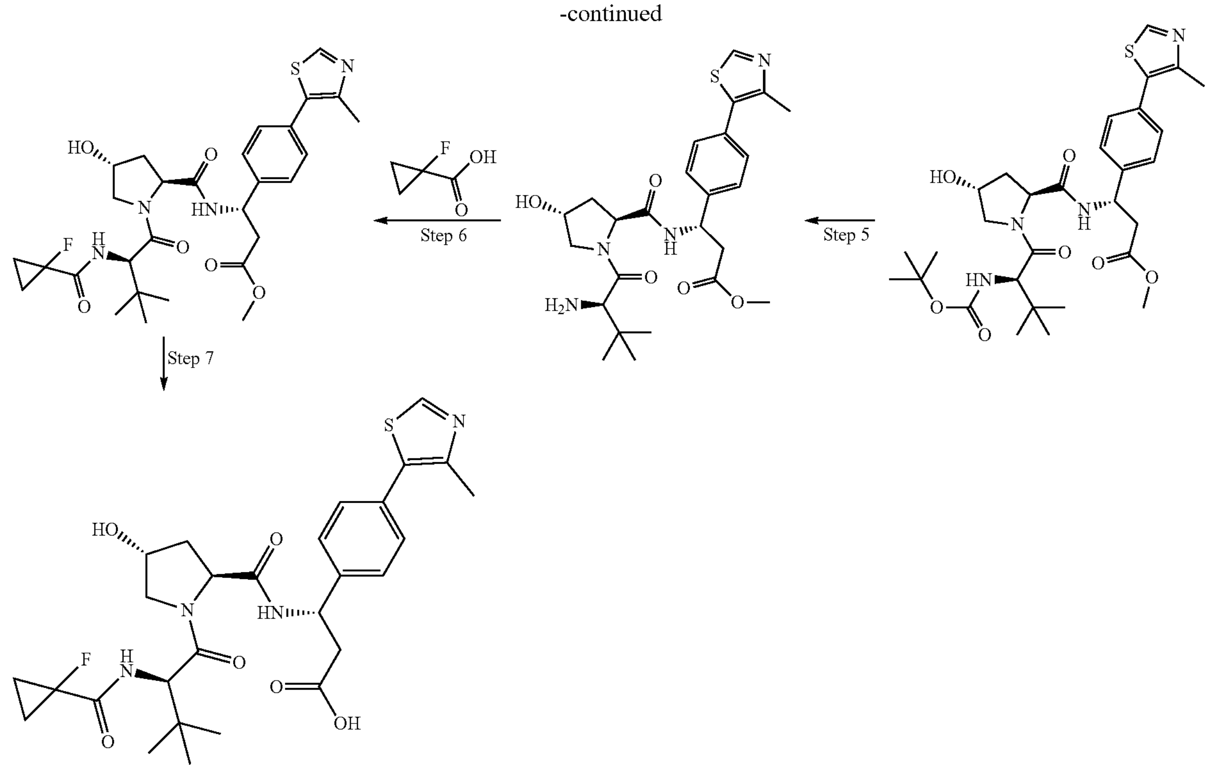

HVB14

Step 1: methyl (3S)-3-amino-3-(4-bromophenyl)propanoate hydrochloride. To a solution of (3S)-3-(4-bromophenyl)-3-{[(tert-butoxy)carbonyl]amino}propanoic acid (8 g, 1.453 mmol, 1.0 eq), in MeOH (140 mL, 0.3 M) at 0° C. was slowly added a cooled 3 M HCl in MeOH (200 mL, 0.15 M). The mixture was stirred at room temperature for 16 h. After that MeOH was removed by evaporation in vacuo, the obtained residue was triturated with $Et_2O$ to afford the desired product methyl (3S)-3-amino-3-(4-bromophenyl) propanoate hydrochloride (yield 90%) as a foam-like white solid: ESI(+)$[M+H]^+$=257.9 and 259.9 (Br pattern); 1H NMR (300 MHz, DMSO-$d_6$): 8.91 (d, J=5.5 Hz, 3H), 7.62 (d, J=8.5 Hz, 2H), 7.54 (d, J=8.6 Hz, 2H), 4.57 (q, J=5.5, 4.9 Hz, 1H), 3.54 (s, 3H), 3.25 (dd, J=16.4, 5.6 Hz, 1H), 3.03 (dd, J=16.3 Hz, 9.0 Hz, 1H).

Step 2: methyl (3S)-3-(4-bromophenyl)-3-{[(2S,4R)-1-[(2R)-2-{[(tert-butoxy)carbonyl]amino}-3,3-dimethylbutanoyl]-4-hydroxypyrrolidin-2-yl]formamido}propanoate 1. HATU (11.52 g, 30,298 mmol, 1.05 eq) dissolved in DMF (0.15M) was slowly added to the mixture of (2S,4R)-1-[(2R)-2-{[(tert-butoxy)carbonyl]amino}-3,3-dimethylbutanoyl]-4-hydroxypyrrolidine-2-carboxylic acid (11.925 g, 34.628 mmol, 1.20 eq.) and DIPEA (7.5 mL, 1.5 eq) in DMF (0.17M) at 0° C. The reaction was stirred at room temperature for 30 min.
2. To a solution of methyl (3S)-3-amino-3-(4-bromophenyl)propanoate hydrochloride (8.5 g, 28.85 mmol, 1.0 eq) in 55 mL of DMF (0.6M) was added DIPEA (20.11 mL, 4 eq) at −40° C. and left to stir at −40° C. for 5 min.
3. Reaction 1 was slowly added to the reaction 2 at −40° C. The mixture was left to stir at room temperature for 16 h.

The reaction mixture was diluted with water following by extraction with DCM organic layer were washed with brine, dried under $Na_2SO_4$, obtained crude was purified via flash chromatography eluted with DCM/MeOH-9/1 to give the product methyl (3S)-3-(4-bromophenyl)-3-{[(2S,4R)-1-[(2R)-2-{[(tert-butoxy)carbonyl]amino}-3,3-dimethylbutanoyl]-4-hydroxypyrrolidin-2-yl]formamido}propanoate (yield 71%) as a pale yellow solid. ESI(+)$[M+H]^+$=585.85.

$^1$H NMR (300 MHz, DMSO-$d_6$) δ 8.50 (d, J=8.1 Hz, 1H), 7.52-7.46 (m, 2H), 7.30-7.21 (m, 2H), 6.45 (d, J=9.2 Hz, 1H), 5.17-5.07 (m, 2H), 4.36 (t, J=8.0 Hz, 1H), 4.25 (s, 1H), 4.12 (d, J=9.3 Hz, 1H), 3.62-3.49 (m, 5H), 2.83-2.76 (m, 1H), 1.99-1.92 (m, 1H), 1.73-1.64 (m, 1H), 1.38 (s, 9H), 0.92 (s, 9H).

Step 3: methyl (3S)-3-{[(2S,4R)-1-[(2R)-2-{[(tert-butoxy)carbonyl]amino}-3,3-dimethylbutanoyl]-4-hydroxypyrrolidin-2-yl]formamido}-3-[4-(4,4,5,5-tetramethyl-1,3,2-dioxaborolan-2-yl)phenyl]propanoate. A mixture of bis(pinacolato)diboron (8.689 g, 34.21 mmol, 2 eq.), potassium acetate (5.037 g, 51.32 mmol, 3 eq), methyl (3S)-3-(4-bromophenyl)-3-{[(2S,4R)-1-[(2R)-2-{[(tert-butoxy)carbonyl]amino}-3,3-dimethylbutanoyl]-4-hydroxypyrrolidin-2-yl]formamido}propanoate (10 g, 14.542 mmol, 17.10 mmol, 1 eq.) dissolved in 285 mL of 1,4-dioxane (0.06M) was stirred a while with argon following by addition of [1,1'-bis(diphenylphosphino)ferrocene]dichloropalladium(II), complex with dichloromethane (1.39 g, 1.71 mmol, 0.1 eq.), then stirred additionally with argon, was placed in a 95° C. pre-heated oil-bath and left to stir for 16 h. The reaction mixture was concentrated, then redissolved in DCM and performed two flash chromatography purifications eluted with DCM/MeOH 98/2 to give the product. Additional flash purification, eluting with Hexane/EtOAc-0=>80%, yielded 8 g of the desired product methyl (3S)-3-{[(2S,4R)-1-[(2R)-

2-{[(tert-butoxy)carbonyl]amino}-3,3-dimethylbutanoyl]-4-hydroxypyrrolidin-2-yl]formamido}-3-[4-(4,4,5,5-tetramethyl-1,3,2-dioxaborolan-2-yl)phenyl]propanoate (yield 71%) as a pale brown foam. ESI(+)[M+H]$^+$=632.0; $^1$H NMR (300 MHz, DMSO-$d_6$) δ 8.49 (d, J=8.1 Hz, 1H), 7.65-7.57 (m, 2H), 7.30 (d, J=8.0 Hz, 2H), 6.44 (d, J=9.2 Hz, 1H), 5.22-5.05 (m, 2H), 4.43-4.34 (m, 1H), 4.25 (s, 1H), 4.13 (d, J=9.4 Hz, 1H), 3.55 (s, 5H), 2.88-2.70 (m, 1H), 1.98-1.90 (m, 1H), 1.68 (ddd, J=12.8, 8.2, 4.7 Hz, 1H), 1.38 (s, 9H), 1.28 (s, 12H), 0.93 (s, 9H).

Step 4: methyl (3S)-3-{[(2S,4R)-1-[(2R)-2-{[(tert-butoxy)carbonyl]amino}-3,3-dimethylbutanoyl]-4-hydroxypyrrolidin-2-yl]formamido}-3-[4-(4-methyl-1,3-thiazol-5-yl)phenyl]propanoate. The reaction mixture of 5-bromo-4-methylthiazole (3.383 g, 19.0 mmol, 1.5 eq), [1,1'-bis (diphenylphosphino)ferrocene]dichloropalladium(II), complex with dichloromethane (1.034 g, 1.266 mmol, 0.1 eq), potassium carbonate (5.02 g, 36.35 mmol, 2.87 eq), methyl (3S)-3-{[(2S,4R)-1-[(2R)-2-{[(tert-butoxy)carbonyl]amino}-3,3-dimethylbutanoyl]-4-hydroxypyrrolidin-2-yl]formamido}-3-[4-(4,4,5,5-tetramethyl-1,3,2-dioxaborolan-2-yl)phenyl]propanoate (8.0 g, 12.667 mmol, 1.0 eq) in the of 1,4-dioxane (210 mL, 0.06M) and water (63.33 ml, 0.2 M) was stirred under argon a while, then putted in a 100° C. pre-heated oil-bath and stirred for 16 h. Then the reaction mixture was filtered through a celite pad, the filtrate was concentrated and purified via a flash chromatography eluted with DCM/MeOH (MeOH 10-30%) to give 4.2 g of the desired product methyl (3S)-3-{[(2S,4R)-1-[(2R)-2-{[(tert-butoxy)carbonyl]amino}-3,3-dimethylbutanoyl]-4-hydroxypyrrolidin-2-yl]formamido}-3-[4-(4-methyl-1,3-thiazol-5-yl)phenyl]propanoate (yield 51%) as a pale brown solid. ESI(+)[M+H]$^+$=589.3; $^1$H NMR (300 MHz, DMSO-$d_6$) δ 8.99 (s, 1H), 8.55 (d, J=7.9 Hz, 1H), 7.49-7.34 (m, 4H), 6.45 (d, J=9.2 Hz, 1H), 5.15-5.08 (m, 2H), 4.40 (t, J=8.1 Hz, 1H), 4.27 (s, 1H), 4.14 (d, J=9.3 Hz, 1H), 3.62-3.54 (m, 2H), 2.75-2.58 (m, 2H), 2.45 (s, 3H), 2.00 (d, J=3.7 Hz, 1H), 1.75 (s, 1H), 1.39 (s, 9H), 0.93 (s, 9H).

Step 5: methyl (3S)-3-{[(2S,4R)-1-[(2R)-2-amino-3,3-dimethylbutanoyl]-4-hydroxypyrrolidin-2-yl]formamido}-3-[4-(4-methyl-1,3-thiazol-5-yl)phenyl]propanoate hydrochloride. To a solution of methyl (3S)-3-{[(2S,4R)-1-[(2R)-2-{[(tert-butoxy)carbonyl]amino}-3,3-dimethylbutanoyl]-4-hydroxypyrrolidin-2-yl]formamido}-3-[4-(4-methyl-1,3-thiazol-5-yl)phenyl]propanoate (4.9 g, 8.1 mmol, 1.0 eq), in MeOH (68 mL, 0.3M) at 0° C. was slowly added a cooled 3M HCl in MeOH (43.5 mL, 0.15M). The mixture was stirred at room temperature for 16 h. After that MeOH was removed by evaporation in vacuo, the obtained residue was triturated with $Et_2O$ to afford the desired product methyl (3S)-3-{[(2S,4R)-1-[(2R)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoate hydrochloride (yield 70%) as a foam-like white solid. ESI(+)[M+H]$^+$=503.3; $^1$H NMR (300 MHz, DMSO-$d_6$) δ 9.06 (s, 1H), 8.74 (d, J=8.1 Hz, 1H), 8.10 (s, 4H), 7.43 (q, J=8.4 Hz, 4H), 5.19 (d, J=7.6 Hz, 1H), 4.51 (d, J=8.4 Hz, 1H), 4.30 (s, 1H), 3.89 (d, J=5.3 Hz, 1H), 3.73 (d, J=11.0 Hz, 1H), 3.61-3.47 (m, 5H), 2.87-2.82 (m, 2H), 2.46 (s, 3H), 2.13-2.00 (m, 1H), 1.77-1.66 (m Hz, 1H), 1.02 (s, 9H).

Step 6: methyl (3S)-3-{[(2S,4R)-1-[(2R)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoate 1. HATU (3.6 g, 9.5 mmol, 1.04 eq.) dissolved in DMF (0.15M) was slowly added to the mixture of 1-Fluorocyclopropanecarboxylic acid (0.983 g, 9.45 mmol, 1.04 eq.) and DIPEA (2.4 mL, 1.5 eq) in DMF (0.17M) at 0° C. The reaction was stirred at room temperature for 30 min.
2. To a solution of methyl (3S)-3-{[(2S,4R)-1-[(2R)-2-amino-3,3-dimethylbutanoyl]-4-hydroxypyrrolidin-2-yl]formamido}-3-[4-(4-methyl-1,3-thiazol-5-yl)phenyl]propanoate (4.9 g, 9.2 mmol, 1.0 eq) in 55 mL DMF (0.16M) was added DIPEA (8.4 mL, 5 eq) at −40° C. and stirred at −40° C. for 5 min.
3. The reaction 1 was slowly added to the reaction 2 at −40° C. The mixture was stirred at room temperature for 16 h.

The reaction mixture was diluted with water following by extraction with DCM organic layer were washed with brine, dried under $Na_2SO_4$, obtained crude was purified via flash chromatography eluted with DCM/MeOH-9/1 to give the product (3S)-3-{[(2S,4R)-1-[(2R)-2-[(1-fluorocyclopropyl) formamido]-3,3-dimethylbutanoyl]-4-hydroxypyrrolidin-2-yl]formamido}-3-[4-(4-methyl-1,3-thiazol-5-yl)phenyl]propanoic acid (yield 47%) as a pale yellow solid. ESI(+)[M+H]=589.35

$^1$H NMR (300 MHz, DMSO-$d_6$) δ 8.99 (s, 1H), 8.59 (d, J=8.1 Hz, 1H), 7.44 (t, J=7.5 Hz, 4H), 7.28 (dd, J=9.2, 2.9 Hz, 1H), 5.25-5.11 (m, 2H), 4.57 (d, J=9.2 Hz, 1H), 4.43 (t, J=8.3 Hz, 1H), 4.27 (s, 1H), 3.63-3.52 (m, 5H), 2.86-2.81 (m, 1H), 2.46 (s, 3H), 2.08-2.00 (m, 1H), 1.79-1.68 (m, 1H), 1.42-1.29 (m, 2H), 1.24-1.18 (m, 2H), 0.96 (d, J=6.4 Hz, 9H).

Step 7: (3S)-3-{[(2S,4R)-1-[(2R)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid. (3S)-3-{[(2S,4R)-1-[(2R)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid (2.8 g, 4.756 mmol, 1.0 eq) and lithium hydroxide monohydrate (0.409 g, 9.518 mmol, 2 eq) were dissolved in the mixture of tetrahydrofuran (2.8 ml, 1.7 M) and water (10.12 ml, 0.47 M) and stirred for 2 h at room temperature. After that THF was removed under vacuo, the obtained water layer residue was neutralized with $KHSO_4$ to pH 4, formed solid was filtered to give the product (3S)-3-{[(2S,4R)-1-[(2S)-2-[(1-fluorocyclopropyl) formamido]-3,3-dimethylbutanoyl]-4-hydroxypyrrolidin-2-yl]formamido}-3-[4-(4-methyl-1,3-thiazol-5-yl)phenyl]propanoic acid (yield 86%) as a white-off solid. LCMS (254 nm): RT=2.787 min, 93.13% purity. ESI(+)[M+H]$^+$=575.24. $^1$H NMR (300 MHz, DMSO-$d_6$) δ 8.99 (s, 1H), 8.55 (d, J=7.6 Hz, 1H), 7.47-7.37 (m, 4H), 7.28 (dd, J=9.2, 3.0 Hz, 1H), 5.17-5.09 (m, 2H), 4.57 (d, J=9.2 Hz, 1H), 4.43 (t, J=8.3 Hz, 1H), 4.27 (s, 1H), 3.59 (dd, J=12.0, 8.3 Hz, 2H), 2.86-2.62 (m, 2H), 2.46 (s, 3H), 2.04 (t, J=10.6 Hz, 1H), 1.73 (ddd, J=13.1, 8.9, 4.5 Hz, 1H), 1.36 (ddd, J=18.2, 5.7, 3.1 Hz, 2H), 1.25-1.16 (m, 2H), 0.96 (s, 9H).

HVB15: 2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]acetic acid

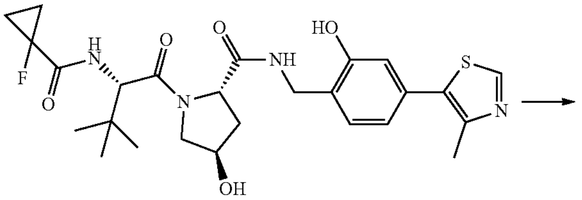

-continued

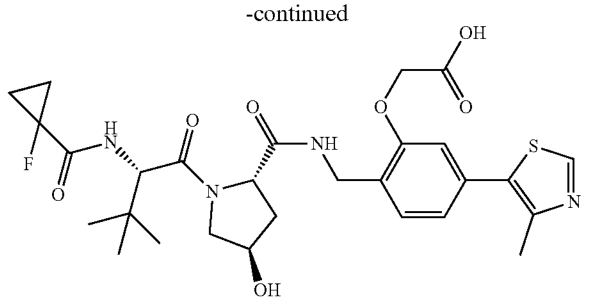

HVB15

Prepared analogously to HVB4, but with tert-butyl bromoacetate in place of tert-butyl 6-bromohexanoate. LCMS: $C_{28}H_{35}FN_4O_7S$ requires: 590.22. found: m/z=591.3[M+H]$^+$.

HVB16: (S)-3-((2S,4R)-1-((R)-2-(1-fluorocyclopropane-1-carboxamido)-3,3-dimethylbutanoyl)-4-hydroxypyrrolidine-2-carboxamido)-3-phenylpropanoic acid

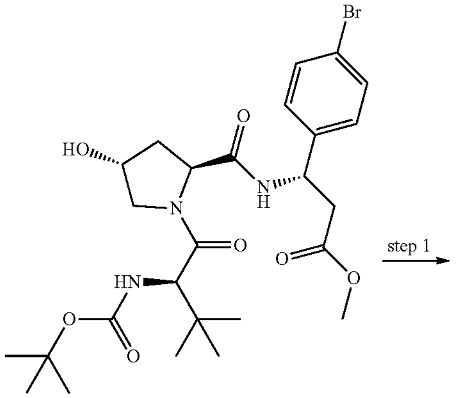

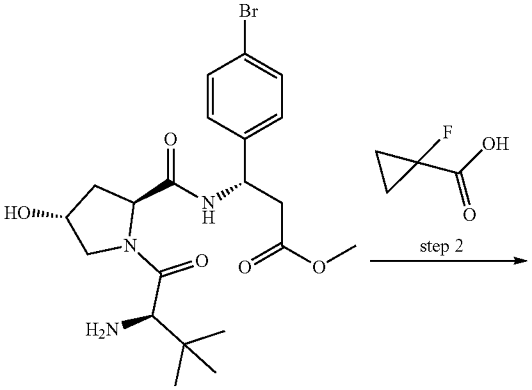

-continued

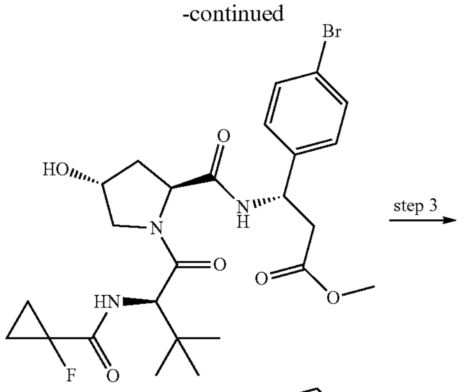

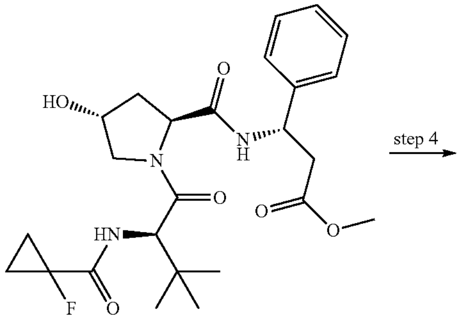

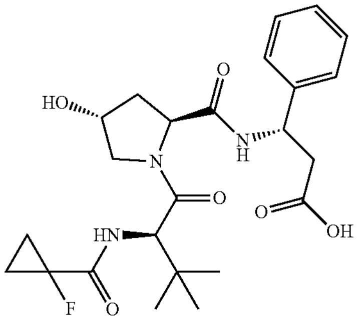

HVB16

Step 1: methyl (3S)-3-{[(2S,4R)-1-[(2R)-2-amino-3,3-dimethylbutanoyl]-4-hydroxypyrrolidin-2-yl]formamido}-3-(4-bromophenyl)propanoate hydrochloride. To a solution of methyl (3S)-3-(4-bromophenyl)-3-{[(2S,4R)-1-[(2R)-2-{[(tert-butoxy)carbonyl]amino}-3,3-dimethylbutanoyl]-4-hydroxypyrrolidin-2-yl]formamido}propanoate (1.5 g, 2.566 mmol, 1.0 eq), in MeOH (21 mL, 0.3M) at 0° C. was slowly added a cooled 3 M methanolic solution of HCl (160 mL, 0.15M). The mixture was stirred at RT for 64 h (weekend). After that MeOH was removed, obtained residue was triturated with $Et_2O$ to give the product methyl (3S)-3-{[(2S,4R)-1-[(2S)-2-amino-3,3-dimethylbutanoyl]-4-hydroxypyrrolidin-2-yl]formamido}-3-(4-bromophenyl)propanoate hydrochloride (1.32 g, 2.534 mmol, 94%) as a pile yellow solid. ESI(−)[M−H]$^-$=482; $^1$H NMR (300 MHz, DMSO-$d_6$) 8.72 (d, J=8.0 Hz, 1H), 8.10 (s, 3H), 7.53-7.48 (m, 2H), 7.30-7.23 (m, 2H), 5.11 (d, J=7.7 Hz, 1H), 4.47 (t, J=8.4 Hz, 1H), 4.28 (s, 1H), 3.88 (d, J=5.1 Hz, 2H), 3.71 (d, J=11.0 Hz, 1H), 3.48 (dd, J=11.0, 3.8 Hz, 1H), 3.17 (s, 3H), 2.88-2.71 (m, 2H), 2.10-1.99 (m, 1H), 1.66 (s, 1H), 1.02 (s, 9H).

Step 2: methyl (3S)-3-(4-bromophenyl)-3-{[(2S,4R)-1-[(2R)-2-[(1-fluorocyclopropyl)formamido]-3,3-dimethylbutanoyl]-4-hydroxypyrrolidin-2-yl]formamido}propanoate 1. To 1-Fluorocyclopropanecarboxylic acid (0.274 g, 2.63 mmol, 1.04 eq.) in 5 mL of DMF (0.5M) was added DIPEA (0.663 mL, 1.5 eq) at 0° C. Then HATU (1 g, 2.635 mmol, 1.04 eq.) was dissolved in 5 mL of DMF and slowly added to the mixture at 0° C. The reaction was stirred at room temperature for 30 min.
2. To a solution of methyl (3S)-3-{[(2S,4R)-1-[(2S)-2-amino-3,3-dimethylbutanoyl]-4-hydroxypyrrolidin-2-yl]formamido}-3-(4-bromophenyl)propanoate hydrochloride (1.320 g, 2.534 mmol, 1.0 eq) in 5 mL of DMF (0.5M) was added DIPEA (2.2 mL, 5 eq) at −40° C. and left to stir at −40° C. for 5 min.
3. Reaction 1 was slowly added to the Reaction 2 at −40° C. The mixture was left to stir at room temperature for 1 h.

After that the obtained reaction mixture was diluted with water following by extraction with DCM organic layer were washed with brine, dried under $Na_2SO_4$ to give the crude product, which was purified by FC eluted with DCM/MeOH-9/1 to give the desired product methyl (3S)-3-(4-bromophenyl)-3-{[(2S,4R)-1-[(2S)-2-[(1-fluorocyclopropyl)formamido]-3,3-dimethylbutanoyl]-4-hydroxypyrrolidin-2-yl]formamido}propanoate (1.117 g, 1.958 mmol, 73%). ESI(+)$[M+H]^+$=570.2

$^1$H NMR (300 MHz, DMSO-$d_6$) δ 8.57 (d, J=8.0 Hz, 1H), 7.55-7.46 (m, 2H), 7.31-7.23 (m, 3H), 5.17-5.09 (m, 2H), 4.57 (d, J=9.1 Hz, 1H), 4.40 (t, J=8.3 Hz, 1H), 4.25 (s, 1H), 3.56 (s, 4H), 3.20-3.03 (m, 1H), 2.84-2.70 (m, 2H), 2.05-1.92 (m, 1H), 1.69 (td, J=8.6, 4.4 Hz, 1H), 1.36 (dd, J=18.5, 3.5 Hz, 1H), 0.95 (d, J=7.0 Hz, 9H).

Step 3: methyl (3S)-3-{[(2S,4R)-1-[(2R)-2-[(1-fluorocyclopropyl)formamido]-3,3-dimethylbutanoyl]-4-hydroxypyrrolidin-2-yl]formamido}-3-phenylpropanoate. Methyl (3S)-3-{[(2S,4R)-1-[(2R)-2-[(1-fluorocyclopropyl)formamido]-3,3-dimethylbutanoyl]-4-hydroxypyrrolidin-2-yl]formamido}-3-phenylpropanoate) (0.834 g, 1.46 mmol, 1 eq) dissolved in i-PrOH (0.5M), was degassed, charged with $Pd(OAc)_2$ (0.4 eq) and left to stir under $H_2$ (1 atm, balloon) for overnight. Conversion was monitored by LCMS, NMR and TLC. After full consumption of the starting material, the reaction mixture was filtrated through a Celite pad, concentrated under reduced pressure to give the desired product methyl (3S)-3-{[(2S,4R)-1-[(2R)-2-[(1-fluorocyclopropyl)formamido]-3,3-dimethylbutanoyl]-4-hydroxypyrrolidin-2-yl]formamido}-3-phenylpropanoate (0.6 g, 1.22 mmol, 87% yield). ESI(−)$[M-H]^-$=490.30; ESI(+)$[M+H]^+$=492.25; $^1$H NMR (300 MHz, DMSO-$d_6$) δ 8.53 (d, J=8.2 Hz, 1H), 7.35-7.20 (m, 6H), 5.23-5.08 (m, 2H), 4.61-4.53 (d, J=9.35 Hz, 1H), 4.42 (t, J=8.2 Hz, 1H), 4.26 (s, 1H), 3.60 (m, 3.62-3.53 Hz, 5H), 2.88-2.70 (m, 2H), 2.05-1.96 (m, 1H), 1.74-1.65 (m, 1H), 1.42-1.31 (m, 2H), 1.25-1.17 (m, 3H), 0.96 (s, 9H).

Step 4: (S)-3-((2S,4R)-1-(R)-2-(1-fluorocyclopropane-1-carboxamido)-3,3-dimethylbutanoyl)-4-hydroxypyrrolidine-2-carboxamido)-3-phenylpropanoic acid. To methyl (3S)-3-{[(2S,4R)-1-[(2R)-2-[(1-fluorocyclopropyl)formamido]-3,3-dimethylbutanoyl]-4-hydroxypyrrolidin-2-yl]formamido}-3-phenylpropanoate (0.6 g, 1.22 mmol, 1 eq) dissolved in the mixture THF/$H_2O$—5/1 (0.5 M) was added lithium hydroxide monohydrate (0.042 g, 2.44 mmol, 2 eq) and left to stir for 16 h at room temperature. The reaction was monitored by TLC and LCMS. THF was evaporated, the water layer residue was neutralized with $NaHSO_4$ (2 eq), the mixture was concentrated, obtained dry residue was triturated with DCM to give the desired product methyl (3S)-3-{[(2S,4R)-1-[(2R)-2-[(1-fluorocyclopropyl)formamido]-3,3-dimethylbutanoyl]-4-hydroxypyrrolidin-2-yl]formamido}-3-phenylpropanoate (0.350 g, 0.732 mmol, 81% yield): LCMS: 254 nm, RT=2.09 min, 87.76%, ESI (−) $[M-H]^-$=475.98; $^1$H NMR (300 MHz, DMSO-$d_6$) δ 12.24 (s, 1H), 8.46 (d, J=8.1 Hz, 1H), 7.33-7.20 (m, 6H), 5.16-5.03 (m, 2H), 4.57 (d, J=9.1 Hz, 1H), 4.42 (t, J=8.3 Hz, 1H), 4.25 (s, 1H), 3.64-3.49 (m, 2H), 2.77 (dd, J=15.7, 6.6 Hz, 1H), 2.64 (dd, J=15.6, 8.2 Hz, 1H), 2.06-1.95 (m, 1H), 1.70 (ddd, J=12.8, 8.7, 4.4 Hz, 1H), 1.42-1.31 (m, 2H), 1.24-1.17 (m, 3H), 0.96 (s, 9H).

HVB17 (2S,4S)-1-((S)-2-amino-3,3-dimethylbutanoyl)-4-hydroxy-N-(4-(4-methylthiazol-5-yl)benzyl)pyrrolidine-2-carboxamide

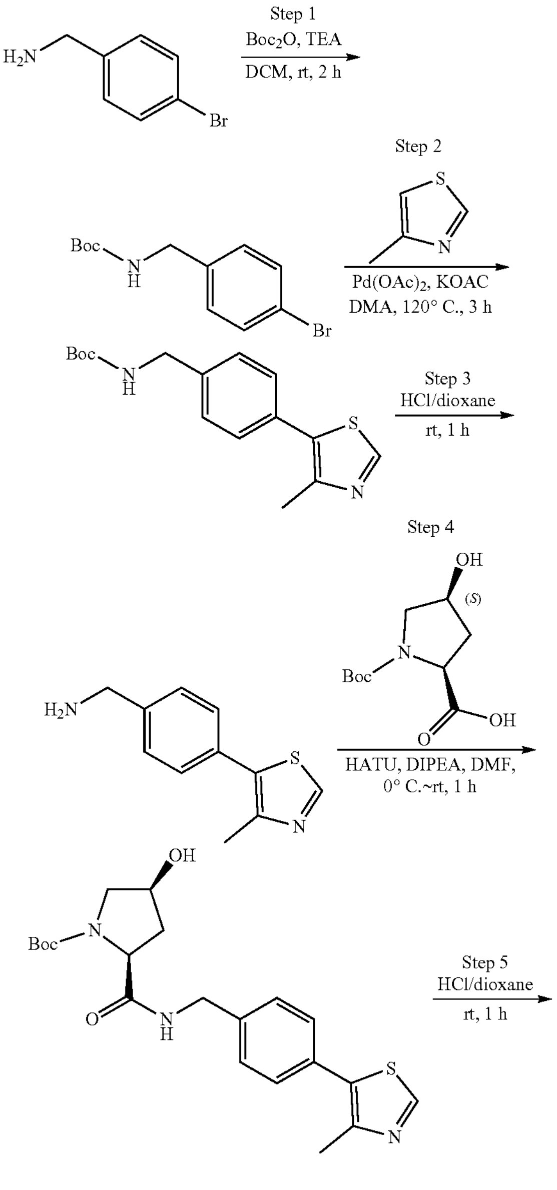

-continued

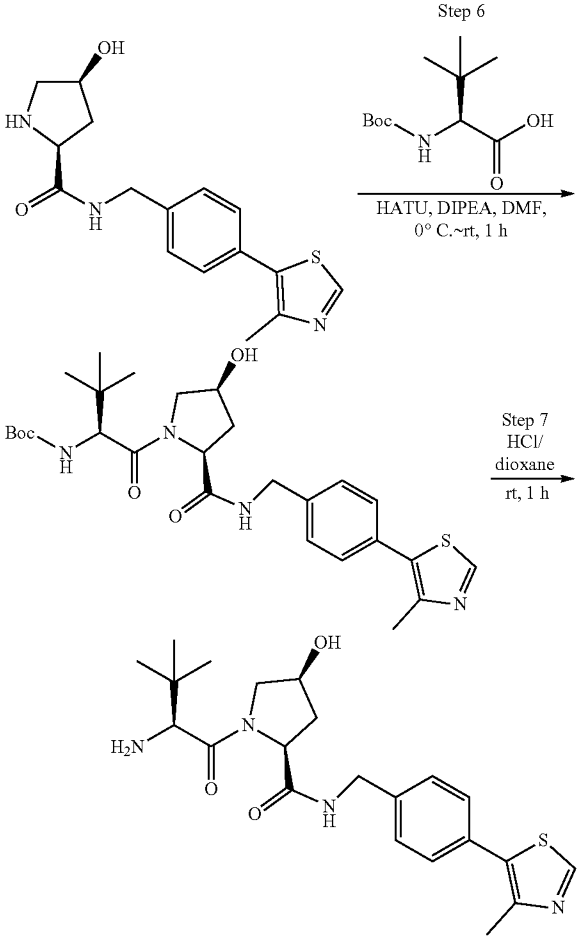

HVB17

Step 1. Synthesis of tert-butyl N-[(4-bromophenyl)methyl]carbamate. To a solution of (4-bromophenyl)methanamine (22.8 g, 122.55 mmol, 15.51 mL, 1 eq) and TEA (18.60 g, 183.82 mmol, 25.59 mL, 1.5 eq) in DCM (150 mL) was added tert-butoxycarbonyl tert-butyl carbonate (29.42 g, 134.80 mmol, 30.97 mL, 1.1 eq). The mixture was stirred at 25° C. for 2 h. TLC (Petroleum ether/ethyl acetate=10:1) showed the material (4-bromophenyl) methanamine was consumed, and a major new spot was detected. The mixture was poured into water (150 mL), the organic layer was separated, washed with 1N HCl aqueous (150 mL) and brine (100 mL), then the organic layer was dried over anhydrous $Na_2SO_4$, filtered, the filtrate was concentrated. The residue was purified by triturated in petroleum ether (120 mL) and collected by filtration, the filter cake was dried under vacuum to afford tert-butyl N-[(4-bromophenyl)methyl]carbamate (26.3 g, 91.91 mmol, 75% yield) as white solid.

Step 2. Synthesis of tert-butyl N-[[4-(4-methylthiazol-5-yl)phenyl]methyl]carbamate. To a stirred solution of tert-butyl N-[(4-bromophenyl)methyl]carbamate (26.3 g, 91.91 mmol, 1 eq) in DMA (150 mL), under an atmosphere of $N_2$, was added 4-methylthiazole (18.23 g, 183.81 mmol, 16.72 mL, 2 eq), KOAc (18.04 g, 183.81 mmol, 2 eq) and $Pd(OAc)_2$ (1.03 g, 4.60 mmol, 0.05 eq). The resulting mixture was stirred at 120° C. for 16 h. LCMS showed a main peak with desired MS detected. TLC (Petroleum ether/ethyl acetate=5:1) showed the material tert-butyl N-[(4-bromophenyl)methyl]carbamate was consumed, and a major new spot was detected. The mixture was poured into water (200 mL), the aqueous mixture was extracted with ethyl acetate (150 mL*2), the combined organic layer was washed with brine (100 mL), dried over anhydrous $Na_2SO_4$, concentrated. The residue was triturated with Petroleum ether:Ethyl acetate=10:1 (80 mL) to afford tert-butyl N-[[4-(4-methylthiazol-5-yl)phenyl]methyl]carbamate (16.8 g, 55.19 mmol, 60.05% yield) as yellow solid. MS[M+H]=305.0. $^1H$ NMR (400 MHz, $CDCl_3$) δ 8.70 (s, 1H), 7.46-7.41 (m, 2H), 7.40-7.34 (m, 2H), 4.98-4.87 (m, 1H), 4.39 (d, J=5.9 Hz, 2H), 2.55 (s, 3H), 1.50 (s, 9H).

Step 3. Synthesis of [4-(4-methylthiazol-5-yl)phenyl]methanamine. A mixture of tert-butyl N-[[4-(4-methylthiazol-5-yl)phenyl]methyl]carbamate (16.8 g, 55.19 mmol, 1 eq) in HCl/dioxane (4 M, 50 mL, 3.62 eq) was stirred at 25° C. for 1 h. LCMS showed a main peak with desired mass was detected. The solvent was evaporated to afford [4-(4-methylthiazol-5-yl)phenyl]methanamine (13.3 g, crude, HCl) as yellow solid, which was used directly in the next step without any purification. $MS[M+H]^+=205.1$.

Step 4. Synthesis of tert-butyl (2S,4S)-4-hydroxy-2-[[4-(4-methylthiazol-5-yl)phenyl]methylcarbamoyl]pyrrolidine-1-carboxylate. To a mixture of (2S,4S)-1-tert-butoxycarbonyl-4-hydroxy-pyrrolidine-2-carboxylic acid (12.77 g, 55.24 mmol, 1.0 eq) and DIPEA (14.28 g, 110.49 mmol, 19.24 mL, 2 eq) in DMF (120 mL) was added HATU (23.11 g, 60.77 mmol, 1.1 eq). The mixture was stirred at 25° C. for 30 min, then [4-(4-methylthiazol-5-yl)phenyl]methanamine (13.3 g, 55.24 mmol, 1 eq, HCl) was added and the formed mixture was stirred at 25° C. for 1.5 h. LCMS showed the material [4-(4-methylthiazol-5-yl)phenyl]methanamine was consumed, and desired mass was detected. The mixture was poured into water (100 mL), the formed aqueous was extracted with ethyl acetate (100 mL*2), the combined organic layer was dried over anhydrous $Na_2SO_4$, concentrated. The residue was purified by chromatography (silica gel, eluting with DCM:MeOH=100:1, 50:1) to afford tert-butyl (2S,4S)-4-hydroxy-2-[[4-(4-methylthiazol-5-yl)phenyl]methylcarbamoyl]pyrrolidine-1-carboxylate (17 g, 38.19 mmol, 69.13% yield, 93.8% purity) as light yellow oil. $MS[M+H]^+=418.3$.

Step 5. Synthesis of (2S,4S)-4-hydroxy-N-[[4-(4-methylthiazol-5-yl)phenyl]methyl]pyrrolidine-2-carboxamide. A mixture of tert-butyl (2S,4S)-4-hydroxy-2-[[4-(4-methylthiazol-5-yl)phenyl]methylcarbamoyl]pyrrolidine-1-carboxylate (5 g, 11.23 mmol, 1 eq) in HCl/dioxane (4 M, 50 mL, 17.80 eq) was stirred at 25° C. for 1 h. LCMS showed the material tert-butyl (2S,4S)-4-hydroxy-2-[[4-(4-methylthiazol-5-yl)phenyl]methylcarbamoyl]pyrrolidine-1-carboxylate was consumed, and a main peak with desired mass was detected. The solvent was evaporated to afford (2S,4S)-4-hydroxy-N-[[4-(4-methylthiazol-5-yl)phenyl]methyl]pyrrolidine-2-carboxamide (4 g, crude, HCl) as light yellow solid, which was without any purification and used directly in the next step. MS $(M+H)^+=318.1$.

Step 6. Synthesis of tert-butyl N-[(1S)-1-[(2S,4S)-4-hydroxy-2-[[4-(4-methylthiazol-5-yl)phenyl]methylcarbamoyl]pyrrolidine-1-carbonyl]-2,2-dimethyl-propyl]carbamate. To a solution of (2S,4S)-4-hydroxy-N-[[4-(4-methylthiazol-5-yl)phenyl]methyl]pyrrolidine-2-carboxamide (4 g, 11.30 mmol, 1 eq, HCl) and (2S)-2-(tert-butoxycarbonylamino)-3,3-dimethyl-butanoic acid (2.61 g, 11.30 mmol, 1 eq) in DMF (30 mL) were added HATU (4.73 g, 12.43 mmol, 1.1 eq) and DIPEA (2.92 g, 22.61 mmol, 3.94 mL, 2 eq) at 0° C., the mixture was then stirred at 25° C. for 2 h. LCMS showed the material (2S,4S)-4-hydroxy-N-[[4-(4-methylthiazol-5-yl)phenyl]methyl]pyrrolidine-2-carboxamide was consumed, and a main peak with desired mass was detected. The mixture was poured into water (100 mL), the resulting aqueous extracted with ethyl acetate (100 mL*2). The combined organic layer was dried over anhydrous $Na_2SO_4$, concentrated. The residue was purified by reverse flash MPLC (FA) to afford tert-butyl-N-[(1S)-1-[(2S,4S)-4-hydroxy-2-[[4-(4-methylthiazol-5-yl)phenyl]methylcarbamoyl]pyrrolidine-1-carbonyl]-2,2-dimethyl-propyl]carbamate (1.65 g, 3.01 mmol, 26.60% yield, 96.7% purity) as light yellow gum. MS[M+H]$^+$=531.2.

Step 7. Synthesis of (2S,4S)-1-[(2S)-2-amino-3,3-dimethyl-butanoyl]-4-hydroxy-N-[[4-(4-methylthiazol-5-yl)phenyl]methyl]pyrrolidine-2-carboxamide. To a solution of tert-butyl N-[(1S)-1-[(2S,4S)-4-hydroxy-2-[[4-(4-methylthiazol-5-yl)phenyl]methylcarbamoyl]pyrrolidine-1-carbonyl]-2,2-dimethyl-propyl]carbamate (3.35 g, 6.31 mmol, 1 eq) in dioxane (10 mL) was added HCl/dioxane (4 M, 20 mL, 12.67 eq). The mixture was stirred at 25° C. for 1 h. LCMS showed a main peak with desired mass was detected. The solvent was evaporated. The residue was triturated in petroleum ether/ethyl acetate (10:1, 80 mL) and collected by filtration to afford (2S,4S)-1-[(2S)-2-amino-3,3-dimethyl-butanoyl]-4-hydroxy-N-[[4-(4-methylthiazol-5-yl)phenyl]methyl]pyrrolidine-2-carboxamide (2.77 g, 5.63 mmol, 89.20% yield, 94.8% purity, HCl) as white powder. MS[M+H]=431.3. $^1H$ NMR (400 MHz, $CD_3OD$) δ 9.78 (s, 1H), 7.63-7.48 (m, 4H), 4.65-4.59 (m, 1H), 4.57-4.54 (m, 1H), 4.06 (s, 1H), 4.00-3.94 (m, 1H), 3.67-3.63 (m, 1H), 3.62 (s, 2H), 2.60 (s, 3H), 2.57-2.49 (m, 1H), 1.99 (d, J=13.4 Hz, 1H), 1.15 (s, 9H).

HVB18: (2S,4R)-1-[(2S)-2-amino-3,3-dimethylbutanoyl]-N-[(1S)-1-(4-bromophenyl)ethyl]-4-hydroxypyrrolidine-2-carboxamide

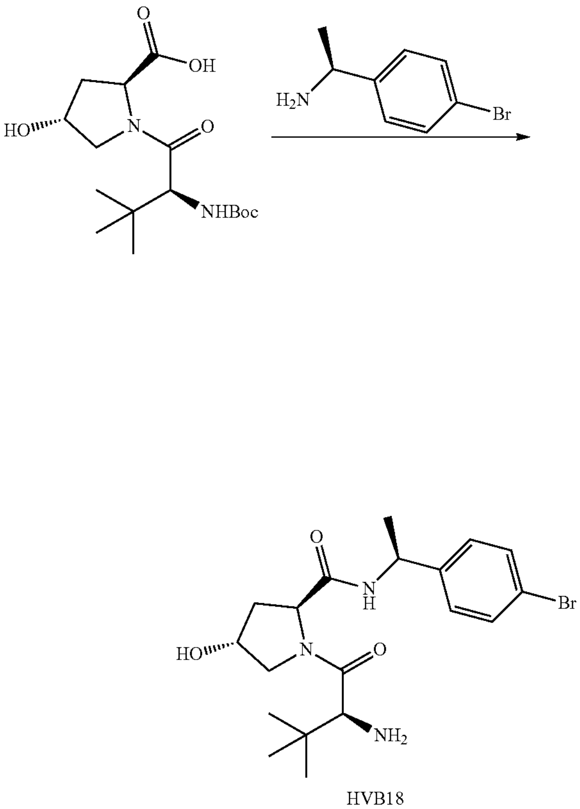

HVB18

Followed same protocol as for the synthesis of (2S,4R)-1-[(2S)-2-[(1-Fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (Scheme B4) but used (S)-1-(4-bromophenyl)ethan-1-amine in place of 2-(aminomethyl)-5-(4-methyl-1,3-thiazol-5-yl)phenol. LCMS: $C_{19}H_{28}BrN_3O_3$ requires: 425.13. found: m/z=426.67[M+H]$^+$.

HVB19: (2S,4R)-1-[(2S)-2-amino-3,3-dimethylbutanoyl]-4-hydroxy-N-[(1S)-1-phenylethyl]pyrrolidine-2-carboxamide

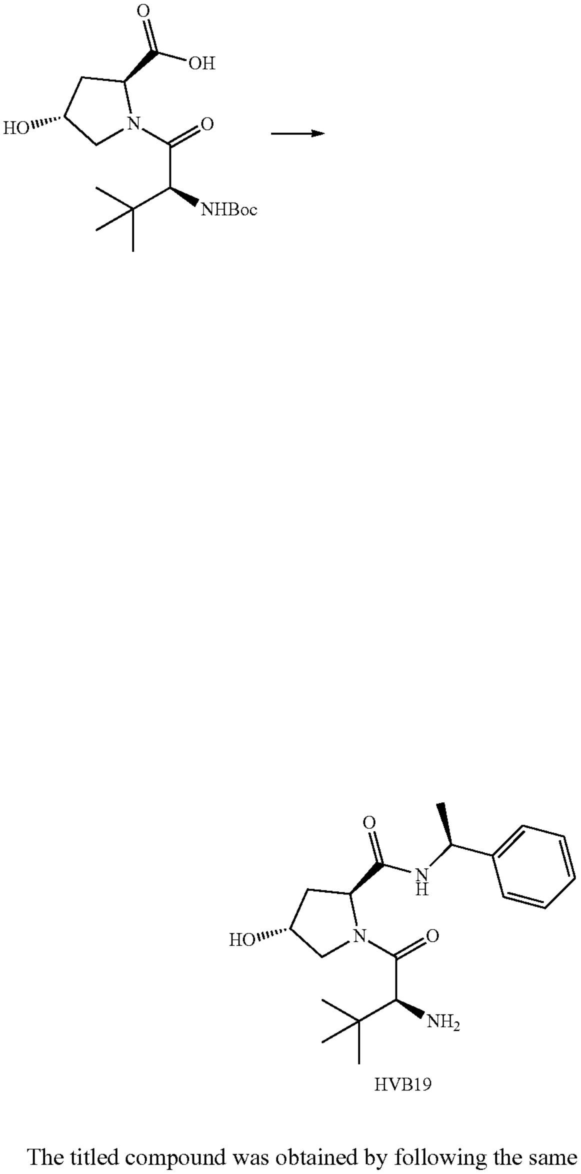

HVB19

The titled compound was obtained by following the same protocol as for the synthesis of (2S,4R)-1-[(2S)-2-[(1-Fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (Scheme B4) but used (S)-1-phenylethan-1-amine in place of 2-(aminomethyl)-5-(4-methyl-1,3-thiazol-5-yl)phenol. LCMS: $C_{19}H_{29}N_3O_3$ requires: 347.22. found: m/z=348.13[M+H]$^+$.

HVB20: (3R)-3-((2R,4S)-4-hydroxy-1-(3-methyl-2-(3-methylisoxazol-5-yl)butanoyl)pyrrolidine-2-carboxamido)-3-(4-(4-methylthiazol-5-yl)phenyl)propanoic acid
Step 1: Methyl (3S)-3-amino-3-(4-bromophenyl)propanoate. To a solution of (3S)-3-(4-bromophenyl)-3-{[(tert-butoxy)carbonyl]amino}propanoic acid (8.0 g, 0.023 mmol, 1.0 eq) in methanol (100 ml, 0.01 M) at 0° C. was slowly
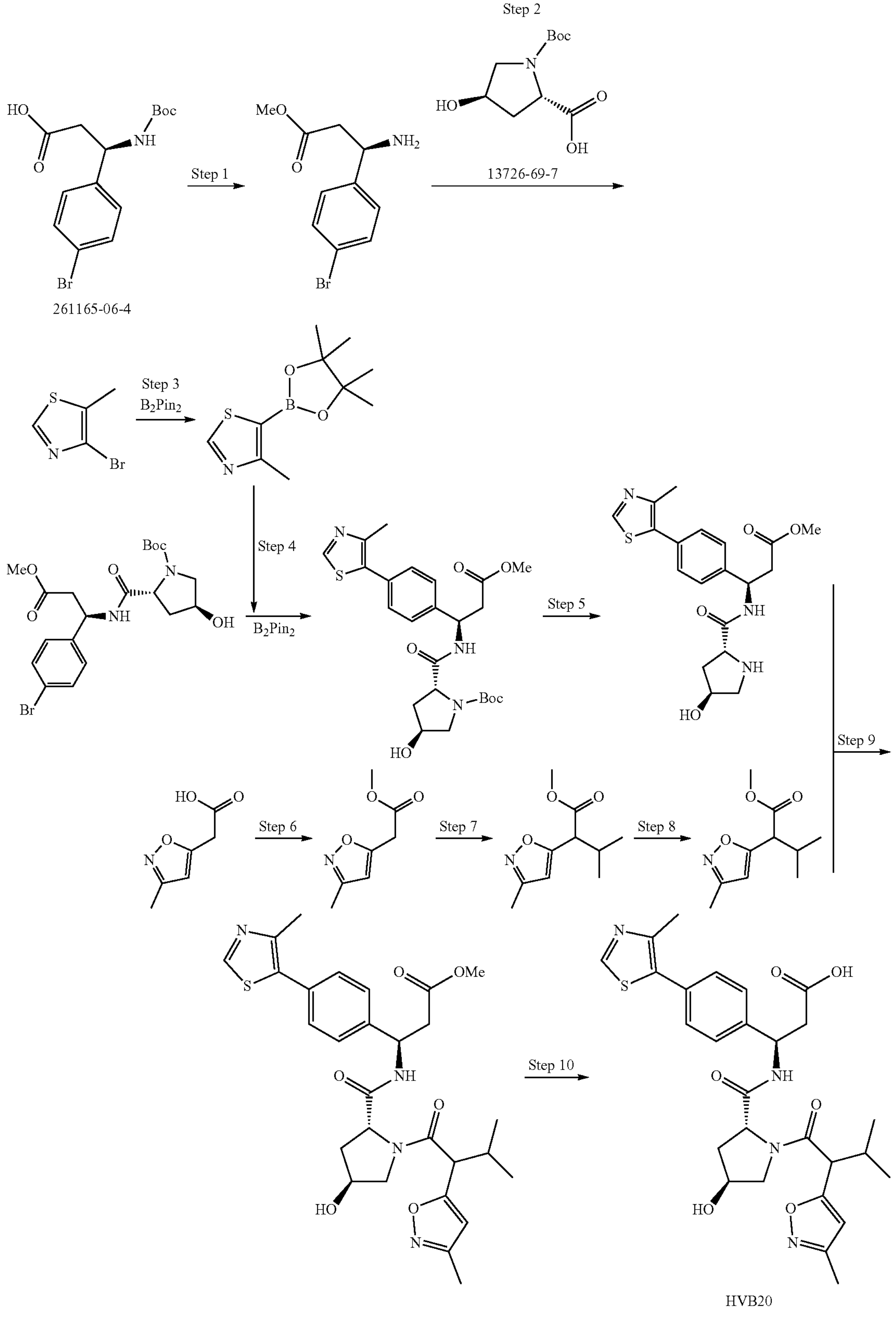

added a cooled solution of HCl (3 M in MeOH, 160 mL, 0.01 M). The mixture was stirred at room temperature for 16 h. The crude reaction was concentrated in vacuo at 30° C. and then, a 3 M solution of HCl in $Et_2O$ (40 ml) was added followed by concentration in vacuo to afford methyl (3S)-3-amino-3-(4-bromophenyl)propanoate a foamy white solid. The product was isolated as a HCl salt and was engaged in the next step without additional purification (5.71 g, 95% yield). ESI(+)$[M+H]^+$=258.00; $^1$H NMR (300 MHz, Methanol-$d_4$), δ: 7.63 (d, J=8.2 Hz, 2H), 7.40 (d, J=8.2 Hz, 2H), 4.73 (t, J=7.1 Hz, 1H), 3.70 (s, 3H), 3.19-2.97 (m, 2H).

Step 2: tert-butyl (2S,4R)-2-{[(1S)-1-(4-bromophenyl)-3-methoxy-3-oxopropyl]carbamo-yl}-4-hydroxypyrrolidine-1-carboxylate. To a solution of (2S,4R)-1-[(tert-butoxy) carbonyl]-4-hydroxypyrrolidine-2-carboxylic acid (5.71 g, 24.7 mmol, 1.15 eq) in DMF (45 mL, 0.5 M) at 0° C. was added DIPEA (6 ml, 1.5 eq). Then, a solution of HATU (8.53 g, 22.5 mmol, 1.04 eq) in DMF (45 ml, 0.5 M) was added slowly to the previous solution at 0° C. The reaction mixture was stirred at room temperature for 0.5 h and was then slowly added at −30° C. to a cooled solution of methyl (3S)-3-amino-3-(4-bromophenyl)propanoate (6.7 g, 21.5 mmol, 1 eq) in DMF (35 mL, 0.6 M) pre-treated with DIPEA (20 mL, 5 eq). The mixture was stirred at −30° C. slowly warmed to RT in 2 h (TLC, UPLC and NMR control). The crude reaction was then thrown on crushed ice and extracted with DCM (6×500 mL). The organic layer was dried over $Na_2SO_4$, concentrated in vacuo, and purified by flash column chromatography (eluent DCM/MeOH 9:1) to afford the desired compound as a foamy white solid (10.54 g, quant. yield). ESI(+)$[M+H]^+$=471.10; $^1$H NMR (300 MHz, DMSO-$d_6$) Methanol-d4) δ 7.47 (t, J=7.9 Hz, 2H), 7.36-7.20 (m, 2H), 5.32 (t, J=7.4 Hz, 1H), 4.29 (dd, J=15.4, 6.9 Hz, 2H), 3.62 (s, 3H), 3.60-3.40 (m, 1H), 3.03-2.73 (m, 2H), 2.34-2.08 (m, 1H), 2.03-1.76 (m, 1H), 1.47 (s, 3H), 1.40-1.29 (s, 6H). Boc protons are missing.

Step 3: Methyl-5-(4,4,5,5-tetramethyl-1,3,2-dioxaborolan-2-yl)-1,3-thiazole. A mixture of 5-bromo-4-methyl-1,3-thiazole (7.5 g, 42.1 mmol, 1 eq), KOAc (12.4 g, 126.4 mmol, 3.4 eq), and 4,4,5,5-tetramethyl-2-(4,4,5,5-tetramethyl-1,3,2-dioxaborolan-2-yl)-1,3,2-dioxaborolane (21.4 g, 1.85 mmol, 2 eq) and $Pd(PPh_3)_4$ (10 g, 20 mol %) were dissolved in dioxane (375 ml, 0.1 M), purged with argon during 10 min and stirred at 95° C. for 16 h. The mixture was then allowed to cool down to RT, filtrated through a pad of celite, concentrated in vacuo and purified by short manual column chromatography (eluent hexane/EtOAc 1:1) to afford of the title product as an off-white solid (10.25 g, 52% yield, contaminated with pinacol derivatives 50% by weight). $^1$H NMR (300 MHz, Chloroform-d), δ: 8.92 (s, 1H), 2.70 (s, 3H), 1.34 (s, 12H).

Step 4: (3S)-3-{[(2S,4R)-1-[(tert-butoxy)carbonyl]-4-hydroxypyrrolidin-2-yl]formami-do}-3-[4-(4-methyl-1,3-thiazol-5-yl)phenyl]propanoic acid methyl ester. A mixture of tert-butyl (2S,4R)-2-{[(1S)-1-(4-bromophenyl)-3-methoxy-3-oxopropyl]carbamoyl}-4-hydroxypyrrolidine-1-carboxylate (9 g, 19.09 mmol, 1 eq), 4-methyl-5-(4,4,5,5-tetramethyl-1,3,2-dioxaborolan-2-yl)-1,3-thiazole (9.91 g, 21 mmol, 1.2 eq), $K_2CO_3$ (13.2 g, 95.5 mmol, 5 eq), Pd(dppf)$Cl_2$.DCM (1.6 g, 10 mol %) in dioxane/$H_2O$ (5:1, 380 mL, 0.05 M) was purged with argon during 20 min and was stirred at 110° C. for 2 h (completion of Suzuki coupling). The mixture was then allowed to cool down to room temperature, filtrated through a pad of celite. The filtrate was concentrated in vacuo, purified by flash column chromatography (eluent DCM/MeOH/AcOH 8:2:0.2% to 6:4:0.2%). The desired product was concentrated in vacuo, dissolved in DCM/MeOH/AcOH 9:1:0.1%, and filtrated to remove eventual silica gel. The filtrate was concentrated in vacuo then precipitated in diethyl ether to afford the desired product as a grey solid (6.6 g, 76% yield). ESI(+)$[M+H]^+$=476.07; $^1$H NMR (300 MHz, Methanol-$d_4$), δ: 8.88 (s, 1H), 7.47 (m, 4H), 5.54-5.28 (m, 1H), 4.33 (d, J=9.9 Hz, 2H), 3.68-3.40 (m, 2H), 3.60 (s, 3H), 2.88 (m, 2H), 2.48 (s, 3H), 2.31-2.14 (m, 1H), 1.99 (s, 1H), 1.48 (s, 3H), 1.33 (s, 6H).

Step 5: methyl (3S)-3-{[(2S,4R)-4-hydroxypyrrolidin-2-yl]formamido}-3-[4-(4-methyl-1,3-thiazol-5-yl)phenyl]propanoate. A mixture of (3S)-3-{[(2S,4R)-1-[(tert-butoxy)carbonyl]-4-hydroxypyrrolidin-2-yl]forma-mido}-3-[4-(4-methyl-1,3-thiazol-5-yl)phenyl]propanoic acid methyl ester (0.3 g, 0.61 mmol, 1 eq) and 2N HCl in methanol (10 eq) was stirred at ambient conditions for 2 h (UPLC and NMR reaction control). The solvent was removed in vacuo and the resulting solid was triturated with dry diethyl ether to give the desired salt product to obtained the desired product as a viscous brown oil (0.22 g, 83% yield). ESI(+)$[M+H]^+$=390.45; $^1$H NMR (300 MHz, DMSO-$d_6$) δ: 9.89 (s, 1H), 9.32 (d, J=7.9 Hz, 1H), 9.03 (s, 1H), 8.65 (s, 1H), 7.51-7.39 (m, 4H), 4.33 (s, 2H), 3.61 (s, 3H), 3.51 (s, 1H), 3.41 (s, 2H), 3.07 (d, J=4.7 Hz, 1H), 2.88 (d, J=7.5 Hz, 2H), 2.33 (s, 1H), 1.78 (m, 1H).

Step 6: Methyl 2-(3-methyl-1,2-oxazol-5-yl)acetate. To a solution of 3-methyl-5-isoxazole acetic acid (0.8 g, 5.67 mmol, 1 eq) in MeOH (10 ml, 0.55 M) the thionyl chloride (1.5 eq) was added dropwise at 0° C. and the resulting mixture was stirred at 50° C. for 4 h. The UPLC monitoring was used. Then, the reaction mixture was poured with saturated ammonia chloride and extracted with EtOAc, washed with saturated $NaHCO_3$, dried and concentrated in vacuo to give the desired product as a brown oil (0.78 g, 89% yield). $^1$H NMR (300 MHz, Chloroform-d), δ: 6.11 (s, 1H), 3.80 (s, 2H), 2.76 (s, 3H), 2.30 (s, 3H).

Step 7: Methyl 3-methyl-2-(3-methyl-1,2-oxazol-5-yl)butanoate. The mixture of methyl 2-(3-methyl-1,2-oxazol-5-yl)acetate (0.14 g, 0.9 mmol, 1 eq), cesium carbonate (0.32 g, 0.99 mmol, 1.1 eq) and 2-iodopropane (0.16 g, 0.94 mmol, 1.05 eq) in DMSO (2.3 ml, 0.4 M) was stirred at 65-70° C. for 5-8 h (LCMS control was applied). After reaction completion, the RM was poured with dilute HCl aqueous solution, extracted with EtOAc twice, dried, and evaporated in vacuo. The crude product was purified with flash chromatography using ELSD (product is not UV active) to give the desired product (0.12 g, 64% yield). $^1$H NMR (300 MHz, DMSO-$d_6$), δ: 6.30 (s, 1H), 3.76 (d, J=8.6 Hz, 1H), 3.66 (s, 3H), 2.35-2.26 (m, 1H), 2.21 (s, 3H), 0.93 (d, J=6.7 Hz, 3H), 0.83 (d, J=6.7 Hz, 3H).

Step 8: 3-Methyl-2-(3-methyl-1,2-oxazol-5-yl)butanoic acid. To a solution of starting methyl 3-methyl-2-(3-methyl-1,2-oxazol-5-yl)butanoate (0.59 g, 2.99 mmol, 1 eq) in THF-Water (3:1; 0.14 M) the sodium hydroxide (0.18 g, 4.5 mmol, 1.5 eq) was added and the resulting mixture was stirred at room temperature until the reaction completion (TLC control). Then, the THF was evaporated under low pressure and water residue was acidified with 1 N aqueous HCl to pH=4-3. The resulting solution was extracted with EtOAc twice, dried and after all volatiles were evaporated, the desired compound was obtained as a white solid (0.5 g, 90% yield). $^1$H NMR (300 MHz, DMSO-$d_6$), δ: 12.84 (s, 1H), 6.27 (s, 1H), 3.58 (d, J=8.7 Hz, 1H), 2.35-2.23 (m, 1H), 2.21 (s, 3H), 0.96 (d, J=6.7 Hz, 3H), 0.82 (d, J=6.7 Hz, 3H).

Step 9: (3S)-3-{[(2S,4R)-4-hydroxy-1-[3-methyl-2-(3-methyl-1,2-oxazol-5-yl)butanoyl]-pyrrolidin-2-yl]formamido}-3-[4-(4-methyl-1,3-thiazol-5-yl)phenyl]propanoic acid. To a solution of methyl (3S)-3-{[(2S,4R)-4-hydroxypyrrolidin-2-yl]formamido}-3-[4-(4-methyl-1,3-thiazol-5-yl)phenyl]propanoate (0.23 g, 0.56 mmol, 1 eq) and 3-methyl-2-(3-methyl-1,2-oxazol-5-yl)butanoic acid (0.11 g, 0.62 mmol, 1.1 eq) in DCM (6 ml, 0.1 M) were added DIPEA (0.22 ml, 1.7 mmol, 3.00 eq) and HATU (0.32 g, 0.84 mmol, 1.5 eq). The mixture was stirred at 25° C. overnight. UPLC control was used. The reaction mixture was quenched with water and extracted with ethyl acetate. The combined organic layers were washed with acidic water, brine, dried over $Na_2SO_4$ and concentrated to get a crude product, which was purified via flash chromatography as a viscous oil (0.28 g, 78% yield). ESI(+)$[M+H]^+$=556.04; $^1H$ NMR (300 MHz, DMSO-$d_6$), δ: 8.72 (s, 1H), 7.47-7.35 (br m, 4H), 6.10 (m, 1H), 5.35 (m, 1H), 4.60 (m, 2H), 3.72 (m, 4H), 3.60 (s, 3H), 2.77 (m, 2H), 2.50 (m, 4H), 2.25 (m, 4H), 2.06 (m, 1H), 1.07 (m, 3H), 0.89 (m, 3H).

Step 10: (3S)-3-{[(2S,4R)-4-hydroxy-1-[3-methyl-2-(3-methyl-1,2-oxazol-5-yl)butanoyl]-pyrrolidin-2-yl]formamido}-3-[4-(4-methyl-1,3-thiazol-5-yl)phenyl]propanoic acid. To a solution of the starting (3S)-3-{[(2S,4R)-4-hydroxy-1-[3-methyl-2-(3-methyl-1,2-oxazol-5-yl)butanoyl]-pyrrolidin-2-yl]formamido}-3-[4-(4-methyl-1,3-thiazol-5-yl)phenyl]propanoic acid (0.28 g, 0.54 mmol, 1 eq) in methanol-water (3:1; 0.14 M) the sodium hydroxide (0.03 g, 0.75 mmol, 1.5 eq) was added and the resulting mixture was stirred at ambient conditions until the completion (UPLC control). Then, the organic solvent was evaporated under low pressure and water residue was acidified with 1 N HCl to pH=4-3. The resulting solution was purified with reverse-phase flash chromatography (5 to 29% acetonitrile in water). After evaporation the title compound was obtained as a white solid (0.1 g, 37% yield). LCMS: 254 nm, RT=2.443 min, 98.32% purity, ESI(+)$[M+H]^+$=542.66; $^1H$ NMR (300 MHz, DMSO-$d_6$), δ: 8.90 (s, 1H), 7.47 (m, 4H), 6.25 (d, J=5.9 Hz, 1H), 5.38 (m, 1H), 4.62-4.37 (m, 2H), 3.94-3.41 (m, 4H), 3.10-2.78 (m, 2H), 2.50 (m, 4H), 2.25 (m, 4H), 1.98 (m, 1H), 1.07 (d, J=7.6 Hz, 3H), 0.94-0.82 (m, 3H).

C. General Schemes for Coupling the IRAK4 Binder and LHM Building Blocks

The L moiety typically has up to five linker segments ($-L_1-L_2-L_3-L_4-L_5-$), one of which is formed by coupling the IRAK4 building block and the LHM block described herein via a bond formation (e.g., amide). The following General Methods A-D illustrate the bond formations by which the building blocks may be coupled to afford the compounds of Formula (I).

General Method A (Amide coupling)

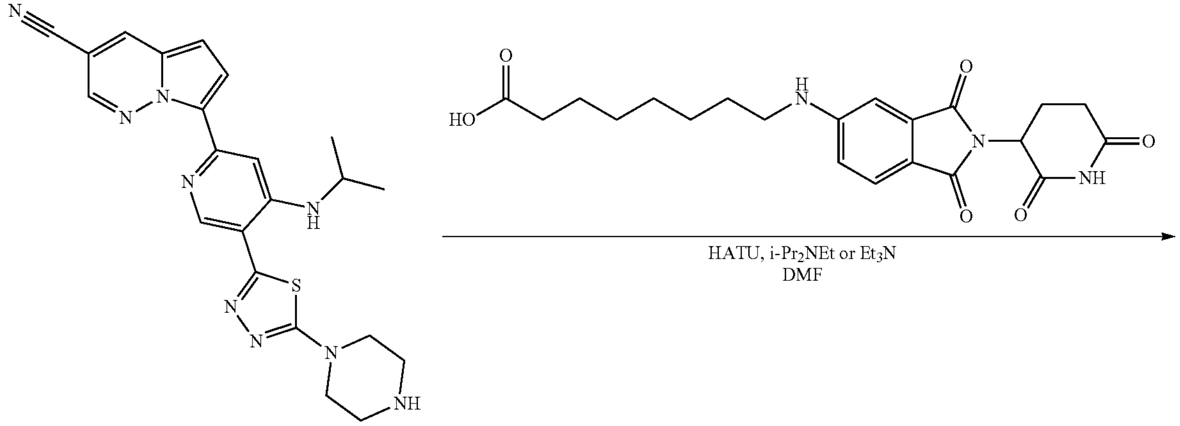

BB4

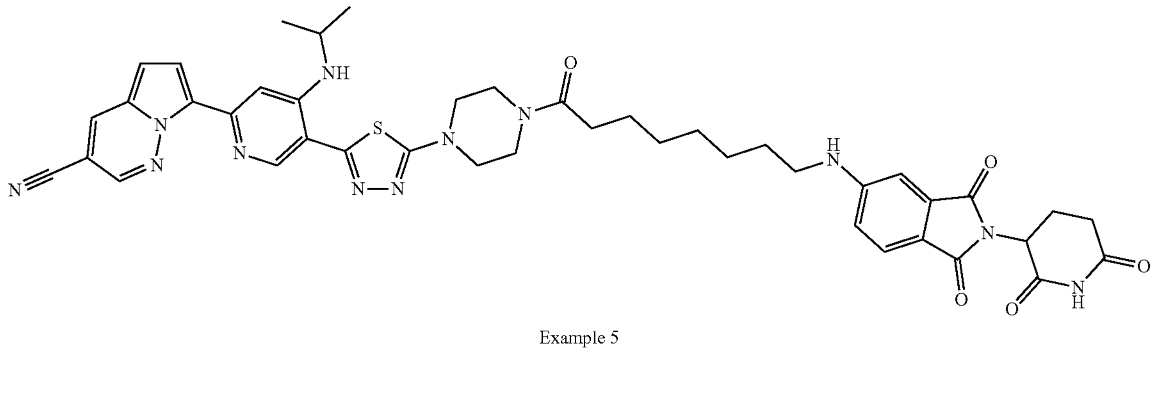

Example 5

-continued
General Method B (Reductive Amination)
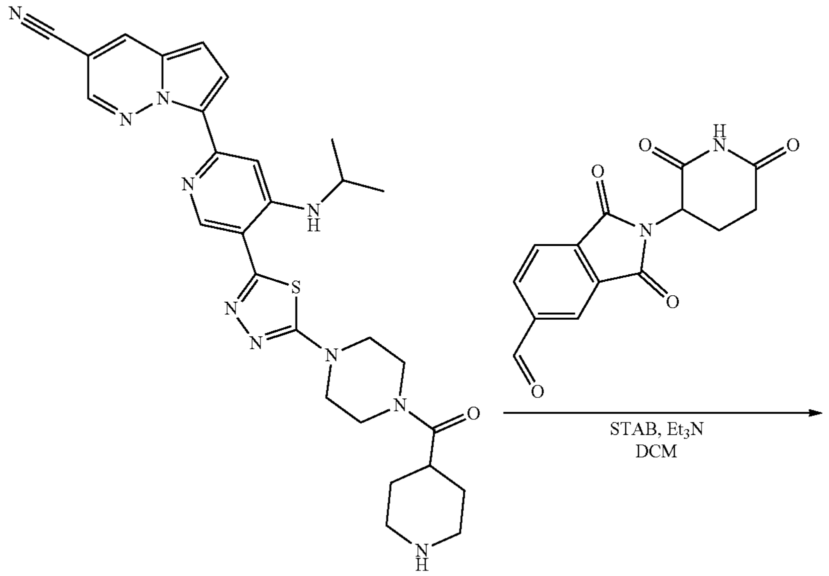
BB5
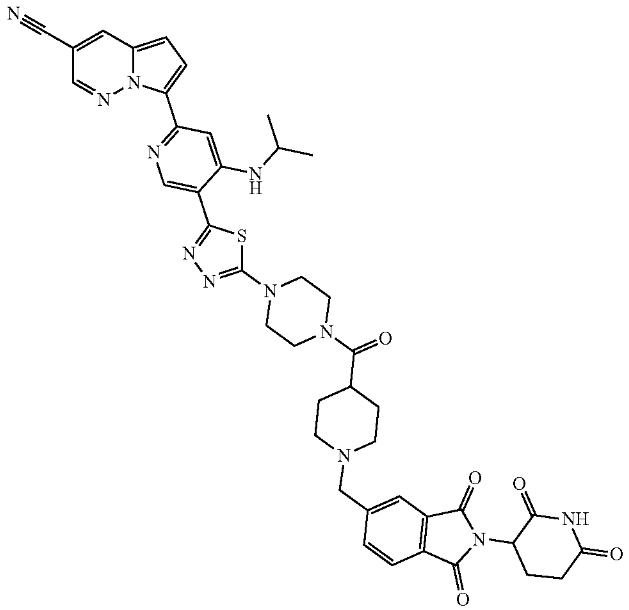
Example 13
General Method C (Displacement)
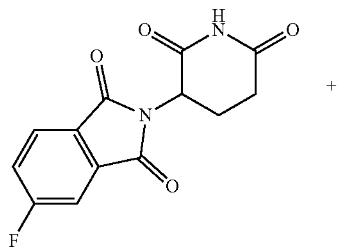

-continued

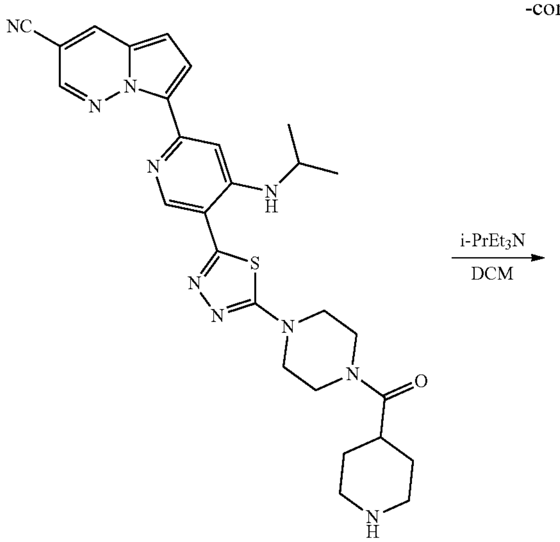

BB5

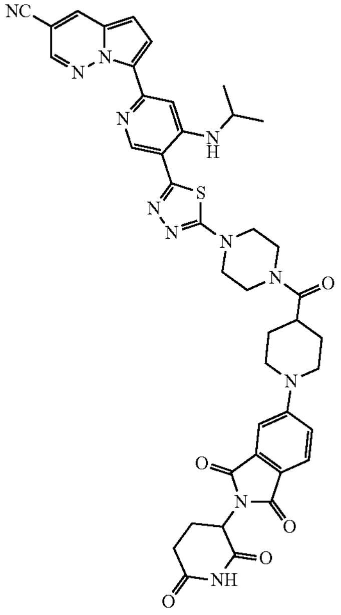

Example 23

General Method D (Amide Coupling. In-Situ BOC-Deprotection)

General Method D is similar to General Method A except that the amine terminal moiety (e.g., of an IRAK4 building block) may be initially protected by BOC. The amide coupling can be carried out via an in-situ BOC-deprotection to form the amide bond with a carboxylic acid terminal moiety (e.g., of an LHM building block). For example, see the synthesis of Example 50.

Definitions

The following description sets forth exemplary methods, parameters and the like. It should be recognized, however, that such description is not intended as a limitation on the scope of the present disclosure but is instead provided as a description of exemplary embodiments.

A dash ("—") that is not between two letters or symbols is used to indicate a point of attachment for a substituent. For example, —$C(O)NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an or branched saturated hydrocarbon chain containing no unsaturation. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., $—(CH_2)_3CH_3$), sec-butyl (i.e., $—CH(CH_3)CH_2CH_3$), isobutyl (i.e., $—CH_2CH(CH_3)_2$) and tert-butyl (i.e., $—C(CH_3)_3$); and "propyl" includes n-propyl (i.e., $—(CH_2)_2CH_3$) and isopropyl (i.e., $—CH(CH_3)_2$).

"Alkylene" or "alkylene chain" refers to a unbranched or branched divalent hydrocarbon chain, linking the rest of the molecule to a radical group, containing no unsaturation and having from 1 to 20 carbon atoms, or more typically 1 to 12 carbon atoms, or 1 to 8 carbon atoms, e.g., methylene, ethylene, propylene, n-butylene, and the like. The alkylene chain may be attached to the rest of the molecule and to the radical group through one carbon within the chain or through any two carbons within the chain.

"Alkenyl" refers to an alkyl group containing at least one carbon-carbon double bond and having from 2 to 20 carbon atoms (i.e., $C_{2-20}$ alkenyl), or more typically 2 to 12 carbon atoms (i.e., $C_{2-12}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkenylene" and "alkenylene chain" refer to a unbranched or branched divalent hydrocarbon chain linking the rest of the molecule to a radical group, containing at least one double bond and having from 2 to 20 carbon atoms, or more typically 2 to 12 carbon atoms, or 2 to 8 carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkynyl" refers to an alkyl group containing at least one carbon-carbon triple bond and having from 2 to 20 carbon atoms (i.e., $C_{2-20}$ alkynyl), or more typically 2 to 12 carbon atoms (i.e., $C_{2-12}$ alkynyl), or more typically 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkynylene" and "alkynylene chain" refer to a unbranched or branched divalent hydrocarbon chain linking the rest of the molecule to a radical group, containing at least one triple bond and having from 2 to 20 carbon atoms, or more typically 2 to 12 carbon atoms, or 2 to 8 carbon atoms. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Amino" refers to the group $—NR^yR^y$ wherein each $R^y$ is independently selected from the group consisting of hydrogen, alkyl, alkenyl, alkynyl, aryl, heterocyclyl, cycloalkyl or heteroaryl, each of which is optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 15 carbon ring atoms (i.e., $C_{6-15}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cyano" refers to the group —CN.

"Keto" or "oxo" refers to a group =O.

"Carbamoyl" refers to both an "O-carbamoyl" group which refers to the group $—O—C(O)NR^yR^z$ and an "N-carbamoyl" group which refers to the group $—NR^yC(O)OR^z$, wherein $R^y$ and $R^z$ are independently selected from the group consisting of hydrogen, alkyl, aryl, haloalkyl, or heteroaryl; each of which may be optionally substituted.

"Carboxyl" or "carboxylic acid" refers to —C(O)OH.

"Ester" refers to both —OC(O)R and —C(O)OR, wherein R is a substituent; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 15 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, cyclohexyl, and bicyclo[2.2.2]octan-1-yl. Cycloalkyl may be attached to the remainder of a molecule by a single ring atom (e.g., as a substituent) or by two ring atoms (e.g., as a linker).

"Ethylene glycol unit" refers to a bivalent monomer having the structure of $—CH_2CH_2O—$, which may be repeated and extended into a longer chain. A linker segment may have up to 12 ethylene glycol units, or more typically up to 6 ethylene glycol units.

"Propylene glycol unit" refers to a bivalent monomer having the structure of $—CH(CH_3)—CH_2O—$, which may be repeated and extended into a longer chain. A linker segment may have up to 12 propylene glycol units, or more typically up to 6 propylene glycol units.

"Halogen" or "halo" includes fluoro, chloro, bromo, and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl ($—CHF_2$) and trifluoromethyl ($—CF_3$).

"Heteroalkyl" refers to an alkyl group in which one or more of the carbon atoms (and any associated hydrogen atoms) are each independently replaced with the same or different heteroatoms such as N, O, S, and the likes. The term "heteroalkyl" includes unbranched or branched saturated chain having carbon and heteroatoms. By way of example, 1, 2 or 3 carbon atoms may be independently replaced with the same or different heteroatoms. Heteroatomic groups include, but are not limited to, —N(R)—, —O—, —S—, —S(O)—, $—S(O)_2—$, and the like, where R is H, alkyl, aryl, cycloalkyl, heteroalkyl, heteroaryl or heterocyclyl, each of which may be optionally substituted. Examples of heteroalkyl groups include $—OCH_3$, $—CH_2OCH_3$, $—SCH_3$, $—CH_2SCH_3$, $—NRCH_3$, and $—CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a 5-15 membered, or more typically, 5-12 membered aromatic group having a single ring, multiple rings, or multiple fused rings, with 1-3 ring heteroatoms independently selected from nitrogen, oxygen, and sulfur. As used herein, heteroaryl includes 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo [1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above. Heteroaryl may be attached to the remainder of a molecule by a single ring atom (e.g., as a substituent) or by two ring atoms (e.g., as a linker).

"Heterocyclyl" refers to a 3-15 membered, or more typically, 5-12 membered, saturated or unsaturated cyclic alkyl group, with 1-3 ring heteroatoms independently selected from nitrogen, oxygen and sulfur. The term "heterocyclyl" includes heterocycloalkenyl groups (i.e., the heterocyclyl group having at least one double bond), bicyclic heterocyclyl groups, bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 3 to 15 ring atoms (e.g., 3-15 membered heterocyclyl, 3-12 membered heterocyclyl, 4 to 10 membered heterocyclyl, 4-8 membered heterocyclyl or 4-6 membered heterocyclyl; having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include pyrrolidinyl, piperidinyl, piperazinyl, oxetanyl, dioxolanyl, azetidinyl, azetidinyl, morpholinyl, thiomorpholinyl, 4-7 membered sultam, 4-7 membered cyclic carbamate, 4-7 membered cyclic carbonate, 4-7 membered cyclic sulfide and morpholinyl. As used herein, heterocyclyl may include a bridged structure (i.e., "bridged heterocyclyl), in which a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, 2,3-dihydro-1H-isoindolyl, and isoindolinyl, where the heterocyclyl can be bound via either ring of the fused system. As used herein, a bicyclic heterocyclyl group is a heterocyclyl group attached at two points to another cyclic group, wherein the other cyclic group may itself be a heterocyclic group, or a carbocyclic group. Heteroaryl may be attached to the remainder of a molecule by a single ring atom (e.g., as a substituent) or by two ring atoms (e.g., as a linker).

"Fused" refers to a ring which is joint to an adjacent ring and share two adjacent ring atoms that form a covalent bond.

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Nitro" refers to the group $—NO_2$.

"Imino" refers to a group that contains a C═N double bond, such as C═N—$R^y$, or ═N—C(O)$R^y$, wherein $R^y$ is selected from the group consisting of hydrogen, alkyl, aryl, cyano, haloalkyl, or heteroaryl; each of which may be optionally substituted. Imino may be a linker segment by attaching to the remainder molecule at the carbon and nitrogen respectively.

"Sulfoximine" or "sulfoximino" refers to a substituted or unsubstituted moiety of the general formula

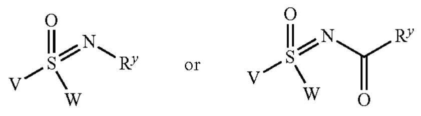

wherein $R^y$ is selected from the group consisting of hydrogen, alkyl, amino, aryl, cyano, haloalkyl, heterocyclyl, or heteroaryl; V and W are each independently selected from a bond, alkyl, amino, aryl, haloalkyl, heterocyclyl or heteroaryl; each of which may be optionally substituted and wherein $R^y$ and V, $R^y$ and W, and V and W together with the atoms to which they are attached may be joined together to form a ring. Sulfoximine may be a linker segment by attaching to the remainder molecule at the sulfur and nitrogen respectively.

"Sulfonyl" refers to the group —$S(O)_2R$, where R is a substituent, or a defined group.

"Alkylsulfonyl" refers to the group —$S(O)_2R$, where R is a substituent, or a defined group.

"Alkylsulfinyl" refers to the group —S(O)R, where R is a substituent, or a defined group.

"Thiocyanate"—SCN.

"Thiol" refers to the group —SR, where R is a substituent, or a defined group.

"Thioxo" or "thione" refer to the group (═S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurrence is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl" or "heteroaryl," then the general term can refer to any antecedent specifically recited term, such as ($C_{1-3}$ alkyl), ($C_{4-6}$ alkyl), —O($C_{1-4}$ alkyl), ($C_{3-10}$ cycloalkyl), O—($C_{3-10}$ cycloalkyl) and the like. For example, "any aryl" includes both "aryl" and "—O(aryl) as well as examples of aryl, such as phenyl or naphthyl and the like. Also, the term "any heterocyclyl" includes both the terms "heterocyclyl" and O-(heterocyclyl)," as well as examples of heterocyclyls, such as oxetanyl, tetrahydropyranyl, morpholino, piperidinyl and the like. In the same manner, the term "any heteroaryl" includes the terms "heteroaryl" and "O-(heteroryl)," as well as specific heteroaryls, such as pyridine and the like.

Some compounds of Formula (I) may exist as a "stereoisomer" or a mixture of stereoisomers. Stereoisomer refers to a compound made up of the same atoms bonded by the same bonds but having different three-dimensional structures, which are not interchangeable. The compounds of the disclosure, or their pharmaceutically acceptable salts may contain one or more asymmetric centers and may thus give rise to enantiomers (two stereoisomers whose molecules are non-superimposable mirror images of one another), diastereomers, and other stereoisomeric forms that may be defined, in terms of absolute stereochemistry, as (R)- or (S)-. The present disclosure is meant to include all such possible isomers, as well as their racemic mixture (i.e., equal amounts of (R) and (S) enantiomers) and optically pure forms. Optically active (+) and (−), (R)- and (S)-isomers may be prepared using chiral synthons or chiral reagents, or resolved using conventional techniques, such as HPLC using a chiral column.

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, or solvates of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Targeted IRAK4 Degradation

The compounds of the present disclosure are demonstrated by cell-based profiling to degrade IRAK4 with selectivity.

The degradation mechanism and selectivity of two representative compounds having CRBN-targeting LHM (Formula (IIA)) and two representative compounds having VHL-targeting LHM (Formula (IIB)) were evaluated and discussed herein. For comparison, 3 compounds known for degrading IRAK4 were also evaluated. Table 1 shows the structures of the selected compounds.

TABLE 1
| Example # | Chemical Structures | LHM Type |
|---|---|---|
| Example 13 | 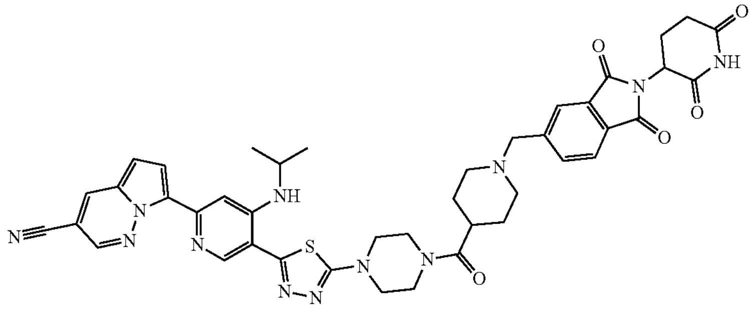 [SMILES: CC(C)Nc1cc(-c2ccc3cc(C#N)cnn23)ncc1-c1nnc(N2CCN(C(=O)C3CCN(Cc4ccc5c(c4)C(=O)N(C4CCC(=O)NC4=O)C5=O)CC3)CC2)s1] | CRBN |
| Example 24 | 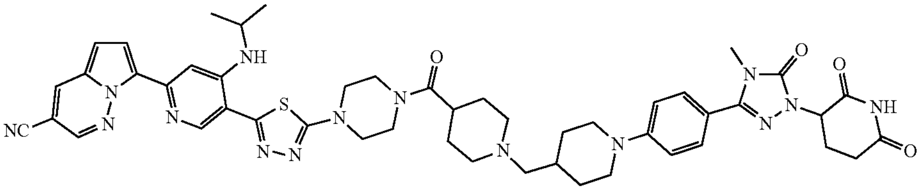 [SMILES: CC(C)Nc1cc(-c2ccc3cc(C#N)cnn23)ncc1-c1nnc(N2CCN(C(=O)C3CCN(CC4CCN(c5ccc(-c6nn(C7CCC(=O)NC7=O)c(=O)n6C)cc5)CC4)CC3)CC2)s1] | CRBN |
| Comparative Compound a1 | 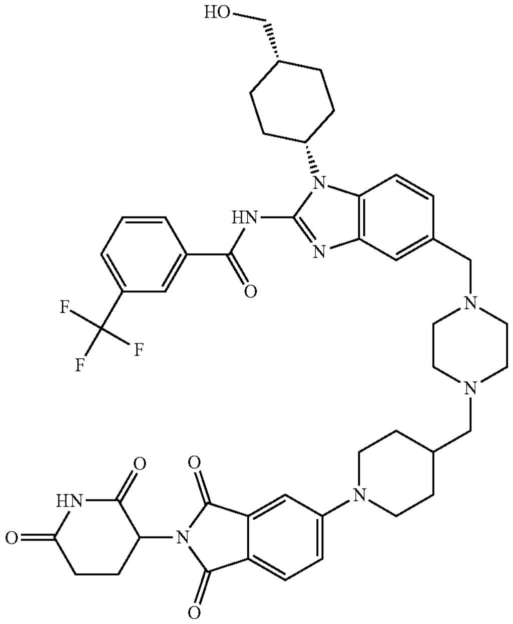 [SMILES: O=C1CCC(N2C(=O)c3ccc(N4CCC(CN5CCN(Cc6ccc7c(c6)nc(NC(=O)c6cccc(C(F)(F)F)c6)n7[C@H]6CC[C@@H](CO)CC6)CC5)CC4)cc3C2=O)C(=O)N1] | CRBN |
| Comparative Compound a2 | 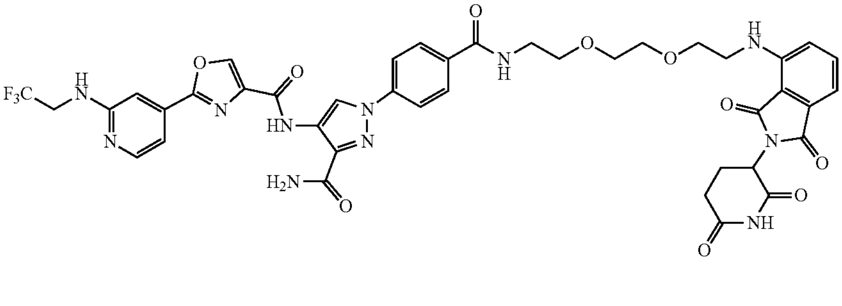 [SMILES: NC(=O)c1nn(-c2ccc(C(=O)NCCOCCOCCNc3cccc4c3C(=O)N(C3CCC(=O)NC3=O)C4=O)cc2)cc1NC(=O)c1coc(-c2ccnc(NCC(F)(F)F)c2)n1] | CRBN |

TABLE 1-continued
| Example # | Chemical Structures | LHM Type |
| --- | --- | --- |
| Example 47 | 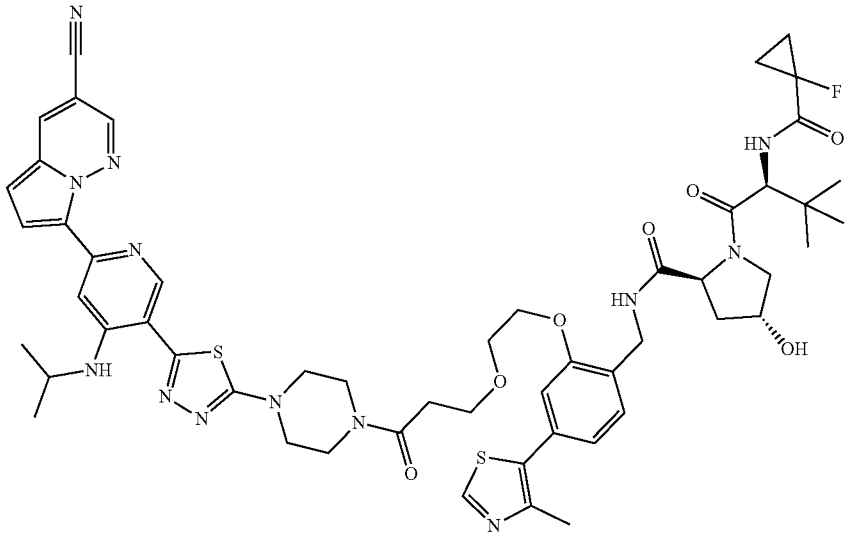 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCC(=O)N2CCN(c3nnc(-c4cnc(-c5ccc6cc(C#N)cnn56)cc4NC(C)C)s3)CC2)c1] | VHL |
| Example 35 | 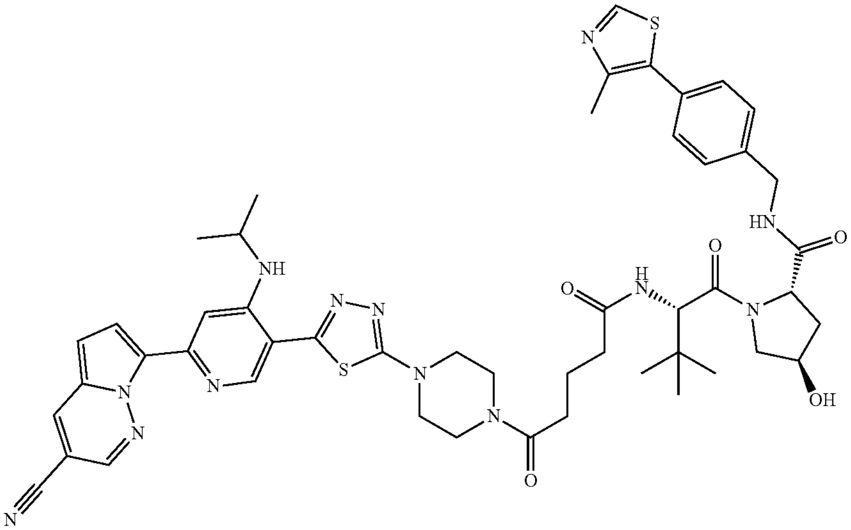 [SMILES: Cc1ncsc1-c1ccc(CNC(=O)[C@@H]2C[C@@H](O)CN2C(=O)[C@@H](NC(=O)CCCC(=O)N2CCN(c3nnc(-c4cnc(-c5ccc6cc(C#N)cnn56)cc4NC(C)C)s3)CC2)C(C)(C)C)cc1] | VHL |

TABLE 1-continued

| Example # | Chemical Structures | LHM Type |
|---|---|---|
| Comparative b1 | 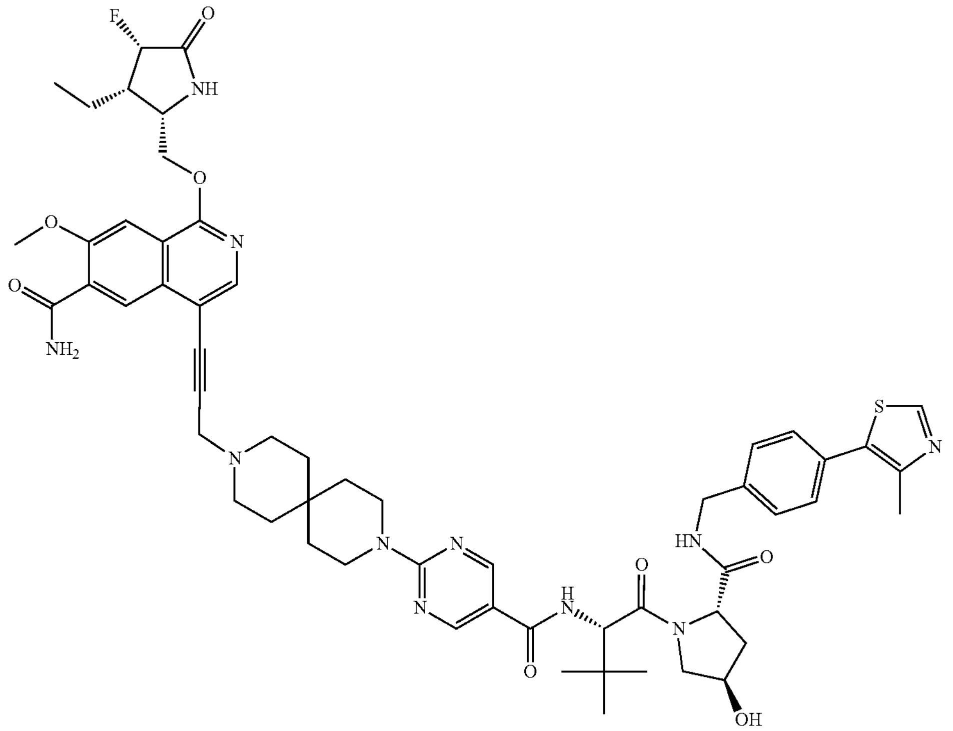 [SMILES: CC[C@@H]1[C@H](F)C(=O)N[C@@H]1COc1ncc(C#CCN2CCC3(CC2)CCN(c2ncc(C(=O)N[C@H](C(=O)N4C[C@H](O)C[C@H]4C(=O)NCc4ccc(-c5scnc5C)cc4)C(C)(C)C)cn2)CC3)c2cc(C(N)=O)c(OC)cc12] | VHL |

More specifically, the selected compounds were evaluated for cellular degradation of IRAK4 using three different assay formats; HiBiT assays, HTRF assays and Western blotting. All the compounds showed consistent, reproducible degradation across these three assays. In particular, among the selected compounds, Compound 47 was shown to be the most efficient degrader with respect to Dmax, achieving 99% degradation as assessed by Western blot analysis. In addition, the representative compounds demonstrated equivalent or superior degradation ($D_{max}$) in comparison to the known compounds with similar LHM (Compound a1, a2 and b1).

Furthermore, to verify that IRAK4 degradation was mediated through the ubiquitin proteasome system, the compounds of Formula (I) were profiled in the presence of a proteasome inhibitor, ligase inhibitor or with excess concentrations of corresponding mono-functional compounds such as a compound with only an IRAK4 binding moiety, or a compound with only an LHM. Pre-treatment under any of these conditions restored IRAK4 protein levels to that of untreated cells, demonstrating on-mechanism activity of the bifunctional compounds.

The specificity of IRAK4 degradation by the compounds of the present disclosure was evaluated by first assessing degradation of CRBN neosubstrates Ikaros, Aiolos and GSPT1, and secondly by assessing the degrader's effect on the highly related target IRAK1. Neosubstrate profiling demonstrated that while one of the known compounds, Comparative Compound a2, degraded both Ikaros and Aiolos, none of Compounds 13, 24, 47, and 35 displayed neosubstrate degradation. Additionally, none of the assayed compounds affected IRAK1 levels, demonstrating specificity for IRAK4 over IRAK1 degradation. Lastly, none of the assayed compounds affected cellular viability as assessed by CellTiter-Glo.

Table 2 summarizes the degradation results for the selected compounds targeting CRBN.

TABLE 2

| Biochemical Assay Data | 13 | 24 | a1 | a2 |
|---|---|---|---|---|
| IRAK4 biochemical $IC_{50}$ (nM) | 0.5 | 0.6 | 3 | 1.2 |
| IRAK4 HiBit $DC_{50}$, μM ($D_{max}$ %) | 0.026 (101) | 0.327 (102) | 0.180 (104) | 0.026 (88) |
| IRAK4 degradation (Western) $DC_{50}$, μM ($D_{max}$ %) | 0.014 (87) | 0.2 (90) | 0.08 (70) | 0.001 (54) |
| IRAK4 HTRF $DC_{50}$, μM ($D_{max}$ %) | 0.05 (>100) | 0.42 (>100) | 0.21 (100) | 0.06 (100) |
| Rescue by proteasome or Nedd8 inhibition | YES | YES | YES | YES |
| Aiolos Degradation $DC_{50}$, μM | >5 | >5 | >5 | 0.02 |
| Ikaros Degradation $DC_{50}$, μM | >5 | >5 | >5 | 0.02 |
| GSPT1 Degradation $DC_{50}$, μM | >10 | >10 | >10 | >10 |

TABLE 2-continued

| Biochemical Assay Data | 13 | 24 | a1 | a2 |
|---|---|---|---|---|
| IRAK1 Degradation $DC_{50}$, μM | >10 | >10 | >10 | >10 |
| Viability assessment $EC_{50}$, μM | >10 | >10 | >10 | >10 |

Table 3 summarizes the degradation results for the selected compounds targeting VHL.

TABLE 3

| Biochemical Assay Data | 47 | 35 | b1 |
|---|---|---|---|
| IRAK4 biochemical IC50 (nm) | 7.3 | 5.2 | 2.3 |
| IRAK4 HiBit DC50, μM (Dmax %) | 0.144 (118) | 0.590 (100) | 0.204 (95) |
| IRAK4 degradation (Western) DC50, μM (Dmax %) | 0.089 (99) | 0.2 (86) | 0.07 (86) |
| IRAK4 HTRF DC50, μM (Dmax %) | 0.14 (>100) | 0.40 (100) | 0.08 (100) |
| Rescue by proteasome or Nedd8 inhibition | YES | YES | YES |
| Aiolos Degradation DC50, μM | >5 | >5 | >5 |
| Ikaros Degradation DC50, μM | >5 | >5 | >5 |
| GSPT1 Degradation DC50, μM | >10 | >10 | >10 |
| IRAK1 Degradation DC50, μM | >10 | >10 | >10 |
| Viability assessment EC50, μM | >10 | >10 | >10 |

Pharmaceutical Composition and Use of the Bifunctional Compounds of Formula (I)

The bifunctional compounds of Formula (I) are demonstrated to degrade IRAK4 and are therefore useful for treating disease indications or disorders involving the function of IRAK4, such as signaling or scaffolding.

Various embodiments provide pharmaceutical compositions of a compound of Formula (I), or any one of the substructures or compounds of Table 5, and a pharmaceutically acceptable carrier.

Further embodiments provide methods for treating cancer, inflammatory disorders, autoimmune disorders or metabolic disorders, comprising administering to a subject in need thereof a therapeutically effective amount of a compound of Formula (I), or any one of the substructures or compounds of Table 5.

Examples of cancer that may be treated include lymphomas, leukemia, including, e.g., acute myeloid leukemia (AML) and myelodysplastic syndrome (MDS), etc.

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of inflammatory disorders include rheumatoid arthritis (RA), inflammatory bowel disease (IBD), Crohn's disease, ulcerative colitis, necrotizing enterocolitis, gout, Lyme disease, arthritis, psoriasis, pelvic inflammatory disease, systemic lupus erythematosus (SLE), Sjogren's syndrome, inflammation associated with gastrointestinal infections, including *C. difficile*, viral myocarditis, acute and chronic tissue injury, non-alcoholic steatohepatitis (NASH), alcoholic hepatitis and kidney disease, including chronic kidney disease and diabetic kidney disease.

A further embodiment provides a method of treating an inflammation related disease or condition, or a metabolic disorder, gastrointestinal disorder, or cancer and the like comprising administering a compound of Formula (I) in combination with one or more compounds useful for the treatment of such diseases to a subject, particularly a human subject, in need thereof.

In some embodiments, a compound of the present disclosure is co-formulated with the additional one or more active ingredients. In some embodiments, the other active ingredient is administered at approximately the same time, in a separate dosage form. In some embodiments, the other active ingredient is administered sequentially, and may be administered at different times in relation to a compound of the present disclosure.

EXAMPLES

Preparation of Compounds of Formula (I)

Example 1

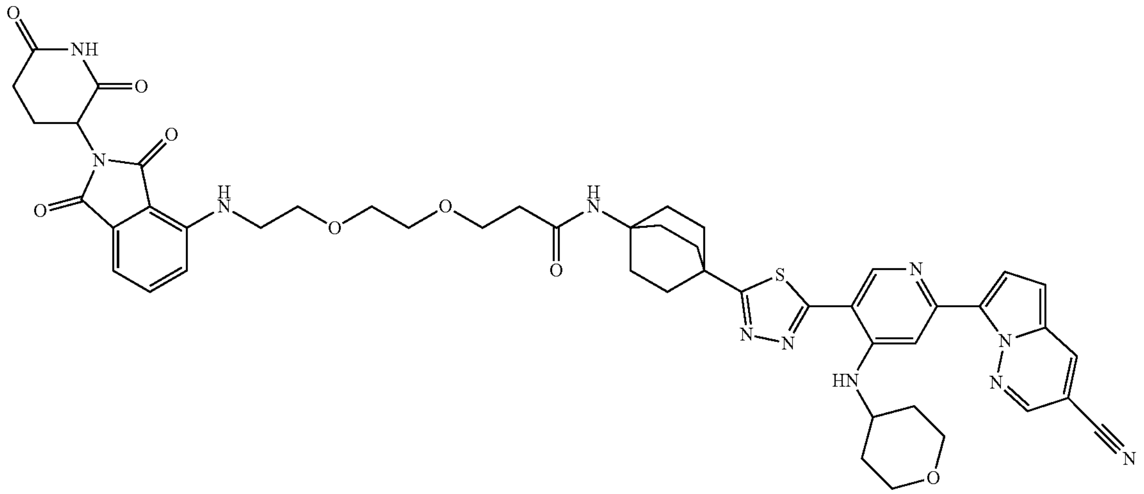 [SMILES: N#Cc1cnn2c(-c3cc(NC4CCOCC4)c(-c4nnc(C56CCC(NC(=O)CCOCCOCCNc7cccc8c7C(=O)N(C7CCC(=O)NC7=O)C8=O)(CC5)CC6)s4)cn3)ccc2c1]

N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)-3-(2-(2-((2-(2,6-dioxopiperidin-3-yl)-1,3-dioxoisoindolin-4-yl)amino)ethoxy)ethoxy)propanamide To a mixture of 7-(5-(5-(4-aminobicyclo[2.2.2]octan-1-yl)-1,3,4-thiadiazol-2-yl)-4-((tetrahydro-2H-pyran-4-yl)amino)pyridin-2-yl)pyrrolo[1,2-b]pyridazine-3-carbonitrile, bis-hydrochloride (BB1, 16.0 mg, 0.0249 mmol), 3-[2-[2-[[2-(2,6-dioxo-3-piperidyl)-1,3-dioxo-isoindolin-4-yl]amino]ethoxy]ethoxy]propanoic acid (13.0 mg, 0.0299 mmol) and HATU (9.97 mg, 0.0262 mmol) in DMF (0.125 mL) was added DIPEA (0.0143 mL, 0.0799 mmol). The resulting solution was stirred at room temperature for 12 h. The crude solution was purified by preparative HPLC (Gemini C18, eluent: 10-64% acetonitrile/H2O/0.1% TFA) and lyophilized to provide N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-6yl)bicyclo[2.2.2]octan-1-yl)-3-(2-(2-((2-(2,6-dioxopiperidin-3-yl)-1,3-dioxoisoindolin-4-yl)amino)ethoxy)ethoxy)propanamide as a TFA salt. ES/MS: 942.476 $(M+H^+)$; $^1H$ NMR (400 MHz, Methanol-d4) δ 10.17 (d, J=7.7 Hz, 1H), 9.03 (s, 1H), 8.68 (s, 1H), 8.66-8.58 (m, 2H), 8.11 (d, J=5.1 Hz, 1H), 7.79 (s, 1H), 7.59 (dd, J=8.6, 7.1 Hz, 1H), 7.21 (d, J=5.1 Hz, 1H), 7.08 (t, J=7.8 Hz, 2H), 6.34 (s, 1H), 4.97 (dd, J=12.2, 5.3 Hz, 1H), 4.01 (dt, J=12.1, 3.9 Hz, 2H), 3.74 (t, J=5.3 Hz, 2H), 3.70-3.56 (m, 9H), 3.49 (t, J=5.3 Hz, 2H), 2.83-2.64 (m, 3H), 2.30 (t, J=6.0 Hz, 2H), 2.19-2.11 (m, 2H), 2.11-2.01 (m, 9H), 1.85-1.73 (m, 3H).

Example 2

N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)-3-(2-(2-(2-((2-(2,6-dioxopiperidin-3-yl)-1,3-dioxoisoindolin-4-yl)amino)ethoxy)ethoxy)ethoxy)propanamide Starting from 7-(5-(5-(4-aminobicyclo[2.2.2]octan-1-yl)-1,3,4-thiadiazol-2-yl)-4-((tetrahydro-2H-pyran-4-yl)amino)pyridin-2-yl)pyrrolo[1,2-b]pyridazine-3-carbonitrile, bis-hydrochloride (BB1 18.0 mg, 0.0281 mmol) N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)-3-(2-(2-(2-((2-(2,6-dioxopiperidin-3-yl)-1,3-dioxoisoindolin-4-yl)amino)ethoxy)ethoxy)ethoxy)propanamide was prepared following the procedure for Example 2, substituting 3-[2-[2-[[2-(2,6-dioxo-3-piperidyl)-1,3-dioxo-isoindolin-4-yl]amino]ethoxy]ethoxy]propanoic acid (13.0 mg, 0.0299 mmol) for 3-(2-(2-(2-((2-(2,6-dioxopiperidin-3-yl)-1,3-dioxoisoindolin-4-yl)amino)ethoxy)ethoxy)ethoxy)propanoic acid (14.8 mg, 0.0309 mmol). ES/MS: 986.572 $(M+H^+)$; $^1H$ NMR (400 MHz, Acetonitrile-$d_3$) δ 10.19 (d, J=7.6 Hz, 1H), 9.12 (s, 1H), 8.68-8.59 (m, 3H), 8.11 (d, J=5.1 Hz, 1H), 7.74 (s, 1H), 7.56 (dd, J=8.6, 7.1 Hz, 1H), 7.22 (d, J=5.1 Hz, 1H), 7.06 (dd, J=19.2, 7.7 Hz, 2H), 6.34 (s, 1H), 4.96 (dd, J=12.4, 5.4 Hz, 1H), 4.01 (dt, J=11.9, 3.8 Hz, 2H), 3.72 (t, J=5.3 Hz, 2H), 3.65 (tt, J=5.3, 3.1 Hz, 6H), 3.61-3.54 (m, 3H), 3.49 (t, J=5.3 Hz, 2H), 2.86-2.58 (m, 2H), 2.31 (t, J=6.1 Hz, 2H), 2.19-2.03 (m, 12H), 1.84-1.73 (m, 2H).

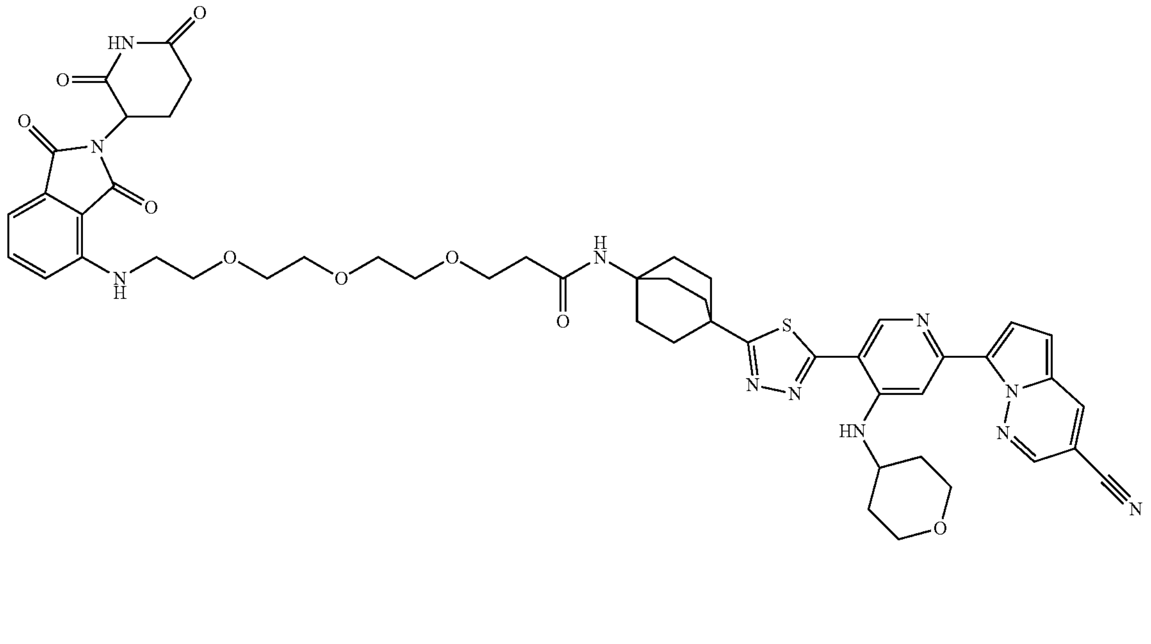 [SMILES: N#Cc1cnn2c(-c3cc(NC4CCOCC4)c(-c4nnc(C56CCC(NC(=O)CCOCCOCCOCCNc7cccc8c7C(=O)N(C7CCC(=O)NC7=O)C8=O)(CC5)CC6)s4)cn3)ccc2c1]

Example 3

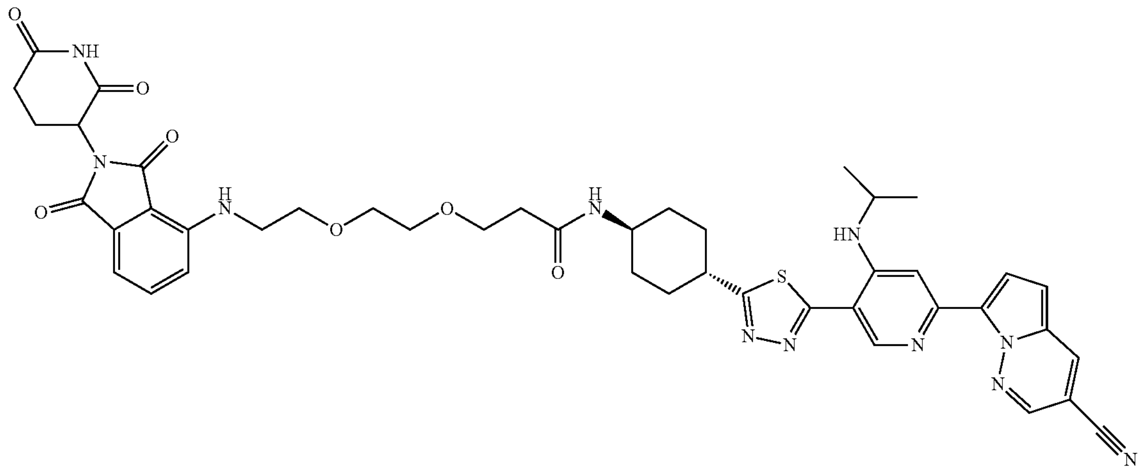 [SMILES: CC(C)Nc1cc(-c2ccc3cc(C#N)cnn23)ncc1-c1nnc([C@H]2CC[C@H](NC(=O)CCOCCOCCNc3cccc4c3C(=O)N(C3CCC(=O)NC3=O)C4=O)CC2)s1]

Synthesis of N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-(2-(2-((2-(2,6-dioxopiperidin-3-yl)-1,3-dioxoisoindolin-4-yl)amino)ethoxy)ethoxy)propanamide To a mixture of 7-(5-(5-((trans)-4-aminocyclohexyl)-1,3,4-thiadiazol-2-yl)-4-(isopropylamino)pyridin-2-yl)pyrrolo[1,2-b]pyridazine-3-carbonitrile, bis-hydrochloride (BB2 10.0 mg, 0.0188 mmol), 3-(2-(2-((2-(2,6-dioxopiperidin-3-yl)-1,3-dioxoisoindolin-4-yl)amino)ethoxy)ethoxy)propanoic acid (10.0 mg, 0.0231 mmol) and HATU (10.0 mg, 0.0263 mmol) in DMF (0.5 mL) was added DIPEA (0.0170 mL, 0.0976 mmol). The resulting solution was stirred at room temperature for 20 min. The crude solution was purified by preparative HPLC (Gemini C18, eluent: 10-45% acetonitrile/H2O/0.1% TFA) and lyophilized to provide N-((trans)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-(2-(2-((2-(2,6-dioxopiperidin-3-yl)-1,3-dioxoisoindolin-4-yl)amino)ethoxy)ethoxy)propenamide as a TFA salt. ES/MS: 874.659 (M+H$^+$); $^1$H NMR (400 MHz, Methanol-d4) δ 8.79 (d, J=2.1 Hz, 1H), 8.72 (d, J=1.8 Hz, 2H), 8.10 (d, J=5.1 Hz, 1H), 7.97 (s, 1H), 7.58 (dd, J=8.6, 7.1 Hz, 1H), 7.26 (d, J=5.1 Hz, 1H), 7.13 (d, J=8.5 Hz, 1H), 7.05 (d, J=7.0 Hz, 1H), 5.09 (dd, J=12.5, 5.5 Hz, 1H), 4.34 (p, J=6.4 Hz, 1H), 3.77 (td, J=5.6, 2.6 Hz, 5H), 3.73-3.62 (m, 3H), 3.60-3.48 (m, 2H), 3.23-3.09 (m, 1H), 2.89 (ddd, J=17.7, 14.3, 5.0 Hz, 1H), 2.83-2.66 (m, 2H), 2.45 (t, J=5.9 Hz, 2H), 2.30-1.99 (m, 5H), 1.81-1.63 (m, 2H), 1.52 (d, J=6.4 Hz, 6H), 1.50-1.35 (m, 3H).

Example 4

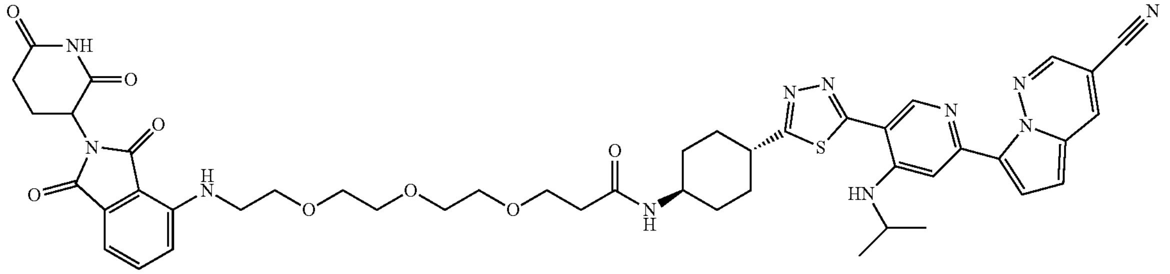 [SMILES: CC(C)Nc1cc(-c2ccc3cc(C#N)cnn23)ncc1-c1nnc([C@H]2CC[C@H](NC(=O)CCOCCOCCOCCNc3cccc4c3C(=O)N(C3CCC(=O)NC3=O)C4=O)CC2)s1]

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-(2-(2-(2-((2-(2,6-dioxopiperidin-3-yl)-1,3-dioxoisoindolin-4-yl)amino)ethoxy)ethoxy)ethoxy)propanamide Starting with 7-(5-(5-((trans)-4-aminocyclohexyl)-1,3,4-thiadiazol-2-yl)-4-(isopropylamino)pyridin-2-yl)pyrrolo[1,2-b]pyridazine-3-carbonitrile, bis-hydrochloride (BB2 10.0 mg, 0.0188 mmol), N-((trans)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-(2-(2-(2-((2-(2,6-dioxopiperidin-3-yl)-1,3-dioxoisoindolin-4-yl)amino)ethoxy)ethoxy)ethoxy)propenamide was prepared following the procedure for Example 3, substituting 3-(2-(2-(2-((2-(2,6-dioxopiperidin-3-yl)-1,3-dioxoisoindolin-4-yl)amino)ethoxy)ethoxy)ethoxy)propanoic acid (10.0 mg, 0.0209 mmol) for 3-(2-(2-((2-(2,6-dioxopiperidin-3-yl)-1,3-dioxoisoindolin-4-yl)amino)ethoxy)ethoxy)propanoic acid (10.0 mg, 0.0231 mmol). ES/MS: 918.750 (M+H$^+$); $^1$H NMR (400 MHz, Methanol-d4) δ 8.79 (d, J=2.2 Hz, 1H), 8.72 (d, J=2.2 Hz, 1H), 8.70 (s, 1H), 8.10 (d, J=5.1 Hz, 1H), 7.97 (s, 1H), 7.55 (dd, J=8.6, 7.1 Hz, 1H), 7.26 (d, J=5.1 Hz, 1H), 7.11 (d, J=8.6 Hz, 1H), 7.01 (d, J=7.0 Hz, 1H), 5.07 (dd, J=12.4, 5.5 Hz, 1H), 4.34 (p, J=6.4 Hz, 1H), 3.80-3.72 (m, 5H), 3.70 (s, 4H), 3.69-3.59 (m, 4H), 3.53 (t, J=5.2 Hz, 2H), 3.24 (tt, J=12.0, 3.6 Hz, 1H), 2.89 (ddd, J=17.8, 14.2, 5.2 Hz, 1H), 2.83-2.65 (m, 2H), 2.44 (t, J=6.0 Hz, 2H), 2.27 (d, J=13.1 Hz, 2H), 2.19-2.04 (m, 3H), 1.75 (qd, J=13.0, 3.3 Hz, 2H), 1.52 (d, J=6.4 Hz, 6H), 1.45 (dd, J=12.8, 3.4 Hz, 2H).

Example 5

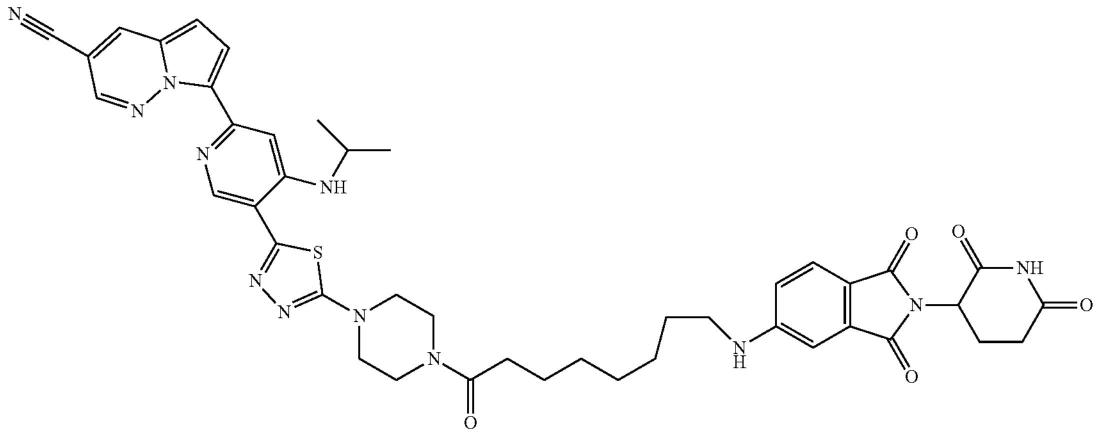 [SMILES: CC(C)Nc1cc(-c2ccc3cc(C#N)cnn23)ncc1-c1nnc(N2CCN(C(=O)CCCCCCCNc3ccc4c(c3)C(=O)N(C3CCC(=O)NC3=O)C4=O)CC2)s1]

7-(5-(5-(4-(8-((2-(2,6-dioxopiperidin-3-yl)-1,3-dioxoisoindolin-5-yl)amino)octanoyl)piperazin-1-yl)-1,3,4-thiadiazol-2-yl)-4-(isopropylamino)pyridin-2-yl)pyrrolo[1,2-b]pyridazine-3-carbonitrile HATU (19 mg, 0.05 mmol) and 8-{[2-(2,6-dioxopiperidin-3-yl)-1,3-dioxoisoindol-5-yl]amino}octanoic acid (14 mg, 0.03 mmol) were dissolved in DMF (0.15 M) and triethylamine (7 mg, 0.07 mmol). The reaction was stirred at room temperature for 10 minutes before addition of 7-[4-(isopropylamino)-5-[5-(piperazin-1-yl)-1,3,4-thiadiazol-2-yl]pyridin-2-yl]pyrrolo[1,2-b]pyridazine-3-carbonitrile (15 mg, 0.03 mmol), BB4. The reaction was then stirred for 16 h, followed by filtration by syringe filter, and purification by HPLC to provide 7-(5-{5-[4-(8-{[2-(2,6-dioxopiperidin-3-yl)-1,3-dioxoisoindol-5-yl]amino}octanoyl)piperazin-1-yl]-1,3,4-thiadiazol-2-yl}-4-(isopropylamino)pyridin-2-yl)pyrrolo[1,2-b]pyridazine-3-carbonitrile (3.6 mg, 13%). LCMS: $C_{43}H_{46}N_{12}O_5S$ requires: 843.0. found: m/z=843.9 $[M+H]^+$; $^1H$ NMR (500 MHz, DMSO-$d_6$) δ 11.06 (s, 1H), 9.50 (s, 1H), 8.98 (d, J=2.1 Hz, 1H), 8.85 (d, J=2.1 Hz, 1H), 8.57 (s, 1H), 8.06 (d, J=4.9 Hz, 1H), 8.02 (s, 1H), 7.57 (d, J=8.3 Hz, 1H), 7.24 (d, J=5.0 Hz, 1H), 7.12 (s, 1H), 6.95 (d, J=2.1 Hz, 1H), 6.85 (dd, J=8.2, 2.1 Hz, 1H), 6.56 (s, 1H), 5.03 (dd, J=12.7, 5.4 Hz, 1H), 4.18 (s, 1H), 3.68 (d, J=4.6 Hz, 1H), 3.64 (s, 2H), 3.58 (d, J=5.8 Hz, 2H), 3.18 (d, J=7.4 Hz, 2H), 2.88 (ddd, J=18.2, 13.8, 5.6 Hz, 1H), 2.60 (s, 1H), 2.39 (d, J=7.5 Hz, 1H), 2.00 (d, J=12.9 Hz, 1H), 1.62-1.54 (m, 2H), 1.53 (d, J=6.8 Hz, 3H), 1.38 (d, J=6.4 Hz, 8H), 1.36-1.32 (m, 6H).

Example 6

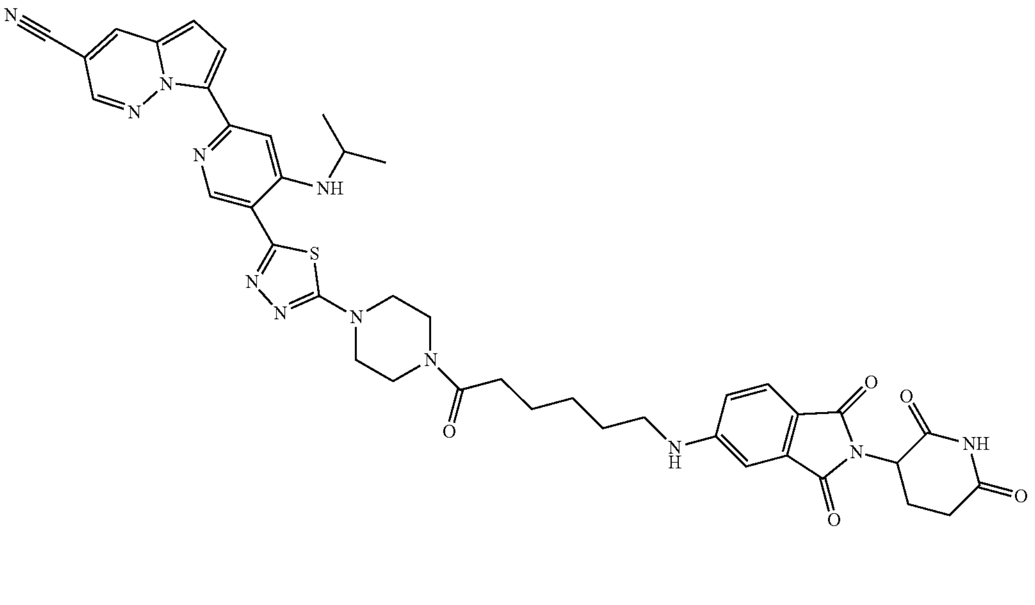 [SMILES: CC(C)Nc1cc(-c2ccc3cc(C#N)cnn23)ncc1-c1nnc(N2CCN(C(=O)CCCCCNc3ccc4c(c3)C(=O)N(C3CCC(=O)NC3=O)C4=O)CC2)s1]

7-(5-(5-(4-(6-((2-(2,6-dioxopiperidin-3-yl)-1,3-dioxoisoindolin-5-yl)amino)hexanoyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 6-((2-(2,6-dioxopiperidin-3-yl)-1,3-dioxoisoindolin-5-yl)amino) hexanoic acid by amide coupling using General Method A. LCMS: $C_{41}H_{42}N_{12}O_5S$ requires: 814.3. found: m/z=815.9 $[M+H]^+$; $^1$H NMR (500 MHz, DMSO-$d_6$) δ 11.06 (s, 1H), 9.20 (s, 1H), 8.94 (d, J=2.3 Hz, 1H), 8.82 (d, J=2.2 Hz, 1H), 8.56 (s, 1H), 8.09 (s, 1H), 8.00 (d, J=4.7 Hz, 1H), 7.55 (dd, J=19.1, 8.3 Hz, 1H), 7.20 (d, J=4.8 Hz, 1H), 7.13 (s, 1H), 6.96 (d, J=2.2 Hz, 1H), 6.85 (ddd, J=10.6, 8.3, 2.1 Hz, 1H), 6.54 (s, 3H), 5.03 (dd, J=12.7, 5.2 Hz, 1H), 4.11 (s, 1H), 3.67 (d, J=5.3 Hz, 2H), 3.18 (s, 2H), 2.88 (ddd, J=16.5, 13.6, 5.4 Hz, 1H), 2.60 (s, 1H), 2.48 (s, 2H), 2.41 (t, J=7.3 Hz, 1H), 2.00 (d, J=12.9 Hz, 1H), 1.60 (tt, J=15.2, 7.6 Hz, 3H), 1.43 (d, J=7.5 Hz, 1H), 1.38 (d, J=6.4 Hz, 6H).

Example 7

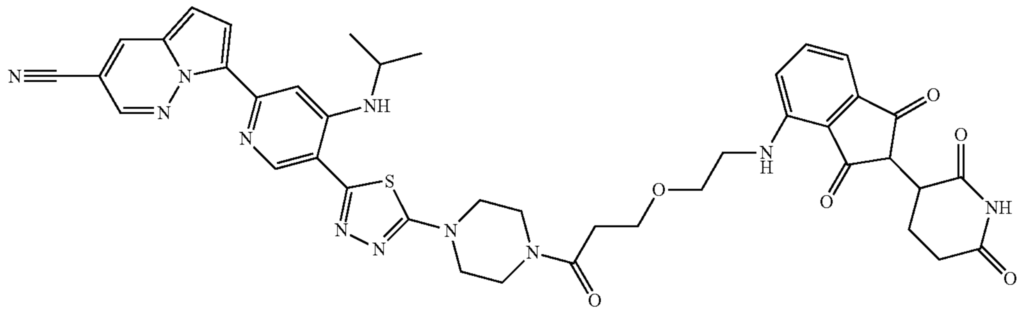 [SMILES: CC(C)Nc1cc(-c2ccc3cc(C#N)cnn23)ncc1-c1nnc(N2CCN(C(=O)CCOCCNc3cccc4c3C(=O)C(C3CCC(=O)NC3=O)C4=O)CC2)s1]

7-(5-(5-(4-(3-(2-((2-(2,6-dioxopiperidin-3-yl)-1,3-dioxoisoindolin-4-yl)amino)ethoxy)propanoyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 3-(2-((2-(2,6-dioxopiperidin-3-yl)-1,3-dioxoisoindolin-4-yl) amino)ethoxy)propanoic acid by amide coupling using General Method A. LCMS: $C_{40}H_{40}N_{12}O_6S$ requires: 816.3 found: m/z=817.7 $[M+H]^+$; $^1$H NMR (500 MHz, DMSO-$d_6$) δ 11.11 (s, 1H), 9.37 (s, 1H), 8.97 (d, J=2.1 Hz, 1H), 8.84 (d, J=2.2 Hz, 1H), 8.52 (s, 1H), 8.05 (d, J=6.1 Hz, 2H), 7.61-7.55 (m, 1H), 7.23 (d, J=4.9 Hz, 1H), 7.14 (d, J=8.6 Hz, 1H), 7.00 (d, J=7.0 Hz, 1H), 6.56 (t, J=5.5 Hz, 1H), 5.06 (dd, J=12.8, 5.4 Hz, 1H), 4.16 (s, 1H), 3.73 (t, J=6.3 Hz, 2H), 3.66 (dt, J=14.4, 5.2 Hz, 6H), 3.61-3.52 (m, 4H), 3.48 (q, J=5.4 Hz, 2H), 2.90 (ddd, J=17.4, 13.8, 5.5 Hz, 1H), 2.67 (t, J=6.3 Hz, 2H), 2.63 (s, 1H), 2.57 (d, J=15.6 Hz, 1H), 2.10-2.03 (m, 1H), 1.39 (d, J=6.3 Hz, 6H).

Example 8

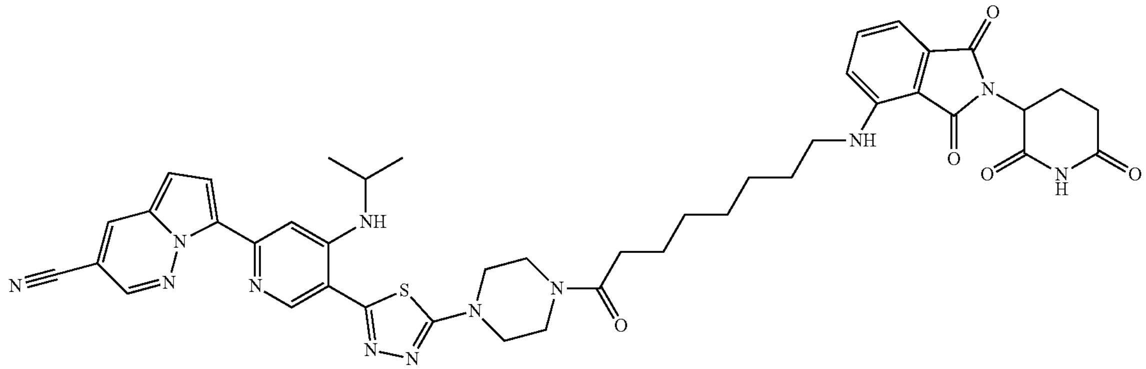 [SMILES: CC(C)Nc1cc(-c2ccc3cc(C#N)cnn23)ncc1-c1nnc(N2CCN(C(=O)CCCCCCCNc3cccc4c3C(=O)N(C3CCC(=O)NC3=O)C4=O)CC2)s1]

7-(5-(5-(4-(8-((2-(2,6-dioxopiperidin-3-yl)-1,3-dioxoisoindolin-4-yl)amino)octanoyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 8-((2-(2,6-dioxopiperidin-3-yl)-1,3-dioxoisoindolin-4-yl)amino) octanoic acid by amide coupling using General Method A. LCMS: $C_{43}H_{46}N_{12}O_5S$ requires: 842.3. found: m/z=843.8 $[M+H]^+$; $^1H$ NMR (500 MHz, DMSO-$d_6$) δ 11.10 (s, 1H), 9.42 (s, 1H), 8.97 (d, J=2.2 Hz, 1H), 8.84 (d, J=2.2 Hz, 1H), 8.56 (s, 1H), 8.04 (d, J=6.6 Hz, 2H), 7.59 (dd, J=8.6, 7.0 Hz, 1H), 7.23 (d, J=4.9 Hz, 1H), 7.11 (d, J=8.6 Hz, 1H), 7.03 (d, J=7.0 Hz, 1H), 6.54 (t, J=6.0 Hz, 1H), 5.06 (dd, J=12.7, 5.5 Hz, 1H), 4.16 (s, 1H), 3.67 (dd, J=7.1, 3.7 Hz, 4H), 3.57 (d, J=5.5 Hz, 2H), 3.31 (q, J=6.4 Hz, 2H), 2.89 (ddd, J=16.8, 13.7, 5.4 Hz, 1H), 2.63-2.56 (m, 1H), 2.49 (s, 1H), 2.38 (t, J=7.4 Hz, 2H), 2.08-2.01 (m, 1H), 1.59 (t, J=6.9 Hz, 2H), 1.53 (t, J=7.2 Hz, 2H), 1.40-1.33 (m, 12H).

Example 9

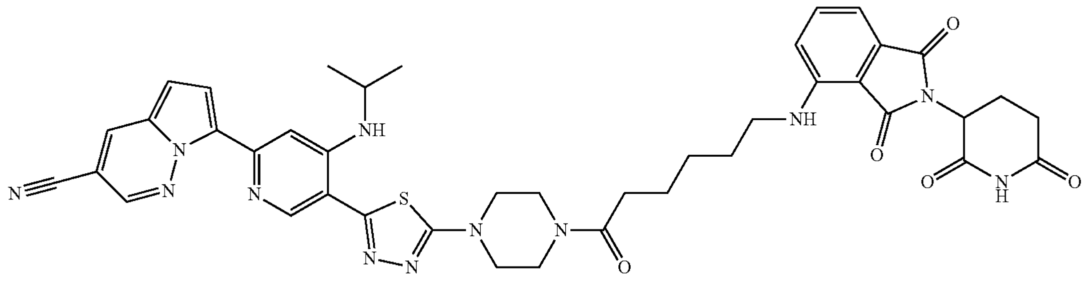 [SMILES: CC(C)Nc1cc(-c2ccc3cc(C#N)cnn23)ncc1-c1nnc(N2CCN(C(=O)CCCCCNc3cccc4c3C(=O)N(C3CCC(=O)NC3=O)C4=O)CC2)s1]

7-(5-(5-(4-(6-((2-(2,6-dioxopiperidin-3-yl)-1,3-dioxoisoindolin-4-yl)amino)hexanoyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 6-((2-(2,6-dioxopiperidin-3-yl)-1,3-dioxoisoindolin-4-yl)amino) hexanoic acid by amide coupling using General Method A. LCMS: $C_{41}H_{42}N_{12}O_5S$ requires: 814.3. found: m/z=817.7 $[M+H]^+$; $^1H$ NMR (500 MHz, DMSO-$d_6$) δ 11.10 (s, 1H), 9.26 (s, 1H), 8.95 (d, J=2.3 Hz, 1H), 8.82 (d, J=2.3 Hz, 1H), 8.56 (s, 1H), 8.08 (s, 1H), 8.01 (d, J=4.9 Hz, 1H), 7.63-7.56 (m, 1H), 7.21 (d, J=4.9 Hz, 1H), 7.12 (d, J=8.6 Hz, 1H), 7.02 (d, J=7.0 Hz, 1H), 6.55 (t, J=6.2 Hz, 1H), 5.06 (dd, J=12.8, 5.4 Hz, 1H), 4.12 (s, 1H), 3.67 (dd, J=6.9, 3.7 Hz, 4H), 3.56 (d, J=5.4 Hz, 2H), 3.32 (q, J=6.6 Hz, 2H), 2.90 (ddd, J=16.8, 13.8, 5.4 Hz, 1H), 2.65-2.56 (m, 1H), 2.41 (t, J=7.4 Hz, 2H), 2.07-2.01 (m, 1H), 1.60 (dp, J=15.1, 7.3 Hz, 4H), 1.38 (d, J=6.4 Hz, 8H).

Example 10

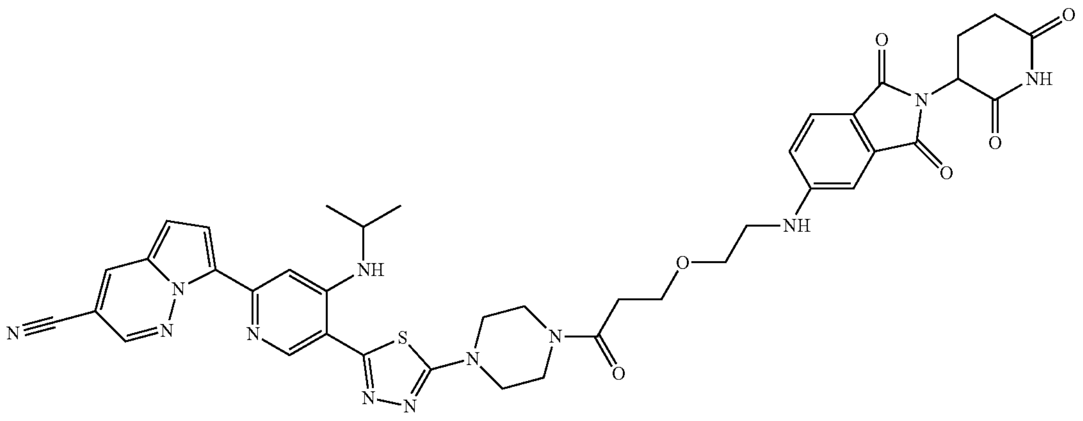 [SMILES: CC(C)Nc1cc(-c2ccc3cc(C#N)cnn23)ncc1-c1nnc(N2CCN(C(=O)CCOCCNc3ccc4c(c3)C(=O)N(C3CCC(=O)NC3=O)C4=O)CC2)s1]

7-(5-(5-(4-(3-(2-((2-(2,6-dioxopiperidin-3-yl)-1,3-dioxoisoindolin-5-yl)amino)ethoxy)propanoyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 3-(2-((2-(2,6-dioxopiperidin-3-yl)-1,3-dioxoisoindolin-5-yl)amino)ethoxy)propanoic acid by amide coupling using General Method A. LCMS: $C_{40}H_{40}N_{12}O_6S$ requires: 816.3. found: m/z=817.6 $[M+H]^+$; $^1H$ NMR (500 MHz, DMSO-$d_6$) δ 11.05 (s, 1H), 9.43 (s, 1H), 8.97 (d, J=2.2 Hz, 1H), 8.84 (d, J=2.2 Hz, 1H), 8.54 (s, 1H), 8.07-8.02 (m, 2H), 7.54 (d, J=8.4 Hz, 1H), 7.23 (d, J=4.9 Hz, 1H), 7.15 (s, 1H), 7.01 (d, J=2.2 Hz, 1H), 6.90 (dd, J=8.4, 2.2 Hz, 1H), 5.01 (dd, J=12.9, 5.4 Hz, 1H), 4.16 (q, J=6.6 Hz, 1H), 3.76-3.58 (m, 8H), 3.57 (s, 2H), 3.36 (t, J=5.4 Hz, 2H), 2.85 (ddd, J=17.4, 14.0, 5.5 Hz, 1H), 2.68 (t, J=6.4 Hz, 2H), 2.58-2.53 (m, 1H), 2.50-2.43 (m, 0H), 1.97 (dtd, J=13.0, 6.1, 2.9 Hz, 1H), 1.38 (d, J=6.3 Hz, 6H).

Example 11

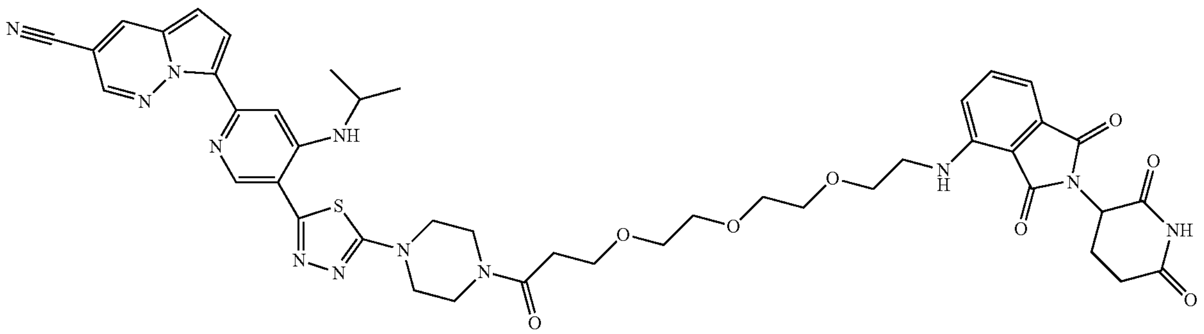 [SMILES: CC(C)Nc1cc(-c2ccc3cc(C#N)cnn23)ncc1-c1nnc(N2CCN(C(=O)CCOCCOCCOCCNc3cccc4c3C(=O)N(C3CCC(=O)NC3=O)C4=O)CC2)s1]

7-(5-(5-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 3-(2-(2-(2-((2-(2,6-dioxopiperidin-3-yl)-1,3-dioxoisoindolin-4-yl)amino)ethoxy)ethoxy)ethoxy)propanoic acid by amide coupling using General Method A. LCMS: $C_{44}H_{48}N_{12}O_8S$ requires: 904.3. found: m/z=906.1 $[M+H]^+$; $^1H$ NMR (500 MHz, DMSO-$d_6$) δ 11.10 (s, 1H), 8.96 (d, J=2.1 Hz, 1H), 8.83 (d, J=2.2 Hz, 1H), 8.53 (s, 1H), 8.07-8.00 (m, 2H), 7.56 (t, J=7.8 Hz, 1H), 7.22 (d, J=4.9 Hz, 1H), 7.13 (d, J=8.6 Hz, 1H), 7.01 (d, J=7.0 Hz, 1H), 6.59 (t, J=5.7 Hz, 1H), 5.06 (dd, J=12.7, 5.4 Hz, 1H), 4.13 (s, 1H), 3.65 (dp, J=17.0, 5.3 Hz, 10H), 3.59-3.46 (m, 10H), 3.46 (d, J=5.6 Hz, 2H), 2.89 (ddd, J=17.5, 13.8, 5.3 Hz, 1H), 2.67-2.56 (m, 3H), 2.05 (dd, J=9.9, 4.4 Hz, 1H), 1.37 (d, J=6.3 Hz, 6H).

Example 12

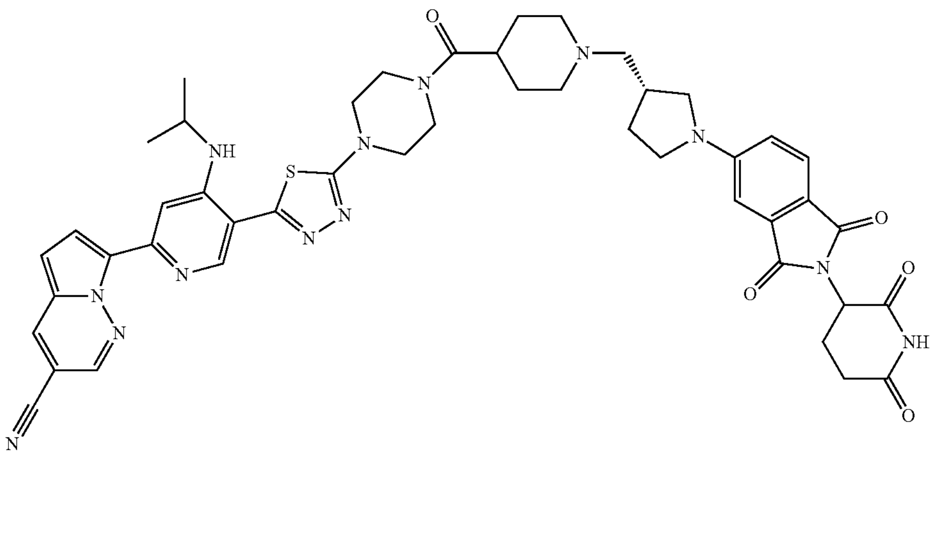 [SMILES: CC(C)Nc1cc(-c2ccc3cc(C#N)cnn23)ncc1-c1nnc(N2CCN(C(=O)C3CCN(C[C@H]4CCN(c5ccc6c(c5)C(=O)N(C5CCC(=O)NC5=O)C6=O)C4)CC3)CC2)s1]

7-(5-(5-(4-(1-(((3R)-1-(2-(2,6-dioxopiperidin-3-yl)-1,3-dioxoisoindolin-5-yl)pyrrolidin-3-yl)methyl)piperidine-4-carbonyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB5 and (3S)-1-(2-(2,6-dioxopiperidin-3-yl)-1,3-dioxoisoindolin-5-yl)pyrrolidine-3-carbaldehyde by reductive amination using General Method B. LCMS: $C_{46}H_{49}N_{13}O_5S$ requires: 895.4. found: m/z=896.8 $[M+H]^+$; $^1H$ NMR (500 MHz, DMSO-$d_6$) δ 11.09 (s, 1H), 9.28 (s, 1H), 9.13 (s, 2H), 8.94 (d, J=2.3 Hz, 1H), 8.81 (d, J=2.2 Hz, 1H), 8.58 (s, 1H), 8.11 (s, 1H), 7.99 (d, J=4.8 Hz, 1H), 7.74-7.68 (m, 1H), 7.21 (d, J=4.9 Hz, 1H), 6.96 (d, J=2.2 Hz, 1H), 6.85 (dd, J=8.5, 2.2 Hz, 1H), 5.08 (dd, J=12.8, 5.4 Hz, 1H), 4.10 (s, 1H), 3.98 (s, 3H), 3.77 (s, 2H), 3.61-3.56 (m, 4H), 3.43 (q, J=8.5 Hz, 1H), 3.27 (dt, J=27.8, 7.7 Hz, 2H), 3.04 (s, 2H), 3.01 (s, 1H), 2.92-2.83 (m, 2H), 2.64-2.57 (m, 1H), 2.28 (s, 1H), 2.03 (d, J=12.1 Hz, 1H), 1.93 (s, 5H), 1.85 (dd, J=12.2, 8.7 Hz, 1H), 1.38 (d, J=6.3 Hz, 7H).

Example 13

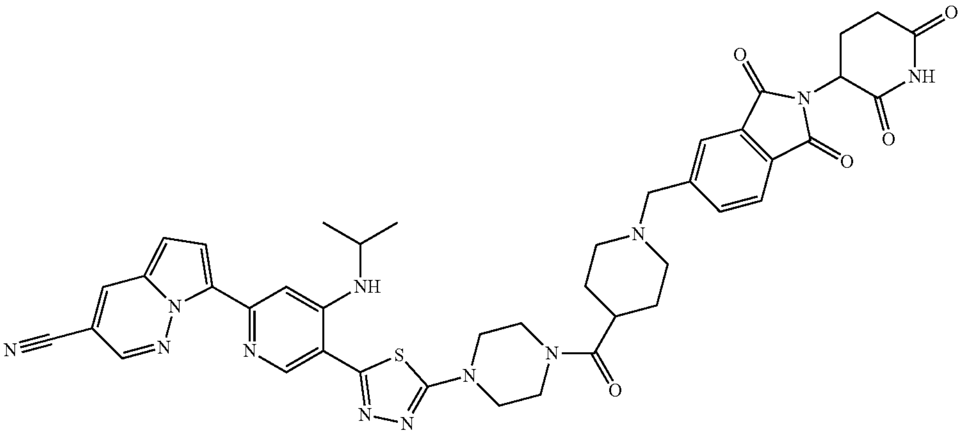 [SMILES: CC(C)Nc1cc(-c2ccc3cc(C#N)cnn23)ncc1-c1nnc(N2CCN(C(=O)C3CCN(Cc4ccc5c(c4)C(=O)N(C4CCC(=O)NC4=O)C5=O)CC3)CC2)s1]

7-(5-(5-(4-(1-((2-(2,6-dioxopiperidin-3-yl)-1,3-dioxoisoindolin-5-yl)methyl)piperidine-4-carbonyl)piperazin-1-yl)-1,3,4-thiadiazol-2-yl)-4-(isopropylamino)pyridin-2-yl)pyrrolo[1,2-b]pyridazine-3-carbonitrile 2-(2,6-dioxopiperidin-3-yl)-1,3-dioxoisoindole-5-carbaldehyde (15 mg, 0.05 mmol), 7-[4-(isopropylamino)-5-{5-[4-(piperidine-4-carbonyl)piperazin-1-yl]-1,3,4-thiadiazol-2-yl}pyridin-2-yl]pyrrolo[1,2-b]pyridazine-3-carbonitrile (BB5, 29 mg, 0.05 mmol) were dissolved in DCE (0.1 M) and triethylamine (0.01 M), then stirred for 10 minutes, after which sodium triacetoxyborohydride (20 mg, 0.1 mmol) was added. The reaction was stirred for 2 h at room temperature, followed by partitioning between DCM and water. The organic layer was separated, dried over magnesium sulfate, and purified by HPLC to provide 7-(5-{5-[4-(1-{[2-(2,6-dioxopiperidin-3-yl)-1,3-dioxoisoindol-5-yl]methyl}piperidine-4-carbonyl)piperazin-1-yl]-1,3,4-thiadiazol-2-yl}-4-(isopropylamino)pyridin-2-yl)pyrrolo[1,2-b]pyridazine-3-carbonitrile (0.007 g, 16%). LCMS: $C_{42}H_{42}N_{12}O_5S$ requires: 826.9. found: m/z=827.9 $[M+H]^+$; $^1H$ NMR (500 MHz, DMSO-$d_6$) δ 11.17 (s, 1H), 9.71 (s, 1H), 8.95 (s, 1H), 8.82 (s, 1H), 8.57 (s, 1H), 8.17 (s, 1H), 8.10 (d, J=6.4 Hz, 2H), 8.03 (dd, J=22.0, 14.0 Hz, 2H), 7.21 (d, J=4.8 Hz, 1H), 5.21 (dd, J=12.8, 5.4 Hz, 1H), 4.55 (s, 2H), 4.11 (s, 2H), 3.73 (s, 14H), 2.96 (d, J=37.5 Hz, 4H), 2.64 (d, J=16.2 Hz, 2H), 2.10 (s, 2H), 1.98-1.67 (m, 4H), 1.37 (d, J=6.2 Hz, 7H), 1.34-1.21 (m, 1H).

Example 14

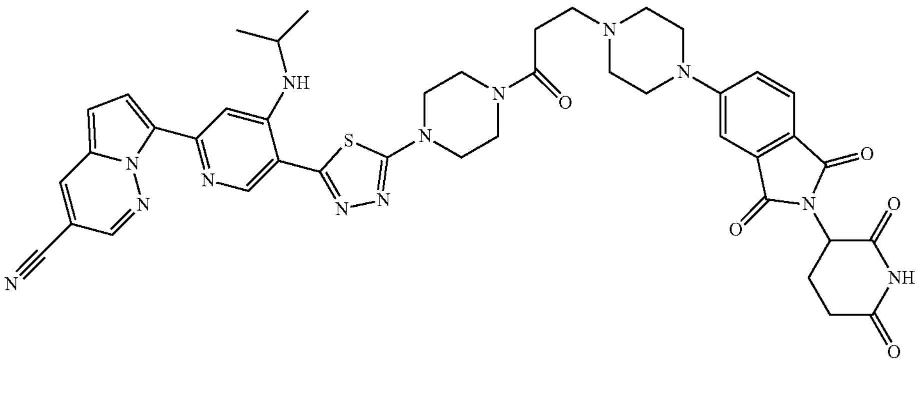 [SMILES: CC(C)Nc1cc(-c2ccc3cc(C#N)cnn23)ncc1-c1nnc(N2CCN(C(=O)CCN3CCN(c4ccc5c(c4)C(=O)N(C4CCC(=O)NC4=O)C5=O)CC3)CC2)s1]

7-(5-(5-(4-(3-(4-(2-(2,6-dioxopiperidin-3-yl)-1,3-dioxoisoindolin-5-yl)piperazin-1-yl)propanoyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 3-(4-(2-(2,6-dioxopiperidin-3-yl)-1,3-dioxoisoindolin-5-yl)piperazin-1-yl)propanoic acid by amide coupling using General Method A. LCMS: $C_{42}H_{43}N_{13}O_5S$ requires: 841.3. found: m/z=842.8 $[M+H]^+$.

Example 15

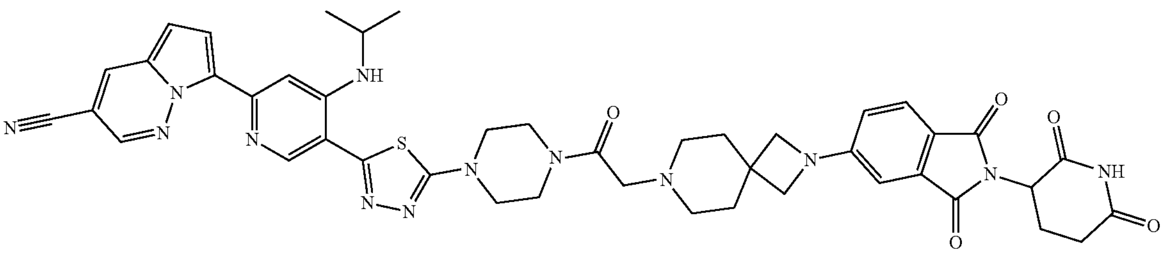 [SMILES: CC(C)Nc1cc(-c2ccc3cc(C#N)cnn23)ncc1-c1nnc(N2CCN(C(=O)CN3CCC4(CC3)CN(c3ccc5c(c3)C(=O)N(C3CCC(=O)NC3=O)C5=O)C4)CC2)s1]

7-(5-(5-(4-(2-(2-(2-(2,6-dioxopiperidin-3-yl)-1,3-dioxoisoindolin-5-yl)-2,7-diazaspiro[3.5]nonan-7-yl)acetyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 2-(2-(2-(2,6-dioxopiperidin-3-yl)-1,3-dioxoisoindolin-5-yl)-2,7-diazaspiro[3.5]nonan-7-yl)acetic acid by amide coupling using General Method A. LCMS: $C_{44}H_{45}N_{13}O_5S$ requires: 867.3. found: m/z=868.8 $[M+H]^+$.

Example 16

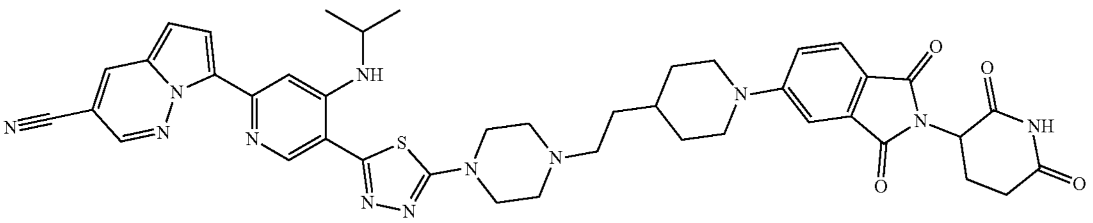 [SMILES: CC(C)Nc1cc(-c2ccc3cc(C#N)cnn23)ncc1-c1nnc(N2CCN(CCC3CCN(c4ccc5c(c4)C(=O)N(C4CCC(=O)NC4=O)C5=O)CC3)CC2)s1]

7-(5-(5-(4-(2-(1-(2-(2,6-dioxopiperidin-3-yl)-1,3-dioxoisoindolin-5-yl)piperidin-4-yl)ethyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 2-(1-(2-(2,6-dioxopiperidin-3-yl)-1,3-dioxoisoindolin-5-yl)piperidin-4-yl)acetaldehyde by reductive amination using General Method B. LCMS: $C_{42}H_{44}N_{12}O_4S$ requires: 812.3. found: m/z=814.0 $[M+H]^+$.

Example 17

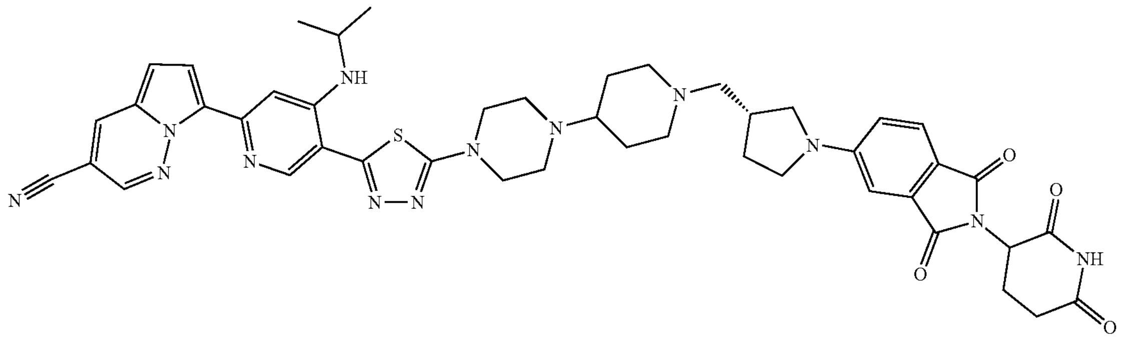 [SMILES: CC(C)Nc1cc(-c2ccc3cc(C#N)cnn23)ncc1-c1nnc(N2CCN(C3CCN(C[C@H]4CCN(c5ccc6c(c5)C(=O)N(C5CCC(=O)NC5=O)C6=O)C4)CC3)CC2)s1]

7-(5-(5-(4-(1-(((3R)-1-(2-(2,6-dioxopiperidin-3-yl)-1,3-dioxoisoindolin-5-yl)pyrrolidin-3-yl)methyl)piperidin-4-yl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB6 and (3S)-1-(2-(2,6-dioxopiperidin-3-yl)-1,3-dioxoisoindolin-5-yl)pyrrolidine-3-carbaldehyde by reductive amination using General Method B. LCMS: $C_{45}H_{49}N_{13}O_4S$ requires: 867.4. found: m/z=868.9 $[M+H]^+$.

Example 18

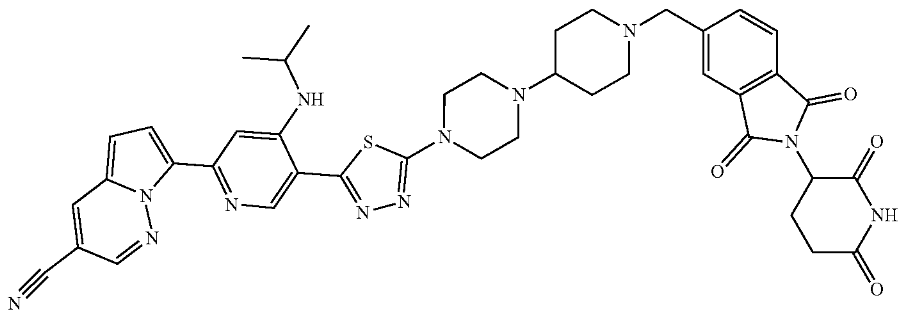 [SMILES: CC(C)Nc1cc(-c2ccc3cc(C#N)cnn23)ncc1-c1nnc(N2CCN(C3CCN(Cc4ccc5c(c4)C(=O)N(C4CCC(=O)NC4=O)C5=O)CC3)CC2)s1]

7-(5-(5-(4-(1-((2-(2,6-dioxopiperidin-3-yl)-1,3-dioxoisoindolin-5-yl)methyl)piperidin-4-yl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB6 and 2-(2,6-dioxopiperidin-3-yl)-1,3-dioxoisoindoline-5-carbaldehyde by reductive amination using General Method B. LCMS: $C_{41}H_{42}N_{12}O_4S$ requires: 798.3. found: m/z=799.8 $[M+H]^+$.

Example 19

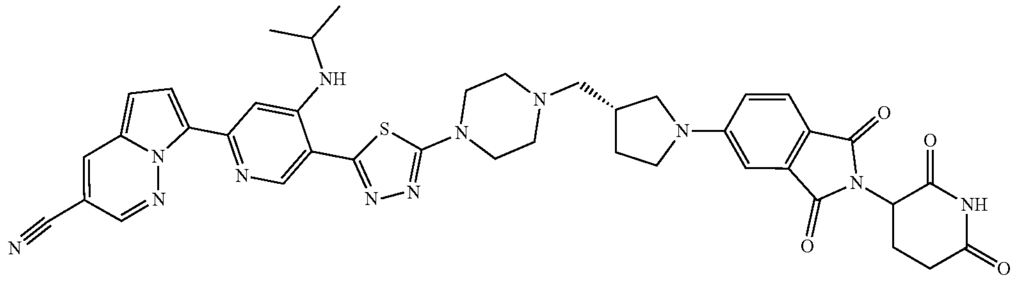 [SMILES: CC(C)Nc1cc(-c2ccc3cc(C#N)cnn23)ncc1-c1nnc(N2CCN(C[C@H]3CCN(c4ccc5c(c4)C(=O)N(C4CCC(=O)NC4=O)C5=O)C3)CC2)s1]

77-(5-(5-(4-(((3R)-1-(2-(2,6-dioxopiperidin-3-yl)-1,3-dioxoisoindolin-5-yl)pyrrolidin-3-yl)methyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and (3S)-1-(2-(2,6-dioxopiperidin-3-yl)-1,3-dioxoisoindolin-5-yl)pyrrolidine-3-carbaldehyde by reductive amination using General Method B. LCMS: $C_{40}H_{40}N_{12}O_4S$ requires: 784.3. found: m/z=785.9[M+H]$^+$; $^1$H NMR (500 MHz, DMSO-$d_6$) δ 11.08 (s, 1H), 9.88 (s, 1H), 8.93 (d, J=2.3 Hz, 1H), 8.80 (d, J=2.3 Hz, 1H), 8.58 (s, 1H), 8.14 (s, 1H), 7.97 (s, 1H), 7.71 (d, J=8.2 Hz, 1H), 7.19 (d, J=4.9 Hz, 1H), 6.97 (d, J=2.3 Hz, 1H), 6.86 (dd, J=8.6, 2.2 Hz, 1H), 6.54 (s, 1H), 5.07 (dd, J=12.8, 5.4 Hz, 1H), 4.15 (s, 3H), 4.08 (s, 2H), 3.76 (s, 3H), 3.66 (s, 4H), 3.58 (s, 1H), 3.46 (t, J=8.8 Hz, 1H), 2.87 (s, 2H), 2.62 (s, 1H), 2.60-2.53 (m, 1H), 2.29 (s, 1H), 2.04 (s, 1H), 1.86 (t, J=10.3 Hz, 1H), 1.37 (d, J=6.3 Hz, 7H).

Example 20

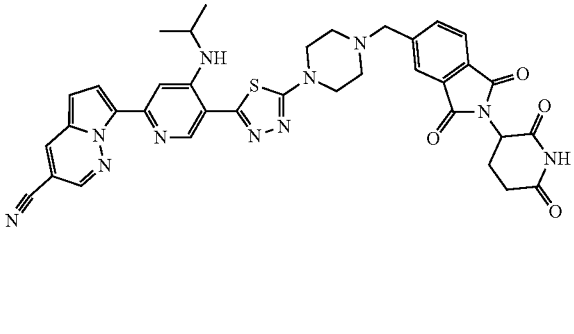 [SMILES: CC(C)Nc1cc(-c2ccc3cc(C#N)cnn23)ncc1-c1nnc(N2CCN(Cc3ccc4c(c3)C(=O)N(C3CCC(=O)NC3=O)C4=O)CC2)s1]

7-(5-(5-(4-((2-(2,6-dioxopiperidin-3-yl)-1,3-dioxoisoindolin-5-yl)methyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 2-(2,6-dioxopiperidin-3-yl)-1,3-dioxoisoindoline-5-carbaldehyde by reductive amination using General Method B. LCMS: $C_{36}H_{33}N_{11}O_{4}S$ requires: 715.2. found: m/z=716.9 [M+H]$^+$.

Example 21

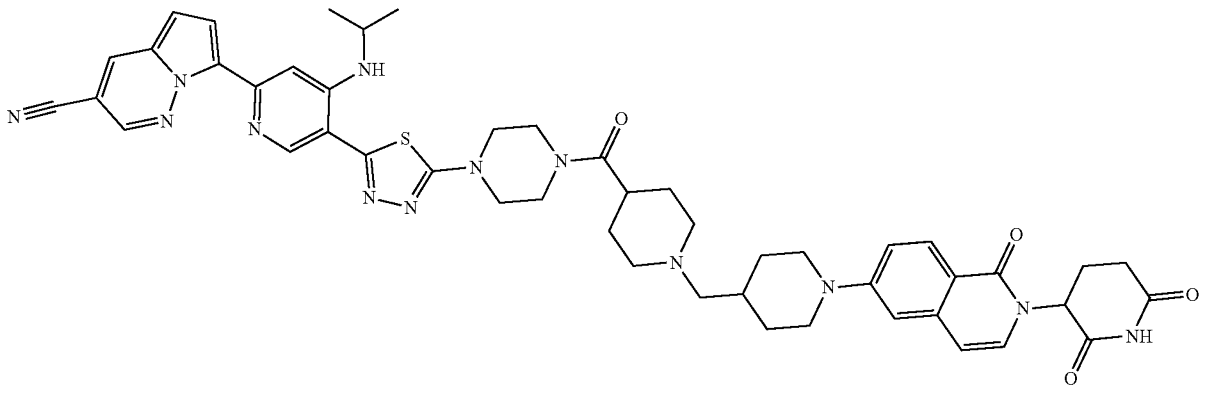 [SMILES: CC(C)Nc1cc(-c2ccc3cc(C#N)cnn23)ncc1-c1nnc(N2CCN(C(=O)C3CCN(CC4CCN(c5ccc6c(=O)n(C7CCC(=O)NC7=O)ccc6c5)CC4)CC3)CC2)s1]

7-(5-(5-(4-(1-((1-(2-(2,6-dioxopiperidin-3-yl)-1-oxo-1,2-dihydroisoquinolin-6-yl)piperidin-4-yl)methyl)piperidine-4-carbonyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB5 and 1-(2-(2,6-dioxopiperidin-3-yl)-1-oxo-1,2-dihydroisoquinolin-6-yl)piperidine-4-carbaldehyde by reductive amination using General Method B. LCMS: $C_{48}H_{53}N_{13}O_4S$ requires: 907.4. found: m/z=909.0[M+H]$^+$; $^1$H NMR (500 MHz, DMSO-$d_6$) δ 11.00 (s, 1H), 9.16 (s, 2H), 8.96-8.92 (m, 1H), 8.81 (d, J=2.3 Hz, 1H), 8.58 (s, 1H), 8.11 (s, 1H), 8.02-7.97 (m, 2H), 7.28 (d, J=7.6 Hz, 1H), 7.24-7.18 (m, 2H), 6.99 (d, J=2.5 Hz, 1H), 6.48 (d, J=7.4 Hz, 1H), 5.43 (s, 1H), 4.11 (s, 1H), 4.02 (d, J=12.5 Hz, 2H), 3.38 (s, 1H), 3.01 (dd, J=13.5, 8.0 Hz, 4H), 2.90 (q, J=17.2, 15.0 Hz, 2H), 2.61 (d, J=14.1 Hz, 2H), 2.12 (s, 1H), 2.03-1.99 (m, 1H), 1.91 (dt, J=27.8, 12.9 Hz, 6H), 1.38 (d, J=6.3 Hz, 7H), 1.34-1.22 (m, 3H).

Example 22

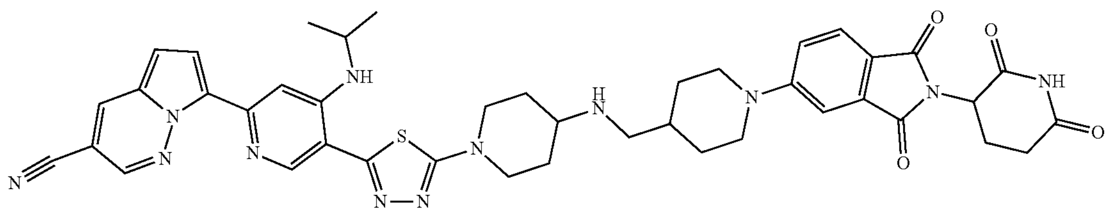 [SMILES: CC(C)Nc1cc(-c2ccc3cc(C#N)cnn23)ncc1-c1nnc(N2CCC(NCC3CCN(c4ccc5c(c4)C(=O)N(C4CCC(=O)NC4=O)C5=O)CC3)CC2)s1]

7-[5-(5-{4-[({1-[2-(2,6-dioxopiperidin-3-yl)-1,3-dioxo-2,3-dihydro-1H-isoindol-5-yl]piperidin-4-yl}methyl)amino]piperidin-1-yl}-1,3,4-thiadiazol-2-yl)-4-[(propan-2-yl)amino]pyridin-2-yl]pyrrolo[1,2-b]pyridazine-3-carbonitrile The title compound was synthesized from BB7 and 1-(2-(2,6-dioxopiperidin-3-yl)-1,3-dioxoisoindolin-5-yl)piperidine-4-carbaldehyde by reductive amination using General Method B. LCMS: $C_{42}H_{44}N_{12}O_4S$ requires: 812.3. found: m/z=813.9 $[M+H]^+$; $^1H$ NMR (500 MHz, DMSO-$d_6$) δ 11.09 (s, 1H), 9.11 (s, 1H), 8.94 (d, J=2.2 Hz, 1H), 8.81 (d, J=2.3 Hz, 1H), 8.56 (s, 1H), 8.47 (s, 2H), 8.11 (s, 1H), 7.99 (t, J=7.1 Hz, 1H), 7.71 (dd, J=13.1, 8.2 Hz, 1H), 7.38 (d, J=2.3 Hz, 1H), 7.32-7.18 (m, 2H), 6.56 (s, 1H), 5.08 (dd, J=12.8, 5.4 Hz, 1H), 4.13 (d, J=13.5 Hz, 2H), 4.06 (d, J=13.1 Hz, 2H), 3.96 (s, 1H), 3.33 (t, J=12.5 Hz, 1H), 3.00 (t, J=12.5 Hz, 1H), 2.96 (s, 3H), 2.94-2.85 (m, 1H), 2.64-2.56 (m, 1H), 2.18 (d, J=12.3 Hz, 2H), 2.01 (s, 1H), 1.98 (s, 1H), 1.86 (d, J=12.8 Hz, 2H), 1.68 (dd, J=13.5, 9.4 Hz, 2H), 1.37 (d, J=6.3 Hz, 5H), 1.32 (s, 1H), 1.30-1.23 (m, 1H).

Example 23

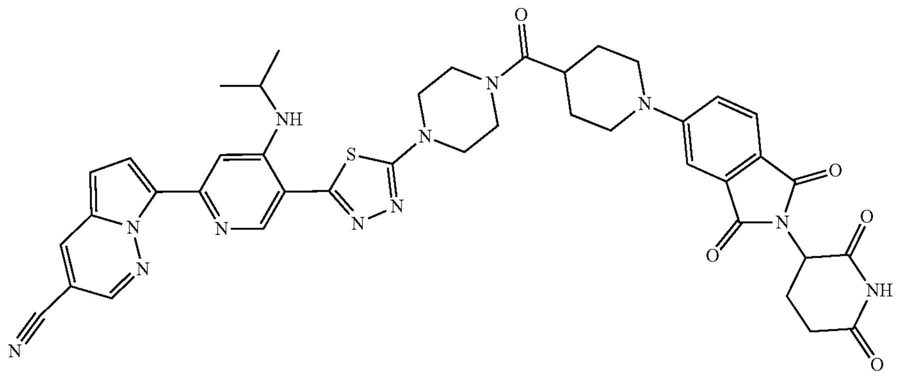 [SMILES: CC(C)Nc1cc(-c2ccc3cc(C#N)cnn23)ncc1-c1nnc(N2CCN(C(=O)C3CCN(c4ccc5c(c4)C(=O)N(C4CCC(=O)NC4=O)C5=O)CC3)CC2)s1]

7-{5-[5-(4-{1-[2-(2,6-dioxopiperidin-3-yl)-1,3-dioxo-2,3-dihydro-1H-isoindol-5-yl]piperidine-4-carbonyl}piperazin-1-yl)-1,3,4-thiadiazol-2-yl]-4-[(propan-2-yl)amino]pyridin-2-yl}pyrrolo[1,2-b]pyridazine-3-carbonitrile 2-(2,6-dioxopiperidin-3-yl)-5-fluoroisoindole-1,3-dione (5 mg, 0.02 mmol) and 7-[4-(isopropylamino)-5-{5-[4-(piperidine-4-carbonyl)piperazin-1-yl]-1,3,4-thiadiazol-2-yl}pyridin-2-yl]pyrrolo[1,2-b]pyridazine-3-carbonitrile (BB5 10 mg, 0.02 mmol) were dissolved in DMF (0.1M) and DIEA was added (0.01M). The reaction was then irradiated in a microwave reactor for 2 h at 110° C. The reaction was then cooled, filtered with a syringe filter and purified by HPLC to provide 7-{5-[5-(4-{1-[2-(2,6-dioxopiperidin-3-yl)-1,3-dioxoisoindol-5-yl]piperidine-4-carbonyl}piperazin-1-yl)-1,3,4-thiadiazol-2-yl]-4-(isopropylamino)pyridin-2-yl}pyrrolo[1,2-b]pyridazine-3-carbonitrile (4.6 mg, 31%). LCMS: $C_{41}H_{40}N_{12}O_5S$ requires: 812.9. found: m/z=813.7 $[M+H]^+$; $^1H$ NMR (500 MHz, DMSO-$d_6$) δ 11.09 (s, 1H), 9.20 (s, 1H), 8.94 (d, J=2.2 Hz, 1H), 8.82 (d, J=2.2 Hz, 1H), 8.57 (s, 1H), 8.10 (s, 1H), 8.00 (d, J=4.8 Hz, 1H), 7.69 (d, J=8.5 Hz, 1H), 7.36 (d, J=2.3 Hz, 1H), 7.27 (dd, J=8.7, 2.3 Hz, 1H), 7.20 (d, J=4.9 Hz, 1H), 6.54 (s, 2H), 5.08 (dd, J=12.8, 5.4 Hz, 1H), 4.10 (d, J=12.6 Hz, 3H), 3.80 (s, 2H), 3.61-3.56 (m, 2H), 3.09 (dt, J=21.6, 11.9 Hz, 3H), 2.90 (t, J=15.7 Hz, 1H), 2.64-2.56 (m, 1H), 2.03 (d, J=12.9 Hz, 1H), 1.77 (d, J=12.2 Hz, 2H), 1.66 (q, J=11.7 Hz, 2H), 1.38 (d, J=6.3 Hz, 7H).

Example 24

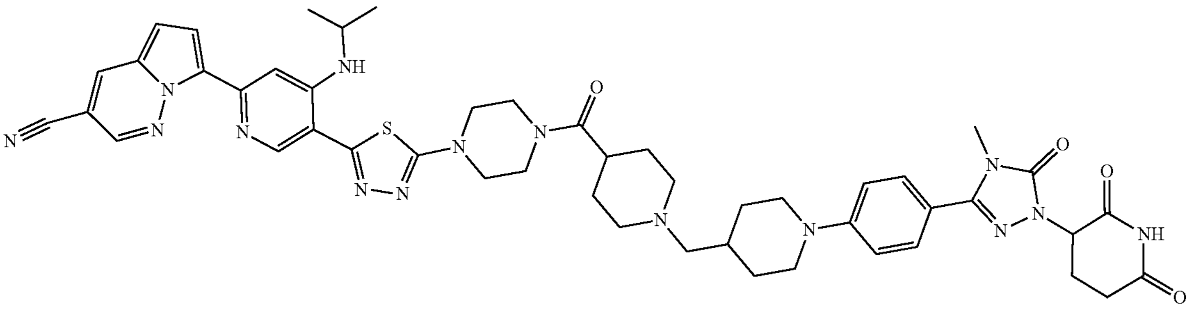 [SMILES: CC(C)Nc1cc(-c2ccc3cc(C#N)cnn23)ncc1-c1nnc(N2CCN(C(=O)C3CCN(CC4CCN(c5ccc(-c6nn(C7CCC(=O)NC7=O)c(=O)n6C)cc5)CC4)CC3)CC2)s1]

7-(5-(5-(4-(1-((1-(4-(1-(2,6-dioxopiperidin-3-yl)-4-methyl-5-oxo-4,5-dihydro-1H-1,2,4-triazol-3-yl)phenyl)piperidin-4-yl)methyl)piperidine-4-carbonyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB5 and 1-(4-(1-(2,6-dioxopiperidin-3-yl)-4-methyl-5-oxo-4,5-dihydro-1H-1,2,4-triazol-3-yl)phenyl)piperidine-4-carbaldehyde by reductive amination using General Method B. LCMS: $C_{48}H_{55}N_{15}O_4S$ requires: 937.4. found: m/z=938.9 $[M+H]^+$; $^1H$ NMR (500 MHz, Acetonitrile-d3) δ 10.01 (d, J=7.3 Hz, 1H), 9.42 (s, 1H), 8.85 (s, 1H), 8.69-8.60 (m, 2H), 8.42 (s, 1H), 8.07 (d, J=5.1 Hz, 1H), 7.63 (s, 1H), 7.54 (d, J=8.4 Hz, 2H), 7.22 (d, J=5.0 Hz, 1H), 7.08 (d, J=8.5 Hz, 2H), 5.04 (dd, J=12.4, 5.3 Hz, 1H), 4.26 (q, J=6.7 Hz, 1H), 3.88 (d, J=12.9 Hz, 2H), 3.83-3.62 (m, 13H), 3.34 (s, 5H), 3.11-2.89 (m, 11H), 2.87-2.75 (m, 4H), 2.62 (td, J=12.6, 5.2 Hz, 2H), 2.32-2.18 (m, 2H), 2.11 (d, J=11.2 Hz, 4H), 1.45 (d, J=6.2 Hz, 8H).

Example 25

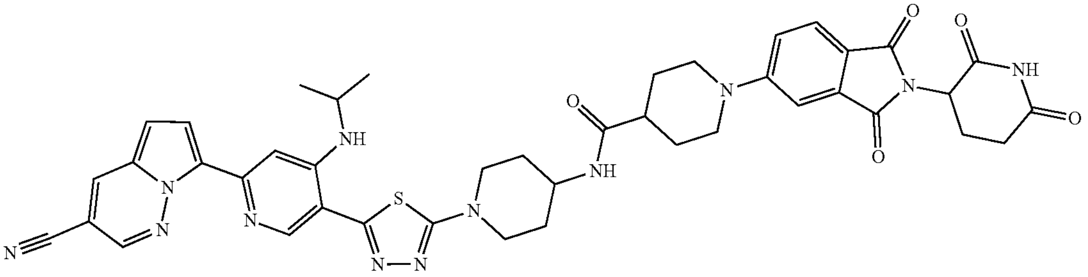 [SMILES: CC(C)Nc1cc(-c2ccc3cc(C#N)cnn23)ncc1-c1nnc(N2CCC(NC(=O)C3CCN(c4ccc5c(c4)C(=O)N(C4CCC(=O)NC4=O)C5=O)CC3)CC2)s1]

N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)-1-(2-(2,6-dioxopiperidin-3-yl)-1,3-dioxoisoindolin-5-yl)piperidine-4-carboxamide Step 1: N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)piperidine-4-carboxamide. 7-(5-(5-(4-aminopiperidin-1-yl)-1,3,4-thiadiazol-2-yl)-4-(isopropylamino)pyridin-2-yl)pyrrolo[1,2-b]pyridazine-3-carbonitrile (BB7 100 mg, 0.22 mmol) was added to a solution of piperidine-4-carboxylic acid (28 mg, 0.22 mmol) and HATU (0.16 g, 0.44 mmol) in DMF (0.15M) and DIEA (0.01M). The reaction was then stirred for 16 h, followed by partitioning between ethyl acetate and water. The organic layer was separated, dried over magnesium sulfate, filtered, and concentrated. The crude material was then dissolved in 4N HCl in dioxane (excess, 3 mL) and stirred for 3 h. The reaction was concentrated to provide N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)piperidine-4-carboxamide (0.11 g, 90%) which was used as-is in the next step. LCMS: $C_{29}H_{34}N_{10}Os$ requires 570.06. found: m/z=571.5 $[M+H]^+$.

Step 2: rac-N-{1-[5-(6-{3-cyanopyrrolo[1,2-b]pyridazin-7-yl}-4-[(propan-2-yl)amino]pyridin-3-yl)-1,3,4-thiadiazol-2-yl]piperidin-4-yl}-1-{2-[(3R)-2,6-dioxopiperidin-3-yl]-1,3-dioxo-2,3-dihydro-1H-isoindol-5-yl}piperidine-4-carboxamide. Synthesized by reacting N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)piperidine-4-carboxamide with 2-(2,6-dioxopiperidin-3-yl)-5-fluoroisoindole-1,3-dione using General Method C to give the title compound. LCMS: $C_{42}H_{42}N_{12}O_5S$ requires: 826.3. found: m/z=827.8 $[M+H]^+$.

Example 26

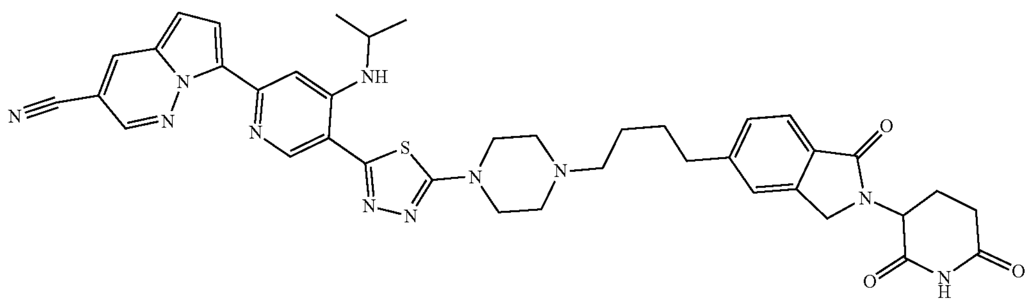 [SMILES: CC(C)Nc1cc(-c2ccc3cc(C#N)cnn23)ncc1-c1nnc(N2CCN(CCCCc3ccc4c(c3)CN(C3CCC(=O)NC3=O)C4=O)CC2)s1]

7-(5-(5-(4-(4-(2-(2,6-dioxopiperidin-3-yl)-1-oxoisoindolin-5-yl)butyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 4-(2-(2,6-dioxopiperidin-3-yl)-1-oxoisoindolin-5-yl)butanal by reductive amination using General Method B. LCMS: $C_{39}H_{41}N_{11}O_3S$ requires: 743.3. found: m/z=744.6 $[M+H]^+$; $^1H$ NMR (500 MHz, DMSO-$d_6$) δ 13.31 (s, 4H), 11.00 (s, 1H), 9.67 (s, 1H), 8.91 (s, 1H), 8.83 (s, 1H), 8.78 (d, J=2.3 Hz, 1H), 8.56 (s, 1H), 8.17 (s, 1H), 8.00 (d, J=7.9 Hz, 4H), 7.93 (s, 1H), 7.75-7.67 (m, 5H), 7.49 (t, J=7.6 Hz, 5H), 7.41 (d, J=7.8 Hz, 1H), 7.25 (td, J=7.6, 1.8 Hz, 4H), 7.18 (d, J=4.8 Hz, 1H), 6.54 (s, 1H), 5.13 (dd, J=13.4, 5.1 Hz, 1H), 4.44 (d, J=17.3 Hz, 1H), 4.32 (d, J=17.2 Hz, 1H), 4.12 (s, 2H), 4.04 (s, 1H), 3.55 (s, 1H), 3.22 (s, 5H), 2.95-2.88 (m, 1H), 2.79 (s, 2H), 2.60 (s, 1H), 2.01 (d, J=12.6 Hz, 1H), 1.69 (s, 4H), 1.37 (d, J=6.2 Hz, 6H).

Example 27

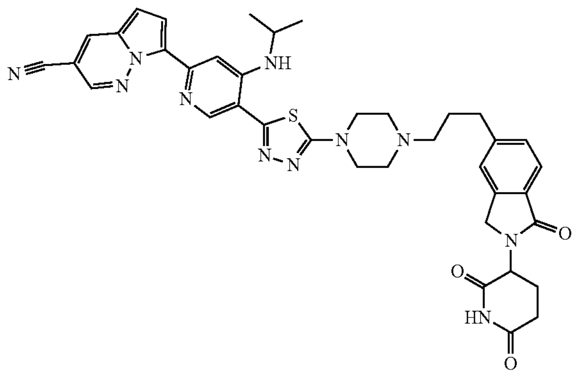 [SMILES: CC(C)Nc1cc(-c2ccc3cc(C#N)cnn23)ncc1-c1nnc(N2CCN(CCCc3ccc4c(c3)CN(C3CCC(=O)NC3=O)C4=O)CC2)s1]

7-(5-(5-(4-(3-(2-(2,6-dioxopiperidin-3-yl)-1-oxoisoindolin-5-yl)propyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 3-(2-(2,6-dioxopiperidin-3-yl)-1-oxoisoindolin-5-yl)propanal by reductive amination using General Method B. LCMS: $C_{38}H_{39}N_{11}O_3S$ requires: 729.3. found: m/z=730.6 $[M+H]^+$.

Example 28

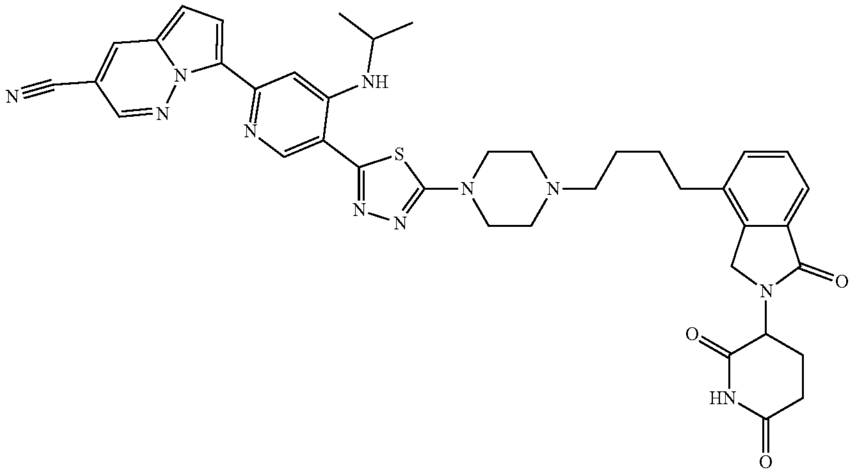 [SMILES: CC(C)Nc1cc(-c2ccc3cc(C#N)cnn23)ncc1-c1nnc(N2CCN(CCCCc3cccc4c3CN(C3CCC(=O)NC3=O)C4=O)CC2)s1]

7-(5-(5-(4-(4-(2-(2,6-dioxopiperidin-3-yl)-1-oxoisoindolin-4-yl)butyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 4-(2-(2,6-dioxopiperidin-3-yl)-1-oxoisoindolin-4-yl)butanal by reductive amination using General Method B. LCMS: $C_{39}H_{41}N_{11}O_3S$ requires: 743.3. found: m/z=744.6 $[M+H]^+$; $^1H$ NMR (500 MHz, DMSO-$d_6$) δ 11.03 (s, 1H), 9.76 (s, 1H), 8.92 (s, 1H), 8.79 (d, J=2.3 Hz, 1H), 8.57 (s, 1H), 8.16 (s, 1H), 7.95 (d, J=4.8 Hz, 1H), 7.62 (dd, J=5.6, 2.9 Hz, 1H), 7.51 (d, J=5.7 Hz, 2H), 7.18 (d, J=4.9 Hz, 1H), 5.18 (dd, J=13.3, 5.1 Hz, 1H), 4.50 (d, J=17.1 Hz, 1H), 4.34 (d, J=17.1 Hz, 1H), 4.12 (s, 2H), 4.06 (s, 1H), 3.02-2.91 (m, 1H), 2.73 (t, J=7.1 Hz, 2H), 2.62 (s, 1H), 2.42 (dd, J=13.2, 4.4 Hz, 1H), 2.08-2.02 (m, 1H), 1.70 (s, 5H), 1.37 (d, J=6.3 Hz, 7H), 1.26 (s, 1H).

Example 29

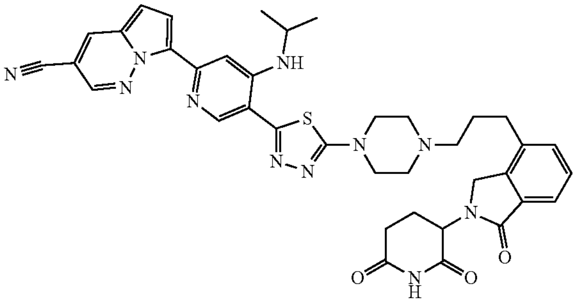 [SMILES: CC(C)Nc1cc(-c2ccc3cc(C#N)cnn23)ncc1-c1nnc(N2CCN(CCCc3cccc4c3CN(C3CCC(=O)NC3=O)C4=O)CC2)s1]

7-(5-(5-(4-(3-(2-(2,6-dioxopiperidin-3-yl)-1-oxoisoindolin-4-yl)propyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 3-(2-(2,6-dioxopiperidin-3-yl)-1-oxoisoindolin-4-yl)propanal by reductive amination using General Method B. LCMS: $C_{38}H_{39}N_{11}O_3S$ requires: 729.3. found: m/z=730.7 $[M+H]^+$; $^1H$ NMR (500 MHz, DMSO-$d_6$) δ 11.02 (d, J=17.7 Hz, 1H), 9.95 (s, 1H), 8.92 (d, J=2.2 Hz, 1H), 8.79 (d, J=2.2 Hz, 1H), 8.57 (s, 1H), 8.15 (s, 1H), 7.95 (d, J=4.8 Hz, 1H), 7.64 (dd, J=6.4, 2.2 Hz, 1H), 7.53 (d, J=6.8 Hz, 2H), 7.18 (d, J=4.9 Hz, 1H), 5.18 (dd, J=13.2, 5.2 Hz, 1H), 4.55-4.42 (m, 1H), 4.35 (d, J=17.1 Hz, 1H), 4.12 (s, 3H), 4.06 (d, J=8.3 Hz, 1H), 3.23 (s, 3H), 2.97 (ddd, J=18.0, 13.6, 5.4 Hz, 1H), 2.90 (s, 1H), 2.74 (t, J=7.4 Hz, 2H), 2.65 (d, J=17.2 Hz, 1H), 2.43-2.37 (m, 1H), 2.09-2.03 (m, 3H), 1.37 (d, J=6.3 Hz, 6H).

Example 30

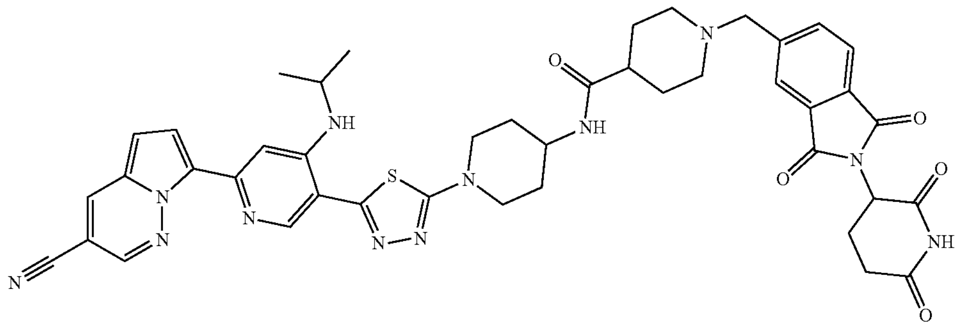 [SMILES: CC(C)Nc1cc(-c2ccc3cc(C#N)cnn23)ncc1-c1nnc(N2CCC(NC(=O)C3CCN(Cc4ccc5c(c4)C(=O)N(C4CCC(=O)NC4=O)C5=O)CC3)CC2)s1]

N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)-1-((2-(2,6-dioxopiperidin-3-yl)-1,3-dioxoisoindolin-5-yl)methyl)piperidine-4-carboxamide Step 1: N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)piperidine-4-carboxamide. 7-(5-(5-(4-aminopiperidin-1-yl)-1,3,4-thiadiazol-2-yl)-4-(isopropylamino)pyridin-2-yl)pyrrolo[1,2-b]pyridazine-3-carbonitrile (BB7 100 mg, 0.22 mmol) was added to a solution of piperidine-4-carboxylic acid (28 mg, 0.22 mmol) and HATU (0.16 g, 0.44 mmol) in DMF (0.15M) and DIEA (0.01M). The reaction was then stirred for 16 h, followed by partitioning between ethyl acetate and water. The organic layer was separated, dried over magnesium sulfate, filtered, and concentrated. The crude material was then dissolved in 4N HCl in dioxane (excess, 3 mL) and stirred for 3 h. The reaction was concentrated to provide N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)piperidine-4-carboxamide (0.11 g, 90%) which was used as-is in the next step. LCMS: $C_{29}H_{34}N_{10}OS$ requires 570.06. found: m/z=571.5 $[M+H]^+$ Step 2: rac-N-{1-[5-(6-{3-cyanopyrrolo[1,2-b]pyridazin-7-yl}-4-[(propan-2-yl)amino]pyridin-3-yl)-1,3,4-thiadiazol-2-yl]piperidin-4-yl}-1-({2-[(3R)-2,6-dioxopiperidin-3-yl]-1,3-dioxo-2,3-dihydro-1H-isoindol-5-yl}methyl)piperidine-4-carboxamide. Synthesized from N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)piperidine-4-carboxamide and 2-(2,6-dioxopiperidin-3-yl)-1,3-dioxoisoindoline-5-carbaldehyde by reductive amination using General Method B to give the title compound. LCMS: $C_{43}H_{44}N_{12}O_5S$ requires: 840.3. found: m/z=841.4 $[M+H]^+$.

Example 31

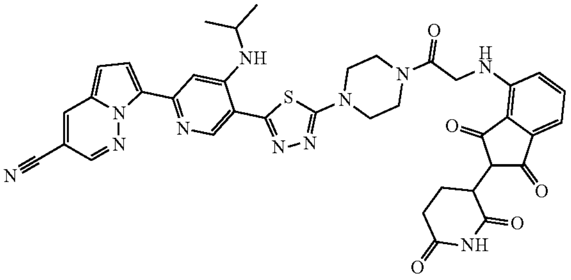 [SMILES: CC(C)Nc1cc(-c2ccc3cc(C#N)cnn23)ncc1-c1nnc(N2CCN(C(=O)CNc3cccc4c3C(=O)C(C3CCC(=O)NC3=O)C4=O)CC2)s1]

7-(5-(5-(4-((2-(2,6-dioxopiperidin-3-yl)-1,3-dioxoisoindolin-4-yl)glycyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and (2-(2,6-dioxopiperidin-3-yl)-1,3-dioxoisoindolin-4-yl)glycine by amide coupling using General Method A. LCMS: $C_{370}H_{34}N_{12}O_5S$ requires: 758.3. found: m/z=759.6 $[M+H]^+$; $^1$H NMR (500 MHz, DMSO-$d_6$) δ 11.12 (s, 1H), 9.01 (s, 1H), 8.91 (d, J=2.2 Hz, 1H), 8.80 (d, J=2.2 Hz, 1H), 8.56 (s, 1H), 8.13 (s, 1H), 7.96 (d, J=4.8 Hz, 1H), 7.68-7.57 (m, 1H), 7.17 (dd, J=16.4, 6.7 Hz, 2H), 7.10 (d, J=6.8 Hz, 2H), 6.53 (s, 0H), 5.09 (dd, J=12.8, 5.5 Hz, 1H), 4.30 (d, J=4.3 Hz, 2H), 4.26 (d, J=5.8 Hz, 1H), 4.06 (s, 1H), 3.74 (d, J=13.9 Hz, 5H), 3.68 (s, 1H), 3.63 (t, J=5.5 Hz, 2H), 2.95-2.85 (m, 1H), 2.65-2.56 (m, 1H), 2.06 (dd, J=11.7, 5.7 Hz, 1H), 1.38 (d, J=6.3 Hz, 5H).

Example 32

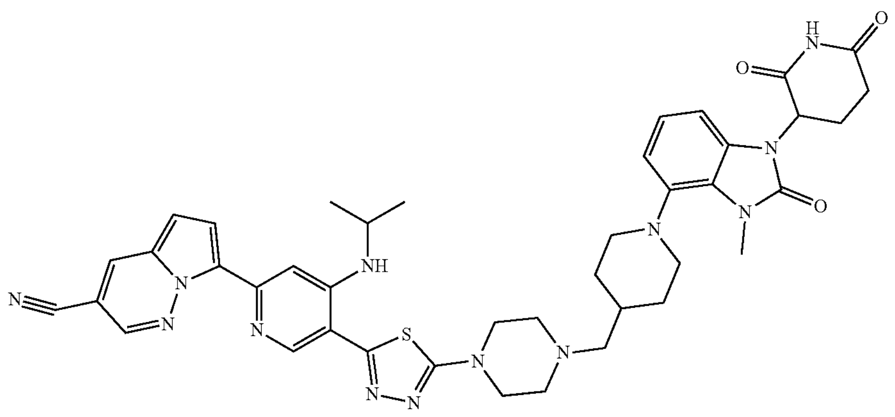 [SMILES: CC(C)Nc1cc(-c2ccc3cc(C#N)cnn23)ncc1-c1nnc(N2CCN(CC3CCN(c4cccc5c4n(C)c(=O)n5C4CCC(=O)NC4=O)CC3)CC2)s1]

7-(5-(5-(4-((1-(1-(2,6-dioxopiperidin-3-yl)-3-methyl-2-oxo-2,3-dihydro-1H-benzo[d]imidazol-4-yl)piperidin-4-yl)methyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 1-(1-(2,6-dioxopiperidin-3-yl)-3-methyl-2-oxo-2,3-dihydro-1H-benzo[d]imidazol-4-yl)piperidine-4-carbaldehyde by amide coupling using General Method A. LCMS: $C_{41}H_{45}N_{13}O_3S$ requires: 799.3. found: m/z=800.8 $[M+H]^+$; $^1H$ NMR (500 MHz, DMSO-$d_6$) δ 11.10 (d, J=5.7 Hz, 1H), 9.68 (s, 1H), 8.95 (d, J=2.1 Hz, 1H), 8.82 (d, J=2.1 Hz, 1H), 8.60 (s, 1H), 8.12 (s, 1H), 8.00 (d, J=4.8 Hz, 1H), 7.21 (d, J=4.9 Hz, 1H), 7.01 (q, J=10.7, 9.4 Hz, 1H), 6.97-6.78 (m, 2H), 5.37 (dt, J=12.5, 5.9 Hz, 1H), 4.13 (s, 2H), 3.19 (d, J=10.6 Hz, 3H), 3.01-2.81 (m, 2H), 2.81-2.59 (m, 4H), 2.06-1.97 (m, 2H), 1.91 (d, J=12.8 Hz, 1H), 1.70-1.43 (m, 2H), 1.38 (d, J=6.3 Hz, 4H).

Example 33

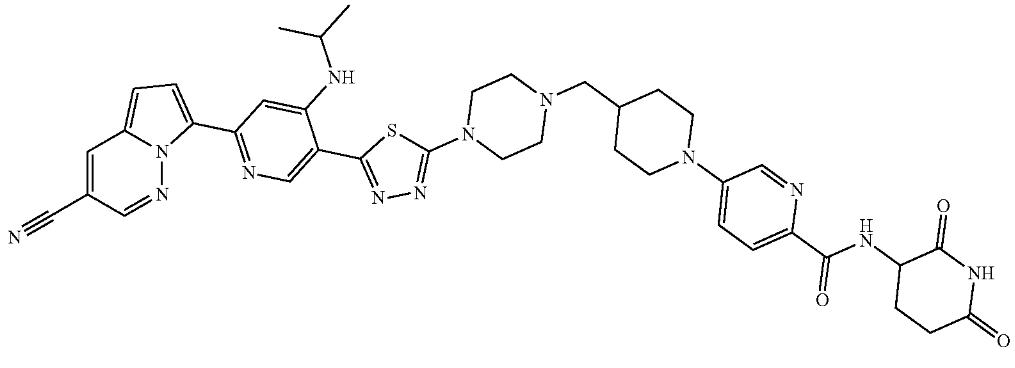 [SMILES: CC(C)Nc1cc(-c2ccc3cc(C#N)cnn23)ncc1-c1nnc(N2CCN(CC3CCN(c4ccc(C(=O)NC5CCC(=O)NC5=O)nc4)CC3)CC2)s1]

5-(4-((4-(5-(6-(3-cyanopyrrolo[1,2-b]pyridazin-7-yl)-4-(isopropylamino)pyridin-3-yl)-1,3,4-thiadiazol-2-yl)piperazin-1-yl)methyl)piperidin-1-yl)-N-(2,6-dioxopiperidin-3-yl)picolinamide The title compound was synthesized from BB4 and N-(2,6-dioxopiperidin-3-yl)-5-(4-formylpiperidin-1-yl)picolinamide by reductive amination using General Method B. LCMS: $C_{39}H_{43}N_{13}O_3S$ requires: 773.3 found: m/z=774.8 $[M+H]^+$; $^1H$ NMR (500 MHz, DMSO-$d_6$) δ 10.85 (s, 1H), 8.85 (d, J=2.3 Hz, 1H), 8.76-8.68 (m, 2H), 8.57 (d, J=7.3 Hz, 1H), 8.51 (s, 1H), 8.32 (d, J=3.0 Hz, 1H), 8.22 (s, 1H), 7.96 (s, 1H), 7.88-7.83 (m, 2H), 7.45-7.39 (m, 1H), 7.13 (d, J=4.7 Hz, 1H), 4.75 (s, 1H), 3.98 (s, 1H), 3.95 (s, 2H), 3.57 (t, J=4.9 Hz, 3H), 2.90 (s, 4H), 2.80 (s, 1H), 2.74 (s, 3H), 2.26 (d, J=6.8 Hz, 2H), 2.18 (s, 1H), 2.03 (s, 1H), 1.85 (d, J=11.8 Hz, 3H), 1.36 (d, J=6.3 Hz, 6H), 1.23 (d, J=14.0 Hz, 3H).

Example 34

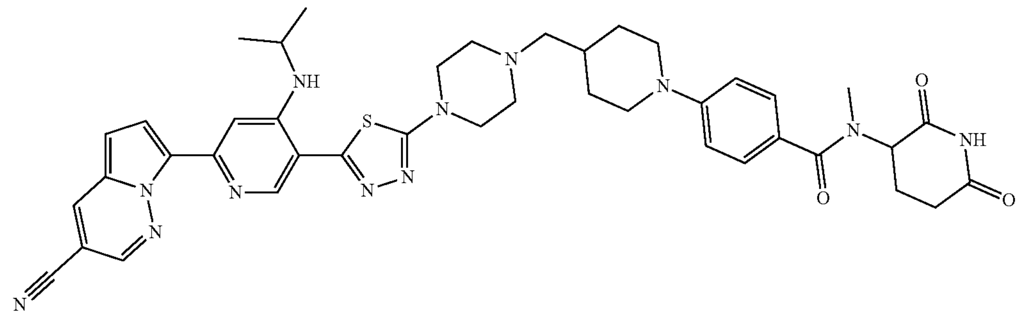 [SMILES: CC(C)Nc1cc(-c2ccc3cc(C#N)cnn23)ncc1-c1nnc(N2CCN(CC3CCN(c4ccc(C(=O)N(C)C5CCC(=O)NC5=O)cc4)CC3)CC2)s1]

4-(4-((4-(5-(6-(3-cyanopyrrolo[1,2-b]pyridazin-7-yl)-4-(isopropylamino)pyridin-3-yl)-1,3,4-thiadiazol-2-yl)piperazin-1-yl)methyl)piperidin-1-yl)-N-(2,6-dioxopiperidin-3-yl)-N-methylbenzamide The title compound was synthesized from BB4 and N-(2,6-dioxopiperidin-3-yl)-4-(4-formylpiperidin-1-yl)-N-methylbenzamide by reductive amination using General Method B. LCMS: $C_{41}H_{46}N_{12}O_3S$ requires: 786.3. found: m/z=787.9 $[M+H]^+$; $^1H$ NMR (500 MHz, DMSO-$d_6$) δ 10.87 (s, 1H), 8.85 (d, J=2.3 Hz, 1H), 8.74 (d, J=2.2 Hz, 1H), 8.57 (d, J=7.0 Hz, 1H), 8.51 (s, 1H), 8.22 (s, 1H), 7.85 (d, J=4.8 Hz, 1H), 7.33 (s, 3H), 7.13 (d, J=4.8 Hz, 1H), 6.96 (d, J=8.4 Hz, 3H), 5.01 (s, 1H), 3.95 (dt, J=13.2, 6.5 Hz, 1H), 3.83 (d, J=12.2 Hz, 2H), 3.56 (d, J=5.4 Hz, 4H), 3.30 (s, 1H), 2.90 (s, 2H), 2.76 (d, J=11.7 Hz, 5H), 2.55 (d, J=4.3 Hz, 3H), 2.48 (s, 3H), 2.40 (s, 1H), 2.25 (d, J=7.0 Hz, 2H), 1.97 (d, J=13.2 Hz, 2H), 1.83 (d, J=13.3 Hz, 2H), 1.77 (s, 1H), 1.36 (d, J=6.3 Hz, 7H), 1.27-1.18 (m, 3H).

Example 35

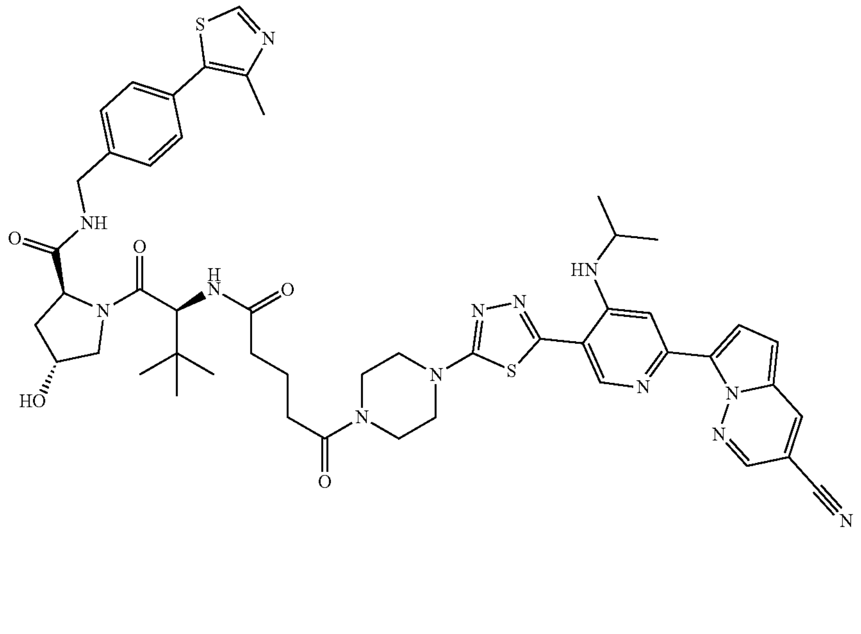 [SMILES: Cc1ncsc1-c1ccc(CNC(=O)[C@@H]2C[C@@H](O)CN2C(=O)[C@@H](NC(=O)CCCC(=O)N2CCN(c3nnc(-c4cnc(-c5ccc6cc(C#N)cnn56)cc4NC(C)C)s3)CC2)C(C)(C)C)cc1]

(2S,4R)-1-((S)-2-(5-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide The title compound was synthesized from BB4 and 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid by amide coupling using General Method A. LCMS: $C_{49}H_{57}N_{13}O_5S_2$ requires: 971.4. found: m/z=973.1 $[M+H]^+$; $^1H$ NMR (500 MHz, Acetonitrile-d3) δ 9.89 (d, J=7.5 Hz, 1H), 8.73 (s, 1H), 8.64-8.55 (m, 2H), 8.46 (s, 1H), 8.07 (d, J=5.1 Hz, 1H), 7.74 (s, 1H), 7.40 (s, 4H), 7.27 (s, 1H), 7.18 (d, J=5.1 Hz, 1H), 6.76 (d, J=8.8 Hz, 1H), 4.57-4.43 (m, 4H), 4.36 (td, J=15.9, 15.5, 5.9 Hz, 2H), 4.20 (dt, J=13.2, 6.6 Hz, 2H), 3.91 (d, J=11.1 Hz, 1H), 3.73 (td, J=10.9, 10.5, 6.2 Hz, 3H), 3.67 (s, 4H), 3.61 (d, J=5.4 Hz, 2H), 2.45 (d, J=7.4 Hz, 6H), 2.40 (dd, J=14.3, 7.3 Hz, 5H), 2.34-2.28 (m, 4H), 2.15 (dd, J=9.3, 5.1 Hz, 3H), 1.88 (p, J=7.1 Hz, 2H), 1.44 (dd, J=6.4, 2.4 Hz, 6H), 1.00 (s, 9H).

Example 36

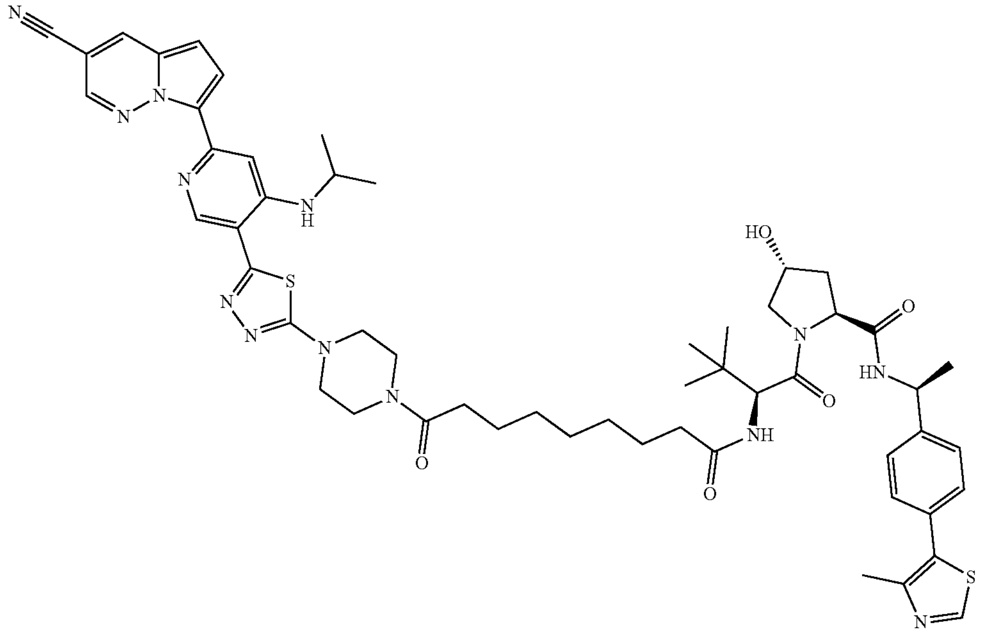 [SMILES: Cc1ncsc1-c1ccc([C@H](C)NC(=O)[C@@H]2C[C@@H](O)CN2C(=O)[C@@H](NC(=O)CCCCCCCC(=O)N2CCN(c3nnc(-c4cnc(-c5ccc6cc(C#N)cnn56)cc4NC(C)C)s3)CC2)C(C)(C)C)cc1]

(2S,4R)-1-((S)-2-(9-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-9-oxononanamido)-3,3-dimethylbutanoyl)-4-hydroxy-N—((S)-1-(4-(4-methylthiazol-5-yl)phenyl)ethyl)pyrrolidine-2-carboxamide The title compound was synthesized from BB4 and 9-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-9-oxononanoic acid by amide coupling using General Method A. LCMS: $C_{54}H_{67}N_{13}O_5S_2$ requires: 1041.5. found: m/z=1043.1 $[M+H]^+$; $^1H$ NMR (500 MHz, DMSO-$d_6$) δ 9.59 (s, 1H), 9.00 (d, J=1.7 Hz, 2H), 8.86 (d, J=2.2 Hz, 1H), 8.58 (s, 1H), 8.37 (d, J=7.8 Hz, 1H), 8.08 (d, J=4.9 Hz, 1H), 8.01 (s, 1H), 7.79 (d, J=9.2 Hz, 1H), 7.47-7.41 (m, 2H), 7.39 (d, J=8.3 Hz, 2H), 7.25 (d, J=4.9 Hz, 1H), 4.93 (p, J=7.0 Hz, 1H), 4.53 (d, J=9.3 Hz, 1H), 4.43 (t, J=8.0 Hz, 1H), 4.29 (s, 1H), 4.24-4.17 (m, 1H), 3.68 (d, J=4.2 Hz, 1H), 3.69-3.60 (m, 5H), 3.59 (dd, J=13.5, 8.5 Hz, 4H), 2.46 (s, 4H), 2.38 (t, J=7.5 Hz, 2H), 2.27 (dt, J=14.6, 7.5 Hz, 1H), 2.13 (dt, J=14.1, 7.1 Hz, 1H), 2.01 (td, J=9.1, 7.5, 4.5 Hz, 1H), 1.80 (ddd, J=12.9, 8.5, 4.6 Hz, 1H), 1.54-1.43 (m, 4H), 1.38 (d, J=6.5 Hz, 9H), 1.32-1.24 (m, 8H), 0.95 (s, 10H).

Example 37

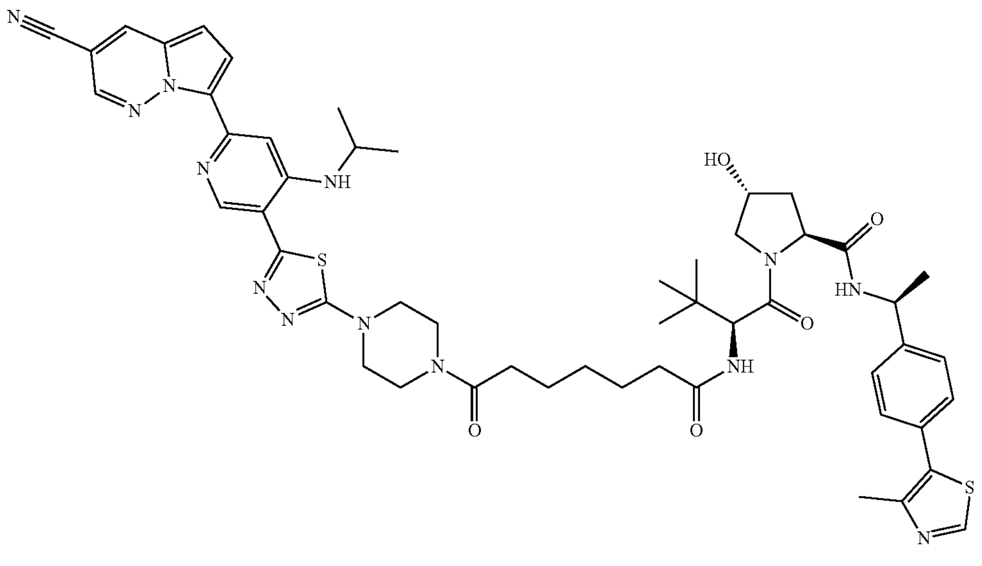 [SMILES: Cc1ncsc1-c1ccc([C@H](C)NC(=O)[C@@H]2C[C@@H](O)CN2C(=O)[C@@H](NC(=O)CCCCCC(=O)N2CCN(c3nnc(-c4cnc(-c5ccc6cc(C#N)cnn56)cc4NC(C)C)s3)CC2)C(C)(C)C)cc1]

(2S,4R)-1-((S)-2-(7-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-7-oxoheptanamido)-3,3-dimethylbutanoyl)-4-hydroxy-N—((S)-1-(4-(4-methylthiazol-5-yl)phenyl)ethyl)pyrrolidine-2-carboxamide Synthesized from BB4 and 7-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-7-oxoheptanoic acid by amide coupling using General Method A. LCMS: $C_{52}H_{63}N_{13}O_5S_2$ requires: 1013.5. found: m/z=1015.3 $[M+H]^+$; $^1H$ NMR (500 MHz, DMSO-$d_6$) δ 9.54 (s, 1H), 8.99 (s, 2H), 8.85 (d, J=2.2 Hz, 1H), 8.58 (s, 1H), 8.37 (d, J=7.8 Hz, 1H), 8.07 (d, J=4.9 Hz, 1H), 8.02 (s, 1H), 7.80 (d, J=9.2 Hz, 1H), 7.47-7.41 (m, 2H), 7.39 (d, J=8.2 Hz, 2H), 7.24 (d, J=4.9 Hz, 1H), 4.93 (p, J=7.1 Hz, 1H), 4.53 (d, J=9.3 Hz, 1H), 4.43 (t, J=8.1 Hz, 1H), 4.29 (s, 1H), 4.19 (d, J=7.3 Hz, 1H), 3.68 (s, 1H), 3.61 (s, 1H), 2.46 (s, 4H), 2.36 (d, J=7.7 Hz, 2H), 2.27 (dt, J=14.7, 7.6 Hz, 1H), 2.14 (dt, J=14.1, 7.3 Hz, 1H), 2.02 (t, J=10.1 Hz, 1H), 1.81 (ddd, J=12.8, 8.5, 4.6 Hz, 1H), 1.51 (dt, J=20.7, 7.3 Hz, 5H), 1.41-1.36 (m, 9H), 1.28 (dq, J=14.3, 6.9, 6.4 Hz, 2H), 0.95 (s, 10H).

Example 38

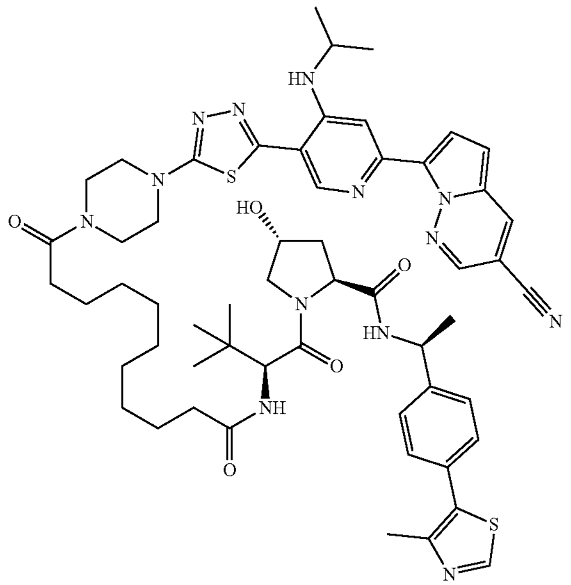 [SMILES: Cc1ncsc1-c1ccc([C@H](C)NC(=O)[C@@H]2C[C@@H](O)CN2C(=O)[C@@H](NC(=O)CCCCCCCCCC(=O)N2CCN(c3nnc(-c4cnc(-c5ccc6cc(C#N)cnn56)cc4NC(C)C)s3)CC2)C(C)(C)C)cc1]

(2S,4R)-1-((S)-2-(11-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-11-oxoundecanamido)-3,3-dimethylbutanoyl)-4-hydroxy-N—((S)-1-(4-(4-methylthiazol-5-yl)phenyl)ethyl)pyrrolidine-2-carboxamide Synthesized from BB4 and 11-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-11-oxoundecanoic acid by amide coupling using General Method A. LCMS: $C_{56}H_{57}N_{13}O_5S_2$ requires: 1069.5. found: m/z=1071.9 $[M+H]^+$; $^1H$ NMR (500 MHz, DMSO-$d_6$) δ 9.40 (s, 1H), 8.98 (d, J=13.2 Hz, 2H), 8.84 (d, J=2.3 Hz, 1H), 8.56 (s, 1H), 8.37 (d, J=7.8 Hz, 1H), 8.04 (s, 2H), 7.79 (d, J=9.3 Hz, 1H), 7.48-7.41 (m, 2H), 7.41-7.32 (m, 2H), 7.22 (d, J=4.9 Hz, 1H), 5.06 (s, 2H), 4.92 (p, J=7.0 Hz, 1H), 4.53 (d, J=9.3 Hz, 1H), 4.43 (t, J=8.0 Hz, 1H), 4.29 (s, 1H), 4.15 (s, 1H), 3.65 (ddt, J=16.3, 10.6, 4.4 Hz, 8H), 3.60 (s, 0H), 3.58 (s, 3H), 2.46 (s, 3H), 2.38 (t, J=7.5 Hz, 2H), 2.26 (dt, J=14.8, 7.7 Hz, 1H), 2.12 (dt, J=14.3, 7.2 Hz, 1H), 2.06-1.98 (m, 1H), 1.80 (ddd, J=12.9, 8.4, 4.6 Hz, 1H), 1.50 (dd, J=18.0, 7.1 Hz, 1H), 1.38 (dd, J=6.7, 2.8 Hz, 10H), 1.28 (d, J=14.2 Hz, 15H), 0.94 (s, 11H).

Example 39

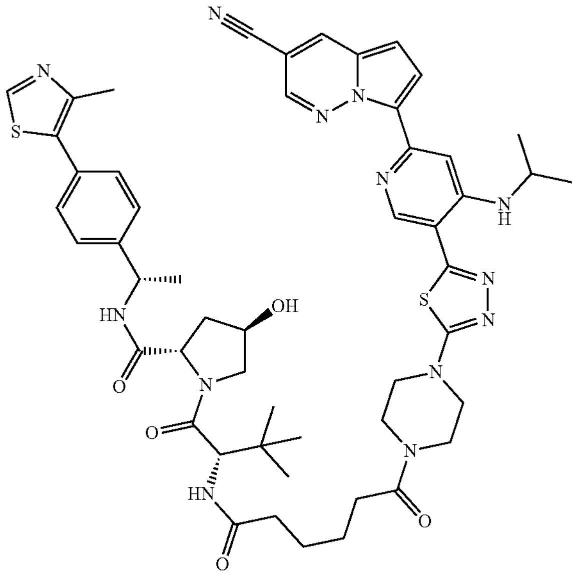 [SMILES: Cc1ncsc1-c1ccc([C@H](C)NC(=O)[C@@H]2C[C@@H](O)CN2C(=O)[C@@H](NC(=O)CCCCC(=O)N2CCN(c3nnc(-c4cnc(-c5ccc6cc(C#N)cnn56)cc4NC(C)C)s3)CC2)C(C)(C)C)cc1]

(2S,4R)-1-((S)-2-(6-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-6-oxohexanamido)-3,3-dimethylbutanoyl)-4-hydroxy-N—((S)-1-(4-(4-methylthiazol-5-yl)phenyl)ethyl)pyrrolidine-2-carboxamide Synthesized from BB4 and 6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexanoic acid by amide coupling using General Method A. LCMS: $C_{51}H_{61}N_{13}O_5S_2$ requires: 999.4. found: m/z=1000.7 $[M+H]^+$; $^1H$ NMR (500 MHz, DMSO-$d_6$) δ 9.66 (s, 1H), 9.03-8.94 (m, 2H), 8.87 (d, J=2.2 Hz, 1H), 8.59 (s, 1H), 8.37 (d, J=7.8 Hz, 1H), 8.10 (d, J=5.0 Hz, 1H), 8.00 (s, 1H), 7.82 (d, J=9.3 Hz, 1H), 7.51-7.33 (m, 5H), 7.26 (d, J=5.0 Hz, 1H), 4.93 (p, J=6.9 Hz, 1H), 4.53 (d, J=9.3 Hz, 1H), 4.44 (t, J=8.0 Hz, 1H), 4.29 (s, 1H), 4.26-4.19 (m, 1H), 3.68 (d, J=7.3 Hz, 7H), 3.64-3.57 (m, 5H), 2.46 (s, 3H), 2.40 (d, J=14.4 Hz, 1H), 2.40 (s, 2H), 2.34-2.27 (m, 1H), 2.20-2.14 (m, 1H), 2.02 (t, J=10.2 Hz, 1H), 1.81 (ddd, J=12.9, 8.6, 4.6 Hz, 1H), 1.57-1.42 (m, 6H), 1.41-1.36 (m, 10H), 0.95 (s, 10H), 0.94 (s, 1H).

Example 40

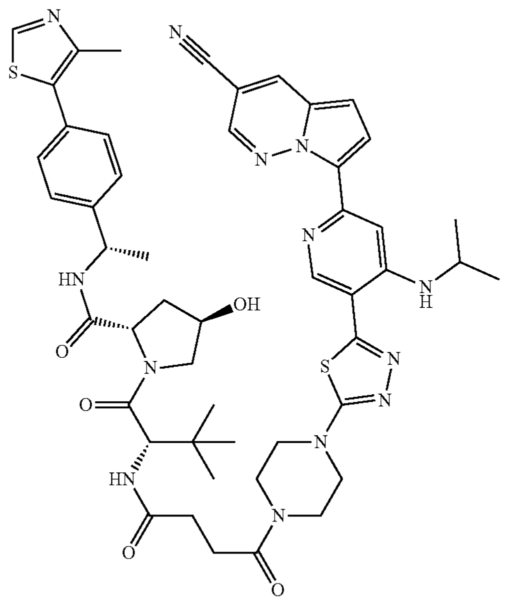 [SMILES: Cc1ncsc1-c1ccc([C@H](C)NC(=O)[C@@H]2C[C@@H](O)CN2C(=O)[C@@H](NC(=O)CCC(=O)N2CCN(c3nnc(-c4cnc(-c5ccc6cc(C#N)cnn56)cc4NC(C)C)s3)CC2)C(C)(C)C)cc1]

(2S,4R)-1-((S)-2-(4-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-4-oxobutanamido)-3,3-dimethylbutanoyl)-4-hydroxy-N—((S)-1-(4-(4-methylthiazol-5-yl)phenyl)ethyl)pyrrolidine-2-carboxamide Synthesized from BB4 and 4-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-4-oxobutanoic acid by amide coupling using General Method A. LCMS: $C_{49}H_{57}N_{13}O_5S_2$ requires: 971.4. found: m/z=972.8 $[M+H]^+$.

Example 41

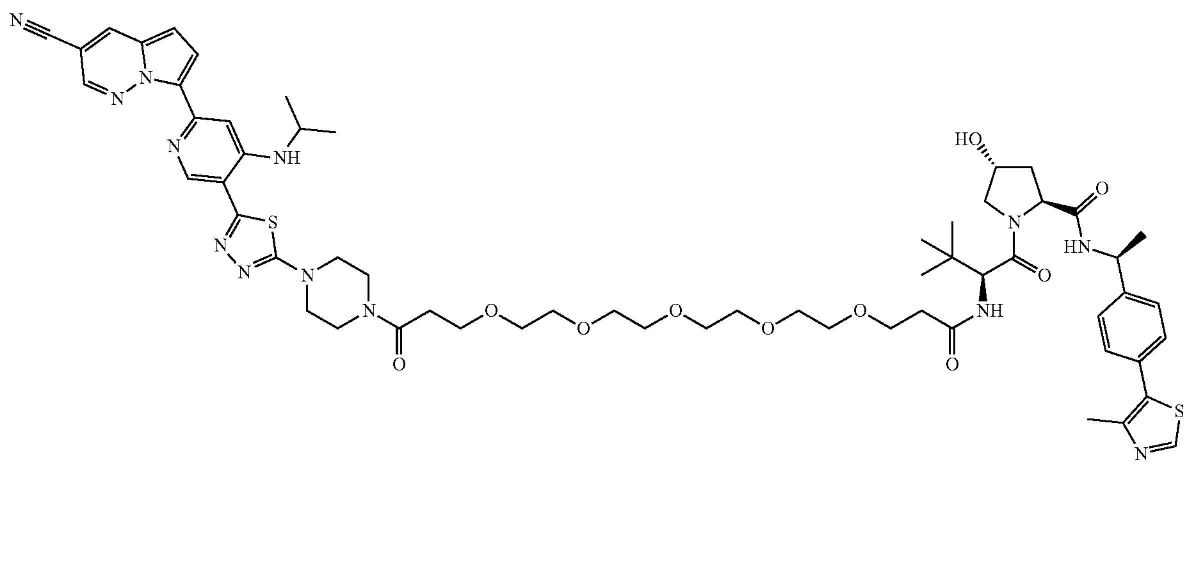 [SMILES: Cc1ncsc1-c1ccc([C@H](C)NC(=O)[C@@H]2C[C@@H](O)CN2C(=O)[C@@H](NC(=O)CCOCCOCCOCCOCCOCCC(=O)N2CCN(c3nnc(-c4cnc(-c5ccc6cc(C#N)cnn56)cc4NC(C)C)s3)CC2)C(C)(C)C)cc1]

(2S,4R)-1-((S)-2-(tert-butyl)-22-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-4,22-dioxo-7,10,13,16,19-pentaoxa-3-azadocosanoyl)-4-hydroxy-N—((S)-1-(4-(4-methylthiazol-5-yl)phenyl)ethyl)pyrrolidine-2-carboxamide The title compound was synthesized from BB4 and (S)-21-((2S,4R)-4-hydroxy-2-(((S)-1-(4-(4-methylthiazol-5-yl)phenyl)ethyl)carbamoyl)pyrrolidine-1-carbonyl)-22,22-dimethyl-19-oxo-4,7,10,13,16-pentaoxa-20-azatricosanoic acid by amide coupling using General Method A. LCMS: $C_{59}H_{77}N_{13}O_{10}S_2$ requires: 1191.5. found: m/z=1193.3 $[M+H]^+$; $^1$H NMR (500 MHz, DMSO-$d_6$) δ 9.37 (s, 1H), 8.97 (d, J=13.7 Hz, 2H), 8.83 (d, J=2.2 Hz, 1H), 8.56 (s, 1H), 8.38 (d, J=7.8 Hz, 1H), 8.04 (d, J=11.6 Hz, 2H), 7.87 (d, J=9.3 Hz, 1H), 7.44 (d, J=8.0 Hz, 2H), 7.38 (d, J=8.3 Hz, 2H), 7.22 (d, J=4.9 Hz, 1H), 4.92 (t, J=7.2 Hz, 1H), 4.53 (d, J=9.3 Hz, 1H), 4.43 (t, J=8.1 Hz, 1H), 4.29 (s, 1H), 4.14 (s, 2H), 3.66 (d, J=6.9 Hz, 2H), 3.59 (ddt, J=12.4, 9.5, 5.2 Hz, 5H), 3.54-3.44 (m, 18H), 2.67 (t, J=6.7 Hz, 2H), 2.46 (s, 3H), 2.37-2.31 (m, 1H), 2.02 (t, J=10.4 Hz, 1H), 1.80 (ddd, J=13.0, 8.5, 4.7 Hz, 1H), 1.38 (dd, J=6.7, 2.8 Hz, 10H), 0.94 (s, 10H).

Example 42

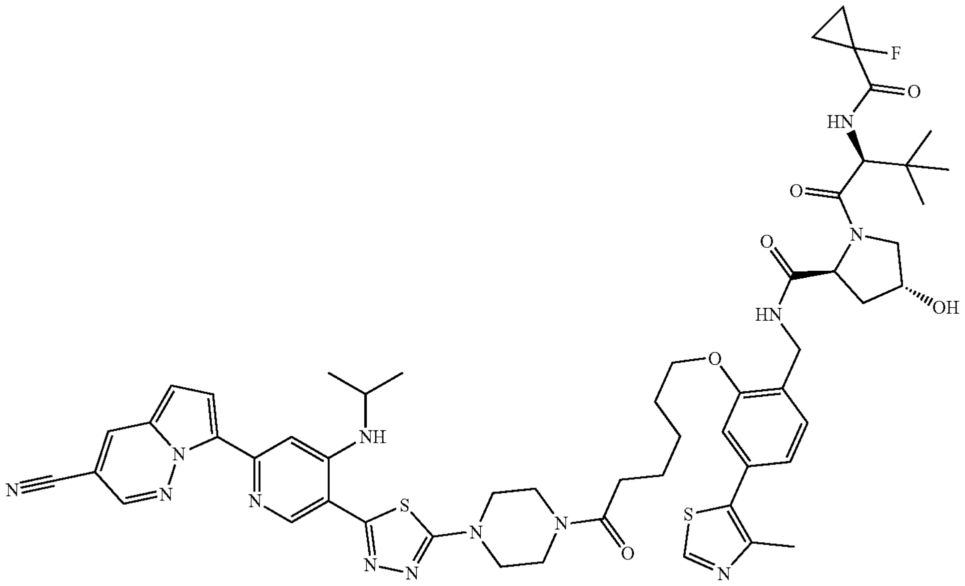 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCC(=O)N2CCN(c3nnc(-c4cnc(-c5ccc6cc(C#N)cnn56)cc4NC(C)C)s3)CC2)c1]

(2S,4R)—N-(2-((6-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-6-oxohexyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB4 and 6-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)hexanoic acid by amide coupling using General Method A. LCMS: $C_{54}H_{64}N_{13}O_6S_2F$ requires: 1073.5. found: m/z=1075.1 $[M+H]^+$; $^1H$ NMR (500 MHz, DMSO-$d_6$) δ 9.51 (s, 1H), 8.99 (d, J=3.7 Hz, 2H), 8.85 (d, J=2.2 Hz, 1H), 8.57 (s, 1H), 8.51 (t, J=6.1 Hz, 1H), 8.09-8.01 (m, 2H), 7.42 (d, J=7.8 Hz, 1H), 7.30 (dd, J=9.2, 2.8 Hz, 1H), 7.24 (d, J=4.9 Hz, 1H), 7.02 (d, J=1.7 Hz, 1H), 6.96 (dd, J=7.7, 1.7 Hz, 1H), 4.61 (d, J=9.2 Hz, 1H), 4.53 (t, J=8.2 Hz, 1H), 4.37 (s, 1H), 4.31 (dd, J=16.5, 6.4 Hz, 1H), 4.22 (dd, J=16.6, 6.1 Hz, 1H), 4.18 (s, 1H), 4.07 (q, J=5.0, 3.5 Hz, 2H), 3.70-3.64 (m, 6H), 3.63 (s, 2H), 3.62-3.55 (m, 2H), 3.27 (dq, J=21.2, 7.2 Hz, 1H), 2.47 (s, 3H), 2.49-2.41 (m, 2H), 2.10 (t, J=10.3 Hz, 1H), 1.93 (ddd, J=13.2, 9.0, 5.0 Hz, 1H), 1.81 (p, J=6.9 Hz, 2H), 1.62 (q, J=7.8 Hz, 2H), 1.58-1.49 (m, 2H), 1.42-1.33 (m, 8H), 1.23 (dd, J=8.4, 2.8 Hz, 2H), 1.09 (t, J=7.1 Hz, 0H), 0.97 (s, 9H), 0.96 (s, 2H).

Example 43

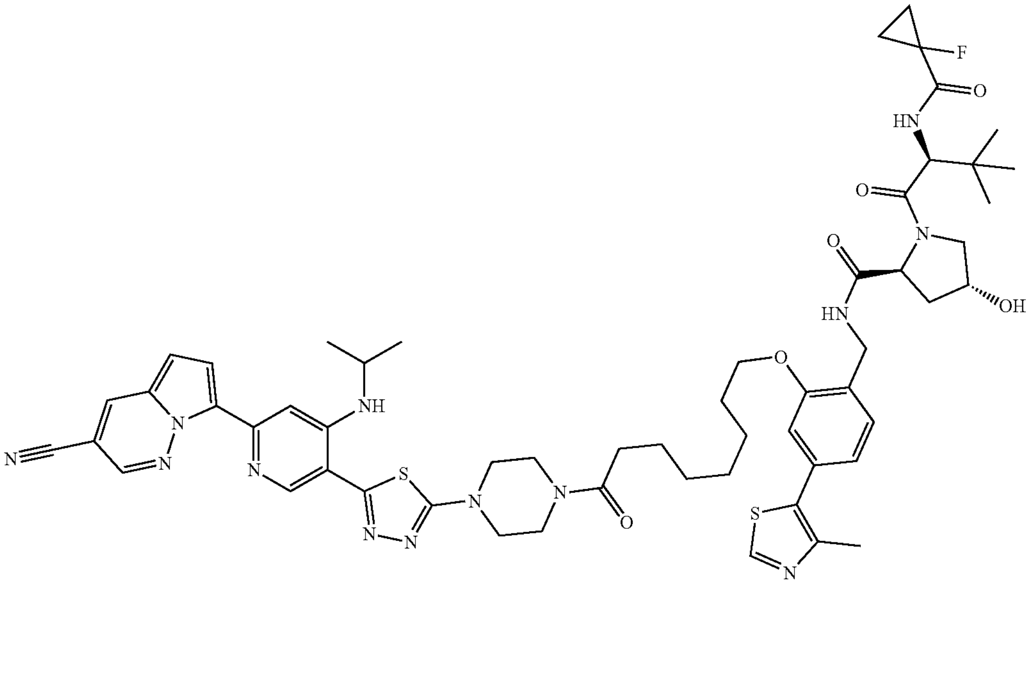 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCC(=O)N2CCN(c3nnc(-c4cnc(-c5ccc6cc(C#N)cnn56)cc4NC(C)C)s3)CC2)c1]

(2S,4R)—N-(2-((8-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-8-oxooctyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB4 and 8-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)octanoic acid by amide coupling using General Method A. LCMS: $C_{56}H_{68}N_{13}O_6S_2F$ requires: 1101.5. found: m/z=1103.0 $[M+H]^+$; $^1H$ NMR (500 MHz, DMSO-$d_6$) δ 9.44 (s, 1H), 8.98 (d, J=7.3 Hz, 2H), 8.84 (d, J=2.3 Hz, 1H), 8.57 (s, 1H), 8.50 (q, J=5.5 Hz, 1H), 8.07-8.02 (m, 1H), 7.41 (d, J=7.8 Hz, 1H), 7.30 (dd, J=9.5, 2.8 Hz, 1H), 7.23 (d, J=4.9 Hz, 1H), 7.02 (d, J=6.3 Hz, 1H), 6.96 (d, J=7.8 Hz, 1H), 5.15 (s, 1H), 4.61 (d, J=9.2 Hz, 1H), 4.53 (t, J=8.2 Hz, 1H), 4.37 (s, 1H), 4.30 (dd, J=16.7, 5.8 Hz, 1H), 4.21 (dd, J=16.5, 5.4 Hz, 1H), 4.19-4.14 (m, 1H), 4.06 (q, J=6.0 Hz, 2H), 3.70-3.62 (m, 2H), 3.62 (s, 2H), 3.59 (d, J=11.3 Hz, 1H), 3.26 (dq, J=14.4, 7.0 Hz, 1H), 2.47 (s, 3H), 2.42-2.36 (m, 2H), 2.25 (t, J=7.4 Hz, 1H), 2.10 (t, J=10.2 Hz, 1H), 1.94 (ddd, J=13.0, 8.9, 4.8 Hz, 1H), 1.77 (p, J=7.2 Hz, 2H), 1.56 (d, J=7.4 Hz, 1H), 1.53 (s, 1H), 1.48 (s, 2H), 1.37 (dd, J=12.5, 6.7 Hz, 12H), 1.25-1.20 (m, 2H), 1.09 (t, J=7.1 Hz, 1H), 1.00 (d, J=7.0 Hz, 1H), 0.97 (s, 10H).

Example 44

(2S,4R)—N-(2-((10-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-10-oxodecyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB4 and 10-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)decanoic acid by amide coupling using General Method A. LCMS: $C_{58}H_{72}N_{13}O_6S_2F$ requires: 1129.5. found: m/z=1131.2 $[M+H]^+$; $^1H$ NMR (500 MHz, DMSO-$d_6$) δ 9.54 (s, 1H), 8.99 (s, 3H), 8.86 (s, 1H), 8.57 (s, 1H), 8.50 (d, J=6.9 Hz, 2H), 8.08 (d, J=4.9 Hz, 1H), 8.01 (s, 1H), 7.41 (d, J=7.8 Hz, 2H), 7.32-7.27 (m, 2H), 7.24 (d, J=4.9 Hz, 1H), 7.01 (s, 2H), 6.96 (d, J=7.7 Hz, 2H), 4.61 (d, J=9.2 Hz, 2H), 4.53 (t, J=8.1 Hz, 2H), 4.37 (s, 2H), 4.30 (dd, J=16.4, 6.0 Hz, 2H), 4.21 (dd, J=15.7, 5.5 Hz, 3H), 4.06 (t, J=6.3 Hz, 4H), 3.70-3.61 (m, 12H), 3.61-3.55 (m, 4H), 3.48 (s, 0H), 2.95 (s, 1H), 2.80 (s, 1H), 2.47 (s, 6H), 2.38 (d, J=15.0 Hz, 1H), 2.26 (t, J=7.5 Hz, 1H), 2.19 (t, J=7.4 Hz, 1H), 2.10 (t, J=10.6 Hz, 2H), 1.93 (ddd, J=13.2, 8.8, 4.6 Hz, 2H), 1.76 (t, J=7.7 Hz, 4H), 1.53 (s, 2H), 1.47 (s, 5H), 1.37 (dd, J=12.4, 6.7 Hz, 12H), 1.30 (d, J=16.0 Hz, 13H), 1.23 (d, J=9.1 Hz, 4H), 0.97 (s, 17H).

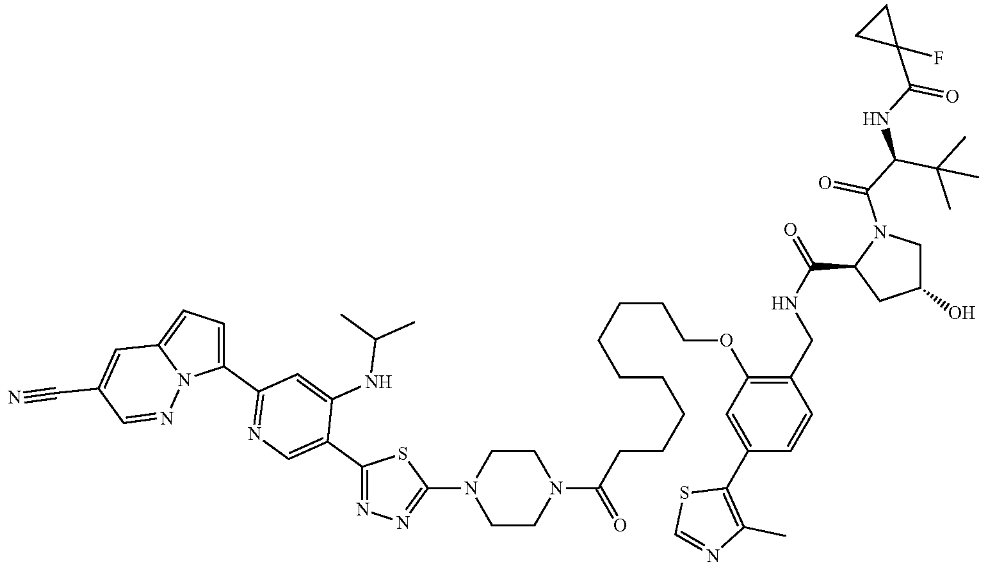 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCCCC(=O)N2CCN(c3nnc(-c4cnc(-c5ccc6cc(C#N)cnn56)cc4NC(C)C)s3)CC2)c1]

Example 45

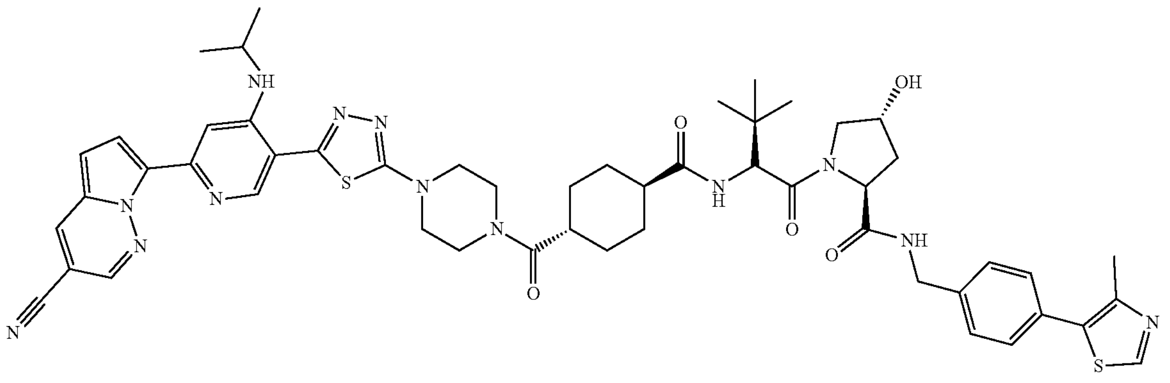

(2S,4R)-1-((S)-2-((1r,4S)-4-(4-(5-(6-(3-cyanopyrrolo[1,2-b]pyridazin-7-yl)-4-(isopropylamino)pyridin-3-yl)-1,3,4-thiadiazol-2-yl)piperazine-1-carbonyl)cyclohexane-1-carboxamido)-3,3-dimethylbutanoyl)-4-hydroxy-N-(4-(4-methylthiazol-5-yl)benzyl)pyrrolidine-2-carboxamide The title compound was synthesized from BB4 and (1SR,4SR)-4-(((S)-1-((2S,4R)-4-hydroxy-2-((4-(4-methyl-1,3-thiazol-5-yl)benzyl)carbamoyl)pyrrolidin-1-yl)-3,3-dimethyl-1-oxobutan-2-yl)carbamoyl)cyclohexane-1-carboxylic acid by amide coupling using General Method A. LCMS: $C_{52}H_{61}N_{13}O_5S_2$ requires: 1011.4. found: m/z=1013.1 $[M+H]^+$.

Example 46

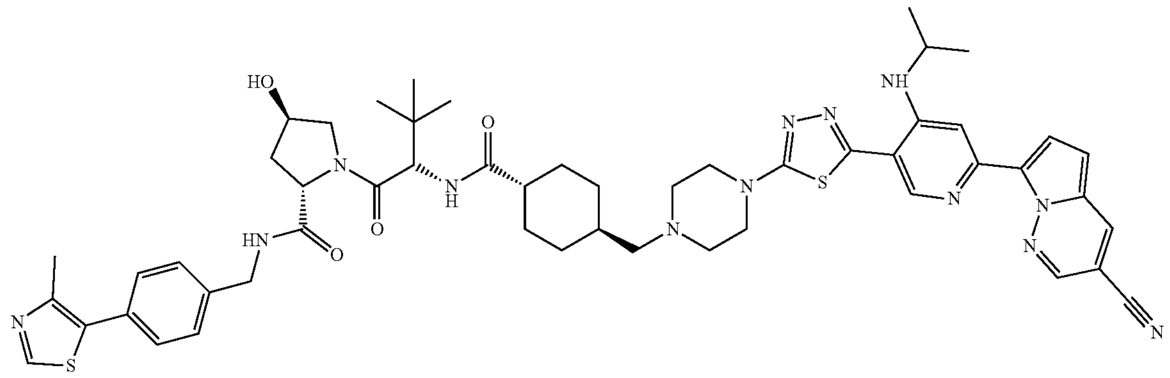

(2S,4R)-1-((S)-2-((1r,4S)-4-((4-(5-(6-(3-cyanopyrrolo[1,2-b]pyridazin-7-yl)-4-(isopropylamino)pyridin-3-yl)-1,3,4-thiadiazol-2-yl)piperazin-1-yl)methyl)cyclohexane-1-carboxamido)-3,3-dimethylbutanoyl)-4-hydroxy-N-(4-(4-methylthiazol-5-yl)benzyl)pyrrolidine-2-carboxamide The title compound was synthesized from BB4 and (2S,4R)-1-((S)-2-((1SR,4SR)-4-formylcyclohexane-1-carboxamido)-3,3-dimethylbutanoyl)-4-hydroxy-N-(4-(4-methylthiazol-5-yl)benzyl)pyrrolidine-2-carboxamide by reductive amination using General Method B. LCMS: $C_{52}H_{63}N_{13}O_4S_2$ requires: 997.5. found: m/z=999.0 $[M+H]^+$.

Example 47

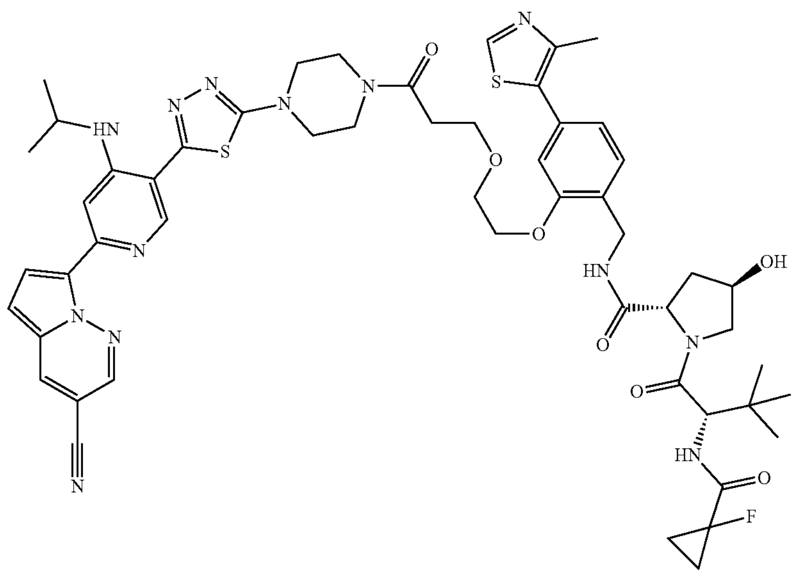 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCC(=O)N2CCN(c3nnc(-c4cnc(-c5ccc6cc(C#N)cnn56)cc4NC(C)C)s3)CC2)c1]

(2S,4R)—N-(2-(2-(3-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-3-oxopropoxy)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB4 and 3-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)propanoic acid by amide coupling using General Method A. LCMS: $C_{53}H_{62}N_{13}O_7S_2F$ requires: 1075.4. found: m/z=1076.9 $[M+H]^+$; $^1H$ NMR (500 MHz, DMSO-$d_6$) δ 9.46 (s, 1H), 9.03-8.93 (m, 2H), 8.85 (d, J=2.3 Hz, 1H), 8.52 (d, J=2.7 Hz, 2H), 8.12-7.96 (m, 2H), 7.42 (dd, J=7.7, 2.5 Hz, 1H), 7.29 (dd, J=9.3, 2.8 Hz, 1H), 7.28-7.19 (m, 1H), 7.03 (d, J=1.9 Hz, 1H), 6.96 (d, J=7.8 Hz, 1H), 4.61 (d, J=9.1 Hz, 1H), 4.54 (t, J=8.2 Hz, 1H), 4.41-4.28 (m, 3H), 4.24-4.12 (m, 5H), 3.79 (q, J=6.4, 5.3 Hz, 10H), 3.67 (t, J=7.9 Hz, 7H), 3.64-3.47 (m, 9H), 2.70 (t, J=6.5 Hz, 2H), 2.45 (d, J=2.6 Hz, 4H), 2.11 (dd, J=12.9, 7.9 Hz, 1H), 1.93 (ddd, J=13.1, 9.1, 4.6 Hz, 1H), 1.38 (dd, J=6.4, 2.5 Hz, 9H), 1.22 (dd, J=8.3, 2.9 Hz, 3H), 0.97 (d, J=2.6 Hz, 10H).

Example 48

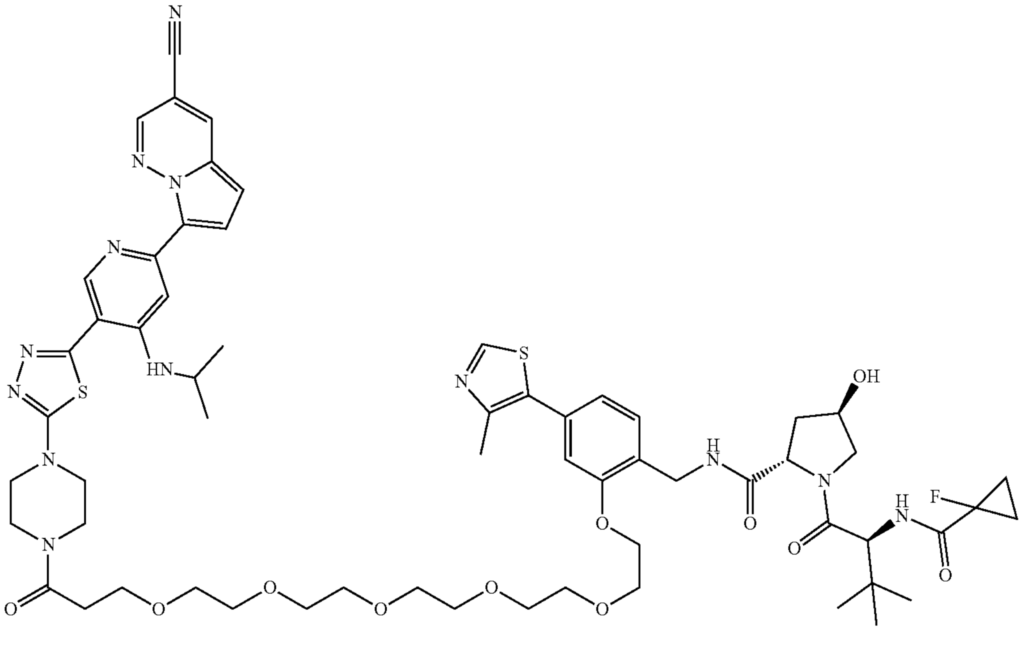 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCOCCOCCC(=O)N2CCN(c3nnc(-c4cnc(-c5ccc6cc(C#N)cnn56)cc4NC(C)C)s3)CC2)c1]

(2S,4R)—N-(2-((18-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-18-oxo-3,6,9,12,15-pentaoxaoctadecyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB4 and 1-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)-3,6,9,12,15-pentaoxaoctadecan-18-oic acid by amide coupling using General Method A. LCMS: $C_{61}H_{78}N_{13}O_{11}S_2F$ requires: 1251.5. found: m/z=1275.2 $[M+Na]^+$; $^1H$ NMR (500 MHz, DMSO-$d_6$) δ 9.01-8.95 (m, 2H), 8.84 (d, J=2.2 Hz, 1H), 8.57 (d, J=7.9 Hz, 1H), 8.49 (t, J=6.0 Hz, 1H), 8.04 (d, J=6.1 Hz, 2H), 7.41 (d, J=7.8 Hz, 1H), 7.29 (dd, J=9.2, 2.9 Hz, 1H), 7.22 (d, J=4.9 Hz, 1H), 7.04 (d, J=1.7 Hz, 1H), 6.99-6.94 (m, 1H), 4.60 (d, J=9.2 Hz, 1H), 4.52 (t, J=8.2 Hz, 1H), 4.36 (s, 1H), 4.31 (dd, J=16.4, 6.2 Hz, 1H), 4.25-4.16 (m, 4H), 3.82-3.77 (m, 2H), 3.67 (t, J=6.5 Hz, 7H), 3.66-3.60 (m, 7H), 3.62-3.52 (m, 2H), 3.50 (d, J=6.6 Hz, 14H), 2.65 (t, J=6.5 Hz, 2H), 2.46 (d, J=2.8 Hz, 3H), 2.14-2.06 (m, 1H), 1.93 (ddd, J=13.1, 9.0, 4.4 Hz, 1H), 1.42-1.30 (m, 9H), 1.27-1.20 (m, 2H), 0.97 (s, 10H).

Example 49

(2S,4R)—N-(2-(2-(2-(2-(3-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-3-oxopropoxy)ethoxy)ethoxy)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB4 and 3-(2-(2-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy)ethoxy)ethoxy)propanoic acid by amide coupling using General Method A. LCMS: $C_{57}H_{70}N_{13}O_9S_2F$ requires: 1163.5 found: m/z=1165.3 $[M+H]^+$; $^1H$ NMR (500 MHz, DMSO-$d_6$) δ 9.49 (s, 1H), 9.01-8.95 (m, 2H), 8.85 (d, J=2.2 Hz, 1H), 8.56 (s, 1H), 8.49 (t, J=6.0 Hz, 1H), 8.06 (d, J=5.0 Hz, 1H), 8.02 (s, 1H), 7.41 (d, J=7.7 Hz, 1H), 7.29 (dd, J=9.4, 2.8 Hz, 1H), 7.24 (d, J=4.9 Hz, 1H), 7.04 (d, J=1.7 Hz, 1H), 6.99-6.94 (m, 1H), 4.60 (d, J=9.2 Hz, 1H), 4.53 (t, J=8.2 Hz, 1H), 4.36 (s, 1H), 4.31 (dd, J=16.5, 6.3 Hz, 1H), 4.25-4.16 (m, 4H), 3.82-3.77 (m, 2H), 3.68-3.48 (m, 16H), 2.65 (t, J=6.5 Hz, 3H), 2.47 (d, J=1.8 Hz, 1H), 2.46 (s, 3H), 2.10 (t, J=10.5 Hz, 1H), 1.93 (ddd, J=13.1, 8.9, 4.5 Hz, 1H), 1.37 (d, J=6.3 Hz, 9H), 1.22 (dd, J=8.3, 2.9 Hz, 2H), 0.97 (s, 11H).

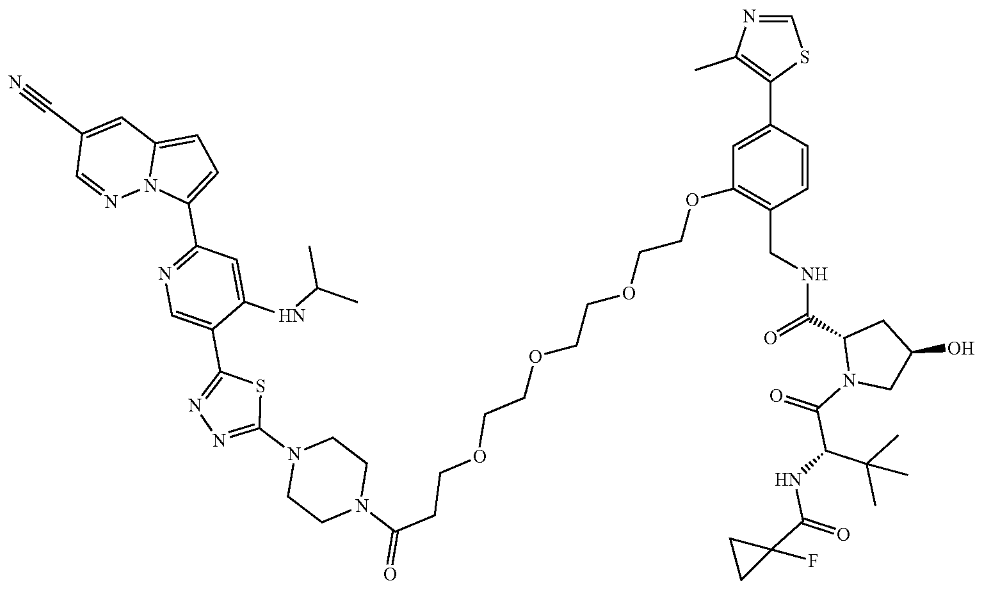 [SMILES: Cc1ncsc1-c1ccc(CNC(=O)[C@@H]2C[C@@H](O)CN2C(=O)[C@@H](NC(=O)C2(F)CC2)C(C)(C)C)c(OCCOCCOCCOCCC(=O)N2CCN(c3nnc(-c4cnc(-c5ccc6cc(C#N)cnn56)cc4NC(C)C)s3)CC2)c1]

Example 50

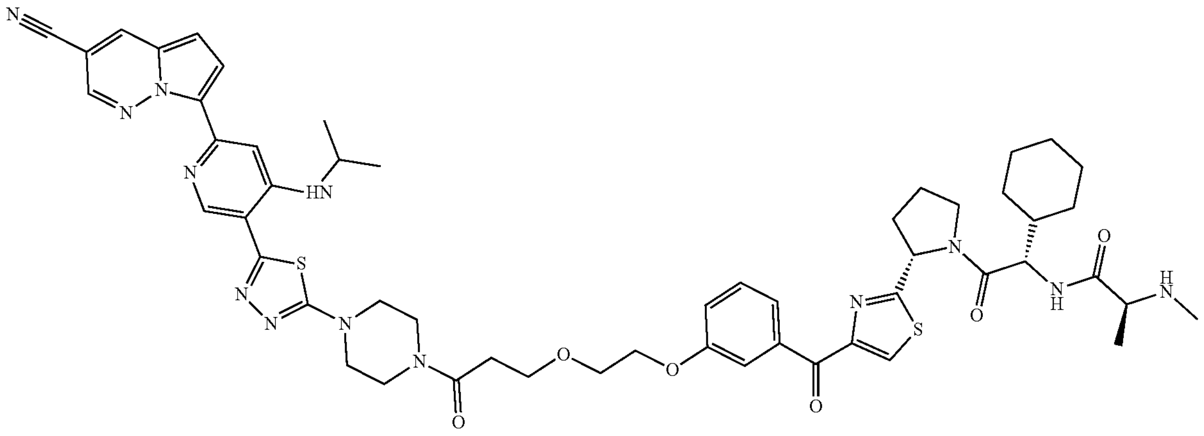 [SMILES: CN[C@@H](C)C(=O)N[C@H](C(=O)N1CCC[C@H]1c1nc(C(=O)c2cccc(OCCOCCC(=O)N3CCN(c4nnc(-c5cnc(-c6ccc7cc(C#N)cnn67)cc5NC(C)C)s4)CC3)c2)cs1)C1CCCCC1]

(S)—N—((S)-2-((S)-2-(4-(3-(2-(3-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-3-oxopropoxy)ethoxy)benzoyl)thiazol-2-yl)pyrrolidin-1-yl)-1-cyclohexyl-2-oxoethyl)-2-(methylamino)propanamide To a mixture of 3-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)propanoic acid (BB4 12 mg) and HA-1 was added a pre-prepared mixture of N,N-diisopropylethylamine (2-3 equiv) in THF (1 mL), then HATU (1.4 equiv) was added and the mixture was stirred at RT for 16 h. The reaction mixture was concentrated under reduced pressure, then added DCM (0.3 mL) and 4M HCl in dioxanes (0.3 mL) and stirred for 3 h. The reaction mixture was concentrated and purified by HPLC to give the title compound. LCMS: $C_{53}H_{36}N_{13}O_6S_2$ requires: 1041.4. found: m/z=1042.9 $[M+H]^+$; $^1H$ NMR (500 MHz, DMSO-$d_6$) δ 8.94 (s, 1H), 8.81 (d, J=2.3 Hz, 1H), 8.79 (s, 2H), 8.73 (d, J=8.0 Hz, 1H), 8.52 (d, J=6.3 Hz, 1H), 8.47 (s, 1H), 8.10 (s, 1H), 7.99 (s, 1H), 7.68-7.60 (m, 2H), 7.44 (t, J=7.9 Hz, 1H), 7.25 (dd, J=8.1, 2.6 Hz, 1H), 7.20 (d, J=4.9 Hz, 1H), 5.38 (dd, J=7.8, 3.2 Hz, 1H), 4.48 (t, J=7.6 Hz, 1H), 4.18 (t, J=4.5 Hz, 3H), 4.09 (s, 1H), 3.87 (q, J=6.5 Hz, 1H), 3.83-3.73 (m, 7H), 3.59 (s, 2H), 3.54 (s, 2H), 2.70 (t, J=6.5 Hz, 2H), 2.27-2.20 (m, 1H), 2.20 (s, 1H), 2.05 (s, 2H), 1.71-1.62 (m, 7H), 1.57 (d, J=10.4 Hz, 2H), 1.36 (dd, J=13.8, 6.6 Hz, 10H), 1.15-1.06 (m, 3H), 1.05 (s, 5H).

Example 51

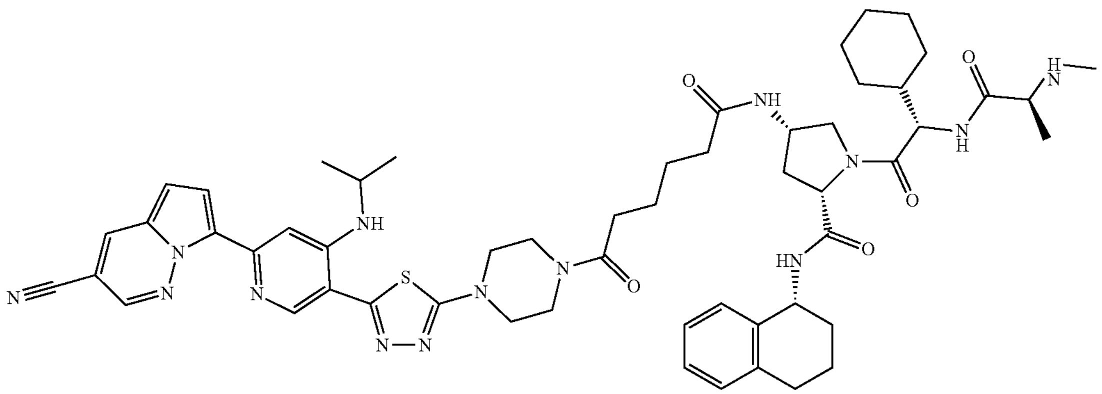 [SMILES: CN[C@@H](C)C(=O)N[C@H](C(=O)N1C[C@@H](NC(=O)CCCCC(=O)N2CCN(c3nnc(-c4cnc(-c5ccc6cc(C#N)cnn56)cc4NC(C)C)s3)CC2)C[C@H]1C(=O)N[C@@H]1CCCc2ccccc21)C1CCCCC1]

(2S,4S)-4-(6-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-6-oxohexanamido)-1-((S)-2-cyclohexyl-2-((S)-2-(methylamino)propanamido)acetyl)-N—((R)-1,2,3,4-tetrahydronaphthalen-1-yl)pyrrolidine-2-carboxamide The title compound was synthesized from BB4 and 6-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-6-oxohexanoic acid by amide coupling using General Method D. LCMS: $C_{55}H_{70}N_{14}O_5S$ requires: 1038.5. found: m/z=1041.1 $[M+H]^+$; $^1H$ NMR (500 MHz, DMSO-$d_6$) δ 9.52 (s, 1H), 8.99 (d, J=2.2 Hz, 1H), 8.85 (d, J=2.3 Hz, 1H), 8.79 (t, J=9.5 Hz, 3H), 8.59 (s, 1H), 8.42 (d, J=8.6 Hz, 1H), 8.16 (t, J=7.7 Hz, 1H), 8.07 (d, J=5.0 Hz, 1H), 8.03 (s, 1H), 7.30 (d, J=7.5 Hz, 1H), 7.24 (d, J=4.9 Hz, 1H), 7.20-7.07 (m, 3H), 4.95 (s, 1H), 4.40 (t, J=8.2 Hz, 1H), 4.29 (dt, J=12.1, 7.9 Hz, 2H), 4.19 (d, J=7.6 Hz, 1H), 4.13 (dd, J=9.7, 7.0 Hz, 1H), 3.88-3.82 (m, 1H), 3.68 (s, 1H), 3.32 (t, J=8.9 Hz, 1H), 2.74 (d, J=7.0 Hz, 3H), 2.40 (t, J=7.0 Hz, 2H), 2.10 (q, J=10.2, 8.4 Hz, 2H), 1.95-1.86 (m, 2H), 1.86 (s, 1H), 1.82-1.61 (m, 7H), 1.53 (s, 5H), 1.38 (d, J=6.4 Hz, 5H), 1.33 (d, J=6.8 Hz, 3H), 1.26-1.12 (m, 3H), 1.06 (d, J=10.6 Hz, 1H), 1.03 (s, 2H).

Example 52

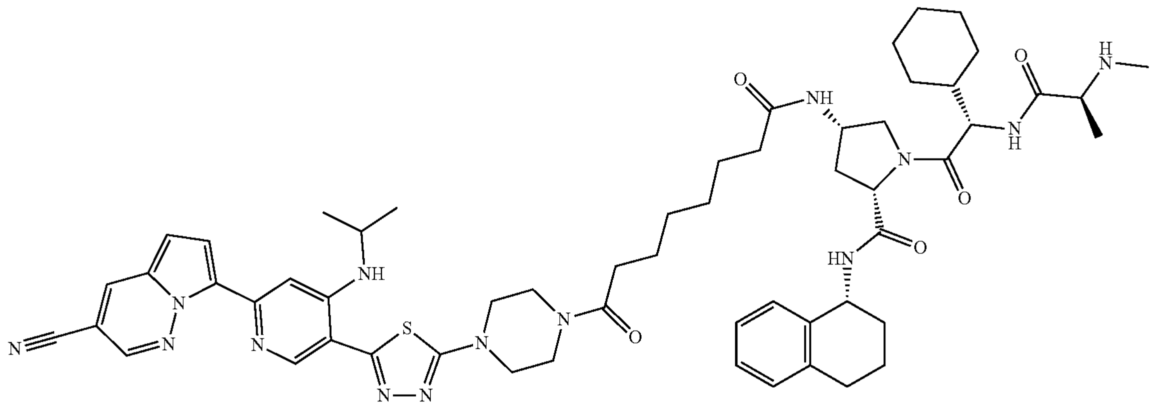 [SMILES: CN[C@@H](C)C(=O)N[C@H](C(=O)N1C[C@@H](NC(=O)CCCCCCC(=O)N2CCN(c3nnc(-c4cnc(-c5ccc6cc(C#N)cnn56)cc4NC(C)C)s3)CC2)C[C@H]1C(=O)N[C@@H]1CCCc2ccccc21)C1CCCCC1]

(2S,4S)-4-(8-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-8-oxooctanamido)-1-((S)-2-cyclohexyl-2-((S)-2-(methylamino)propanamido)acetyl)-N—((R)-1,2,3,4-tetrahydronaphthalen-1-yl)pyrrolidine-2-carboxamide The title compound was synthesized from BB4 and 8-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-8-oxooctanoic acid (synthesis of related intermediates are described in patent WO2016169989) by amide coupling using General Method D. LCMS: $C_{57}H_{74}N_{14}O_5S$ requires: 1066.6. found: m/z=1068.0 $[M+H]^+$; $^1H$ NMR (500 MHz, DMSO-$d_6$) δ 9.27 (s, 1H), 8.95 (d, J=2.2 Hz, 1H), 8.84-8.75 (m, 3H), 8.57 (s, 1H), 8.42 (dd, J=8.7, 5.3 Hz, 1H), 8.14 (t, J=6.6 Hz, 1H), 8.08 (s, 1H), 8.01 (d, J=4.9 Hz, 1H), 7.30 (d, J=7.5 Hz, 1H), 7.21 (d, J=4.9 Hz, 1H), 7.16 (dd, J=8.6, 6.2 Hz, 1H), 7.12 (q, J=8.8, 7.3 Hz, 2H), 4.95 (q, J=7.1 Hz, 1H), 4.40 (t, J=8.1 Hz, 1H), 4.30 (td, J=8.2, 3.7 Hz, 2H), 4.17-4.08 (m, 2H), 3.86 (q, J=6.6 Hz, 1H), 3.75-3.65 (m, 2H), 3.65 (dd, J=8.9, 3.7 Hz, 3H), 3.32 (q, J=8.0, 7.6 Hz, 1H), 2.74 (s, 3H), 2.38 (t, J=7.4 Hz, 3H), 2.07 (q, J=7.5 Hz, 2H), 1.92 (d, J=13.2 Hz, 1H), 1.87 (d, J=7.4 Hz, 2H), 1.82-1.59 (m, 3H), 1.51 (p, J=7.1 Hz, 4H), 1.40-1.24 (m, 11H), 1.16 (p, J=12.4 Hz, 2H).

Example 53

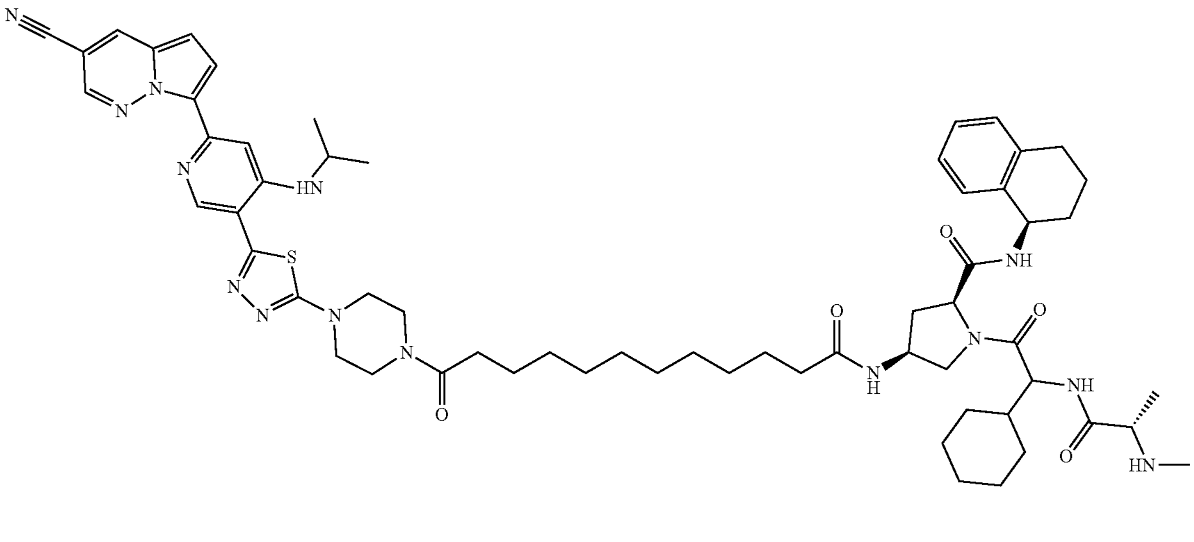 [SMILES: CN[C@@H](C)C(=O)NC(C(=O)N1C[C@@H](NC(=O)CCCCCCCCCCC(=O)N2CCN(c3nnc(-c4cnc(-c5ccc6cc(C#N)cnn56)cc4NC(C)C)s3)CC2)C[C@H]1C(=O)N[C@@H]1CCCc2ccccc21)C1CCCCC1]

(2S,4S)-4-(12-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-12-oxododecanamido)-1-((S)-2-cyclohexyl-2-((S)-2-(methylamino)propanamido)acetyl)-N—((R)-1,2,3,4-tetrahydronaphthalen-1-yl)pyrrolidine-2-carboxamide The title compound was synthesized from BB4 and 12-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-12-oxododecanoic acid by amide coupling using General Method D. LCMS: $C_{61}H_{82}N_{14}O_5S$ requires: 1122.6. found: m/z=1124.2 $[M+H]^+$; $^1H$ NMR (500 MHz, DMSO-$d_6$) δ 9.25 (s, 1H), 8.95 (d, J=2.2 Hz, 1H), 8.82 (d, J=2.2 Hz, 1H), 8.78 (d, J=9.2 Hz, 2H), 8.56 (s, 1H), 8.42 (d, J=8.7 Hz, 1H), 8.14 (d, J=7.6 Hz, 1H), 8.08 (s, 1H), 8.01 (d, J=4.8 Hz, 1H), 7.30 (d, J=7.6 Hz, 1H), 7.21 (d, J=4.9 Hz, 1H), 7.16 (t, J=7.4 Hz, 1H), 7.10 (t, J=7.6 Hz, 2H), 4.95 (s, 1H), 4.40 (t, J=8.2 Hz, 1H), 4.29 (dt, J=11.8, 7.6 Hz, 2H), 4.14-4.07 (m, 2H), 3.86 (q, J=6.4 Hz, 1H), 3.66 (dt, J=11.6, 6.5 Hz, 6H), 3.31 (q, J=8.2, 7.6 Hz, 1H), 2.74 (s, 3H), 2.38 (q, J=7.6 Hz, 3H), 2.05 (q, J=7.5 Hz, 2H), 1.92 (d, J=12.5 Hz, 1H), 1.89-1.83 (m, 2H), 1.82-1.76 (m, 1H), 1.76-1.59 (m, 7H), 1.51 (q, J=7.2 Hz, 5H), 1.38 (s, 3H), 1.39-1.24 (m, 20H), 1.16 (tt, J=22.8, 10.1 Hz, 3H), 1.03 (s, 3H).

Example 54

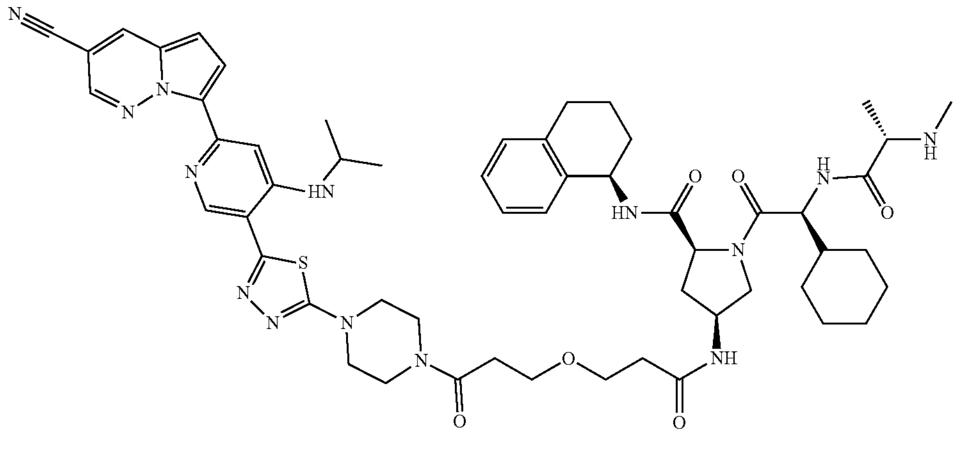 [SMILES: CN[C@@H](C)C(=O)N[C@H](C(=O)N1C[C@@H](NC(=O)CCOCCC(=O)N2CCN(c3nnc(-c4cnc(-c5ccc6cc(C#N)cnn56)cc4NC(C)C)s3)CC2)C[C@H]1C(=O)N[C@@H]1CCCc2ccccc21)C1CCCCC1]

(2S,4S)-4-(3-(3-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-3-oxopropoxy)propanamido)-1-((S)-2-cyclohexyl-2-((S)-2-(methylamino)propanamido)acetyl)-N—((R)-1,2,3,4-tetrahydronaphthalen-1-yl)pyrrolidine-2-carboxamide The title compound was synthesized from BB4 and 3-(3-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-3-oxopropoxy)propanoic acid by amide coupling using General Method D. LCMS: $C_{55}H_{70}N_{14}O_6S$ requires: 1054.5. found: m/z=1056.0 $[M+H]^+$; $^1H$ NMR (500 MHz, DMSO-$d_6$) δ 8.93 (s, 1H), 8.82-8.76 (m, 4H), 8.55 (s, 1H), 8.39 (d, J=8.7 Hz, 1H), 8.19 (d, J=7.5 Hz, 1H), 8.11 (s, 1H), 7.97 (s, 1H), 7.31 (d, J=7.5 Hz, 1H), 7.20 (d, J=4.9 Hz, 1H), 7.18-7.06 (m, 3H), 6.55 (s, 1H), 4.95 (s, 1H), 4.40 (t, J=8.2 Hz, 1H), 4.33-4.21 (m, 2H), 4.16 (s, 1H), 4.08 (s, 1H), 3.86 (q, J=6.7 Hz, 1H), 3.74-3.58 (m, 3H), 3.31 (t, J=9.1 Hz, 1H), 2.66 (d, J=6.6 Hz, 1H), 2.33 (t, J=6.4 Hz, 1H), 1.93 (d, J=11.2 Hz, 1H), 1.86 (d, J=5.3 Hz, 1H), 1.74 (dd, J=23.2, 13.8 Hz, 5H), 1.62 (d, J=9.4 Hz, 1H), 1.35 (dd, J=18.9, 6.6 Hz, 8H), 1.16 (dt, J=24.0, 12.2 Hz, 2H), 1.07-0.99 (m, 2H).

Example 55

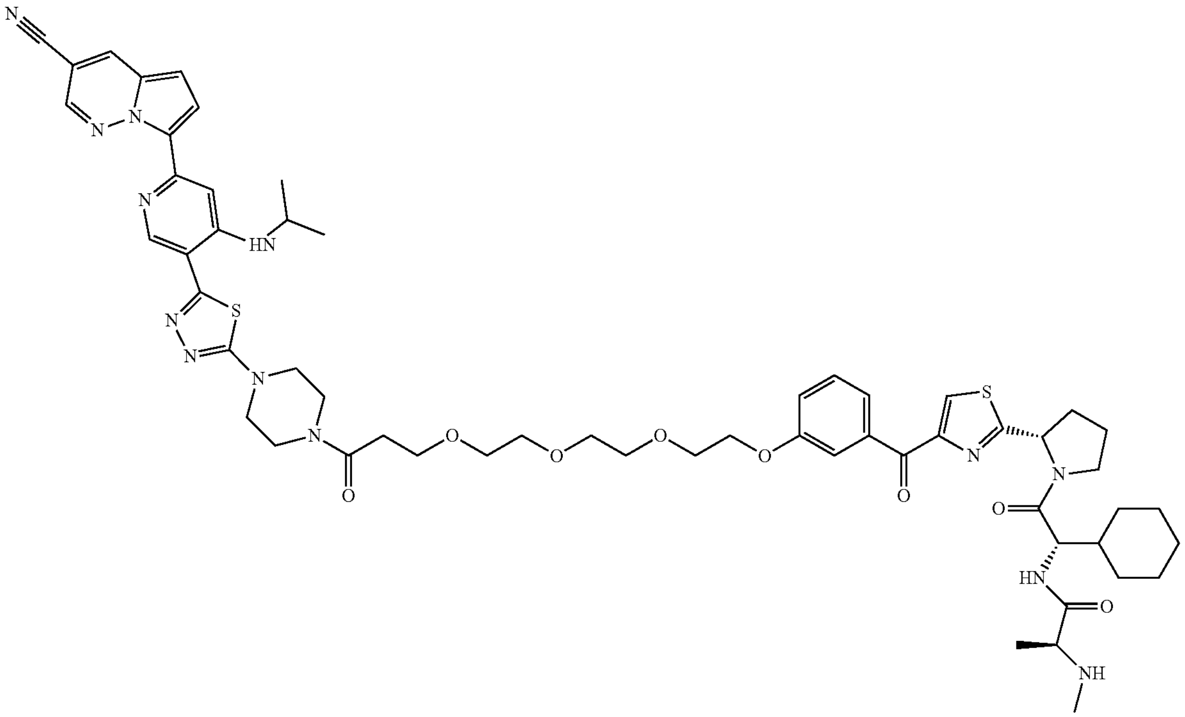 [SMILES: CN[C@@H](C)C(=O)N[C@H](C(=O)N1CCC[C@H]1c1nc(C(=O)c2cccc(OCCOCCOCCOCCC(=O)N3CCN(c4nnc(-c5cnc(-c6ccc7cc(C#N)cnn67)cc5NC(C)C)s4)CC3)c2)cs1)C1CCCCC1]

(S)—N—((S)-2-((S)-2-(4-(3-(2-(2-(2-(3-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-3-oxopropoxy)ethoxy)ethoxy)ethoxy)benzoyl)thiazol-2-yl)pyrrolidin-1-yl)-1-cyclohexyl-2-oxoethyl)-2-(methylamino)propanamide The title compound was synthesized from BB4 and 3-(2-(2-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)ethoxy)ethoxy) propanoic acid (*J. Biol. Chem,* 2017, 292: 4556-4570) by amide coupling using General Method D. LCMS: $C_{57}H_{71}N_{13}O_8S_2$ requires: 1129.5. found: m/z=1053.0 $[M+Na]^+$; $^1H$ NMR (500 MHz, DMSO-$d_6$) δ 8.79 (s, 2H), 8.76-8.70 (m, 1H), 8.54-8.47 (m, 1H), 7.68 (d, J=7.7 Hz, 1H), 7.65 (dd, J=11.5, 9.0 Hz, 1H), 7.47 (q, J=9.1, 8.6 Hz, 1H), 7.30-7.23 (m, 1H), 6.53 (s, 2H), 5.41 (dd, J=7.4, 3.7 Hz, 1H), 4.49 (s, 1H), 4.17 (s, 2H), 4.01 (s, 2H), 3.81-3.75 (m, 1H), 3.78 (s, 2H), 3.66 (t, J=6.3 Hz, 3H), 3.65-3.58 (m, 4H), 3.61-3.52 (m, 5H), 3.50 (d, J=4.9 Hz, 1H), 3.33-3.20 (m, 2H), 2.55 (s, 1H), 2.24 (s, 3H), 2.06 (d, J=15.4 Hz, 2H), 1.69 (s, 3H), 1.65 (s, 2H), 1.57 (s, 2H), 1.40-1.32 (m, 5H), 1.13 (d, J=7.0 Hz, 1H), 1.08 (dd, J=8.4, 5.8 Hz, 2H), 0.99 (t, J=7.1 Hz, 1H).

Example 56

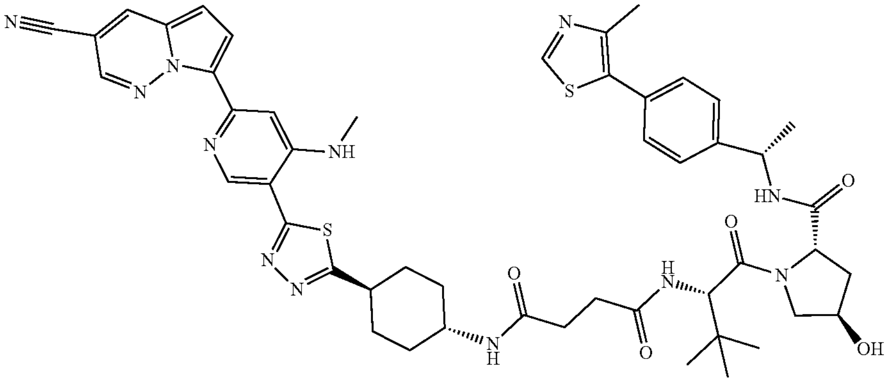 [SMILES: CNc1cc(-c2ccc3cc(C#N)cnn23)ncc1-c1nnc([C@H]2CC[C@H](NC(=O)CCC(=O)N[C@H](C(=O)N3C[C@H](O)C[C@H]3C(=O)N[C@@H](C)c3ccc(-c4scnc4C)cc3)C(C)(C)C)CC2)s1]

$N_1$-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-$N_4$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)succinamide The title compound was synthesized from BB3 and 4-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-4-oxobutanoic acid by amide coupling using General Method A. LCMS: $C_{49}H_{56}N_{12}O_5S_2$ requires: 956.4. found: m/z=958.0 $[M+H]^+$.

Example 57

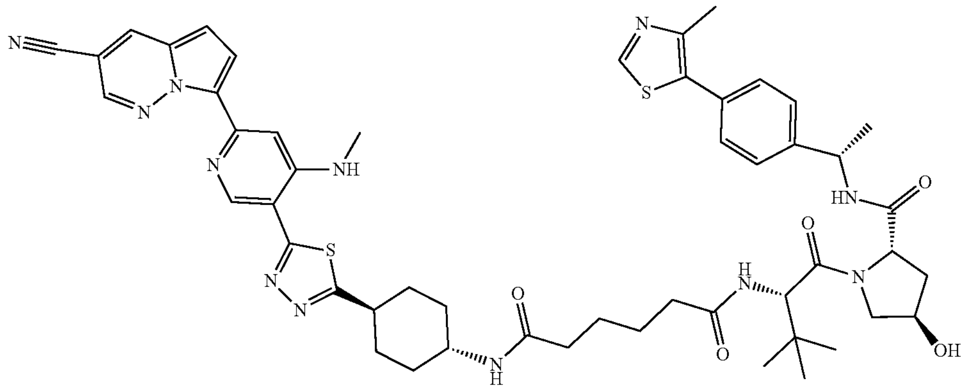 [SMILES: CNc1cc(-c2ccc3cc(C#N)cnn23)ncc1-c1nnc([C@H]2CC[C@H](NC(=O)CCCCC(=O)N[C@H](C(=O)N3C[C@H](O)C[C@H]3C(=O)N[C@@H](C)c3ccc(-c4scnc4C)cc3)C(C)(C)C)CC2)s1]

$N_1$-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-$N_6$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)adipamide The title compound was synthesized from BB3 and 6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexanoic acid by amide coupling using General Method A. LCMS: $C_{51}H_{60}N_{12}O_5S_2$ requires: 984.4. found: m/z=985.9 $[M+H]^+$.

Example 58

(2S,4R)—N-(2-(2-(3-(((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)amino)-3-oxopropoxy)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB3 and 3-(2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)

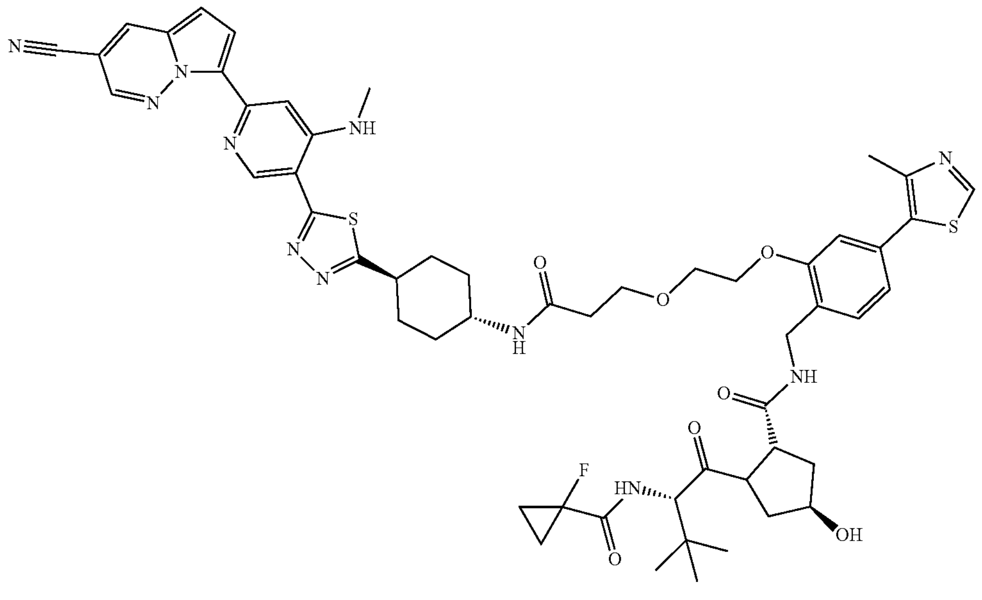

ethoxy)propanoic acid by amide coupling using General Method A. LCMS: $C_{53}H_{61}FN_{12}O_7S_2$ requires: 1060.4. found: m/z=1062.0 $[M+H]^+$.

Example 59

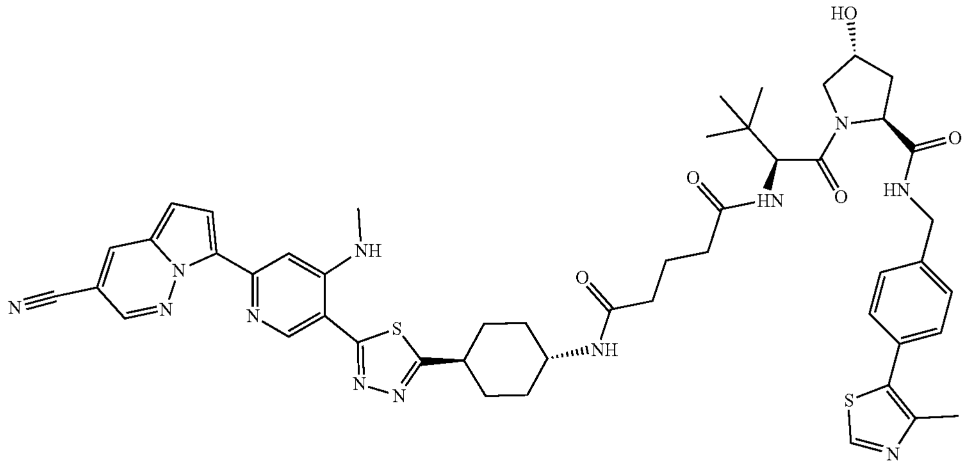 [SMILES: CNc1cc(-c2ccc3cc(C#N)cnn23)ncc1-c1nnc([C@H]2CC[C@H](NC(=O)CCCC(=O)N[C@H](C(=O)N3C[C@H](O)C[C@H]3C(=O)NCc3ccc(-c4scnc4C)cc3)C(C)(C)C)CC2)s1]

N1-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide The title compound was synthesized from BB3 and 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid by amide coupling using General Method A. LCMS: $C_{49}H_{56}N_{12}O_5S_2$ requires: 956.4. found: m/z=957.9 $[M+H]^+$; $^1H$ NMR (500 MHz, DMSO-$d_6$) δ 9.00 (s, 1H), 8.57 (t, J=5.8 Hz, 1H), 8.05 (s, 1H), 7.89 (dt, J=13.0, 8.1 Hz, 1H), 7.41 (ddt, J=8.7, 6.2, 3.8 Hz, 4H), 6.51 (s, 2H), 4.59-4.49 (m, 1H), 4.51-4.40 (m, 2H), 4.37 (d, J=8.0 Hz, 1H), 4.23 (dd, J=15.8, 5.4 Hz, 1H), 3.94 (s, OH), 3.72-3.62 (m, 2H), 3.20 (d, J=4.8 Hz, 1H), 2.45 (s, 3H), 2.32-2.23 (m, 1H), 2.19 (ddd, J=17.6, 14.8, 7.8 Hz, 2H), 1.91 (dq, J=12.8, 4.7 Hz, 1H), 1.78-1.66 (m, 3H), 1.39 (d, J=12.2 Hz, 0H), 1.28 (d, J=6.8 Hz, 3H), 1.13 (d, J=6.6 Hz, 2H), 0.99-0.90 (m, 10H).

Example 60

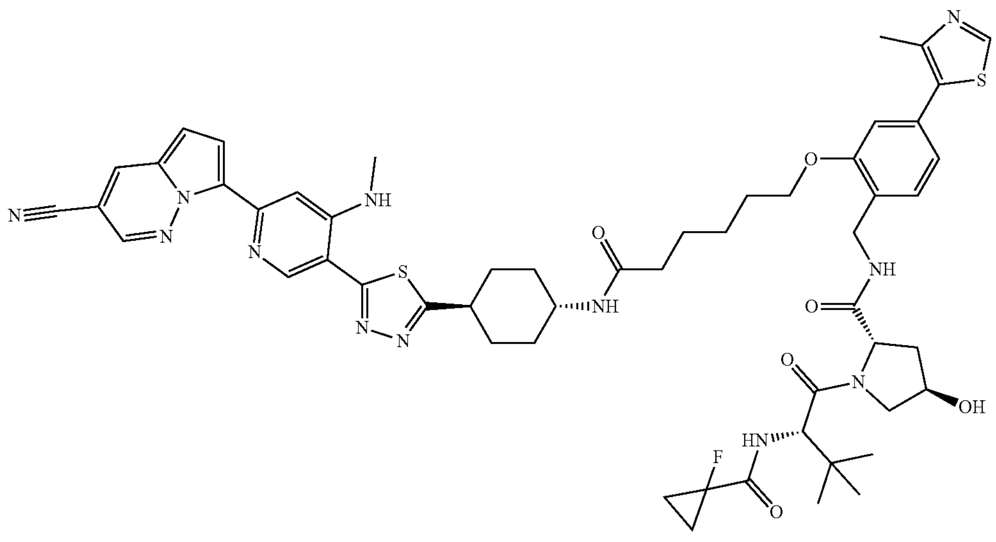 [SMILES: CNc1cc(-c2ccc3cc(C#N)cnn23)ncc1-c1nnc([C@H]2CC[C@H](NC(=O)CCCCCOc3cc(-c4scnc4C)ccc3CNC(=O)[C@@H]3C[C@@H](O)CN3C(=O)[C@@H](NC(=O)C3(F)CC3)C(C)(C)C)CC2)s1]

(2S,4R)—N-(2-((6-(((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)amino)-6-oxo-hexyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB3 and 6-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)hexanoic acid by amide coupling using General Method A. LCMS: $C_{54}H_{63}FN_{12}O_6S_2$ requires: 1058.4. found: m/z=1059.9 $[M+H]^+$; $^1H$ NMR (500 MHz, DMSO-$d_6$) δ 9.00 (d, J=2.4

Hz, 2H), 8.94 (s, 1H), 8.82 (s, 1H), 8.73 (s, 1H), 8.55-8.48 (m, 2H), 8.11 (s, 1H), 8.00 (s, 1H), 7.79 (d, J=7.6 Hz, 1H), 7.42 (t, J=7.0 Hz, 2H), 7.30 (d, J=9.1 Hz, 2H), 7.20 (d, J=4.9 Hz, 1H), 7.00 (d, J=9.9 Hz, 3H), 6.96 (d, J=7.9 Hz, 2H), 6.53 (s, 5H), 4.61 (d, J=9.2 Hz, 2H), 4.53 (t, J=7.7 Hz, 2H), 4.36 (s, 2H), 4.30 (dd, J=15.9, 8.6 Hz, 2H), 4.21 (dd, J=16.6, 6.0 Hz, 2H), 4.05 (d, J=5.5 Hz, 5H), 3.64 (q, J=11.6, 11.0 Hz, 7H), 3.23 (s, 1H), 3.17 (d, J=4.8 Hz, 3H), 2.95 (s, 0H), 2.47 (d, J=3.3 Hz, 7H), 2.26 (t, J=7.1 Hz, 2H), 2.19 (d, J=14.5 Hz, 3H), 2.10 (t, J=9.3 Hz, 4H), 1.93 (d, J=11.3 Hz, 4H), 1.77 (s, 5H), 1.71-1.56 (m, 2H), 1.59 (s, 3H), 1.49 (dd, J=16.2, 8.2 Hz, 4H), 1.39 (s, 7H), 1.36 (d, J=9.1 Hz, 2H), 1.32 (s, 1H), 1.23 (d, J=9.1 Hz, 5H), 1.19 (d, J=6.7 Hz, 1H), 0.99 (s, 1H), 0.97 (s, 16H).

Example 61

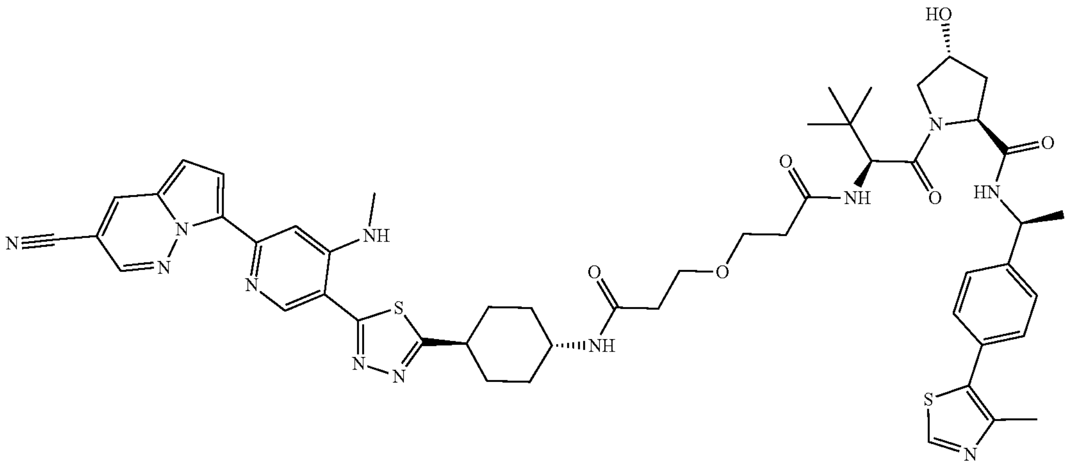 [SMILES: CNc1cc(-c2ccc3cc(C#N)cnn23)ncc1-c1nnc([C@H]2CC[C@H](NC(=O)CCOCCC(=O)N[C@H](C(=O)N3C[C@H](O)C[C@H]3C(=O)N[C@@H](C)c3ccc(-c4scnc4C)cc3)C(C)(C)C)CC2)s1]

(2S,4R)-1-((S)-2-(3-(3-(((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)amino)-3-oxopropoxy)propanamido)-3,3-dimethylbutanoyl)-4-hydroxy-N—((S)-1-(4-(4-methylthiazol-5-yl)phenyl)ethyl)pyrrolidine-2-carboxamide The title compound was synthesized from BB3 and 3-(3-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropoxy)propanoic acid by amide coupling using General Method A. LCMS: $C_{51}H_{60}N_{12}O_6S_2$ requires: 1000.4. found: m/z=1002.0 $[M+H]^+$.

Example 62

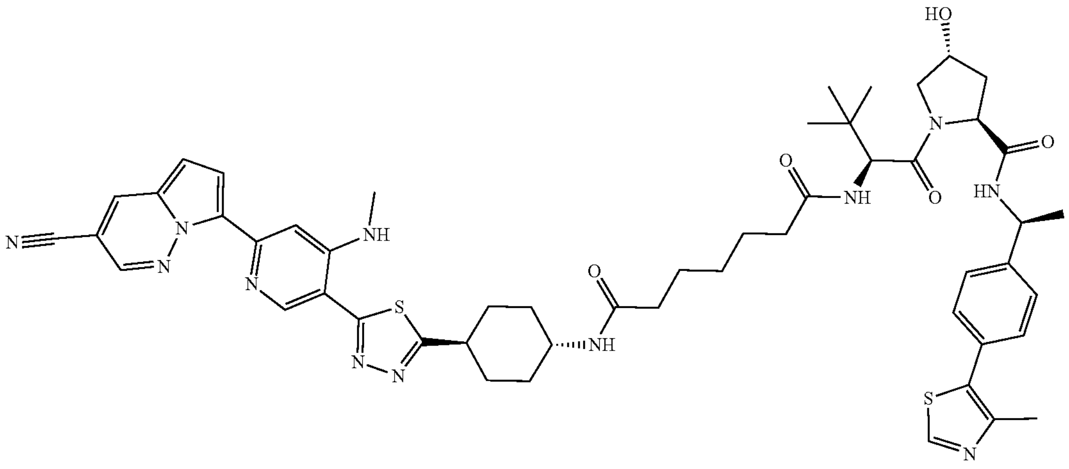 [SMILES: CNc1cc(-c2ccc3cc(C#N)cnn23)ncc1-c1nnc([C@H]2CC[C@H](NC(=O)CCCCCC(=O)N[C@H](C(=O)N3C[C@H](O)C[C@H]3C(=O)N[C@@H](C)c3ccc(-c4scnc4C)cc3)C(C)(C)C)CC2)s1]

N$_1$-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-N$_7$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)heptanediamide The title compound was synthesized from BB3 and 7-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-7-oxoheptanoic acid by amide coupling using General Method A. LCMS: $C_{52}H_{62}N_{12}O_5S_2$ requires: 998.4. found: m/z=1000.1 $[M+H]^+$; $^1H$ NMR (500 MHz, DMSO-$d_6$) δ 8.98 (d, J=17.4 Hz, 2H), 8.84 (d, J=2.2 Hz, 1H), 8.73 (s, 1H), 8.38 (d, J=7.8 Hz, 1H), 8.05 (d, J=14.4 Hz, 2H), 7.80 (d, J=9.3 Hz, 1H), 7.76 (d, J=7.6 Hz, 1H), 7.45 (d, J=8.1 Hz, 2H), 7.39 (d, J=8.1 Hz, 2H), 7.22 (d, J=5.0 Hz, 1H), 4.92 (q, J=7.0 Hz, 1H), 4.53 (d, J=9.3 Hz, 1H), 4.43 (t, J=8.0 Hz, 1H), 4.29 (s, 1H), 3.62 (q, J=7.8 Hz, 3H), 3.25 (t, J=12.2 Hz, 1H), 3.19 (d, J=4.8 Hz, 3H), 2.47 (s, 3H), 2.26 (dt, J=15.1, 7.6 Hz, 1H), 2.21 (s, 1H), 2.19 (s, 1H), 2.13 (dt, J=14.0, 7.3 Hz, 1H), 2.05 (t, J=7.4 Hz, 3H), 1.93 (d, J=12.3 Hz, 2H), 1.84-1.76 (m, 1H), 1.74-1.63 (m, 2H), 1.51 (d, J=8.1 Hz, 1H), 1.49 (s, 4H), 1.39 (d, J=7.2 Hz, 5H), 1.24 (q, J=8.0 Hz, 3H), 1.12 (dd, J=11.5, 6.7 Hz, 1H), 1.09-0.99 (m, 1H), 0.95 (s, 8H), 0.94 (d, J=3.4 Hz, 2H).

Example 63

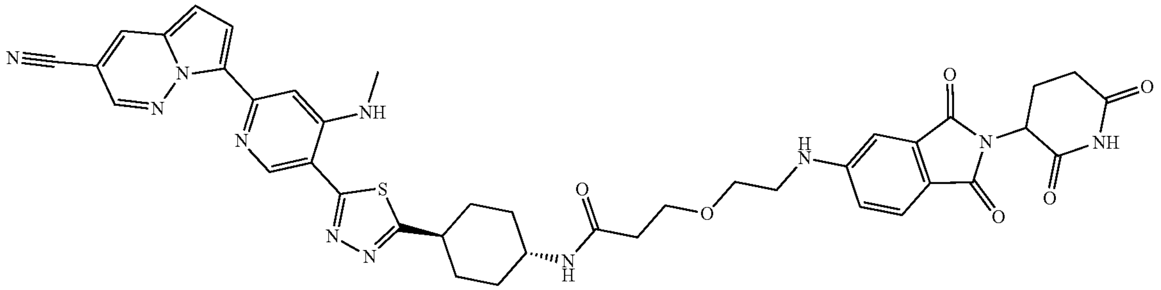 [SMILES: CNc1cc(-c2ccc3cc(C#N)cnn23)ncc1-c1nnc([C@H]2CC[C@H](NC(=O)CCOCCNc3ccc4c(c3)C(=O)N(C3CCC(=O)NC3=O)C4=O)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-3-(2-((2-(2,6-dioxopiperidin-3-yl)-1,3-dioxoisoindolin-5-yl)amino)ethoxy)propanamide The title compound was synthesized from BB3 and 3-(2-((2-(2,6-dioxopiperidin-3-yl)-1,3-dioxoisoindolin-5-yl)amino)ethoxy)propanoic acid by amide coupling using General Method A. LCMS: $C_{40}H_{39}N_{11}O_6S$ requires: 801.3. found: m/z=803.0 $[M+H]^+$; $^1H$ NMR (500 MHz, DMSO-$d_6$) δ 11.06 (s, 1H), 9.31 (s, 1H), 8.97 (d, J=2.2 Hz, 1H), 8.85 (d, J=2.2 Hz, 1H), 8.73 (s, 1H), 8.05 (d, J=5.7 Hz, 2H), 7.82 (dd, J=25.0, 7.7 Hz, 1H), 7.58 (d, J=8.3 Hz, 1H), 7.23 (d, J=4.9 Hz, 1H), 7.14 (s, 1H), 7.02 (d, J=2.2 Hz, 1H), 6.91 (dd, J=8.4, 2.2 Hz, 1H), 5.04 (dd, J=12.9, 5.4 Hz, 1H), 3.67 (q, J=6.2 Hz, 2H), 3.65-3.56 (m, 2H), 3.27-3.16 (m, 4H), 2.88 (ddd, J=17.2, 14.1, 5.8 Hz, 1H), 2.61-2.53 (m, 1H), 2.49 (s, 3H), 2.35 (t, J=6.4 Hz, 2H), 2.17 (d, J=13.0 Hz, 2H), 2.02-1.96 (m, 1H), 1.91 (d, J=12.6 Hz, 2H), 1.69 (d, J=12.1 Hz, 1H), 1.67-1.61 (m, 1H), 1.36 (q, J=12.5 Hz, 2H).

Example 64

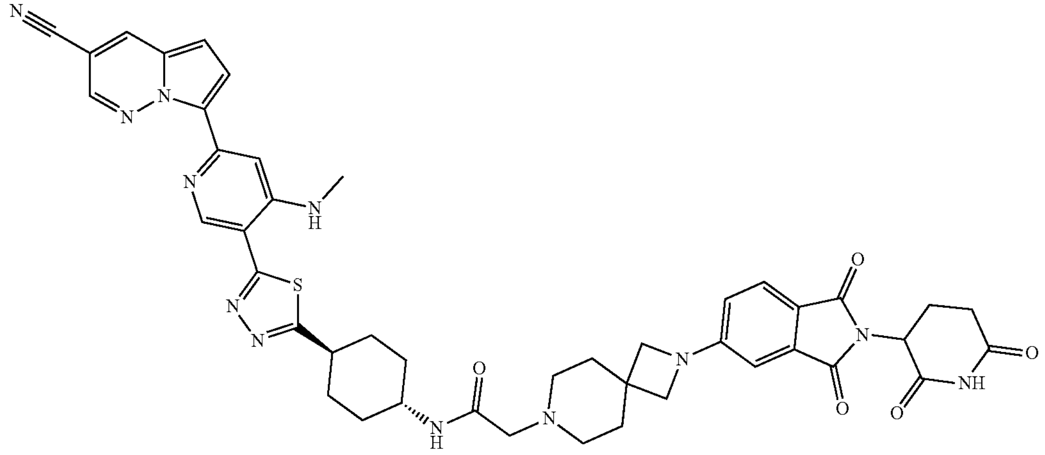 [SMILES: CNc1cc(-c2ccc3cc(C#N)cnn23)ncc1-c1nnc([C@H]2CC[C@H](NC(=O)CN3CCC4(CC3)CN(c3ccc5c(c3)C(=O)N(C3CCC(=O)NC3=O)C5=O)C4)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-2-(2-(2-(2,6-dioxopiperidin-3-yl)-1,3-dioxoisoindolin-5-yl)-2,7-diazaspiro[3.5]nonan-7-yl)acetamide The title compound was synthesized from BB3 and 2-(2-(2-(2,6-dioxopiperidin-3-yl)-1,3-dioxoisoindolin-5-yl)-2,7-diazaspiro[3.5]nonan-7-yl)acetic acid by amide coupling using General Method A. LCMS: $C_{44}H_{44}N_{12}O_5S$ requires: 852.3. found: m/z=854.1 $[M+H]^+$; $^1H$ NMR (500 MHz, DMSO-$d_6$) δ 11.09 (s, 1H), 9.73 (s, 1H), 9.09 (s, 2H), 8.95 (d, J=2.2 Hz, 1H), 8.83 (d, J=2.2 Hz, 1H), 8.74 (s, 1H), 8.60 (d, J=7.6 Hz, 1H), 8.12 (s, 1H), 8.01 (d, J=4.7 Hz, 1H), 7.70 (d, J=8.2 Hz, 1H), 7.21 (d, J=4.9 Hz, 1H), 6.79 (s, 1H), 6.67 (d, J=8.3 Hz, 1H), 5.07 (dd, J=12.8, 5.6 Hz, 1H), 3.92 (d, J=10.5 Hz, 3H), 3.83 (s, 2H), 3.76 (s, 2H), 3.45 (d, J=11.6 Hz, 3H), 3.18 (d, J=4.9 Hz, 3H), 3.11 (s, 2H), 2.94-2.85 (m, 1H), 2.62 (s, 1H), 2.57 (d, J=12.3 Hz, 3H), 2.23 (d, J=12.5 Hz, 2H), 2.13 (d, J=13.5 Hz, 1H), 2.02 (s, 7H), 1.74 (q, J=12.4, 11.9 Hz, 3H), 1.53-1.42 (m, 2H).

Example 65

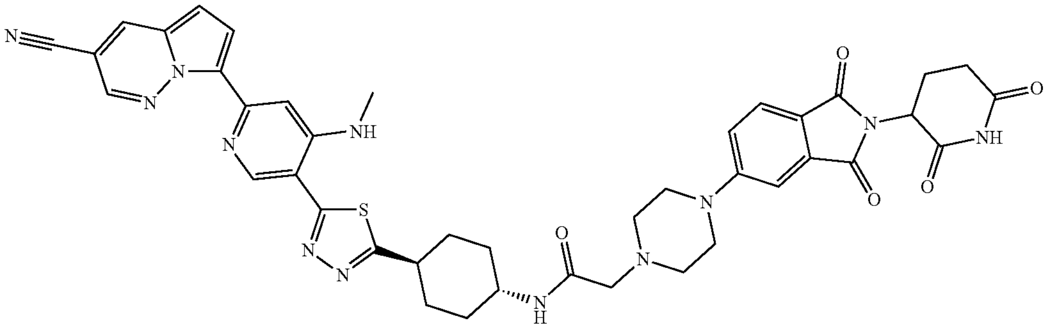 [SMILES: CNc1cc(-c2ccc3cc(C#N)cnn23)ncc1-c1nnc([C@H]2CC[C@H](NC(=O)CN3CCN(c4ccc5c(c4)C(=O)N(C4CCC(=O)NC4=O)C5=O)CC3)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-2-(4-(2-(2,6-dioxopiperidin-3-yl)-1,3-dioxoisoindolin-5-yl)piperazin-1-yl)acetamide The title compound was synthesized from BB3 and 3-(4-(2-(2,6-dioxopiperidin-3-yl)-1,3-dioxoisoindolin-5-yl)piperazin-1-yl)propanoic acid by amide coupling using General Method A. LCMS: $C_{41}H_{40}N_{12}O_5S$ requires: 812.3. found: m/z=813.9 $[M+H]^+$; $^1H$ NMR (500 MHz, DMSO) δ 11.11 (s, 1H), 10.27 (s, 1H), 9.09 (s, 2H), 8.94 (d, J=2.2 Hz, 1H), 8.82 (d, J=2.3 Hz, 1H), 8.73 (s, 1H), 8.60 (s, 1H), 8.11 (s, 1H), 8.00 (d, J=4.7 Hz, 1H), 7.76 (dd, J=23.6, 8.4 Hz, 1H), 7.48 (d, J=2.3 Hz, 1H), 7.35 (dd, J=8.7, 2.4 Hz, 1H), 7.21 (d, J=5.0 Hz, 1H), 5.11 (dd, J=12.8, 5.4 Hz, 1H), 4.19 (s, 9H), 3.99 (s, 3H), 3.76 (s, 2H), 3.55 (s, 1H), 3.40 (s, 1H), 3.34-3.26 (m, 2H), 3.18 (d, J=4.9 Hz, 4H), 2.96-2.85 (m, 1H), 2.65-2.53 (m, 2H), 2.49 (s, 1H), 2.23 (d, J=12.8 Hz, 3H), 2.04-1.97 (m, 3H), 1.80-1.69 (m, 2H), 1.49 (d, J=11.7 Hz, 1H), 1.47-1.42 (m, 1H), 1.24 (d, J=3.1 Hz, 1H).

Example 66

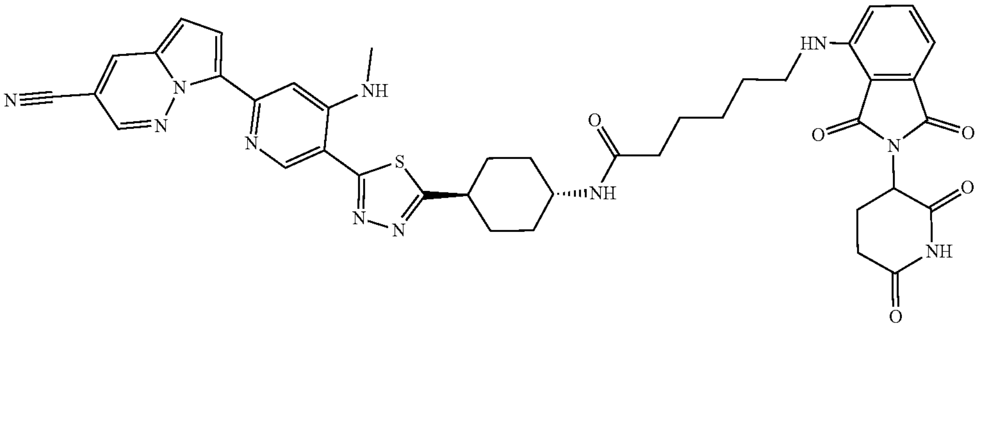 [SMILES: CNc1cc(-c2ccc3cc(C#N)cnn23)ncc1-c1nnc([C@H]2CC[C@H](NC(=O)CCCCCNc3cccc4c3C(=O)N(C3CCC(=O)NC3=O)C4=O)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-6-((2-(2,6-dioxopiperidin-3-yl)-1,3-dioxoisoindolin-4-yl)amino)hexanamide The title compound was synthesized from BB3 and 6-((2-(2,6-dioxopiperidin-3-yl)-1,3-dioxoisoindolin-4-yl)amino) hexanoic acid by amide coupling using General Method A. LCMS: $C_{41}H_{41}N_{11}O_5S$ requires: 799.3. found: m/z=800.9 $[M+H]^+$; $^1H$ NMR (500 MHz, DMSO-$d_6$) δ 11.10 (s, 1H), 9.34 (s, 1H), 8.97 (d, J=2.2 Hz, 1H), 8.85 (d, J=2.2 Hz, 1H), 8.74 (s, 1H), 8.08-8.02 (m, 2H), 7.77 (d, J=7.8 Hz, 1H), 7.60 (dd, J=8.6, 7.1 Hz, 1H), 7.23 (d, J=4.9 Hz, 1H), 7.11 (d, J=8.6 Hz, 1H), 7.04 (d, J=7.0 Hz, 1H), 6.54 (s, 1H), 5.06 (dd, J=12.7, 5.4 Hz, 1H), 3.64 (dq, J=7.8, 4.0 Hz, 0H), 3.32 (t, J=6.3 Hz, 2H), 3.28-3.18 (m, 3H), 2.89 (ddd, J=16.9, 13.8, 5.4 Hz, 1H), 2.64-2.53 (m, 2H), 2.19 (d, J=12.4 Hz, 2H), 2.06 (dt, J=18.9, 6.1 Hz, 2H), 1.96-1.89 (m, 2H), 1.62 (ddq, J=52.5, 15.3, 8.9, 7.5 Hz, 5H), 1.42-1.37 (m, 1H), 1.37-1.31 (m, 3H).

Example 67

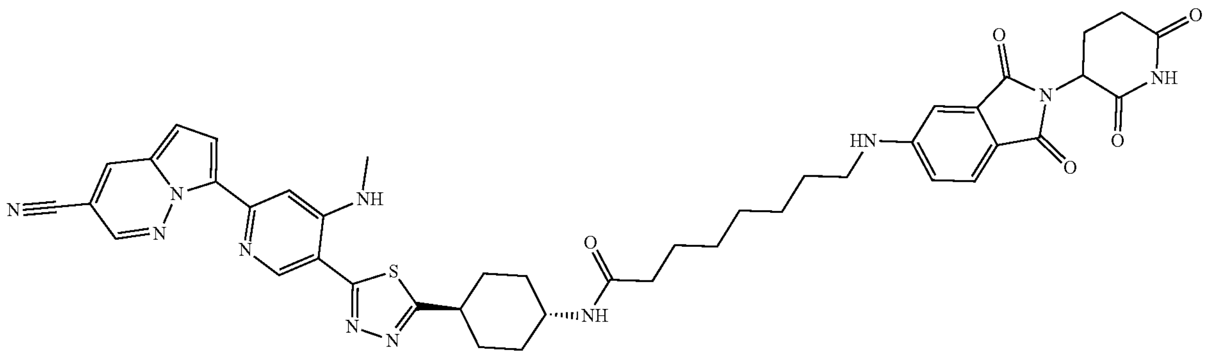 [SMILES: CNc1cc(-c2ccc3cc(C#N)cnn23)ncc1-c1nnc([C@H]2CC[C@H](NC(=O)CCCCCCCNc3ccc4c(c3)C(=O)N(C3CCC(=O)NC3=O)C4=O)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-8-((2-(2,6-dioxopiperidin-3-yl)-1,3-dioxoisoindolin-5-yl)amino)octanamide The title compound was synthesized from BB3 and 8-((2-(2,6-dioxopiperidin-3-yl)-1,3-dioxoisoindolin-4-yl)amino) octanoic acid by amide coupling using General Method A. LCMS: $C_{43}H_{45}N_{11}O_5S$ requires: 827.3. found: m/z=829.0 $[M+H]^+$; $^1H$ NMR (500 MHz, DMSO-$d_6$) δ 11.06 (s, 1H), 9.34 (s, 1H), 8.97 (d, J=2.3 Hz, 1H), 8.85 (d, J=2.2 Hz, 1H), 8.73 (s, 1H), 8.08-8.02 (m, 2H), 7.76 (d, J=7.7 Hz, 1H), 7.60-7.50 (m, 1H), 7.23 (d, J=5.0 Hz, 1H), 7.12 (s, 1H), 6.96 (d, J=2.1 Hz, 1H), 6.86 (dd, J=8.4, 2.1 Hz, 1H), 5.04 (dd, J=12.7, 5.4 Hz, 1H), 3.28-3.15 (m, 6H), 2.93-2.83 (m, 1H), 2.60 (s, 1H), 2.56 (d, J=4.7 Hz, 1H), 2.22-2.16 (m, 2H), 2.07 (t, J=7.3 Hz, 2H), 2.00 (d, J=12.2 Hz, 1H), 1.96-1.90 (m, 2H), 1.73-1.62 (m, 2H), 1.55 (dt, J=31.3, 7.3 Hz, 3H), 1.39 (d, J=4.0 Hz, 1H), 1.36 (s, 4H), 1.32-1.25 (m, 1H).

Example 68

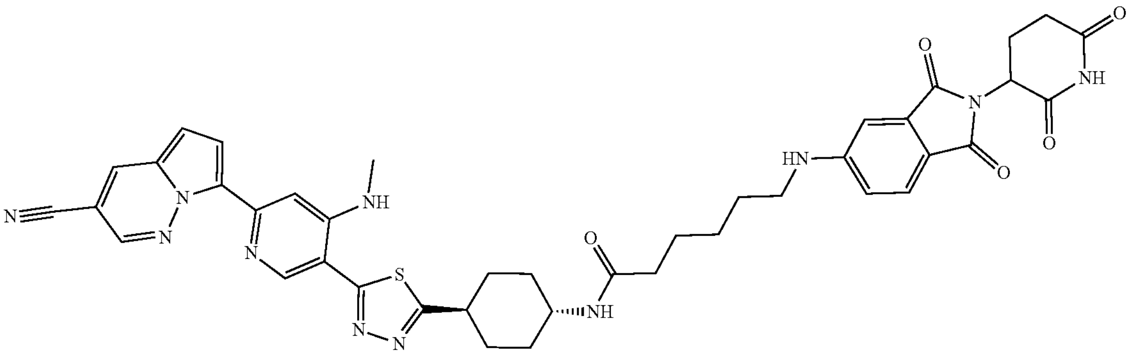 [SMILES: CNc1cc(-c2ccc3cc(C#N)cnn23)ncc1-c1nnc([C@H]2CC[C@H](NC(=O)CCCCCNc3ccc4c(c3)C(=O)N(C3CCC(=O)NC3=O)C4=O)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-6-((2-(2,6-dioxopiperidin-3-yl)-1,3-dioxoisoindolin-5-yl)amino)hexanamide The title compound was synthesized from BB3 and 6-((2-(2,6-dioxopiperidin-3-yl)-1,3-dioxoisoindolin-5-yl)amino) hexanoic acid by amide coupling using General Method A. LCMS: $C_{41}H_{41}N_{11}O_5S$ requires: 799.3. found: m/z=801.0 $[M+H]^+$; $^1H$ NMR (500 MHz, DMSO-$d_6$) δ 11.06 (s, 1H), 9.36 (s, 1H), 8.98 (d, J=2.2 Hz, 1H), 8.85 (d, J=2.2 Hz, 1H), 8.74 (s, 1H), 8.09-8.02 (m, 2H), 7.77 (d, J=7.8 Hz, 1H), 7.58 (d, J=8.4 Hz, 1H), 7.23 (d, J=5.0 Hz, 1H), 7.12 (s, 1H), 6.96 (d, J=2.2 Hz, 1H), 6.86 (dd, J=8.5, 2.2 Hz, 1H), 5.04 (dd, J=12.8, 5.6 Hz, 1H), 3.63 (dq, J=8.3, 4.3 Hz, 1H), 3.28-3.14 (m, 6H), 2.89 (ddd, J=14.2, 10.5, 7.1 Hz, 1H), 2.62-2.53 (m, 2H), 2.19 (d, J=12.5 Hz, 3H), 2.09 (t, J=7.3 Hz, 2H), 2.04-1.96 (m, 1H), 1.95-1.88 (m, 2H), 1.62 (dtd, J=53.0, 14.9, 14.1, 8.9 Hz, 7H), 1.36 (dt, J=14.9, 6.3 Hz, 4H).

Example 69

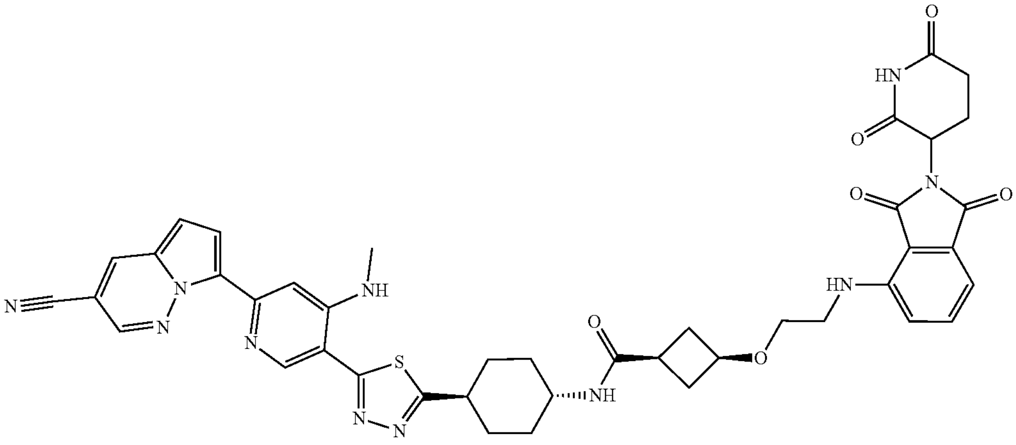 [SMILES: CNc1cc(-c2ccc3cc(C#N)cnn23)ncc1-c1nnc([C@H]2CC[C@H](NC(=O)[C@H]3C[C@@H](OCCNc4cccc5c4C(=O)N(C4CCC(=O)NC4=O)C5=O)C3)CC2)s1]

(1s,3S)—N-((1r,4R)-4-(5-(6-(3-cyanopyrrolo[1,2-b] pyridazin-7-yl)-4-(methylamino)pyridin-3-yl)-1,3,4-thiadiazol-2-yl)cyclohexyl)-3-(2-((2-(2,6-dioxopiperidin-3-yl)-1,3-dioxoisoindolin-4-yl)amino)ethoxy) cyclobutane-1-carboxamide The title compound was synthesized from BB3 and (1s, 3s)-3-(2-((2-(2,6-dioxopiperidin-3-yl)-1,3-dioxoisoindolin-4-yl)amino)ethoxy)cyclobutane-1-carboxylic acid by amide coupling using General Method A. LCMS: $C_{42}H_{41}N_{11}O_6S$ requires: 827.3. found: m/z=829.1 $[M+H]^+$; $^1H$ NMR (500 MHz, DMSO-$d_6$) δ 11.10 (s, 1H), 9.28 (s, 1H), 8.96 (d, J=2.3 Hz, 1H), 8.84 (d, J=2.2 Hz, 1H), 8.73 (s, 1H), 8.05 (d, J=5.6 Hz, 2H), 7.76 (d, J=7.7 Hz, 1H), 7.60 (dd, J=8.6, 7.1 Hz, 1H), 7.22 (d, J=4.9 Hz, 1H), 7.16 (d, J=8.6 Hz, 1H), 7.06 (d, J=7.0 Hz, 1H), 6.60 (d, J=6.0 Hz, 1H), 5.08 (dd, J=12.8, 5.4 Hz, 1H), 3.89 (p, J=7.6 Hz, 1H), 3.49 (dd, J=21.0, 5.2 Hz, 4H), 3.28-3.17 (m, 4H), 2.90 (ddd, J=16.4, 13.5, 5.3 Hz, 1H), 2.64-2.53 (m, 2H), 2.46 (d, J=8.8 Hz, 1H), 2.31 (q, J=8.4 Hz, 2H), 2.22-2.16 (m, 2H), 2.09-1.94 (m, 3H), 1.92 (dd, J=13.2, 3.6 Hz, 2H), 1.74-1.68 (m, 1H), 1.68-1.63 (m, 1H), 1.43-1.32 (m, 2H).

Example 70

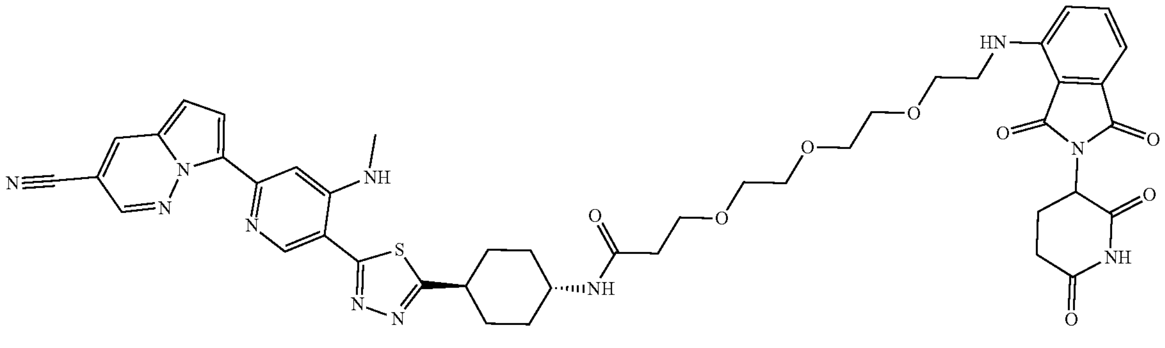 [SMILES: CNc1cc(-c2ccc3cc(C#N)cnn23)ncc1-c1nnc([C@H]2CC[C@H](NC(=O)CCOCCOCCOCCNc3cccc4c3C(=O)N(C3CCC(=O)NC3=O)C4=O)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-3-(2-(2-(2-((2-(2,6-dioxopiperidin-3-yl)-1,3-dioxoisoindolin-4-yl)amino)ethoxy)ethoxy)ethoxy)propenamide The title compound was synthesized from BB3 and 3-(2-(2-(2-((2-(2,6-dioxopiperidin-3-yl)-1,3-dioxoisoindolin-4-yl)amino)ethoxy)ethoxy)ethoxy)propanoic acid by amide coupling using General Method A. LCMS: $C_{44}H_{47}N_{11}O_8S$ requires: 889.3. found: m/z=891.0 $[M+H]^+$; $^1H$ NMR (500 MHz, DMSO-$d_6$) δ 11.10 (s, 1H), 9.34 (s, 1H), 8.97 (d, J=2.2 Hz, 1H), 8.85 (d, J=2.2 Hz, 1H), 8.73 (s, 1H), 8.08-8.02 (m, 2H), 7.82 (d, J=7.8 Hz, 1H), 7.59 (dd, J=8.6, 7.0 Hz, 1H), 7.23 (d, J=4.9 Hz, 1H), 7.16 (d, J=8.6 Hz, 1H), 7.05 (d, J=7.0 Hz, 1H), 6.62 (t, J=5.8 Hz, 1H), 5.07 (dd, J=12.8, 5.5 Hz, 1H), 3.67-3.52 (m, 7H), 3.55-3.45 (m, 5H), 3.29-3.22 (m, 1H), 3.20 (d, J=4.9 Hz, 3H), 2.90 (ddd, J=16.7, 13.7, 5.5 Hz, 1H), 2.62 (s, 1H), 2.57 (d, J=14.2 Hz, 1H), 2.31 (t, J=6.4 Hz, 2H), 2.22-2.15 (m, 2H), 2.04 (td, J=7.3, 6.7, 3.1 Hz, 1H), 1.97-1.90 (m, 2H), 1.73-1.67 (m, 1H), 1.67-1.62 (m, 1H), 1.38 (dt, J=13.4, 10.3 Hz, 2H).

Example 71

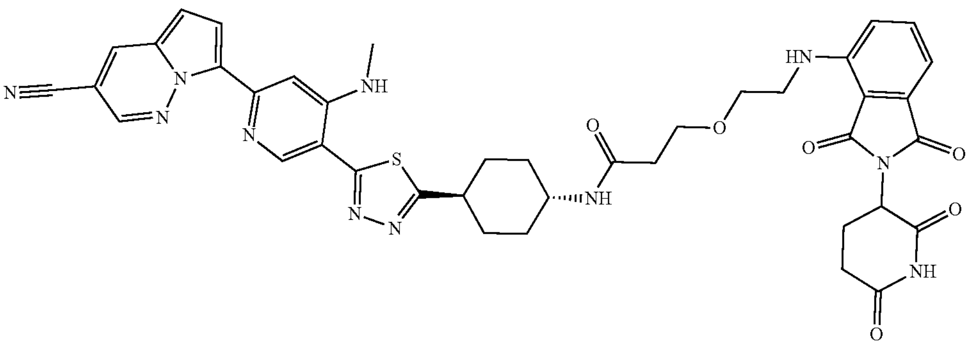 [SMILES: CNc1cc(-c2ccc3cc(C#N)cnn23)ncc1-c1nnc([C@H]2CC[C@H](NC(=O)CCOCCNc3cccc4c3C(=O)N(C3CCC(=O)NC3=O)C4=O)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-3-(2-((2-(2,6-dioxopiperidin-3-yl)-1,3-dioxoisoindolin-4-yl)amino)ethoxy)propanamide The title compound was synthesized from BB3 and 3-(2-((2-(2,6-dioxopiperidin-3-yl)-1,3-dioxoisoindolin-4-yl)amino)ethoxy)propanoic acid by amide coupling using General Method A. LCMS: $C_{40}H_{39}N_{11}O_6S$ requires: 801.3. found: m/z=802.9 $[M+H]^+$; $^1H$ NMR (500 MHz, DMSO-$d_6$) δ 11.11 (s, 1H), 9.28 (s, 1H), 8.96 (d, J=2.2 Hz, 1H), 8.84 (d, J=2.2 Hz, 1H), 8.73 (s, 1H), 8.05 (d, J=7.4 Hz, 2H), 7.83 (d, J=7.7 Hz, 1H), 7.61 (dd, J=8.6, 7.1 Hz, 1H), 7.22 (d, J=4.9 Hz, 1H), 7.16 (d, J=8.6 Hz, 1H), 7.07 (d, J=7.0 Hz, 1H), 6.58 (d, J=6.3 Hz, 1H), 5.07 (dd, J=12.8, 5.5 Hz, 1H), 3.71-3.61 (m, 2H), 3.61 (t, J=5.4 Hz, 2H), 3.48 (q, J=5.5 Hz, 2H), 3.26-3.18 (m, 4H), 2.95-2.86 (m, 1H), 2.62 (s, 1H), 2.57 (d, J=17.1 Hz, 2H), 2.49 (s, 3H), 2.34 (t, J=6.4 Hz, 2H), 2.17 (d, J=12.2 Hz, 2H), 2.08-2.01 (m, 1H), 1.93 (d, J=12.1 Hz, 2H), 1.72-1.67 (m, 1H), 1.67-1.61 (m, 1H), 1.36 (dt, J=13.3, 10.3 Hz, 2H).

Example 72

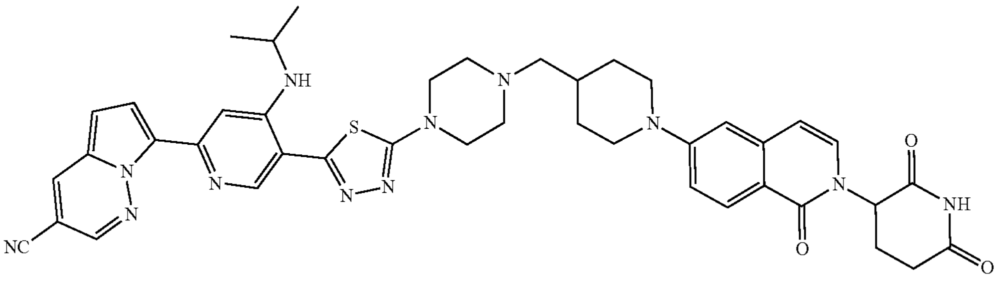 [SMILES: CC(C)Nc1cc(-c2ccc3cc(C#N)cnn23)ncc1-c1nnc(N2CCN(CC3CCN(c4ccc5c(=O)n(C6CCC(=O)NC6=O)ccc5c4)CC3)CC2)s1]

7-(5-(5-(4-((1-(2-(2,6-dioxopiperidin-3-yl)-1-oxo-1,2-dihydroisoquinolin-6-yl)piperidin-4-yl)methyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB4 and 1-(2-(2,6-dioxopiperidin-3-yl)-1-oxo-1,2-dihydroisoquinolin-6-yl)piperidine-4-carbaldehyde by reductive amination using General Method B. LCMS: $C_{42}H_{44}N_{12}O_3S$ requires: 797.0. found: m/z=798.0 $[M+H]^+$; $^1H$ NMR (500 MHz, Methanol-d4) δ 8.79 (d, J=2.1 Hz, 1H), 8.70 (s, 1H), 8.57 (s, 1H), 8.11 (dd, J=14.2, 7.0 Hz, 2H), 7.93 (s, 1H), 7.25 (dd, J=9.9, 5.6 Hz, 3H), 7.01 (d, J=2.1 Hz, 1H), 6.62 (d, J=7.4 Hz, 1H), 4.32 (p, J=6.3 Hz, 1H), 4.11 (d, J=13.0 Hz, 2H), 3.99 (d, J=29.4 Hz, 2H), 3.54 (s, 4H), 3.18 (s, 3H), 3.02 (t, J=12.5 Hz, 3H), 2.94-2.70 (m, 5H), 2.22 (s, 2H), 1.99 (d, J=13.0 Hz, 2H), 1.50 (d, J=6.3 Hz, 8H).

Example 73

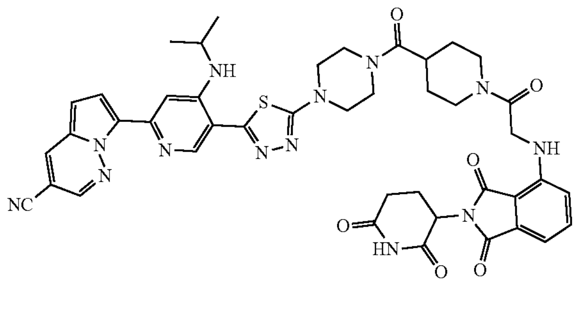 [SMILES: CC(C)Nc1cc(-c2ccc3cc(C#N)cnn23)ncc1-c1nnc(N2CCN(C(=O)C3CCN(C(=O)CNc4cccc5c4C(=O)N(C4CCC(=O)NC4=O)C5=O)CC3)CC2)s1]

7-(5-(5-(4-(1-((2-(2,6-dioxopiperidin-3-yl)-1,3-dioxoisoindolin-4-yl)glycyl)piperidine-4-carbonyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB5 and (2-(2,6-dioxopiperidin-3-yl)-1,3-dioxoisoindolin-4-yl)glycine by amide coupling using General Method A. LCMS: $C_{43}H_{43}N_{13}O_6S$ requires: 870.0. found: m/z=871.1 $[M+H]^+$; $^1H$ NMR (500 MHz, Methanol-$d_4$) δ 8.78 (d, J=2.2 Hz, 1H), 8.70 (d, J=2.2 Hz, 1H), 8.52 (s, 1H), 8.08 (d, J=5.2 Hz, 1H), 7.90 (s, 1H), 7.59 (t, J=7.8 Hz, 1H), 7.25 (d, J=5.1 Hz, 1H), 7.07 (dd, J=36.3, 7.8 Hz, 2H), 5.09 (dd, J=12.6, 5.5 Hz, 1H), 4.57 (d, J=13.2 Hz, 1H), 4.35-4.16 (m, 3H), 4.05 (d, J=13.8 Hz, 1H), 3.95-3.76 (m, 5H), 3.70 (s, 2H), 3.12 (s, 1H), 2.95-2.70 (m, 4H), 2.14 (d, J=11.8 Hz, 1H), 1.95-1.73 (m, 3H), 1.73-1.55 (m, 2H), 1.49 (d, J=6.3 Hz, 6H).

Example 74

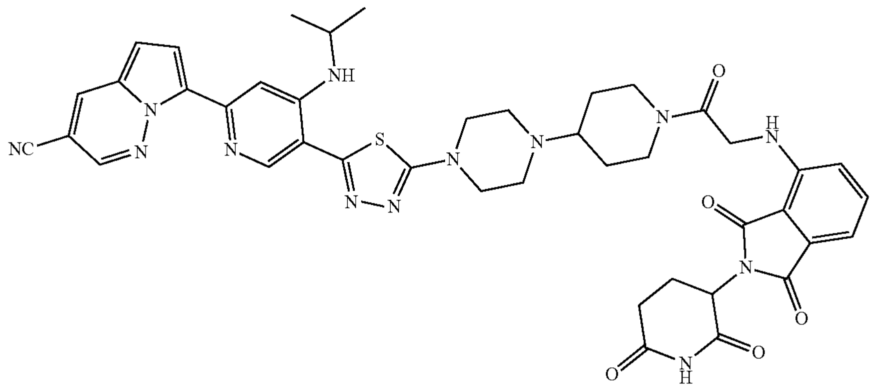 [SMILES: CC(C)Nc1cc(-c2ccc3cc(C#N)cnn23)ncc1-c1nnc(N2CCN(C3CCN(C(=O)CNc4cccc5c4C(=O)N(C4CCC(=O)NC4=O)C5=O)CC3)CC2)s1]

7-(5-(5-(4-(1-((2-(2,6-dioxopiperidin-3-yl)-1,3-dioxoisoindolin-4-yl)glycyl)piperidin-4-yl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB6 and (2-(2,6-dioxopiperidin-3-yl)-1,3-dioxoisoindolin-4-yl)glycine by amide coupling using General Method A. LCMS: $C_{42}H_{43}N_{13}O_5S$ requires: 842.0. found: m/z=843.0 $[M+H]^+$; $^1H$ NMR (500 MHz, Methanol-d4) δ 8.78 (d, J=2.1 Hz, 1H), 8.70 (d, J=2.2 Hz, 1H), 8.55 (s, 1H), 8.09 (d, J=5.1 Hz, 1H), 7.93 (s, 1H), 7.61 (t, J=8.1 Hz, 1H), 7.25 (d, J=5.0 Hz, 1H), 7.14 (dd, J=7.3, 3.4 Hz, 1H), 7.06 (dd, J=8.1, 4.1 Hz, 1H), 5.10 (dt, J=12.0, 6.0 Hz, 1H), 4.41-4.14 (m, 4H), 3.98 (s, 3H), 3.51 (s, 6H), 2.91-2.72 (m, 4H), 2.68 (s, 2H), 2.31-2.09 (m, 3H), 1.73 (ddd, J=69.0, 23.3, 12.3 Hz, 3H), 1.49 (d, J=6.4 Hz, 6H).

Example 75

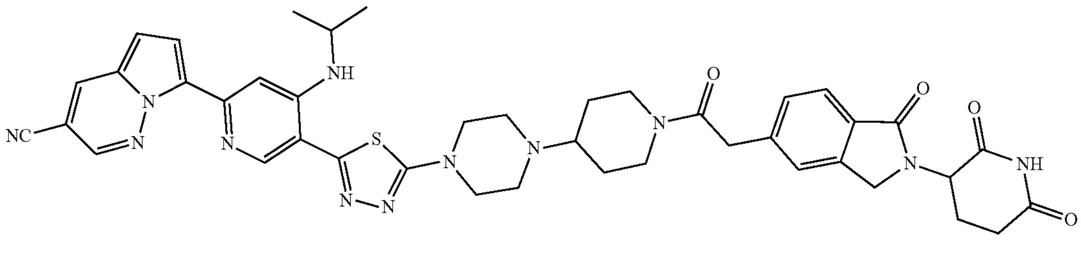 [SMILES: CC(C)Nc1cc(-c2ccc3cc(C#N)cnn23)ncc1-c1nnc(N2CCN(C3CCN(C(=O)Cc4ccc5c(c4)CN(C4CCC(=O)NC4=O)C5=O)CC3)CC2)s1]

7-(5-(5-(4-(1-(2-(2-(2,6-dioxopiperidin-3-yl)-1-oxoisoindolin-5-yl)acetyl)piperidin-4-yl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB6 and 2-(2-(2,6-dioxopiperidin-3-yl)-1-oxoisoindolin-5-yl)acetic acid by amide coupling using General Method A. LCMS: $C_{42}H_{44}N_{12}O_4S$ requires: 813.0. found: m/z=813.8 $[M+H]^+$.

Example 76

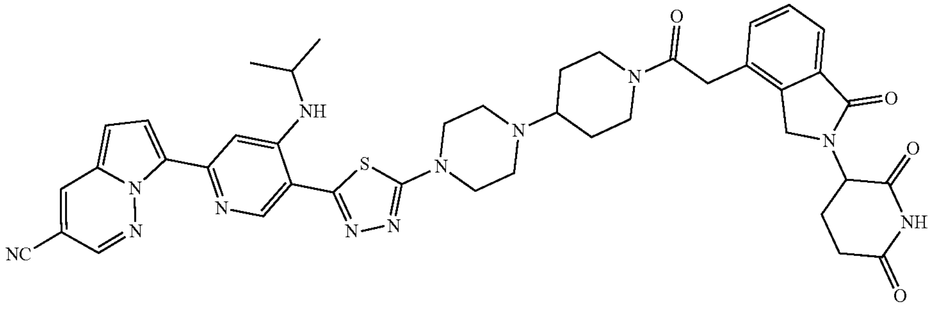 [SMILES: CC(C)Nc1cc(-c2ccc3cc(C#N)cnn23)ncc1-c1nnc(N2CCN(C3CCN(C(=O)Cc4cccc5c4CN(C4CCC(=O)NC4=O)C5=O)CC3)CC2)s1]

7-(5-(5-(4-(1-(2-(2-(2,6-dioxopiperidin-3-yl)-1-oxoisoindolin-4-yl)acetyl)piperidin-4-yl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB6 and 2-(2-(2,6-dioxopiperidin-3-yl)-1-oxoisoindolin-4-yl)acetic acid by amide coupling using General Method A. LCMS: $C_{42}H_{44}N_{12}O_4S$ requires: 813.0. found: m/z=813.8 $[M+H]^+$; $^1H$ NMR (500 MHz, Methanol-$d_4$) δ 8.78 (d, J=2.1 Hz, 1H), 8.69 (d, J=2.2 Hz, 1H), 8.55 (s, 1H), 8.09 (d, J=5.1 Hz, 1H), 7.93 (s, 1H), 7.81-7.69 (m, 1H), 7.61-7.46 (m, 3H), 7.25 (d, J=5.0 Hz, 1H), 5.28-5.10 (m, 1H), 4.57-4.42 (m, 2H), 4.38-4.16 (m, 3H), 4.10-3.86 (m, 6H), 3.43 (s, 4H), 3.21 (s, 1H), 2.98-2.69 (m, 4H), 2.58-2.43 (m, 1H), 2.42-2.25 (m, 1H), 2.25-2.09 (m, 3H), 1.64-1.54 (m, 1H), 1.49 (d, J=6.3 Hz, 6H), 1.36 (dd, J=23.0, 16.5 Hz, 2H).

Example 77

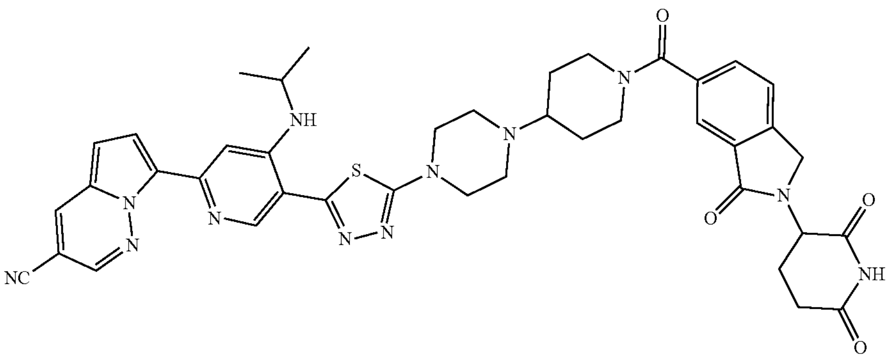 [SMILES: CC(C)Nc1cc(-c2ccc3cc(C#N)cnn23)ncc1-c1nnc(N2CCN(C3CCN(C(=O)c4ccc5c(c4)C(=O)N(C4CCC(=O)NC4=O)C5)CC3)CC2)s1]

7-(5-(5-(4-(1-(2-(2,6-dioxopiperidin-3-yl)-3-oxoisoindoline-5-carbonyl)piperidin-4-yl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB6 and 2-(2,6-dioxopiperidin-3-yl)-3-oxoisoindoline-5-carboxylic acid by amide coupling using General Method A. LCMS: $C_{41}H_{42}N_{12}O_4S$ requires: 798.9. found: m/z=799.8 $[M+H]^+$; $^1H$ NMR (500 MHz, Methanol-$d_4$) δ 7.98-7.85 (m, 3H), 7.83 (dd, J=8.2, 2.1 Hz, 1H), 7.51 (t, J=8.1 Hz, 1H), 7.41 (d, J=7.8 Hz, 1H), 7.28 (dt, J=7.9, 1.5 Hz, 1H), 5.55 (t, J=8.0 Hz, 1H), 4.60 (t, J=14.3 Hz, 1H), 4.00 (t, J=14.3 Hz, 1H), 3.43 (d, J=13.0 Hz, 1H), 3.04-2.75 (m, 2H), 2.27 (td, J=12.8, 4.7 Hz, 1H), 2.19 (d, J=8.8 Hz, 3H), 2.06 (d, J=1.3 Hz, 3H), 1.89-1.76 (m, 2H), 1.76-1.58 (m, 2H).

Example 78

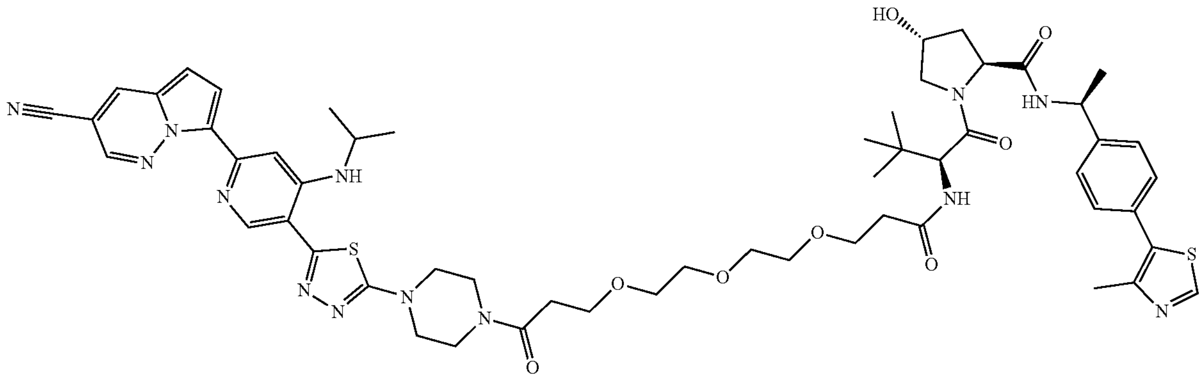 [SMILES: Cc1ncsc1-c1ccc([C@H](C)NC(=O)[C@@H]2C[C@@H](O)CN2C(=O)[C@@H](NC(=O)CCOCCOCCOCCC(=O)N2CCN(c3nnc(-c4cnc(-c5ccc6cc(C#N)cnn56)cc4NC(C)C)s3)CC2)C(C)(C)C)cc1]

(2S,4R)-1-((S)-2-(tert-butyl)-16-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-4,16-dioxo-7,10,13-trioxa-3-azahexadecanoyl)-4-hydroxy-N—((S)-1-(4-(4-methylthiazol-5-yl)phenyl)ethyl)pyrrolidine-2-carboxamide The title compound was synthesized from BB4 and (S)-15-((2S,4R)-4-hydroxy-2-(((S)-1-(4-(4-methylthiazol-5-yl)phenyl)ethyl)carbamoyl)pyrrolidine-1-carbonyl)-16,16-dimethyl-13-oxo-4,7,10-trioxa-14-azaheptadecanoic acid by amide coupling using General Method A. LCMS: $C_{55}H_{69}N_{13}O_8S_2$ requires: 1103.5. found: m/z=1105.1 $[M+H]^+$.

Example 79

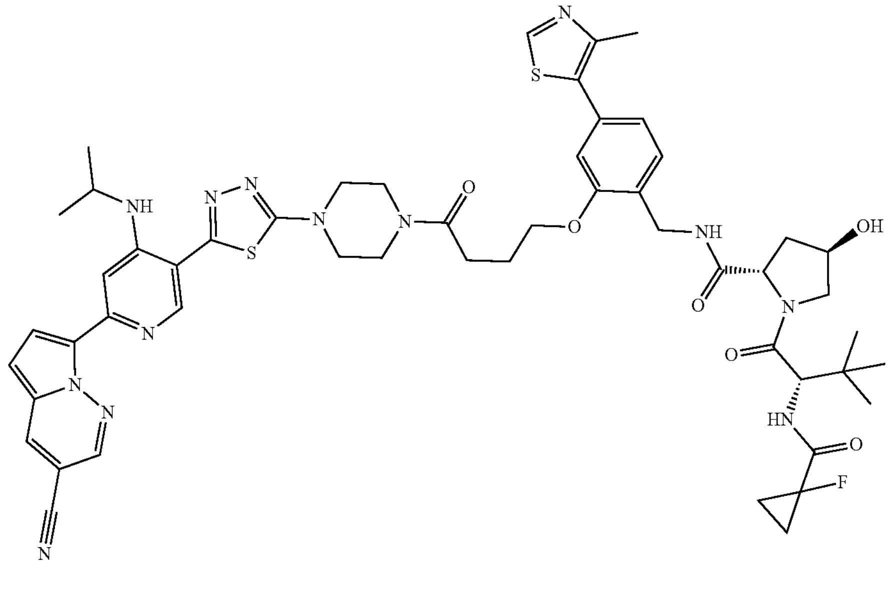 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCC(=O)N2CCN(c3nnc(-c4cnc(-c5ccc6cc(C#N)cnn56)cc4NC(C)C)s3)CC2)c1]

(2S,4R)—N-(2-(4-(4-(5-(6-(3-cyanopyrrolo[1,2-b]pyridazin-7-yl)-4-(isopropylamino)pyridin-3-yl)-1,3,4-thiadiazol-2-yl)piperazin-1-yl)-4-oxobutoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB4 and 4-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)butanoic acid by amide coupling using General Method A. LCMS: $C_{52}H_{60}FN_{13}O_6S_2$ requires: 1045.4. found: m/z=1047.2 $[M+H]^+$; $^1H$ NMR (500 MHz, Methanol-$d_4$) δ 8.91 (s, 1H), 8.79 (d, J=2.1 Hz, 1H), 8.70 (d, J=2.2 Hz, 1H), 8.52 (d, J=8.4 Hz, 1H), 8.09 (d, J=5.0 Hz, 1H), 7.90 (s, 1H), 7.52 (dd, J=18.5, 8.3 Hz, 2H), 7.26 (d, J=5.0 Hz, 1H), 7.04 (d, J=9.1 Hz, 2H), 4.77 (d, J=9.4 Hz, 2H), 4.66 (t, J=8.3 Hz, 1H), 4.50 (d, J=25.9 Hz, 3H), 4.41-4.19 (m, 3H), 4.18 (d, J=5.8 Hz, 2H), 3.90-3.78 (m, 6H), 3.72 (dt, J=34.8, 5.1 Hz, 5H), 2.78 (t, J=7.1 Hz, 2H), 2.30-2.08 (m, 5H), 1.49 (d, J=6.3 Hz, 7H), 1.43-1.24 (m, 5H), 1.05 (s, 10H).

Example 80

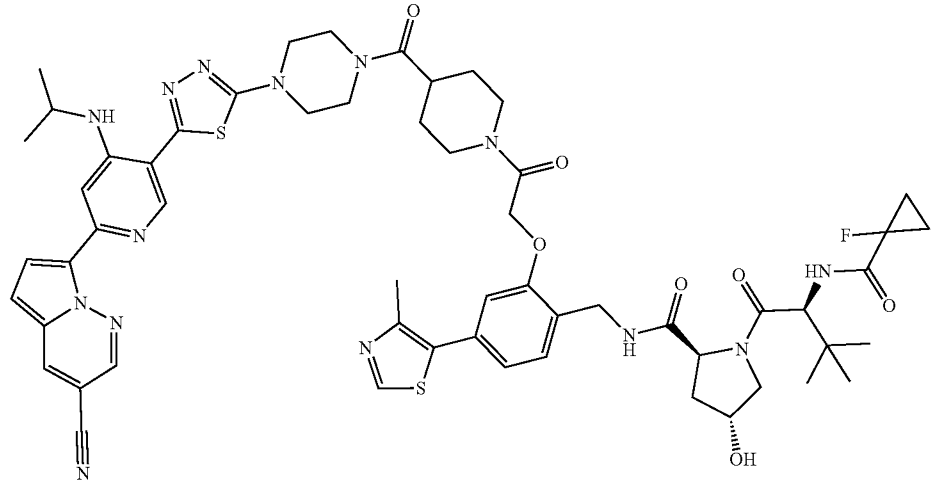 [SMILES: Cc1ncsc1-c1ccc(CNC(=O)[C@@H]2C[C@@H](O)CN2C(=O)[C@@H](NC(=O)C2(F)CC2)C(C)(C)C)c(OCC(=O)N2CCC(C(=O)N3CCN(c4nnc(-c5cnc(-c6ccc7cc(C#N)cnn67)cc5NC(C)C)s4)CC3)CC2)c1]

(2S,4R)—N-(2-(2-(4-(4-(5-(6-(3-cyanopyrrolo[1,2-b]pyridazin-7-yl)-4-(isopropylamino)pyridin-3-yl)-1,3,4-thiadiazol-2-yl)piperazine-1-carbonyl)piperidin-1-yl)-2-oxoethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB5 and 2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)acetic acid by amide coupling using General Method A. LCMS: $C_{56}H_{65}FN_{14}O_7S_2$ requires: 1129.4. found: m/z=1151.9 $[M+Na]^+$; $^1H$ NMR (500 MHz, DMSO-$d_6$) δ 9.61 (s, 1H), 9.00 (s, 3H), 8.86 (s, 1H), 8.59 (d, J=5.7 Hz, 2H), 8.10 (d, J=4.8 Hz, 1H), 8.01 (s, 1H), 7.42 (d, J=7.7 Hz, 1H), 7.31 (d, J=9.3 Hz, 1H), 7.25 (d, J=5.0 Hz, 1H), 7.10-6.80 (m, 3H), 5.10-4.87 (m, 3H), 4.71-4.43 (m, 3H), 4.40-4.10 (m, 9H), 3.85-3.61 (m, 36H), 3.02 (s, 3H), 2.76 (t, J=10.5 Hz, 2H), 2.46 (s, 5H), 2.21-2.02 (m, 3H), 1.93 (ddd, J=13.2, 9.0, 4.5 Hz, 2H), 1.75-1.58 (m, 4H), 1.43-1.31 (m, 11H), 1.29-1.11 (m, 5H).

Example 81

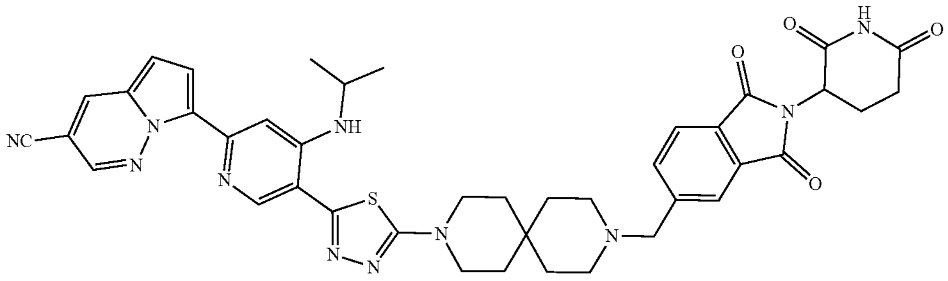 [SMILES: CC(C)Nc1cc(-c2ccc3cc(C#N)cnn23)ncc1-c1nnc(N2CCC3(CCN(Cc4ccc5c(c4)C(=O)N(C4CCC(=O)NC4=O)C5=O)CC3)CC2)s1]

7-(5-(5-(9-((2-(2,6-dioxopiperidin-3-yl)-1,3-dioxoisoindolin-5-yl)methyl)-3,9-diazaspiro[5.5]undecan-3-yl)-1,3,4-thiadiazol-2-yl)-4-(isopropylamino)pyridin-2-yl)pyrrolo[1,2-b]pyridazine-3-carbonitrile The title compound was synthesized from BB8 and 2-(2,6-dioxopiperidin-3-yl)-1,3-dioxoisoindoline-5-carbaldehyde by reductive amination using General Method B. LCMS: $C_{41}H_{41}N_{11}O_4S$ requires: 783.9. found: m/z=784.8 $[M+H]^+$; $^1H$ NMR (500 MHz, DMSO-$d_6$) δ 11.17 (s, 1H), 9.62 (s, 1H), 9.36 (s, 1H), 8.96 (d, J=2.1 Hz, 1H), 8.83 (d, J=2.1 Hz, 1H), 8.56 (s, 1H), 8.21-7.89 (m, 5H), 7.22 (d, J=4.9 Hz, 1H), 5.21 (dd, J=12.8, 5.5 Hz, 1H), 4.57 (s, 2H), 4.14 (dd, J=12.9, 6.5 Hz, 2H), 3.27-3.07 (m, 5H), 2.92 (ddd, J=17.8, 12.7, 5.3 Hz, 2H), 2.69-2.56 (m, 3H), 2.15-2.01 (m, 1H), 1.96 (d, J=14.3 Hz, 2H), 1.81 (s, 2H), 1.57 (t, J=12.7 Hz, 5H), 1.38 (d, J=6.2 Hz, 7H).

Example 82

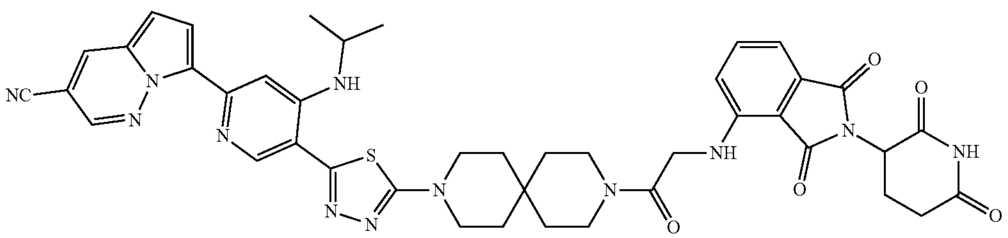 [SMILES: CC(C)Nc1cc(-c2ccc3cc(C#N)cnn23)ncc1-c1nnc(N2CCC3(CCN(C(=O)CNc4cccc5c4C(=O)N(C4CCC(=O)NC4=O)C5=O)CC3)CC2)s1]

7-(5-(5-(9-((2-(2,6-dioxopiperidin-3-yl)-1,3-dioxoisoindolin-4-yl)glycyl)-3,9-diazaspiro[5.5]undecan-3-yl)-1,3,4-thiadiazol-2-yl)-4-(isopropylamino)pyridin-2-yl)pyrrolo[1,2-b]pyridazine-3-carbonitrile The title compound was synthesized from BB8 and (2-(2,6-dioxopiperidin-3-yl)-1,3-dioxoisoindolin-4-yl)glycine by amide coupling using General Method A.

LCMS: $C_{42}H_{42}N_{12}O_5S$ requires: 826.9. found: m/z=827.8 $[M+H]^+$; $^1H$ NMR (500 MHz, DMSO-$d_6$) δ 11.12 (s, 1H), 9.56 (s, 1H), 8.99 (d, J=2.2 Hz, 1H), 8.85 (d, J=2.2 Hz, 1H), 8.56 (s, 1H), 8.12-7.92 (m, 2H), 7.63 (t, J=7.8 Hz, 1H), 7.24 (d, J=4.9 Hz, 1H), 7.12 (dd, J=27.1, 7.8 Hz, 3H), 5.09 (dd, J=12.8, 5.4 Hz, 1H), 4.20 (d, J=10.7 Hz, 4H), 3.00-2.85 (m, 2H), 2.70-2.57 (m, 3H), 2.06 (dd, J=11.2, 5.8 Hz, 1H), 1.71-1.40 (m, 10H), 1.39 (d, J=6.3 Hz, 6H).

Example 83

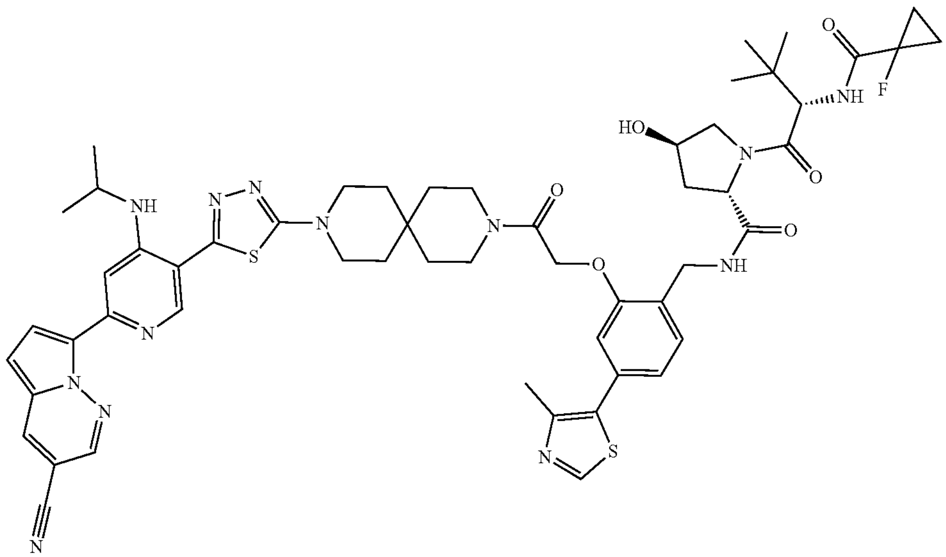 [SMILES: Cc1ncsc1-c1ccc(CNC(=O)[C@@H]2C[C@@H](O)CN2C(=O)[C@@H](NC(=O)C2(F)CC2)C(C)(C)C)c(OCC(=O)N2CCC3(CC2)CCN(c2nnc(-c4cnc(-c5ccc6cc(C#N)cnn56)cc4NC(C)C)s2)CC3)c1]

(2S,4R)—N-(2-(2-(9-(5-(6-(3-cyanopyrrolo[1,2-b]pyridazin-7-yl)-4-(isopropylamino)pyridin-3-yl)-1,3,4-thiadiazol-2-yl)-3,9-diazaspiro[5.5]undecan-3-yl)-2-oxoethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB8 and 2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)acetic acid by amide coupling using General Method A. LCMS: $C_{55}H_{64}FN_{13}O_6S_2$ requires: 1085.5. found: m/z=1109.0 $[M+Na]^+$; $^1H$ NMR (500 MHz, DMSO-$d_6$) δ 9.00 (d, J=5.1 Hz, 1H), 8.86 (d, J=2.3 Hz, 1H), 8.66-8.47 (m, 1H), 8.09 (d, J=5.1 Hz, 1H), 7.42 (d, J=7.7 Hz, 1H), 7.34-7.17 (m, 1H), 7.11-6.84 (m, 1H), 5.00 (d, J=6.4 Hz, 1H), 4.61 (d, J=9.2 Hz, 1H), 4.52 (t, J=8.3 Hz, 1H), 4.43-4.27 (m, 2H), 4.27-4.13 (m, 2H), 3.51 (q, J=5.6 Hz, 3H), 2.46 (d, J=2.5 Hz, 2H), 2.16-1.99 (m, 1H), 1.93 (ddd, J=13.1, 9.0, 4.5 Hz, 1H), 1.69-1.45 (m, 4H), 1.39 (d, J=6.3 Hz, 4H), 1.28-1.18 (m, 2H), 0.97 (s, 5H).

Example 84

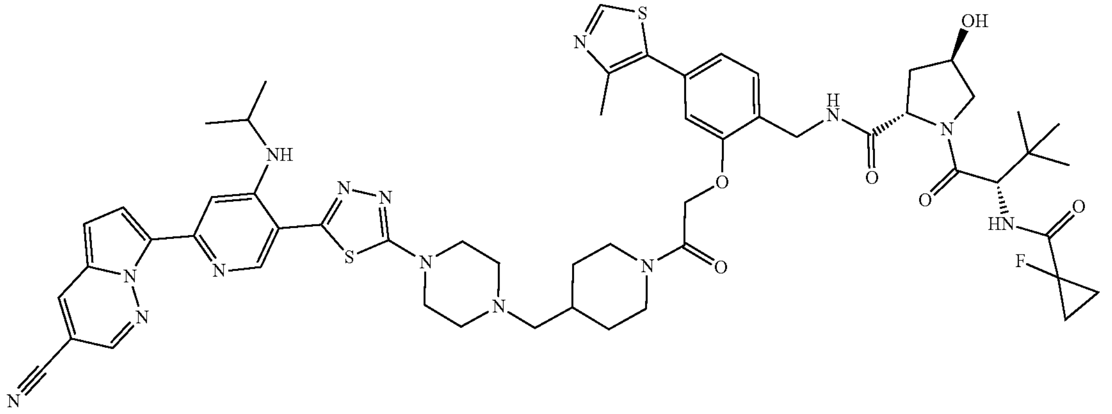 [SMILES: Cc1ncsc1-c1ccc(CNC(=O)[C@@H]2C[C@@H](O)CN2C(=O)[C@@H](NC(=O)C2(F)CC2)C(C)(C)C)c(OCC(=O)N2CCC(CN3CCN(c4nnc(-c5cnc(-c6ccc7cc(C#N)cnn67)cc5NC(C)C)s4)CC3)CC2)c1]

(2S,4R)—N-(2-(2-(4-((4-(5-(6-(3-cyanopyrrolo[1,2-b]pyridazin-7-yl)-4-(isopropylamino)pyridin-3-yl)-1,3,4-thiadiazol-2-yl)piperazin-1-yl)methyl)piperidin-1-yl)-2-oxoethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB25 and 2-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)acetic acid by amide coupling using General Method A. LCMS: $C_{56}H_{67}FN_{14}O_6S_2$ requires: 1114.5. found: m/z=1138.1 $[M+Na]^+$; $^1H$ NMR (500 MHz, DMSO-$d_6$) δ 9.71 (s, 1H), 9.27 (s, 1H), 9.07-8.89 (m, 2H), 8.83 (d, J=2.2 Hz, 1H), 8.60 (d, J=7.1 Hz, 2H), 8.10 (s, 1H), 8.03 (d, J=4.8 Hz, 1H), 7.43 (d, J=7.7 Hz, 1H), 7.30 (dd, J=9.3, 2.8 Hz, 1H), 7.22 (d, J=4.9 Hz, 1H), 7.04-6.92 (m, 2H), 5.10-4.93 (m, 3H), 4.61 (d, J=9.2 Hz, 2H), 4.52 (t, J=8.2 Hz, 2H), 4.39-4.29 (m, 6H), 4.17-4.09 (m, 5H), 3.94 (d, J=13.5 Hz, 4H), 3.71-3.59 (m, 7H), 3.27 (s, 3H), 3.12 (s, 3H), 2.69 (t, J=12.5 Hz, 2H), 2.46 (s, 4H), 2.22-2.00 (m, 2H), 1.92 (ddd, J=13.0, 8.8, 4.5 Hz, 1H), 1.83 (d, J=12.4 Hz, 2H), 1.38 (d, J=6.3 Hz, 10H), 1.29-1.18 (m, 4H), 1.13-1.04 (m, 1H), 0.98 (s, 11H).

Example 85

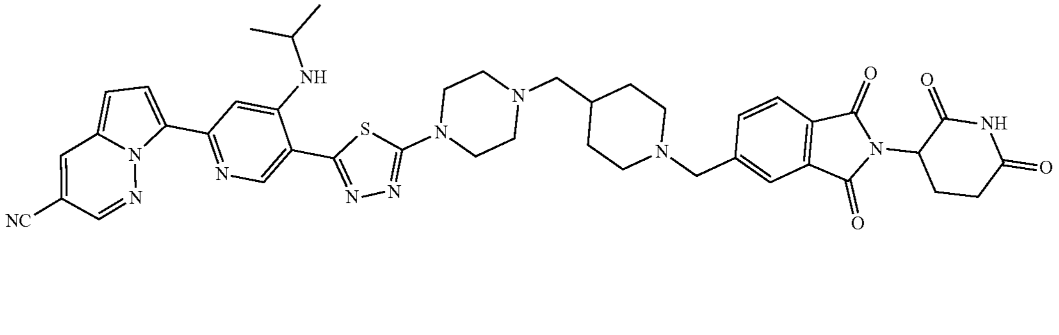 [SMILES: CC(C)Nc1cc(-c2ccc3cc(C#N)cnn23)ncc1-c1nnc(N2CCN(CC3CCN(Cc4ccc5c(c4)C(=O)N(C4CCC(=O)NC4=O)C5=O)CC3)CC2)s1]

7-(5-(5-(4-((1-((2-(2,6-dioxopiperidin-3-yl)-1,3-dioxoisoindolin-5-yl)methyl)piperidin-4-yl)methyl)piperazin-1-yl)-1,3,4-thiadiazol-2-yl)-4-(isopropylamino)pyridin-2-yl)pyrrolo[1,2-b]pyridazine-3-carbonitrile The title compound was synthesized from BB25 and 2-(2,6-dioxopiperidin-3-yl)-1,3-dioxoisoindoline-5-carbaldehyde by reductive amination using General Method B. LCMS: $C_{42}H_{44}N_{12}O_4S$ requires: 813.0. found: m/z=813.8 $[M+H]^+$.

Example 86

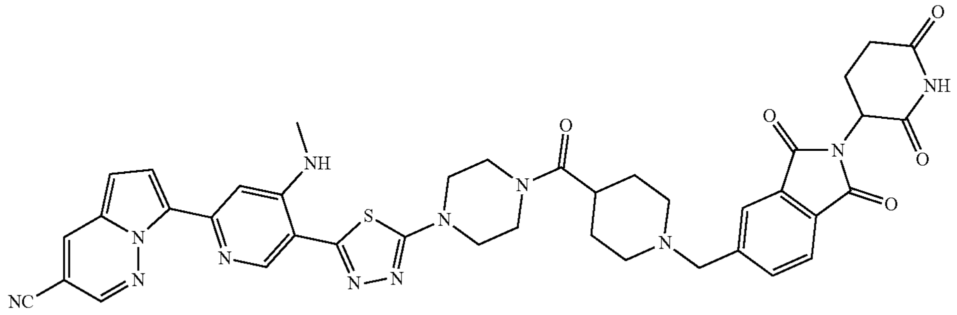 [SMILES: CNc1cc(-c2ccc3cc(C#N)cnn23)ncc1-c1nnc(N2CCN(C(=O)C3CCN(Cc4ccc5c(c4)C(=O)N(C4CCC(=O)NC4=O)C5=O)CC3)CC2)s1]

7-(5-(5-(4-(1-((2-(2,6-dioxopiperidin-3-yl)-1,3-dioxoisoindolin-5-yl)methyl)piperidine-4-carbonyl)piperazin-1-yl)-1,3,4-thiadiazol-2-yl)-4-(methylamino)pyridin-2-yl)pyrrolo[1,2-b]pyridazine-3-carbonitrile The title compound was synthesized from BB9 and 2-(2,6-dioxopiperidin-3-yl)-1,3-dioxoisoindoline-5-carbaldehyde by reductive amination using General Method B. LCMS: $C_{40}H_{38}N_{12}O_5S$ requires: 798.3. found: m/z=799.6 $[M+H]^+$.

Example 87

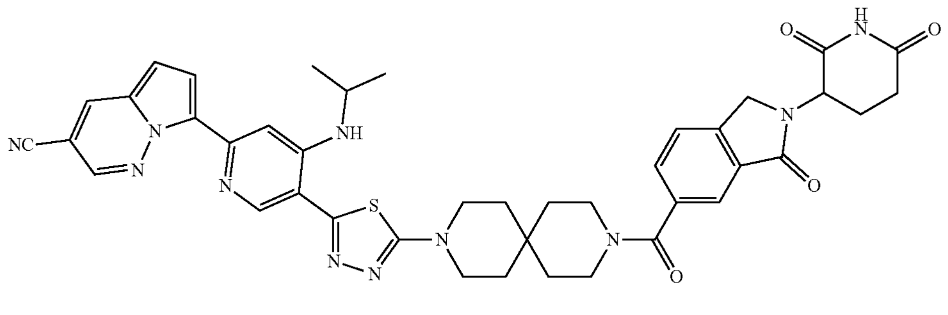 [SMILES: CC(C)Nc1cc(-c2ccc3cc(C#N)cnn23)ncc1-c1nnc(N2CCC3(CCN(C(=O)c4ccc5c(c4)C(=O)N(C4CCC(=O)NC4=O)C5)CC3)CC2)s1]

7-(5-(5-(9-(2-(2,6-dioxopiperidin-3-yl)-3-oxoisoindoline-5-carbonyl)-3,9-diazaspiro[5.5]undecan-3-yl)-1,3,4-thiadiazol-2-yl)-4-(isopropylamino)pyridin-2-yl)pyrrolo[1,2-b]pyridazine-3-carbonitrile The title compound was synthesized from BB8 and 2-(2,6-dioxopiperidin-3-yl)-3-oxoisoindoline-5-carboxylic acid by amide coupling using General Method A. LCMS: $C_{41}H_{41}N_{11}O_4S$ requires: 783.9. found: m/z=784.7 $[M+H]^+$; $^1H$ NMR (500 MHz, DMSO-$d_6$) δ 11.02 (s, 1H), 9.50 (s, 0H), 8.98 (s, 1H), 8.84 (s, 1H), 8.54 (s, 1H), 8.14-8.00 (m, 2H), 7.72 (d, J=7.6 Hz, 2H), 7.67 (d, J=7.9 Hz, 1H), 7.23 (d, J=5.0 Hz, 1H), 5.15 (dd, J=13.3, 5.1 Hz, 1H), 4.53 (d, J=17.6 Hz, 1H), 4.40 (d, J=17.6 Hz, 1H), 4.19-4.14 (m, 1H), 3.62 (s, 3H), 3.35 (s, 1H), 2.94 (ddd, J=17.8, 13.6, 5.4 Hz, 1H), 2.61 (s, 1H), 2.42 (dt, J=13.2, 6.7 Hz, 2H), 2.04 (d, J=12.2 Hz, 1H), 1.69 (s, 3H), 1.63 (s, 1H), 1.53 (s, 1H), 1.38 (d, J=6.2 Hz, 7H).

Example 88

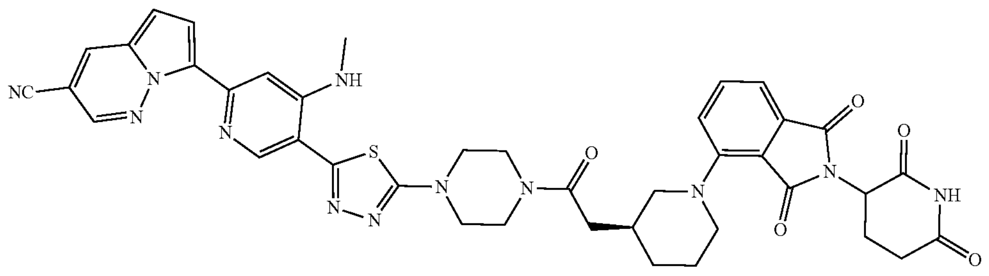 [SMILES: CNc1cc(-c2ccc3cc(C#N)cnn23)ncc1-c1nnc(N2CCN(C(=O)C[C@@H]3CCCN(c4cccc5c4C(=O)N(C4CCC(=O)NC4=O)C5=O)C3)CC2)s1]

7-(5-(5-(4-(2-((3S)-1-(2-(2,6-dioxopiperidin-3-yl)-1,3-dioxoisoindolin-4-yl)piperidin-3-yl)acetyl)piperazin-1-yl)-1,3,4-thiadiazol-2-yl)-4-(methylamino)pyridin-2-yl)pyrrolo[1,2-b]pyridazine-3-carbonitrile The title compound was synthesized from BB10 2-((3S)-1-(2-(2,6-dioxopiperidin-3-yl)-1,3-dioxoisoindolin-4-yl)piperidin-3-yl)acetic acid by amide coupling using General Method A. LCMS: $C_{40}H_{38}N_{12}O_5S$ requires: 798.9. found: m/z=799.5 $[M+H]^+$; $^1H$ NMR (500 MHz, Acetonitrile-$d_3$) δ 8.66-8.55 (m, 2H), 8.40 (d, J=7.4 Hz, 1H), 8.10 (t, J=4.9 Hz, 1H), 7.68-7.60 (m, 2H), 7.40-7.28 (m, 3H), 7.21 (d, J=5.1 Hz, 1H), 5.05-4.85 (m, 1H), 3.86-3.49 (m, 13H), 3.29 (d, J=5.0 Hz, 4H), 3.03 (s, 2H), 2.71 (s, 6H), 2.42 (s, 3H), 1.75 (s, 3H), 1.30 (s, 4H), 1.22-1.07 (m, 3H).

Example 89

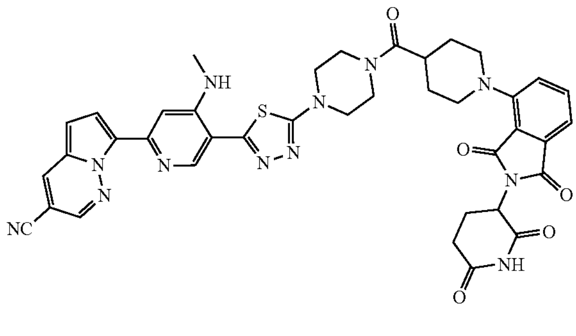 [SMILES: CNc1cc(-c2ccc3cc(C#N)cnn23)ncc1-c1nnc(N2CCN(C(=O)C3CCN(c4cccc5c4C(=O)N(C4CCC(=O)NC4=O)C5=O)CC3)CC2)s1]

7-(5-(5-(4-(1-(2-(2,6-dioxopiperidin-3-yl)-1,3-dioxoisoindolin-4-yl)piperidine-4-carbonyl)piperazin-1-yl)-1,3,4-thiadiazol-2-yl)-4-(methylamino)pyridin-2-yl)pyrrolo[1,2-b]pyridazine-3-carbonitrile The title compound was synthesized from BB9 and 2-(2,6-dioxopiperidin-3-yl)-4-fluoroisoindoline-1,3-dione by substitution using General Method C. LCMS: $C_{39}H_{36}N_{12}O_5S$ requires: 784.86. found: m/z=785.5 $[M+H]^+$; $^1H$ NMR (500 MHz, Acetonitrile-$d_3$) δ 8.91 (s, 1H), 8.60 (d, J=11.1 Hz, 2H), 7.68 (s, 1H), 7.35 (t, J=8.0 Hz, 2H), 7.19 (s, 1H), 3.79 (s, 9H), 3.66 (d, J=31.0 Hz, 4H), 3.25 (d, J=5.2 Hz, 4H), 2.75 (s, 3H), 2.53 (s, 1H), 1.30 (s, 4H).

Example 90

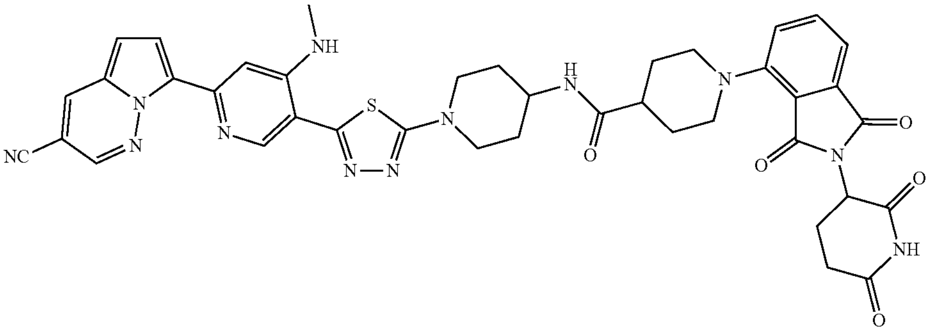 [SMILES: CNc1cc(-c2ccc3cc(C#N)cnn23)ncc1-c1nnc(N2CCC(NC(=O)C3CCN(c4cccc5c4C(=O)N(C4CCC(=O)NC4=O)C5=O)CC3)CC2)s1]

N-(1-(5-(6-(3-cyanopyrrolo[1,2-b]pyridazin-7-yl)-4-(methylamino)pyridin-3-yl)-1,3,4-thiadiazol-2-yl)piperidin-4-yl)-1-(2-(2,6-dioxopiperidin-3-yl)-1,3-dioxoisoindolin-4-yl)piperidine-4-carboxamide The title compound was synthesized from BB11 and 1-(2-(2,6-dioxopiperidin-3-yl)-1,3-dioxoisoindolin-4-yl)piperidine-4-carboxylic acid by amide coupling using General Method A. LCMS: $C_{40}H_{38}N_{12}O_5S$ requires: 798.9. found: m/z=799.5 $[M+H]^+$; $^1H$ NMR (500 MHz, Acetonitrile-$d_3$) δ 9.89 (s, 1H), 8.91 (s, 1H), 8.62 (dd, J=11.7, 2.2 Hz, 2H), 8.38 (s, 1H), 8.07 (d, J=5.1 Hz, 1H), 7.71-7.59 (m, 2H), 7.33 (dd, J=18.0, 7.8 Hz, 2H), 7.20 (d, J=5.1 Hz, 1H), 6.47 (d, J=7.7 Hz, 1H), 5.01 (dd, J=12.2, 5.2 Hz, 1H), 4.00 (d, J=12.7 Hz, 4H), 3.77 (s, 3H), 3.43 (t, J=12.3 Hz, 3H), 3.27 (d, J=5.1 Hz, 4H), 2.82-2.61 (m, 5H), 2.53 (s, 2H), 2.02 (s, 6H), 1.90 (d, J=3.9 Hz, 6H), 1.64 (d, J=12.2 Hz, 3H).

Example 91

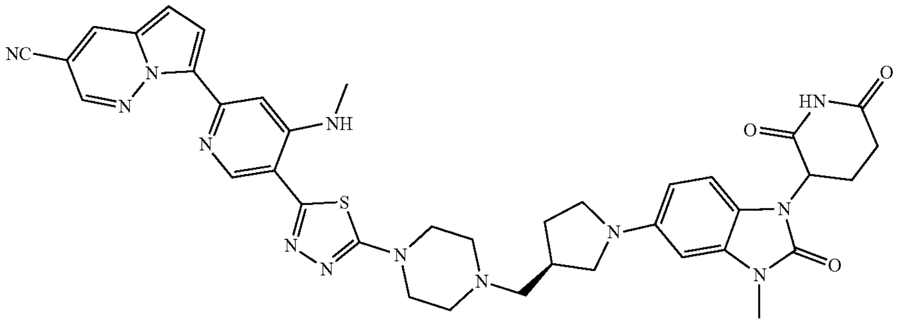 [SMILES: CNc1cc(-c2ccc3cc(C#N)cnn23)ncc1-c1nnc(N2CCN(C[C@H]3CCN(c4ccc5c(c4)n(C)c(=O)n5C4CCC(=O)NC4=O)C3)CC2)s1]

7-(5-(5-(4-(((3R)-1-(1-(2,6-dioxopiperidin-3-yl)-3-methyl-2-oxo-2,3-dihydro-1H-benzo[d]imidazol-5-yl)pyrrolidin-3-yl)methyl)piperazin-1-yl)-1,3,4-thiadiazol-2-yl)-4-(methylamino)pyridin-2-yl)pyrrolo[1,2-b]pyridazine-3-carbonitrile The title compound was synthesized from BB10 and (3S)-1-(1-(2,6-dioxopiperidin-3-yl)-3-methyl-2-oxo-2,3-dihydro-1H-benzo[d]imidazol-5-yl)pyrrolidine-3-carbaldehyde by reductive amination using General Method B. $^{1}$H NMR (500 MHz, DMSO-$d_6$) δ 11.06 (d, J=6.9 Hz, 1H), 8.96 (s, 1H), 8.83 (s, 1H), 8.58 (s, 1H), 8.03 (d, J=6.4 Hz, 1H), 7.22 (d, J=4.8 Hz, 1H), 6.95-6.80 (m, 1H), 6.42 (s, 1H), 6.32-6.14 (m, 1H), 5.28 (td, J=11.2, 9.1, 5.5 Hz, 1H), 4.70 (d, J=2.6 Hz, 1H), 3.18 (d, J=4.8 Hz, 4H), 3.05 (dt, J=14.9, 8.6 Hz, 2H), 2.97-2.77 (m, 3H), 2.74-2.57 (m, 4H), 2.26 (s, 1H), 2.11 (d, J=7.4 Hz, 2H), 1.99 (dd, J=10.7, 5.6 Hz, 1H), 1.79 (ddd, J=20.3, 12.4, 8.5 Hz, 1H).

Example 92

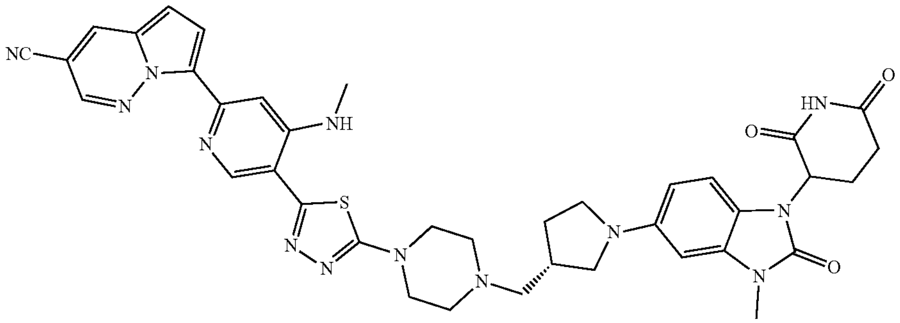 [SMILES: CNc1cc(-c2ccc3cc(C#N)cnn23)ncc1-c1nnc(N2CCN(C[C@@H]3CCN(c4ccc5c(c4)n(C)c(=O)n5C4CCC(=O)NC4=O)C3)CC2)s1]

7-(5-(5-(4-(((3S)-1-(1-(2,6-dioxopiperidin-3-yl)-3-methyl-2-oxo-2,3-dihydro-1H-benzo[d]imidazol-5-yl)pyrrolidin-3-yl)methyl)piperazin-1-yl)-1,3,4-thiadiazol-2-yl)-4-(methylamino)pyridin-2-yl)pyrrolo[1,2-b]pyridazine-3-carbonitrile The title compound was synthesized from BB10 and (3R)-1-(1-(2,6-dioxopiperidin-3-yl)-3-methyl-2-oxo-2,3-dihydro-1H-benzo[d]imidazol-5-yl)pyrrolidine-3-carbaldehyde by reductive amination using General Method B. LCMS: $C_{38}H_{39}N_{13}O_3S$ requires: 757.9. found: m/z=758.6 $[M+H]^+$; $^{1}$H NMR (500 MHz, DMSO-$d_6$) δ 11.06 (d, J=7.2 Hz, 1H), 8.95 (s, 1H), 8.82 (s, 1H), 8.57 (s, 1H), 8.03 (d, J=23.4 Hz, 1H), 7.21 (d, J=4.9 Hz, 1H), 6.93 (dd, J=18.6, 8.4 Hz, 1H), 6.42 (d, J=2.2 Hz, 1H), 6.27 (d, J=8.7 Hz, 1H), 5.36-5.14 (m, 1H), 3.17 (d, J=5.0 Hz, 3H), 3.07 (t, J=8.1 Hz, 2H), 2.99-2.73 (m, 3H), 2.73-2.58 (m, 4H), 2.26 (s, 1H), 2.16-2.03 (m, 1H), 2.03-1.87 (m, 1H), 1.81 (t, J=10.5 Hz, 1H).

Example 93

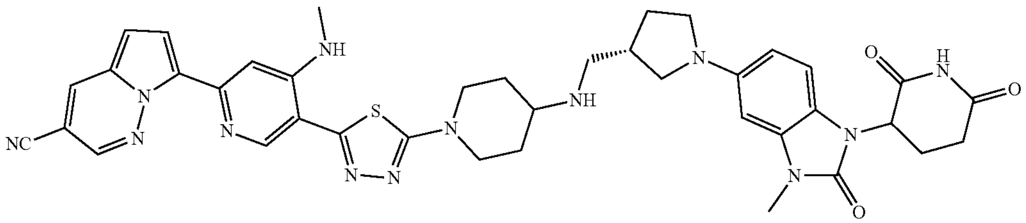 [SMILES: CNc1cc(-c2ccc3cc(C#N)cnn23)ncc1-c1nnc(N2CCC(NC[C@@H]3CCN(c4ccc5c(c4)n(C)c(=O)n5C4CCC(=O)NC4=O)C3)CC2)s1]

7-(5-(5-(4-((((3S)-1-(1-(2,6-dioxopiperidin-3-yl)-3-methyl-2-oxo-2,3-dihydro-1H-benzo[d]imidazol-5-yl)pyrrolidin-3-yl)methyl)amino)piperidin-1-yl)-1,3,4-thiadiazol-2-yl)-4-(methylamino)pyridin-2-yl)pyrrolo[1,2-b]pyridazine-3-carbonitrile The title compound was synthesized from BB11 and (3R)-1-(1-(2,6-dioxopiperidin-3-yl)-3-methyl-2-oxo-2,3-dihydro-1H-benzo[d]imidazol-5-yl)pyrrolidine-3-carbaldehyde by reductive amination using General Method B. LCMS: $C_{39}H_{41}N_{13}O_3S$ requires: 771.9. found: m/z=772.6 $[M+H]^+$.

Example 94

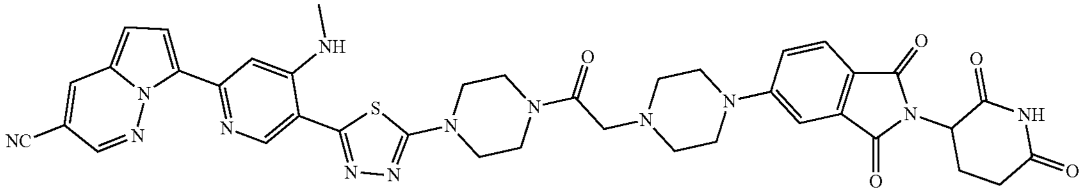 [SMILES: CNc1cc(-c2ccc3cc(C#N)cnn23)ncc1-c1nnc(N2CCN(C(=O)CN3CCN(c4ccc5c(c4)C(=O)N(C4CCC(=O)NC4=O)C5=O)CC3)CC2)s1]

7-(5-(5-(4-(2-(4-(2-(2,6-dioxopiperidin-3-yl)-1,3-dioxoisoindolin-5-yl)piperazin-1-yl)acetyl)piperazin-1-yl)-1,3,4-thiadiazol-2-yl)-4-(methylamino)pyridin-2-yl)pyrrolo[1,2-b]pyridazine-3-carbonitrile The title compound was synthesized from BB10 and 2-(4-(2-(2,6-dioxopiperidin-3-yl)-1,3-dioxoisoindolin-5-yl)piperazin-1-yl)acetic acid by amide coupling using General Method A. LCMS: $C_{39}H_{37}N_{13}O_5S$ requires: 799.3. found: m/z=800.5 $[M+H]^+$; $^1H$ NMR (500 MHz, Methanol-$d_4$) δ 8.78 (d, J=2.1 Hz, 1H), 8.69 (d, J=2.2 Hz, 1H), 8.52 (s, 1H), 8.10 (d, J=5.1 Hz, 1H), 7.86 (s, 1H), 7.79 (d, J=8.5 Hz, 1H), 7.51 (d, J=2.3 Hz, 1H), 7.38 (dd, J=8.4, 2.3 Hz, 1H), 7.25 (d, J=5.0 Hz, 1H), 5.12 (dd, J=12.4, 5.5 Hz, 1H), 4.32 (s, 2H), 3.91 (t, J=5.3 Hz, 3H), 3.83 (t, J=5.2 Hz, 3H), 3.75 (dd, J=12.0, 5.8 Hz, 6H), 2.89 (ddd, J=18.6, 14.1, 5.3 Hz, 1H), 2.82-2.69 (m, 2H), 2.20-2.05 (m, 1H).

Example 95

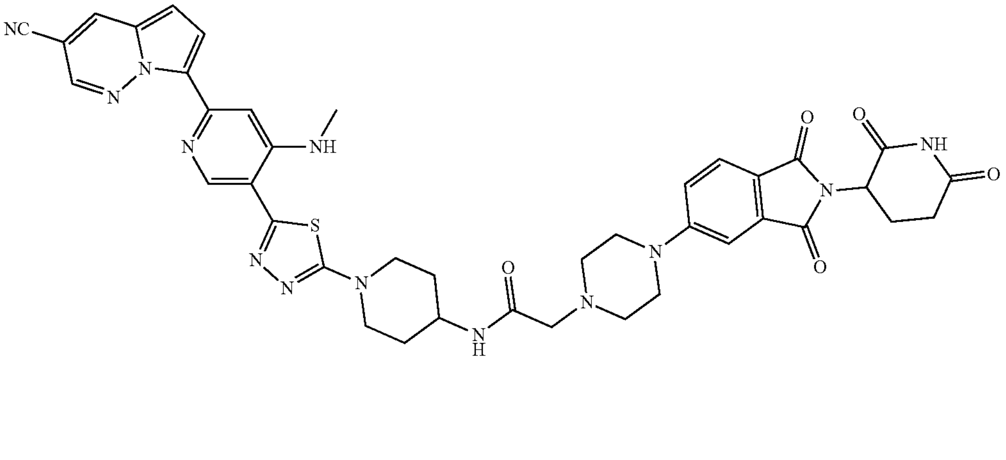 [SMILES: CNc1cc(-c2ccc3cc(C#N)cnn23)ncc1-c1nnc(N2CCC(NC(=O)CN3CCN(c4ccc5c(c4)C(=O)N(C4CCC(=O)NC4=O)C5=O)CC3)CC2)s1]

N-(1-(5-(6-(3-cyanopyrrolo[1,2-b]pyridazin-7-yl)-4-(methylamino)pyridin-3-yl)-1,3,4-thiadiazol-2-yl)piperidin-4-yl)-2-(4-(2-(2,6-dioxopiperidin-3-yl)-1,3-dioxoisoindolin-5-yl)piperazin-1-yl)acetamide The title compound was synthesized from BB11 and 2-(4-(2-(2,6-dioxopiperidin-3-yl)-1,3-dioxoisoindolin-5-yl)piperazin-1-yl)acetic acid by amide coupling using General Method A. LCMS: $C_{40}H_{39}N_{13}O_5S$ requires: 813.3. found: m/z 25=814.6 $[M+H]^+$.

Example 96

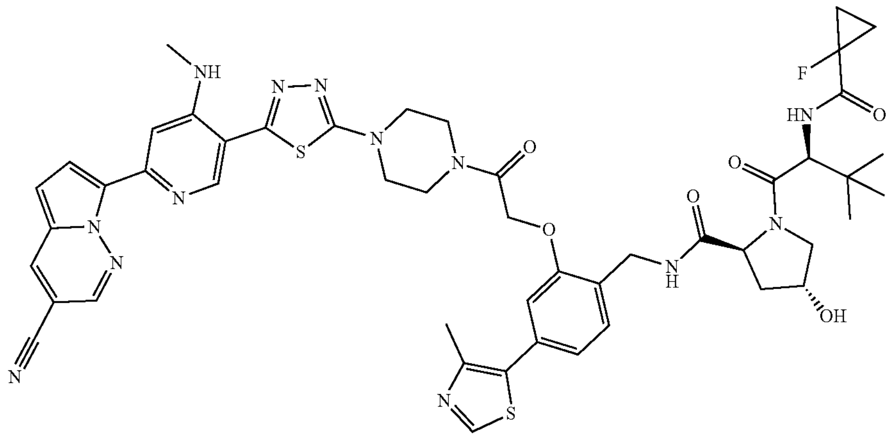 [SMILES: CNc1cc(-c2ccc3cc(C#N)cnn23)ncc1-c1nnc(N2CCN(C(=O)COc3cc(-c4scnc4C)ccc3CNC(=O)[C@@H]3C[C@@H](O)CN3C(=O)[C@@H](NC(=O)C3(F)CC3)C(C)(C)C)CC2)s1]

(2S,4R)—N-(2-(2-(4-(5-(6-(3-cyanopyrrolo[1,2-b]pyridazin-7-yl)-4-(methylamino)pyridin-3-yl)-1,3,4-thiadiazol-2-yl)piperazin-1-yl)-2-oxoethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB10 and 2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]acetic acid by amide coupling using General Method A. LCMS: $C_{48}H_{52}FN_{13}O_6S_2$ requires: 989.4. found: m/z=990.8 $[M+H]^+$; $^1H$ NMR (500 MHz, DMSO-$d_6$) δ 9.49 (s, 1H), 9.00 (s, 2H), 8.87 (d, J=2.1 Hz, 1H), 8.58 (d, J=12.2 Hz, 2H), 8.10 (d, J=4.9 Hz, 1H), 7.94 (s, 1H), 7.44 (d, J=7.8 Hz, 1H), 7.28 (dd, J=23.2, 7.1 Hz, 2H), 7.06 (s, 1H), 7.00 (d, J=7.8 Hz, 1H), 5.07 (s, 2H), 4.61 (d, J=9.2 Hz, 1H), 4.53 (t, J=8.3 Hz, 1H), 4.43-4.23 (m, 5H), 3.22 (d, J=4.8 Hz, 5H), 2.15-1.99 (m, 1H), 1.93 (ddd, J=13.0, 8.7, 4.4 Hz, 1H), 1.37 (dt, J=19.6, 11.6 Hz, 3H), 1.29-1.10 (m, 3H).

Example 97

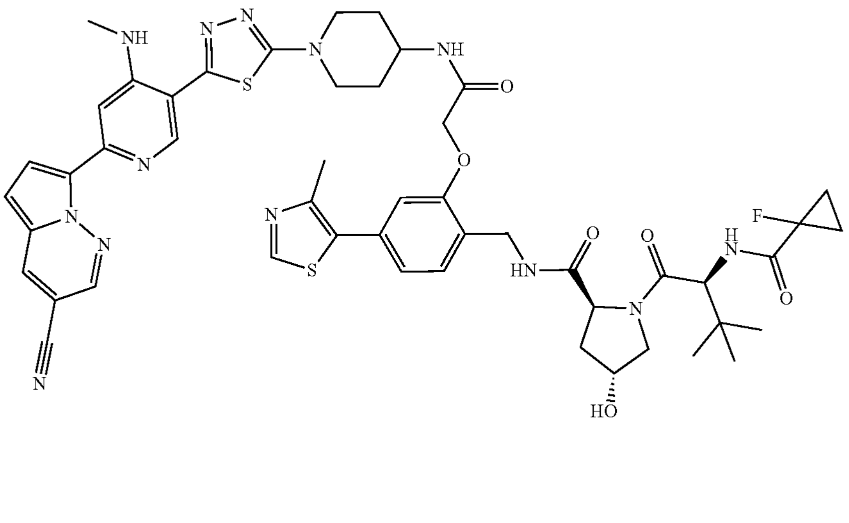 [SMILES: CNc1cc(-c2ccc3cc(C#N)cnn23)ncc1-c1nnc(N2CCC(NC(=O)COc3cc(-c4scnc4C)ccc3CNC(=O)[C@@H]3C[C@@H](O)CN3C(=O)[C@@H](NC(=O)C3(F)CC3)C(C)(C)C)CC2)s1]

(2S,4R)—N-(2-(2-((1-(5-(6-(3-cyanopyrrolo[1,2-b]pyridazin-7-yl)-4-(methylamino)pyridin-3-yl)-1,3,4-thiadiazol-2-yl)piperidin-4-yl)amino)-2-oxoethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB11 and 2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]acetic acid by amide coupling using General Method A. LCMS: $C_{49}H_{54}FN_{13}O_6S_2$ requires: 1003.4. found: m/z=1026.9 $[M+Na]^+$; $^1H$ NMR (500 MHz, DMSO-$d_6$) δ 9.00 (d, J=12.1 Hz, 3H), 8.85 (s, 1H), 8.66-8.39 (m, 2H), 8.15 (d, J=7.8 Hz, 1H), 8.08 (s, 1H), 7.95 (s, 1H), 7.43 (d, J=7.8 Hz, 1H), 7.25 (t, J=6.7 Hz, 3H), 7.05 (d, J=7.7 Hz, 1H), 6.99 (s, 1H), 4.66-4.38 (m, 8H), 4.34 (s, 2H), 4.25 (dd, J=15.4, 5.5 Hz, 2H), 4.05 (s, 2H), 3.96 (d, J=12.6 Hz, 4H), 3.21 (d, J=4.8 Hz, 5H), 2.04 (t, J=10.2 Hz, 1H), 1.96-1.80 (m, 4H), 1.72 (dt, J=17.5, 10.8 Hz, 2H), 1.35 (dt, J=18.3, 10.9 Hz, 3H), 1.27-1.08 (m, 5H), 0.97 (s, 3H).

Example 98

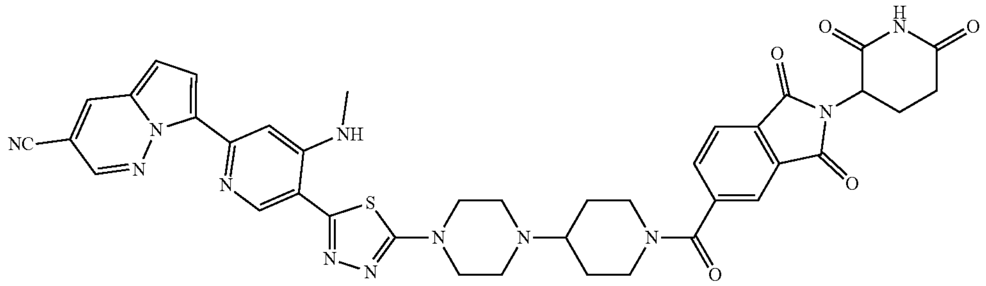 [SMILES: CNc1cc(-c2ccc3cc(C#N)cnn23)ncc1-c1nnc(N2CCN(C3CCN(C(=O)c4ccc5c(c4)C(=O)N(C4CCC(=O)NC4=O)C5=O)CC3)CC2)s1]

7-(5-(5-(4-(1-(2-(2,6-dioxopiperidin-3-yl)-1,3-dioxoisoindoline-5-carbonyl)piperidin-4-yl)piperazin-1-yl)-1,3,4-thiadiazol-2-yl)-4-(methylamino)pyridin-2-yl)pyrrolo[1,2-b]pyridazine-3-carbonitrile The title compound was synthesized from BB12 and rac-(R)-2-(2,6-dioxopiperidin-3-yl)-1,3-dioxoisoindoline-5-carboxylic acid by amide coupling using General Method A. LCMS: $C_{39}H_{36}N_{12}O_5S$ requires: 784.3. found: m/z=785.6 $[M+H]^+$; $^1H$ NMR (500 MHz, DMSO-$d_6$) δ 11.17 (d, J=2.6 Hz, 1H), 8.94 (s, 1H), 8.82 (s, 1H), 8.57 (d, J=2.6 Hz, 1H), 8.11-7.99 (m, 2H), 7.99-7.86 (m, 2H), 7.20 (d, J=3.9 Hz, 1H), 5.21 (ddd, J=12.9, 5.4, 2.6 Hz, 1H), 4.67 (s, 1H), 4.14 (s, 2H), 3.17 (d, J=4.7 Hz, 7H), 2.91 (d, J=13.8 Hz, 5H), 2.62 (s, 5H), 2.30-2.00 (m, 3H), 1.97 (s, 1H), 1.73 (s, 2H).

Example 99

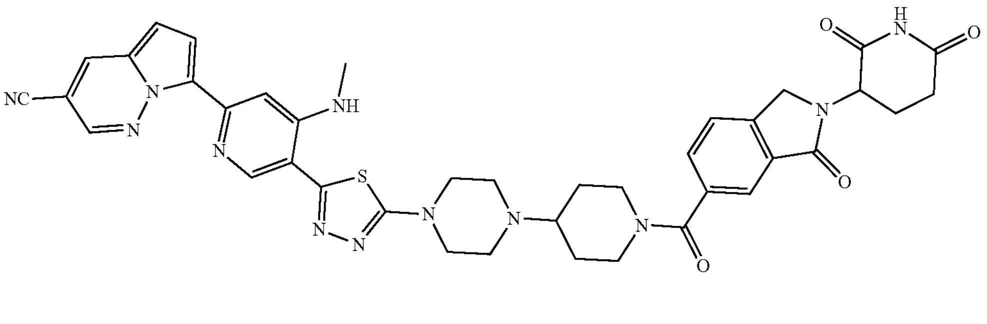 [SMILES: CNc1cc(-c2ccc3cc(C#N)cnn23)ncc1-c1nnc(N2CCN(C3CCN(C(=O)c4ccc5c(c4)C(=O)N(C4CCC(=O)NC4=O)C5)CC3)CC2)s1]

7-(5-(5-(4-(1-(2-(2,6-dioxopiperidin-3-yl)-3-oxoisoindoline-5-carbonyl)piperidin-4-yl)piperazin-1-yl)-1,3,4-thiadiazol-2-yl)-4-(methylamino)pyridin-2-yl)pyrrolo[1,2-b]pyridazine-3-carbonitrile The title compound was synthesized from BB12 and 2-(2,6-dioxopiperidin-3-yl)-3-oxoisoindoline-5-carboxylic acid by amide coupling using General Method A LCMS: $C_{39}H_{38}N_{12}O_4S$ requires: 770.3. found: m/z=771.8 $[M+H]^+$.

Example 100

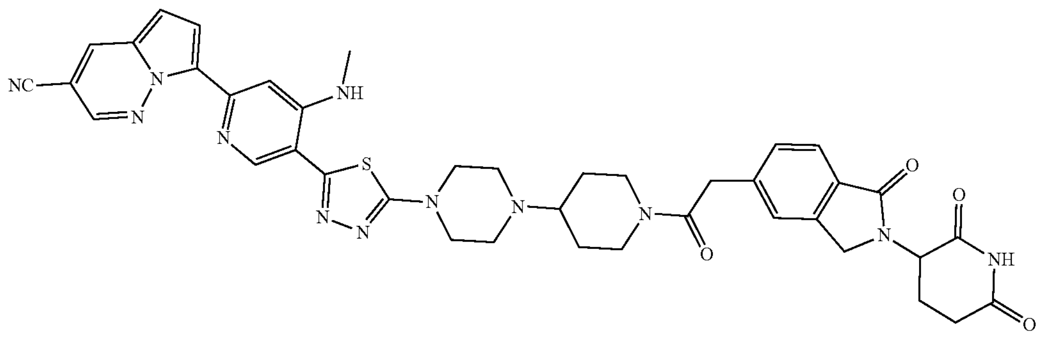 [SMILES: CNc1cc(-c2ccc3cc(C#N)cnn23)ncc1-c1nnc(N2CCN(C3CCN(C(=O)Cc4ccc5c(c4)CN(C4CCC(=O)NC4=O)C5=O)CC3)CC2)s1]

7-(5-(5-(4-(1-(2-(2-(2,6-dioxopiperidin-3-yl)-1-oxoisoindolin-5-yl)acetyl)piperidin-4-yl)piperazin-1-yl)-1,3,4-thiadiazol-2-yl)-4-(methylamino)pyridin-2-yl)pyrrolo[1,2-b]pyridazine-3-carbonitrile The title compound was synthesized from BB12 and 2-(2-(2,6-dioxopiperidin-3-yl)-1-oxoisoindolin-5-yl)acetic acid by amide coupling using General Method A. LCMS: $C_{40}H_{40}N_{12}O_4S$ requires: 784.9. found: m/z=785.6 $[M+H]^+$; $^1H$ NMR (500 MHz, DMSO-$d_6$) δ 10.99 (d, J=16.3 Hz, 1H), 8.94 (s, 1H), 8.89-8.68 (m, 1H), 8.56 (s, 1H), 8.02 (d, J=34.1 Hz, 2H), 7.81-7.59 (m, 1H), 7.49 (s, 1H), 7.43-7.29 (m, 1H), 7.20 (d, J=4.9 Hz, 1H), 5.13 (dd, J=13.6, 5.5 Hz, 1H), 4.57 (d, J=12.6 Hz, 1H), 4.49-4.26 (m, 3H), 4.16 (s, 3H), 3.91 (s, 2H), 3.16 (d, J=4.9 Hz, 3H), 2.92 (d, J=12.3 Hz, 2H), 2.62 (d, J=13.7 Hz, 4H), 2.39 (s, 2H), 2.14-1.84 (m, 3H), 1.48 (d, J=16.5 Hz, 2H).

Example 101

$N_1$-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-N3-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)bicyclo[1.1.1]pentane-1,3-dicarboxamide Step 1. 3-(((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)carbamoyl)bicyclo[1.1.1]pentane-1-carboxylic acid. To a vial was added 3-(tert-butoxycarbonyl)bicyclo[1.1.1]pentane-1-carboxylic acid (9.00 mg, 0.04 mmol), HATU (12 mg, 0.03 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide, DCM (1 mL) and N,N-diisopropylethylamine (27 uL, 0.02 g, 0.16 mmol). The reaction mixture was vortexed and stirred at RT, turning a bright yellow in color. The reaction mixture was monitored for completion, and after approximately 2 hrs, trifluoroacetic acid (0.1 mL, 1.3 mmol) was added and the reaction mixture immediately became homogeneous. De-protection progress was monitored by LCMS taking approximately 3 hrs stirring at RT after which the reaction mixture was concentrated on the rotovap, re-dissolved with DCM and re-concentrated to give 3-(((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)carbamoyl)bicyclo[1.1.1]pentane-1-carboxylic acid which

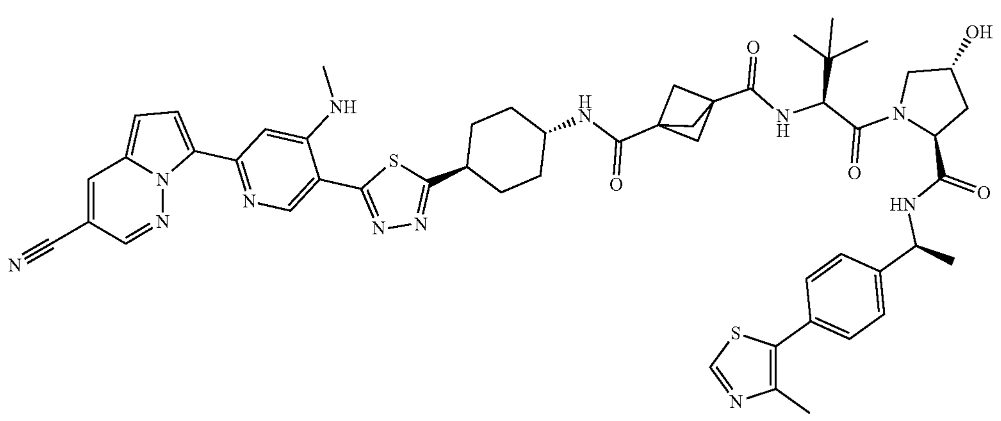 [SMILES: CNc1cc(-c2ccc3cc(C#N)cnn23)ncc1-c1nnc([C@H]2CC[C@H](NC(=O)C34CC(C(=O)N[C@H](C(=O)N5C[C@H](O)C[C@H]5C(=O)N[C@@H](C)c5ccc(-c6scnc6C)cc5)C(C)(C)C)(C3)C4)CC2)s1]

was used directly in the next step without further purification. LCMS: $C_{29}H_{28}N_{8}O_{3}S$ requires: 568.2. found: m/z=569.6 $[M+H]^+$ Step 2. $N_1$-[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]-N3-[(1rs,4rs)-4-[5-(6-{3-cyanopyrrolo[1,2-b]pyridazin-7-yl}-4-(methylamino)pyridin-3-yl)-1,3,4-thiadiazol-2-yl]cyclohexyl]bicyclo[1.1.1]pentane-1,3-dicarboxamide. To 3-(((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)carbamoyl)bicyclo[1.1.1]pentane-1-carboxylic acid was added BB3 (13 mg, 0.03 mmol), HATU (23 mg), DCM (1.5 mL) and Hunig's base (0.1 mL). The reaction mixture was stirred at RT overnight, then the crude reaction mixture was loaded directly onto a silica gel cartridge and purified by column chromatography (0-6% MeOH/DCM stepped gradient, 0.5% each step) to give the crude product as a yellow film. Further purification by reverse-phase HPLC gave the title compound. LCMS: $C_{52}H_{58}N_{12}O_5S_2$ requires: 994.4. found: m/z=995.8 $[M+H]^+$; $^1H$ NMR (500 MHz, Acetonitrile-$d_3$) δ 10.04 (s, 1H), 8.80 (s, 1H), 8.68-8.60 (m, 3H), 8.09 (d, J=5.1 Hz, 1H), 7.65 (s, 1H), 7.51-7.46 (m, 2H), 7.42 (d, J=7.9 Hz, 2H), 7.22 (d, J=5.0 Hz, 1H), 7.12 (d, J=7.6 Hz, 1H), 6.45 (d, J=9.2 Hz, 1H), 6.38 (d, J=8.0 Hz, 1H), 6.14 (s, 2H), 5.56 (s, 2H), 4.98 (q, J=7.3 Hz, 1H), 4.60 (d, J=9.2 Hz, 1H), 4.48 (t, J=8.1 Hz, 1H), 4.40 (s, 1H), 3.76 (d, J=11.8 Hz, 2H), 3.67 (dd, J=10.9, 4.0 Hz, 1H), 3.29 (d, J=17.2 Hz, 2H), 2.78 (s, 1H), 2.55 (s, 21H), 2.29 (d, J=13.0 Hz, 2H), 2.20 (s, 5H), 2.15 (d, J=28.2 Hz, 1H), 2.04 (td, J=9.9, 8.5, 4.0 Hz, 3H), 1.95 (s, 1H), 1.88 (s, 4H), 1.82-1.73 (m, 2H), 1.57-1.42 (m, 5H), 1.38-1.28 (m, 2H), 1.32 (s, 1H), 1.01 (s, 9H).

Example 102

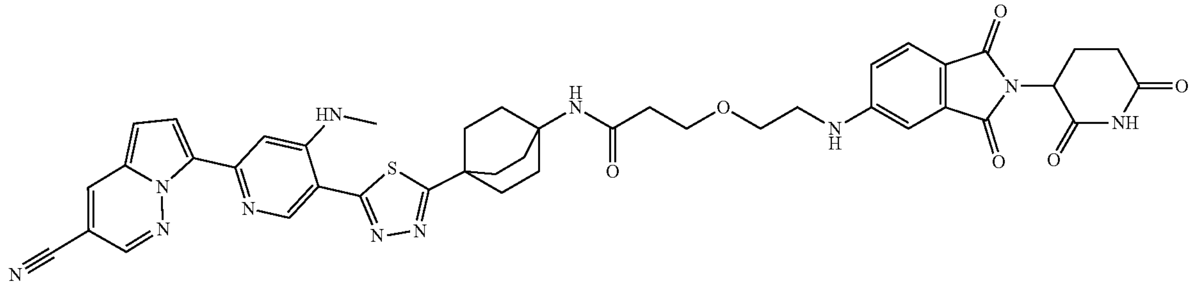 [SMILES: CNc1cc(-c2ccc3cc(C#N)cnn23)ncc1-c1nnc(C23CCC(NC(=O)CCOCCNc4ccc5c(c4)C(=O)N(C4CCC(=O)NC4=O)C5=O)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-3-(2-((2-(2,6-dioxopiperidin-3-yl)-1,3-dioxoisoindolin-5-yl)amino)ethoxy)propanamide The title compound was synthesized from BB13 and 3-(2-((2-(2,6-dioxopiperidin-3-yl)-1,3-dioxoisoindolin-5-yl)amino)ethoxy)propanoic acid by amide coupling using General Method A. LCMS: $C_{42}H_{41}N_{11}O_6S$ requires: 827.3. found: m/z=828.6 $[M+H]^+$; $^1H$ NMR (500 MHz, DMSO-$d_6$) δ 11.06 (s, 1H), 9.36 (s, 1H), 8.98 (d, J=2.1 Hz, 1H), 8.85 (d, J=2.2 Hz, 1H), 8.72 (s, 1H), 8.09-8.01 (m, 2H), 7.59 (d, J=8.4 Hz, 1H), 7.49 (s, 1H), 7.23 (d, J=4.9 Hz, 1H), 7.15 (s, 1H), 7.03 (d, J=2.1 Hz, 1H), 6.91 (dd, J=8.4, 2.2 Hz, 1H), 5.04 (dd, J=13.0, 5.4 Hz, 1H), 3.64 (t, J=6.4 Hz, 2H), 3.59 (t, J=5.4 Hz, 2H), 3.36 (s, 1H), 3.20 (d, J=4.9 Hz, 3H), 2.88 (ddd, J=19.2, 14.5, 5.7 Hz, 1H), 2.57 (d, J=17.2 Hz, 1H), 2.33 (t, J=6.4 Hz, 2H), 2.01 (ddt, J=34.4, 12.3, 6.6 Hz, 14H).

Example 103

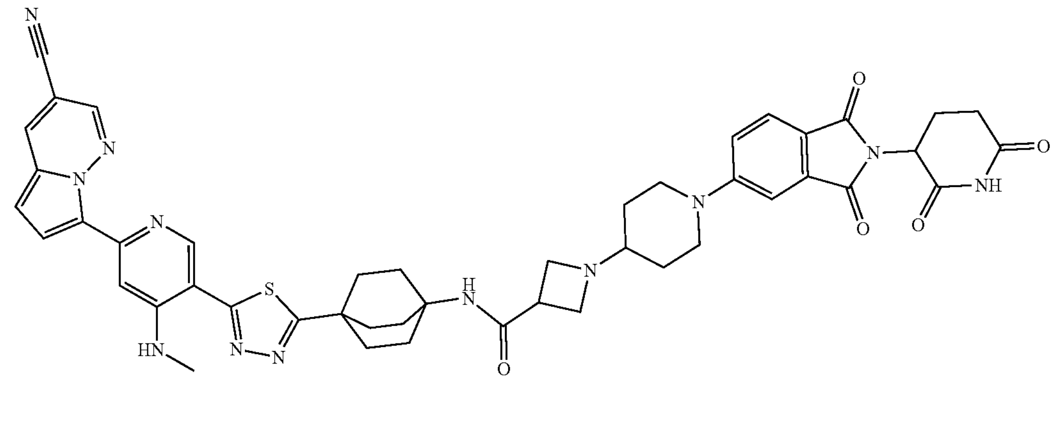 [SMILES: CNc1cc(-c2ccc3cc(C#N)cnn23)ncc1-c1nnc(C23CCC(NC(=O)C4CN(C5CCN(c6ccc7c(c6)C(=O)N(C6CCC(=O)NC6=O)C7=O)CC5)C4)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-1-(1-(2-(2,6-dioxopiperidin-3-yl)-1,3-dioxoisoindolin-5-yl)piperidin-4-yl)azetidine-3-carboxamide The title compound was synthesized from BB13 and 1-(1-(2-(2,6-dioxopiperidin-3-yl)-1,3-dioxoisoindolin-5-yl)piperidin-4-yl)azetidine-3-carboxylic acid by amide coupling using General Method A. LCMS: $C_{46}H_{46}N_{12}O_5S$ requires: 878.3. found: m/z=879.6 $[M+H]^+$; $^1H$ NMR (500 MHz, DMSO-$d_6$) δ 11.09 (s, 1H), 8.92 (s, 1H), 8.80 (s, 1H), 8.71 (s, 1H), 8.14 (s, 1H), 7.96 (s, 1H), 7.91 (s, 0H), 7.85 (s, 1H), 7.72 (d, J=8.5 Hz, 1H), 7.42 (s, 1H), 7.35-7.29 (m, 1H), 7.18 (d, J=4.8 Hz, 1H), 5.09 (dd, J=12.8, 5.4 Hz, 1H), 4.31 (s, 1H), 4.21-4.14 (m, 4H), 4.06 (s, 1H), 3.15 (d, J=4.8 Hz, 3H), 3.01 (s, 1H), 2.92 (d, J=14.3 Hz, 2H), 2.62 (s, 1H), 2.10 (d, J=8.8 Hz, 5H), 2.05 (s, 0H), 2.03 (s, 11H), 1.40 (d, J=13.1 Hz, 1H), 1.32 (d, J=11.6 Hz, 2H), 1.25 (s, 1H).

Example 104

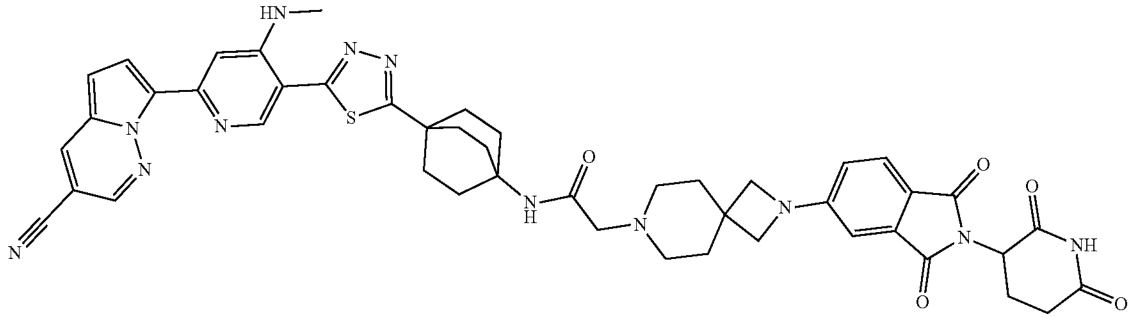 [SMILES: CNc1cc(-c2ccc3cc(C#N)cnn23)ncc1-c1nnc(C23CCC(NC(=O)CN4CCC5(CC4)CN(c4ccc6c(c4)C(=O)N(C4CCC(=O)NC4=O)C6=O)C5)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-2-(2-(2-(2,6-dioxopiperidin-3-yl)-1,3-dioxoisoindolin-5-yl)-2,7-diazaspiro[3.5]nonan-7-yl)acetamide The title compound was synthesized from BB13 and 2-(2-(2-(2,6-dioxopiperidin-3-yl)-1,3-dioxoisoindolin-5-yl)-2,7-diazaspiro[3.5]nonan-7-yl)acetic acid by amide coupling using General Method A. LCMS: $C_{46}H_{46}N_{12}O_5S$ requires: 878.3. found: m/z=879.9 $[M+H]^+$; $^1H$ NMR (500 MHz, DMSO-$d_6$) δ 11.09 (s, 1H), 9.60 (s, 1H), 8.92 (s, 1H), 8.80 (s, 1H), 8.71 (s, 1H), 8.26 (s, 1H), 8.15 (s, 1H), 7.96 (s, 1H), 7.69 (d, J=8.2 Hz, 1H), 7.19 (d, J=4.8 Hz, 1H), 6.79 (s, 1H), 6.67 (d, J=8.2 Hz, 1H), 5.07 (dd, J=12.8, 5.7 Hz, 1H), 3.89 (d, J=9.9 Hz, 3H), 3.83 (s, 2H), 3.19-3.01 (m, 3H), 2.88 (d, J=12.0 Hz, 1H), 2.11 (s, 6H), 2.06 (s, 2H), 2.04 (s, 9H), 1.25 (s, 2H).

Example 105

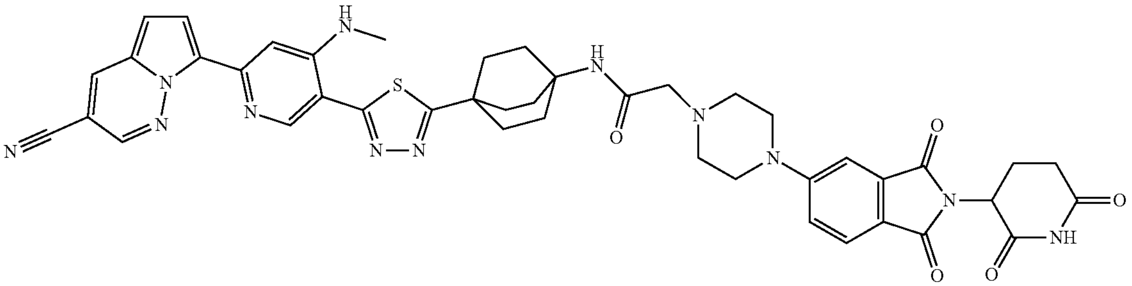 [SMILES: CNc1cc(-c2ccc3cc(C#N)cnn23)ncc1-c1nnc(C23CCC(NC(=O)CN4CCN(c5ccc6c(c5)C(=O)N(C5CCC(=O)NC5=O)C6=O)CC4)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl) bicyclo[2.2.2]octan-1-yl)-2-(4-(2-(2,6-dioxopiperidin-3-yl)-1,3-dioxoisoindolin-5-yl)piperazin-1-yl) acetamide The title compound was synthesized from BB13 and 2-(4-(2-(2,6-dioxopiperidin-3-yl)-1,3-dioxoisoindolin-5-yl) piperazin-1-yl)acetic acid by amide coupling using General Method A. LCMS: $C_{43}H_{42}N_{12}O_5S$ requires: 838.3. found: m/z=839.7 $[M+H]^+$; $^1H$ NMR (500 MHz, DMSO-$d_6$) δ 11.11 (s, 1H), 10.15 (s, 1H), 8.93 (s, 1H), 8.81 (d, J=2.1 Hz, 1H), 8.72 (s, 1H), 8.28 (s, 1H), 8.13 (s, 1H), 7.98 (s, 1H), 7.79 (d, J=8.3 Hz, 1H), 7.48 (s, 1H), 7.35 (d, J=8.6 Hz, 1H), 7.19 (d, J=4.8 Hz, 1H), 5.11 (dd, J=12.8, 5.5 Hz, 1H), 3.96 (s, 2H), 3.16 (d, J=4.8 Hz, 3H), 2.89 (d, J=12.2 Hz, 1H), 2.63 (s, 1H), 2.59 (s, 1H), 2.48 (s, 2H), 2.12 (dt, J=8.5, 5.6 Hz, 6H), 2.08-2.02 (m, 7H), 1.25 (s, 1H).

Example 106

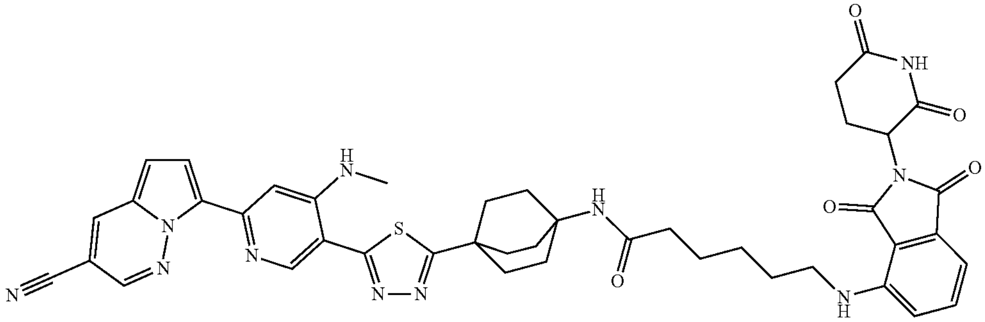 [SMILES: CNc1cc(-c2ccc3cc(C#N)cnn23)ncc1-c1nnc(C23CCC(NC(=O)CCCCCNc4cccc5c4C(=O)N(C4CCC(=O)NC4=O)C5=O)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl) bicyclo[2.2.2]octan-1-yl)-6-((2-(2,6-dioxopiperidin-3-yl)-1,3-dioxoisoindolin-4-yl)amino)hexanamide The title compound was synthesized from BB13 and 6-((2-(2,6-dioxopiperidin-3-yl)-1,3-dioxoisoindolin-4-yl) amino)hexanoic acid by amide coupling using General Method A. LCMS: $C_{43}H_{43}N_{11}O_5S$ requires: 825.3. found: m/z=826.7 $[M+H]^+$; $^1H$ NMR (500 MHz, DMSO-$d_6$) δ 11.10 (s, 1H), 9.30 (s, 1H), 8.97 (d, J=2.2 Hz, 1H), 8.84 (d, J=2.3 Hz, 1H), 8.72 (s, 1H), 8.04 (d, J=4.5 Hz, 2H), 7.64-7.57 (m, 1H), 7.41 (s, 1H), 7.22 (d, J=4.9 Hz, 1H), 7.11 (d, J=8.6 Hz, 1H), 7.04 (d, J=7.0 Hz, 1H), 6.53 (t, J=6.1 Hz, 1H), 5.06 (dd, J=12.7, 5.4 Hz, 1H), 3.19 (d, J=4.8 Hz, 3H), 2.92-2.84 (m, 1H), 2.62 (s, 1H), 2.51 (s, 3H), 2.09-2.01 (m, 8H), 2.04-1.96 (m, 4H), 1.96 (d, J=6.6 Hz, 3H), 1.56 (dp, J=29.8, 7.1 Hz, 4H), 1.33 (p, J=7.8 Hz, 2H).

Example 107

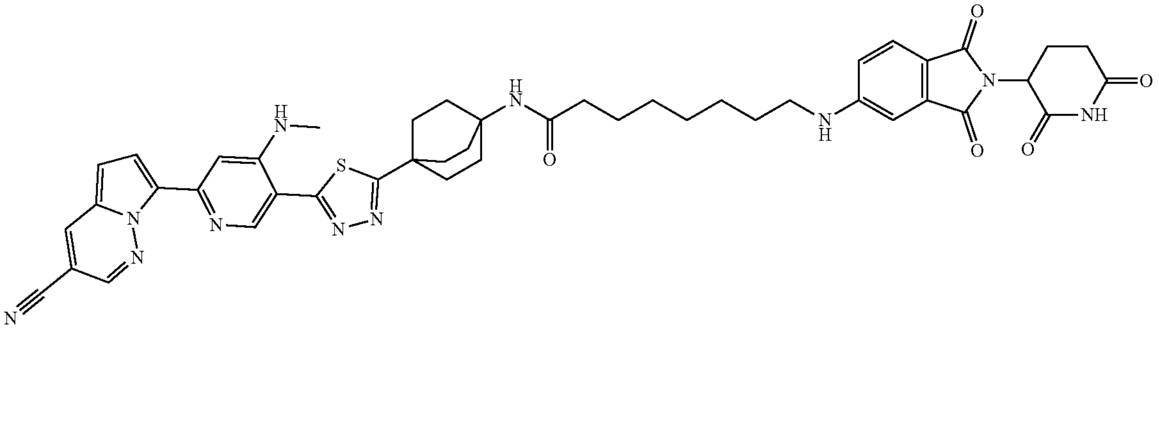 [SMILES: CNc1cc(-c2ccc3cc(C#N)cnn23)ncc1-c1nnc(C23CCC(NC(=O)CCCCCCCNc4ccc5c(c4)C(=O)N(C4CCC(=O)NC4=O)C5=O)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-8-((2-(2,6-dioxopiperidin-3-yl)-1,3-dioxoisoindolin-5-yl)amino)octanamide The title compound was synthesized from BB13 and 8-((2-(2,6-dioxopiperidin-3-yl)-1,3-dioxoisoindolin-5-yl)amino)octanoic acid by amide coupling using General Method A. LCMS: $C_{45}H_{47}N_{11}O_5S$ requires: 853.3. found: m/z=854.7 $[M+H]^+$; $^1H$ NMR (500 MHz, DMSO-$d_6$) δ 11.06 (s, 1H), 9.27 (s, 1H), 8.96 (d, J=2.3 Hz, 1H), 8.84 (d, J=2.2 Hz, 1H), 8.72 (s, 1H), 8.07-8.01 (m, 2H), 7.58 (d, J=8.4 Hz, 1H), 7.40 (s, 1H), 7.22 (d, J=4.9 Hz, 1H), 7.12 (s, 1H), 6.96 (d, J=2.2 Hz, 1H), 6.86 (dd, J=8.3, 2.2 Hz, 1H), 5.03 (dd, J=12.7, 5.4 Hz, 1H), 3.18 (t, J=6.1 Hz, 5H), 2.56 (s, 0H), 2.50 (s, 3H), 2.09-1.95 (m, 16H), 1.58 (p, J=7.1 Hz, 2H), 1.50 (q, J=7.5 Hz, 2H), 1.41-1.30 (m, 5H), 1.29-1.23 (m, 3H).

Example 108

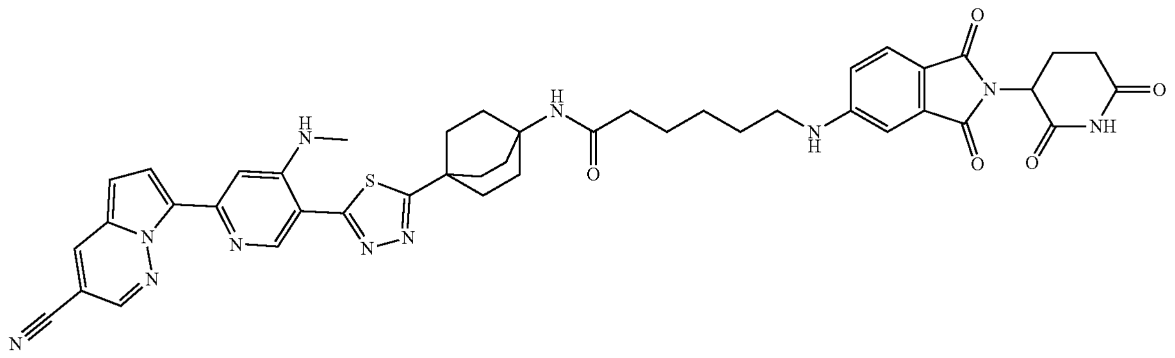 [SMILES: CNc1cc(-c2ccc3cc(C#N)cnn23)ncc1-c1nnc(C23CCC(NC(=O)CCCCCNc4ccc5c(c4)C(=O)N(C4CCC(=O)NC4=O)C5=O)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-6-((2-(2,6-dioxopiperidin-3-yl)-1,3-dioxoisoindolin-5-yl)amino)hexanamide The title compound was synthesized from BB13 and 6-((2-(2,6-dioxopiperidin-3-yl)-1,3-dioxoisoindolin-5-yl)amino)hexanoic acid by amide coupling using General Method A. LCMS: $C_{43}H_{43}N_{11}O_5S$ requires: 825.3. found: m/z=826.7 $[M+H]^+$; $^1H$ NMR (500 MHz, DMSO-$d_6$) δ 11.06 (s, 1H), 8.96 (d, J=2.2 Hz, 1H), 8.84 (d, J=2.2 Hz, 1H), 8.72 (s, 1H), 8.05 (d, J=15.2 Hz, 2H), 7.58 (d, J=8.3 Hz, 1H), 7.41 (s, 1H), 7.22 (d, J=4.9 Hz, 1H), 7.13 (s, 1H), 6.96 (d, J=2.2 Hz, 1H), 6.86 (dd, J=8.5, 2.2 Hz, 1H), 5.04 (dd, J=12.8, 5.5 Hz, 1H), 3.18 (d, J=5.1 Hz, 4H), 2.59 (s, 1H), 2.55 (s, OH), 2.50 (s, 3H), 2.47 (d, J=1.9 Hz, 1H), 2.06 (t, J=7.4 Hz, 7H), 2.00 (s, 1H), 1.97 (dd, J=11.0, 5.1 Hz, 7H), 1.56 (dt, J=25.7, 7.4 Hz, 4H), 1.40-1.31 (m, 2H), 1.25 (s, 1H).

Example 109

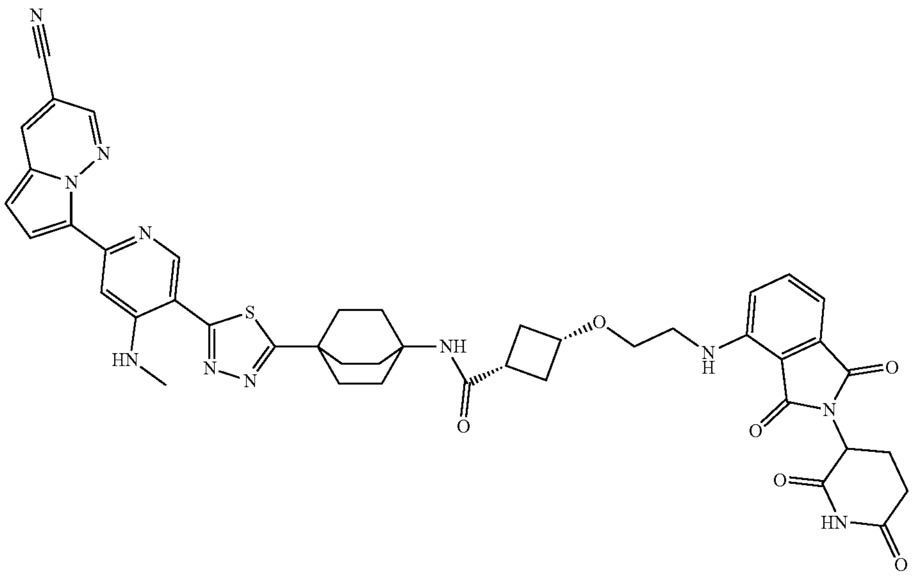 [SMILES: CNc1cc(-c2ccc3cc(C#N)cnn23)ncc1-c1nnc(C23CCC(NC(=O)[C@H]4C[C@@H](OCCNc5cccc6c5C(=O)N(C5CCC(=O)NC5=O)C6=O)C4)(CC2)CC3)s1]

(1s,3s)-N-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-3-(2-((2-(2,6-dioxopiperidin-3-yl)-1,3-dioxoisoindolin-4-yl)amino)ethoxy)cyclobutane-1-carboxamide The title compound was synthesized from BB13 and (3-(2-((2-(2,6-dioxopiperidin-3-yl)-1,3-dioxoisoindolin-4-yl)amino)ethoxy)-cis-cyclobutane-1-carboxylic acid by amide coupling using General Method A. LCMS: $C_{44}H_{43}N_{11}O_6S$ requires: 853.3. found: m/z=854.7 $[M+H]^+$; $^1H$ NMR (500 MHz, DMSO-$d_6$) δ 11.11 (s, 1H), 8.95 (s, 1H), 8.83 (d, J=2.2 Hz, 1H), 8.72 (s, 1H), 8.07 (s, 1H), 8.03 (s, 1H), 7.64-7.57 (m, 1H), 7.40 (s, 1H), 7.21 (d, J=4.9 Hz, 1H), 7.16 (d, J=8.6 Hz, 1H), 7.06 (d, J=7.1 Hz, 1H), 6.59 (s, 1H), 5.08 (dd, J=12.8, 5.5 Hz, 1H), 3.90-3.84 (m, 1H), 3.18 (d, J=4.8 Hz, 3H), 2.60 (d, J=17.5 Hz, 2H), 2.49-2.45 (m, 2H), 2.28 (s, 2H), 2.07 (dd, J=10.8, 5.2 Hz, 7H), 2.01-1.92 (m, 9H), 1.25 (s, 1H).

Example 110

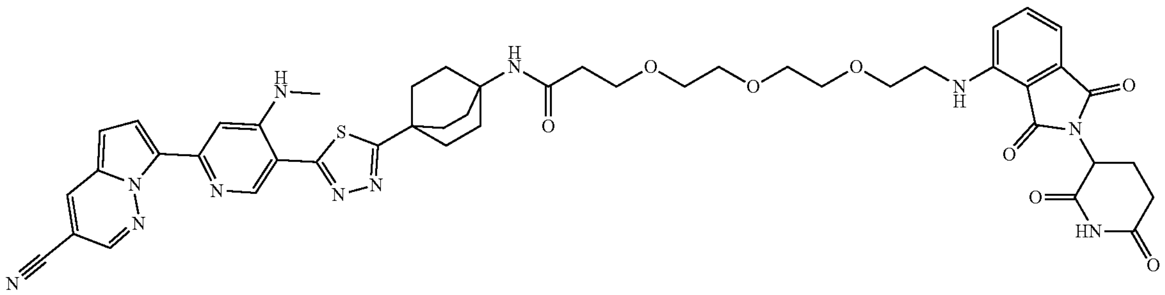 [SMILES: CNc1cc(-c2ccc3cc(C#N)cnn23)ncc1-c1nnc(C23CCC(NC(=O)CCOCCOCCOCCNc4cccc5c4C(=O)N(C4CCC(=O)NC4=O)C5=O)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-3-(2-(2-(2-((2-(2,6-dioxopiperidin-3-yl)-1,3-dioxoisoindolin-4-yl)amino)ethoxy)ethoxy)ethoxy)propanamide The title compound was synthesized from BB13 and 3-(2-(2-(2-((2-(2,6-dioxopiperidin-3-yl)-1,3-dioxoisoindolin-4-yl)amino)ethoxy)ethoxy)ethoxy)propanoic acid by amide coupling using General Method A. LCMS: $C_{46}H_{49}N_{11}O_8S$ requires: 915.3. found: m/z=916.8 $[M+H]^+$; $^1H$ NMR (500 MHz, DMSO-$d_6$) δ 11.10 (s, 1H), 8.96 (d, J=2.2 Hz, 1H), 8.84 (d, J=2.2 Hz, 1H), 8.71 (s, 1H), 8.04 (d, J=7.9 Hz, 2H), 7.63-7.56 (m, 1H), 7.46 (s, 1H), 7.22 (d, J=4.9 Hz, 1H), 7.16 (d, J=8.6 Hz, 1H), 7.05 (d, J=7.1 Hz, 1H), 6.62 (t, J=5.8 Hz, 1H), 5.07 (dd, J=12.7, 5.5 Hz, 1H), 3.64 (t, J=5.4 Hz, 2H), 3.60-3.54 (m, 5H), 3.54-3.47 (m, 3H), 3.19 (d, J=4.8 Hz, 3H), 2.88 (d, J=12.6 Hz, 1H), 2.62 (s, 1H), 2.57 (d, J=14.5 Hz, 1H), 2.50 (s, 3H), 2.29 (t, J=6.5 Hz, 2H), 2.09-1.95 (m, 13H), 1.25 (s, 1H).

Example 111

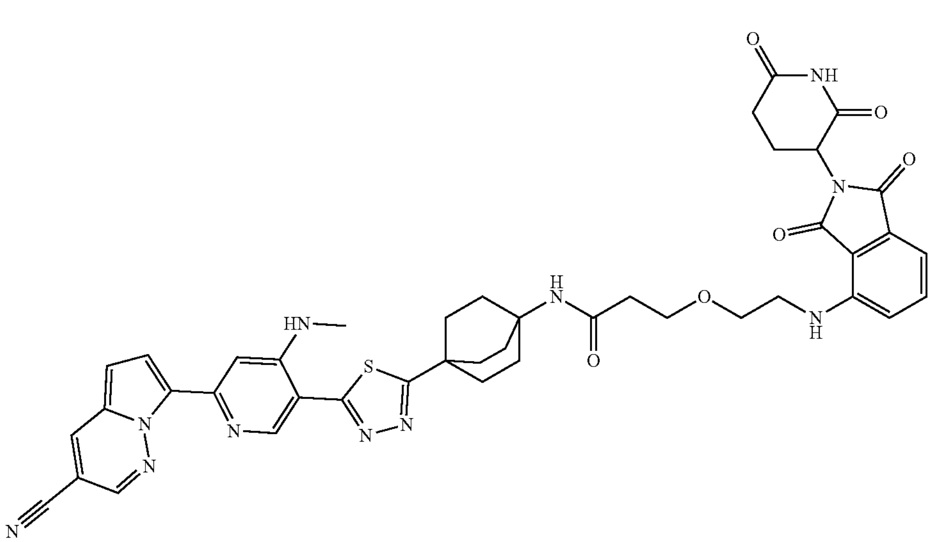 [SMILES: CNc1cc(-c2ccc3cc(C#N)cnn23)ncc1-c1nnc(C23CCC(NC(=O)CCOCCNc4cccc5c4C(=O)N(C4CCC(=O)NC4=O)C5=O)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-3-(2-((2-(2,6-dioxopiperidin-3-yl)-1,3-dioxoisoindolin-4-yl)amino)ethoxy)propenamide The title compound was synthesized from BB13 and 3-(2-((2-(2,6-dioxopiperidin-3-yl)-1,3-dioxoisoindolin-4-yl)amino)ethoxy)propanoic acid by amide coupling using General Method A. LCMS: $C_{42}H_{41}N_{11}O_6S$ requires: 827.3. found: m/z=828.8 $[M+H]^+$; $^1H$ NMR (500 MHz, DMSO-$d_6$) δ 11.11 (s, 1H), 9.30 (s, 1H), 8.96 (d, J=2.1 Hz, 1H), 8.84 (d, J=2.2 Hz, 1H), 8.72 (s, 1H), 8.04 (d, J=5.5 Hz, 2H), 7.64-7.58 (m, 1H), 7.48 (s, 1H), 7.22 (d, J=4.9 Hz, 1H), 7.16 (d, J=8.6 Hz, 1H), 7.07 (d, J=7.0 Hz, 1H), 6.59 (t, J=5.9 Hz, 1H), 5.07 (dd, J=12.9, 5.4 Hz, 1H), 3.62 (dt, J=19.8, 5.9 Hz, 4H), 3.19 (d, J=4.8 Hz, 3H), 2.89 (d, J=12.6 Hz, 0H), 2.62 (s, 1H), 2.59 (s, 1H), 2.32 (t, J=6.4 Hz, 2H), 2.01 (ddt, J=33.8, 11.8, 6.2 Hz, 13H), 1.25 (s, 1H).

Example 112

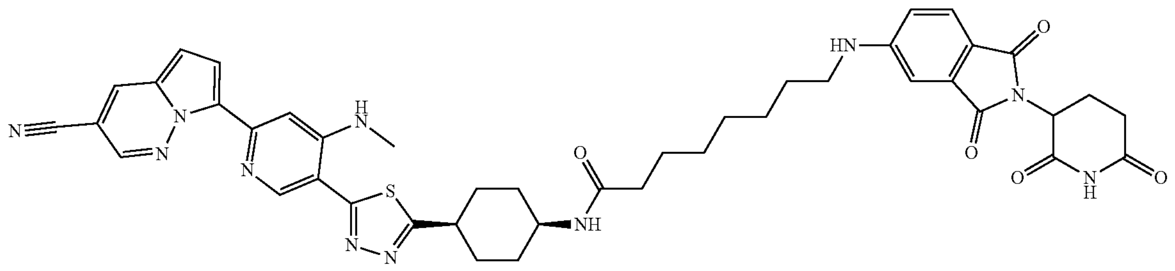 [SMILES: CNc1cc(-c2ccc3cc(C#N)cnn23)ncc1-c1nnc([C@H]2CC[C@@H](NC(=O)CCCCCCCNc3ccc4c(c3)C(=O)N(C3CCC(=O)NC3=O)C4=O)CC2)s1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-8-((2-(2,6-dioxopiperidin-3-yl)-1,3-dioxoisoindolin-5-yl)amino)octanamide The title compound was synthesized from BB14 and 8-((2-(2,6-dioxopiperidin-3-yl)-1,3-dioxoisoindolin-5-yl)amino)octanoic acid by amide coupling using General Method A. LCMS: $C_{43}H_{45}N_{11}O_5S$ requires: 827.3. found: m/z=828.6 $[M+H]^+$ Example 113

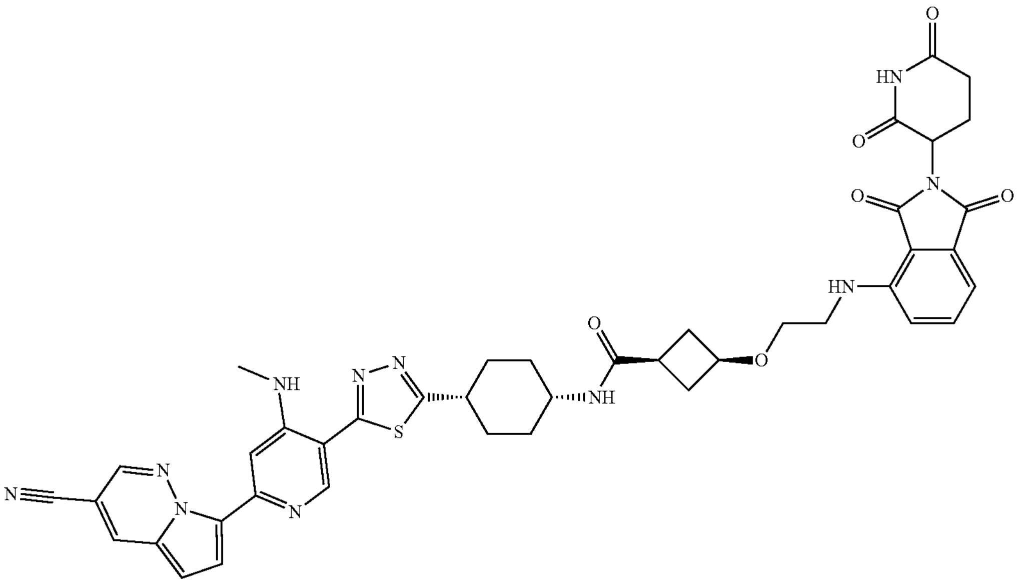 [SMILES: CNc1cc(-c2ccc3cc(C#N)cnn23)ncc1-c1nnc([C@H]2CC[C@@H](NC(=O)[C@H]3C[C@@H](OCCNc4cccc5c4C(=O)N(C4CCC(=O)NC4=O)C5=O)C3)CC2)s1]

(1s,3S)—N-((1s,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-3-(2-((2-(2,6-dioxopiperidin-3-yl)-1,3-dioxoisoindolin-4-yl)amino)ethoxy)cyclobutane-1-carboxamide The title compound was synthesized from BB14 and (3-(2-((2-(2,6-dioxopiperidin-3-yl)-1,3-dioxoisoindolin-4-yl)amino)ethoxy)-cis-cyclobutane-1-carboxylic acid by amide coupling using General Method A. LCMS: $C_{42}H_{41}N_{11}O_6S$ requires: 827.3. found: m/z=828.6 $[M+H]^+$ Example 114

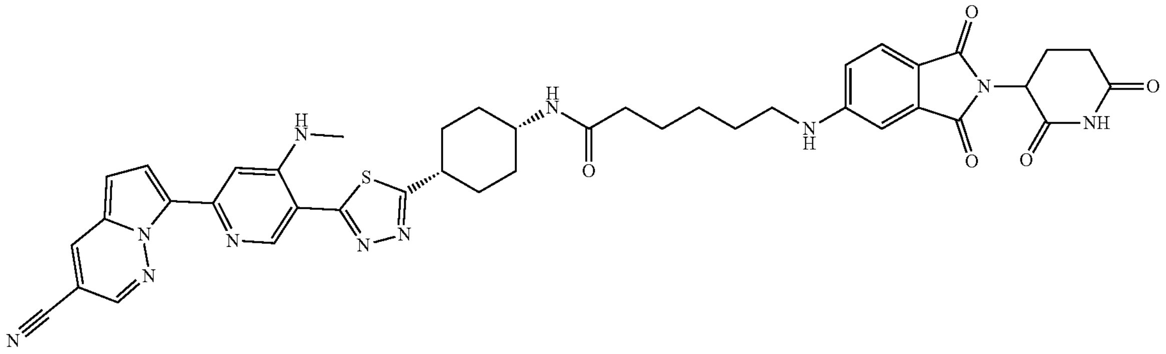 [SMILES: CNc1cc(-c2ccc3cc(C#N)cnn23)ncc1-c1nnc([C@H]2CC[C@@H](NC(=O)CCCCCNc3ccc4c(c3)C(=O)N(C3CCC(=O)NC3=O)C4=O)CC2)s1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-6-((2-(2,6-dioxopiperidin-3-yl)-1,3-dioxoisoindolin-5-yl)amino)hexanamide The title compound was synthesized from BB14 and 6-((2-(2,6-dioxopiperidin-3-yl)-1,3-dioxoisoindolin-5-yl)amino)hexanoic acid by amide coupling using General Method A. LCMS: $C_{41}H_{41}N_{11}O_5S$ requires: 799.3. found: m/z=800.2 $[M+H]^+$; $^1H$ NMR (500 MHz, Acetonitrile-$d_3$) δ 9.99 (s, 1H), 8.89 (s, 1H), 8.73-8.50 (m, 2H), 8.11 (d, J=5.2 Hz, 2H), 7.71 (s, 1H), 7.50 (d, J=8.3 Hz, 1H), 7.22 (d, J=5.1 Hz, 1H), 6.92 (d, J=2.2 Hz, 1H), 6.80 (dd, J=8.4, 2.2 Hz, 1H), 6.45 (d, J=7.4 Hz, 1H), 4.89 (dd, J=12.6, 5.5 Hz, 1H), 4.00 (s, 1H), 3.39 (s, 1H), 3.30 (d, J=5.0 Hz, 1H), 3.22 (t, J=7.0 Hz, 1H), 2.91-2.10 (m, 16H), 2.04 (d, J=4.3 Hz, 2H), 1.79 (d, J=5.3 Hz, 2H), 1.65 (d, J=8.2 Hz, 2H), 1.44 (s, 2H).

Example 115

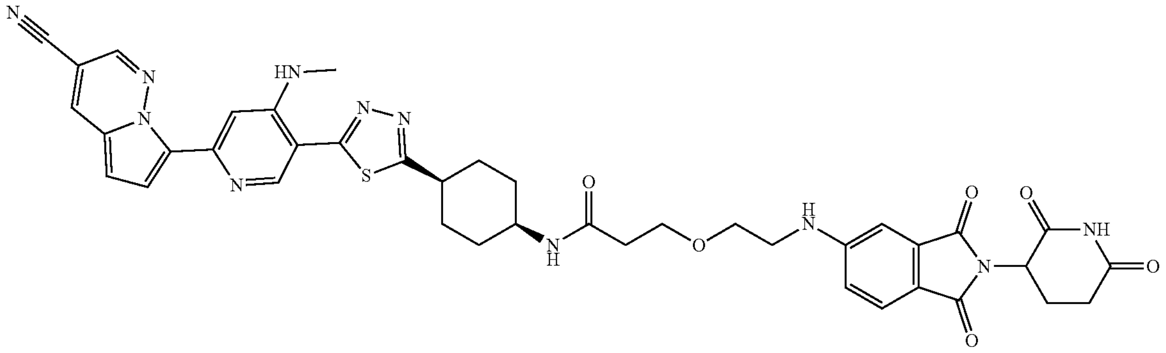 [SMILES: CNc1cc(-c2ccc3cc(C#N)cnn23)ncc1-c1nnc([C@H]2CC[C@@H](NC(=O)CCOCCNc3ccc4c(c3)C(=O)N(C3CCC(=O)NC3=O)C4=O)CC2)s1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-3-(2-((2-(2,6-dioxopiperidin-3-yl)-1,3-dioxoisoindolin-5-yl)amino)ethoxy)propanamide The title compound was synthesized from BB14 and 3-(2-((2-(2,6-dioxopiperidin-3-yl)-1,3-dioxoisoindolin-5-yl)amino)ethoxy)propanoic acid by amide coupling using General Method A. LCMS: $C_{40}H_{39}N_{11}O_6S$ requires: 801.3. found: m/z=802.6 $[M+H]^+$; $^1H$ NMR (500 MHz, Acetonitrile-$d_3$) δ 10.02 (s, 1H), 8.90 (s, 1H), 8.70-8.60 (m, 1H), 8.48 (s, 1H), 8.09 (d, J=5.0 Hz, 1H), 7.56 (s, 1H), 7.46 (d, J=8.3 Hz, 1H), 7.23 (d, J=5.1 Hz, 1H), 6.94 (d, J=2.2 Hz, 1H), 6.81 (dd, J=8.3, 2.2 Hz, 1H), 6.67 (d, J=7.3 Hz, 1H), 4.86 (dd, J=12.7, 5.4 Hz, 1H), 4.04 (s, 1H), 3.82-3.60 (m, 5H), 3.39 (s, 4H), 3.33 (dd, J=33.0, 5.2 Hz, 7H), 3.07 (s, 6H), 2.88-2.51 (m, 6H), 2.43 (t, J=5.7 Hz, 2H), 2.10-1.99 (m, 3H), 1.81 (d, J=4.9 Hz, 3H).

Example 116

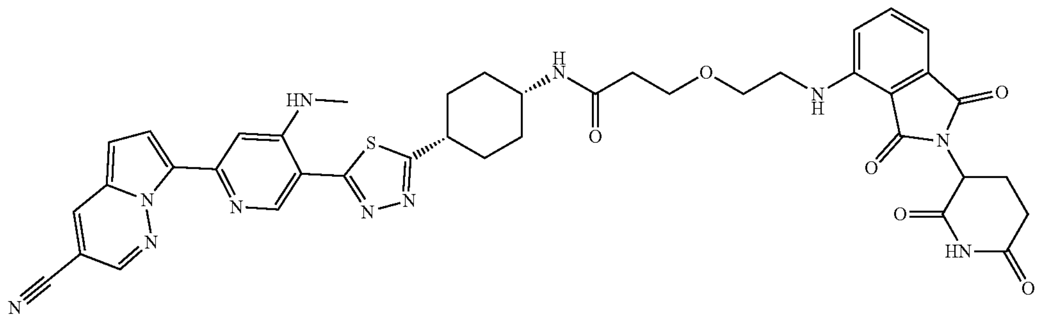 [SMILES: CNc1cc(-c2ccc3cc(C#N)cnn23)ncc1-c1nnc([C@H]2CC[C@@H](NC(=O)CCOCCNc3cccc4c3C(=O)N(C3CCC(=O)NC3=O)C4=O)CC2)s1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-3-(2-((2-(2,6-dioxopiperidin-3-yl)-1,3-dioxoisoindolin-4-yl)amino)ethoxy)propanamide The title compound was synthesized from BB14 and 3-(2-((2-(2,6-dioxopiperidin-3-yl)-1,3-dioxoisoindolin-4-yl)amino)ethoxy)propanoic acid by amide coupling using General Method A. LCMS: $C_{40}H_{39}N_{11}O_6S$ requires: 801.3. found: m/z=802.6 $[M+H]^+$; $^1H$ NMR (500 MHz, Acetonitrile-$d_3$) δ 10.00 (s, 1H), 9.00 (s, 1H), 8.69-8.61 (m, 1H), 8.50 (s, 1H), 8.10 (d, J=5.1 Hz, 1H), 7.61 (s, 1H), 7.46 (dd, J=8.6, 7.1 Hz, 1H), 7.23 (d, J=5.0 Hz, 1H), 6.99 (d, J=8.5 Hz, 1H), 6.91 (d, J=7.0 Hz, 1H), 6.60 (d, J=6.9 Hz, 1H), 4.93 (dd, J=12.8, 5.4 Hz, 1H), 4.02 (s, 1H), 3.72 (dt, J=35.5, 5.6 Hz, 3H), 3.45 (d, J=5.3 Hz, 2H), 3.31 (d, J=5.0 Hz, 4H), 3.25-2.45 (m, 13H), 2.42 (t, J=5.9 Hz, 2H), 2.17-2.01 (m, 2H), 1.79 (d, J=4.6 Hz, 3H).

Example 117

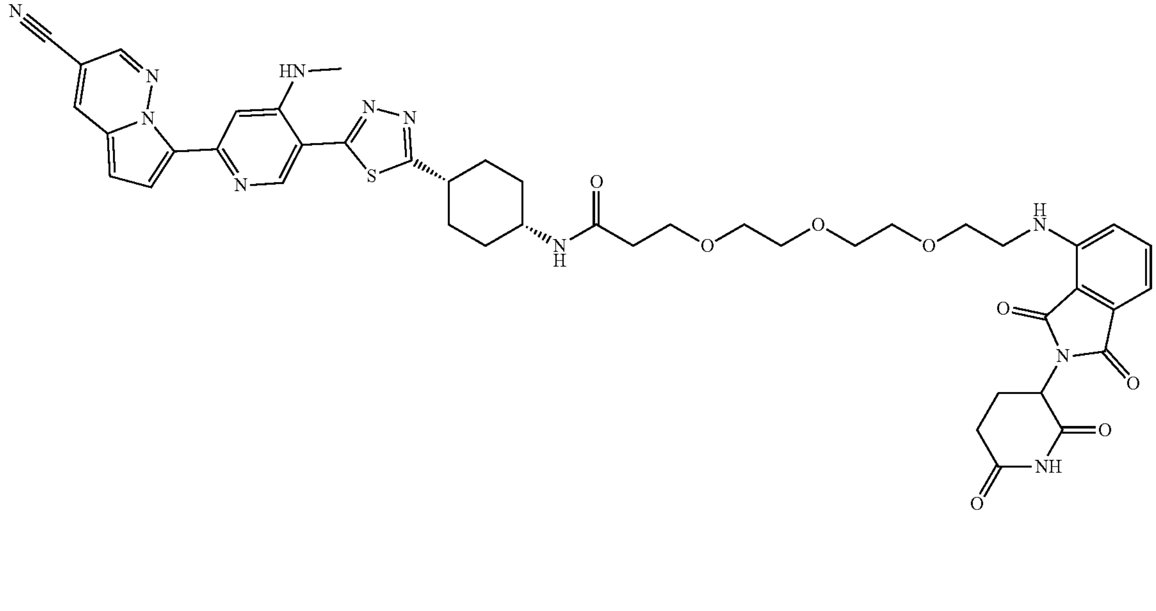 [SMILES: CNc1cc(-c2ccc3cc(C#N)cnn23)ncc1-c1nnc([C@H]2CC[C@@H](NC(=O)CCOCCOCCOCCNc3cccc4c3C(=O)N(C3CCC(=O)NC3=O)C4=O)CC2)s1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-3-(2-(2-(2-((2-(2,6-dioxopiperidin-3-yl)-1,3-dioxoisoindolin-4-yl)amino)ethoxy)ethoxy)ethoxy)propanamide The title compound was synthesized from BB14 and 3-(2-(2-(2-((2-(2,6-dioxopiperidin-3-yl)-1,3-dioxoisoindolin-4-yl)amino)ethoxy)ethoxy)ethoxy)propanoic acid by amide coupling using General Method A. LCMS: $C_{44}H_{47}N_{11}O_8S$ requires: 889.3. found: m/z=890.6 $[M+H]^+$; $^1H$ NMR (500 MHz, Acetonitrile-$d_3$) δ 9.92 (s, 1H), 9.16 (s, 1H), 8.60 (dd, J=6.4, 2.7 Hz, 2H), 8.05 (d, J=5.0 Hz, 1H), 7.66 (s, 1H), 7.37 (t, J=7.9 Hz, 1H), 7.18 (d, J=5.0 Hz, 1H), 6.89 (d, J=8.6 Hz, 1H), 6.82 (d, J=7.0 Hz, 1H), 6.74 (d, J=7.7 Hz, 1H), 6.32 (s, 1H), 5.02-4.84 (m, 2H), 4.02 (d, J=6.4 Hz, 2H), 3.68 (t, J=5.9 Hz, 2H), 3.64-3.50 (m, 4H), 3.34 (d, J=5.2 Hz, 2H), 3.26 (d, J=5.0 Hz, 1H), 2.83-2.55 (m, 5H), 1.97 (p, J=2.4 Hz, 10H), 1.80 (d, J=5.9 Hz, 2H).

Example 118

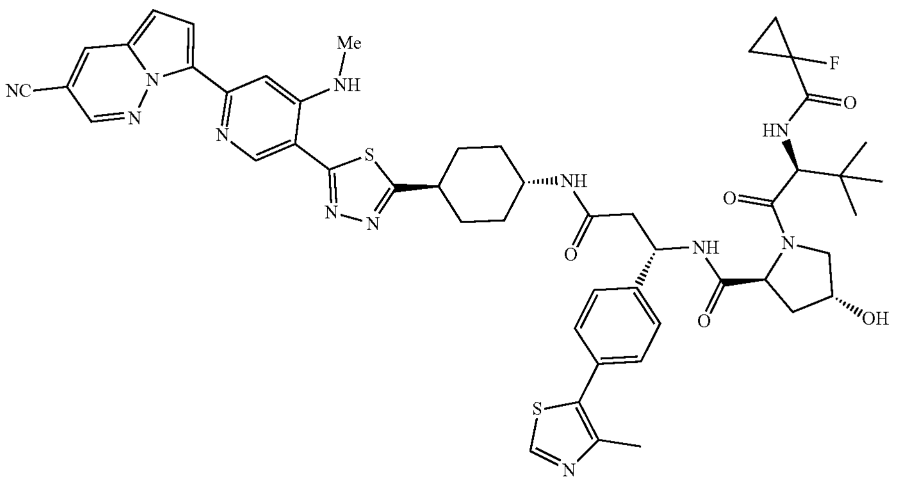 [SMILES: CNc1cc(-c2ccc3cc(C#N)cnn23)ncc1-c1nnc([C@H]2CC[C@H](NC(=O)C[C@H](NC(=O)[C@@H]3C[C@@H](O)CN3C(=O)[C@@H](NC(=O)C3(F)CC3)C(C)(C)C)c3ccc(-c4scnc4C)cc3)CC2)s1]

(2S,4R)—N—((S)-3-(((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB3 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{50}H_{55}FN_{12}O_5S_2$ requires: 986.4. found: m/z=988.1 $[M+H]^+$; $^1H$ NMR (500 MHz, Acetonitrile-$d_3$) δ 10.04 (s, 1H), 8.81 (s, 1H), 8.72-8.60 (m, 2H), 8.52 (s, 1H), 8.08 (d, J=5.1 Hz, 1H), 7.63 (s, 1H), 7.56 (s, 1H), 7.53-7.33 (m, 3H), 7.22 (d, J=5.1 Hz, 1H), 7.11 (d, J=9.3 Hz, 1H), 6.62 (d, J=7.9 Hz, 1H), 5.26 (d, J=7.0 Hz, 1H), 4.69 (d, J=9.1 Hz, 1H), 4.53 (s, 2H), 4.43 (s, 1H), 3.88-3.66 (m, 3H), 3.31 (d, J=5.1 Hz, 4H), 3.22-2.59 (m, 18H), 2.52 (s, 3H), 2.22 (d, J=13.8 Hz, 4H), 1.74 (dd, J=12.3, 3.3 Hz, 3H), 1.44-1.21 (m, 5H), 1.07 (s, 4H).

Example 119

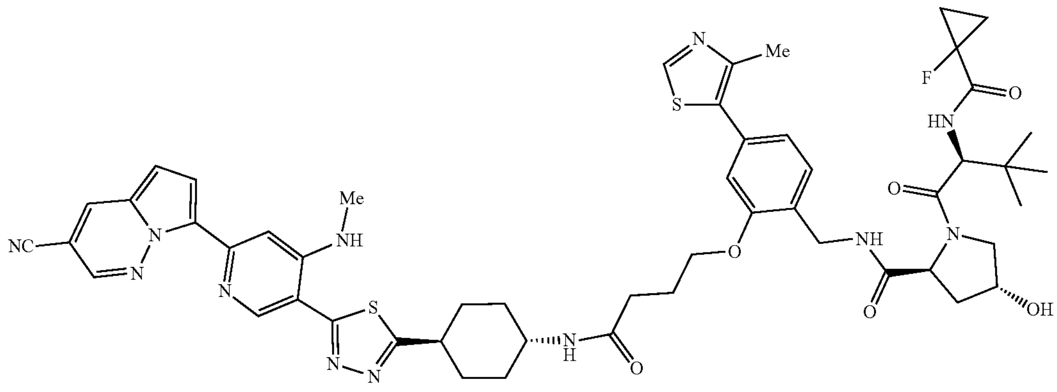 [SMILES: CNc1cc(-c2ccc3cc(C#N)cnn23)ncc1-c1nnc([C@H]2CC[C@H](NC(=O)CCCOc3cc(-c4scnc4C)ccc3CNC(=O)[C@@H]3C[C@@H](O)CN3C(=O)[C@@H](NC(=O)C3(F)CC3)C(C)(C)C)CC2)s1]

(2S,4R)—N-(2-(4-(((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)amino)-4-oxobutoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB3 and 4-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]butanoic acid by amide coupling using General Method A. LCMS: $C_{52}H_{59}FN_{12}O_6S_2$ requires: 1030.4. found: m/z=1031.9 $[M+H]^+$; $^1H$ NMR (500 MHz, Acetonitrile-$d_3$) δ 9.97 (s, 2H), 8.78 (s, 1H), 8.64 (d, J=12.2 Hz, 2H), 8.11 (d, J=5.1 Hz, 1H), 7.71 (s, 1H), 7.42 (d, J=7.8 Hz, 1H), 7.28 (s, 1H), 7.22 (d, J=5.1 Hz, 1H), 7.13-6.96 (m, 2H), 6.63 (d, J=8.0 Hz, 1H), 4.68 (d, J=9.3 Hz, 2H), 4.57 (s, 2H), 4.50-4.35 (m, 2H), 4.11 (t, J=5.7 Hz, 2H), 3.86-3.68 (m, 3H), 3.30 (d, J=5.0 Hz, 2H), 3.23 (s, 1H), 2.02 (s, 1H), 1.97 (q, J=2.6 Hz, 14H), 1.76 (s, 2H), 1.31 (td, J=27.9, 25.2, 11.1 Hz, 5H), 1.00 (s, 4H).

Example 120

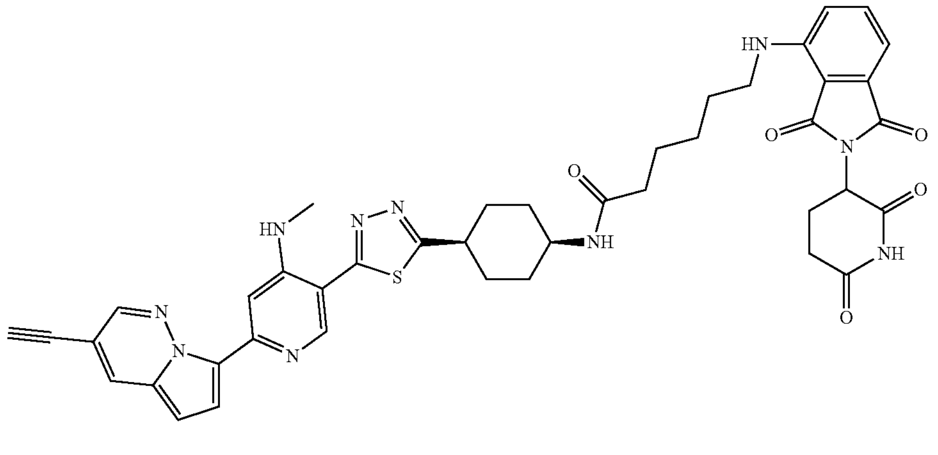 [SMILES: C#Cc1cnn2c(-c3cc(NC)c(-c4nnc([C@H]5CC[C@@H](NC(=O)CCCCCNc6cccc7c6C(=O)N(C6CCC(=O)NC6=O)C7=O)CC5)s4)cn3)ccc2c1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-6-((2-(2,6-dioxopiperidin-3-yl)-1,3-dioxoisoindolin-4-yl)amino)hexanamide The title compound was synthesized from BB14 and 6-((2-(2,6-dioxopiperidin-3-yl)-1,3-dioxoisoindolin-4-yl)amino)hexanoic acid by amide coupling using General Method A. LCMS: $C_{41}H_{41}N_{11}O_5S$ requires: 799.3. found: m/z=800.7 $[M+H]^+$; $^1H$ NMR (500 MHz, Acetonitrile-$d_3$) δ 9.89 (s, 2H), 8.98 (s, 2H), 8.72-8.52 (m, 3H), 8.11 (d, J=5.1 Hz, 2H), 7.80 (s, 1H), 7.51 (t, J=7.8 Hz, 2H), 7.20 (d, J=5.0 Hz, 2H), 6.99 (dd, J=20.5, 7.8 Hz, 3H), 6.46 (s, 2H), 6.30 (s, 2H), 4.93 (dd, J=12.7, 5.4 Hz, 3H), 4.00 (d, J=6.7 Hz, 2H), 3.38 (t, J=4.6 Hz, 2H), 3.29 (t, J=7.7 Hz, 3H), 2.89-2.51 (m, 9H), 1.78 (d, J=6.0 Hz, 3H), 1.67 (dt, J=11.4, 7.3 Hz, 4H), 1.44 (d, J=7.1 Hz, 3H).

Example 121

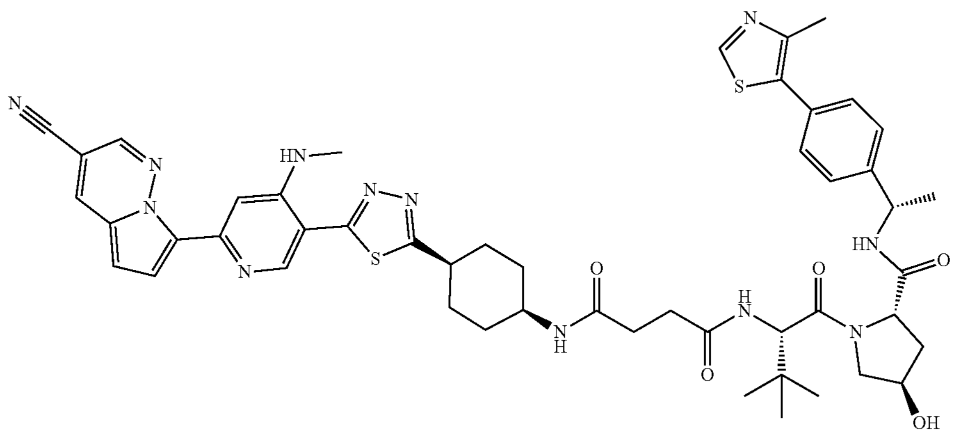 [SMILES: CNc1cc(-c2ccc3cc(C#N)cnn23)ncc1-c1nnc([C@H]2CC[C@@H](NC(=O)CCC(=O)N[C@H](C(=O)N3C[C@H](O)C[C@H]3C(=O)N[C@@H](C)c3ccc(-c4scnc4C)cc3)C(C)(C)C)CC2)s1]

$N_1$-((1s,4R)-4-(5-(6-(3-cyanopyrrolo[1,2-b]pyridazin-7-yl)-4-(methylamino)pyridin-3-yl)-1,3,4-thiadiazol-2-yl)cyclohexyl)-$N_4$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)succinamide The title compound was synthesized from BB14 and 3-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}propanoic acid by amide coupling using General Method A. LCMS: $C_{49}H_{56}N_{12}O_5S_2$ requires: 956.4. found: m/z=957.9 $[M+H]^+$; $^1H$ NMR (500 MHz, Acetonitrile-$d_3$) δ 10.02 (s, 2H), 8.77 (s, 1H), 8.73-8.53 (m, 3H), 8.10 (d, J=5.0 Hz, 2H), 7.66 (s, 1H), 7.56-7.31 (m, 4H), 7.20 (dd, J=20.2, 6.3 Hz, 2H), 6.96 (d, J=8.8 Hz, 2H), 6.71 (s, 2H), 5.03-4.87 (m, 2H), 4.59-4.43 (m, 3H), 4.38 (s, 2H), 4.00 (s, 2H), 3.80 (d, J=11.0 Hz, 2H), 3.64 (dd, J=11.1, 4.0 Hz, 2H), 3.40 (dt, J=8.9, 4.4 Hz, 2H), 3.30 (d, J=5.1 Hz, 3H), 2.05 (dd, J=8.8, 4.2 Hz, 7H), 1.88-1.67 (m, 5H), 1.45 (d, J=6.9 Hz, 4H), 1.30 (s, 2H), 1.00 (s, 7H).

Example 122

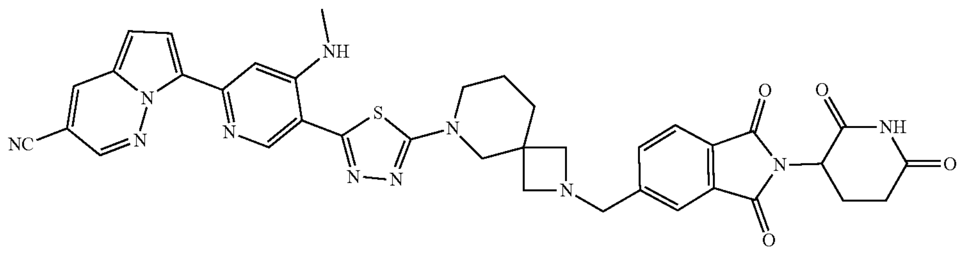 [SMILES: CNc1cc(-c2ccc3cc(C#N)cnn23)ncc1-c1nnc(N2CCCC3(CN(Cc4ccc5c(c4)C(=O)N(C4CCC(=O)NC4=O)C5=O)C3)C2)s1]

7-(5-(5-(2-((2-(2,6-dioxopiperidin-3-yl)-1,3-dioxoisoindolin-5-yl)methyl)-2,6-diazaspiro[3.5]nonan-6-yl)-1,3,4-thiadiazol-2-yl)-4-(methylamino)pyridin-2-yl)pyrrolo[1,2-b]pyridazine-3-carbonitrile The title compound was synthesized from BB15 and 2-(2,6-dioxopiperidin-3-yl)-1,3-dioxoisoindoline-5-carbaldehyde by reductive amination using General Method B. LCMS: $C_{37}H_{33}N_{11}O_4S$ requires: 727.2. found: m/z=728.5 $[M+H]^+$; $^1H$ NMR (500 MHz, Methanol-$d_4$) δ 8.81-8.75 (m, 1H), 8.72-8.64 (m, 1H), 8.50 (d, J=4.7 Hz, 1H), 8.11 (d, J=4.4 Hz, 2H), 8.07-7.96 (m, 2H), 7.86 (d, J=4.6 Hz, 1H), 7.26 (t, J=5.0 Hz, 1H), 5.19 (dd, J=12.6, 5.3 Hz, 1H), 4.70 (d, J=4.5 Hz, 2H), 4.15 (d, J=14.0 Hz, 4H), 3.99 (d, J=4.6 Hz, 2H), 3.67-3.49 (m, 3H), 2.90 (ddd, J=19.0, 14.3, 5.1 Hz, 1H), 2.83-2.67 (m, 2H), 2.25-2.12 (m, 1H), 2.10 (q, J=5.4 Hz, 2H), 1.83 (d, J=7.5 Hz, 2H).

Example 123

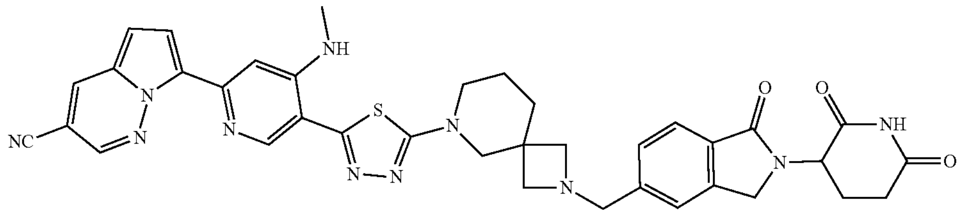 [SMILES: CNc1cc(-c2ccc3cc(C#N)cnn23)ncc1-c1nnc(N2CCCC3(CN(Cc4ccc5c(c4)CN(C4CCC(=O)NC4=O)C5=O)C3)C2)s1]

7-(5-(5-(2-((2-(2,6-dioxopiperidin-3-yl)-1-oxoisoindolin-5-yl)methyl)-2,6-diazaspiro[3.5]nonan-6-yl)-1,3,4-thiadiazol-2-yl)-4-(methylamino)pyridin-2-yl)pyrrolo[1,2-b]pyridazine-3-carbonitrile The title compound was synthesized from BB15 and 2-(2,6-dioxopiperidin-3-yl)-1-oxoisoindoline-5-carbaldehyde by amide coupling using General Method A. LCMS: $C_{37}H_{35}N_{11}O_3S$ requires: 713.3. found: m/z=714.7 $[M+H]^+$; $^1H$ NMR (500 MHz, Methanol-$d_4$) δ 8.78 (d, J=2.1 Hz, 1H), 8.69 (d, J=2.1 Hz, 1H), 8.50 (d, J=9.8 Hz, 1H), 8.11 (d, J=5.0 Hz, 1H), 7.93 (t, J=9.4 Hz, 1H), 7.85 (d, J=3.4 Hz, 1H), 7.78 (s, 1H), 7.70 (d, J=8.0 Hz, 1H), 7.25 (d, J=5.1 Hz, 1H), 5.20 (dd, J=13.3, 5.1 Hz, 1H), 4.58 (dd, J=27.6, 16.7 Hz, 4H), 4.12 (s, 3H), 3.99-3.85 (m, 3H), 3.59 (t, J=5.4 Hz, 2H), 2.93 (ddd, J=18.5, 13.5, 5.4 Hz, 1H), 2.81 (ddd, J=17.5, 4.6, 2.3 Hz, 1H), 2.51 (td, J=13.3, 4.7 Hz, 1H), 2.29-2.10 (m, 1H), 2.10-2.00 (m, 2H), 1.83 (s, 3H).

Example 124

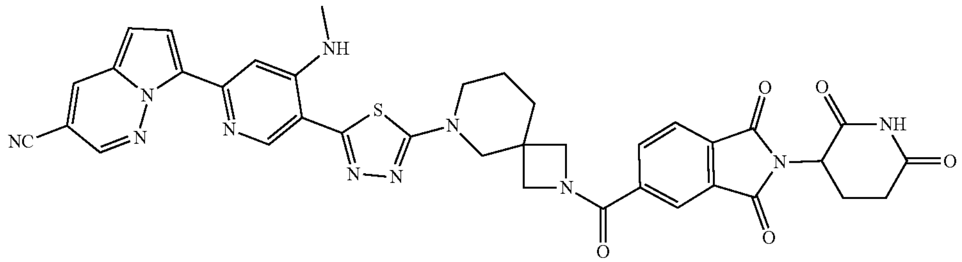 [SMILES: CNc1cc(-c2ccc3cc(C#N)cnn23)ncc1-c1nnc(N2CCCC3(CN(C(=O)c4ccc5c(c4)C(=O)N(C4CCC(=O)NC4=O)C5=O)C3)C2)s1]

7-(5-(5-(2-(2-(2,6-dioxopiperidin-3-yl)-1,3-dioxoisoindoline-5-carbonyl)-2,6-diazaspiro[3.5]nonan-6-yl)-1,3,4-thiadiazol-2-yl)-4-(methylamino)pyridin-2-yl)pyrrolo[1,2-b]pyridazine-3-carbonitrile The title compound was synthesized from BB15 and 2-(2,6-dioxopiperidin-3-yl)-1,3-dioxoisoindoline-5-carboxylic acid by amide coupling using General Method A. LCMS: $C_{37}H_{31}N_{11}O_5S$ requires: 741.2. found: m/z=742.6 $[M+H]^+$; $^1H$ NMR (500 MHz, Methanol-$d_4$) δ 8.78 (d, J=2.1 Hz, 1H), 8.70 (d, J=2.2 Hz, 1H), 8.48 (s, 1H), 8.23-8.12 (m, 2H), 8.10 (d, J=5.1 Hz, 1H), 8.01 (d, J=7.7 Hz, 1H), 7.82 (s, 1H), 7.25 (d, J=5.0 Hz, 1H), 5.18 (dd, J=12.6, 5.5 Hz, 1H), 4.20 (s, 2H), 4.12-3.95 (m, 3H), 3.92 (d, J=6.1 Hz, 2H), 3.64 (t, J=5.6 Hz, 3H), 2.88 (ddd, J=18.9, 14.2, 5.3 Hz, 1H), 2.81-2.71 (m, 2H), 2.22-2.09 (m, 1H), 2.04 (t, J=6.0 Hz, 2H), 1.89-1.69 (m, 2H), 1.35 (dd, J=7.0, 4.5 Hz, 1H).

Example 125

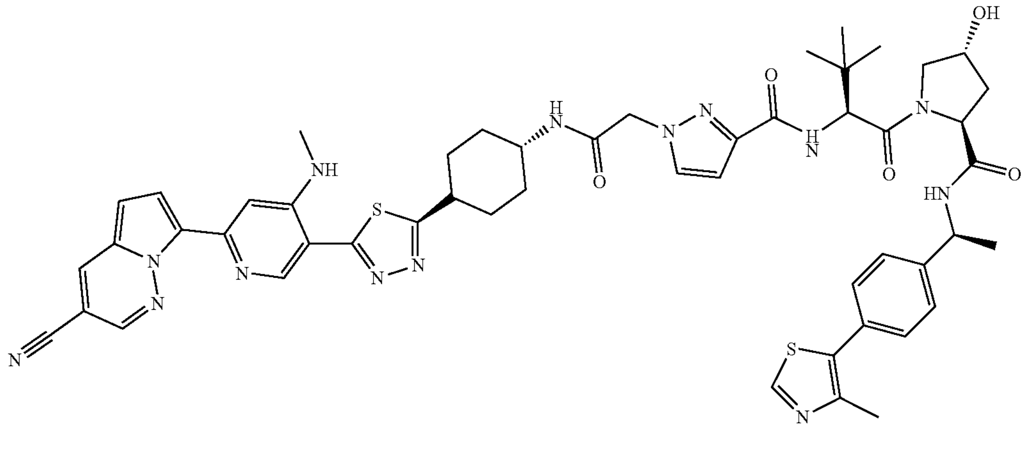

1-(2-(((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)amino)-2-oxoethyl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-1H-pyrazole-3-carboxamide BB3 (25 mg, 0.05 mmol), [3-(tert-butoxycarbonyl)pyrazol-1-yl]acetic acid (11 mg, 0.05 mml) and HATU (19 mg, 0.05 mmol) were combined and suspended in 2 mL dichloromethane. DIPEA (0.04 mL, 0.25 mmol) was added and the mixture was stirred overnight at room temperature. Concentrated in vacuo, then resuspended in 2 mL dichloromethane. Added 0.2 mL of trifluoroacetic acid and stirred overnight at room temperature. Concentrated reaction to a crude oil. Added HATU (19 mg, 0.05 mmol) followed by (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (22 mg, 0.05 mmol). Suspended in 2 mL DMF, added DIPEA (0.04 mL, 0.25 mmol) and stirred overnight at room temperature. Purified by prep-HPLC to give the title compound. LCMS: $C_{51}H_{56}N_{14}O_5S_2$ requires: 1008.4. found: m/z=1009.8 $[M+H]^+$; $^1H$ NMR (500 MHz, Acetonitrile-$d_3$) δ 8.75 (d, J=2.0 Hz, 1H), 8.69-8.55 (m, 1H), 8.10 (d, J=5.1 Hz, 1H), 7.78-7.65 (m, 1H), 7.53-7.38 (m, 2H), 7.19 (dd, J=21.8, 6.3 Hz, 1H), 6.74 (d, J=2.4 Hz, 1H), 6.66 (d, J=7.9 Hz, 1H), 4.98 (d, J=7.1 Hz, 1H), 4.83 (s, 1H), 4.78 (d, J=9.4 Hz, 1H), 4.52 (t, J=8.2 Hz, 1H), 4.41 (s, 1H), 3.82 (d, J=11.2 Hz, 2H), 3.73 (d, J=4.0 Hz, 1H), 3.29 (d, J=5.2 Hz, 3H), 2.49 (s, 2H), 1.97 (p, J=2.5 Hz, 13H), 1.84-1.69 (m, 2H), 1.47 (d, J=7.2 Hz, 2H), 1.07 (s, 3H).

Example 126

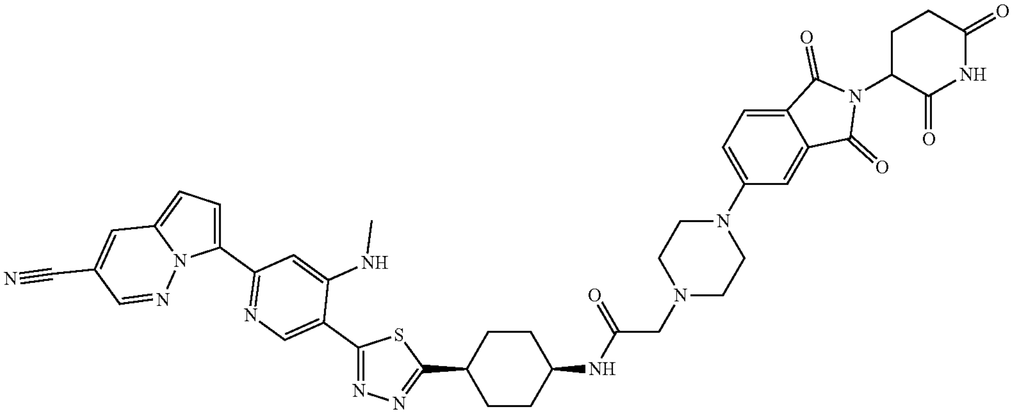 [SMILES: CNc1cc(-c2ccc3cc(C#N)cnn23)ncc1-c1nnc([C@H]2CC[C@@H](NC(=O)CN3CCN(c4ccc5c(c4)C(=O)N(C4CCC(=O)NC4=O)C5=O)CC3)CC2)s1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-2-(4-(2-(2,6-dioxopiperidin-3-yl)-1,3-dioxoisoindolin-5-yl)piperazin-1-yl)acetamide The title compound was synthesized from BB14 and 2-(4-(2-(2,6-dioxopiperidin-3-yl)-1,3-dioxoisoindolin-5-yl)piperazin-1-yl)acetic acid by amide coupling using General Method A. LCMS: $C_{41}H_{40}N_{12}O_5S$ requires: 812.3. found: m/z=813.6 $[M+H]^+$; $^1H$ NMR (500 MHz, DMSO-$d_6$) δ 11.10 (d, J=3.2 Hz, 1H), 10.25 (s, 1H), 9.08 (s, 2H), 8.94 (d, J=2.2 Hz, 1H), 8.82 (t, J=3.3 Hz, 1H), 8.74 (s, 1H), 8.59 (s, 1H), 8.12 (d, J=16.6 Hz, 1H), 7.99 (d, J=4.8 Hz, 1H), 7.78 (dd, J=8.6, 3.5 Hz, 1H), 7.48 (d, J=2.4 Hz, 1H), 7.34 (dd, J=8.8, 2.4 Hz, 1H), 7.21 (t, J=4.9 Hz, 1H), 5.10 (dd, J=12.7, 5.4 Hz, 1H), 4.20 (s, 2H), 4.02 (s, 3H), 3.57 (s, 1H), 3.43 (s, 2H), 3.30 (s, 1H), 3.18 (d, J=4.9 Hz, 3H), 2.97-2.85 (m, 2H), 2.62 (s, 1H), 2.04 (s, 5H), 2.02 (d, J=5.4 Hz, 1H), 1.79 (s, 2H), 1.73 (s, 3H), 1.43 (s, 1H), 1.25 (s, 1H).

Example 127

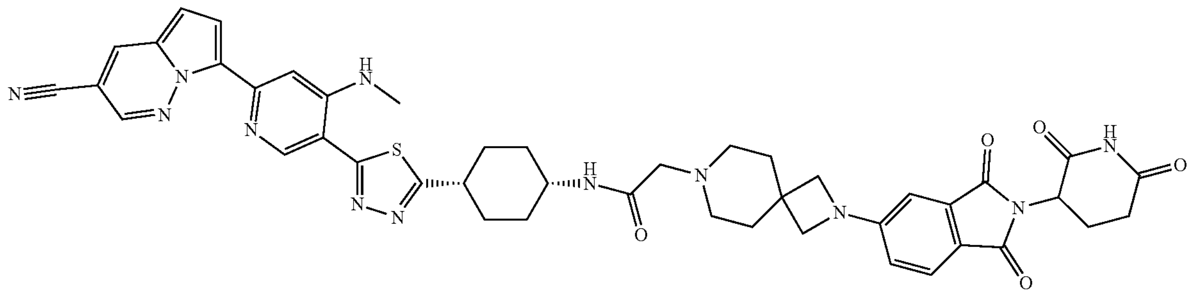 [SMILES: CNc1cc(-c2ccc3cc(C#N)cnn23)ncc1-c1nnc([C@H]2CC[C@@H](NC(=O)CN3CCC4(CC3)CN(c3ccc5c(c3)C(=O)N(C3CCC(=O)NC3=O)C5=O)C4)CC2)s1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-2-(2-(2-(2,6-dioxopiperidin-3-yl)-1,3-dioxoisoindolin-5-yl)-2,7-diazaspiro[3.5]nonan-7-yl)acetamide The title compound was synthesized from BB14 and 2-(2-(2-(2,6-dioxopiperidin-3-yl)-1,3-dioxoisoindolin-5-yl)-2,7-diazaspiro[3.5]nonan-7-yl)acetic acid by amide coupling using General Method A. LCMS: $C_{44}H_{44}N_{12}O_5S$ requires: 852.3. found: m/z=853.6 $[M+H]^+$; $^1H$ NMR (500 MHz, DMSO-$d_6$) δ 11.08 (s, 1H), 9.70 (s, 1H), 8.93 (s, 1H), 8.81 (d, J=2.3 Hz, 1H), 8.74 (s, 1H), 8.56 (d, J=7.2 Hz, 1H), 8.15 (s, 1H), 7.98 (s, 1H), 7.69 (d, J=8.2 Hz, 1H), 7.20 (d, J=4.9 Hz, 1H), 6.78 (s, 1H), 6.66 (d, J=8.9 Hz, 1H), 5.06 (dd, J=12.6, 5.5 Hz, 1H), 4.02 (s, 1H), 3.94 (d, J=4.2 Hz, 2H), 3.90 (s, 2H), 3.82 (s, 2H), 3.17 (d, J=4.9 Hz, 3H), 3.09 (s, 2H), 2.89 (s, 1H), 2.61 (s, 1H), 2.12 (d, J=13.9 Hz, 2H), 2.03 (s, 8H), 1.79 (s, 2H), 1.73 (s, 2H), 1.25 (s, 1H).

Example 128

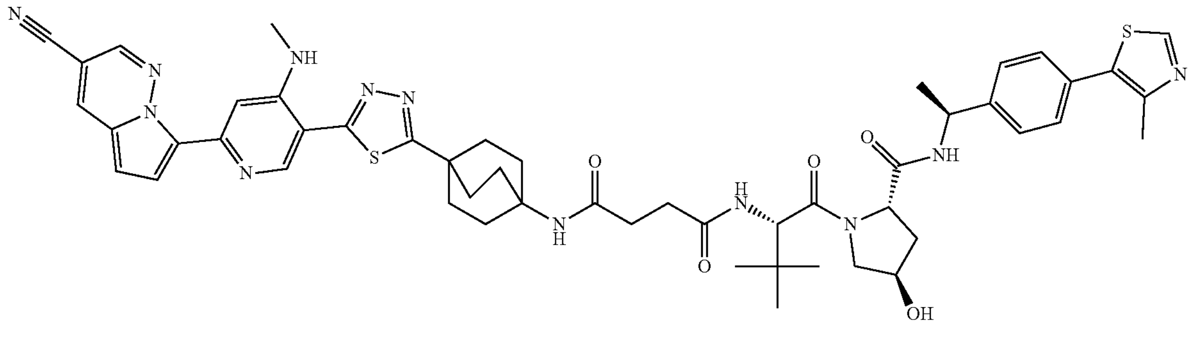 [SMILES: CNc1cc(-c2ccc3cc(C#N)cnn23)ncc1-c1nnc(C23CCC(NC(=O)CCC(=O)N[C@H](C(=O)N4C[C@H](O)C[C@H]4C(=O)N[C@@H](C)c4ccc(-c5scnc5C)cc4)C(C)(C)C)(CC2)CC3)s1]

N1-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-$N_4$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)succinamide The title compound was synthesized from BB13 and 3-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}propanoic acid by amide coupling using General Method A. LCMS: $C_{51}H_{58}N_{12}O_5S_2$ requires: 982.4. found: m/z=983.7 $[M+H]^+$; $^1H$ NMR (500 MHz, DMSO-$d_6$) δ 8.99 (d, J=7.2 Hz, 2H), 8.86 (d, J=2.2 Hz, 2H), 8.73 (s, 2H), 8.38 (d, J=7.7 Hz, 2H), 8.08-7.98 (m, 2H), 7.85 (d, J=9.2 Hz, 2H), 7.58-7.33 (m, 6H), 7.24 (d, J=4.9 Hz, 2H), 4.93 (t, J=7.2 Hz, 2H), 4.52 (d, J=9.3 Hz, 2H), 4.44 (t, J=8.0 Hz, 2H), 4.30 (s, 2H), 3.20 (d, J=4.8 Hz, 5H), 2.47 (s, 3H), 2.43-2.24 (m, 5H), 2.04 (ddt, J=35.1, 12.1, 6.5 Hz, 10H), 1.81 (ddd, J=12.9, 8.5, 4.8 Hz, 2H), 1.39 (d, J=6.9 Hz, 3H), 0.95 (s, 7H).

Example 129

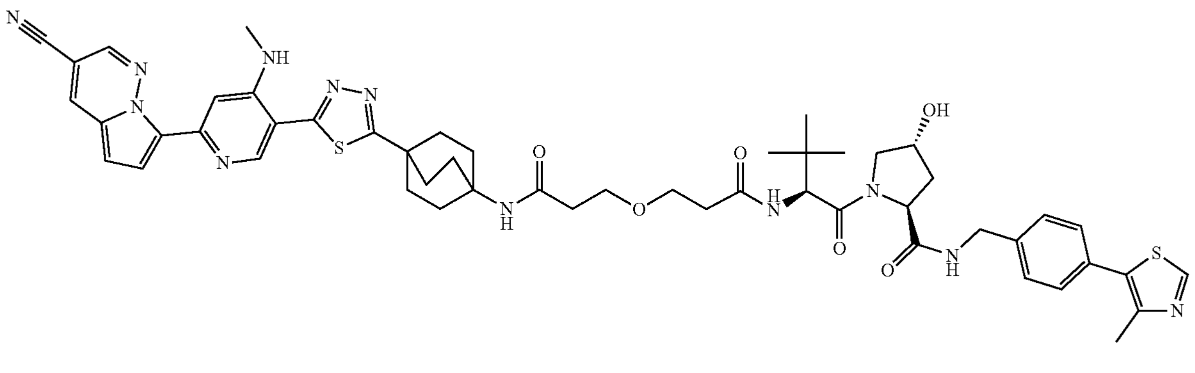 [SMILES: CNc1cc(-c2ccc3cc(C#N)cnn23)ncc1-c1nnc(C23CCC(NC(=O)CCOCCC(=O)N[C@H](C(=O)N4C[C@H](O)C[C@H]4C(=O)NCc4ccc(-c5scnc5C)cc4)C(C)(C)C)(CC2)CC3)s1]

((2S,4R)-1-((S)-2-(3-(3-((4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)amino)-3-oxopropoxy)propanamido)-3,3-dimethylbutanoyl)-4-hydroxy-N-(4-(4-methylthiazol-5-yl)benzyl)pyrrolidine-2-carboxamide The title compound was synthesized from BB13 and 3-[3-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-3-oxo-propoxy]propanoic acid by amide coupling using General Method A. LCMS: $C_{52}H_{60}N_{12}O_6S_2$ requires: 1012.42. found: m/z=1013.71 $[M+H]^+$; $^1H$ NMR (500 MHz, DMSO-$d_6$) δ 9.03-8.94 (m, 2H), 8.85 (d, J=2.3 Hz, 2H), 8.73 (s, 2H), 8.58 (t, J=6.1 Hz, 2H), 8.05 (s, 2H), 7.93 (s, 2H), 7.51-7.29 (m, 5H), 7.23 (d, J=4.9 Hz, 1H), 4.56 (d, J=9.4 Hz, 2H), 4.50-4.40 (m, 2H), 4.37 (s, 1H), 4.31-4.22 (m, 2H), 3.70-3.57 (m, 5H), 3.19 (d, J=4.9 Hz, 5H), 2.46 (s, 5H), 2.29 (s, 3H), 2.18-1.92 (m, 11H), 0.96 (s, 9H).

Example 130

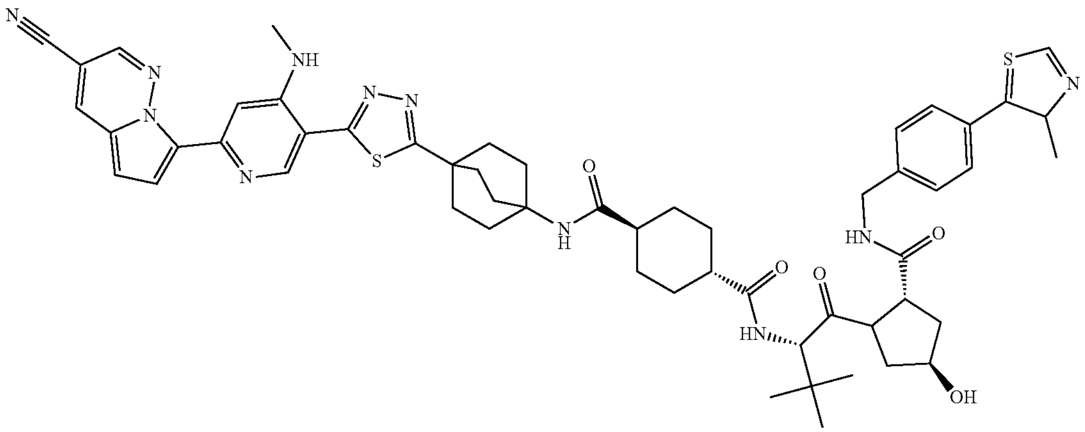

(1S,4r)-$N_1$-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-$N_4$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)cyclohexane-1,4-dicarboxamide The title compound was synthesized from BB13 and 4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamoyl)-trans-cyclohexane-1-carboxylic acid by amide coupling using General Method A. LCMS: $C_{54}H_{62}N_{12}O_5S_2$ requires: 1022.44. found: m/z=1023.78 $[M+H]^+$; $^1H$ NMR (500 MHz, DMSO-$d_6$) δ 9.00 (s, 3H), 8.95 (s, 2H), 8.83 (s, 2H), 8.72 (s, 3H), 8.57 (t, J=6.1 Hz, 2H), 8.05 (d, J=23.8 Hz, 5H), 7.77 (d, J=9.3 Hz, 3H), 7.42 (q, J=8.1 Hz, 4H), 7.35 (s, 3H), 7.21 (d, J=5.0 Hz, 2H), 4.52 (d, J=9.2 Hz, 3H), 4.49-4.41 (m, 3H), 4.37 (s, 3H), 4.23 (dd, J=15.9, 5.6 Hz, 4H), 3.70-3.56 (m, 6H), 3.18 (d, J=4.9 Hz, 6H), 2.46 (s, 12H), 2.17-1.91 (m, 14H), 1.84-1.60 (m, 8H), 1.33 (d, J=9.5 Hz, 4H), 0.95 (s, 7H).

Example 131

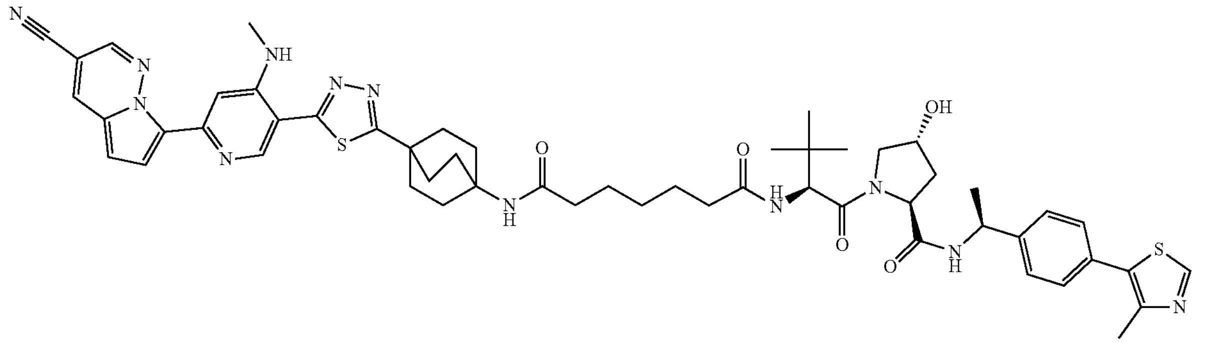 [SMILES: CNc1cc(-c2ccc3cc(C#N)cnn23)ncc1-c1nnc(C23CCC(NC(=O)CCCCCC(=O)N[C@H](C(=O)N4C[C@H](O)C[C@H]4C(=O)N[C@@H](C)c4ccc(-c5scnc5C)cc4)C(C)(C)C)(CC2)CC3)s1]

N1-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-N7-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)heptanediamide The title compound was synthesized from BB13 and 6-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}hexanoic acid by amide coupling using General Method A. LCMS: $C_{54}H_{64}N_{12}O_5S_2$ requires: 1024.5. found: m/z=1026.1 $[M+H]^+$ Example 132

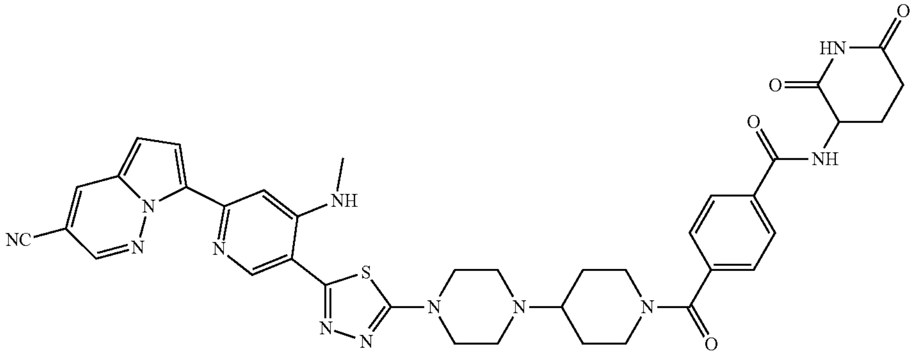 [SMILES: CNc1cc(-c2ccc3cc(C#N)cnn23)ncc1-c1nnc(N2CCN(C3CCN(C(=O)c4ccc(C(=O)NC5CCC(=O)NC5=O)cc4)CC3)CC2)s1]

4-(4-(4-(5-(6-(3-cyanopyrrolo[1,2-b]pyridazin-7-yl)-4-(methylamino)pyridin-3-yl)-1,3,4-thiadiazol-2-yl)piperazin-1-yl)piperidine-1-carbonyl)-N-(2,6-dioxopiperidin-3-yl)benzamide The title compound was synthesized from BB12 and 4-((2,6-dioxopiperidin-3-yl)carbamoyl)benzoic acid by amide coupling using General Method A. LCMS: $C_{38}H_{38}N_{12}O_4S$ requires: 758.9. found: m/z=759.8 $[M+H]^+$; $^1H$ NMR (500 MHz, Methanol-$d_4$) δ 8.79 (dd, J=14.2, 2.2 Hz, 1H), 8.70 (dd, J=5.9, 2.1 Hz, 1H), 8.53 (s, 1H), 8.11 (t, J=5.4 Hz, 1H), 8.00 (d, J=8.1 Hz, 1H), 7.87 (s, 1H), 7.64-7.48 (m, 1H), 7.26 (dd, J=13.7, 5.0 Hz, 1H), 3.94 (s, 4H), 3.41 (s, 11H), 3.13 (d, J=11.3 Hz, 2H), 3.07-2.93 (m, 1H), 2.87 (ddd, J=18.4, 12.0, 6.5 Hz, 1H), 2.79-2.65 (m, 1H), 2.24 (td, J=12.8, 11.4, 4.0 Hz, 2H), 2.06 (d, J=44.6 Hz, 1H), 1.76 (s, 2H).

Example 133

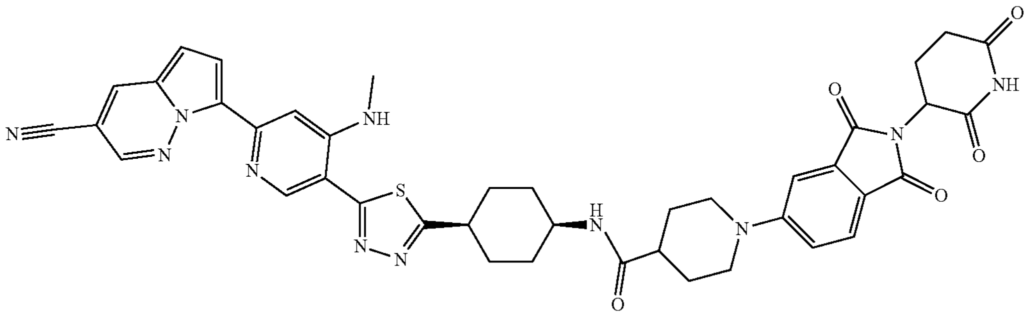 [SMILES: CNc1cc(-c2ccc3cc(C#N)cnn23)ncc1-c1nnc([C@H]2CC[C@@H](NC(=O)C3CCN(c4ccc5c(c4)C(=O)N(C4CCC(=O)NC4=O)C5=O)CC3)CC2)s1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-1-(2-(2,6-dioxopiperidin-3-yl)-1,3-dioxoisoindolin-5-yl)piperidine-4-carboxamide The title compound was synthesized from BB14 and 1-(2-(2,6-dioxopiperidin-3-yl)-1,3-dioxoisoindolin-5-yl)piperidine-4-carboxylic acid by amide coupling using General Method A. LCMS: $C_{41}H_{39}N_{11}O_5S$ requires: 797.3. found: m/z=798.6 $[M+H]^+$; $^1H$ NMR (500 MHz, DMSO-$d_6$) δ 11.08 (s, 1H), 8.96 (s, 1H), 8.84 (s, 1H), 8.74 (d, J=9.3 Hz, 1H), 8.10 (s, 1H), 8.03 (s, 1H), 7.82 (d, J=7.3 Hz, 1H), 7.67 (d, J=8.4 Hz, 1H), 7.34 (d, J=2.4 Hz, 1H), 7.29-7.20 (m, 2H), 5.07 (dd, J=12.7, 5.4 Hz, 1H), 4.09 (d, J=12.9 Hz, 2H), 3.88 (s, 1H), 3.20 (d, J=4.8 Hz, 3H), 3.00 (t, J=12.0 Hz, 2H), 2.89 (s, 0H), 2.61 (s, 1H), 2.51 (s, 5H), 2.04 (s, 2H), 1.98 (s, 4H), 1.74 (dd, J=16.2, 12.6 Hz, 2H), 1.67 (s, 6H), 1.25 (s, 1H).

Example 134

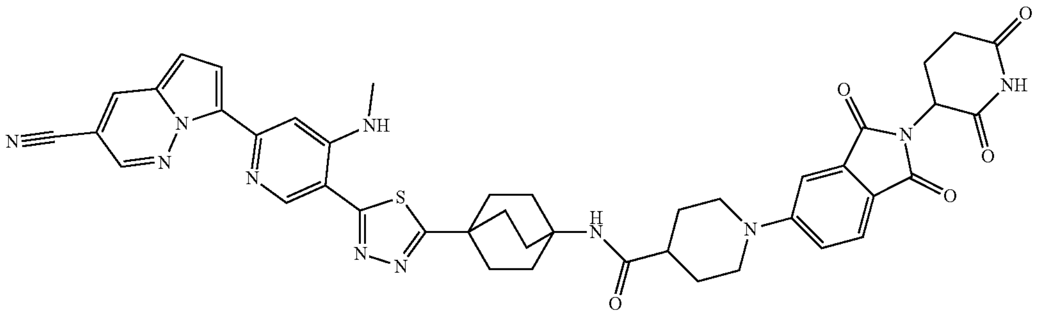 [SMILES: CNc1cc(-c2ccc3cc(C#N)cnn23)ncc1-c1nnc(C23CCC(NC(=O)C4CCN(c5ccc6c(c5)C(=O)N(C5CCC(=O)NC5=O)C6=O)CC4)(CC2)CC3)s1]

N-(4-(5-(6-(3-cyanopyrrolo[1,2-b]pyridazin-7-yl)-4-(methylamino)pyridin-3-yl)-1,3,4-thiadiazol-2-yl) bicyclo[2.2.2]octan-1-yl)-1-(2-(2,6-dioxopiperidin-3-yl)-1,3-dioxoisoindolin-5-yl)piperidine-4-carboxamide The title compound was synthesized from BB13 and 1-(2-(2,6-dioxopiperidin-3-yl)-1,3-dioxoisoindolin-5-yl)piperidine-4-carboxylic acid by amide coupling using General Method A. LCMS: $C_{43}H_{41}N_{11}O_5S$ requires: 823.3. found: m/z=824.6 $[M+H]^+$; $^1H$ NMR (500 MHz, DMSO-$d_6$) δ 11.09 (s, 1H), 8.96 (s, 1H), 8.84 (s, 1H), 8.72 (s, 1H), 8.04 (d, J=7.3 Hz, 2H), 7.68 (d, J=8.4 Hz, 1H), 7.48 (s, 1H), 7.34 (s, 1H), 7.26 (d, J=8.7 Hz, 1H), 7.22 (d, J=4.9 Hz, 1H), 5.08 (dd, J=12.8, 5.5 Hz, 1H), 4.08 (d, J=12.6 Hz, 2H), 3.19 (d, J=4.8 Hz, 3H), 2.97 (d, J=12.1 Hz, 2H), 2.90 (s, 1H), 2.62 (s, 1H), 2.12-1.96 (m, 13H), 1.74 (d, J=13.1 Hz, 2H), 1.62 (d, J=10.5 Hz, 1H), 1.58 (s, 1H), 1.25 (s, 1H).

Example 135

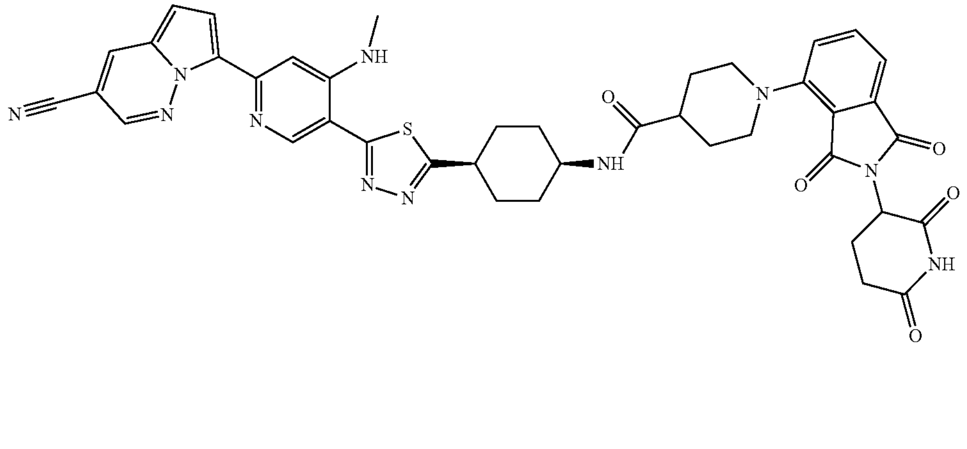 [SMILES: CNc1cc(-c2ccc3cc(C#N)cnn23)ncc1-c1nnc([C@H]2CC[C@@H](NC(=O)C3CCN(c4cccc5c4C(=O)N(C4CCC(=O)NC4=O)C5=O)CC3)CC2)s1]

N-((1s,4s)-4-(5-(6-(3-cyanopyrrolo[1,2-b]pyridazin-7-yl)-4-(methylamino)pyridin-3-yl)-1,3,4-thiadiazol-2-yl)cyclohexyl)-1-(2-(2,6-dioxopiperidin-3-yl)-1,3-dioxoisoindolin-4-yl)piperidine-4-carboxamide The title compound was synthesized from BB14 and 1-(2-(2,6-dioxopiperidin-3-yl)-1,3-dioxoisoindolin-4-yl)piperidine-4-carboxylic acid by amide coupling using General Method A. LCMS: $C_{41}H_{39}N_{11}O_5S$ requires: 797.3. found: m/z=798.6 $[M+H]^+$; $^1H$ NMR (500 MHz, DMSO-$d_6$) δ 11.10 (d, J=4.9 Hz, 1H), 8.96 (s, 1H), 8.84 (s, 1H), 8.75 (d, J=6.5 Hz, 1H), 8.09 (s, 1H), 8.04 (s, 1H), 7.82 (d, J=7.4 Hz, 1H), 7.69 (t, J=7.7 Hz, 1H), 7.35 (t, J=8.5 Hz, 2H), 7.22 (d, J=4.9 Hz, 1H), 5.10 (dd, J=12.7, 5.4 Hz, 1H), 3.90 (s, 1H), 3.74 (d, J=12.0 Hz, 2H), 3.20 (d, J=4.8 Hz, 3H), 2.90 (s, 3H), 2.62 (s, 1H), 2.06 (dd, J=21.3, 9.3 Hz, 3H), 1.99 (s, 3H), 1.79 (s, 5H), 1.70 (s, 3H), 1.25 (s, 1H).

Example 136

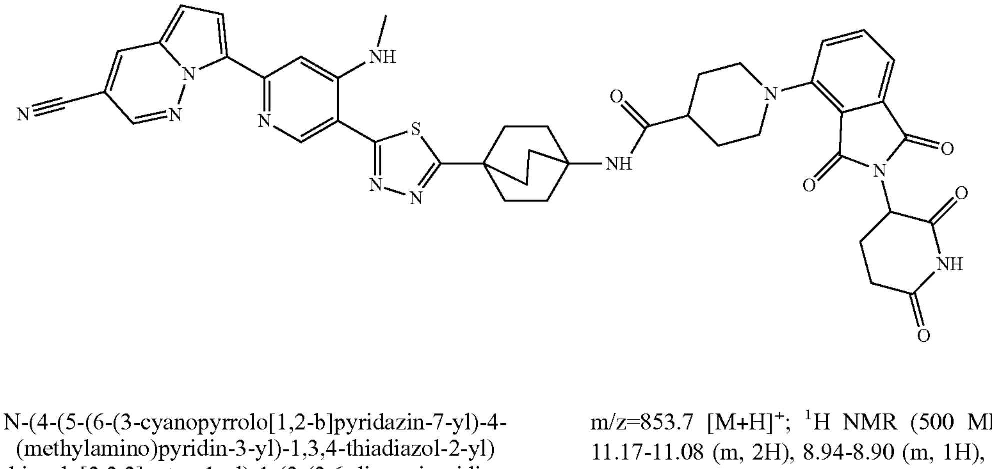

N-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-1-(2-(2,6-dioxopiperidin-3-yl)-1,3-dioxoisoindolin-4-yl)piperidine-4-carboxamide The title compound was synthesized from BB13 and 1-(2-(2,6-dioxopiperidin-3-yl)-1,3-dioxoisoindolin-4-yl)piperidine-4-carboxylic acid by amide coupling using General Method A. LCMS: $C_{44}H_{44}N_{12}O_5S$ requires: 852.3. found: m/z=853.7 $[M+H]^+$; $^1H$ NMR (500 MHz, DMSO-$d_6$) δ 11.17-11.08 (m, 2H), 8.94-8.90 (m, 1H), 8.81 (s, 1H), 8.72 (s, 1H), 8.22-8.14 (m, 2H), 7.96 (s, 1H), 7.72 (d, J=8.4 Hz, 1H), 7.42 (s, 1H), 7.32 (d, J=8.6 Hz, 1H), 7.19 (d, J=4.9 Hz, 1H), 5.09 (dd, J=12.7, 5.5 Hz, 1H), 4.35 (s, 1H), 4.20 (s, 6H), 4.10 (s, 1H), 3.27 (s, 2H), 3.15 (d, J=4.6 Hz, 5H), 2.95 (s, 1H), 2.91 (s, 3H), 2.62 (s, 1H), 2.48 (s, 6H), 2.22 (d, J=11.2 Hz, 3H), 2.05 (s, 4H), 1.98 (s, 5H), 1.71 (d, J=13.0 Hz, 4H), 1.41 (s, 5H), 1.25 (s, 3H).

Example 137

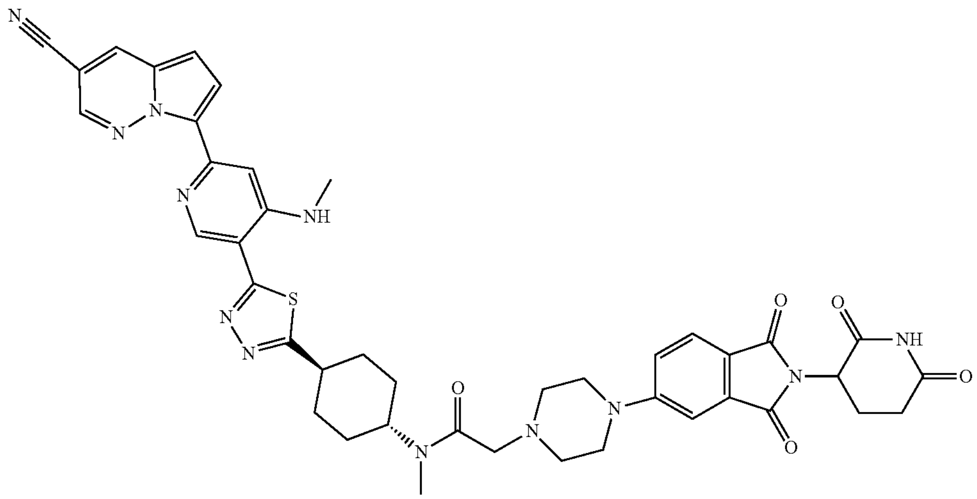 [SMILES: CNc1cc(-c2ccc3cc(C#N)cnn23)ncc1-c1nnc([C@H]2CC[C@H](N(C)C(=O)CN3CCN(c4ccc5c(c4)C(=O)N(C4CCC(=O)NC4=O)C5=O)CC3)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-2-(4-(2-(2,6-dioxopiperidin-3-yl)-1,3-dioxoisoindolin-5-yl)piperazin-1-yl)-N-methylacetamide The title compound was synthesized from BB18 and 2-(4-(2-(2,6-dioxopiperidin-3-yl)-1,3-dioxoisoindolin-5-yl)piperazin-1-yl)acetic acid by amide coupling using General Method A. LCMS: $C_{42}H_{42}N_{12}O_5S$ requires: 826.3. found: m/z=827.3 $[M+H]^+$ Example 138

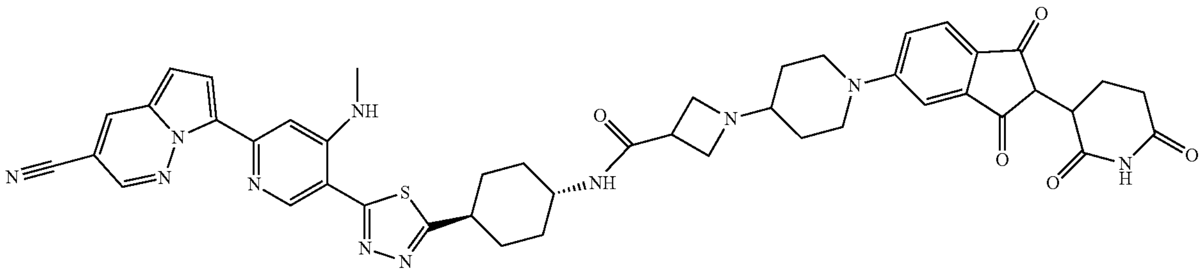 [SMILES: CNc1cc(-c2ccc3cc(C#N)cnn23)ncc1-c1nnc([C@H]2CC[C@H](NC(=O)C3CN(C4CCN(c5ccc6c(c5)C(=O)C(C5CCC(=O)NC5=O)C6=O)CC4)C3)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-1-(1-(2-(2,6-dioxopiperidin-3-yl)-1,3-dioxoisoindolin-5-yl)piperidin-4-yl)azetidine-3-carboxamide The title compound was synthesized from BB3 and 1-(1-(2-(2,6-dioxopiperidin-3-yl)-1,3-dioxoisoindolin-5-yl)piperidin-4-yl)azetidine-3-carboxylic acid (HCB13) by amide coupling using General Method A. LCMS: $C_{44}H_{44}N_{12}O_5S$ requires: 852.3. found: m/z=853.7 $[M+H]^+$; $^1H$ NMR (500 MHz, DMSO-$d_6$) δ 11.17-11.08 (m, 2H), 8.94-8.90 (m, 1H), 8.81 (s, 1H), 8.72 (s, 1H), 8.22-8.14 (m, 2H), 7.96 (s, 1H), 7.72 (d, J=8.4 Hz, 1H), 7.42 (s, 1H), 7.32 (d, J=8.6 Hz, 1H), 7.19 (d, J=4.9 Hz, 1H), 5.09 (dd, J=12.7, 5.5 Hz, 1H), 4.35 (s, 1H), 4.20 (s, 6H), 4.10 (s, 1H), 3.27 (s, 2H), 3.15 (d, J=4.6 Hz, 5H), 2.95 (s, 1H), 2.91 (s, 3H), 2.62 (s, 1H), 2.48 (s, 6H), 2.22 (d, J=11.2 Hz, 3H), 2.05 (s, 4H), 1.98 (s, 5H), 1.71 (d, J=13.0 Hz, 4H), 1.41 (s, 5H), 1.25 (s, 3H).

Example 139

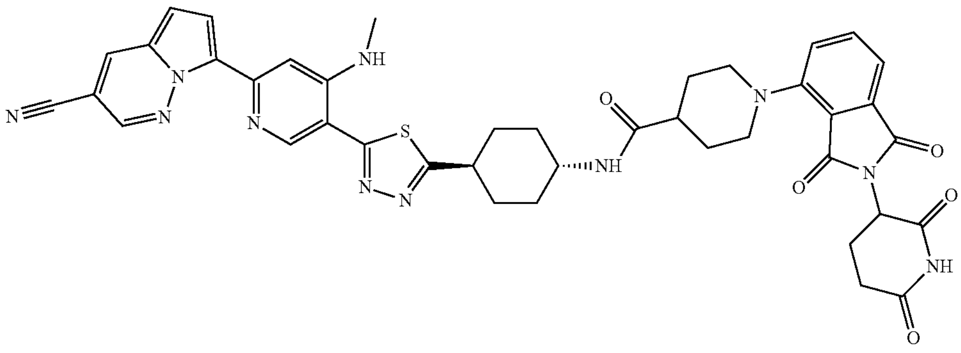 [SMILES: CNc1cc(-c2ccc3cc(C#N)cnn23)ncc1-c1nnc([C@H]2CC[C@H](NC(=O)C3CCN(c4cccc5c4C(=O)N(C4CCC(=O)NC4=O)C5=O)CC3)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-1-(2-(2,6-dioxopiperidin-3-yl)-1,3-dioxoisoindolin-4-yl)piperidine-4-carboxamide The title compound was synthesized from BB3 and 1-(2-(2,6-dioxopiperidin-3-yl)-1,3-dioxoisoindolin-4-yl)piperidine-4-carboxylic acid by amide coupling using General Method A. LCMS: $C_{41}H_{39}N_{11}O_5S$ requires: 797.3. found: m/z=798.5 $[M+H]^+$; $^1H$ NMR (500 MHz, DMSO-$d_6$) δ 11.10 (s, 1H), 8.95 (s, 1H), 8.83 (s, 1H), 8.73 (s, 1H), 8.09 (s, 1H), 8.02 (s, 1H), 7.83 (d, J=7.8 Hz, 1H), 7.70 (t, J=7.7 Hz, 1H), 7.40-7.33 (m, 2H), 7.21 (d, J=4.9 Hz, 1H), 5.11 (dd, J=12.8, 5.5 Hz, 1H), 3.74 (d, J=11.8 Hz, 2H), 3.25 (s, 1H), 3.18 (d, J=4.7 Hz, 3H), 2.90 (s, 4H), 2.61 (d, J=17.8 Hz, 2H), 2.33 (s, 2H), 2.21 (d, J=12.7 Hz, 2H), 2.07-2.01 (m, 2H), 1.95 (d, J=12.0 Hz, 2H), 1.80 (s, 4H), 1.70 (q, J=12.6 Hz, 2H), 1.44 (t, J=12.3 Hz, 2H), 1.25 (s, 3H).

Example 140

(2S,4R)—N—((S)-3-((4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB13 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{52}H_{57}FN_{12}O_5S_2$ requires: 1012.4. found: m/z=1013.7 $[M+H]^+$; $^1H$ NMR (500 MHz, DMSO-$d_6$) δ 8.99 (d, J=17.8 Hz, 2H), 8.85 (d, J=2.2 Hz, 1H), 8.72 (s, 2H), 8.55 (d, J=7.9 Hz, 1H), 8.04 (d, J=8.5 Hz, 2H), 7.47-7.30 (m, 4H), 7.23 (d, J=4.9 Hz, 2H), 5.16 (d, J=7.6 Hz, 2H), 4.60 (d, J=9.2 Hz, 1H), 4.49 (s, 2H), 4.30 (s, 2H), 3.19 (d, J=4.7 Hz, 4H), 2.03 (d, J=8.3 Hz, 6H), 1.96-1.80 (m, 5H), 1.77 (s, 2H), 1.43-1.29 (m, 3H), 1.27-1.17 (m, 3H), 1.00 (s, 9H).

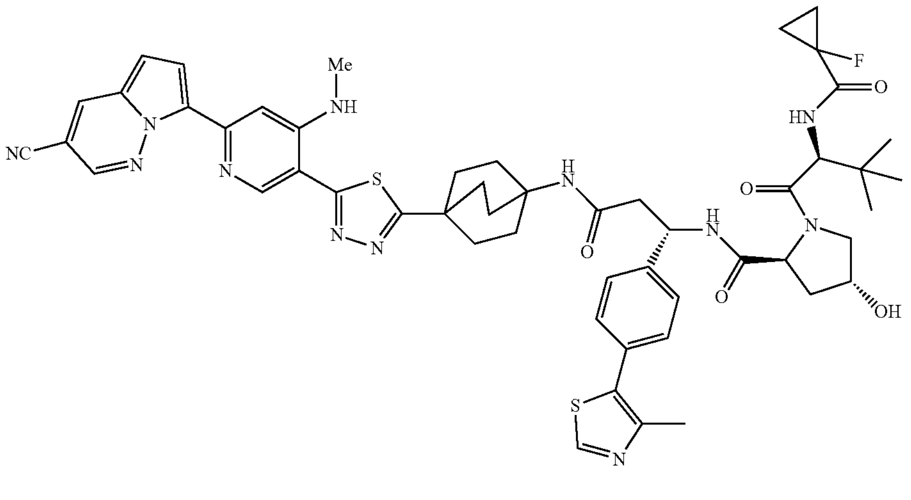 [SMILES: CNc1cc(-c2ccc3cc(C#N)cnn23)ncc1-c1nnc(C23CCC(NC(=O)C[C@H](NC(=O)[C@@H]4C[C@@H](O)CN4C(=O)[C@@H](NC(=O)C4(F)CC4)C(C)(C)C)c4ccc(-c5scnc5C)cc4)(CC2)CC3)s1]

Example 141

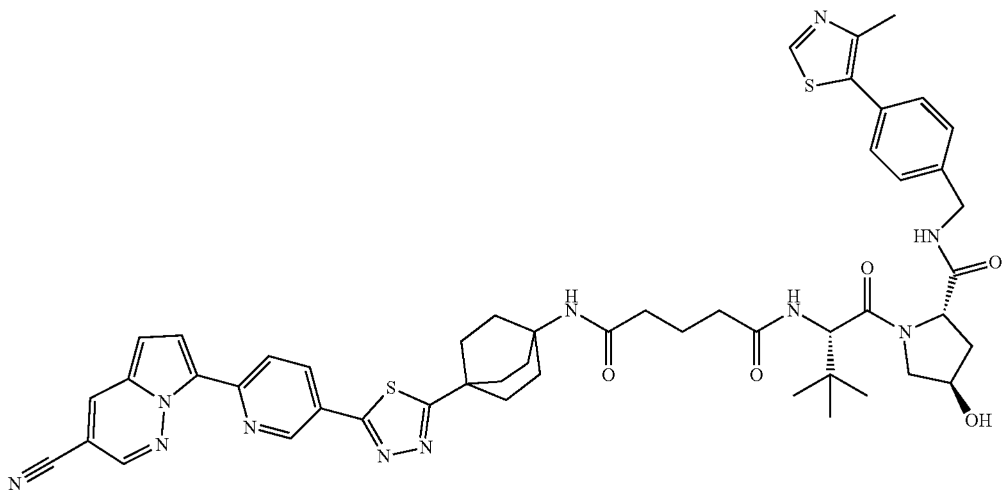 [SMILES: Cc1ncsc1-c1ccc(CNC(=O)[C@@H]2C[C@@H](O)CN2C(=O)[C@@H](NC(=O)CCCC(=O)NC23CCC(c4nnc(-c5ccc(-c6ccc7cc(C#N)cnn67)nc5)s4)(CC2)CC3)C(C)(C)C)cc1]

$N_1$-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide The title compound was synthesized from BB13 and 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid by amide coupling using General Method A. LCMS: $C_{51}H_{58}N_{12}O_5S_2$ requires: 982.4. found: m/z=983.7 $[M+H]^+$; $^1H$ NMR (500 MHz, DMSO-$d_6$) δ 9.00 (s, 2H), 8.96 (s, 2H), 8.84 (s, 2H), 8.72 (s, 4H), 8.57 (s, 3H), 8.07 (s, 5H), 7.89 (d, J=9.4 Hz, 3H), 7.47-7.36 (m, 5H), 7.22 (d, J=4.9 Hz, 3H), 4.55 (d, J=9.1 Hz, 3H), 4.52-4.42 (m, 4H), 4.37 (s, 4H), 4.23 (d, J=10.5 Hz, 5H), 3.75-3.62 (m, 5H), 3.18 (s, 5H), 2.29-2.09 (m, 7H), 2.11-1.91 (m, 13H), 1.70 (d, J=9.9 Hz, 6H), 0.96 (s, 9H).

Example 142

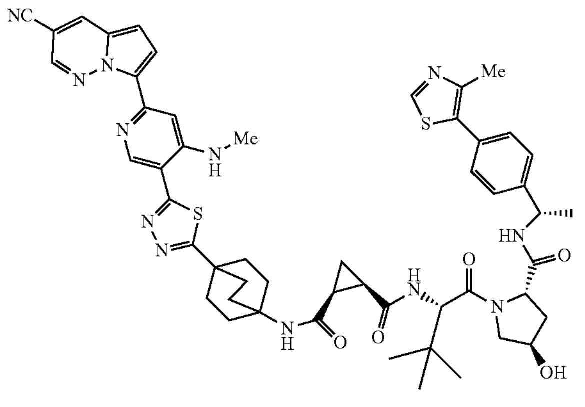 [SMILES: CNc1cc(-c2ccc3cc(C#N)cnn23)ncc1-c1nnc(C23CCC(NC(=O)[C@H]4C[C@H]4C(=O)N[C@H](C(=O)N4C[C@H](O)C[C@H]4C(=O)N[C@@H](C)c4ccc(-c5scnc5C)cc4)C(C)(C)C)(CC2)CC3)s1]

(1RS,2SR)—$N_1$-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-$N_2$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)cyclopropane-1,2-dicarboxamide (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (100 mg, 0.22 mmol) was dissolved in dichloromethane (5 mL) and to which 3-oxabicyclo[3.1.0]hexane-2,4-dione (25 mg, 0.22 mmol) was added. Stirred for 1 hour at room temperature. Concentrated reaction to provide a crude oil. Added BB13 (38 mg, 0.09 mmol) and HATU (34 mg, 0.09 mmol) and suspended in DMF (2 mL). Added DIPEA (0.04 mL, 0.09 mmol) and stirred overnight at room temperature. Purified by prep-HPLC to give the title compound. LCMS: $C_{52}H_{58}N_{12}O_5S_2$ requires: 994.4. found: m/z=995.7 $[M+H]^+$; $^1H$ NMR (500 MHz, DMSO-$d_6$) δ 8.98 (d, J=8.7 Hz, 3H), 8.85 (d, J=2.2 Hz, 2H), 8.72 (d, J=4.3 Hz, 4H), 8.39 (d, J=7.5 Hz, 3H), 8.06 (dd, J=17.0, 8.8 Hz, 5H), 7.80 (s, 2H), 7.49-7.33 (m, 5H), 7.23 (d, J=4.9 Hz, 3H), 4.93 (s, 4H), 4.54 (d, J=9.2 Hz, 2H), 4.45 (s, 3H), 4.31 (d, J=4.5 Hz, 2H), 3.20 (d, J=4.8 Hz, 7H), 2.13-1.92 (m, 15H), 1.83 (d, J=7.0 Hz, 3H), 1.40 (d, J=6.9 Hz, 4H), 1.32-1.15 (m, 5H), 0.95 (s, 9H).

Example 143

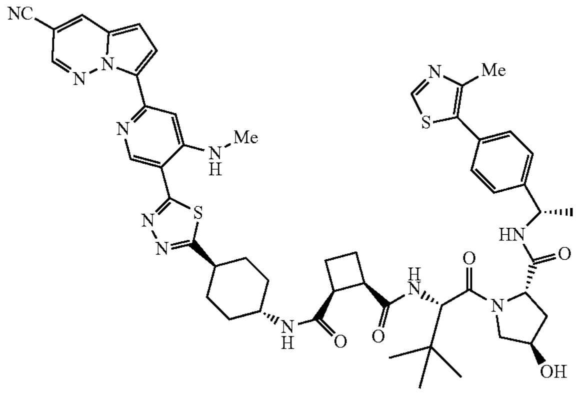 [SMILES: CNc1cc(-c2ccc3cc(C#N)cnn23)ncc1-c1nnc([C@H]2CC[C@H](NC(=O)[C@H]3CC[C@H]3C(=O)N[C@H](C(=O)N3C[C@H](O)C[C@H]3C(=O)N[C@@H](C)c3ccc(-c4scnc4C)cc3)C(C)(C)C)CC2)s1]

(1RS,2SR)—$N_1$-((1r,4R)-4-(5-(6-(3-cyanopyrrolo[1,2-b]pyridazin-7-yl)-4-(methylamino)pyridin-3-yl)-1,3,4-thiadiazol-2-yl)cyclohexyl)-$N_2$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)cyclobutane-1,2-dicarboxamide (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (100 mg, 0.22 mmol) was dissolved in dichloromethane (5 mL) and to which 3-oxabicyclo[3.2.0]heptane-2,4-dione (28 mg, 0.22 mmol) was added. Stirred for 1 hour at room temperature. Concentrated reaction to provide a crude oil. Added BB3 (36 mg, 0.09 mmol) and HATU (34 mg, 0.09 mmol) and suspended in DMF (2 mL). Added DIPEA (0.04 mL, 0.09 mmol) and stirred overnight at room temperature. Purified by prep-HPLC to give the title compound. LCMS: $C_{51}H_{58}N_{12}O_5S_2$ requires: 982.4. found: m/z=983.7 $[M+H]^+$; $^1H$ NMR (500 MHz, DMSO-$d_6$) δ 8.98 (s, 3H), 8.85 (d, J=2.2 Hz, 2H), 8.74 (s, 3H), 8.32 (d, J=7.7 Hz, 3H), 8.05 (d, J=16.6 Hz, 4H), 7.52-7.27 (m, 7H), 7.23 (d, J=5.0 Hz, 2H), 4.93 (t, J=7.2 Hz, 3H), 4.53 (d, J=9.4 Hz, 3H), 4.44 (t, J=8.0 Hz, 2H), 4.29 (s, 3H), 3.20 (d, J=4.9 Hz, 7H), 2.45 (s, 6H), 2.22 (s, 6H), 2.03 (d, J=11.3 Hz, 4H), 1.92 (s, 3H), 1.82 (s, 3H), 1.66 (d, J=13.3 Hz, 4H), 1.39 (d, J=6.8 Hz, 5H), 0.94 (s, 9H).

Example 144

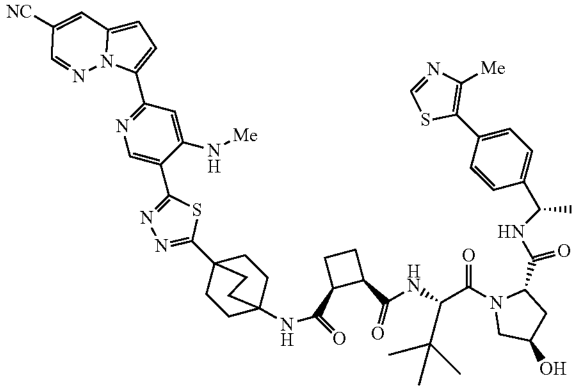 [SMILES: CNc1cc(-c2ccc3cc(C#N)cnn23)ncc1-c1nnc(C23CCC(NC(=O)[C@H]4CC[C@H]4C(=O)N[C@H](C(=O)N4C[C@H](O)C[C@H]4C(=O)N[C@@H](C)c4ccc(-c5scnc5C)cc4)C(C)(C)C)(CC2)CC3)s1]

(1RS,2SR)—$N_1$-(4-(5-(6-(3-cyanopyrrolo[1,2-b]pyridazin-7-yl)-4-(methylamino)pyridin-3-yl)-1,3,4-thiadiazol-2-yl)bicyclo[2.2.2]octan-1-yl)-$N_2$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)cyclobutane-1,2-dicarboxamide (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (100 mg, 0.22 mmol) was dissolved in dichloromethane (5 mL) and to which 3-oxabicyclo[3.2.0]heptane-2,4-dione (28 mg, 0.22 mmol) was added. Stirred for 1 hour at room temperature. Concentrated reaction to provide a crude oil. Added BB13 (38 mg, 0.09 mmol) and HATU (34 mg, 0.09 mmol) and suspended in DMF (2 mL). Added DIPEA (0.04 mL, 0.09 mmol) and stirred overnight at room temperature. Purified by prep-HPLC to give the title compound. LCMS: $C_{53}H_{60}N_{12}O_5S_2$ requires: 1008.4. found: m/z=1009.7 $[M+H]^+$; $^1H$ NMR (500 MHz, DMSO-$d_6$) δ 8.98 (d, J=2.7 Hz, 2H), 8.86 (d, J=2.2 Hz, 1H), 8.73 (s, 1H), 8.36 (d, J=7.7 Hz, 1H), 8.14-7.98 (m, 2H), 7.53-7.35 (m, 3H), 7.26 (dd, J=25.7, 7.1 Hz, 2H), 6.91 (s, 1H), 4.93 (d, J=7.2 Hz, 1H), 4.57 (d, J=9.3 Hz, 1H), 4.45 (t, J=7.7 Hz, 2H), 4.33 (t, J=4.1 Hz, 1H), 3.34 (d, J=7.3 Hz, 2H), 3.20 (d, J=4.8 Hz, 3H), 2.46 (s, 3H), 2.19-1.76 (m, 11H), 1.39 (d, J=7.0 Hz, 2H), 0.95 (s, 5H).

Example 145

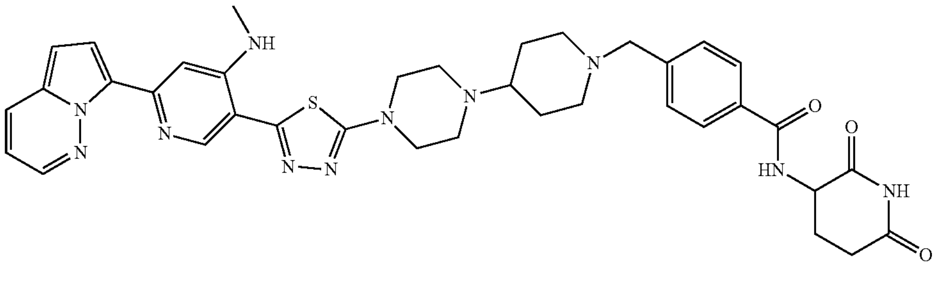 [SMILES: CNc1cc(-c2ccc3cccnn23)ncc1-c1nnc(N2CCN(C3CCN(Cc4ccc(C(=O)NC5CCC(=O)NC5=O)cc4)CC3)CC2)s1]

4-((4-(4-(5-(6-(3-cyanopyrrolo[1,2-b]pyridazin-7-yl)-4-(methylamino)pyridin-3-yl)-1,3,4-thiadiazol-2-yl)piperazin-1-yl)piperidin-1-yl)methyl)-N-(2,6-dioxopiperidin-3-yl)benzamide The title compound was synthesized from BB12 and N-(2,6-dioxopiperidin-3-yl)-4-formylbenzamide by reductive amination using General Method B. LCMS: $C_{38}H_{40}N_{12}O_3S$ requires: 744.3. found: m/z=745.7 $[M+H]^+$; $^1H$ NMR (500 MHz, DMSO-$d_6$) δ 10.90 (s, 1H), 8.92 (d, J=14.5 Hz, 1H), 8.86 (d, J=8.4 Hz, 1H), 8.81 (s, 1H), 8.55 (d, J=3.3 Hz, 1H), 8.06 (q, J=8.3 Hz, 2H), 7.98 (t, J=9.2 Hz, 2H), 7.63 (d, J=7.9 Hz, 2H), 7.20 (d, J=4.8 Hz, 1H), 4.81 (ddd, J=13.2, 8.6, 5.3 Hz, 1H), 4.36 (s, 1H), 3.15 (d, J=4.9 Hz, 5H), 3.02-2.92 (m, 3H), 2.90 (s, 2H), 2.82 (d, J=12.6 Hz, 2H), 2.74 (s, 1H), 2.21-2.06 (m, 3H), 2.00 (s, 2H), 1.77 (s, 2H), 1.24 (d, J=6.9 Hz, 1H).

Example 146

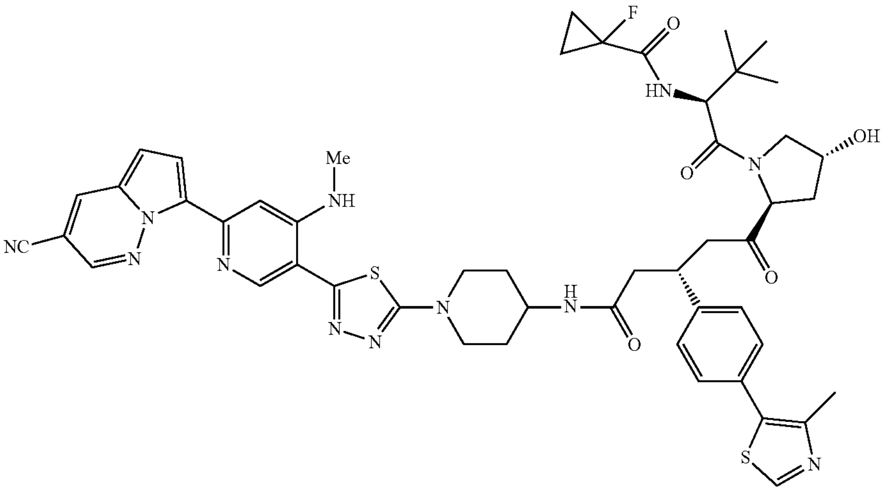 [SMILES: CNc1cc(-c2ccc3cc(C#N)cnn23)ncc1-c1nnc(N2CCC(NC(=O)C[C@H](CC(=O)[C@@H]3C[C@@H](O)CN3C(=O)[C@@H](NC(=O)C3(F)CC3)C(C)(C)C)c3ccc(-c4scnc4C)cc3)CC2)s1]

(2S,4R)—N—((S)-3-((1-(5-(6-(3-cyanopyrrolo[1,2-b]pyridazin-7-yl)-4-(methylamino)pyridin-3-yl)-1,3,4-thiadiazol-2-yl)piperidin-4-yl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB11 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{49}H_{54}FN_{13}O_5S_2$ requires: 987.4. found: m/z=988.7 $[M+H]^+$; $^1H$ NMR (500 MHz, DMSO-$d_6$) δ 9.00 (d, J=3.8 Hz, 2H), 8.86 (d, J=2.2 Hz, 2H), 8.58 (d, J=7.9 Hz, 1H), 8.50 (s, 2H), 8.09 (d, J=4.8 Hz, 2H), 7.99-7.78 (m, 3H), 7.55-7.33 (m, 4H), 7.33-7.14 (m, 3H), 5.20 (d, J=7.5 Hz, 3H), 4.59 (d, J=9.2 Hz, 1H), 4.47 (t, J=8.3 Hz, 2H), 4.29 (s, 2H), 3.85 (d, J=11.9 Hz, 2H), 3.75 (d, J=13.3 Hz, 2H), 3.67-3.51 (m, 4H), 3.21 (d, J=4.9 Hz, 3H), 2.70-2.53 (m, 4H), 2.15-1.97 (m, 3H), 1.88-1.66 (m, 4H), 1.49 (d, J=10.9 Hz, 2H), 1.35 (s, 3H), 1.26-1.14 (m, 2H), 0.98 (d, J=12.9 Hz, 9H).

Example 147

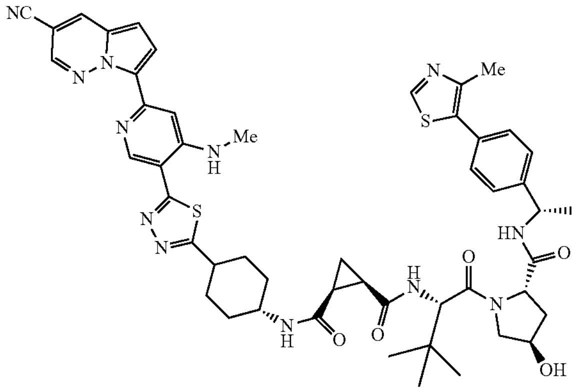

(1RS,2SR)—$N_1$-((1r,4R)-4-(5-(6-(3-cyanopyrrolo[1,2-b]pyridazin-7-yl)-4-(methylamino)pyridin-3-yl)-1,3,4-thiadiazol-2-yl)cyclohexyl)-$N_2$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)cyclopropane-1,2-dicarboxamide (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (100 mg, 0.22 mmol) was dissolved in dichloromethane (5 mL) and to which 3-oxabicyclo[3.1.0]hexane-2,4-dione (25 mg, 0.22 mmol) was added. Stirred for 1 hour at room temperature. Concentrated reaction to provide a crude oil. Added BB3 (36 mg, 0.09 mmol) and HATU (34 mg, 0.09 mmol) and suspended in DMF (2 mL). Added DIPEA (0.04 mL, 0.09 mmol) and stirred overnight at room temperature. Purified by prep-HPLC to give the title compound. LCMS: $C_{50}H_{56}N_{12}O_5S_2$ requires: 968.4. found: m/z=969.8 $[M+H]^+$; $^1H$ NMR (500 MHz, DMSO-$d_6$) δ 8.98 (d, J=12.5 Hz, 2H), 8.84 (d, J=2.2

Hz, 2H), 8.73 (s, 2H), 8.38 (d, J=7.8 Hz, 2H), 8.19 (d, J=7.9 Hz, 1H), 8.05 (d, J=7.0 Hz, 3H), 8.00 (d, J=9.2 Hz, 1H), 7.51-7.32 (m, 4H), 7.22 (d, J=4.9 Hz, 2H), 4.92 (t, J=7.2 Hz, 2H), 4.52 (d, J=9.1 Hz, 2H), 4.44 (t, J=8.0 Hz, 2H), 4.29 (s, 2H), 3.72-3.51 (m, 6H), 3.20 (d, J=4.8 Hz, 3H), 2.22 (d, J=13.1 Hz, 3H), 2.07-1.86 (m, 5H), 1.86-1.76 (m, 2H), 1.76-1.55 (m, 4H), 1.48-1.29 (m, 5H), 1.29-1.13 (m, 3H), 0.94 (s, 9H).

Example 148

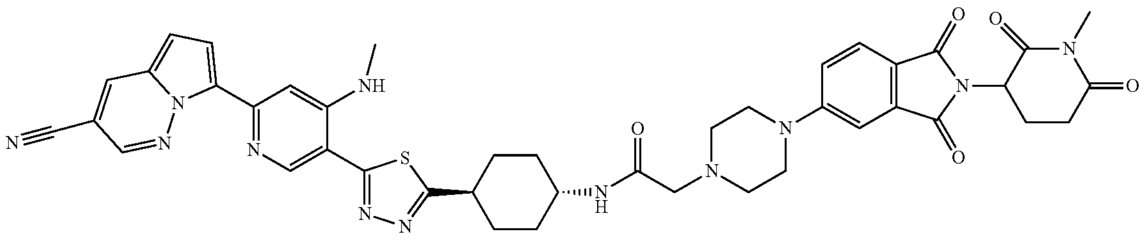 [SMILES: CNc1cc(-c2ccc3cc(C#N)cnn23)ncc1-c1nnc([C@H]2CC[C@H](NC(=O)CN3CCN(c4ccc5c(c4)C(=O)N(C4CCC(=O)N(C)C4=O)C5=O)CC3)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-2-(4-(2-(1-methyl-2,6-dioxopiperidin-3-yl)-1,3-dioxoisoindolin-5-yl)piperazin-1-yl)acetamide The title compound was synthesized from BB3 and 2-(4-(2-(1-methyl-2,6-dioxopiperidin-3-yl)-1,3-dioxoisoindolin-5-yl)piperazin-1-yl)acetic acid by amide coupling using General Method A. LCMS: $C_{42}H_{42}N_{12}O_5S$ requires: 826.3. found: m/z=827.6 $[M+H]^+$; $^1H$ NMR (500 MHz, DMSO-$d_6$) δ 10.28 (s, 1H), 9.05 (s, 2H), 8.94 (s, 1H), 8.82 (d, J=2.2 Hz, 1H), 8.73 (s, 1H), 8.60 (s, 1H), 8.12 (s, 1H), 8.00 (d, J=4.8 Hz, 1H), 7.79 (d, J=8.4 Hz, 1H), 7.48 (s, 1H), 7.36 (d, J=8.9 Hz, 1H), 7.20 (d, J=4.9 Hz, 1H), 5.18 (dd, J=13.0, 5.4 Hz, 1H), 4.21 (s, 2H), 3.99 (s, 2H), 3.17 (d, J=4.9 Hz, 3H), 3.03 (s, 3H), 2.96 (d, J=12.8 Hz, 1H), 2.82-2.75 (m, 1H), 2.23 (d, J=12.5 Hz, 2H), 2.07 (dd, J=11.6, 5.7 Hz, 1H), 2.04-1.97 (m, 2H), 1.74 (q, J=12.6, 11.6 Hz, 2H), 1.47 (tt, J=13.9, 6.9 Hz, 2H).

Example 149

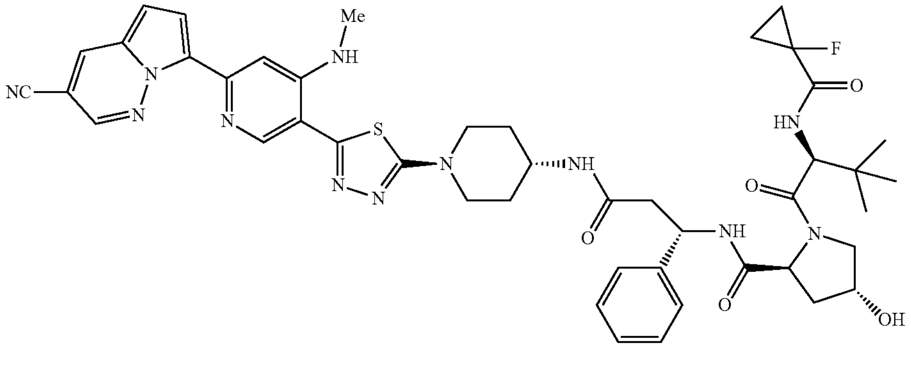

(2S,4R)—N—((S)-3-(((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)amino)-3-oxo-1-phenylpropyl)-1-((S)-2-(1-fluorocyclopropane-1-carboxamido)-3,3-dimethylbutanoyl)-4-hydroxypyrrolidine-2-carboxamide The title compound was synthesized from BB3 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-phenylpropanoic acid by amide coupling using General Method A. LCMS: $C_{46}H_{52}FN_{11}O_5S$ requires: 889.4. found: m/z=890.8 $[M+H]^+$; $^1H$ NMR (500 MHz, DMSO-$d_6$) δ 8.97 (d, J=2.3 Hz, 1H), 8.85 (d, J=2.2 Hz, 1H), 8.73 (s, 1H), 8.50 (d, J=8.1 Hz, 2H), 8.18-7.94 (m, 2H), 7.79 (d, J=7.9 Hz, 2H), 7.39-7.18 (m, 5H), 5.17 (d, J=7.7 Hz, 2H), 4.59 (d, J=9.2 Hz, 1H), 4.47 (t, J=8.2 Hz, 2H), 4.28 (s, 2H), 3.87-3.34 (m, 16H), 3.20 (d, J=4.9 Hz, 4H), 2.19-1.98 (m, 3H), 1.88 (d, J=12.8 Hz, 2H), 1.83-1.56 (m, 4H), 1.36 (dd, J=11.8, 8.1 Hz, 3H), 1.28-1.16 (m, 3H), 0.99 (s, 9H).

Example 150

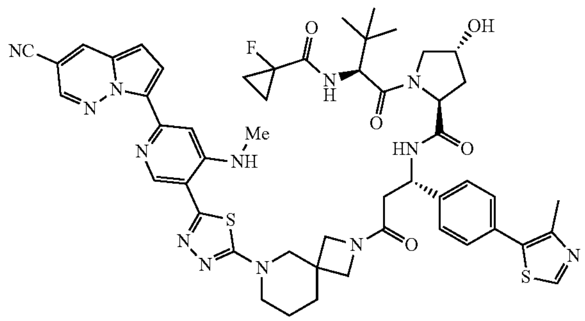 [SMILES: CNc1cc(-c2ccc3cc(C#N)cnn23)ncc1-c1nnc(N2CCCC3(CN(C(=O)C[C@H](NC(=O)[C@@H]4C[C@@H](O)CN4C(=O)[C@@H](NC(=O)C4(F)CC4)C(C)(C)C)c4ccc(-c5scnc5C)cc4)C3)C2)s1]

(2S,4R)—N—((S)-3-(6-(5-(6-(3-cyanopyrrolo[1,2-b]pyridazin-7-yl)-4-(methylamino)pyridin-3-yl)-1,3,4-thiadiazol-2-yl)-2,6-diazaspiro[3.5]nonan-2-yl)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB15 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{51}H_{56}FN_{13}O_5S_2$ requires: 1013.4. found: m/z=1014.7 $[M+H]^+$; $^1H$ NMR (500 MHz, DMSO-$d_6$) δ 8.98 (d, J=23.4 Hz, 2H), 8.87 (d, J=2.2 Hz, 1H), 8.57 (s, 1H), 8.48 (d, J=4.3 Hz, 1H), 8.10 (d, J=5.0 Hz, 1H), 7.92 (s, 1H), 7.58-7.36 (m, 3H), 7.26 (d, J=5.1 Hz, 2H), 5.17 (d, J=7.7 Hz, 2H), 4.60 (t, J=10.6 Hz, 1H), 4.47 (d, J=8.8 Hz, 1H), 4.31 (d, J=18.0 Hz, 2H), 4.01-3.39 (m, 18H), 3.22 (d, J=4.9 Hz, 3H), 2.74-2.57 (m, 2H), 2.05 (d, J=9.6 Hz, 1H), 1.93-1.71 (m, 2H), 1.65 (s, 3H), 1.45-1.29 (m, 2H), 1.29-1.11 (m, 3H), 0.98 (d, J=6.1 Hz, 9H).

Example 151

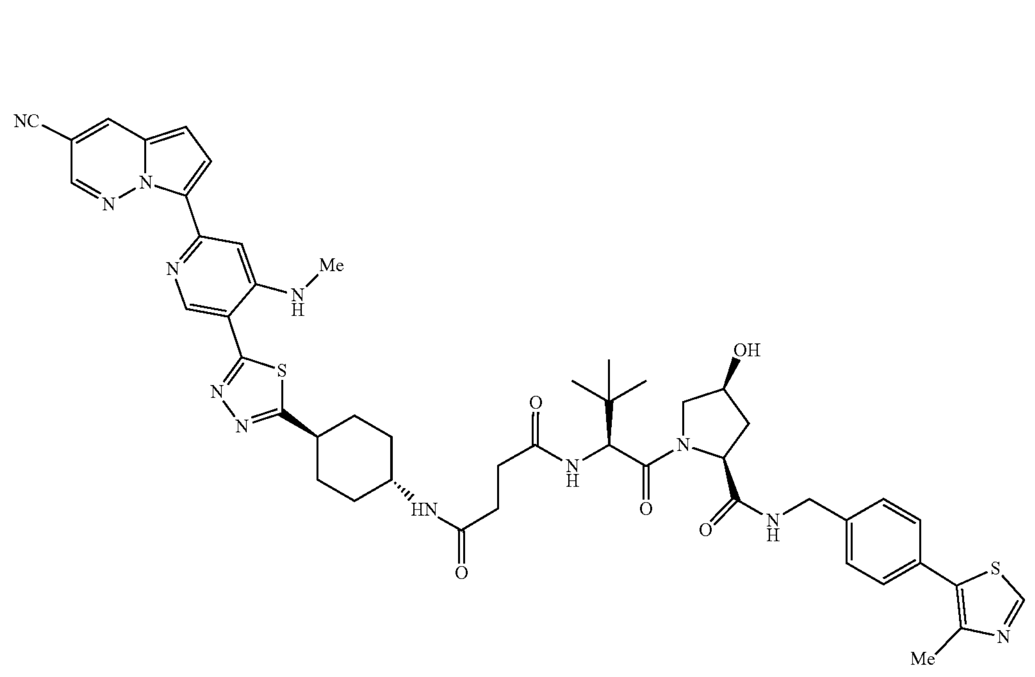 [SMILES: CNc1cc(-c2ccc3cc(C#N)cnn23)ncc1-c1nnc([C@H]2CC[C@H](NC(=O)CCC(=O)N[C@H](C(=O)N3C[C@@H](O)C[C@H]3C(=O)NCc3ccc(-c4scnc4C)cc3)C(C)(C)C)CC2)s1]

N1-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-$N_4$—((S)-1-((2S,4S)-4-hydroxy-2-((4-(4-methylthiazol-5-yl)benzyl)carbamoyl)pyrrolidin-1-yl)-3,3-dimethyl-1-oxobutan-2-yl)succinamide (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (15 mg, 0.03 mmol) was dissolved in dichloromethane (1 mL) and to which succinic anhydride (3 mg, 0.03 mmol) was added. Stirred for 1 hour at room temperature. Concentrated reaction to provide a crude oil. Added BB3 (12 mg, 0.03 mmol) and HATU (11 mg, 0.03 mmol) and suspended in DMF (1 mL). Added DIPEA (0.01 mL, 0.07 mmol) and stirred overnight at room temperature. Purified by prep-HPLC to give the title compound. LCMS: $C_{48}H_{54}N_{12}O_5S_2$ requires: 942.4. found: m/z=943.8 $[M+H]^+$; $^1H$ NMR (500 MHz, DMSO-$d_6$) δ 9.09-8.94 (m, 1H), 8.85 (d, J=2.2 Hz, 1H), 8.74 (s, 1H), 8.64 (s, 1H), 8.12-7.97 (m, 2H), 7.92 (d, J=8.8 Hz, 1H), 7.81 (d, J=7.7 Hz, 1H), 7.53-7.36 (m, 2H), 7.23 (d, J=4.8 Hz, 2H), 4.53-4.38 (m, 2H), 4.38-4.29 (m, 1H), 4.31-4.18 (m, 2H), 3.94 (dd, J=10.1, 5.7 Hz, 1H), 3.64 (s, 3H), 3.20 (d, J=4.8 Hz, 2H), 2.46 (s, 1H), 2.42-2.23 (m, 3H), 2.20 (d, J=12.6 Hz, 2H), 1.93 (d, J=12.4 Hz, 2H), 1.75 (d, J=6.4 Hz, 1H), 1.73-1.52 (m, 2H), 1.38 (d, J=12.5 Hz, 2H), 0.97 (s, 9H).

Example 152

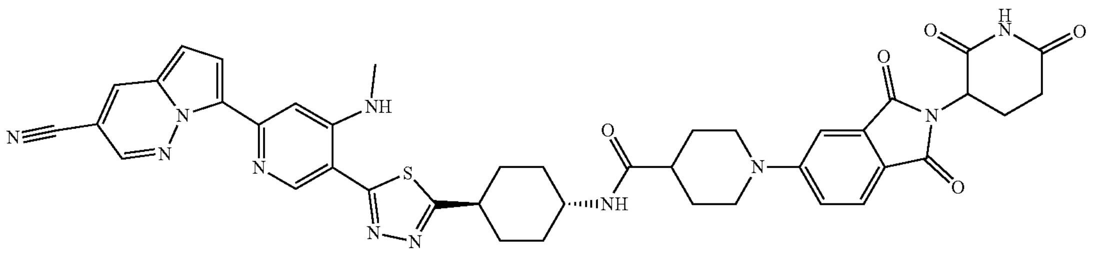 [SMILES: CNc1cc(-c2ccc3cc(C#N)cnn23)ncc1-c1nnc([C@H]2CC[C@H](NC(=O)C3CCN(c4ccc5c(c4)C(=O)N(C4CCC(=O)NC4=O)C5=O)CC3)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-1-(2-(2,6-dioxopiperidin-3-yl)-1,3-dioxoisoindolin-5-yl)piperidine-4-carboxamide The title compound was synthesized from BB3 and 1-(2-(2,6-dioxopiperidin-3-yl)-1,3-dioxoisoindolin-5-yl)piperidine-4-carboxylic acid by amide coupling using General Method A. LCMS: $C_{41}H_{39}N_{11}O_5S$ requires: 797.3. found: m/z=798.6 $[M+H]^+$; $^1H$ NMR (500 MHz, DMSO-$d_6$) δ 11.09 (s, 1H), 9.30 (s, 1H), 8.97 (s, 1H), 8.84 (s, 1H), 8.73 (s, 1H), 8.05 (s, 2H), 7.83 (d, J=7.8 Hz, 1H), 7.68 (d, J=8.5 Hz, 1H), 7.35 (d, J=2.3 Hz, 1H), 7.27 (d, J=8.9 Hz, 1H), 7.22 (d, J=4.9 Hz, 1H), 5.08 (dd, J=12.7, 5.4 Hz, 1H), 4.09 (d, J=12.8 Hz, 2H), 3.26 (s, 1H), 3.20 (d, J=4.8 Hz, 3H), 3.02 (t, J=12.2 Hz, 2H), 2.90 (t, J=16.0 Hz, 1H), 2.62 (s, 1H), 2.58 (s, 1H), 2.51 (d, J=5.6 Hz, 18H), 2.20 (d, J=12.7 Hz, 2H), 2.03 (d, J=12.2 Hz, 1H), 1.96-1.90 (m, 3H), 1.77 (d, J=12.6 Hz, 2H), 1.74-1.63 (m, 3H), 1.62 (s, 1H), 1.46-1.41 (m, 1H), 1.41-1.36 (m, 1H).

Example 153

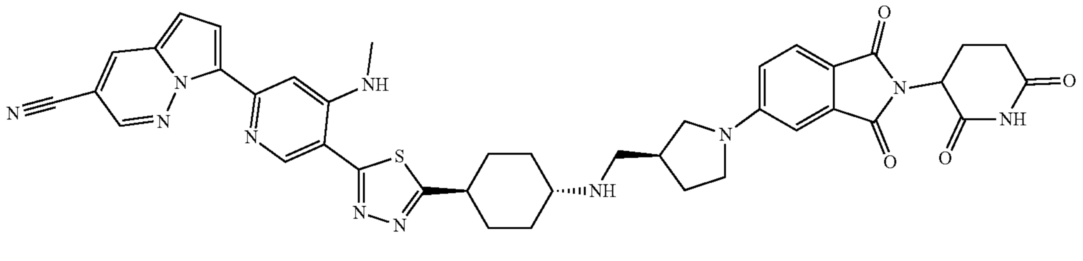 [SMILES: CNc1cc(-c2ccc3cc(C#N)cnn23)ncc1-c1nnc([C@H]2CC[C@H](NC[C@@H]3CCN(c4ccc5c(c4)C(=O)N(C4CCC(=O)NC4=O)C5=O)C3)CC2)s1]

7-(5-(5-((1S,4r)-4-((((3S)-1-(2-(2,6-dioxopiperidin-3-yl)-1,3-dioxoisoindolin-5-yl)pyrrolidin-3-yl)methyl)amino)cyclohexyl)-1,3,4-thiadiazol-2-yl)-4-(methylamino)pyridin-2-yl)pyrrolo[1,2-b]pyridazine-3-carbonitrile The title compound was synthesized from BB3 and (3R)-1-(2-(2,6-dioxopiperidin-3-yl)-1,3-dioxoisoindolin-5-yl)pyrrolidine-3-carbaldehyde by reductive amination using General Method B. LCMS: $C_{40}H_{39}N_{11}O_4S$ requires: 769.3. found: m/z=770.3 $[M+H]^+$ Example 154

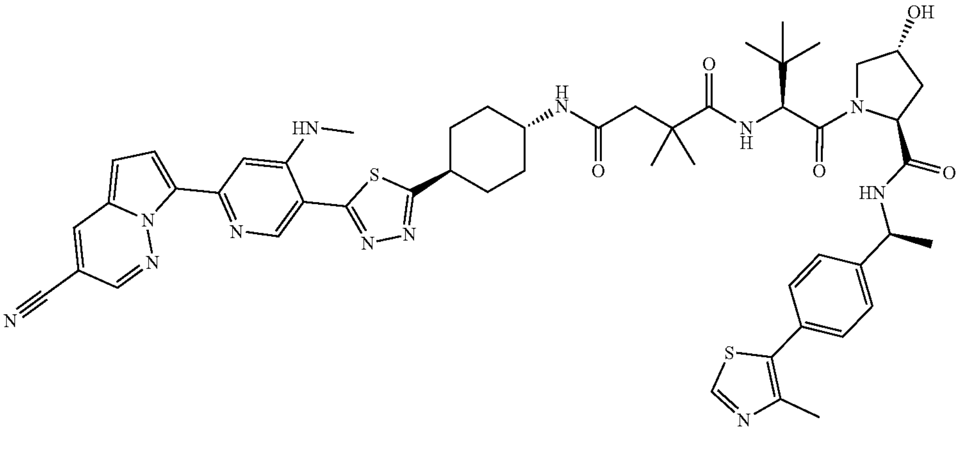 [SMILES: CNc1cc(-c2ccc3cc(C#N)cnn23)ncc1-c1nnc([C@H]2CC[C@H](NC(=O)CC(C)(C)C(=O)N[C@H](C(=O)N3C[C@H](O)C[C@H]3C(=O)N[C@@H](C)c3ccc(-c4scnc4C)cc3)C(C)(C)C)CC2)s1]

N4-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-$N_1$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-2,2-dimethylsuccinamide (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (100 mg, 0.22 mmol) was dissolved in dichloromethane (3 mL) and to which 3,3-dimethyloxolane-2,5-dione (30 mg, 0.22 mmol) was added. Stirred overnight at room temperature. Concentrated reaction to provide a crude oil. Added BB3 (25 mg, 0.06 mmol) and HATU (22 mg, 0.03 mmol) and suspended in DMF (2 mL). Added DIPEA (0.03 mL, 0.14 mmol) and stirred overnight at room temperature. Purified by prep-HPLC to give the title compound. LCMS: $C_{51}H_{60}N_{12}O_5S_2$ requires: 984.4. found: m/z=985.7 $[M+H]^+$; $^1H$ NMR (500 MHz, DMSO-$d_6$) δ 8.98 (d, J=13.9 Hz, 2H), 8.84 (d, J=2.3 Hz, 2H), 8.74 (s, 1H), 8.39 (d, J=7.8 Hz, 1H), 8.19 (d, J=8.7 Hz, 2H), 8.08-7.97 (m, 2H), 7.50-7.34 (m, 3H), 7.22 (d, J=4.9 Hz, 2H), 4.98-4.84 (m, 2H), 4.57-4.41 (m, 3H), 4.31 (s, 2H), 3.62 (d, J=4.7 Hz, 3H), 3.20 (d, J=4.8 Hz, 3H), 2.21 (d, J=12.5 Hz, 3H), 2.02 (d, J=9.5 Hz, 2H), 1.96 (d, J=13.0 Hz, 2H), 1.80 (dd, J=8.5, 4.2 Hz, 2H), 1.71 (d, J=12.3 Hz, 2H), 1.39 (d, J=6.9 Hz, 4H), 1.16 (s, 4H), 0.97 (d, J=9.1 Hz, 7H).

Example 155

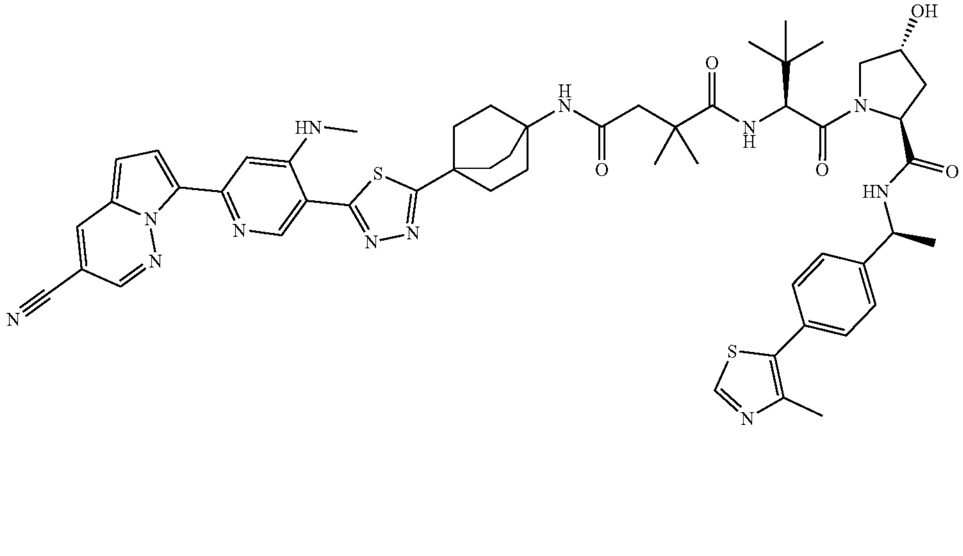 [SMILES: CNc1cc(-c2ccc3cc(C#N)cnn23)ncc1-c1nnc(C2CCC(NC(=O)CC(C)(C)C(=O)N[C@H](C(=O)N3C[C@H](O)C[C@H]3C(=O)N[C@@H](C)c3ccc(-c4scnc4C)cc3)C(C)(C)C)CC2)s1]

N4-(4-(5-(6-(3-cyanopyrrolo[1,2-b]pyridazin-7-yl)-4-(methylamino)pyridin-3-yl)-1,3,4-thiadiazol-2-yl) bicyclo[2.2.2]octan-1-yl)-$N_1$—((S)-1-((2S,4R)-4-hydroxy-2-(((S)-1-(4-(4-methylthiazol-5-yl)phenyl) ethyl)carbamoyl)pyrrolidin-1-yl)-3,3-dimethyl-1-oxobutan-2-yl)-2,2-dimethylsuccinamide (2S,4R)-1-((S)-2-amino-3,3-dimethylbutanoyl)-4-hydroxy-N—((S)-1-(4-(4-methylthiazol-5-yl)phenyl)ethyl) pyrrolidine-2-carboxamide (100 mg, 0.22 mmol) was dissolved in dichloromethane (3 mL) and to which 3,3-dimethyloxolane-2,5-dione (30 mg, 0.22 mmol) was added. Stirred overnight at room temperature. Concentrated reaction to provide a crude oil. Added BB13 (25 mg, 0.06 mmol) and HATU (22 mg, 0.03 mmol) and suspended in DMF (2 mL). Added DIPEA (0.03 mL, 0.14 mmol) and stirred overnight at room temperature. Purified by prep-HPLC to give the title compound. LCMS: $C_{53}H_{62}N_{12}O_5S_2$ requires: 1010.4. found: m/z=1011.9 $[M+H]^+$; $^1H$ NMR (500 MHz, DMSO-$d_6$) δ 8.98 (d, J=14.8 Hz, 3H), 8.84 (d, J=2.3 Hz, 2H), 8.73 (s, 2H), 8.40 (d, J=7.7 Hz, 1H), 8.16-7.92 (m, 4H), 7.64 (s, 2H), 7.54-7.32 (m, 5H), 7.22 (d, J=4.9 Hz, 2H), 4.98-4.86 (m, 2H), 4.55-4.37 (m, 4H), 4.31 (s, 2H), 3.67-3.51 (m, 4H), 3.19 (d, J=4.9 Hz, 5H), 2.16-1.85 (m, 12H), 1.87-1.73 (m, 3H), 1.40 (d, J=7.0 Hz, 3H), 1.25 (s, 3H), 1.15 (d, J=14.1 Hz, 6H), 0.97 (d, J=9.4 Hz, 7H).

Example 156

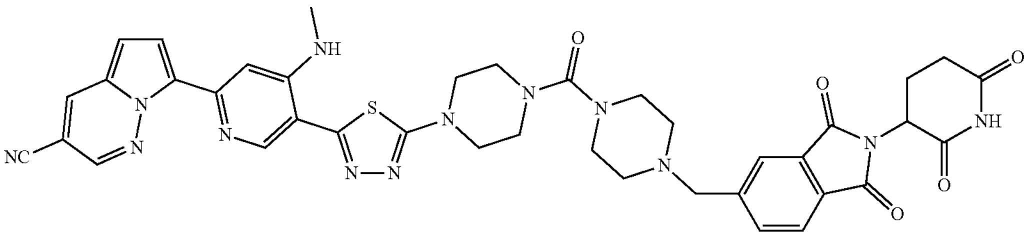 [SMILES: CNc1cc(-c2ccc3cc(C#N)cnn23)ncc1-c1nnc(N2CCN(C(=O)N3CCN(Cc4ccc5c(c4)C(=O)N(C4CCC(=O)NC4=O)C5=O)CC3)CC2)s1]

7-(5-(5-(4-(4-((2-(2,6-dioxopiperidin-3-yl)-1,3-dioxoisoindolin-5-yl)methyl)piperazine-1-carbonyl) piperazin-1-yl)-1,3,4-thiadiazol-2-yl)-4-(methylamino)pyridin-2-yl)pyrrolo[1,2-b]pyridazine-3-carbonitrile The title compound was synthesized from BB16 and rac-(R)-2-(2,6-dioxopiperidin-3-yl)-1,3-dioxoisoindoline-5-carbaldehyde by reductive amination using General Method B. LCMS: $C_{39}H_{37}N_{13}O_5S$ requires: 799.3. found: m/z=800.8 $[M+H]^+$.

Example 157

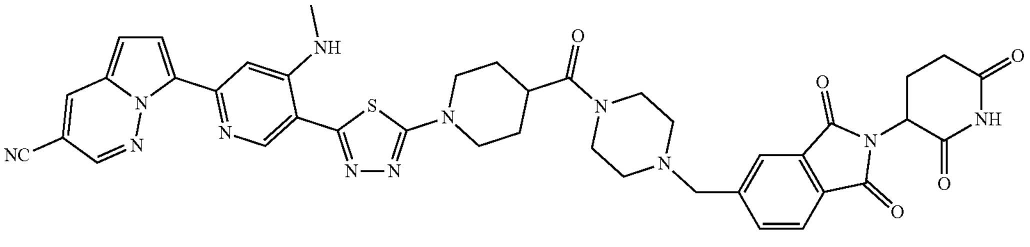 [SMILES: CNc1cc(-c2ccc3cc(C#N)cnn23)ncc1-c1nnc(N2CCC(C(=O)N3CCN(Cc4ccc5c(c4)C(=O)N(C4CCC(=O)NC4=O)C5=O)CC3)CC2)s1]

7-(5-(5-(4-(4-((2-(2,6-dioxopiperidin-3-yl)-1,3-dioxoisoindolin-5-yl)methyl)piperazine-1-carbonyl) piperidin-1-yl)-1,3,4-thiadiazol-2-yl)-4-(methylamino)pyridin-2-yl)pyrrolo[1,2-b]pyridazine-3-carbonitrile The title compound was synthesized from BB17 and rac-(R)-2-(2,6-dioxopiperidin-3-yl)-1,3-dioxoisoindoline-5-carbaldehyde by reductive amination using General Method B. LCMS: $C_{40}H_{38}N_{12}O_5S$ requires: 798.3. found: m/z=799.8 $[M+H]^+$.

Example 158

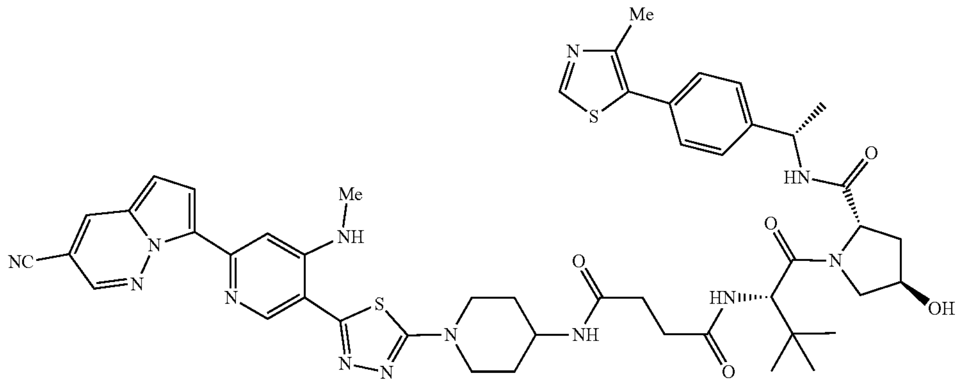 [SMILES: CNc1cc(-c2ccc3cc(C#N)cnn23)ncc1-c1nnc(N2CCC(NC(=O)CCC(=O)N[C@H](C(=O)N3C[C@H](O)C[C@H]3C(=O)N[C@@H](C)c3ccc(-c4scnc4C)cc3)C(C)(C)C)CC2)s1]

$N_1$-(1-(5-(6-(3-cyanopyrrolo[1,2-b]pyridazin-7-yl)-4-(methylamino)pyridin-3-yl)-1,3,4-thiadiazol-2-yl)piperidin-4-yl)-$N_4$—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)succinamide The title compound was synthesized from BB11 and 3-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}propanoic acid by amide coupling using General Method A. LCMS: $C_{48}H_{55}N_{13}O_5S_2$ requires: 957.4. found: m/z=958.7 $[M+H]^+$; $^1H$ NMR (500 MHz, DMSO-$d_6$) δ 8.99 (d, J=7.2 Hz, 1H), 8.85 (s, 1H), 8.52 (s, 1H), 8.38 (d, J=7.8 Hz, 1H), 8.07 (s, 1H), 7.98-7.79 (m, 2H), 7.50-7.35 (m, 2H), 7.24 (d, J=4.8 Hz, 1H), 4.93 (t, J=7.2 Hz, 1H), 4.52 (d, J=9.2 Hz, 1H), 4.43 (t, J=8.1 Hz, 1H), 4.29 (s, 1H), 3.91 (d, J=14.4 Hz, 2H), 3.62 (s, 2H), 3.24-3.15 (m, 2H), 2.46 (s, 1H), 2.43-2.25 (m, 3H), 2.01 (d, J=10.1 Hz, 1H), 1.96-1.85 (m, 1H), 1.85-1.65 (m, 2H), 1.61-1.43 (m, 2H), 1.39 (d, J=7.0 Hz, 1H), 1.25 (s, 1H), 0.95 (s, 9H).

Example 159

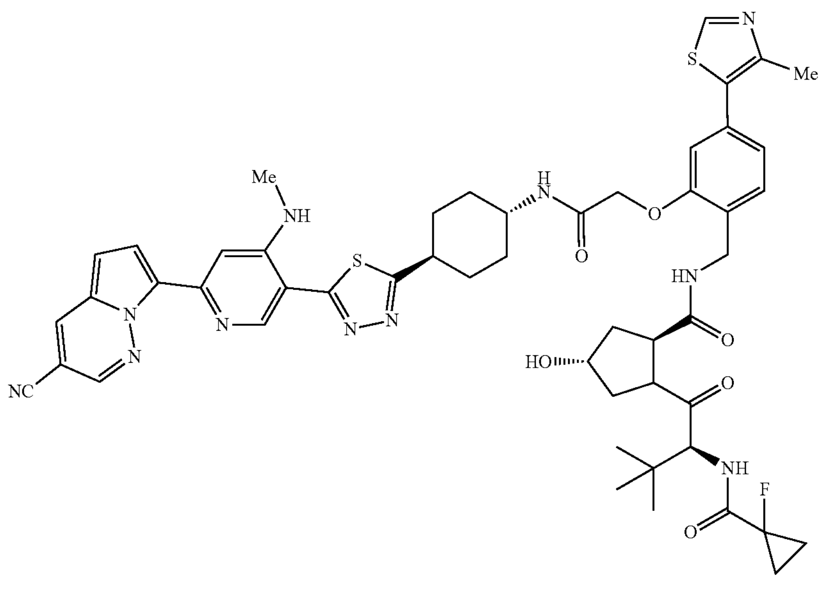 [SMILES: CNc1cc(-c2ccc3cc(C#N)cnn23)ncc1-c1nnc([C@H]2CC[C@H](NC(=O)COc3cc(-c4scnc4C)ccc3CNC(=O)[C@@H]3C[C@@H](O)CC3C(=O)[C@@H](NC(=O)C3(F)CC3)C(C)(C)C)CC2)s1]

(2S,4R)—N-(2-(2-(((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)amino)-2-oxoethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB3 and 2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]acetic acid by amide coupling using General Method A. LCMS: $C_{50}H_{55}FN_{12}O_6S_2$ requires: 1002.4. found: m/z=1003.7 $[M+H]^+$; $^1H$ NMR (500 MHz, DMSO-$d_6$) δ 9.01 (s, 1H), 8.96 (s, 1H), 8.84 (s, 1H), 8.74 (s, 1H), 8.56 (t, J=6.0 Hz, 1H), 8.15-7.99 (m, 2H), 7.45 (d, J=7.8 Hz, 1H), 7.29 (d, J=9.4 Hz, 1H), 7.22 (d, J=4.9 Hz, 1H), 7.04 (d, J=7.8 Hz, 1H), 6.99 (s, 1H), 4.67-4.55 (m, 2H), 4.55-4.42 (m, 2H), 4.38 (s, 1H), 4.28 (dd, J=15.6, 5.6 Hz, 2H), 3.73-3.59 (m, 2H), 3.19 (d, J=4.9 Hz, 3H), 2.48 (s, 2H), 2.22 (d, J=12.4 Hz, 2H), 2.07 (t, J=10.7 Hz, 1H), 2.00-1.84 (m, 2H), 1.72 (d, J=12.9 Hz, 2H), 1.57 (t, J=11.6 Hz, 2H), 1.38 (dd, J=18.8, 10.5 Hz, 2H), 1.32-1.19 (m, 2H), 0.98 (d, J=9.5 Hz, 9H).

Example 160

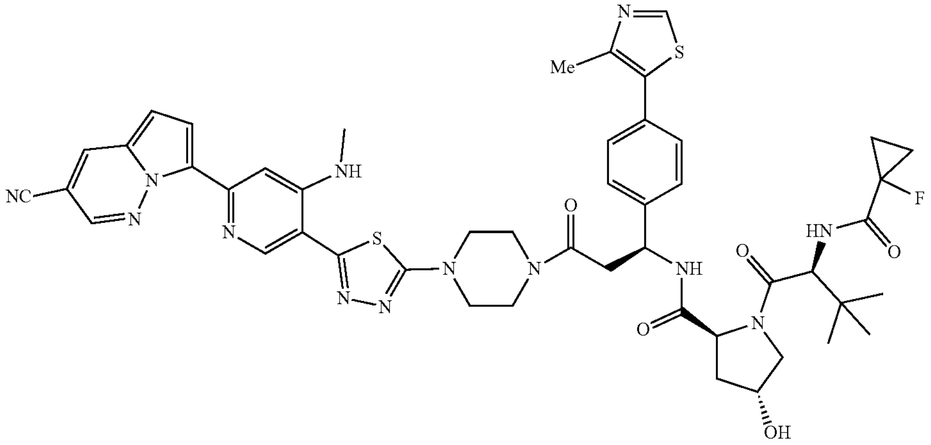 [SMILES: CNc1cc(-c2ccc3cc(C#N)cnn23)ncc1-c1nnc(N2CCN(C(=O)C[C@H](NC(=O)[C@@H]3C[C@@H](O)CN3C(=O)[C@@H](NC(=O)C3(F)CC3)C(C)(C)C)c3ccc(-c4scnc4C)cc3)CC2)s1]

(2S,4R)—N—((S)-3-(4-(5-(6-(3-cyanopyrrolo[1,2-b]pyridazin-7-yl)-4-(methylamino)pyridin-3-yl)-1,3,4-thiadiazol-2-yl)piperazin-1-yl)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB10 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{48}H_{52}FN_{13}O_5S_2$ requires: 973.4. found: m/z=974.8 $[M+H]^+$; $^1H$ NMR (500 MHz, DMSO-$d_6$) δ 9.58 (s, 1H), 9.07-8.93 (m, 2H), 8.87 (d, J=2.2 Hz, 1H), 8.62-8.50 (m, 2H), 8.12 (d, J=5.0 Hz, 1H), 7.91 (s, 1H), 7.46 (s, 3H), 7.26 (d, J=5.0 Hz, 1H), 7.21 (dd, J=9.2, 2.9 Hz, 1H), 5.27 (d, J=7.4 Hz, 1H), 4.58 (d, J=9.2 Hz, 1H), 4.47 (t, J=8.3 Hz, 1H), 4.29 (s, 2H), 3.23 (d, J=4.9 Hz, 3H), 2.93 (t, J=7.6 Hz, 2H), 2.45 (s, 3H), 2.08 (dd, J=12.7, 8.0 Hz, 1H), 1.77 (dt, J=8.7, 5.1 Hz, 1H), 1.45-1.11 (m, 4H), 0.97 (s, 9H).

Example 161

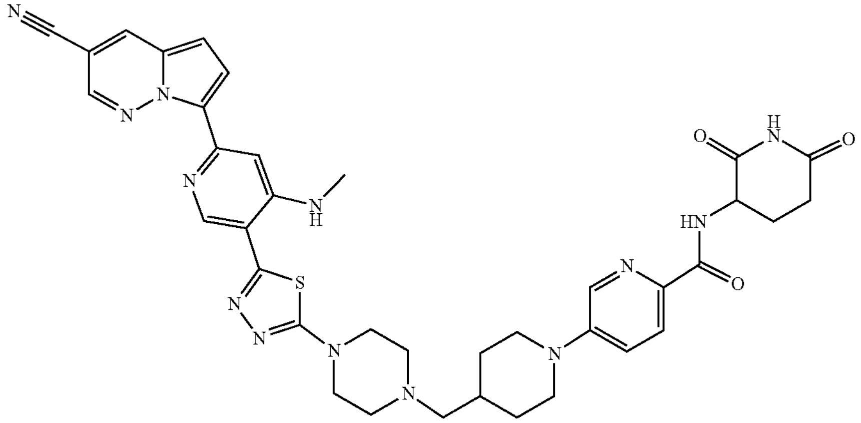 [SMILES: CNc1cc(-c2ccc3cc(C#N)cnn23)ncc1-c1nnc(N2CCN(CC3CCN(c4ccc(C(=O)NC5CCC(=O)NC5=O)nc4)CC3)CC2)s1]

5-(4-((4-(5-(6-(3-cyanopyrrolo[1,2-b]pyridazin-7-yl)-4-(methylamino)pyridin-3-yl)-1,3,4-thiadiazol-2-yl)piperazin-1-yl)methyl)piperidin-1-yl)-N-(2,6-dioxopiperidin-3-yl)picolinamide The title compound was synthesized from BB10 and N-(2,6-dioxopiperidin-3-yl)-5-(4-formylpiperidin-1-yl)pyridine-2-carboxamide by reductive amination using General Method B. LCMS: $C_{37}H_{39}N_{13}O_3S$ requires: 745.3. found: m/z=746.6 $[M+H]^+$ Example 162

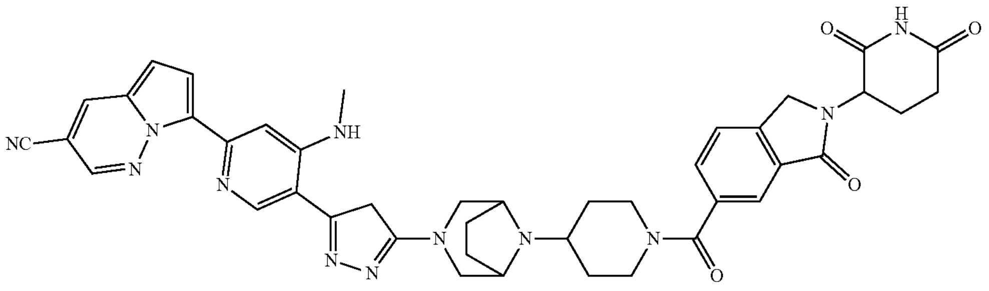 [SMILES: CNc1cc(-c2ccc3cc(C#N)cnn23)ncc1C1=NN=C(N2CC3CCC(C2)N3C2CCN(C(=O)c3ccc4c(c3)C(=O)N(C3CCC(=O)NC3=O)C4)CC2)C1]

7-(5-(5-(8-(1-(2-(2,6-dioxopiperidin-3-yl)-3-oxoisoindoline-5-carbonyl)piperidin-4-yl)-3,8-diazabicyclo[3.2.1]octan-3-yl)-1,3,4-thiadiazol-2-yl)-4-(methylamino)pyridin-2-yl)pyrrolo[1,2-b]pyridazine-3-carbonitrile The title compound was synthesized from BB20 and 2-(2,6-dioxopiperidin-3-yl)-3-oxoisoindoline-5-carboxylic acid by amide coupling using General Method A. LCMS: $C_{41}H_{40}N_{12}O_4S$ requires: 796.3. found: m/z=797.8 $[M+H]^+$; $^1H$ NMR (500 MHz, DMSO-$d_6$) δ 11.03 (s, 1H), 9.89 (d, J=38.0 Hz, 1H), 9.07 (d, J=27.1 Hz, 1H), 8.95 (d, J=2.2 Hz, 1H), 8.82 (d, J=2.2 Hz, 1H), 8.58 (s, 1H), 8.02 (d, J=6.7 Hz, 2H), 7.81-7.62 (m, 3H), 7.22 (d, J=4.9 Hz, 1H), 5.15 (dd, J=13.2, 5.1 Hz, 1H), 4.58-4.36 (m, 4H), 3.94 (d, J=23.8 Hz, 3H), 3.18 (d, J=4.9 Hz, 4H), 2.94 (ddd, J=17.4, 13.2, 5.2 Hz, 2H), 2.63 (d, J=17.3 Hz, 1H), 2.45-2.32 (m, 1H), 2.26 (s, 2H), 2.15 (s, 2H), 2.03 (d, J=6.5 Hz, 2H), 1.61 (s, 2H).

Example 163

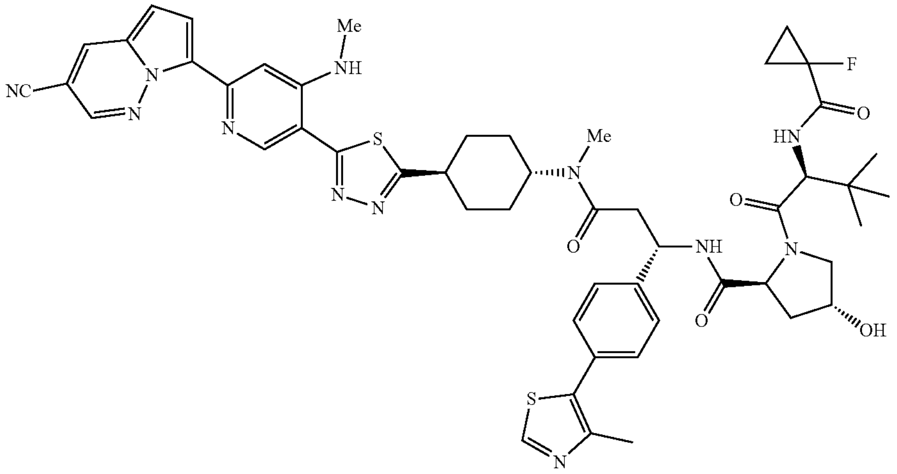 [SMILES: CNc1cc(-c2ccc3cc(C#N)cnn23)ncc1-c1nnc([C@H]2CC[C@H](N(C)C(=O)C[C@H](NC(=O)[C@@H]3C[C@@H](O)CN3C(=O)[C@@H](NC(=O)C3(F)CC3)C(C)(C)C)c3ccc(-c4scnc4C)cc3)CC2)s1]

(2S,4R)—N—((S)-3-(((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)(methyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB18 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{51}H_{57}FN_{12}O_5S_2$ requires: 1000.4. found: m/z=1001.8 $[M+H]^+$; $^1H$ NMR (500 MHz, DMSO-$d_6$) δ 9.08-8.94 (m, 1H), 8.86 (d, J=2.4 Hz, 1H), 8.74 (d, J=3.7 Hz, 1H), 8.51 (t, J=9.2 Hz, 1H), 8.12-7.94 (m, 2H), 7.44 (dd, J=7.5, 4.4 Hz, 2H), 7.37-7.17 (m, 2H), 5.32-5.16 (m, 1H), 4.59 (d, J=8.9 Hz, 1H), 4.47 (d, J=2.8 Hz, 1H), 4.40 (d, J=28.6 Hz, 1H), 4.30 (s, 1H), 3.21 (d, J=4.9 Hz, 3H), 2.95 (d, J=6.9 Hz, 1H), 2.86 (dd, J=13.6, 6.3 Hz, 1H), 2.79 (s, 1H), 2.67 (d, J=24.6 Hz, 2H), 2.47 (s, 2H), 2.21 (d, J=17.2 Hz, 2H), 2.06 (dd, J=13.0, 8.1 Hz, 1H), 1.73 (ddd, J=37.4, 20.9, 11.9 Hz, 4H), 1.55 (d, J=4.8 Hz, 1H), 1.49-1.26 (m, 2H), 1.26-1.16 (m, 1H), 0.99 (q, J=5.4, 4.6 Hz, 9H).

Example 164

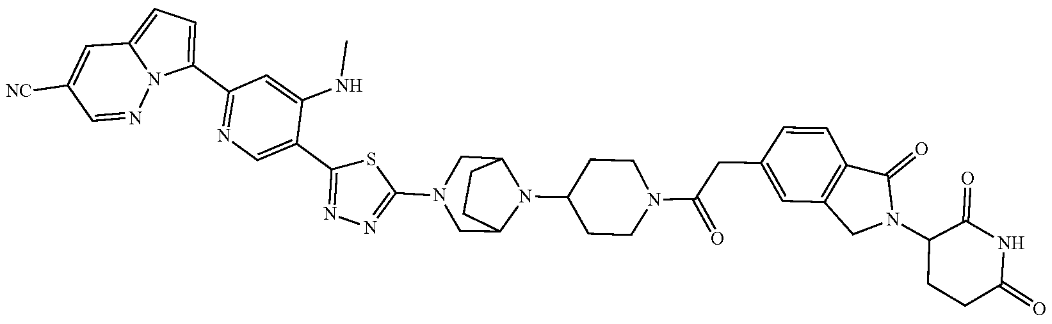 [SMILES: CNc1cc(-c2ccc3cc(C#N)cnn23)ncc1-c1nnc(N2CC3CCC(C2)N3C2CCN(C(=O)Cc3ccc4c(c3)CN(C3CCC(=O)NC3=O)C4=O)CC2)s1]

7-(5-(5-(8-(1-(2-(2-(2,6-dioxopiperidin-3-yl)-1-oxoisoindolin-5-yl)acetyl)piperidin-4-yl)-3,8-diazabicyclo[3.2.1]octan-3-yl)-1,3,4-thiadiazol-2-yl)-4-(methylamino)pyridin-2-yl)pyrrolo[1,2-b]pyridazine-3-carbonitrile The title compound was synthesized from BB20 and 2-(2-(2,6-dioxopiperidin-3-yl)-1-oxoisoindolin-5-yl)acetic acid by amide coupling using General Method A. LCMS: $C_{42}H_{42}N_{12}O_4S$ requires: 810.3. found: m/z=811.7 $[M+H]^+$; $^1H$ NMR (500 MHz, DMSO-$d_6$) δ 11.00 (d, J=7.0 Hz, 2H), 9.70 (d, J=37.6 Hz, 1H), 8.97 (s, 1H), 8.83 (s, 1H), 8.58 (d, J=14.1 Hz, 1H), 8.11-7.89 (m, 2H), 7.70 (dd, J=17.0, 7.8 Hz, 2H), 7.51 (s, 1H), 7.42 (q, J=8.1, 7.3 Hz, 1H), 7.34 (d, J=8.1 Hz, 1H), 7.23 (d, J=4.9 Hz, 1H), 5.12 (dd, J=13.2, 5.3 Hz, 2H), 4.56 (s, 2H), 4.45 (q, J=9.3 Hz, 4H), 4.32 (dd, J=17.4, 8.2 Hz, 3H), 3.93 (d, J=25.7 Hz, 6H), 3.19 (d, J=4.8 Hz, 5H), 2.62 (d, J=15.7 Hz, 4H), 2.45-2.31 (m, 3H), 2.23 (s, 4H), 2.12 (s, 2H), 2.02 (dd, J=12.5, 6.8 Hz, 4H), 1.39 (s, 2H).

Example 165

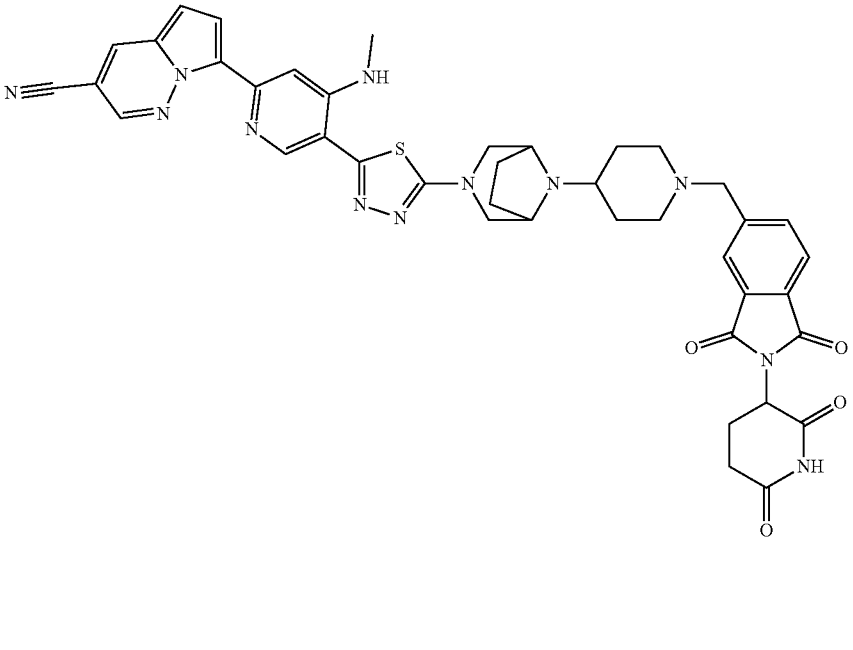 [SMILES: CNc1cc(-c2ccc3cc(C#N)cnn23)ncc1-c1nnc(N2CC3CCC(C2)N3C2CCN(Cc3ccc4c(c3)C(=O)N(C3CCC(=O)NC3=O)C4=O)CC2)s1]

7-(5-(5-(8-(1-((2-(2,6-dioxopiperidin-3-yl)-1,3-dioxoisoindolin-5-yl)methyl)piperidin-4-yl)-3,8-diazabicyclo[3.2.1]octan-3-yl)-1,3,4-thiadiazol-2-yl)-4-(methylamino)pyridin-2-yl)pyrrolo[1,2-b]pyridazine-3-carbonitrile The title compound was synthesized from BB20 and 2-(2,6-dioxopiperidin-3-yl)-1,3-dioxoisoindoline-5-carbaldehyde by amide coupling using General Method A. LCMS: $C_{41}H_{40}N_{12}O_4S$ requires: 796.3. found: m/z=797.6 $[M+H]^+$.

Example 166

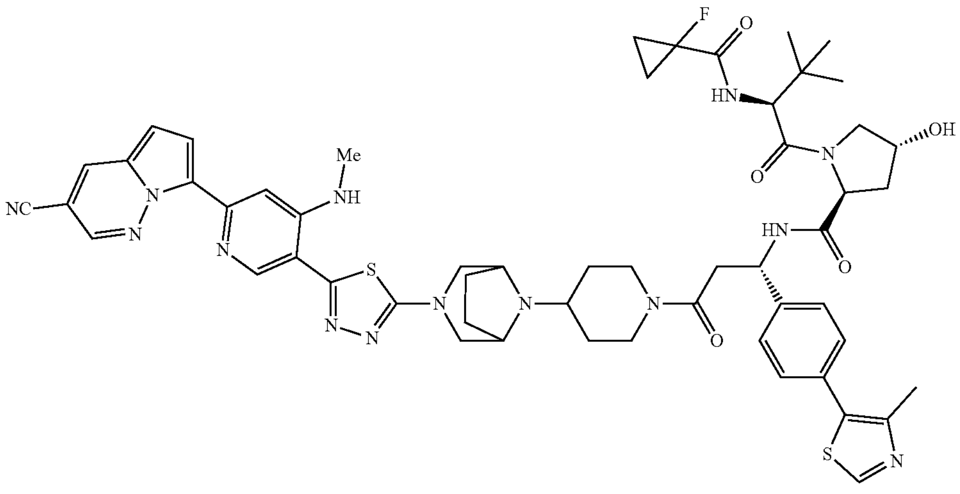 [SMILES: CNc1cc(-c2ccc3cc(C#N)cnn23)ncc1-c1nnc(N2CC3CCC(C2)N3C2CCN(C(=O)C[C@H](NC(=O)[C@@H]3C[C@@H](O)CN3C(=O)[C@@H](NC(=O)C3(F)CC3)C(C)(C)C)c3ccc(-c4scnc4C)cc3)CC2)s1]

(2S,4R)—N-((1S)-3-(4-(3-(5-(6-(3-cyanopyrrolo[1,2-b]pyridazin-7-yl)-4-(methylamino)pyridin-3-yl)-1,3,4-thiadiazol-2-yl)-3,8-diazabicyclo[3.2.1]octan-8-yl)piperidin-1-yl)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB20 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{55}H_{63}FN_{14}O_5S_5$ requires: 1083.3. found: m/z=1084.8 $[M+H]^+$; $^1$H NMR (500 MHz, DMSO-$d_6$) δ 9.72 (d, J=48.0 Hz, 1H), 8.99 (d, J=23.8 Hz, 2H), 8.83 (s, 1H), 8.59 (d, J=14.1 Hz, 1H), 8.55-8.25 (m, 1H), 8.09-7.89 (m, 2H), 7.44 (d, J=9.7 Hz, 5H), 7.24 (dd, J=16.7, 7.2 Hz, 2H), 5.21 (d, J=6.8 Hz, 2H), 4.59 (d, J=9.0 Hz, 2H), 4.46 (t, J=8.4 Hz, 3H), 4.31 (s, 3H), 3.18 (s, 5H), 2.30-1.94 (m, 8H), 1.78 (d, J=12.9 Hz, 1H), 1.36 (d, J=16.7 Hz, 4H), 1.28-1.15 (m, 4H), 0.99 (d, J=5.4 Hz, 12H).

Example 167

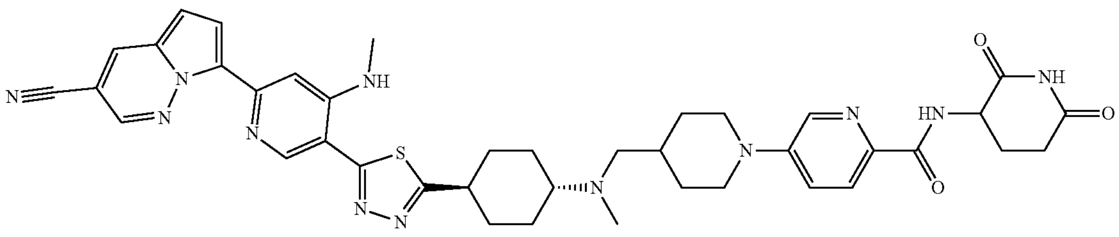 [SMILES: CNc1cc(-c2ccc3cc(C#N)cnn23)ncc1-c1nnc([C@H]2CC[C@H](N(C)CC3CCN(c4ccc(C(=O)NC5CCC(=O)NC5=O)nc4)CC3)CC2)s1]

5-(4-((((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)(methyl)amino)methyl)piperidin-1-yl)-N-(2,6-dioxopiperidin-3-yl)picolinamide The title compound was synthesized from BB18 and N-(2,6-dioxopiperidin-3-yl)-5-(4-formylpiperidin-1-yl)pyridine-2-carboxamide by amide coupling using General Method A. LCMS: $C_{40}H_{44}N_{12}O_3S$ requires: 772.3. found: m/z=773.7 $[M+H]^+$; $^1$H NMR (500 MHz, DMSO-$d_6$) δ 10.87 (s, 1H), 9.08 (s, 1H), 8.93 (d, J=15.0 Hz, 2H), 8.82 (s, 1H), 8.72 (d, J=20.0 Hz, 2H), 8.35 (d, J=13.5 Hz, 1H), 8.13 (d, J=16.1 Hz, 1H), 8.00 (d, J=5.0 Hz, 1H), 7.88 (d, J=8.8 Hz, 1H), 7.46 (d, J=9.2 Hz, 1H), 7.21 (d, J=4.9 Hz, 1H), 3.18 (s, 6H), 2.82 (d, J=5.1 Hz, 5H), 2.32 (s, 4H), 2.23-1.96 (m, 7H), 1.77 (q, J=12.5, 10.4 Hz, 6H), 1.25-1.04 (m, 4H).

Example 168

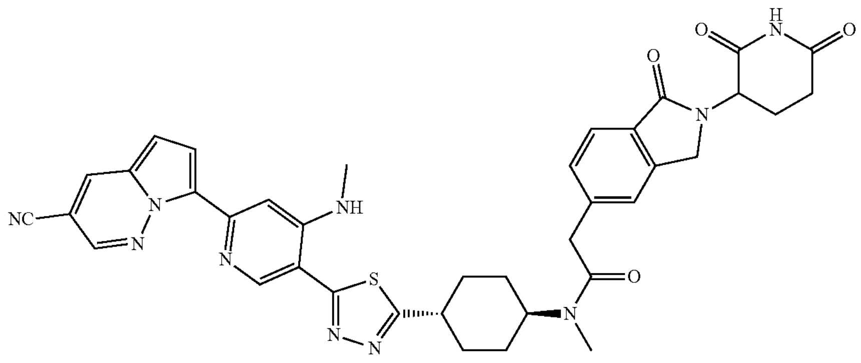 [SMILES: CNc1cc(-c2ccc3cc(C#N)cnn23)ncc1-c1nnc([C@H]2CC[C@H](N(C)C(=O)Cc3ccc4c(c3)CN(C3CCC(=O)NC3=O)C4=O)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-2-(2-(2,6-dioxopiperidin-3-yl)-1-oxoisoindolin-5-yl)-N-methylacetamide The title compound was synthesized from BB18 and 2-(2-(2,6-dioxopiperidin-3-yl)-1-oxoisoindolin-5-yl)acetic acid by amide coupling using General Method A. LCMS: $C_{38}H_{36}N_{10}O_4S$ requires: 728.3. found: m/z=729.6 $[M+H]^+$; $^1H$ NMR (500 MHz, DMSO-$d_6$) δ 11.00 (s, 1H), 8.95 (s, 1H), 8.83 (s, 1H), 8.73 (d, J=3.9 Hz, 1H), 8.10-7.94 (m, 1H), 7.69 (d, J=7.8 Hz, 1H), 7.57-7.33 (m, 2H), 7.21 (d, J=4.9 Hz, 1H), 5.12 (d, J=13.1 Hz, 1H), 4.46 (d, J=17.3 Hz, 2H), 4.32 (d, J=17.3 Hz, 1H), 3.96 (s, 2H), 3.87 (s, 1H), 2.92 (s, 2H), 2.77 (s, 1H), 2.55 (s, 2H), 2.27-2.10 (m, 2H), 1.97 (d, J=50.9 Hz, 1H), 1.87-1.52 (m, 5H).

Example 169

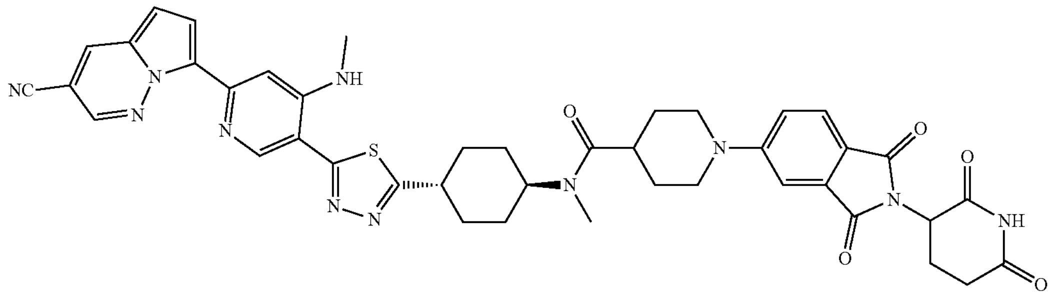 [SMILES: CNc1cc(-c2ccc3cc(C#N)cnn23)ncc1-c1nnc([C@H]2CC[C@H](N(C)C(=O)C3CCN(c4ccc5c(c4)C(=O)N(C4CCC(=O)NC4=O)C5=O)CC3)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-1-(2-(2,6-dioxopiperidin-3-yl)-1,3-dioxoisoindolin-5-yl)-N-methylpiperidine-4-carboxamide The title compound was synthesized from BB18 and 1-(2-(2,6-dioxopiperidin-3-yl)-1,3-dioxoisoindolin-5-yl)piperidine-4-carboxylic acid by amide coupling using General Method A. LCMS: $C_{42}H_{41}N_{11}O_5S$ requires: 811.3. found: m/z=812.6 $[M+H]^+$; $^1H$ NMR (500 MHz, Methanol-$d_4$) δ 8.80 (s, 1H), 8.72 (d, J=3.7 Hz, 2H), 8.13 (d, J=5.2 Hz, 1H), 7.91 (s, 1H), 7.71 (d, J=8.5 Hz, 1H), 7.39 (d, J=2.3 Hz, 1H), 7.27 (d, J=5.0 Hz, 1H), 4.13 (d, J=13.0 Hz, 2H), 3.12 (d, J=12.1 Hz, 4H), 3.00 (d, J=23.1 Hz, 1H), 2.91-2.85 (m, 2H), 2.76 (t, J=14.9 Hz, 2H), 2.40 (s, 2H), 2.16 (d, J=18.0 Hz, 2H), 1.99 (d, J=27.0 Hz, 3H), 1.92-1.77 (m, 6H).

Example 170

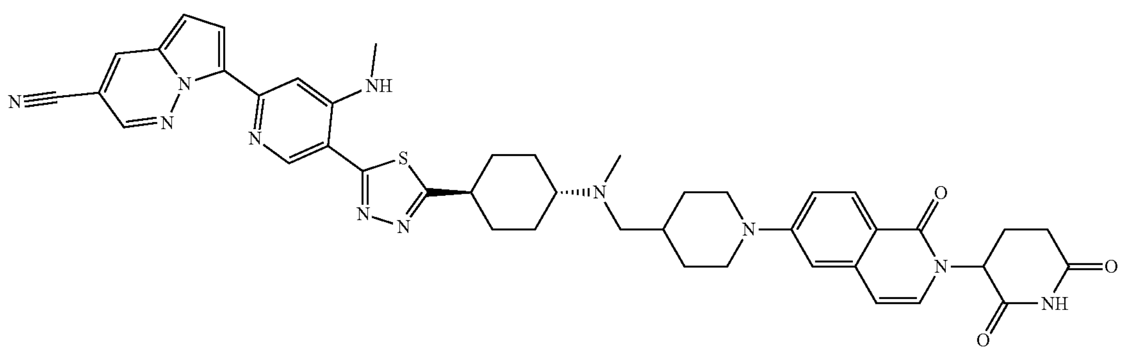 [SMILES: CNc1cc(-c2ccc3cc(C#N)cnn23)ncc1-c1nnc([C@H]2CC[C@H](N(C)CC3CCN(c4ccc5c(=O)n(C6CCC(=O)NC6=O)ccc5c4)CC3)CC2)s1]

7-(5-(5-((1r,4r)-4-(((1-(2-(2,6-dioxopiperidin-3-yl)-1-oxo-1,2-dihydroisoquinolin-6-yl)piperidin-4-yl)methyl)(methyl)amino)cyclohexyl)-1,3,4-thiadiazol-2-yl)-4-(methylamino)pyridin-2-yl)pyrrolo[1,2-b]pyridazine-3-carbonitrile The title compound was synthesized from BB18 and 1-[2-(2,6-dioxopiperidin-3-yl)-1-oxoisoquinolin-6-yl]piperidine-4-carbaldehyde by reductive amination using General Method B. LCMS: $C_{43}H_{45}N_{11}O_3S$ requires: 795.3. found: m/z=796.6 $[M+H]^+$.

Example 171

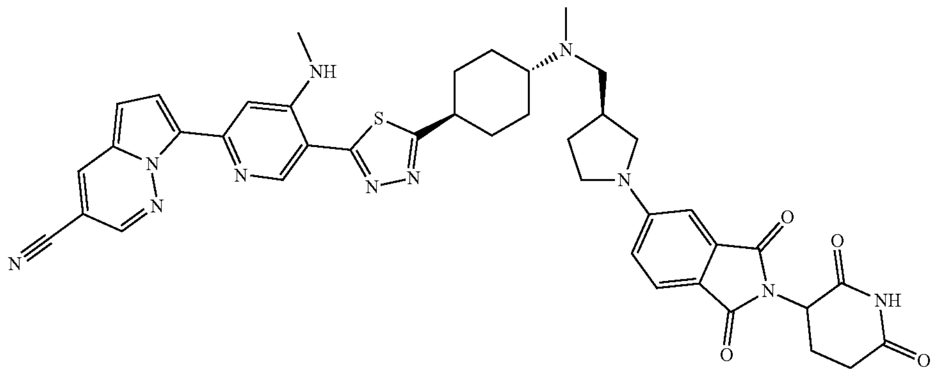 [SMILES: CNc1cc(-c2ccc3cc(C#N)cnn23)ncc1-c1nnc([C@H]2CC[C@H](N(C)C[C@@H]3CCN(c4ccc5c(c4)C(=O)N(C4CCC(=O)NC4=O)C5=O)C3)CC2)s1]

7-(5-(5-((1S,4r)-4-((((3S)-1-(2-(2,6-dioxopiperidin-3-yl)-1,3-dioxoisoindolin-5-yl)pyrrolidin-3-yl)methyl)(methyl)amino)cyclohexyl)-1,3,4-thiadiazol-2-yl)-4-(methylamino)pyridin-2-yl)pyrrolo[1,2-b]pyridazine-3-carbonitrile The title compound was synthesized from BB18 and (3S)-1-(2-(2,6-dioxopiperidin-3-yl)-1,3-dioxoisoindolin-5-yl)pyrrolidine-3-carbaldehyde by reductive amination using General Method B. LCMS: $C_{41}H_{41}N_{11}O_4S$ requires: 783.3. found: m/z=784.6 $[M+H]^+$; $^1H$ NMR (500 MHz, Methanol-$d_4$) δ 8.79 (d, J=2.2 Hz, 1H), 8.72 (d, J=13.8 Hz, 2H), 8.12 (d, J=5.1 Hz, 1H), 7.93 (s, 1H), 7.71 (d, J=8.3 Hz, 1H), 7.26 (d, J=5.0 Hz, 1H), 7.06 (d, J=2.2 Hz, 1H), 7.02-6.74 (m, 1H), 5.09 (dd, J=12.4, 5.4 Hz, 1H), 3.85-3.76 (m, 1H), 3.67 (d, J=8.0 Hz, 1H), 3.62-3.48 (m, 3H), 3.02 (s, 3H), 2.94-2.82 (m, 2H), 2.83-2.67 (m, 3H), 2.49 (d, J=24.8 Hz, 3H), 2.32 (s, 2H), 2.13 (d, J=11.7 Hz, 2H), 1.94 (s, 5H).

Example 172

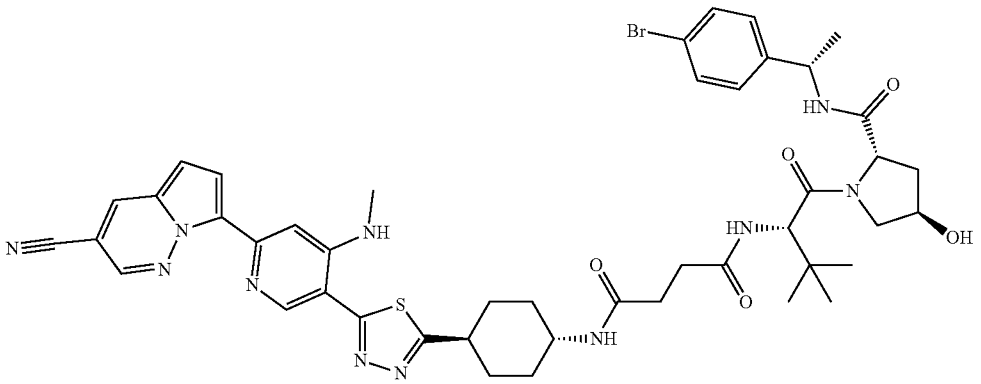 [SMILES: CNc1cc(-c2ccc3cc(C#N)cnn23)ncc1-c1nnc([C@H]2CC[C@H](NC(=O)CCC(=O)N[C@H](C(=O)N3C[C@H](O)C[C@H]3C(=O)N[C@@H](C)c3ccc(Br)cc3)C(C)(C)C)CC2)s1]

$N_1$—((S)-1-((2S,4R)-2-(((S)-1-(4-bromophenyl)ethyl)carbamoyl)-4-hydroxypyrrolidin-1-yl)-3,3-dimethyl-1-oxobutan-2-yl)-$N_4$-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)succinamide (2S,4R)-1-[(2S)-2-amino-3,3-dimethylbutanoyl]-N-[(1S)-1-(4-bromophenyl)ethyl]-4-hydroxypyrrolidine-2-carboxamide (50 mg, 0.12 mmol) was dissolved in DMF (2 mL) and to which succinic anhydride (12 mg, 0.03 mmol) was added. Stirred for 2 hours at room temperature. Added BB3 (30 mg, 0.06 mmol) and HATU (22 mg, 0.06 mmol) and suspended in DMF (1 mL). Stirred overnight at room temperature. Purified by prep-HPLC to give the title compound. LCMS: $C_{45}H_{52}BrN_{11}O_5S$ requires: 937.3. found: m/z=938.6 $[M+H]^+$; $^1H$ NMR (500 MHz, DMSO-$d_6$) δ 8.93 (s, 1H), 8.82 (s, 1H), 8.72 (s, 2H), 8.36 (d, J=7.7 Hz, 1H), 8.12 (s, 1H), 8.00 (s, 1H), 7.84 (dd, J=17.2, 8.5 Hz, 2H), 7.56-7.45 (m, 2H), 7.25 (d, J=8.1 Hz, 1H), 7.20 (d, J=5.0 Hz, 1H), 4.92-4.77 (m, 2H), 4.51 (d, J=9.2 Hz, 2H), 4.41 (t, J=8.0 Hz, 1H), 4.28 (s, 1H), 3.17 (d, J=4.8 Hz, 2H), 2.20 (d, J=12.7 Hz, 2H), 1.96 (dd, J=27.5, 11.1 Hz, 2H), 1.72 (dd, J=40.0, 10.0 Hz, 3H), 1.34 (d, J=7.0 Hz, 4H), 0.94 (s, 9H).

Example 173

N1-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-$N_4$—((S)-1-((2S,4R)-4-hydroxy-2-(((S)-1-phenylethyl)carbamoyl)pyrrolidin-1-yl)-3,3-dimethyl-1-oxobutan-2-yl)succinamide (2S,4R)-1-[(2S)-2-amino-3,3-dimethylbutanoyl]-4-hydroxy-N-[(1 S)-1-phenylethyl]pyrrolidine-2-carboxamide (20 mg, 0.06 mmol) was dissolved in DMF (1 mL) and to which succinic anhydride (6 mg, 0.06 mmol) was added. Stirred for 5 hours at room temperature. Added BB3 (12 mg, 0.03 mmol) and HATU (10 mg, 0.03 mmol) and suspended in DMF (1 mL). Added DIPEA (0.01 mL, 0.07 mmol) and stirred overnight at room temperature. Purified by prep-HPLC to give the title compound. LCMS: $C_{45}H_{53}N_{11}O_5S$ requires: 859.4. found: m/z=860.8 $[M+H]^+$; $^1H$ NMR (500 MHz, DMSO-$d_6$) δ 8.96 (s, 1H), 8.84 (s, 1H), 8.74 (s, 1H), 8.32 (d, J=8.0 Hz, 1H), 8.06 (d, J=15.3 Hz, 1H), 7.85 (dd, J=18.6, 8.5 Hz, 1H), 7.31 (d, J=8.5 Hz, 2H), 7.22 (d, J=4.4 Hz, 1H), 4.97-4.84 (m, 1H), 4.52 (d, J=9.2 Hz, 1H), 4.43 (t, J=8.1 Hz, 1H), 4.29 (s, 1H), 3.62 (s, 3H), 3.20 (d, J=4.8 Hz, 1H), 2.31 (s, 2H), 2.21 (d, J=12.6 Hz, 1H), 2.02-1.88 (m, 1H), 1.84-1.58 (m, 2H), 1.36 (d, J=7.2 Hz, 2H), 0.95 (s, 9H).

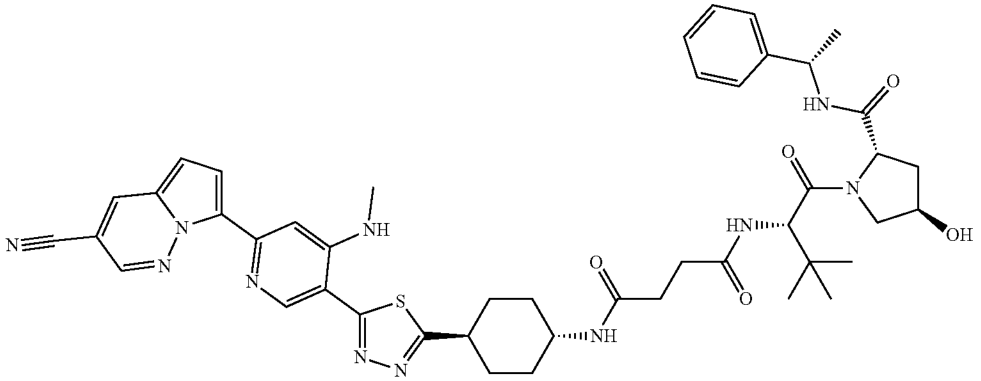 [SMILES: CNc1cc(-c2ccc3cc(C#N)cnn23)ncc1-c1nnc([C@H]2CC[C@H](NC(=O)CCC(=O)N[C@H](C(=O)N3C[C@H](O)C[C@H]3C(=O)N[C@@H](C)c3ccccc3)C(C)(C)C)CC2)s1]

Example 174

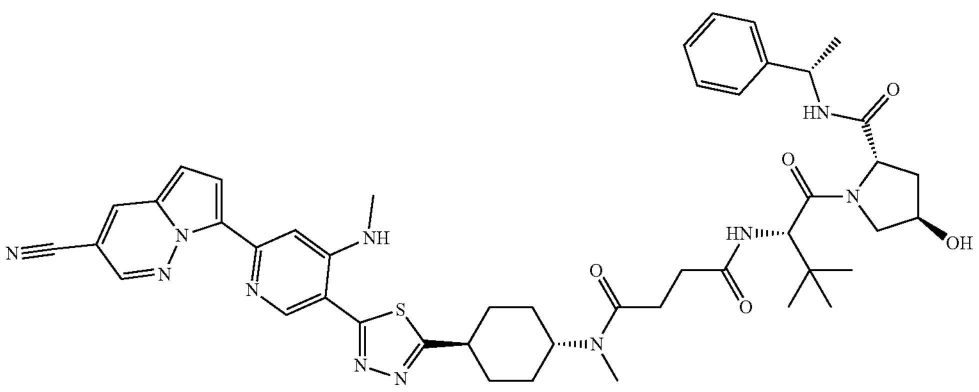 [SMILES: CNc1cc(-c2ccc3cc(C#N)cnn23)ncc1-c1nnc([C@H]2CC[C@H](N(C)C(=O)CCC(=O)N[C@H](C(=O)N3C[C@H](O)C[C@H]3C(=O)N[C@@H](C)c3ccccc3)C(C)(C)C)CC2)s1]

N1-((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)-$N_4$—((S)-1-((2S,4R)-4-hydroxy-2-(((S)-1-phenylethyl)carbamoyl)pyrrolidin-1-yl)-3,3-dimethyl-1-oxobutan-2-yl)-$N_1$-methylsuccinamide (2S,4R)-1-[(2S)-2-amino-3,3-dimethylbutanoyl]-4-hydroxy-N-[(1S)-1-phenylethyl]pyrrolidine-2-carboxamide (20 mg, 0.06 mmol) was dissolved in DMF (1 mL) and to which succinic anhydride (6 mg, 0.06 mmol) was added. Stirred for 5 hours at room temperature. Added BB18 (12 mg, 0.03 mmol) and HATU (10 mg, 0.03 mmol) and suspended in DMF (1 mL). Added DIPEA (0.01 mL, 0.07 mmol) and stirred overnight at room temperature. Purified by prep-HPLC to give the title compound. LCMS: $C_{46}H_{55}N_{11}O_5S$ requires: 873.4. found: m/z=874.8 $[M+H]^+$; $^1H$ NMR (500 MHz, DMSO-$d_6$) δ 8.99 (s, 1H), 8.86 (s, 2H), 8.75 (s, 1H), 8.32 (d, J=8.0 Hz, 2H), 8.06 (dd, J=15.0, 4.5 Hz, 3H), 7.87 (d, J=9.0 Hz, 2H), 7.37-7.25 (m, 3H), 7.23 (d, J=7.6 Hz, 2H), 5.02-4.83 (m, 3H), 4.52 (d, J=9.2 Hz, 2H), 4.43 (t, J=8.1 Hz, 2H), 4.29 (s, 2H), 3.22 (d, J=5.0 Hz, 2H), 2.88 (s, 2H), 2.75 (s, 3H), 2.25 (s, 2H), 2.00 (s, 2H), 1.95-1.72 (m, 5H), 1.64 (s, 3H), 1.36 (d, J=7.0 Hz, 3H), 0.96 (s, 9H).

Example 175

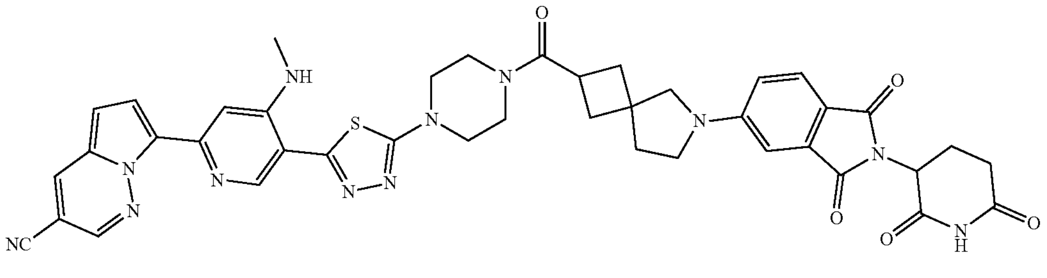 [SMILES: CNc1cc(-c2ccc3cc(C#N)cnn23)ncc1-c1nnc(N2CCN(C(=O)C3CC4(CCN(c5ccc6c(c5)C(=O)N(C5CCC(=O)NC5=O)C6=O)C4)C3)CC2)s1]

7-(5-(5-(4-(6-(2-(2,6-dioxopiperidin-3-yl)-1,3-dioxoisoindolin-5-yl)-6-azaspiro[3.4]octane-2-carbonyl)piperazin-1-yl)-1,3,4-thiadiazol-2-yl)-4-(methylamino)pyridin-2-yl)pyrrolo[1,2-b]pyridazine-3-carbonitrile The title compound was synthesized from BB10 and 6-(2-(2,6-dioxopiperidin-3-yl)-1,3-dioxoisoindolin-5-yl)-6-azaspiro[3.4]octane-2-carboxylic acid by amide coupling using General Method A. LCMS: $C_{41}H_{38}N_{12}O_5S$ requires: 810.3. found: m/z=811.6 $[M+H]^+$; $^1H$ NMR (500 MHz, Methanol-$d_4$) δ 8.78 (d, J=2.2 Hz, 1H), 8.70 (d, J=2.2 Hz, 1H), 8.50 (s, 1H), 8.10 (d, J=5.0 Hz, 1H), 7.83 (s, 1H), 7.66 (dd, J=11.5, 8.4 Hz, 1H), 7.25 (d, J=5.1 Hz, 1H), 7.08-6.91 (m, 1H), 6.84 (dd, J=19.8, 8.4 Hz, 1H), 5.08 (dd, J=12.2, 6.0 Hz, 1H), 3.84 (s, 2H), 3.72 (d, J=10.1 Hz, 6H), 3.61-3.35 (m, 5H), 2.87 (d, J=15.9 Hz, 1H), 2.73 (dd, J=33.4, 18.4 Hz, 3H), 2.38 (qd, J=23.3, 20.0, 11.1 Hz, 3H), 2.28-2.18 (m, 1H), 2.18-1.99 (m, 2H).

Example 176

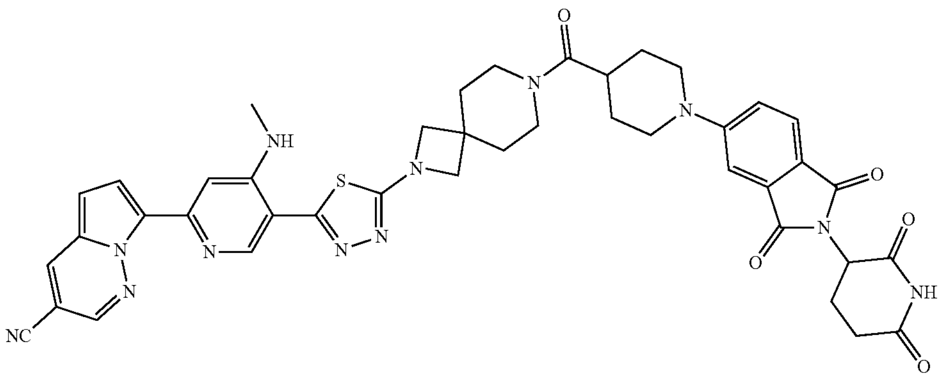 [SMILES: CNc1cc(-c2ccc3cc(C#N)cnn23)ncc1-c1nnc(N2CC3(CCN(C(=O)C4CCN(c5ccc6c(c5)C(=O)N(C5CCC(=O)NC5=O)C6=O)CC4)CC3)C2)s1]

7-(5-(5-(7-(1-(2-(2,6-dioxopiperidin-3-yl)-1,3-dioxoisoindolin-5-yl)piperidine-4-carbonyl)-2,7-diazaspiro[3.5]nonan-2-yl)-1,3,4-thiadiazol-2-yl)-4-(methylamino)pyridin-2-yl)pyrrolo[1,2-b]pyridazine-3-carbonitrile The title compound was synthesized from BB21 and 1-(2-(2,6-dioxopiperidin-3-yl)-1,3-dioxoisoindolin-5-yl)piperidine-4-carboxylic acid by amide coupling using General Method A. LCMS: $C_{42}H_{40}N_{12}O_5S$ requires: 824.3. found: m/z=825.7 $[M+H]^+$; $^1H$ NMR (500 MHz, Methanol-$d_4$) δ 8.79 (d, J=2.1 Hz, 1H), 8.70 (d, J=2.2 Hz, 1H), 8.49 (s, 1H), 8.11 (d, J=5.1 Hz, 1H), 7.83 (s, 1H), 7.69 (d, J=8.5 Hz, 1H), 7.38 (d, J=2.3 Hz, 1H), 7.26 (dd, J=6.0, 3.8 Hz, 2H), 5.09 (dd, J=12.3, 5.5 Hz, 1H), 4.11 (d, J=8.4 Hz, 6H), 3.67 (d, J=22.2 Hz, 4H), 3.20-2.91 (m, 3H), 2.91-2.62 (m, 3H), 2.25-2.07 (m, 1H), 2.02 (s, 2H), 1.89 (d, J=25.7 Hz, 5H).

Example 177

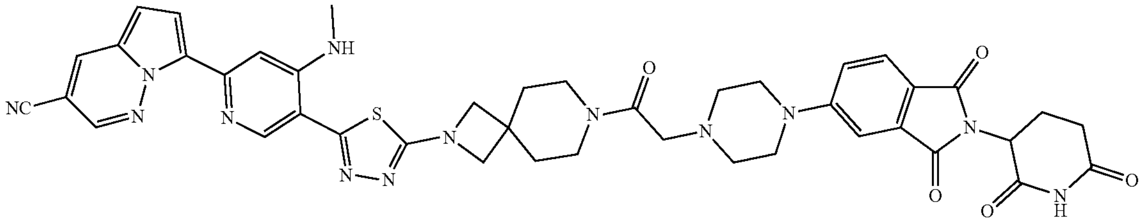 [SMILES: CNc1cc(-c2ccc3cc(C#N)cnn23)ncc1-c1nnc(N2CC3(CCN(C(=O)CN4CCN(c5ccc6c(c5)C(=O)N(C5CCC(=O)NC5=O)C6=O)CC4)CC3)C2)s1]

7-(5-(5-(7-(2-(4-(2-(2,6-dioxopiperidin-3-yl)-1,3-dioxoisoindolin-5-yl)piperazin-1-yl)acetyl)-2,7-diazaspiro[3.5]nonan-2-yl)-1,3,4-thiadiazol-2-yl)-4-(methylamino)pyridin-2-yl)pyrrolo[1,2-b]pyridazine-3-carbonitrile The title compound was synthesized from BB21 and 2-(4-(2-(2,6-dioxopiperidin-3-yl)-1,3-dioxoisoindolin-5-yl)piperazin-1-yl)acetic acid by amide coupling using General Method A. LCMS: $C_{42}H_{41}N_{13}O_5S$ requires: 839.3. found: m/z=840.7 $[M+H]^+$; $^1H$ NMR (500 MHz, Methanol-$d_4$) δ 8.79 (d, J=2.1 Hz, 1H), 8.70 (d, J=2.2 Hz, 1H), 8.50 (s, 1H), 8.11 (d, J=5.0 Hz, 1H), 7.90-7.70 (m, 2H), 7.52 (d, J=2.3 Hz, 1H), 7.39 (dd, J=8.5, 2.4 Hz, 1H), 7.25 (d, J=5.0 Hz, 1H), 5.12 (dd, J=12.5, 5.5 Hz, 1H), 4.41 (s, 2H), 4.11 (s, 5H), 3.71 (t, J=5.7 Hz, 3H), 3.57 (s, 3H), 3.48 (d, J=5.8 Hz, 3H), 2.89 (ddd, J=17.7, 14.1, 5.4 Hz, 1H), 2.82-2.54 (m, 2H), 2.18-2.08 (m, 1H), 2.00 (dt, J=30.5, 5.7 Hz, 4H).

Example 178

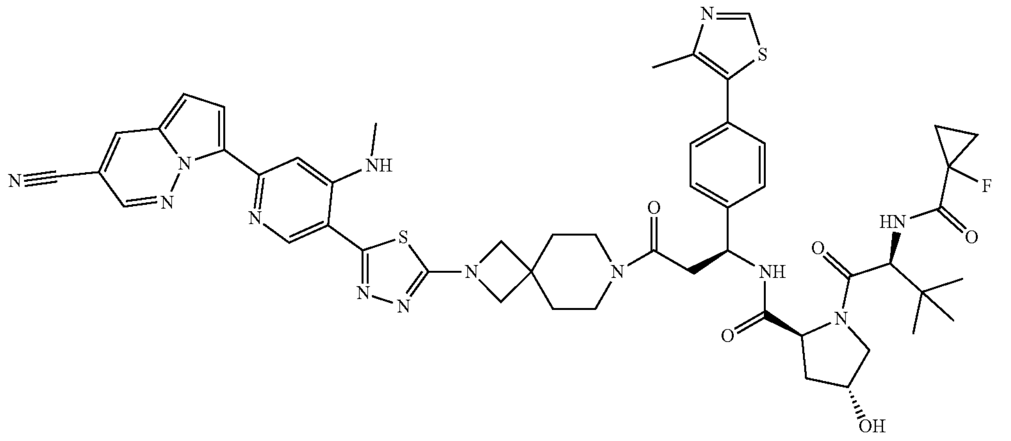 [SMILES: CNc1cc(-c2ccc3cc(C#N)cnn23)ncc1-c1nnc(N2CC3(CCN(C(=O)C[C@H](NC(=O)[C@@H]4C[C@@H](O)CN4C(=O)[C@@H](NC(=O)C4(F)CC4)C(C)(C)C)c4ccc(-c5scnc5C)cc4)CC3)C2)s1]

((2S,4R)—N—((S)-3-(2-(5-(6-(3-cyanopyrrolo[1,2-b]pyridazin-7-yl)-4-(methylamino)pyridin-3-yl)-1,3,4-thiadiazol-2-yl)-2,7-diazaspiro[3.5]nonan-7-yl)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB21 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{51}H_{56}FN_{13}O_5S_2$ requires: 1013.4. found: m/z=1014.8 $[M+H]^+$; $^1H$ NMR (500 MHz, DMSO-$d_6$) δ 9.00 (d, J=19.1 Hz, 2H), 8.85 (s, 1H), 8.54 (q, J=7.9, 6.5 Hz, 2H), 8.07 (s, 1H), 7.95 (s, 1H), 7.44 (q, J=8.2 Hz, 3H), 7.26 (dd, J=14.7, 7.0 Hz, 2H), 5.23 (d, J=7.7 Hz, 2H), 4.60 (d, J=9.1 Hz, 2H), 4.47 (t, J=8.3 Hz, 2H), 4.30 (s, 2H), 3.93 (d, J=22.2 Hz, 4H), 3.20 (d, J=4.7 Hz, 3H), 2.88 (dd, J=13.6, 7.0 Hz, 4H), 2.08 (d, J=11.5 Hz, 2H), 1.73 (d, J=53.4 Hz, 5H), 1.40 (dd, J=19.1, 9.2 Hz, 3H), 1.25 (s, 2H), 0.99 (d, J=12.3 Hz, 9H).

Example 179

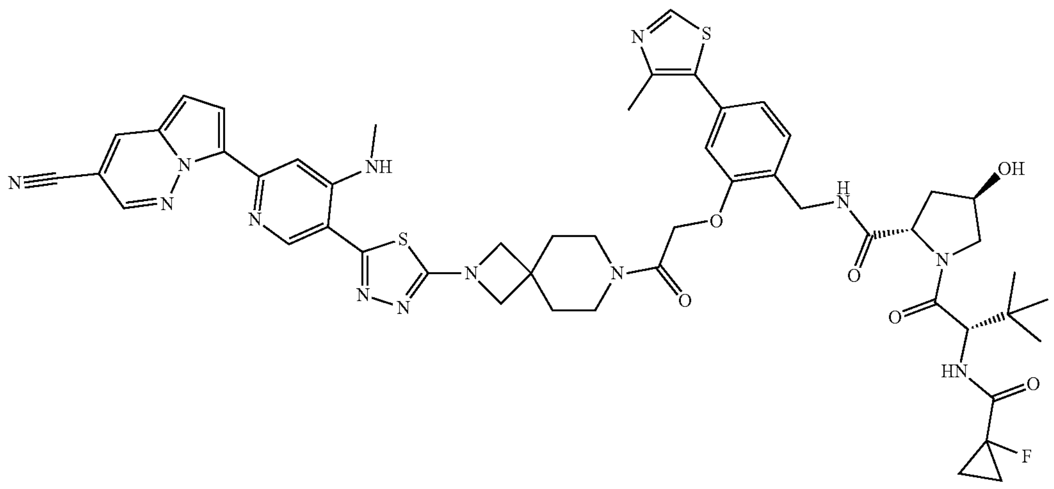 [SMILES: CNc1cc(-c2ccc3cc(C#N)cnn23)ncc1-c1nnc(N2CC3(CCN(C(=O)COc4cc(-c5scnc5C)ccc4CNC(=O)[C@@H]4C[C@@H](O)CN4C(=O)[C@@H](NC(=O)C4(F)CC4)C(C)(C)C)CC3)C2)s1]

(2S,4R)—N-(2-(2-(2-(5-(6-(3-cyanopyrrolo[1,2-b]pyridazin-7-yl)-4-(methylamino)pyridin-3-yl)-1,3,4-thiadiazol-2-yl)-2,7-diazaspiro[3.5]nonan-7-yl)-2-oxoethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide The title compound was synthesized from BB21 and 2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]acetic acid by amide coupling using General Method A. LCMS: $C_{51}H_{56}FN_{13}O_6S_2$ requires: 1029.4. found: m/z=1030.7 $[M+H]^+$; $^1H$ NMR (500 MHz, DMSO-$d_6$) δ 8.99 (d, J=10.3 Hz, 1H), 8.85 (s, 1H), 8.58 (d, J=21.1 Hz, 1H), 8.07 (s, 1H), 7.95 (s, 1H), 7.42 (d, J=7.7 Hz, 1H), 7.27 (dd, J=29.1, 7.1 Hz, 2H), 7.12-6.92 (m, 2H), 5.00 (s, 1H), 4.61 (d, J=9.1 Hz, 1H), 4.52 (s, 1H), 4.43-4.22 (m, 2H), 3.99 (s, 2H), 2.08 (s, 1H), 1.90 (s, 2H), 1.79 (s, 1H), 1.42-1.32 (m, 1H), 1.24 (s, 2H), 0.97 (s, 9H).

Example 180

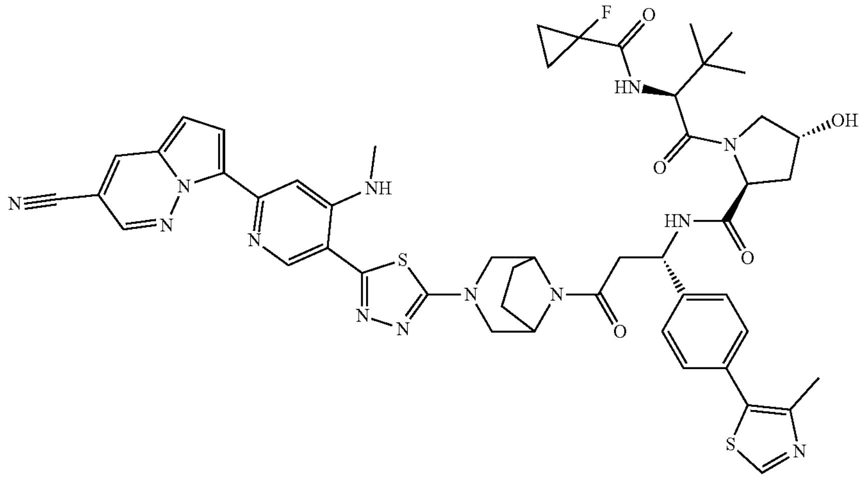 [SMILES: CNc1cc(-c2ccc3cc(C#N)cnn23)ncc1-c1nnc(N2CC3CCC(C2)N3C(=O)C[C@H](NC(=O)[C@@H]2C[C@@H](O)CN2C(=O)[C@@H](NC(=O)C2(F)CC2)C(C)(C)C)c2ccc(-c3scnc3C)cc2)s1]

(2S,4R)—N-((1S)-3-(3-(5-(6-(3-cyanopyrrolo[1,2-b]pyridazin-7-yl)-4-(methylamino)pyridin-3-yl)-1,3,4-thiadiazol-2-yl)-3,8-diazabicyclo[3.2.1]octan-8-yl)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB19 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{55}H_{54}FN_{13}O_5S_2$ requires: 999.4. found: m/z=1000.7 $[M+H]^+$; $^1H$ NMR (500 MHz, DMSO-$d_6$) δ 8.98 (d, J=22.0 Hz, 1H), 8.92-8.77 (m, 1H), 8.64 (s, 1H), 8.49 (d, J=26.5 Hz, 1H), 8.11 (s, 1H), 7.91 (s, 1H), 7.42 (dd, J=17.4, 8.2 Hz, 2H), 7.26 (t, J=4.6 Hz, 2H), 5.35-5.22 (m, 1H), 4.71 (d, J=11.3 Hz, 1H), 4.58 (d, J=9.2 Hz, 1H), 4.46 (dd, J=20.4, 12.0 Hz, 1H), 4.28 (s, 1H), 3.22 (s, 2H), 2.85 (d, J=7.2 Hz, 2H), 2.08 (s, 2H), 1.88 (s, 1H), 1.74 (d, J=23.1 Hz, 3H), 1.36 (d, J=10.1 Hz, 1H), 1.30-1.13 (m, 2H), 0.97 (d, J=7.4 Hz, 9H).

Example 181

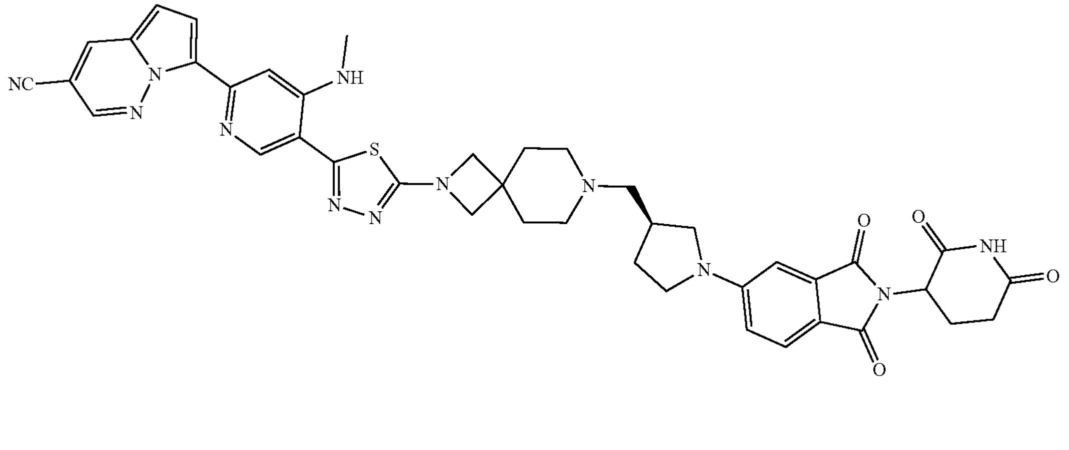 [SMILES: CNc1cc(-c2ccc3cc(C#N)cnn23)ncc1-c1nnc(N2CC3(CCN(C[C@@H]4CCN(c5ccc6c(c5)C(=O)N(C5CCC(=O)NC5=O)C6=O)C4)CC3)C2)s1]

7-(5-(5-(7-(((3S)-1-(2-(2,6-dioxopiperidin-3-yl)-1,3-dioxoisoindolin-5-yl)pyrrolidin-3-yl)methyl)-2,7-diazaspiro[3.5]nonan-2-yl)-1,3,4-thiadiazol-2-yl)-4-(methylamino)pyridin-2-yl)pyrrolo[1,2-b]pyridazine-3-carbonitrile The title compound was synthesized from BB21 and (3S)-1-(2-(2,6-dioxopiperidin-3-yl)-1,3-dioxoisoindolin-5-yl)pyrrolidine-3-carbaldehyde by reductive amination using General Method B. LCMS: $C_{41}H_{40}N_{12}O_4S$ requires: 796.3. found: m/z=797.9 $[M+H]^+$; $^1H$ NMR (500 MHz, Methanol-$d_4$) δ 8.86-8.75 (m, 1H), 8.70 (dd, J=4.7, 2.4 Hz, 1H), 8.55-8.40 (m, 1H), 8.11 (q, J=4.9, 4.1 Hz, 1H), 7.86 (dt, J=12.0, 3.7 Hz, 1H), 7.71 (dt, J=8.0, 3.6 Hz, 1H), 7.26 (t, J=4.7 Hz, 1H), 7.19-6.98 (m, 1H), 6.91 (d, J=7.1 Hz, 1H), 5.14-5.04 (m, 1H), 4.27-4.01 (m, 4H), 3.87-3.47 (m, 5H), 3.03-2.82 (m, 2H), 2.82-2.63 (m, 2H), 2.43 (s, 2H), 2.16 (p, J=12.2, 11.1 Hz, 3H), 2.03-1.82 (m, 2H).

Example 182

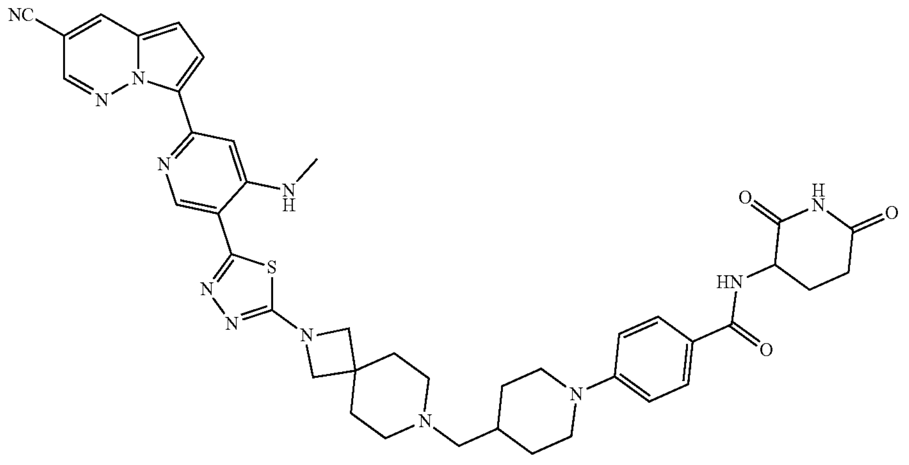 [SMILES: CNc1cc(-c2ccc3cc(C#N)cnn23)ncc1-c1nnc(N2CC3(CCN(CC4CCN(c5ccc(C(=O)NC6CCC(=O)NC6=O)cc5)CC4)CC3)C2)s1]

4-(4-((2-(5-(6-(3-cyanopyrrolo[1,2-b]pyridazin-7-yl)-4-(methylamino)pyridin-3-yl)-1,3,4-thiadiazol-2-yl)-2,7-diazaspiro[3.5]nonan-7-yl)methyl)piperidin-1-yl)-N-(2,6-dioxopiperidin-3-yl)benzamide The title compound was synthesized from BB21 and N-(2,6-dioxopiperidin-3-yl)-5-(4-formylpiperidin-1-yl) pyridine-2-carboxamide by reductive amination using General Method B. LCMS: $C_{41}H_{44}N_{12}O_3S$ requires: 784.3. found: m/z=785.9 $[M+H]^+$; $^1H$ NMR (500 MHz, Methanol-$d_4$) δ 8.77 (d, J=2.1 Hz, 1H), 8.69 (d, J=2.1 Hz, 1H), 8.50 (d, J=2.4 Hz, 1H), 8.11 (d, J=5.0 Hz, 1H), 7.88-7.72 (m, 3H), 7.25 (d, J=5.0 Hz, 1H), 7.03 (d, J=8.7 Hz, 2H), 4.19 (d, J=5.9 Hz, 2H), 4.14-4.03 (m, 2H), 3.99 (d, J=12.9 Hz, 2H), 3.67 (d, J=12.9 Hz, 2H), 3.12 (d, J=6.8 Hz, 3H), 3.04-2.68 (m, 4H), 2.39 (d, J=14.5 Hz, 2H), 2.25-2.06 (m, 5H), 1.93 (d, J=12.9 Hz, 1H), 1.53-1.40 (m, 2H).

Example 183

(2S,4R)—N—((S)-3-(((1r,3S)-3-(5-(6-(3-cyanopyrrolo[1,2-b]pyridazin-7-yl)-4-(methylamino)pyridin-3-yl)-1,3,4-thiadiazol-2-yl)cyclobutyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide The title compound was synthesized from BB24 and (3S)-3-{[(2S,4R)-1-[(2S)-2-[(1-fluorocyclopropyl)formamido]-3,3-dimethylbutanoyl]-4-hydroxypyrrolidin-2-yl]formamido}-3-[4-(4-methyl-1,3-thiazol-5-yl)phenyl]propanoic acid by amide coupling using General Method A. LCMS: $C_{48}H_{51}FN_{12}O_5S_2$ requires: 958.4. found: m/z=959.8 $[M+H]^+$; $^1H$ NMR (500 MHz, DMSO-$d_6$) δ 9.09-8.92 (m, 1H), 8.87 (s, 1H), 8.74 (s, 1H), 8.60 (d, J=8.1 Hz, 1H), 8.35 (d, J=7.2 Hz, 1H), 8.13-7.98 (m, 1H), 7.56-7.33 (m, 2H), 7.25 (d, J=5.5 Hz, 1H), 5.21 (d, J=8.0 Hz, 1H), 4.60 (d, J=9.1 Hz, 1H), 4.48 (d, J=9.8 Hz, 2H), 4.31 (s, 2H), 3.22 (d, J=4.6 Hz, 2H), 2.16-1.97 (m, 1H), 1.77 (s, 1H), 1.46-1.32 (m, 1H), 1.24 (d, J=8.8 Hz, 2H), 1.00 (s, 3H).

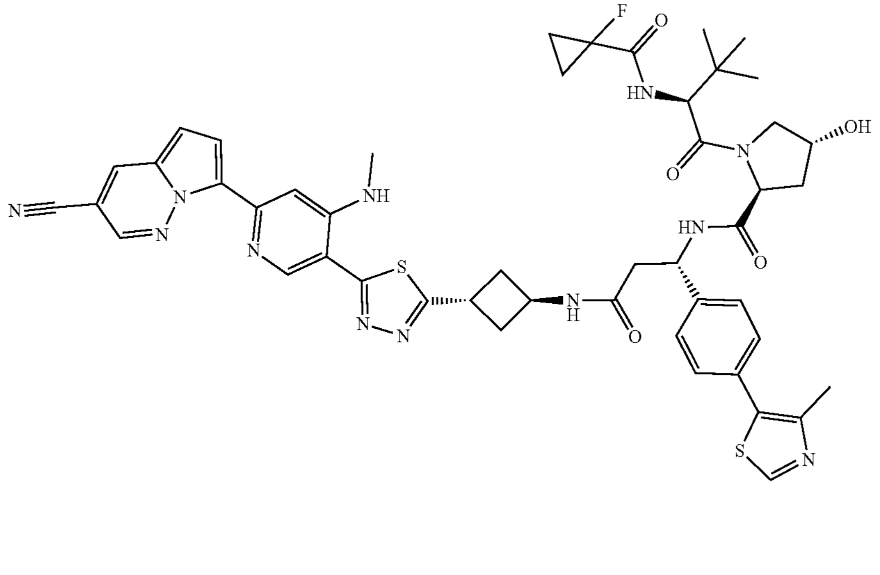 [SMILES: CNc1cc(-c2ccc3cc(C#N)cnn23)ncc1-c1nnc([C@H]2C[C@H](NC(=O)C[C@H](NC(=O)[C@@H]3C[C@@H](O)CN3C(=O)[C@@H](NC(=O)C3(F)CC3)C(C)(C)C)c3ccc(-c4scnc4C)cc3)C2)s1]

Example 184

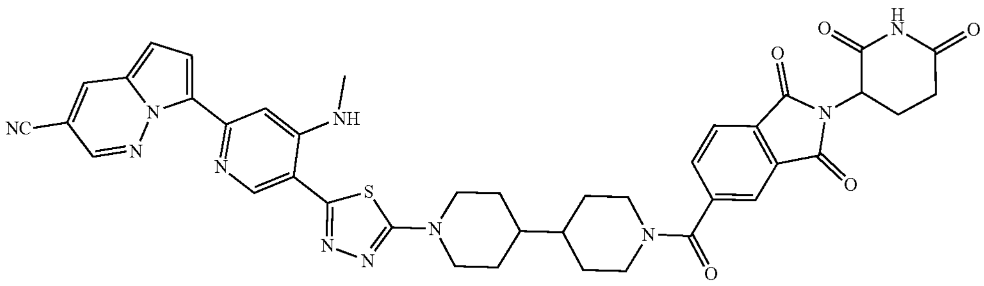 [SMILES: CNc1cc(-c2ccc3cc(C#N)cnn23)ncc1-c1nnc(N2CCC(C3CCN(C(=O)c4ccc5c(c4)C(=O)N(C4CCC(=O)NC4=O)C5=O)CC3)CC2)s1]

7-(5-(5-(1'-(2-(2,6-dioxopiperidin-3-yl)-1,3-dioxoisoindoline-5-carbonyl)-[4,4'-bipiperidin]-1-yl)-1,3,4-thiadiazol-2-yl)-4-(methylamino)pyridin-2-yl)pyrrolo[1,2-b]pyridazine-3-carbonitrile The title compound was synthesized from BB22 and 2-(2,6-dioxopiperidin-3-yl)-1,3-dioxoisoindoline-5-carboxylic acid by amide coupling using General Method A. LCMS: $C_{39}H_{36}N_{12}O_5S$ requires: 783.3. found: m/z=784.5 $[M+H]^+$; $^1H$ NMR (500 MHz, DMSO-$d_6$) δ 11.16 (s, 1H), 8.99 (s, 1H), 8.86 (s, 1H), 8.52 (s, 1H), 8.09 (s, 1H), 8.00 (d, J=7.6 Hz, 1H), 7.93-7.78 (m, 3H), 7.25 (d, J=4.8 Hz, 1H), 5.19 (dd, J=12.6, 5.3 Hz, 1H), 4.56 (s, 1H), 3.99 (d, J=12.6 Hz, 2H), 3.50 (d, J=13.1 Hz, 1H), 3.24 (dd, J=26.1, 8.7 Hz, 5H), 3.07 (s, 1H), 2.91 (t, J=13.9 Hz, 1H), 2.78 (s, 1H), 2.09 (s, 1H), 1.84 (s, 3H), 1.64 (s, 1H), 1.46 (s, 2H), 1.34 (d, J=12.7 Hz, 2H), 1.25 (t, J=8.2 Hz, 3H).

Example 185

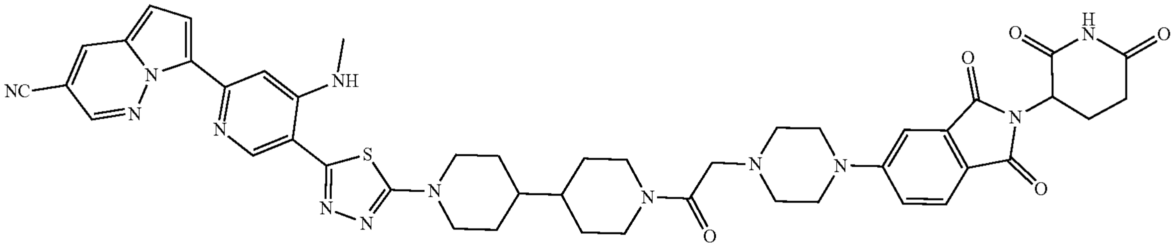 [SMILES: CNc1cc(-c2ccc3cc(C#N)cnn23)ncc1-c1nnc(N2CCC(C3CCN(C(=O)CN4CCN(c5ccc6c(c5)C(=O)N(C5CCC(=O)NC5=O)C6=O)CC4)CC3)CC2)s1]

7-(5-(5-(1'-(2-(4-(2-(2,6-dioxopiperidin-3-yl)-1,3-dioxoisoindolin-5-yl)piperazin-1-yl)acetyl)-[4,4'-bipiperidin]-1-yl)-1,3,4-thiadiazol-2-yl)-4-(methylamino)pyridin-2-yl)pyrrolo[1,2-b]pyridazine-3-carbonitrile The title compound was synthesized from BB22 and 2-(4-(2-(2,6-dioxopiperidin-3-yl)-1,3-dioxoisoindolin-5-yl)piperazin-1-yl)acetic acid by amide coupling using General Method A. LCMS: $C_{45}H_{47}N_{13}O_5S$ requires: 882.0, found: m/z=882.4 $[M+H]^+$; $^1H$ NMR (500 MHz, DMSO-$d_6$) δ 11.11 (s, 1H), 10.05 (s, 1H), 8.94 (s, 1H), 8.81 (s, 1H), 8.51 (s, 1H), 8.01 (s, 2H), 7.85-7.75 (m, 1H), 7.49 (s, 1H), 7.35 (d, J=8.6 Hz, 1H), 7.20 (s, 1H), 5.11 (d, J=13.1 Hz, 1H), 4.43 (t, J=22.6 Hz, 3H), 4.18 (s, 2H), 3.98 (s, 3H), 3.30-3.07 (m, 10H), 3.04 (s, 2H), 2.05 (s, 1H), 1.83 (d, J=14.8 Hz, 4H), 1.40 (d, J=48.5 Hz, 5H), 1.23 (d, J=21.5 Hz, 1H), 1.08 (s, 1H).

Example 186

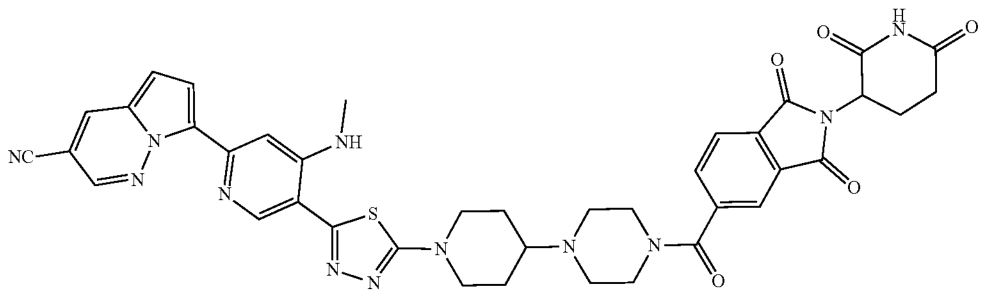 [SMILES: CNc1cc(-c2ccc3cc(C#N)cnn23)ncc1-c1nnc(N2CCC(N3CCN(C(=O)c4ccc5c(c4)C(=O)N(C4CCC(=O)NC4=O)C5=O)CC3)CC2)s1]

7-(5-(5-(4-(4-(2-(2,6-dioxopiperidin-3-yl)-1,3-di-oxoisoindoline-5-carbonyl)piperazin-1-yl)piperidin-1-yl)-1,3,4-thiadiazol-2-yl)-4-(methylamino)pyridin-2-yl)pyrrolo[1,2-b]pyridazine-3-carbonitrile The title compound was synthesized from BB23 and 2-(2,6-dioxopiperidin-3-yl)-1,3-dioxoisoindoline-5-carboxylic acid by amide coupling using General Method A. LCMS: $C_{39}H_{36}N_{12}O_5S$ requires: 784.3. found: m/z=785.3 $[M+H]^+$; $^1H$ NMR (500 MHz, DMSO-$d_6$) δ 11.16 (s, 1H), 9.98 (s, 1H), 9.25 (s, 1H), 8.97 (s, 1H), 8.84 (s, 1H), 8.55 (s, 1H), 8.06 (p, J=5.2 Hz, 2H), 8.03-7.83 (m, 2H), 7.23 (d, J=5.0 Hz, 1H), 5.20 (dd, J=12.8, 5.5 Hz, 1H), 4.12 (d, J=12.8 Hz, 2H), 3.19 (d, J=5.0 Hz, 3H), 3.00-2.81 (m, 2H), 2.76-2.56 (m, 2H), 2.20 (d, J=11.4 Hz, 2H), 2.15-2.01 (m, 1H), 1.92-1.66 (m, 2H), 1.32-0.91 (m, 2H).

Example 187

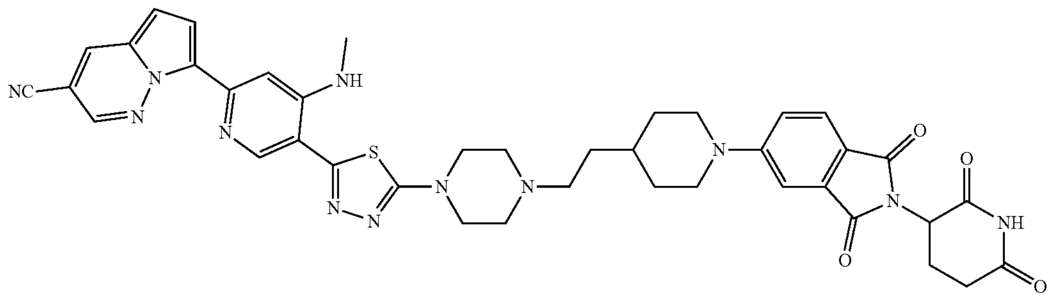 [SMILES: CNc1cc(-c2ccc3cc(C#N)cnn23)ncc1-c1nnc(N2CCN(CCC3CCN(c4ccc5c(c4)C(=O)N(C4CCC(=O)NC4=O)C5=O)CC3)CC2)s1]

7-(5-(5-(4-(2-(1-(2-(2,6-dioxopiperidin-3-yl)-1,3-dioxoisoindolin-5-yl)piperidin-4-yl)ethyl)piperazin-1-yl)-1,3,4-thiadiazol-2-yl)-4-(methylamino)pyridin-2-yl)pyrrolo[1,2-b]pyridazine-3-carbonitrile The title compound was synthesized from BB10 and 2-(1-(2-(2,6-dioxopiperidin-3-yl)-1,3-dioxoisoindolin-5-yl)piperidin-4-yl)acetaldehyde by reductive amination using General Method B. LCMS: $C_{40}H_{40}N_{12}O_4S$ requires: 784.3. found: m/z=785.4 $[M+H]^+$; $^1H$ NMR (500 MHz, Methanol-$d_4$) δ 8.79 (d, J=2.3 Hz, 1H), 8.70 (d, J=2.3 Hz, 1H), 8.55 (s, 1H), 8.12 (d, J=5.1 Hz, 1H), 7.86 (s, 1H), 7.69 (d, J=8.5 Hz, 2H), 7.37 (d, J=2.3 Hz, 2H), 7.25 (dd, J=9.0, 3.2 Hz, 3H), 5.09 (dd, J=12.5, 5.4 Hz, 1H), 4.09 (d, J=13.1 Hz, 5H), 3.57 (s, 3H), 3.04 (t, J=12.8 Hz, 4H), 2.94-2.81 (m, 2H), 2.82-2.62 (m, 4H), 2.15-2.02 (m, 2H), 1.91 (d, J=13.1 Hz, 3H), 1.84-1.68 (m, 5H), 1.48-1.35 (m, 3H).

Example 188

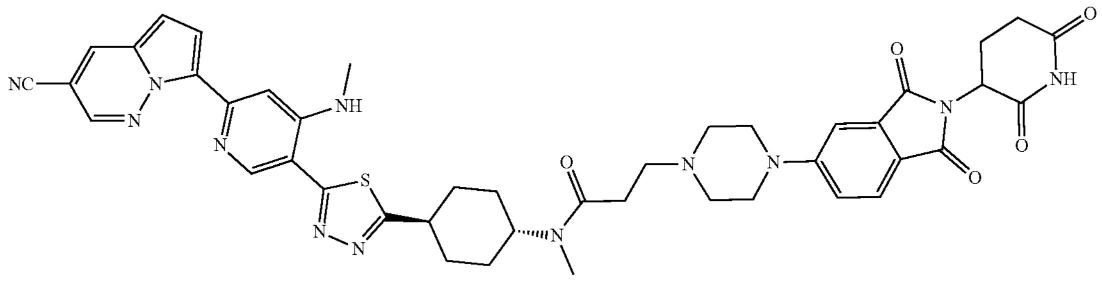 [SMILES: CNc1cc(-c2ccc3cc(C#N)cnn23)ncc1-c1nnc([C@H]2CC[C@H](N(C)C(=O)CCN3CCN(c4ccc5c(c4)C(=O)N(C4CCC(=O)NC4=O)C5=O)CC3)CC2)s1]

N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)-3-(4-(2-(2,6-dioxopiperidin-3-yl)-1,3-dioxoisoindolin-5-yl)piperazin-1-yl)-N-methylpropanamide The title compound was synthesized from BB18 and 3-{4-[2-(2,6-dioxopiperidin-3-yl)-1,3-dioxoisoindol-5-yl]piperazin-1-yl}propanoic acid by amide coupling using General Method A. LCMS: $C_{43}H_{44}N_{12}O_5S$ requires: 840.3. found: m/z=841.8 $[M+H]^+$; $^1H$ NMR (500 MHz, Methanol-$d_4$) δ 8.79 (d, J=2.3 Hz, 1H), 8.75-8.63 (m, 1H), 8.12 (dd, J=5.1, 1.8 Hz, 1H), 8.01-7.85 (m, 1H), 7.80 (d, J=8.5 Hz, 1H), 7.52 (d, J=2.3 Hz, 1H), 7.39 (dd, J=8.5, 2.4 Hz, 1H), 7.26 (dd, J=5.2, 1.7 Hz, 1H), 5.12 (dd, J=12.4, 5.5 Hz, 2H), 3.58 (t, J=6.5 Hz, 2H), 3.11 (t, J=6.4 Hz, 1H), 3.03 (d, J=7.4 Hz, 3H), 2.97-2.83 (m, 3H), 2.83-2.60 (m, 3H), 2.42 (d, J=13.6 Hz, 2H), 2.19-2.04 (m, 2H), 1.99 (q, J=11.8, 10.0 Hz, 2H), 1.92-1.75 (m, 4H).

Example 189

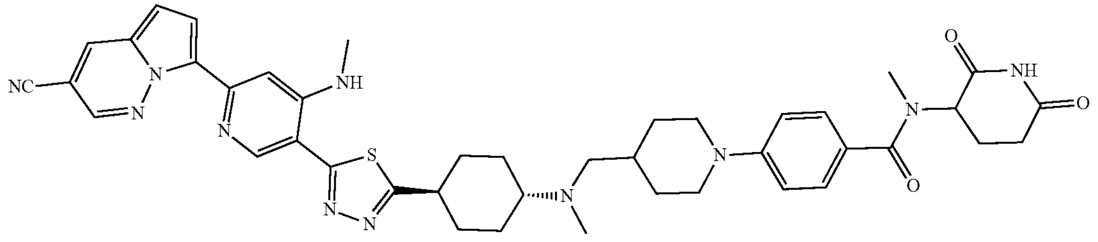 [SMILES: CNc1cc(-c2ccc3cc(C#N)cnn23)ncc1-c1nnc([C@H]2CC[C@H](N(C)CC3CCN(c4ccc(C(=O)N(C)C5CCC(=O)NC5=O)cc4)CC3)CC2)s1]

4-(4-((((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)(methyl)amino)methyl)piperidin-1-yl)-N-(2,6-dioxopiperidin-3-yl)-N-methylbenzamide The title compound was synthesized from BB18 and N-(2,6-dioxopiperidin-3-yl)-4-(4-formylpiperidin-1-yl)-N-methylbenzamide by reductive amination using General Method B. LCMS: $C_{42}H_{47}N_{11}O_3S$ requires: 785.4. found: m/z=786.4 $[M+H]^+$; $^1H$ NMR (500 MHz, Methanol-$d_4$) δ 8.80 (d, J=2.2 Hz, 1H), 8.77-8.64 (m, 2H), 8.13 (d, J=5.0 Hz, 1H), 7.93 (d, J=3.5 Hz, 1H), 7.42 (d, J=33.2 Hz, 2H), 7.26 (d, J=5.0 Hz, 1H), 7.05 (d, J=8.4 Hz, 2H), 3.95 (d, J=12.7 Hz, 2H), 3.52 (s, 2H), 3.37 (s, 4H), 3.09 (d, J=17.9 Hz, 3H), 2.97 (s, 4H), 2.92 (d, J=14.9 Hz, 2H), 2.86-2.60 (m, 2H), 2.50 (s, 3H), 2.29 (d, J=27.0 Hz, 2H), 2.13 (d, J=24.5 Hz, 2H), 2.00 (d, J=10.4 Hz, 2H), 1.92 (d, J=7.8 Hz, 4H), 1.50 (t, J=14.6 Hz, 2H).

Example 190

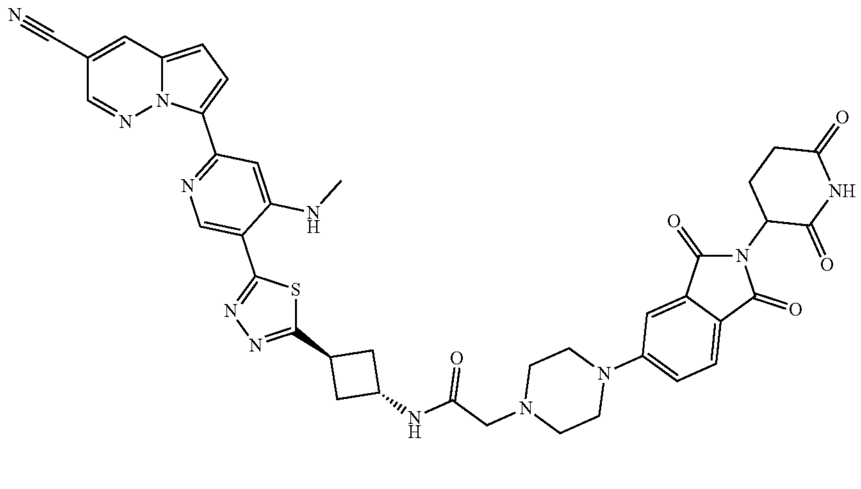 [SMILES: CNc1cc(-c2ccc3cc(C#N)cnn23)ncc1-c1nnc([C@H]2C[C@H](NC(=O)CN3CCN(c4ccc5c(c4)C(=O)N(C4CCC(=O)NC4=O)C5=O)CC3)C2)s1]

N-((1r,3r)-3-(5-(6-(3-cyanopyrrolo[1,2-b]pyridazin-7-yl)-4-(methylamino)pyridin-3-yl)-1,3,4-thiadiazol-2-yl)cyclobutyl)-2-(4-(2-(2,6-dioxopiperidin-3-yl)-1,3-dioxoisoindolin-5-yl)piperazin-1-yl)acetamide The title compound was synthesized from BB24 and 2-(4-(2-(2,6-dioxopiperidin-3-yl)-1,3-dioxoisoindolin-5-yl)piperazin-1-yl)acetic acid by amide coupling using General Method A. LCMS: $C_{39}H_{36}N_{12}O_5S$ requires: 784.3. found: m/z=785.3 $[M+H]^+$; $^1H$ NMR (500 MHz, DMSO) δ 11.10 (s, 1H), 10.27 (s, 1H), 9.07 (s, 2H), 8.93 (d, J=2.4 Hz, 1H), 8.82 (d, J=2.4 Hz, 1H), 8.73 (d, J=7.6 Hz, 1H), 8.14 (s, 1H), 7.99 (d, J=4.8 Hz, 1H), 7.78 (d, J=8.4 Hz, 1H), 7.48 (s, 1H), 7.35 (dd, J=8.6, 2.3 Hz, 1H), 7.20 (d, J=4.8 Hz, 1H), 5.11 (dd, J=12.8, 5.4 Hz, 1H), 4.63 (q, J=7.7 Hz, 1H), 4.19 (s, 3H), 4.09 (dt, J=9.4, 5.0 Hz, 1H), 4.01 (s, 2H), 3.25 (s, 1H), 3.18 (d, J=5.0 Hz, 3H), 2.90 (td, J=15.8, 13.6, 5.5 Hz, 1H), 2.70 (d, J=10.7 Hz, 2H), 2.63 (s, 2H), 2.61 (d, J=13.6 Hz, 1H), 2.04 (dd, J=12.3, 6.4 Hz, 1H).

Example 191

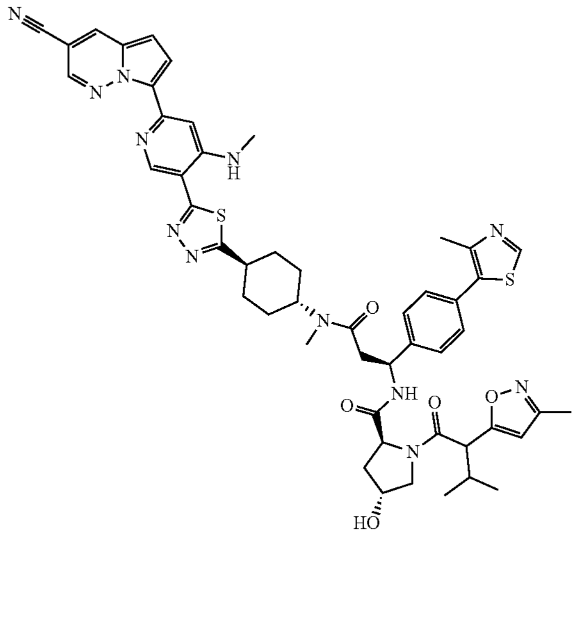 [SMILES: CNc1cc(-c2ccc3cc(C#N)cnn23)ncc1-c1nnc([C@H]2CC[C@H](N(C)C(=O)C[C@H](NC(=O)[C@@H]3C[C@@H](O)CN3C(=O)C(c3cc(C)no3)C(C)C)c3ccc(-c4scnc4C)cc3)CC2)s1]

(2S,4R)—N—((S)-3-(((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)(methyl)amino)-1-(4-(4-methylthiazol-5-yl)phenyl)-3-oxopropyl)-4-hydroxy-1-(3-methyl-2-(3-methylisoxazol-5-yl)butanoyl)pyrrolidine-2-carboxamide The title compound was synthesized from BB18 and (3S)-3-((2S,4R)-4-hydroxy-1-(3-methyl-2-(3-methylisoxazol-5-yl)butanoyl)pyrrolidine-2-carboxamido)-3-(4-(4-methylthiazol-5-yl)phenyl)propanoic acid by amide coupling using General Method A. LCMS: $C_{50}H_{54}N_{12}O_5S_2$ requires: 966.4. found: m/z=967.4 $[M+H]^+$; $^1H$ NMR (500 MHz, DMSO-$d_6$) δ 9.07-8.93 (m, 1H), 8.85 (t, J=2.7 Hz, 1H), 8.73 (d, J=3.6 Hz, 1H), 8.05 (d, J=11.8 Hz, 1H), 7.54-7.38 (m, 1H), 7.35 (d, J=7.9 Hz, 1H), 7.23 (d, J=4.9 Hz, 1H), 6.22 (dd, J=19.6, 16.1 Hz, 2H), 5.25 (dd, J=14.1, 7.2 Hz, 1H), 4.47-4.13 (m, 3H), 3.20 (d, J=4.4 Hz, 3H), 2.91-2.63 (m, 3H), 1.88-1.53 (m, 4H), 0.98 (d, J=6.3 Hz, 1H).

Example 192

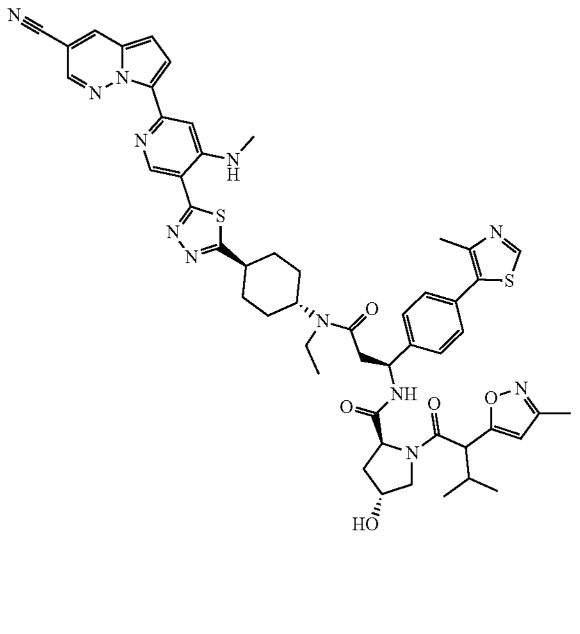 [SMILES: CCN(C(=O)C[C@H](NC(=O)[C@@H]1C[C@@H](O)CN1C(=O)C(c1cc(C)no1)C(C)C)c1ccc(-c2scnc2C)cc1)[C@H]1CC[C@H](c2nnc(-c3cnc(-c4ccc5cc(C#N)cnn45)cc3NC)s2)CC1]

(2S,4R)—N—((S)-3-(((1r,4S)-4-(5-(6-(3-cyanopyrrolo[1,2-b]pyridazin-7-yl)-4-(methylamino)pyridin-3-yl)-1,3,4-thiadiazol-2-yl)cyclohexyl)(ethyl)amino)-1-(4-(4-methylthiazol-5-yl)phenyl)-3-oxopropyl)-4-hydroxy-1-(3-methyl-2-(3-methylisoxazol-5-yl)butanoyl)pyrrolidine-2-carboxamide The title compound was synthesized from BB26 and (3S)-3-((2S,4R)-4-hydroxy-1-(3-methyl-2-(3-methylisoxazol-5-yl)butanoyl)pyrrolidine-2-carboxamido)-3-(4-(4-methylthiazol-5-yl)phenyl)propanoic acid by amide coupling using General Method A. LCMS: $C_{51}H_{56}N_{12}O_5S_2$ requires: 980.4. found: m/z=981.6 $[M+H]^+$; $^1H$ NMR (500 MHz, DMSO-$d_6$) δ 9.07-8.91 (m, 1H), 8.85 (d, J=3.7 Hz, 1H), 8.73 (d, J=3.0 Hz, 1H), 8.04 (s, 1H), 7.56-7.29 (m, 2H), 7.22 (t, J=4.2 Hz, 1H), 6.33-6.08 (m, 2H), 5.31-5.17 (m, 1H), 4.45-4.10 (m, 2H), 3.88 (s, 1H), 3.76 (d, J=9.5 Hz, 1H), 3.19 (d, J=4.1 Hz, 2H), 2.29-2.18 (m, 2H), 1.84-1.62 (m, 3H), 1.05-0.94 (m, 6H), 0.86-0.66 (m, 2H).

Biological Data

Biological Example 1

IRAK4 Biochemical HTRF Kinase Assay

The binding capacities of certain bifunctional compounds of Formula (I) were determined using the CisBio HTRF KinEASE STK S1 Kit (#62ST1PEB, contains 5× Kinase buffer, 1× Detection Buffer, anti-phospho-serine/threonine-cryptate, Streptavidin-XL665, and STK-S1), which measures the phosphorylation of a biotinylated peptide substrate by IRAK4, according to the manufacturer's protocol. Briefly, test compounds in DMSO were serially diluted into 384 Plus White Proxiplate (PerkinElmer, #6008280) using a Labcyte Echo 550 Liquid Handler, at a concentration of 50× final in 200 nL of 100% DMSO. 7.8 μl of kinase solution, containing 1.28 nM IRAK4 in 1× Kinase Buffer (supplemented with 3 mM MgCl2, 0.01% Triton X-100, and 1 mM DTT) was added to each compound containing well and incubated at ambient temperature for 30 min. 2 μl of a reaction solution containing 5 μM STK-S1, 10 mM ATP, and 10 mM $MgCl_2$ were added to each well to a final volume of 10 μl. Assay controls include wells containing kinase with no compound (DMSO only) and wells containing no kinase and no compound (DMSO only). The reactions were allowed to proceed at ambient temperature for 90 minutes. The reactions were stopped by addition of 10 ul Detection Buffer containing 2× anti-phospho-serine/threonine antibody cryptate and 125 nM Streptavidin-XL665. The plates were incubated for 60 minutes at ambient temperature and then read on an Envision Multilabel Reader (PerkinElmer). HTRF ratio was calculated as (acceptor signal at 665 nm/donor signal at 620 nm)×104 and data was normalized to % inhibition using control wells with no compound as 0% and wells with no kinase and no compound as −100% inhibition. For $IC_{50}$ determination, the compounds were tested at sixteen concentrations in duplicate and curve-fitting was performed by non-linear regression analysis using GraphPad Priam.

Biological Example 2

IRAK4 Degradation HiBiT Assay

Compound dilution series (11-point, 3.16-fold dilutions in DMSO, columns 1-11 and 12-22) at 500× the final required concentrations were prepared in Labcyte LDV 384-well plates (cat. no. LP-0200) using a Labcyte Echo 550 Liquid Handler. The 500× solutions ranged from 5 mM to 0.5 μM (final assay concentration range 10 μM to 0.1 nM). Using the Echo, the 500× solutions were stamped into white, 384-well assay plates (Corning, cat. no. 3570) at 60 nL/well. The following assay plate controls were also stamped at 60 nL/well: DMSO in wells E23-P23 (NC, Negative Control, maximum signal), 5 mM solution control compound a1 in wells A23-D23 and M24-P24 (AC, Active Control, minimum signal/background, 10 μM final assay concentration), control compound a1 dilution series in wells A23-D23 (12-point, 4-fold dilutions). C-terminal HiBiT-tagged Jurkat cells (polyclonal cell line or clone 8D5) were plated at 1×106 cells/mL, 30 μL/well (3×104 cells/well) in complete RPMI (10% FBS, 1% L-glutamine). Cells were incubated for 4 hrs at 32° C./6% $CO_2$.

Following incubation, 30 uL of complete Nano-Glo HiBiT Lytic Detection Reagent (Nano-Glo HiBiT Lytic Buffer with 1:50 Nano-Glo HiBiT Lytic Substrate and 1:100 LgBiT Protein; Promega cat. no. N3040) was added. Cells were further incubated for 10 min at room temperature (RT). Luminescence units (LU) were read on an EnVision plate reader (Perkin Elmer, 0.1 sec per well). Percent IRAK4 remaining per sample was calculated as follows:

$$\%\ IRAK4\ \text{remaining} = \left[\frac{\text{sample } LU - \text{average } AC\ LU}{\text{average } NC\ LU - \text{avereage } AC\ LU}\right] \times 100$$

Using Graphpad Prism, % IRAK4 remaining values were plotted as a function of compound concentration. To determine $DC_{50}$ and $D_{max}$ values, resulting curves were fit to the Prism curve-fitting equation "log(inhibitor) vs response–Variable slope (four parameters)" (reported best fit value $IC_{50}$ used as $DC_{50}$). Table 4 summarizes the biological data of Compounds 1-71 obtained from the assays described in Biological Example 1 and Biological Example 2.

TABLE 4

Biological Assay Data of bifunctional compounds

| Example No. | IRAK4 HTRF biochemical: $IC_{50}$ (uM) | Cellular IRAK4 HiBiT: $DC_{50}$ (uM) | Cellular IRAK4 HiBiT: $D_{max}$ (%) |
|---|---|---|---|
| 1 | 0.0018 | 0.0238 | 65 |
| 2 | 0.0016 | 0.0278 | 71 |
| 3 | 0.0023 | 0.0320 | 91 |
| 4 | 0.0018 | 0.0518 | 97 |
| 5 | 0.0038 | 0.0840 | 57 |
| 6 | 0.0026 | 0.0746 | 82 |
| 7 | 0.0092 | 0.2275 | 39 |
| 8 | 0.0008 | 0.0538 | 100 |
| 9 | 0.0029 | 0.2175 | 125 |
| 10 | 0.0010 | 0.0491 | 103 |
| 11 | 0.0013 | 0.1278 | 104 |
| 12 | 0.0012 | 0.1083 | 92 |
| 13 | 0.0005 | 0.0256 | 101 |
| 14 | 0.0008 | 0.0427 | 99 |
| 15 | 0.0010 | 0.0827 | 81 |
| 16 | 0.0017 | 0.1273 | 62 |
| 17 | 0.0014 | 0.1393 | 69 |
| 18 | 0.0019 | 0.1229 | 88 |
| 19 | 0.0022 | 0.0901 | 79 |
| 20 | 0.0020 | 0.6544 | 29 |
| 21 | 0.0005 | 0.2506 | 103 |
| 22 | 0.0008 | 0.2315 | 96 |
| 23 | 0.0015 | 0.1844 | 97 |
| 24 | 0.0006 | 0.3273 | 102 |
| 25 | 0.0078 | 0.1878 | 69 |
| 26 | 0.0009 | 0.0942 | 87 |
| 27 | 0.0003 | 0.0706 | 57 |
| 28 | 0.0004 | 0.0530 | 70 |
| 29 | 0.0008 | 0.1354 | 90 |
| 30 | 0.0009 | 0.0734 | 95 |
| 31 | 0.0018 | 0.1058 | 39 |
| 32 | 0.0023 | 0.1521 | 37 |

TABLE 4-continued

| Biological Assay Data of bifunctional compounds | | | |
|---|---|---|---|
| Example No. | IRAK4 HTRF biochemical: $IC_{50}$ (uM) | Cellular IRAK4 HiBiT: $DC_{50}$ (uM) | Cellular IRAK4 HiBiT: $D_{max}$ (%) |
| 33 | 0.0021 | >10 | 14 |
| 34 | 0.0020 | 0.3255 | 85 |
| 35 | 0.0052 | 0.5899 | 100 |
| 36 | 0.0134 | 0.3154 | 84 |
| 37 | 0.0060 | 0.2400 | 98 |
| 38 | 0.0104 | 0.1277 | 34 |
| 39 | 0.0050 | 0.3571 | 97 |
| 40 | 0.0036 | 0.4195 | 53 |
| 41 | 0.0013 | 0.8717 | 44 |
| 42 | 0.0173 | 0.3364 | 104 |
| 43 | 0.0241 | 1.1673 | 78 |
| 44 | 0.7021 | >10 | 33 |
| 45 | 0.0190 | 4.3335 | 67 |
| 46 | 0.0154 | 1.5747 | 78 |
| 47 | 0.0073 | 0.1436 | 118 |
| 48 | 0.0040 | 0.6905 | 119 |
| 49 | 0.0046 | 0.2308 | 111 |
| 50 | 0.0031 | 0.1974 | 67 |
| 51 | 0.0020 | 0.6380 | 48 |
| 52 | 0.0019 | 0.4224 | 70 |
| 53 | 0.0058 | 0.9933 | 48 |
| 54 | 0.0006 | 0.8161 | 48 |
| 55 | 0.0066 | 0.9337 | 45 |
| 56 | 0.00279 | 0.0776 | 115 |
| 57 | 0.00290 | 0.0896 | 107 |
| 58 | 0.00526 | 0.0728 | 115 |
| 59 | 0.00093 | 0.1631 | 89 |
| 60 | 0.00355 | 0.1586 | 105 |
| 61 | 0.00398 | 0.5914 | 117 |
| 62 | 0.00151 | 0.0745 | 103 |
| 63 | 0.00070 | 0.0081 | 80 |
| 64 | 0.00089 | 0.0173 | 110 |
| 65 | 0.00095 | 0.0051 | 109 |
| 67 | 0.00161 | 0.0104 | 53 |
| 68 | 0.00179 | 0.0475 | 82 |
| 69 | 0.00081 | 0.0126 | 98 |
| 70 | 0.00086 | 0.0063 | 68 |
| 71 | 0.00077 | 0.0129 | 93 |

Biological Example 3

IRAK4 Degradation HTRF Assay

Compound dilution series (11-point, 3.16-fold dilutions in DMSO, columns 1-11) at 500× the final required concentrations were prepared in 96-well culture plate (Falcon, cat. no. 353077) using a Labcyte Echo 550 Liquid Handler. The 500× solutions ranged from 5 mM to 0.5 μM (final assay concentration range 10 μM to 0.1 nM). Using the Echo, the 500× solutions were stamped into assay plates at 400 nL/well. DMSO was stamped into wells A12-H12 at 400 nL/well (NC, Negative Control, maximum signal). Wild-type Jurkat cells were plated at $1\times10^6$ cells/mL, 200 L/well ($2\times10^5$ cells/well) in complete RPMI (10% FBS, 1% L-glutamine, 1% pen-strep, 0.1% β-mercaptoethanol). Cells were incubated for 4 hrs at 32° C./6% $CO_2$. Following incubation, plates were centrifuged for 5 min at 1600 rpm. Media was removed and cell pellets were lysed in 50 μL lysis buffer (RTPA buffer (Fisher, P189901), cOmplete Mini EDTA-free protease inhibitor (Sigma 11836170001), Protease Inhibitor Cocktail (Sigma, P2714), Phosphatase Inhibitor Cocktail 2 and 3 (Sigma, P5726 and P0044), Benzonase (Sigma, E1014)). Cells were incubated 30 min at room temperature with gentle shaking. 16 μL each lysate was transferred to 96-well detection plate included in Cisbio Total IRAK4 HTRF Assay Kit (cat. no. 63ADK108PEG). To the lysates was added 2 μL each of Total-IRAK4 d2 antibody and Total-IRAK4 Cryptate antibody (Cisbio Total IRAK4 HTRF Assay Kit). Plates were incubated overnight at RT. Fluorescence emission at 665 nm and 620 nm was read using an EnVision plate reader. The HTRF Ratio was calculated per sample using the following equation:

$$\text{HTRF Ratio}=(665\text{ nm signal}/620\text{ nm signal})\times 10{,}000$$

Percent IRAK4 remaining per sample was calculated as follows:

$$\%\ IRAK4\ \text{remaining} = \left[\frac{\text{sample } HTRF\ \text{Ratio}-\text{average } AC\ HTRF\ \text{Ratio}}{\text{average } NC\ HTRF\ \text{Ratio}-avereage\ AC\ HTRF\ \text{Ratio}}\right]\times 100$$

Using Graphpad Prism, % IRAK4 remaining values were plotted as a function of compound concentration. To determine $DC_{50}$ and $D_{max}$ values, resulting curves were fit to the Prism curve-fitting equation "log(inhibitor) vs response–Variable slope (four parameters)" (reported best fit value $IC_{50}$ used as $DC_{50}$).

For selected compounds of Formula (I) as well as certain known IRAK4 degrades, see, e.g., compounds of Table 1, IRAK4 degradation as observed by the IRAK4 HiBiT assay was confirmed in wild-type Jurkat cells by HTRF analysis. HTRF Ratio decreases indicated that all seven compounds induced IRAK4 degradation (4 hrs) with varying potencies and levels of degradation. $DC_{50}$ values obtained by HTRF correlated well with those obtained by both the HiBiT assay and by Western (see Table 2 and Table 3). $D_{max}$ values confirmed the observation made by HiBiT assay and by Western that maximum IRAK4 degradation among the tested compounds was achieved with Compound 47. $DC_{50}$ and $D_{max}$ values are summarized in Tables 2 and 3.

Degradation of compounds of Examples 1-192 were measured in multiple runs using HTRF assay and HiBit assay, the results of which are summarized in Table 5.

TABLE 5

| Example | IRAK4 HTRF biochemical: IC50 (μM) | Cellular IRAK4 HiBiT: DC50 (μM) | Cellular IRAK4 HiBiT: Dmax (%) |
|---|---|---|---|
| 1 | 0.0020 | 0.0229 | 60 |
| 2 | 0.0018 | 0.0272 | 75 |
| 3 | 0.0019 | 0.0301 | 90 |
| 4 | 0.0017 | 0.0525 | 98 |
| 5 | 0.0039 | 0.0712 | 57 |
| 6 | 0.0026 | 0.07 | 69 |
| 7 | 0.0092 | 0.229 | 39 |
| 8 | 0.0008 | 0.0538 | 100 |
| 9 | 0.0029 | 0.217 | 125 |
| 10 | 0.0010 | 0.0491 | 103 |
| 11 | 0.0013 | 0.128 | 104 |
| 12 | 0.0012 | 0.0981 | 91 |
| 13 | 0.0008 | 0.027 | 100 |
| 14 | 0.0008 | 0.0372 | 97 |
| 15 | 0.0010 | 0.0869 | 85 |
| 16 | 0.0017 | 0.19 | 53 |
| 17 | 0.0014 | 0.168 | 77 |
| 18 | 0.0019 | 0.113 | 87 |
| 19 | 0.0022 | 0.0906 | 67 |
| 20 | 0.0020 | 0.66 | 29 |
| 21 | 0.0005 | 0.251 | 101 |
| 22 | 0.0008 | 0.231 | 99 |
| 23 | 0.0015 | 0.057 | 108 |
| 24 | 0.0006 | 0.31 | 112 |
| 25 | 0.0078 | 0.16 | 77 |
| 26 | 0.0009 | 0.0941 | 87 |
| 27 | 0.0012 | 0.0707 | 57 |
| 28 | 0.0005 | 0.0531 | 70 |
| 29 | 0.0011 | 0.136 | 90 |

TABLE 5-continued

| Example | IRAK4 HTRF biochemical: IC50 (μM) | Cellular IRAK4 HiBiT: DC50 (μM) | Cellular IRAK4 HiBiT: Dmax (%) |
|---|---|---|---|
| 30 | 0.0011 | 0.0735 | 95 |
| 31 | 0.0017 | 0.105 | 39 |
| 32 | 0.0025 | 0.153 | 37 |
| 33 | 0.0021 | >9.98 | na |
| 34 | 0.0020 | 0.326 | 85 |
| 35 | 0.0052 | 0.235 | 100 |
| 36 | 0.0134 | 0.287 | 85 |
| 37 | 0.0060 | 0.22 | 98 |
| 38 | 0.0104 | 0.128 | 34 |
| 39 | 0.0050 | 0.357 | 97 |
| 40 | 0.0036 | 0.419 | 53 |
| 41 | 0.0013 | 1.33 | 47 |
| 42 | 0.0173 | 0.315 | 104 |
| 43 | 0.0240 | 1.09 | 67 |
| 44 | 0.7020 | >9.98 | na |
| 45 | 0.0190 | 2.49 | 83 |
| 46 | 0.0154 | 1.24 | 73 |
| 47 | 0.0058 | 0.144 | 118 |
| 48 | 0.0040 | 0.691 | 119 |
| 49 | 0.0046 | 0.231 | 111 |
| 50 | 0.0032 | 0.197 | 67 |
| 51 | 0.0020 | 0.502 | 47 |
| 52 | 0.0019 | 0.422 | 70 |
| 53 | 0.0058 | 8.75 | 82 |
| 54 | 0.0006 | 0.794 | 48 |
| 55 | 0.0066 | 0.937 | 45 |
| 56 | 0.0015 | 0.0529 | 117 |
| 57 | 0.0029 | 0.0814 | 114 |
| 58 | 0.0053 | 0.0737 | 118 |
| 59 | 0.0009 | 0.16 | 101 |
| 60 | 0.0035 | 0.111 | 112 |
| 61 | 0.0040 | 0.399 | 121 |
| 62 | 0.0015 | 0.0582 | 111 |
| 63 | 0.0006 | 0.0076 | 85 |
| 64 | 0.0008 | 0.0149 | 112 |
| 65 | 0.0008 | 0.0169 | 111 |
| 66 | 0.0016 | 0.0112 | 54 |
| 67 | 0.0018 | 0.0457 | 86 |
| 68 | 0.0008 | 0.0143 | 101 |
| 69 | 0.0009 | 0.00671 | 73 |
| 70 | 0.0008 | 0.0108 | 100 |
| 71 | 0.0008 | 0.00587 | 52 |
| 72 | 0.0031 | 0.189 | 94 |
| 73 | 0.0019 | 0.0252 | 69 |
| 74 | 0.0025 | 0.0289 | 82 |
| 75 | 0.0008 | 0.00859 | 111 |
| 76 | 0.0008 | 0.0131 | 100 |
| 77 | 0.0005 | 0.0151 | 114 |
| 78 | 0.0024 | 0.332 | 74 |
| 79 | 0.0098 | 0.137 | 113 |
| 80 | 0.0037 | 0.313 | 115 |
| 81 | 0.0018 | 0.0649 | 81 |
| 82 | 0.0031 | 0.0728 | 61 |
| 83 | 0.0068 | 0.319 | 109 |
| 84 | 0.0055 | 0.247 | 115 |
| 85 | 0.0021 | >0.97 | na |
| 86 | 0.0011 | 0.0185 | 105 |
| 87 | 0.0024 | 0.0158 | 70 |
| 88 | 0.0014 | >3.33 | na |
| 89 | 0.0009 | >9.98 | na |
| 90 | 0.0008 | >9.98 | na |
| 91 | 0.0016 | >0.97 | na |
| 92 | 0.0010 | >0.97 | na |
| 93 | 0.0009 | >9.98 | na |
| 94 | 0.0006 | 0.321 | 113 |
| 95 | 0.0008 | 0.00974 | 108 |
| 96 | 0.0013 | 0.905 | 90 |
| 97 | 0.0048 | 0.265 | 59 |
| 98 | 0.0003 | 0.00658 | 109 |
| 99 | 0.0003 | 0.00359 | 116 |
| 100 | 0.0004 | 0.00441 | 111 |
| 101 | 0.0024 | 0.0422 | 117 |
| 102 | 0.0008 | 0.0253 | 91 |
| 103 | 0.0010 | 0.0733 | 99 |
| 104 | 0.0015 | 0.0499 | 77 |
| 105 | 0.0012 | 0.0398 | 106 |
| 106 | 0.0020 | 0.0438 | 45 |
| 107 | 0.0026 | 0.0997 | 44 |
| 108 | 0.0014 | 0.0457 | 70 |
| 109 | 0.0014 | 0.0216 | 64 |
| 110 | 0.0007 | 0.0342 | 93 |
| 111 | 0.0011 | 0.0158 | 59 |
| 112 | 0.0102 | 0.171 | 57 |
| 113 | 0.0012 | 0.032 | 76 |
| 114 | 0.0029 | 0.0726 | 82 |
| 115 | 0.0022 | 0.0447 | 78 |
| 116 | 0.0022 | 0.0463 | 60 |
| 117 | 0.0012 | 0.0271 | 20 |
| 118 | 0.0014 | 0.0352 | 118 |
| 119 | 0.0022 | 0.116 | 117 |
| 120 | 0.0011 | 0.0334 | 32 |
| 121 | 0.0012 | 1.08 | 95 |
| 122 | 0.0011 | >9.98 | na |
| 123 | 0.0021 | >9.98 | na |
| 124 | 0.0019 | >9.98 | na |
| 125 | 0.0017 | 0.166 | 116 |
| 126 | 0.0009 | 0.0631 | 111 |
| 127 | 0.0008 | 0.187 | 58 |
| 128 | 0.0017 | 0.432 | 139 |
| 129 | 0.0012 | 0.356 | 115 |
| 130 | 0.0018 | 0.126 | 110 |
| 131 | 0.0021 | 0.124 | 109 |
| 132 | 0.0006 | >9.98 | na |
| 133 | 0.0009 | 0.0514 | 111 |
| 134 | 0.0009 | 0.0641 | 103 |
| 135 | 0.0010 | 0.774 | 46 |
| 136 | 0.0016 | 0.0219 | 35 |
| 137 | 0.0226 | 0.0191 | 108 |
| 138 | 0.0008 | 0.0655 | 116 |
| 139 | 0.0009 | 0.0106 | 24 |
| 140 | 0.0023 | 0.0889 | 111 |
| 141 | 0.0014 | 1.91 | 133 |
| 142 | 0.0019 | 0.258 | 115 |
| 143 | 0.0016 | 0.87 | 37 |
| 144 | 0.0015 | 0.429 | 89 |
| 145 | 0.0018 | 0.109 | 49 |
| 146 | 0.0029 | 0.231 | 77 |
| 147 | 0.0015 | 0.508 | 80 |
| 148 | 0.0014 | >9.98 | na |
| 149 | 0.0008 | >9.98 | na |
| 150 | 0.0055 | 0.441 | 113 |
| 151 | 0.0009 | >6.98 | na |
| 152 | 0.0009 | 0.063 | 113 |
| 153 | 0.0005 | 0.0548 | 68 |
| 154 | 0.0028 | 0.544 | 68 |
| 155 | 0.0024 | 0.519 | 90 |
| 156 | 0.0008 | 0.0155 | 109 |
| 157 | 0.0010 | 0.0176 | 104 |
| 158 | 0.0016 | 1.21 | 74 |
| 159 | 0.0021 | 0.111 | 116 |
| 160 | 0.0011 | 0.0858 | 97 |
| 161 | 0.0014 | 0.0246 | 56 |
| 162 | 0.0004 | 0.0105 | 110 |
| 163 | 0.0010 | 0.0659 | 113 |
| 164 | 0.0004 | 0.00564 | 109 |
| 165 | 0.0004 | 0.021 | 100 |
| 166 | 0.0010 | 0.0677 | 114 |
| 167 | 0.0005 | 0.0201 | 107 |
| 168 | 0.0006 | 0.00263 | 20 |
| 169 | 0.0008 | 0.032 | 104 |
| 170 | 0.0005 | 0.0293 | 103 |
| 171 | 0.0004 | 0.0129 | 77 |
| 172 | 0.0015 | 2.52 | 28 |
| 173 | 0.0004 | 0.612 | 16 |
| 174 | 0.0006 | 1.34 | 34 |
| 175 | 0.0005 | 0.0191 | 91 |
| 176 | 0.0005 | 0.0315 | 105 |
| 177 | 0.0005 | 0.0148 | 105 |
| 178 | 0.0007 | 0.0428 | 113 |
| 179 | 0.0007 | 0.057 | 85 |
| 180 | 0.0005 | 0.0916 | 110 |
| 181 | 0.0006 | 0.00694 | 41 |

TABLE 5-continued

| Example | IRAK4 HTRF biochemical: IC50 (μM) | Cellular IRAK4 HiBiT: DC50 (μM) | Cellular IRAK4 HiBiT: Dmax (%) |
|---|---|---|---|
| 182 | 0.0005 | 0.159 | 120 |
| 183 | 0.0023 | 0.222 | 111 |
| 184 | 0.0009 | 0.0714 | 96 |
| 185 | 0.0015 | 0.126 | 89 |
| 186 | 0.0003 | 0.0171 | 96 |
| 187 | 0.0009 | 0.0883 | 95 |
| 188 | 0.0005 | 0.016 | 108 |
| 189 | 0.0003 | 0.192 | 62 |
| 190 | 0.0010 | 0.00775 | 105 |
| 191 | 0.0015 | 0.04819 | 110 |
| 192 | 0.0014 | 0.05056 | 103 |

Biological Example 4

Western Assay for IRAK4, IRAK1 and GSPT1 Degradation

Compound dilution series (11-point, 3.16-fold dilutions in DMSO, columns 1-11) at 500× the final required concentrations were prepared in 96-well culture plate (Falcon, cat. no. 353077) using a Labcyte Echo 550 Liquid Handler. The 500× solutions ranged from 5 mM to 0.5 μM (final assay concentration range 10 μM to 0.1 nM). Using the Echo, the 500× solutions were stamped into assay plates at 500 nL/well. DMSO was stamped into wells A12-H12 at 500 nL/well (NC, Negative Control, maximum signal). Wild-type Jurkat cells were plated at $4\times10^6$ cells/mL, 250 μL/well ($1\times10^6$ cells/well) in complete RPMI (10% FBS, 1% L-glutamine, 1% pen-strep, 0.1% β-mercaptoethanol). Cells were incubated for 4 hrs at 32° C./6% $CO_2$ for IRAK4 and IRAK1, and 24 hrs for GSPT1. Following incubation, plates were centrifuged for 5 min at 1600 rpm. Media was removed and cell pellets were lysed in 50 μL lysis buffer (RIPA buffer (Fisher, PI89901), cOmplete Mini EDTA-free protease inhibitor (Sigma 11836170001), Protease Inhibitor Cocktail (Sigma, P2714), Phosphatase Inhibitor Cocktail 2 and 3 (Sigma, P5726 and P0044), Benzonase (Sigma, E1014)). Cells were lysed overnight at −20° C. Plates were centrifuged for 5 min at 1600 rpm and lysate supernatants were transferred to storage plates. Protein levels were determined by BCA Assay performed according to manufacturer's protocol (EMD Millipore, cat. no. 71285-3). Samples were combined with (4×) LDS Sample Buffer and (10×) Reducing Agent and $H_2O$ to equally load 10 ug protein per lane of a 26-well NuPAGE 4-12% Bis-Tris protein gel (1.0 mm, Thermo cat. no. NP0326). Samples were separated by running gels at constant 200 V in NuPAGE MES SDS Running Buffer. Following electrophoresis, proteins were transferred to nitrocellulose membranes using an iBlot Gel Transfer Device and iBlot Gel Transfer Stacks (Thermo cat. no. IB21001 and IB301001) and transfer method PO (20V 1 min, 23V 4 min, 25V 2 min). Membranes were blocked for 1 hr in 5% milk solution (TBS (0.2% Tween-20)).

Following blocking, membranes were incubated with primary antibody overnight at 4° C. with gentle shaking. The primary antibodies and dilutions used were as follows: IRAK4—abcam ab3200612, 1:500; IRAK1—Cell Signaling Technologies D51G7 #4504, 1:500; GSPT1—Cell Signaling Technologies #14980, 1:500). Blots were washed 3× in TBS (0.2% Tween-20), 5-10 min per wash. Following washes, blots were incubated in secondary HRP-conjugated antibody (Promega anti-Rabbit IgG (H+L) HRP, cat. no. W4011), 1:5000 in 5% milk solution (TBS (0.2% Tween-20)), for 1 hr at room temperature with gentle shaking. Blots were washed 3× in TBS (0.2% Tween-20), 5-10 min per wash. Blots were incubated with 1:1 mix of ECL reagents 1 & 2 (Amersham ECL Western Blotting Detection Reagent, cat. no. RPN2106) for 2-3 min at room temperature. Bands were visualized using a Protein Simple imager. Blots were then re-probed with a combination of anti-actin antibody (Sigma Monoclonal Mouse Anti-3-Actin (clone AC-15), cat. no. A5441) and secondary HRP-conjugated antibody (Promega anti-Mouse IgG (H+L) HRP, cat. no. W4021) and similar steps were taken for incubation, wash, detection and visualization steps as above. The data was analyzed using Alpha View software. The densitometric reading for each sample band was normalized to that of the corresponding actin band per lane. Approximate % IRAK4 remaining per sample was calculated as follows:

$$\%\ \text{remaining} = \left[\frac{\text{sample normalized densitometric reading}}{\textit{DMSO}\ \text{normalized densitometric reading}}\right]\times 100$$

Using Graphpad Prism, % IRAK4 remaining values were plotted as a function of compound concentration. To determine approximate $DC_{50}$ and $D_{max}$ values, resulting curves were fit to the Prism curve-fitting equation "log(inhibitor) vs response−Variable slope (four parameters)" (reported best fit value $IC_{50}$ used as $DC_{50}$).

Results obtained from the Compounds of Table 1 demonstrated that IRAK4 degraders had no effect on IRAK1 or GSPT1 levels. $DC_{50}$ values are summarized in Tables 2 and 3.

Biological Example 5

IRAK4 Degradation Competition/Rescue Assay

Using a Labcyte Echo 550 Liquid Handler, 30 nL of 1000 μM DMSO solutions of the Validation set compounds were stamped into white, 384-well assay plates (Corning, cat. no. 3570; final assay concentration 1 μM). DMSO controls were also stamped at 30 nL/well (NC, Negative Control, maximum signal). C-terminal HiBiT-tagged Jurkat cells (clone 8D5) were plated in 24-well plates (Costar, cat. no. 3524) at $1\times10^6$ cells/mL in complete RPMI (10% FBS, 1% L-glutamine). For the Rescue (proteasome or Nedd8 inhibition) assays, cells were treated with either Nedd8 inhibitor (Boston Biochem Nedd8-E1 Enzyme (NAE Inhibitor), cat. no. I-502; 5 μM final assay concentration) or MG-132 (Enzo Life Sciences, cat. no. BML-PI102-0025; 20 or 50 μM final assay concentration). For the Competition assays, cells were treated with 10 or 20 μM (final assay concentration) of mono-functional compounds such as a compound with only an IRAK4 binding moiety, or a compound with only an LHM. Pre-treated cells were incubated for 1 hr at 32° C./6% $CO_2$. Following incubation, the pre-treated cells were plated into the pre-stamped assay plates at $1\times10^6$ cells/mL, 30 μL/well ($3\times10^4$ cells/well) and further incubated for 4 hrs. The HiBiT assay was then carried out as outlined in Biological Example 2.

It was observed that IRAK4 degradation induced by the bifunctional degraders (1 μM) of Table 1 was rescued by 1 hr pre-treatment of the cells with either Nedd8i (5 μM) or a proteasome inhibitor, MG-132 (20 μM or 50 μM). Furthermore, IRAK4 degradation induced by the bifunctional degraders (1 μM) of Table 1 was rescued by 1 hr pre-treatment of the cells with either the corresponding mono-functional compounds, i.e., compounds having only the IRAK4 binder moiety or only LHM.

Biological Example 6

Flow Cytometry-Based Assay for Aiolos and Ikaros Degradation

Jurkat cells (Clone E6-1) were treated with DMSO or compound for 24 hours and then fixed and permeabilized using a Foxp3/Transcription Factor Fixation/Permeabilization Kit (eBioscience, cat. no. 00-5523). Cells were stained with fluorophore-conjugated antibodies against Ikaros (Biolegend 368414) and Aiolos (Biolegend, cat. no. 371106). An additional set of DMSO-treated cells was stained with fluorophore-conjugated isotype control antibodies (Biolegend, cat. no. 400254 and 400136). Stained cells were run on an Attune N×T Acoustic Focusing Flow Cytometer (Thermo-Fisher, cat. no. A29004), and data was analyzed using FlowJo (v10.5.3) and GraphPad Prism (v7.00) software. Single cells were gated, and the geometric mean fluorescence intensities (MFIs) of Ikaros and Aiolos were calculated. The MFI of the isotype control was calculated for each analyte and used to quantify background staining. Percent Ikaros or Aiolos degradation was calculated for each compound-treated sample using the following equation:

% Degradation=100*(Sample MFI−Isotype MFI)/(DMSO MFI−Isotype MFI)

Among the bifunctional compounds of Table 1, only Comparative Compound a2 induced neosubstrate degradation, demonstrating a similar profile to Pomalidomide. The $DC_{50}$ and $D_{max}$ values are summarized in Tables 2-3.

Biological Example 7

Viability Assay (Celltiter-Glo)

Compound dilution series (11-point, 3.16-fold dilutions in DMSO, columns 1-11 and 12-22) at 500× the final required concentrations were prepared in Labcyte LDV 384-well plates (cat. no. LP-0200) using a Labcyte Echo 550 Liquid Handler. The 500× solutions ranged from 5 mM to 0.5 μM (final assay concentration range 10 μM to 0.1 nM). Using the Echo, the 500× solutions were stamped into white, 384-well assay plates (Corning, cat. no. 3570) at 60 nL/well. DMSO was stamped into empty wells at 60 nL/well (NC, Negative Control, maximum signal). Wild-type Jurkat cells were plated at $1\times10^6$ cells/mL, 200 μL/well ($2\times10^5$ cells/well) in complete RPMI (10% FBS, 1% L-glutamine, 1% pen-strep, 0.1% β-mercaptoethanol). Cells were incubated for 4 hrs at 32° C./6% $CO_2$. Following incubation, the CellTiter-Glo assay was performed according to manufacturer's instructions (Promega CellTiter-Glo Luminescent Cell Viability Assay, cat. no. G7570). Cells were further incubated for 10 min at room temperature (RT). Luminescence units (LU) were read on an EnVision plate reader (0.1 sec per well). Percent IRAK4 remaining per sample was calculated as follows:

$$\% \, IRAK4 \text{ remaining} = \left[\frac{\text{sample } LU}{\text{average } NC\ LU}\right]\times 100$$

Using Graphpad Prism, % IRAK4 remaining values were plotted as a function of compound concentration. To determine $IC_{50}$ values, resulting curves were fit to the Prism curve-fitting equation "log(inhibitor) vs response−Variable slope (four parameters)" (reported best fit value $IC_{50}$).

CellTiter-Glo assay measurements demonstrated that degrader treatment of IRAK4 C-terminally tagged HiBiT Jurkat cell line (clone 8D5) cells had no effect on cellular viability during the time-frame where these compounds induce maximum IRAK4 degradation in both the HiBiT, HTRF and Western assays (4 hrs). $EC_{50}$ values are summarized in Tables 2-3.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound of Formula (I)

Formula (I)

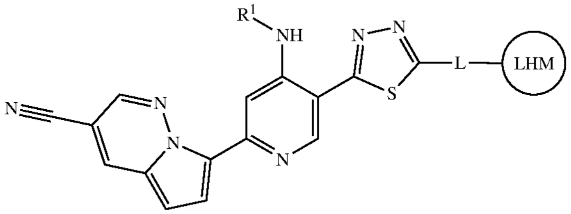

or a pharmaceutically acceptable salt or isotopic form thereof, wherein:

$R^1$ is $C_{1-10}$ alkyl optionally substituted with 1-3 $R^a$; $C_{3-10}$ cycloalkyl optionally substituted with 1-3 $R^a$; or 3-12 membered heterocyclyl optionally substituted with 1-3 $R^a$;

L is $-L_1-L_2-L_3-L_4-L_5-$, each $L_1$, $L_2$, $L_3$, $L_4$ and $L_5$ being independently:

a) $C_{3-12}$ cycloalkyl optionally substituted with 1-3 $R^b$;

b) $C_{6-12}$ aryl optionally substituted with 1-3 $R^b$;

c) 3-12 membered heterocyclyl optionally substituted with 1-3 $R^b$;

d) 5-12 membered heteroaryl optionally substituted with 1-3 $R^b$;

e) direct bond;

f) $C_{1-12}$ alkylene chain optionally substituted with 1-3 $R^d$;

g) $C_{2-12}$ alkenylene chain optionally substituted with 1-3 $R^d$;

h) $C_{2-12}$ alkynylene chain optionally substituted with 1 to 3 $R^d$;

i) 1-6 ethylene glycol units;

j) 1-6 propylene glycol units;

k) —C(O)—, —C(O)O—, —O—, —N($R^c$)—, —S—, —C(S)—, —C(S)—O—, —$S(O)_2$—, —S(O)=N—, —$S(O)_2NH$—, —C(O)—N($R^c$)—, —C=N—, —O—C(O)—N($R^c$)—, or —O—C(O)—O—;

LHM is a ligase harness moiety;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —$OR^c$;

each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—$R^c$, —N($R^c$)C(O)O—$R^c$, —N($R^c$)C(O)N($R^c$)($R^c$), —N($R^c$)S(O)$_2$($R^c$), —NRCS(O)$_2$N($R^c$)($R^c$), —N($R^c$)S(O)$_2$O($R^c$), —OC(O) $R^c$, —OC(O)—N($R^c$)($R^c$), —Si($R^c$)$_3$, —S—$R^c$, —S(O) $R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^d$;

each $R^c$ is independently hydrogen or $C_{1-6}$ alkyl; and each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

2. The compound of claim 1 having the following structure:

Formula (I')

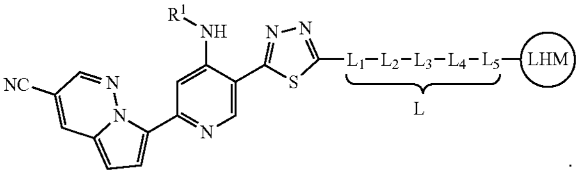

.

3. The compound of claim 1, wherein LHM targets cereblon and has the following structure:

Formula (IIA)

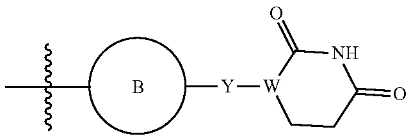

wherein,

W is —C($R^g$)— or —N—;

Y is direct bond, $C_{1-4}$ alkylene chain, —C(O)—, —C(O)O—, —O—, —N($R^g$)—, —S—C(S)—, —C(S)—O—, —O—C(O)O—, —C(O)—N($R^g$)—, or —O—C(O)—N($R^g$)—;

B ring is $C_{6-12}$ aryl, 5-12 membered heteroaryl, or 3-12 membered heterocyclyl, each being optionally substituted with 1 to 3 $R^j$;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—$R^g$, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O) $R^g$, —S(O)(NH)$R^g$, —S(O)$_2R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$;

$R^g$ is hydrogen or $C_{1-6}$ alkyl; and each $R^k$ is independently halo, oxo, —CN, —OH, $C_{1-6}$ alkyl optionally substituted with 1 to 3 fluoro, $C_{3-8}$ cycloalkyl, or —O—$C_{1-6}$ alkyl optionally substituted with 1 to 3 fluoro.

4. The compound of claim 3, wherein Y is direct bond and Formula (IIA) has the following structure:

Formula (IIA1)

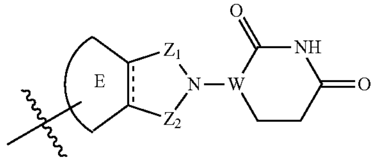

wherein,

W is —C($R^g$)— or —N—;

$Z_1$ is —C(O)—, —C(S)—, —C(N$R^g$)—, —C($R^g$)$_2$—, —N═, —N($R^g$)—, —C($R^g$)$_2$—C(O)—, —C(O)—N($R^g$)—, —C$R^g$═C$R^g$—, —C($R^g$)$_2$—C(S)—, —C($R^g$)═N—, or —C($R^g$)$_2$—C($R^g$)$_2$—;

$Z_2$ is —C(O)—, —C(S)—, —C(N$R^g$)—, —N($R^g$)—, —N═, or —C($R^g$)$_2$—;

$R^g$ is hydrogen or $C_{1-6}$ alkyl; and

E ring is phenyl, 5-6 membered heteroaryl or 5-6 membered heterocyclyl, each being optionally substituted with 1 to 3 $R^j$.

5. The compound of claim 4, wherein $Z_2$ is —C(O)— and Formula (IIA1) has the following structure:

(Formula IIA1')

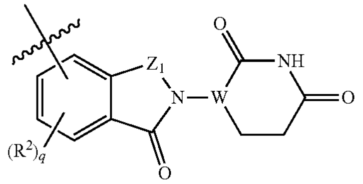

wherein,

W is —C($R^g$)— or —N—;

$Z_1$ is —C(O)—, —C(S)—, —C(N$R^g$)—, —C($R^g$)$_2$—, —C($R^g$)$_2$—C(O)—, —C(O)—N($R^g$)—, —C$R^g$═C$R^g$—, —C($R^g$)═N—, —C($R^g$)$_2$—C(S)—, or —C($R^g$)$_2$—C($R^g$)$_2$—;

q is 0, 1 or 2;

$R^g$ is hydrogen or $C_{1-6}$ alkyl; and $R^2$ is $C_{1-6}$alkyl, halo, halo $C_{1-6}$alkyl, —N($R^g$)$_2$, CN, nitro, hydroxyl, or —O—$C_{1-4}$alkyl.

6. The compound of claim 5 wherein

W is —CH—; and $Z_1$ is —C(O)—, —$CH_2$—, —$CH_2$—C(O)—, or —CH═CH—.

7. The compound of claim 6, wherein Formula (IIA1') has one of the following structures:
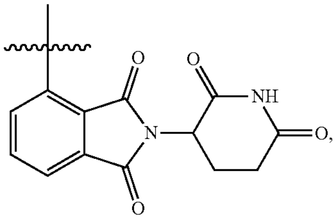
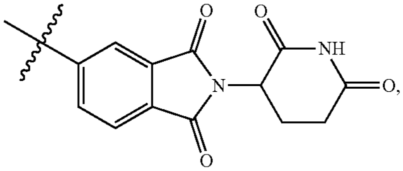
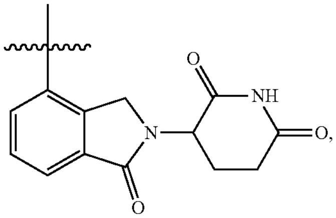
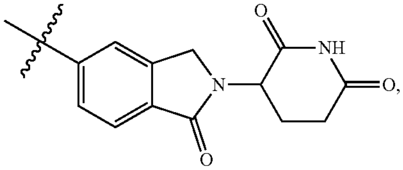
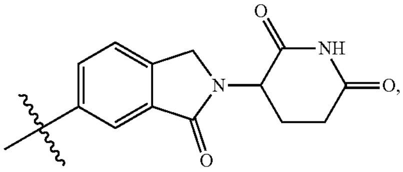
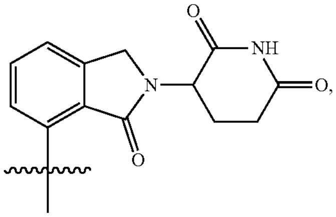
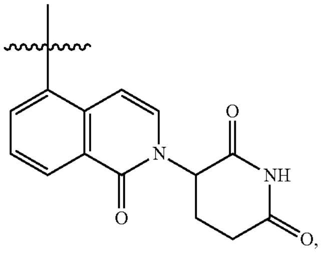
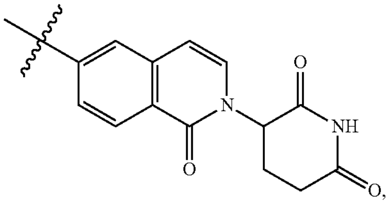
-continued
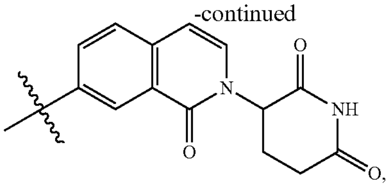
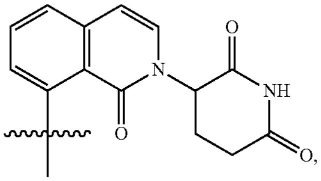
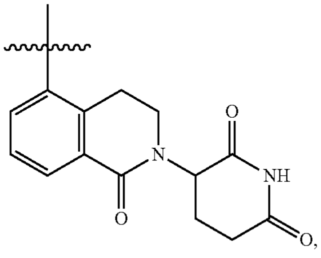
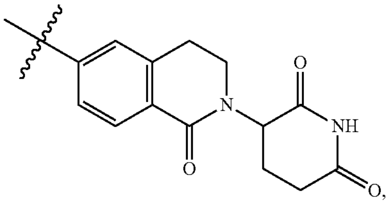
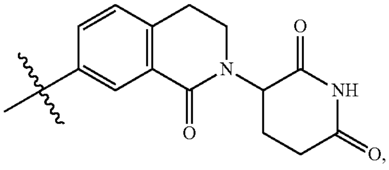
or
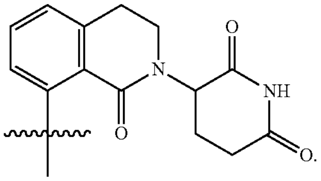
8. The compound of claim 3 wherein Formula (IIA) has the following structure:
(Formula IIA2)
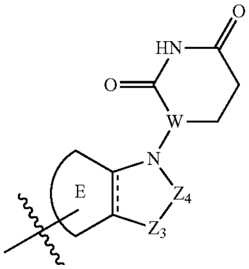
wherein,
W is —C($R^g$)— or —N—;
$Z_3$ is —C(O)—, —C(S)—, —C($NR^g$)—, —C($R^g$)$_2$—, —N═, —N($R^g$)—, —C($R^g$)$_2$—C(O)—, —C(O)—N($R^g$)—, —$CR^g$═$CR^g$—, —C($R^g$)$_2$—C(S)—, —C($R^g$)═N—, —C($R^g$)$_2$—C($R^g$)$_2$—, —C($R^g$)$_2$—O—, —C($R^g$)$_2$—S—, —O—, or —S—;

$Z_4$ is —C(O)—, —C(S)—, —C(N$R^g$)—, —N($R^g$)—, —N═, —O—, —S—, or —C($R^g$)$_2$—;

$R^g$ is hydrogen or $C_{1-6}$ alkyl;

E ring is phenyl, 5-6 membered heteroaryl or 5-6 membered heterocyclyl, each being optionally substituted with 1 to 3 $R^j$;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—$R^g$, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O) $R^g$, —S(O)(NH)$R^g$, —S(O)$_2R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$; and each $R^k$ is independently halo, oxo, —CN, —OH, $C_{1-6}$ alkyl optionally substituted with 1 to 3 fluoro, $C_{3-8}$ cycloalkyl, or —O—$C_{1-6}$ alkyl optionally substituted with 1 to 3 fluoro.

9. The compound of claim 8 wherein

W is —CH—;

$Z_3$ is —C($R^g$)$_2$—, —N($R^g$)—, —C($R^g$)$_2$—C(O)—, —C(O)—N($R^g$)—, —C$R^g$═C$R^g$—, —C($R^g$)$_2$—C(S)—, —C($R^g$)═N—, —C($R^g$)$_2$—C($R^g$)$_2$—, —C($R^g$)$_2$—O—, or —C($R^g$)$_2$—S—; and $Z_4$ is —C(O)—, —C(S)—, —C(N$R^g$)—, or —C($R^g$)$_2$—.

10. The compound of claim 9, wherein Formula (IIA2) has the following structure:

Formula (IIA2')

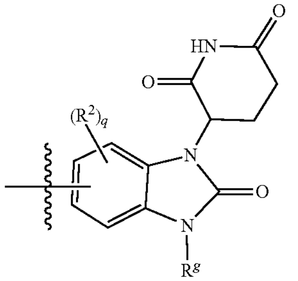

wherein, q is 0, 1 or 2;

$R^g$ is hydrogen or $C_{1-6}$ alkyl; and $R^2$ is $C_{1-6}$alkyl, halo, halo $C_{1-6}$alkyl, —N($R^g$)$_2$, CN, nitro, hydroxyl, or —O—$C_{1-4}$alkyl.

11. The compound of claim 10 wherein Formula (IIA2') has the following structures:

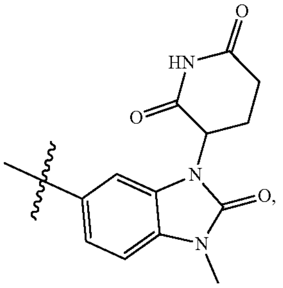

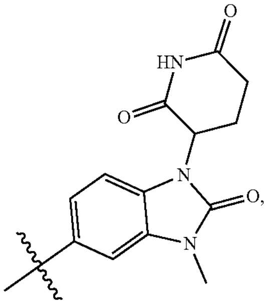

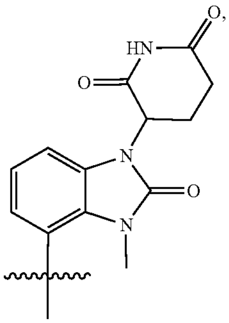

or

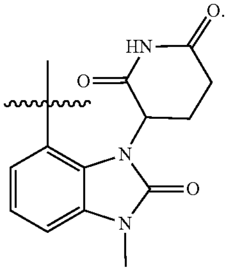

12. The compound of claim 3, wherein

W is —CH—;

Y is direct bond, $C_{1-4}$ alkylene chain, —C(O)—, —C(O)O—, —O—, —N($R^g$)—, —S—, —C(S)—, —C(S)—O—, —O—C(O)O—, —C(O)—N($R^g$)—, —O—C(O)—N($R^g$)—; and B ring is phenyl, 5-6 membered heteroaryl, or 5-6 membered heterocyclyl, each being optionally substituted with 1 to 3 $R^j$;

$R^g$ is hydrogen or $C_{1-6}$ alkyl;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—$R^g$, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O) $R^g$, —S(O)(NH)$R^g$, —S(O)$_2R^g$ or —S(O)$_2$N ($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$; and each $R^k$ is independently halo, oxo, —CN, —OH, $C_{1-6}$ alkyl optionally substituted with 1 to 3 fluoro, $C_{3-8}$ cycloalkyl, or —O—$C_{1-6}$ alkyl optionally substituted with 1 to 3 fluoro.

13. The compound of claim 12 wherein Formula (IIA) has one of the following structures:

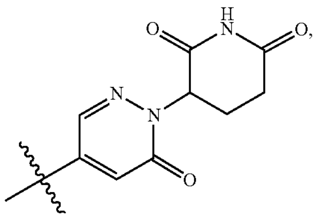

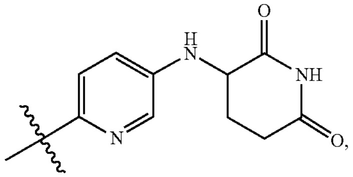

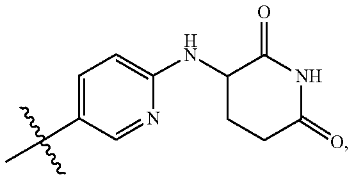

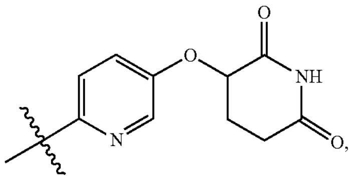

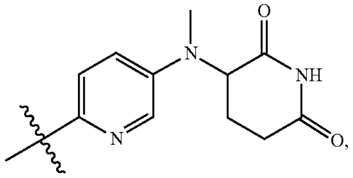

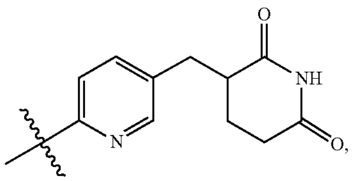

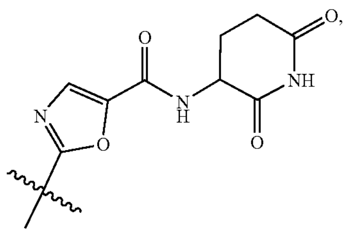

-continued

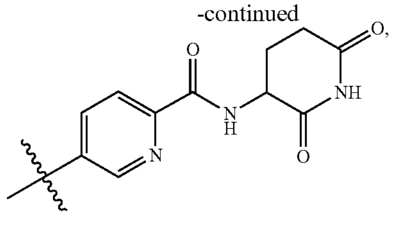

or

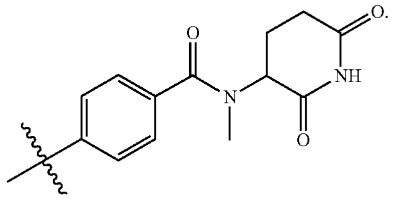

14. The compound of claim 1, wherein LHM targets cereblon and has the following structure:

Formula (IIB)

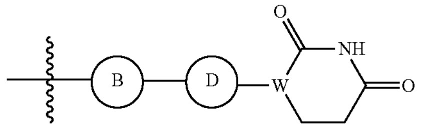

wherein,

W is —C($R^g$)— or —N—;

D ring is phenyl, 5-6 membered heteroaryl, or 5-6 membered heterocyclyl, each being optionally substituted with 1 to 3 $R^j$;

B ring is $C_{6-12}$ aryl, 5-12 membered heteroaryl, or 3-12 membered heterocyclyl, each being optionally substituted with 1 to 3 $R^j$;

$R^g$ is hydrogen or $C_{1-6}$ alkyl;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—$R^g$, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O) $R^g$, —S(O)(NH)$R^g$, —S(O)$_2$$R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$; and each $R^k$ is independently halo, oxo, —CN, —OH, $C_{1-6}$ alkyl optionally substituted with 1 to 3 fluoro, $C_{3-8}$ cycloalkyl, or —O—$C_{1-6}$ alkyl optionally substituted with 1 to 3 fluoro.

15. The compound of claim 14, wherein Formula (IIB) has the following structure:

Formula (IIB1)

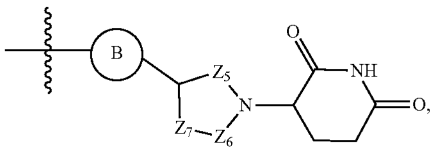

wherein $Z_5$ is —C(O)—, —C(S)—, —C(NR$^g$)—, —N(R$^g$)—, —N═, or —C(R$^g$)$_2$—;

$Z_6$ is —C(O)—, —C(S)—, —C(NR$^g$)—, —C(R$^g$)$_2$—, —N═, —N(R$^g$)—, —C(R$^g$)$_2$—C(O)—, —C(O)—N(R$^g$)—, —CR$^g$═CR$^g$—, —C(R$^g$)$_2$—C(S)—, —C(R$^g$)═N—, or —C(R$^g$)$_2$—C(R$^g$)$_2$—;

$Z_7$ is —C(O)—, —C(S)—, —C(NR$^g$)—, —N(R$^g$)—, —O—, —S—, —N═, or —C(R$^g$)$_2$—; and R$^g$ is hydrogen or $C_{1-6}$ alkyl.

16. The compound of claim 15 wherein Formula (IIB1) has the following structure:

Formula (IB1')

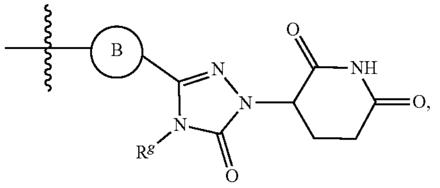

or

Formula (IIB")

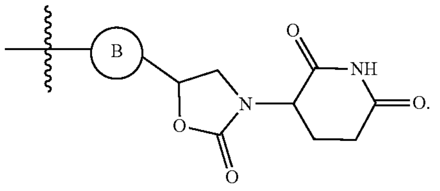

17. The compound of claim 16 wherein Formula (IB1') has the following structure:

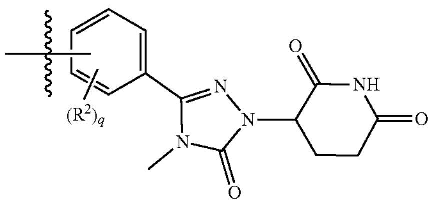

wherein, q is 0, 1 or 2; and $R^2$ is $C_{1-6}$alkyl, halo, halo $C_{1-6}$alkyl, —N(R$^c$)$_2$, CN, nitro, hydroxyl, or —O—$C_{1-4}$alkyl.

18. The compound of claim 1 wherein LHM targets Von Hippel-Lindau (VHL) ligase and has one of the following structures:

Formula (IIIA)

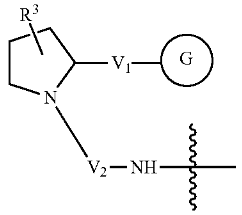

Formula (IIIB)

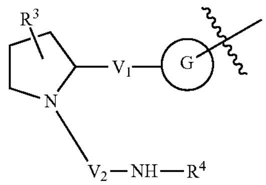

Formula (IIIC)

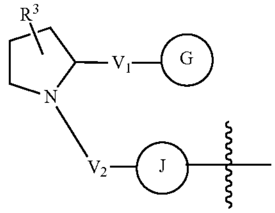

Formula (IIID)

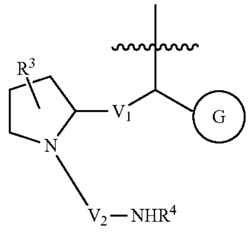

Formula (IIIE)

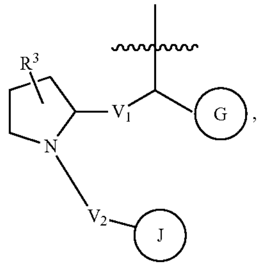

wherein, $V_1$ is —C(O)—, —C(O)O—, —C(O)O—C(R$^e$)$_2$—, —C(O)—N(R$^e$)—, —C(O)—C(R$^e$)$_2$—, or —C(O)—N(R$^e$)—C(R$^e$)$_2$—;

$V_2$ is —C(O)—C(R$^e$)$_2$—;

G ring is phenyl, 5-6 membered heteroaryl or 5-6 membered heterocyclyl, each being optionally substituted with 1 to 3 R$^j$;

J ring is 5-12 membered heteroaryl or 5-12 membered heterocyclyl, each being optionally substituted with 1 to 3 R$^j$;

each R$^e$ is independently hydrogen, $C_{1-6}$ alkyl or $C_{3-8}$ cycloalkyl;

each R$^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—R$^g$, —C(O)—R$^g$, —C(O)O—R$^g$, —C(O)—N(R$^g$)(R$^g$), —$N(R^g)(R^g)$, —$N(R^g)C(O)$—$R^g$, —$N(R^g)C(O)O$—$R^g$, —$N(R^g)C(O)N(R^g)(R^g)$, —$N(R^g)S(O)_2(R^g)$, —$NR^gS(O)_2N(R^g)(R^g)$, —$N(R^g)S(O)_2O(R^g)$, —$OC(O)R^g$, —$OC(O)$—$N(R^g)(R^g)$, —$Si(R^g)_3$, —S—$R^g$, —S(O) $R^g$, —$S(O)(NH)R^g$, —$S(O)_2R^g$ or —$S(O)_2N(R^g)(R^g)$, wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$, each $R^g$ is independently hydrogen or $C_{1-6}$ alkyl;

each $R^k$ is independently halo, oxo, —CN, —OH, $C_{1-6}$ alkyl optionally substituted with 1 to 3 fluoro, $C_{3-8}$ cycloalkyl, or —O—$C_{1-6}$ alkyl optionally substituted with 1 to 3 fluoro;

$R^3$ is hydrogen or hydroxyl; and $R^4$ is —$C(O)R^f$, wherein $R^f$ is $C_{1-6}$ alkyl or $C_{3-8}$ cycloalkyl, each being optionally substituted with halo or —CN.

19. The compound of claim 18 wherein Formulae (IIIA), (IIIB), (IIIC) and (IIID) have the structures represented by Formulae (IIIA1), (IIIB1), (IIIC1), (IIID1), (IIIE1), respectively:

Formula (IIIA1)

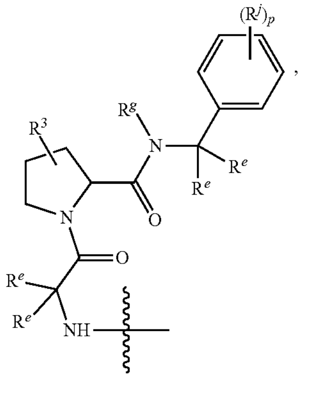

Formula (IIIB1)

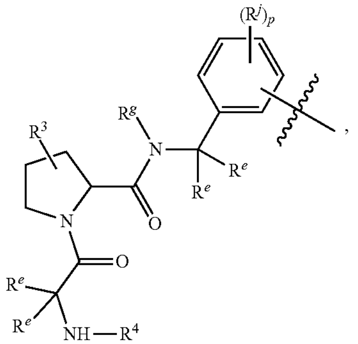

-continued

Formula (IIIC1)

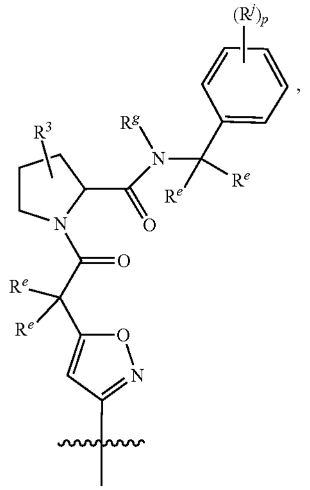

Formula (IIID1)

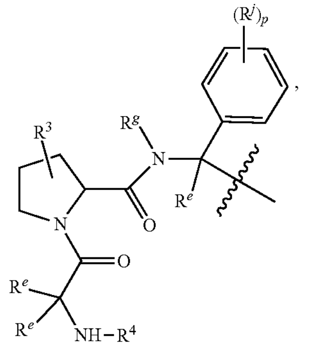

Formula (IIIE1)

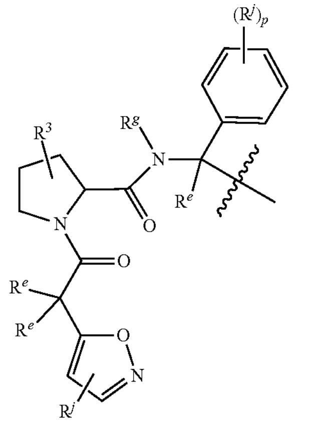

wherein, p is 0 or 1;

$R^j$ is 5-6 member heteroaryl optionally substituted with 1 to 3 $R^k$;

each $R^k$ is independently halo, oxo, —CN, —OH, $C_{1-6}$ alkyl, $C_{3-8}$ cycloalkyl, or —O—$C_{1-6}$ alkyl;

each $R^e$ is independently hydrogen, $C_{1-6}$ alkyl or $C_{3-8}$ cycloalkyl;

each $R^g$ is independently hydrogen or $C_{1-6}$ alkyl;

$R^3$ is hydrogen or hydroxyl; and $R^4$ is —$C(O)R^f$, wherein $R^f$ is $C_{1-6}$ alkyl or $C_{3-8}$ cycloalkyl, each being optionally substituted with halo or —CN.

20. The compound of claim 19 wherein p is 1 and $R^j$ is thiazolyl, oxazolyl, isoxazolyl, pyrazolyl, imidazolyl, 1,2,4-oxadiazolyl, 1,3,4-oxadiazolyl, each being optionally substituted with $C_{1-6}$ alkyl, $C_{3-8}$ cycloalkyl, halo, CN, haloalkyl, or hydroxyalkyl.
21. The compound of claim 20 having one of the following structures:
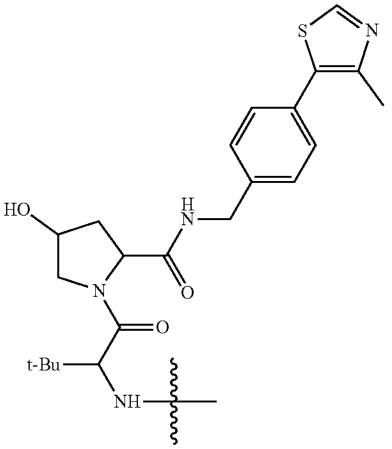
,
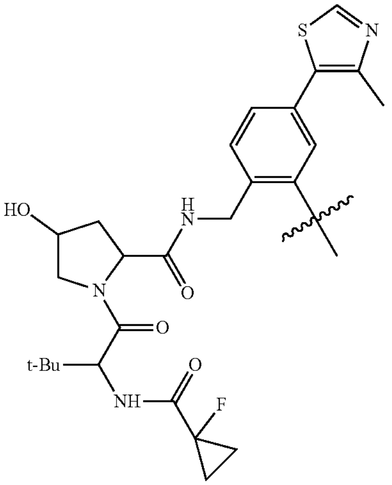
,
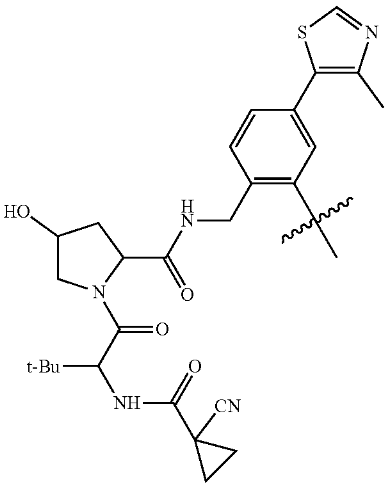
,
-continued
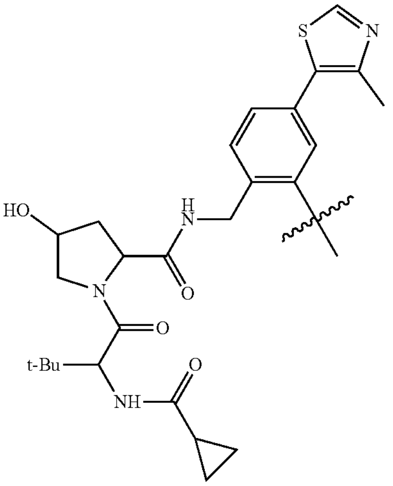
,
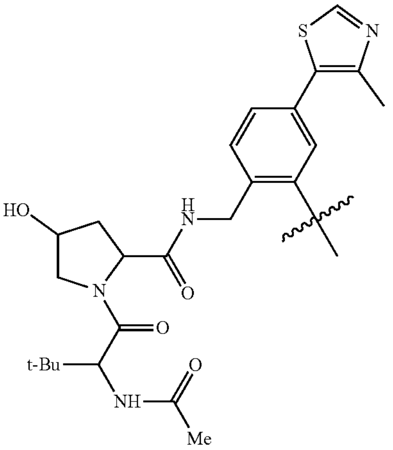
,
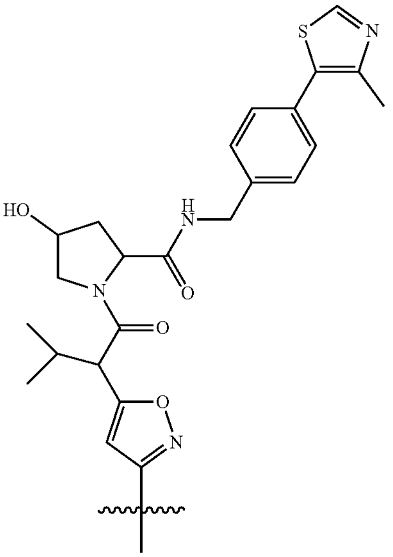
, -continued
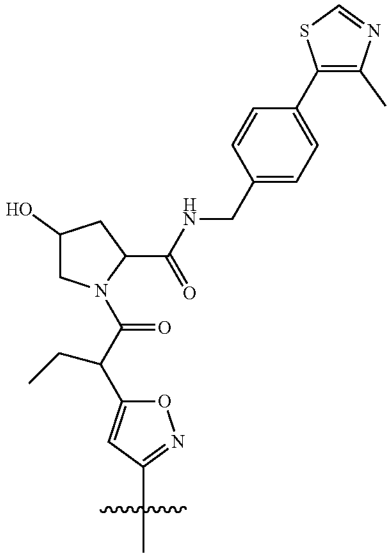
,
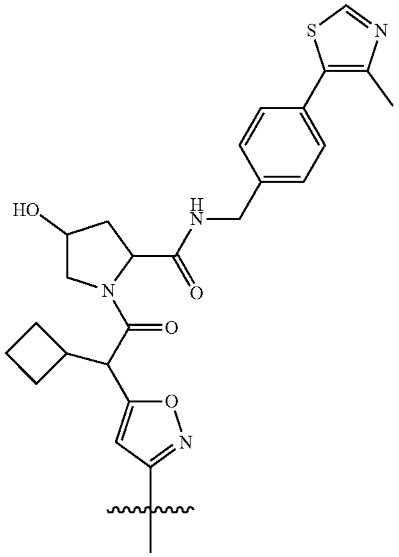
,
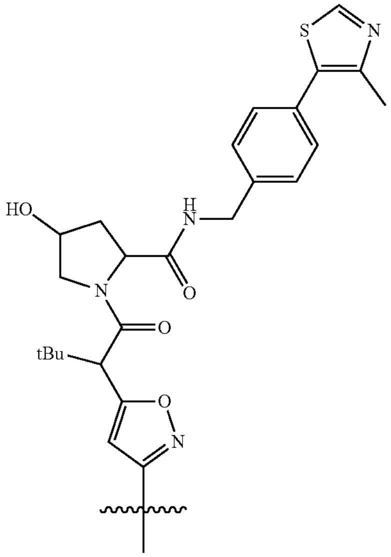
,
-continued
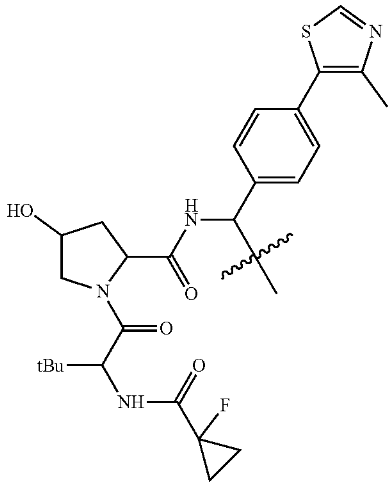
, or
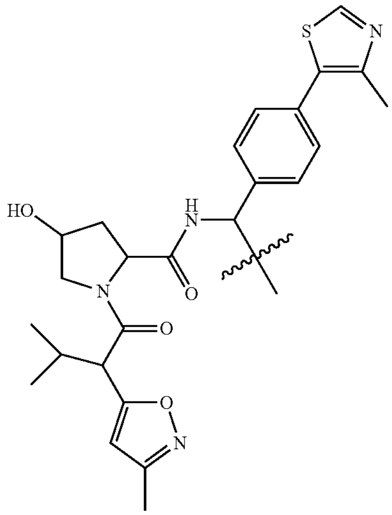
.
22. The compound of claim 19 wherein p is 0 and Formula (IIIA), (IIIB) or (IIIC), (IIID) has any one of the following structures:
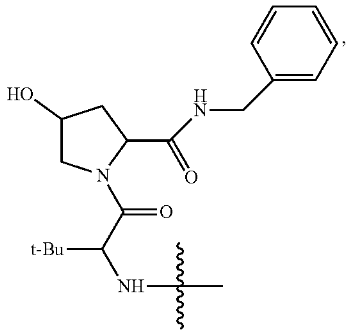
,

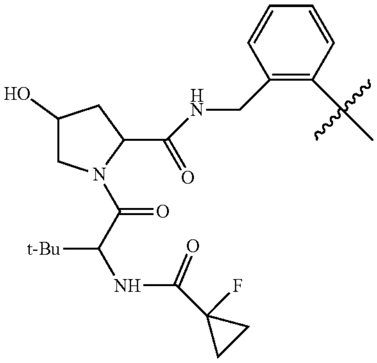
,
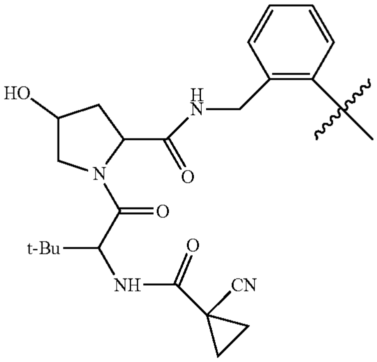
,
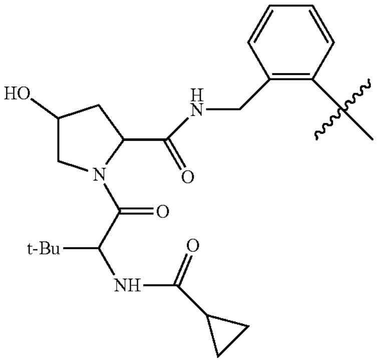
,
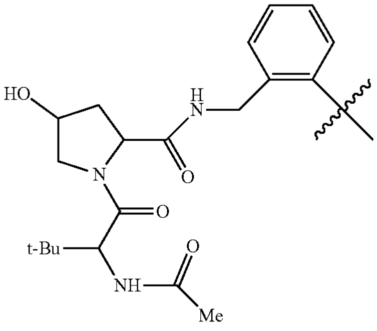
,
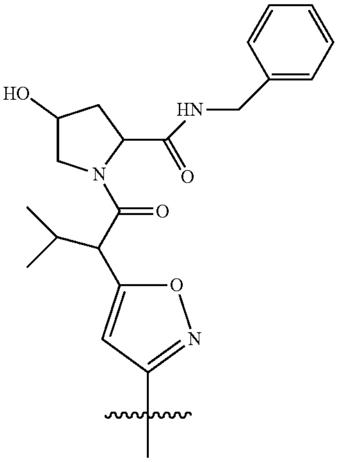
,
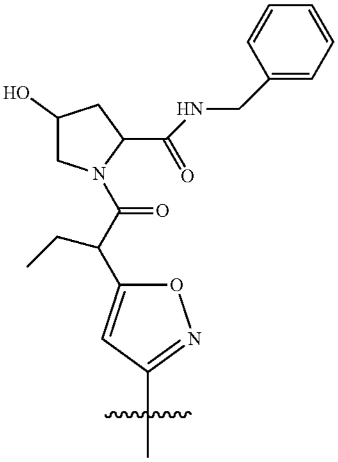
,
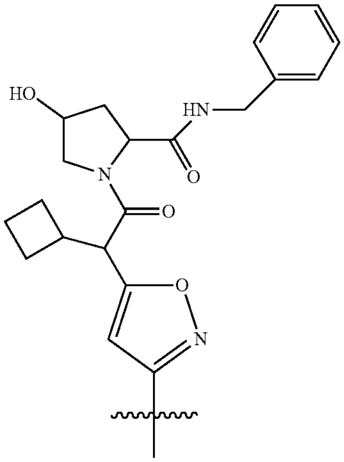
, -continued

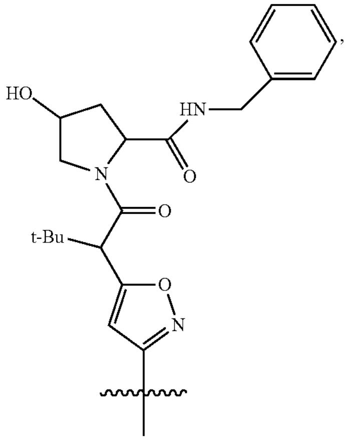

, or

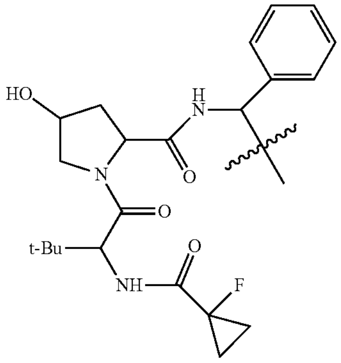

.

23. The compound of claim 1 wherein LHM targets inhibitor of apoptosis proteins (IAP) ligase and has one of the following structures:

Formula (IVA)

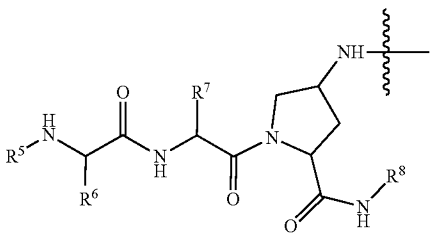

,

Formula (IVB)

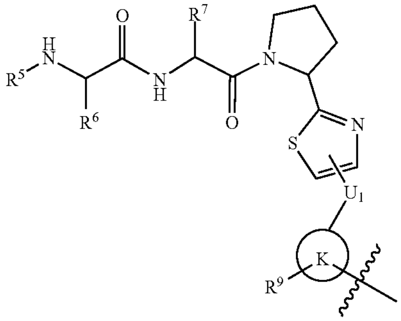

,

-continued

Formula (IVC)

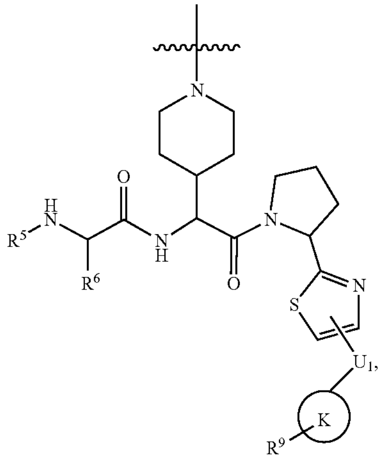

or

Formula (IVD)

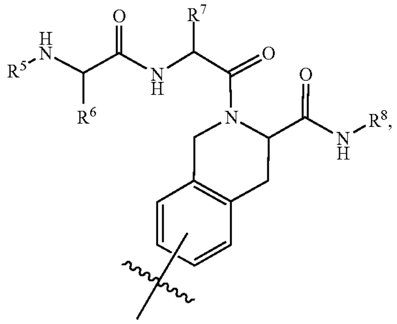

wherein, each $R^5$ is independently hydrogen or $C_{1-6}$ alkyl;

each $R^6$ is independently hydrogen, or $C_{1-6}$ alkyl;

each $R^7$ is independently hydrogen, $C_{1-6}$ alkyl, or $C_{3-8}$ cycloalkyl;

each $R^8$ is independently aryl, 5-12 membered cycloalkyl, 5-12 membered heteroaryl or 5-12 membered heterocyclyl, each being optionally substituted with 1 to 3 $R^j$;

each $R^9$ is independently hydrogen, halo, or $C_{1-6}$ alkyl;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—$R^g$, —N($R^g$)C(O)N($R^g$)($R^g$), —N($R^g$)S$(O)_2$($R^g$), —N$R^g$S$(O)_2$N($R^g$)($R^g$), —N($R^g$)S$(O)_2$O($R^g$), —OC(O)$R^g$, —OC(O)—N($R^g$)($R^g$), —Si$(R^g)_3$, —S—$R^g$, —S(O) $R^g$, —S(O)(NH)$R^g$, —S$(O)_2R^g$ or —S$(O)_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^k$;

each $R^g$ is independently hydrogen or $C_{1-6}$ alkyl;

each $R^k$ is independently halo, oxo, —CN, —OH, $C_{1-6}$ alkyl optionally substituted with 1 to 3 fluoro, $C_{3-8}$ cycloalkyl, or —O—$C_{1-6}$ alkyl optionally substituted with 1 to 3 fluoro;

$U_1$ is direct bond or —C(O)—;

Z is —CH— or —N—; and

K ring is phenyl or naphthyl.

24. The compound of claim 23 wherein Formulae (IVA), (IVB), (IVC) and (IVD) has the following structure, respectively:

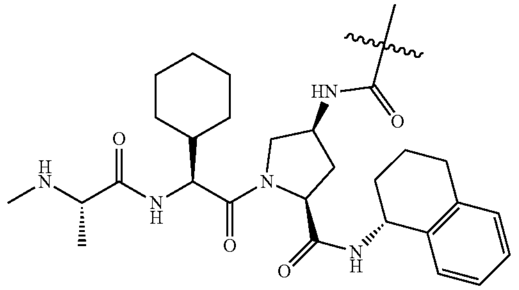
,
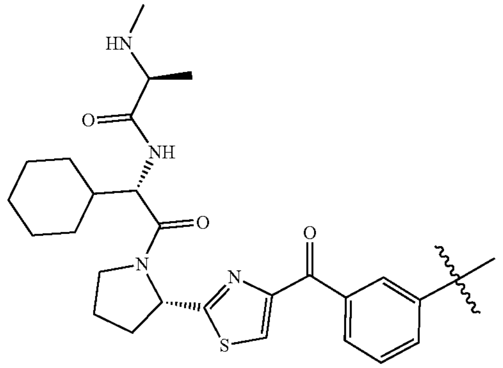
,
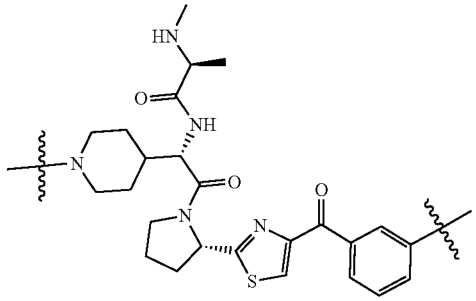
, or
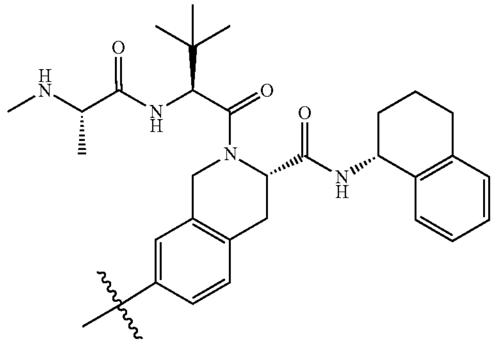
.
25. The compound of claim 1, wherein $L_1$ has any one of the following ring structures:
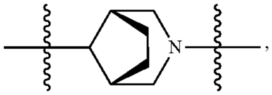
,
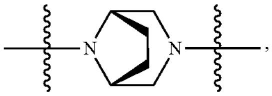
,
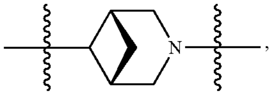
,
-continued
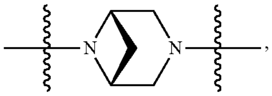
,
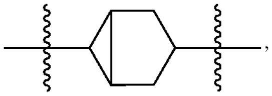
,
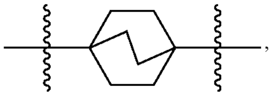
,
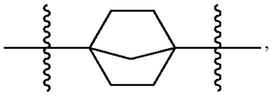
,
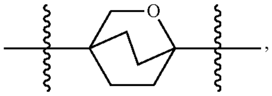
,
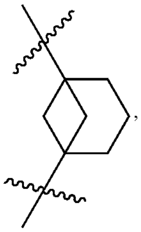
,
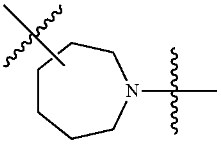
,
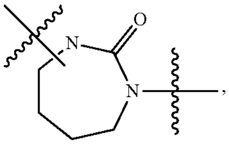
,
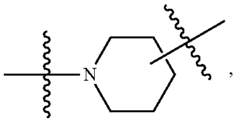
,
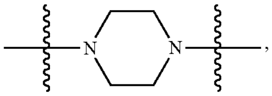
,
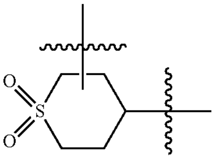
,
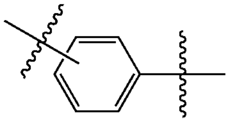
,
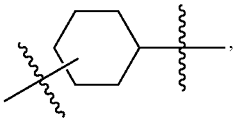
,
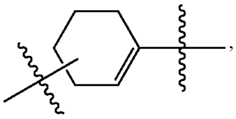
,
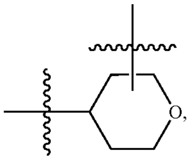
,
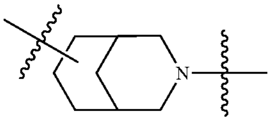
,
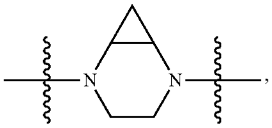
,
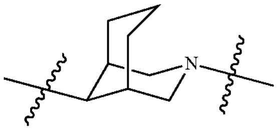
,
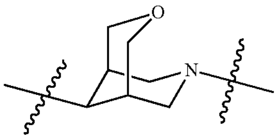
, -continued

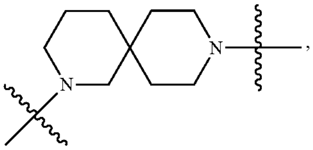,

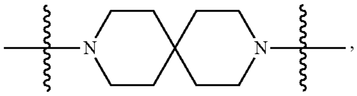,

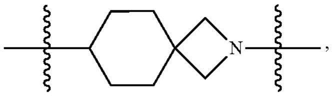,

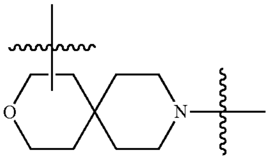,

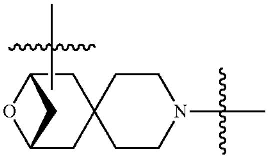, 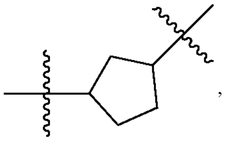,

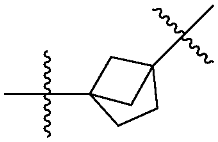, 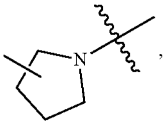,

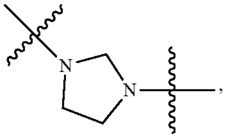, 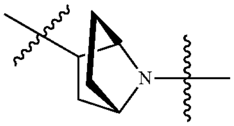,

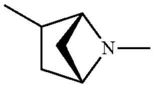, 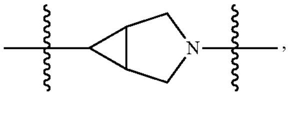,

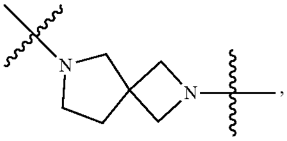,

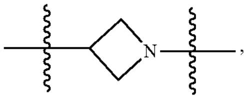, 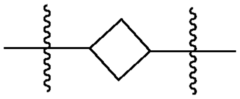,

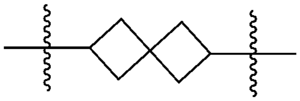,

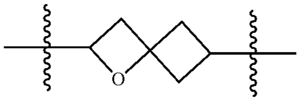,

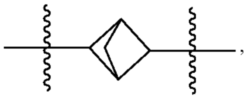, 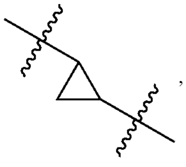,

-continued

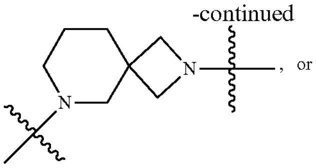, or

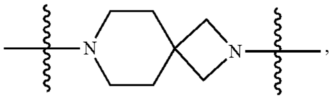, wherein each ring may be optionally substituted by 1 to 3 $R^b$, each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 3-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—$R^c$, —N($R^c$)C(O)O—$R^c$, —N($R^c$)C(O)N($R^c$)($R^c$), —N($R^c$)S(O)$_2$($R^c$), —NRCS(O)$_2$N($R^c$)($R^c$), —N($R^c$)S(O)$_2$O($R^c$), —OC(O)$R^c$, —OC(O)—N($R^c$)($R^c$), —Si($R^c$)$_3$, —S—$R^c$, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 3-12 membered heterocyclyl may be optionally substituted with 1 to 3 $R^d$; and $R^d$ is independently halo, oxo, —CN, —OH, $C_{1-6}$ alkyl, $C_{3-8}$ cycloalkyl optionally substituted with 1 to 3 fluoro, or —O—$C_{1-6}$ alkyl optionally substituted with 1 to 3 fluoro.

26. The compound of claim 25, wherein $L_1$ has any one of the following ring structures:

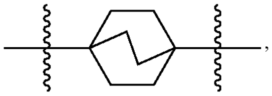,

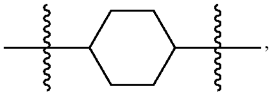,

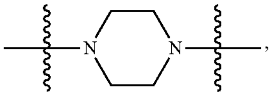,

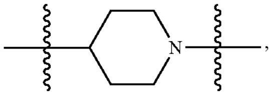,

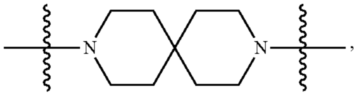,

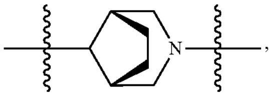,

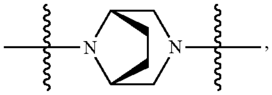,

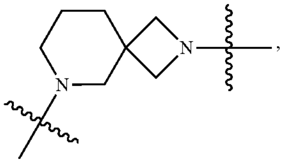,

-continued

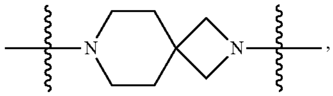,

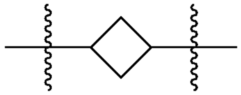 or

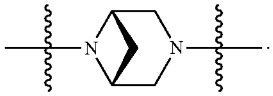.

27. The compound of claim 25, wherein $-L_2-L_3-L_4-L_5-$ is $-C(O)-$, $-NH-C(O)-$, $-C(O)-(CH_2)_n-$, $-C(O)-(CH_2)_n-C(O)-$, $-C(O)-(CH_2)_n-O-$, $-(CH_2)_n-$, $-C(O)-(CH_2)_n-NH-$, $-C(O)-(CH_2CH_2O)_m-$, $-C(O)-(CH_2CH_2O)_m-(CH_2)_n-C(O)-$, $-C(O)-(CH_2CH_2O)_m-(CH_2)_n-NH-$, $-C(O)-(CH_2CH_2O)_m-(CH_2)_n-$, $-NH-C(O)-(CH_2CH_2O)_m-(CH_2)_n-C(O)-$, $-NH-C(O)-(CH_2CH_2O)_m-(CH_2)_n-NH-$, $-NH-C(O)-(CH_2)_n-C(O)-$, $-NH-C(O)-(CH_2CH_2O)_m-$, $-NH-C(O)-(CH_2)_n-O-$, $-NH-C(O)-(CH_2)_n-NH-$ or $-NH-C(O)-(CH_2CH_2O)_m-(CH_2)_n-$, wherein m is an integer of 1 to 6, and n is an integer of 1 to 12, and wherein one or two hydrogens of each of the above linker moieties may be replaced by $C_{1-3}$ alkyl.

28. The compound of claim 27, wherein $L_1$ is

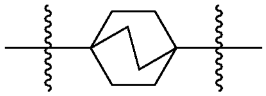, and L has the one of the following structures:

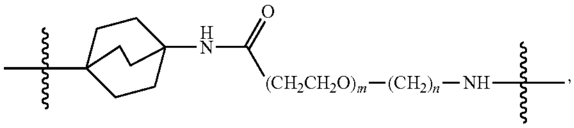,

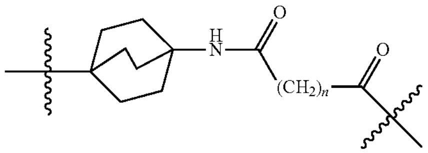,

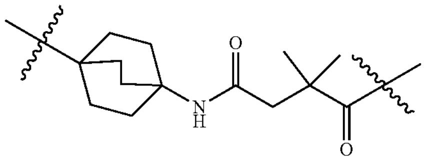 or

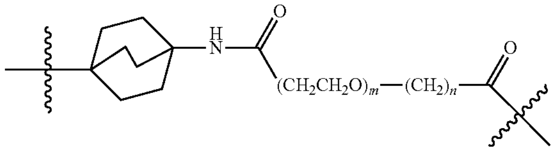, wherein, m is 1, 2, 3, 4, 5 or 6 and n is 2, 3, 4, 5, or 6.

29. The compound of claim 27, wherein $L_1$ is

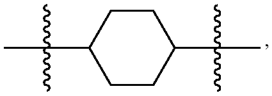, and L has the following structure:

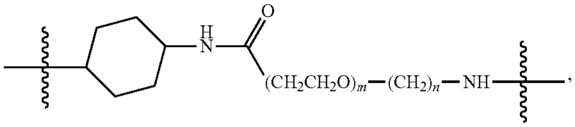, wherein m is 1, 2, 3, 4, 5 or 6 and n is 2, 4, or 6.

30. The compound of claim 27, wherein $L_1$ is

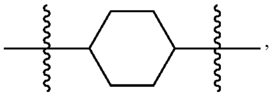, and L has the following structure:

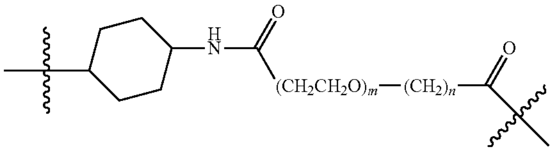

wherein, m is 1, 2, 3, 4, 5 or 6 and n is 2, 4, or 6.

31. The compound of claim 27, wherein $L_1$ is

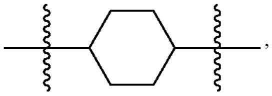, and L has the following structure:

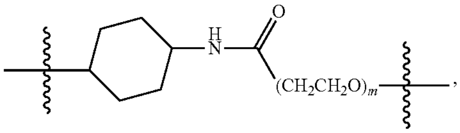, wherein m is 1, 2, 3, 4, 5 or 6.

32. The compound of claim 27, wherein $L_1$ is

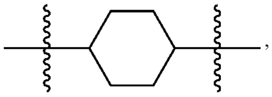, and L has the following structure:

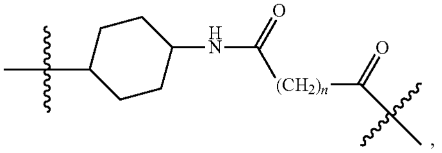

wherein n is 1, 2, 3, 4, 5, 6, 7 or 8.

33. The compound of claim 27, wherein $L_1$ is

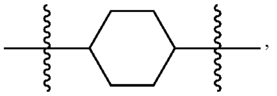

and L has the following structure:

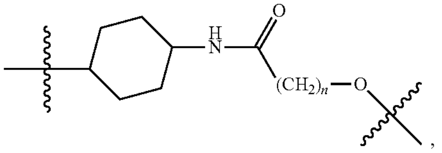

wherein n is 2, 3, 4, 5 or 6.

34. The compound of claim 27, wherein $L_1$ is

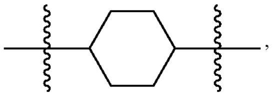 [SMILES: *C1CCC(*)CC1]

and L has the following structure:

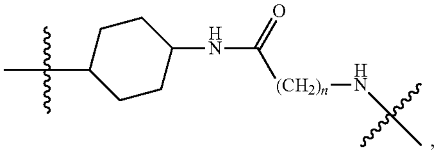

wherein n is 4, 5, 6, 7 or 8.

35. The compound of claim 27, wherein $L_1$ is

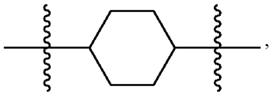

and L has the following structure:

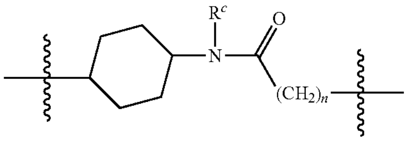

or

-continued

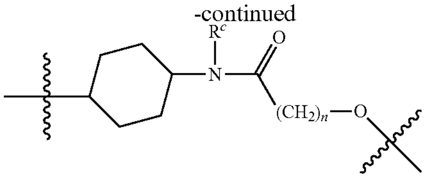

wherein $R^c$ is hydrogen or $C_{1-3}$alkyl, n is 1, 2 or 3.

36. The compound of claim 27, wherein $L_1$ is

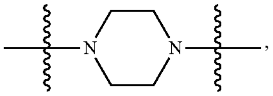

and L has the following structure:

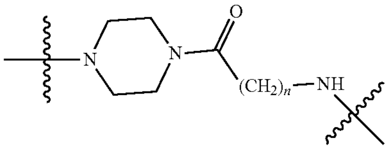

wherein n is 1, 2, 3, 4, 5, 6, 7 or 8.

37. The compound of claim 27, wherein $L_1$ is

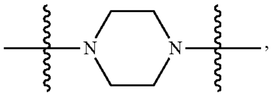 [SMILES: *N1CCN(*)CC1]

and L has the following structure:

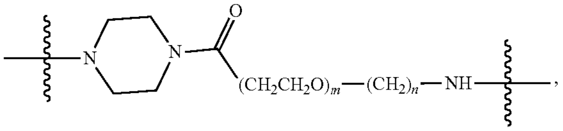

wherein, m is 1, 2, 3, 4, 5 or 6 and n is 2, 4, or 6.

38. The compound of claim 27, wherein $L_1$ is

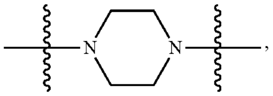 [SMILES: *N1CCN(*)CC1]

and L has the following structure:

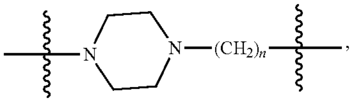

wherein n is 1, 2, 3, 4, 5, or 6.

39. The compound of claim 27, wherein $L_1$ is

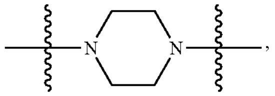

and L has the following structure:

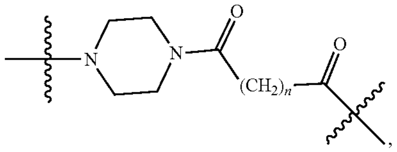

wherein n is 1, 2, 3, 4, 5, 6, 7, 8, 9 or 10.

40. The compound of claim 27, wherein $L_1$ is

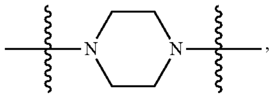 [SMILES: *N1CCN(*)CC1]

and L has the following structure:

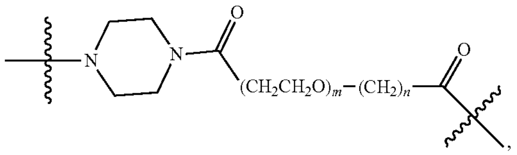

wherein, m is 1, 2, 3, 4, 5 or 6 and n is 2, 4, or 6.

41. The compound of claim 27, wherein $L_1$ is

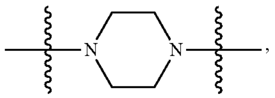

and L has the following structure:

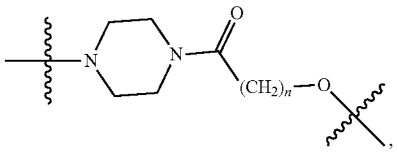

wherein n is 1, 2, 3, 4, 5, 6, 7, 8 or 9.

42. The compound of claim 27, wherein $L_1$ is

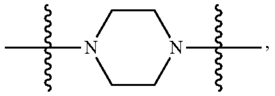 [SMILES: *N1CCN(*)CC1]

and L has the following structure:

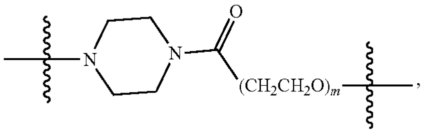

wherein m is 1, 2, 3, 4, 5, 6, 7 or 8.

43. The compound of claim 27, wherein $L_1$ is

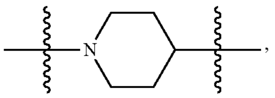

and L has one of the following structures:

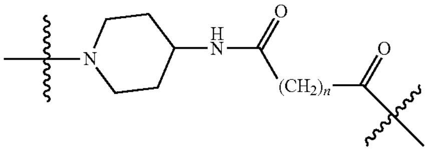

, wherein, n is 1, 2, 3, 4, 5, 6, 7 or 8.

44. The compound of claim 27, wherein $L_1$ is

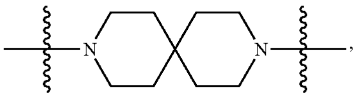

and L has one of the following structures:

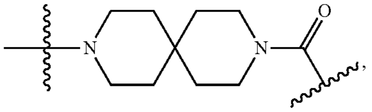

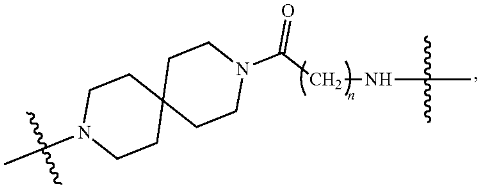

or

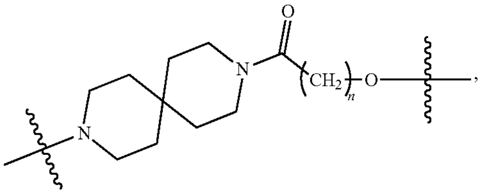

wherein n is 1, 2 or 3.

45. The compound of claim 27, wherein $L_1$ is

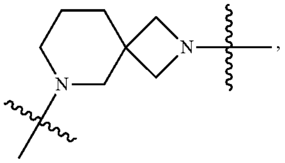 [SMILES: *N1CCCC2(C1)CN(*)C2]

and L has one of the following structures:

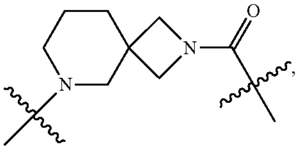

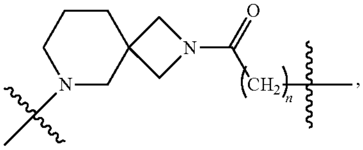

or

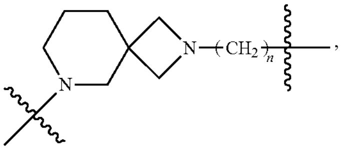

wherein n is 1, 2, 3, 4, 5, 6, 7, 8, or 9.

46. The compound of claim 27, wherein $L_1$ is

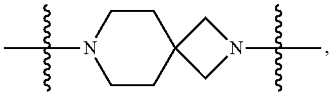

and L has one of the following structures:

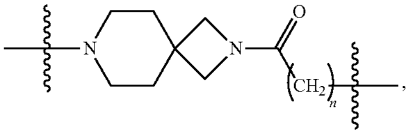

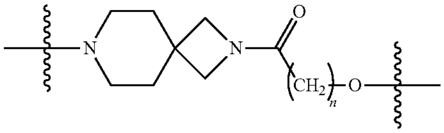

or

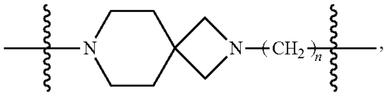

wherein n is 1, 2, 3, 4, 5, 6, 7, 8, or 9.

47. The compound of claim 27, wherein $L_1$ is

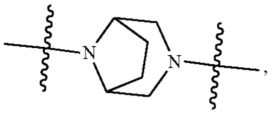 [SMILES: *N1CC2CCC(C1)N2*]

and L has the following structure:

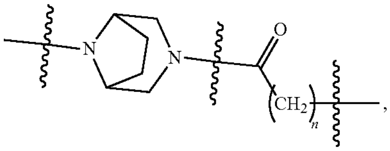

wherein n is 1, 2, or 3.

48. The compound of claim 27, wherein $L_1$ is

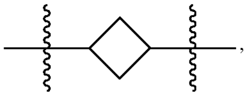

and L has the following structure:

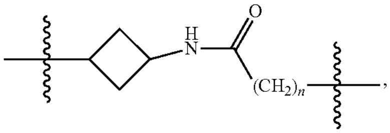

wherein n is 1, 2, or 3.

49. The compound of claim 27, wherein $L_1$ is

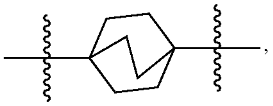

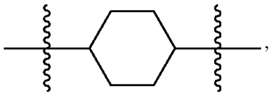

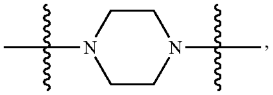

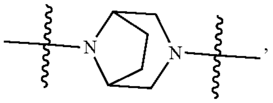

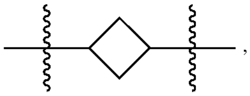

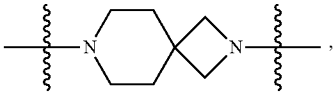

or

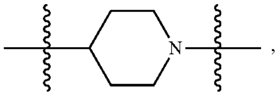

and $-L_2-L_3-L_4-L_5-$ is one of the following structures:

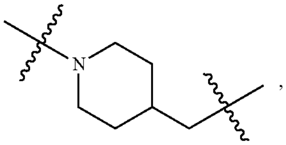

-continued
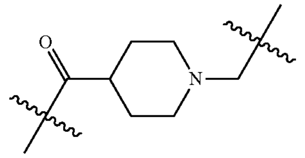
,
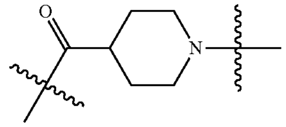
,
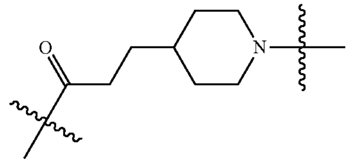
,
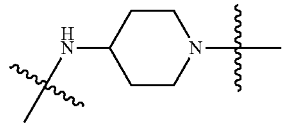
,
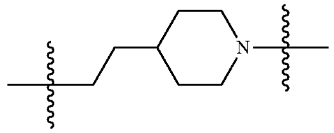
,
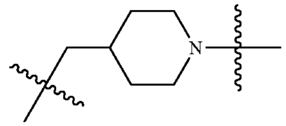
,
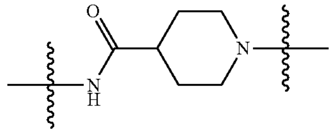
,
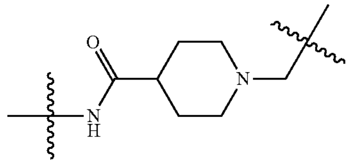
,
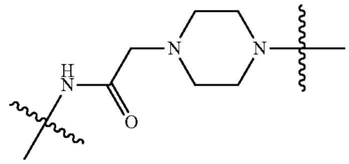
,
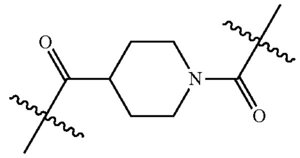
,
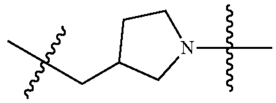
,
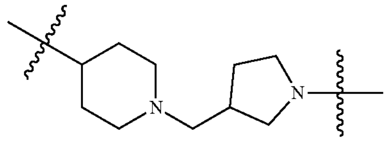
,
-continued
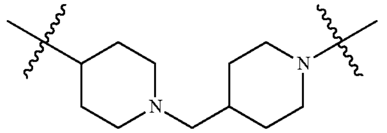
,
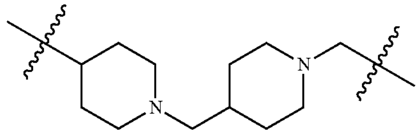
,
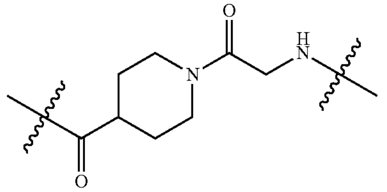
,
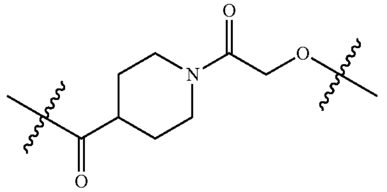
,
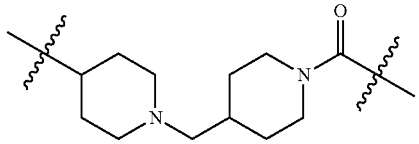
,
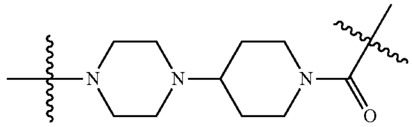
,
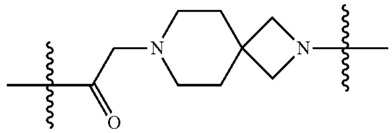
,
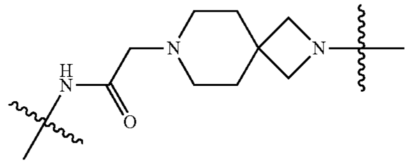
,
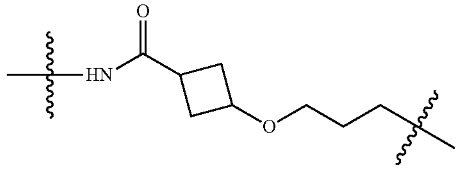
,
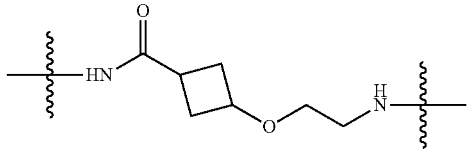
,
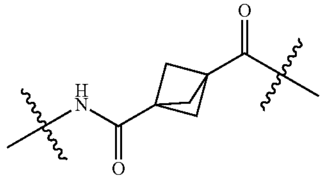

-continued
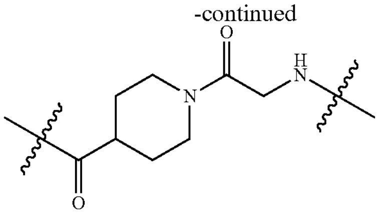
,
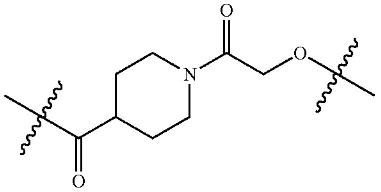
,
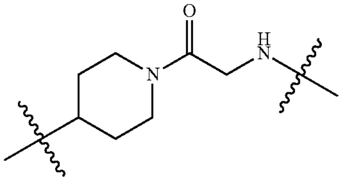
,
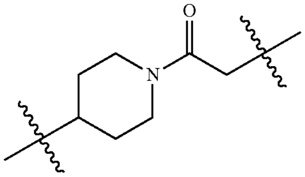
,
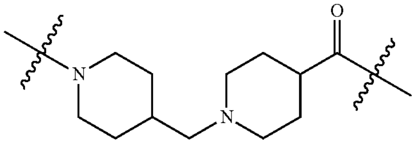
,
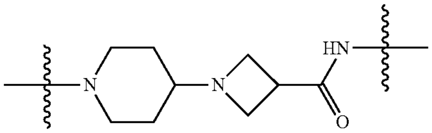
,
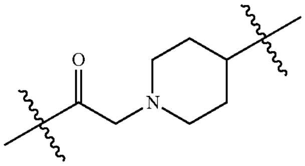
,
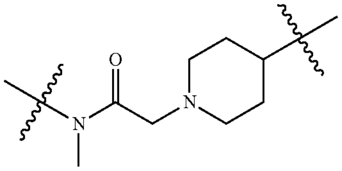
,
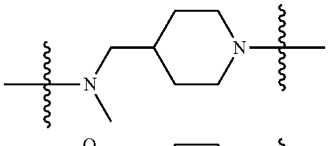
,
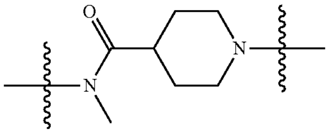
,
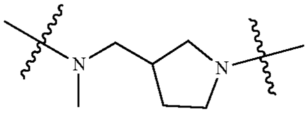
,
-continued
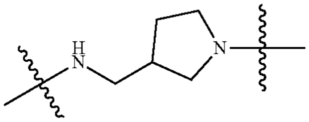
,
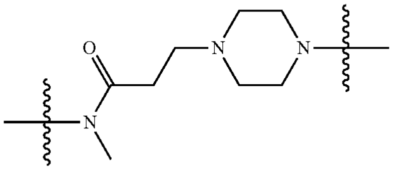
,
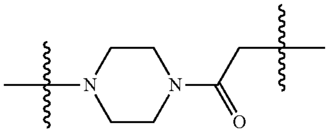
,
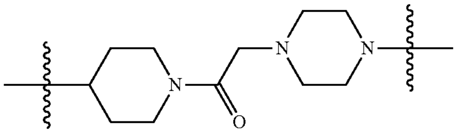
,
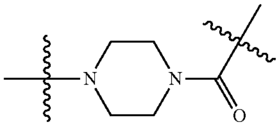
,
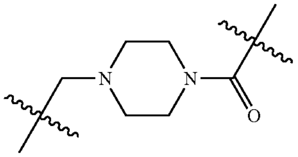
,
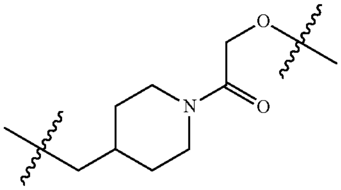
,
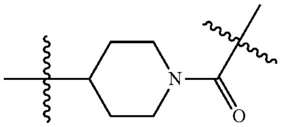
,
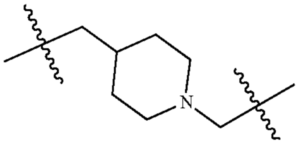
,
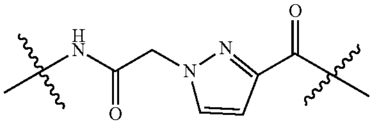
,
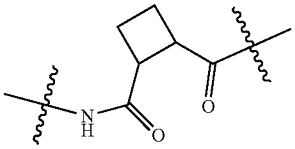
,
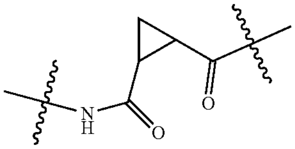
, -continued
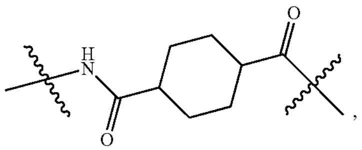
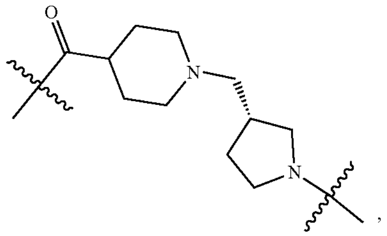
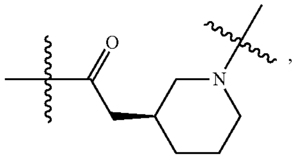
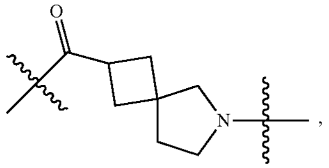
or
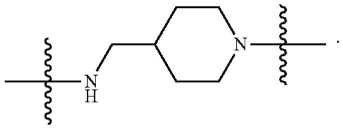
50. The compounds of claim 1 wherein L has one of the following structures:
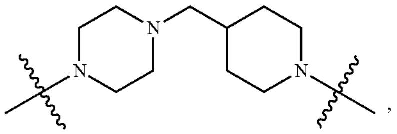
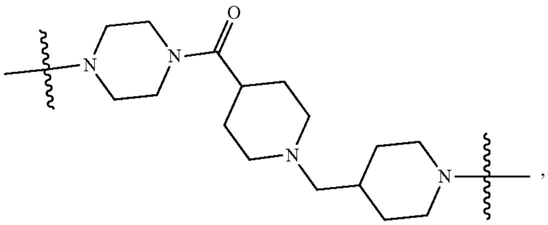
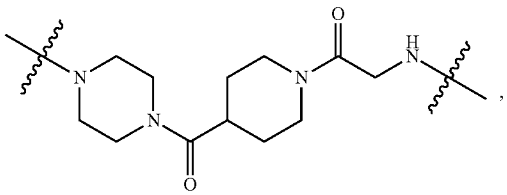
-continued
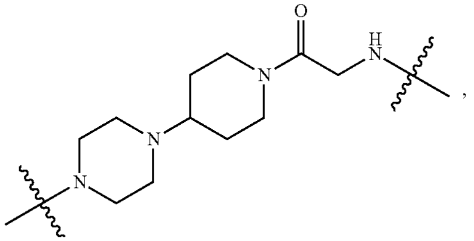
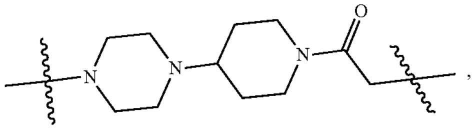
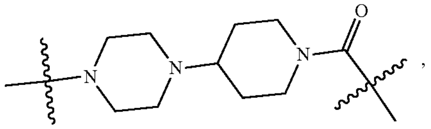
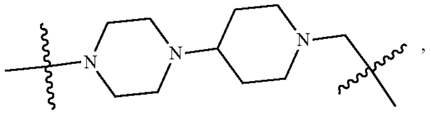
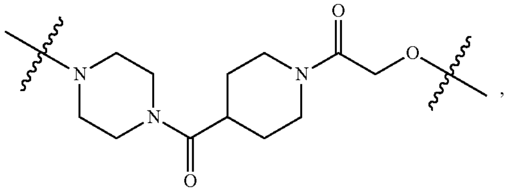
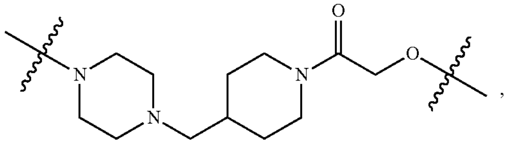
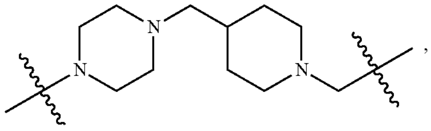
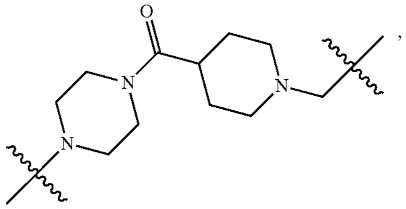
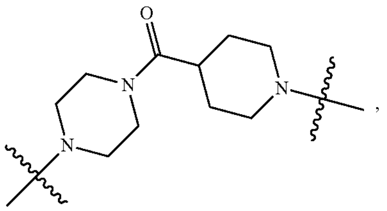
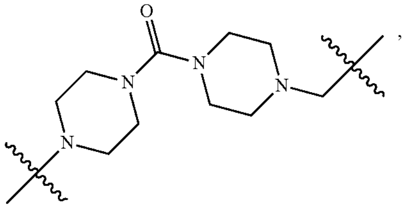

-continued
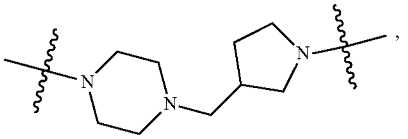
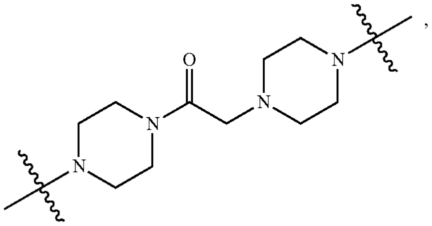
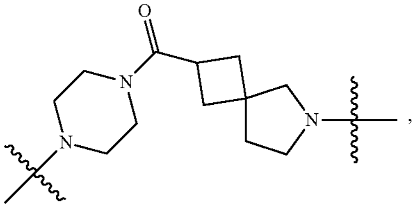
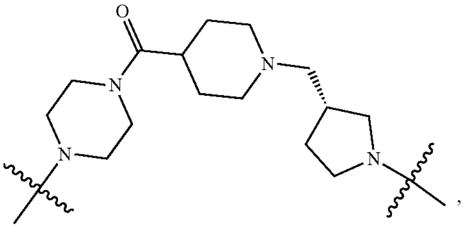
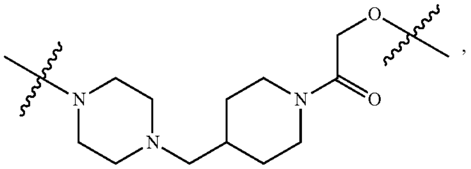
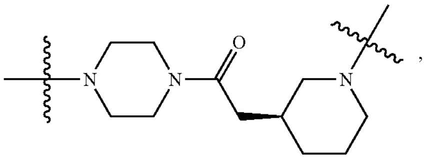
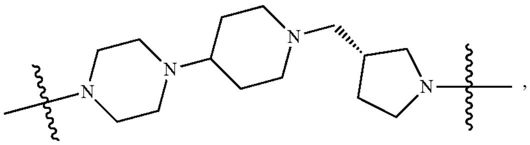
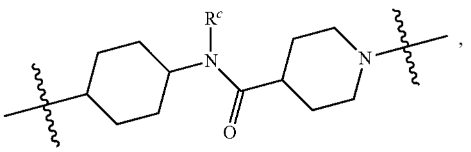
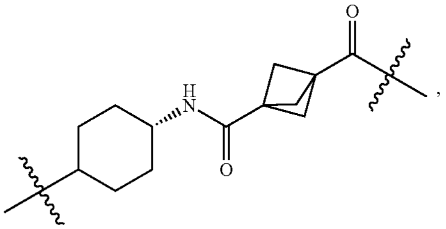
-continued
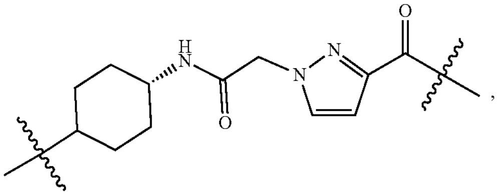
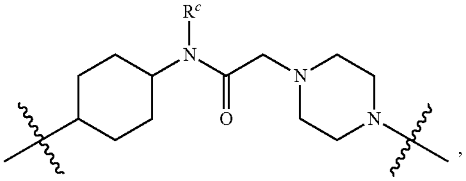
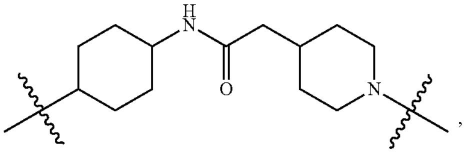
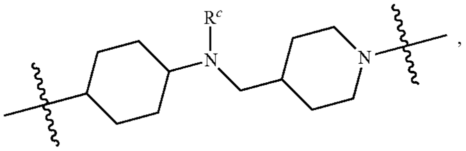
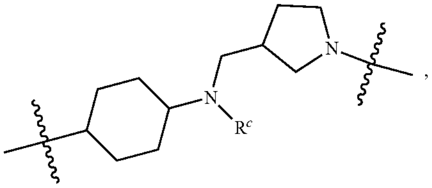
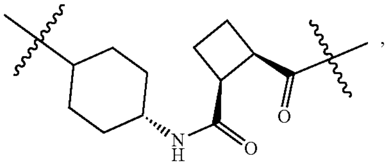
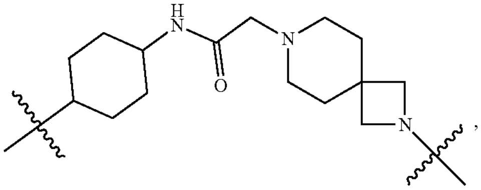
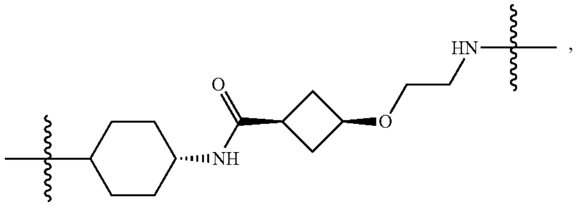
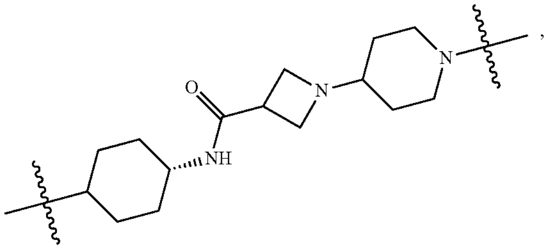

-continued
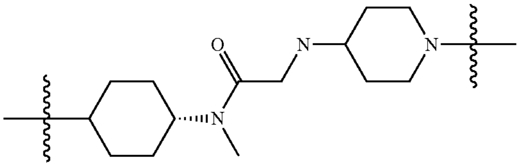
,
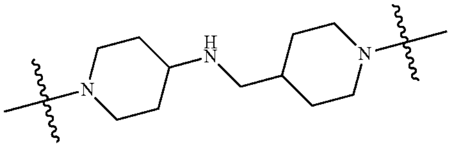
,
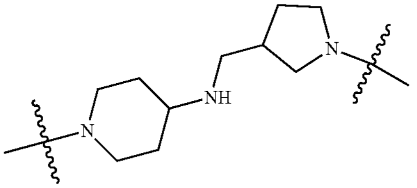
,
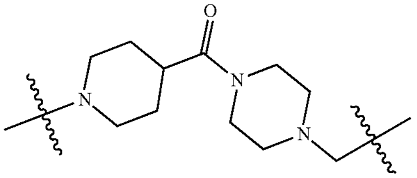
,
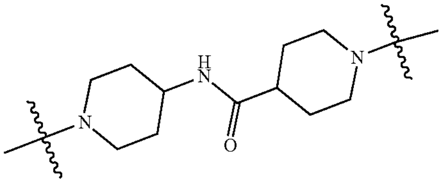
,
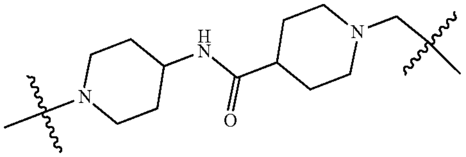
,
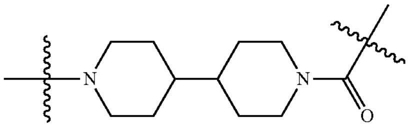
,
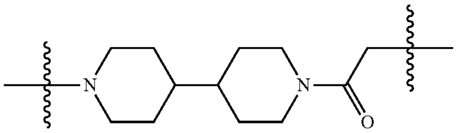
,
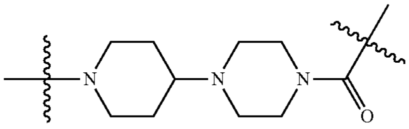
,
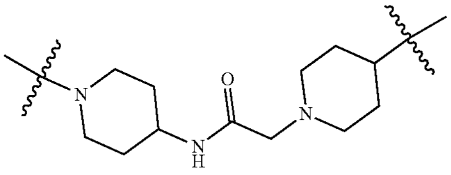
,
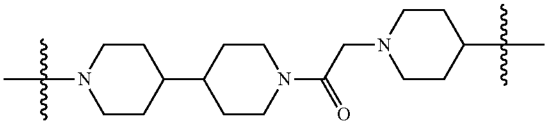
,
-continued
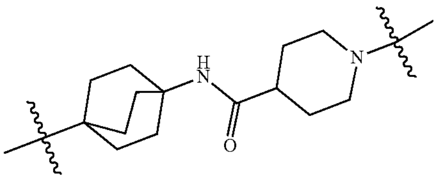
,
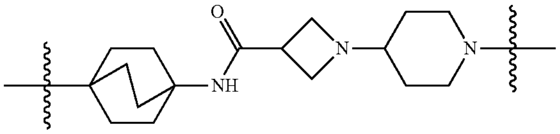
,
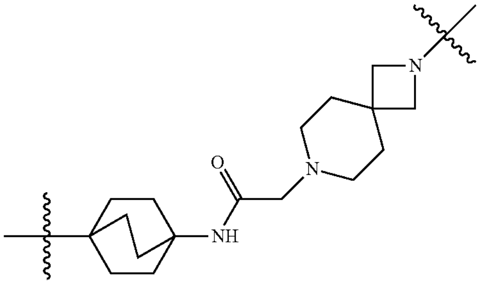
,
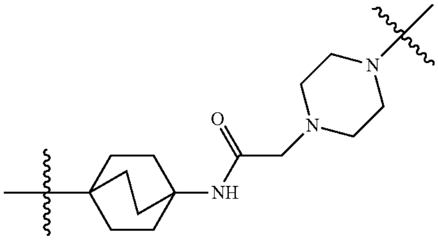
,
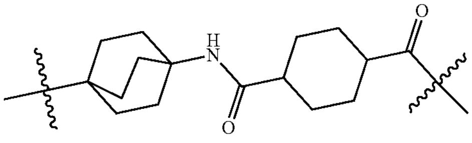
,
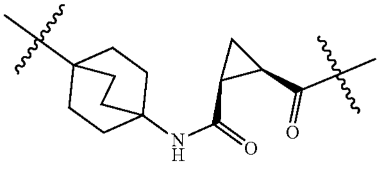
,
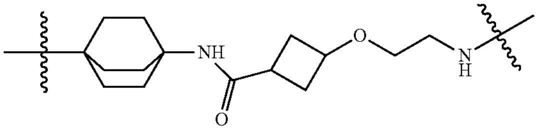
,
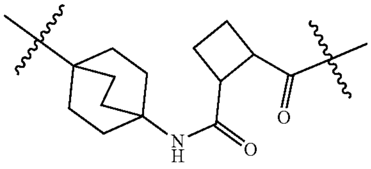
,
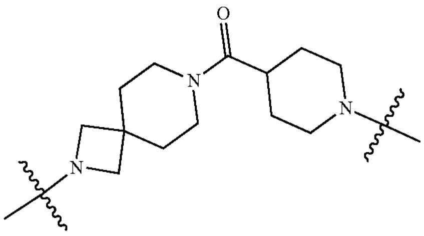
, -continued
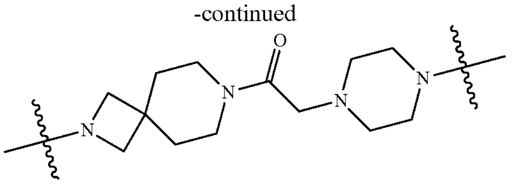
,
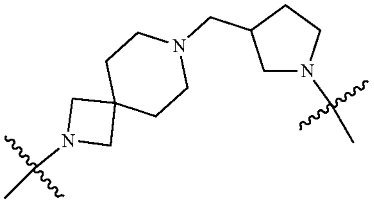
,
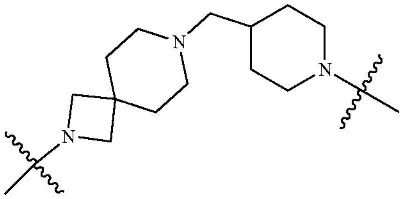
,
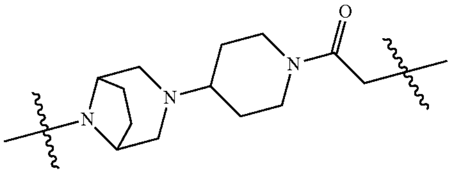
,
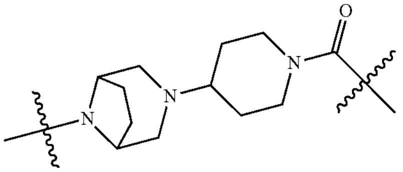
,
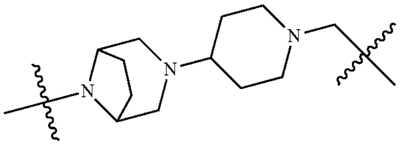
, or
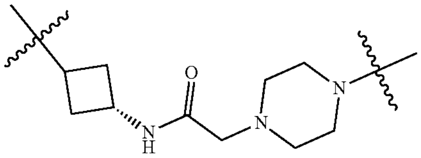
,
wherein $R^c$ is H or $C_{1-3}$alkyl.
51. The compounds of claim 1 wherein L or a partial L has one of the following structures:
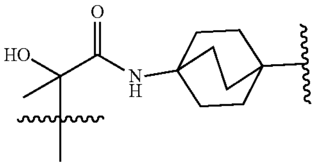
,
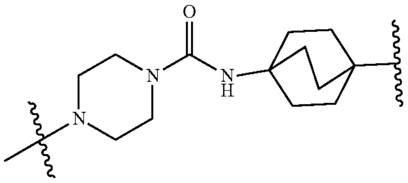
,
-continued
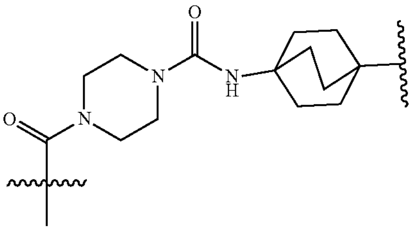
,
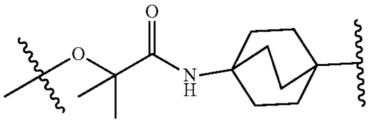
,
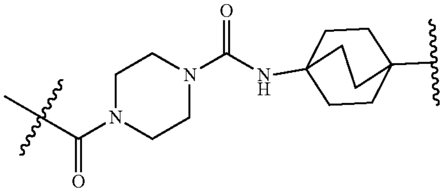
,
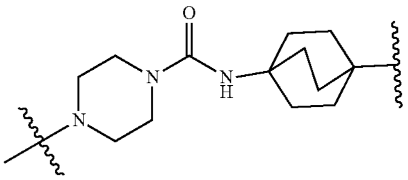
,
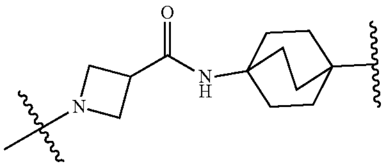
,
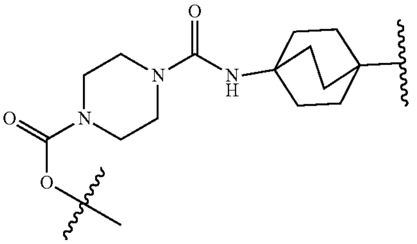
,
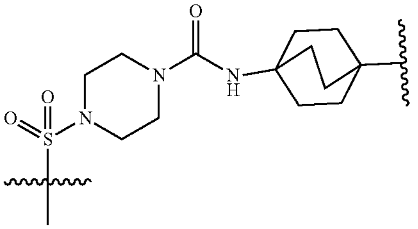
,
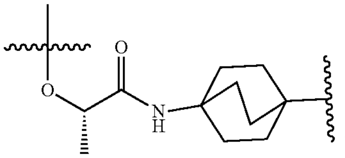
,
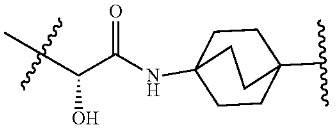
, -continued
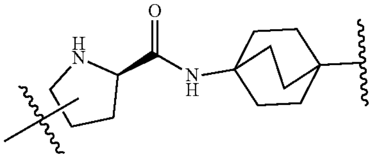,
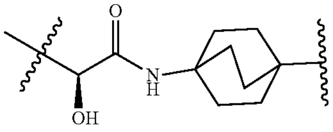, 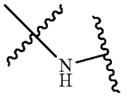,
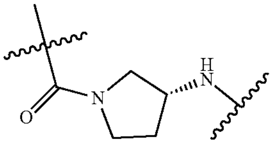,
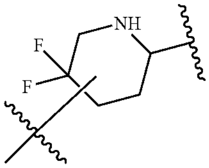,
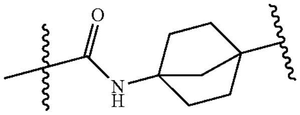,
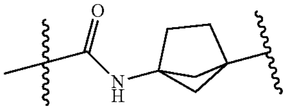,
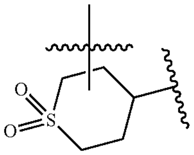, 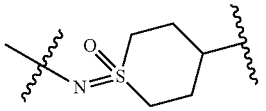,
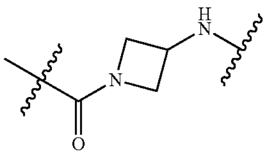, 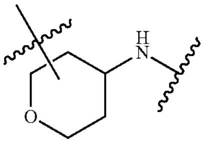,
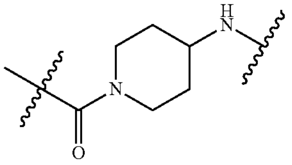,
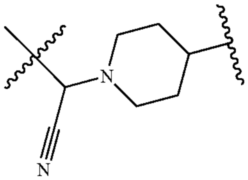, 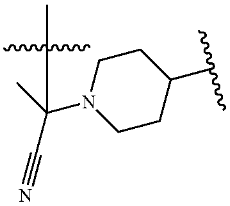,
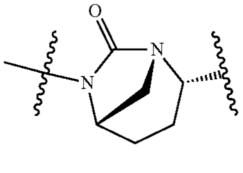,
-continued
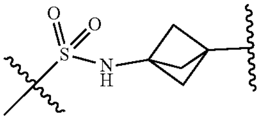,
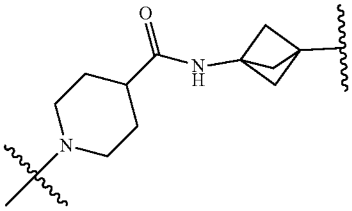,
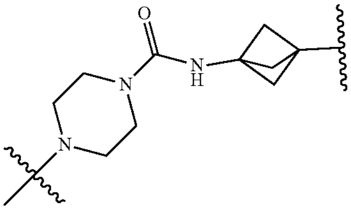,
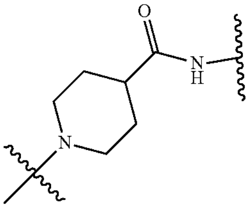,
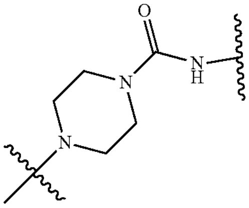,
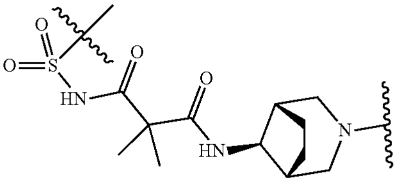,
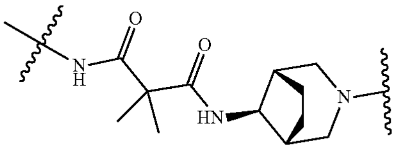,
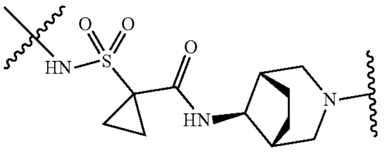,
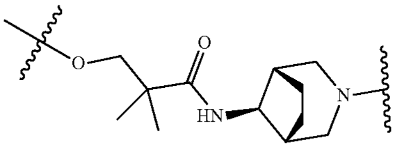, -continued
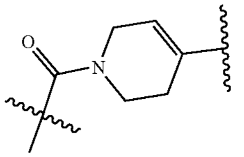,
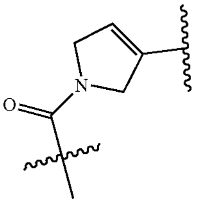,
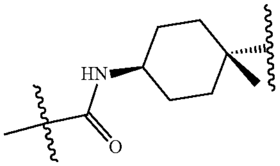,
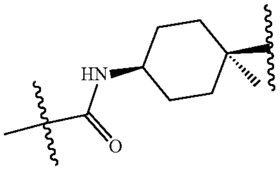,
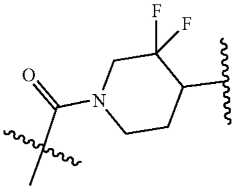,
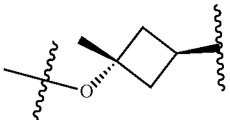,
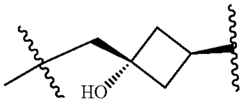,
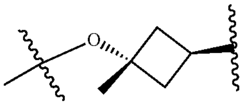,
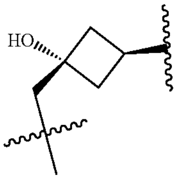,
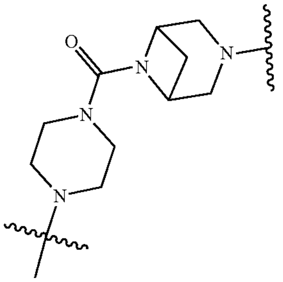,
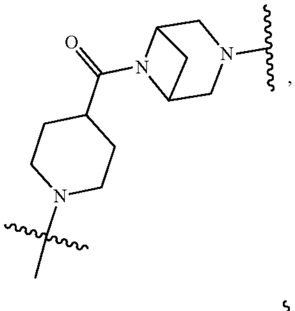,
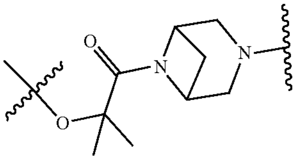,
-continued
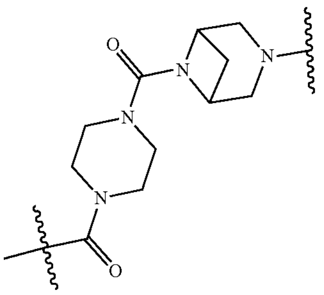,
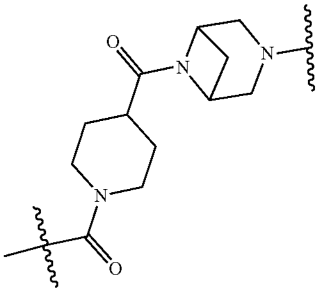,
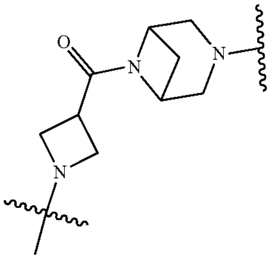,
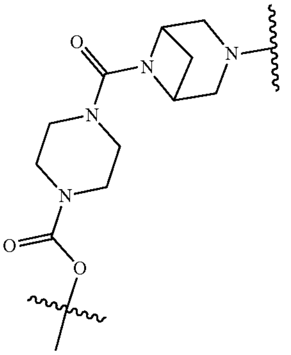,
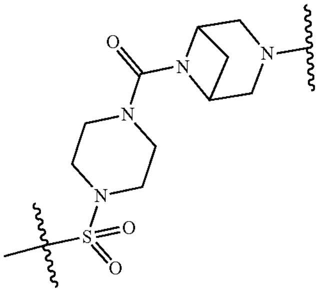,
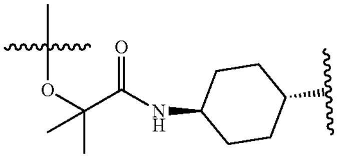, -continued
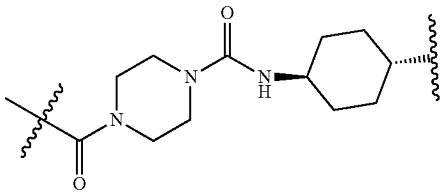,
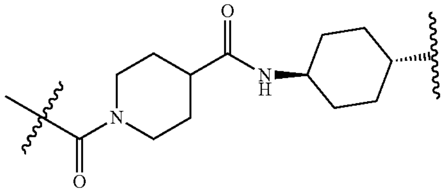,
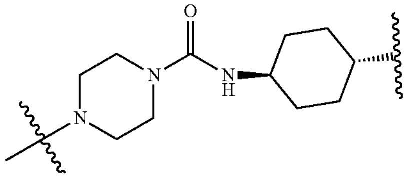,
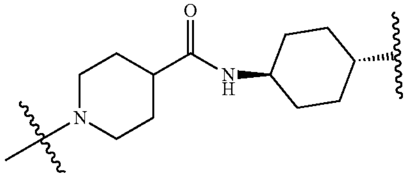,
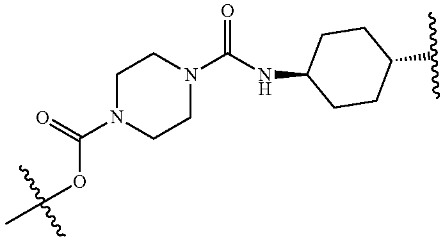,
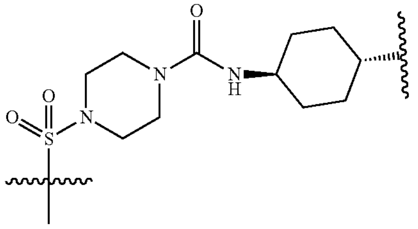,
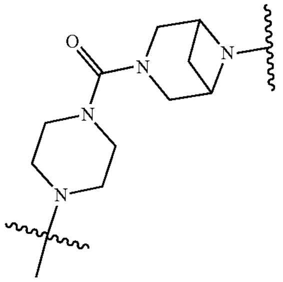,
-continued
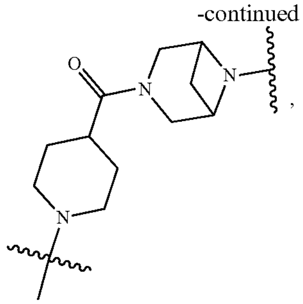,
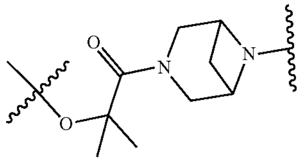,
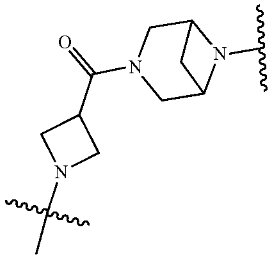,
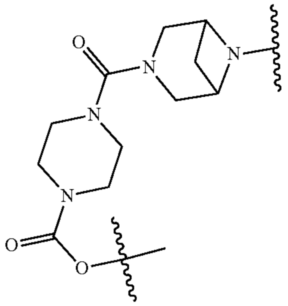,
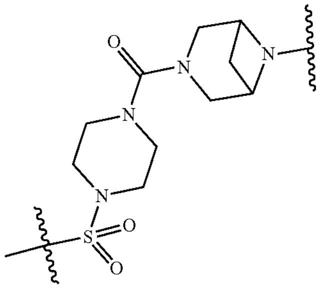,
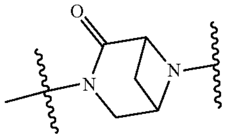,
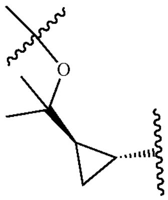,
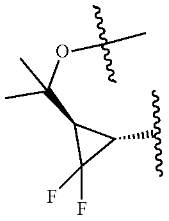,
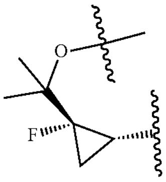, -continued
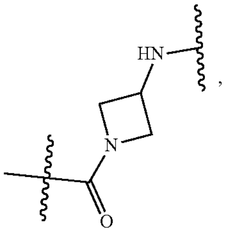,
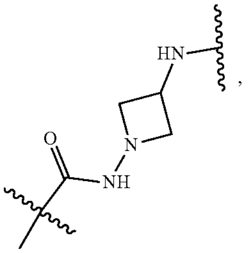,
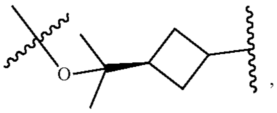,
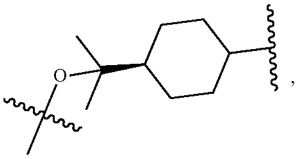,
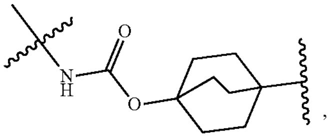,
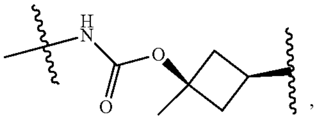,
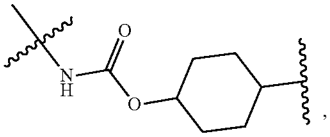,
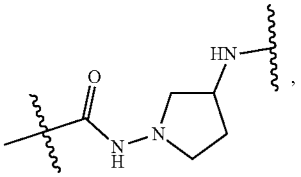,
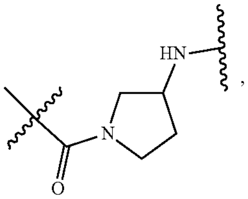,
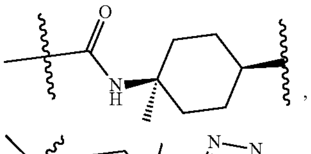,
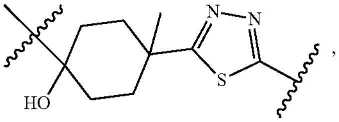,
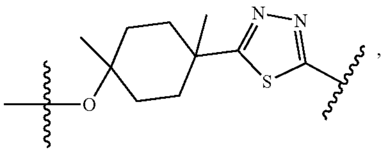,
-continued
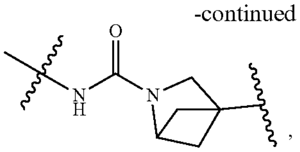,
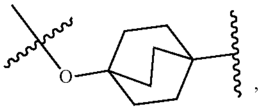,
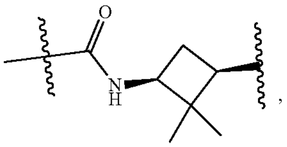,
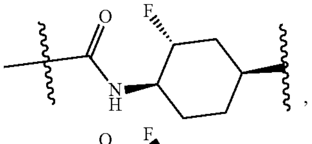,
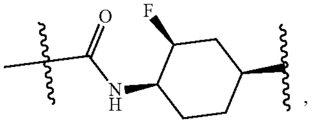,
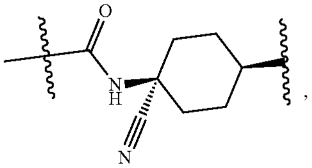,
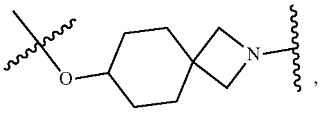,
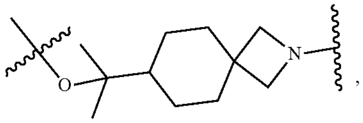,
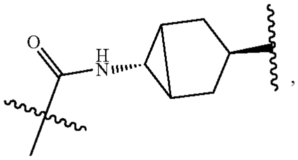,
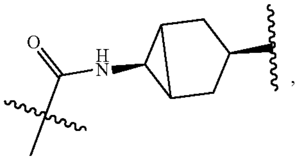,
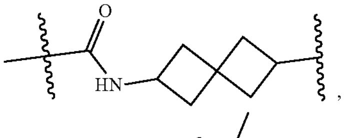, or
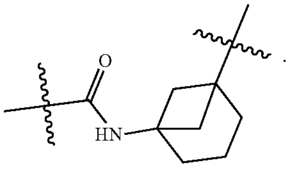.
52. The compound of claim 1, wherein $R^1$ is:
a) $C_{1-5}$ alkyl optionally substituted with halo, —OH, or —CN;

b) 4-8 membered heterocyclyl optionally substituted with halo, $C_{1-5}$ alkyl, —OH, or —CN;
c) $C_{3-10}$ cycloalkyl optionally substituted with halo, $C_{1-5}$ alkyl, —OH, or —CN.
53. The compound of claim 52 wherein $R^1$ is oxetane, tetrahydrofuran or tetrahydropyran optionally substituted with F, $C_{1-3}$ alkyl, —OH, or —CN.
54. The compound of claim 52, wherein
the
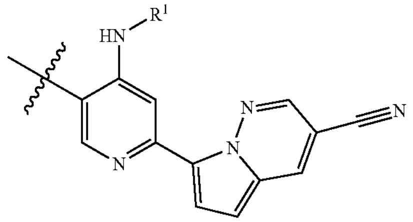
moiety is:
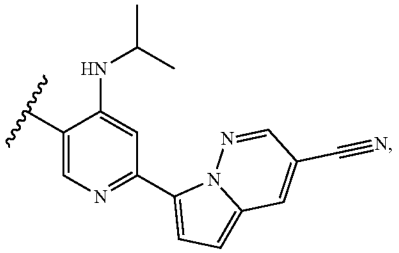
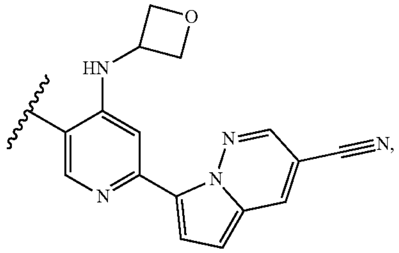
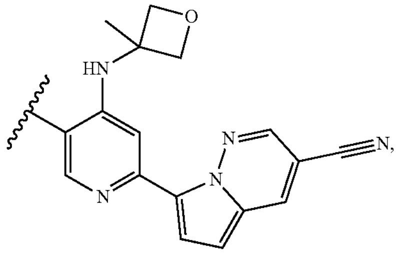
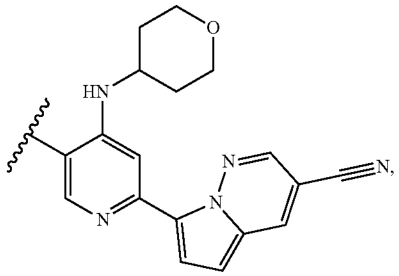
-continued
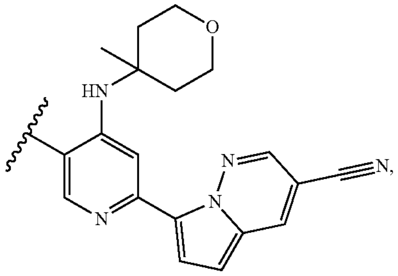
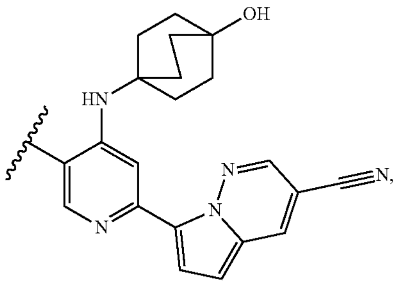
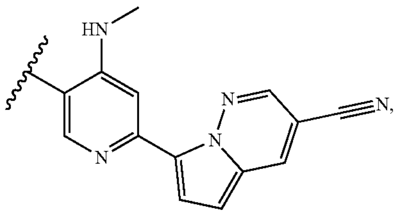
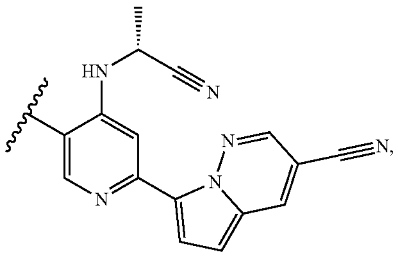
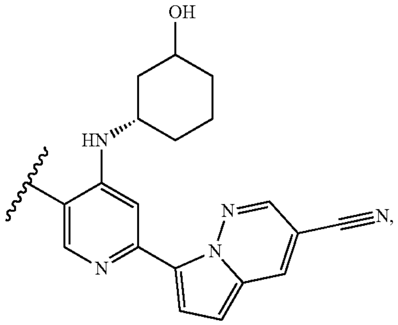

-continued
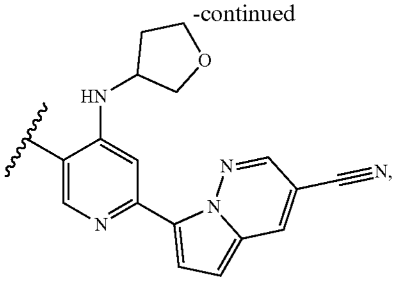
or
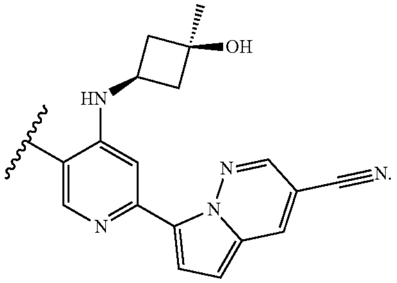
55. The compound of claim 52, wherein the
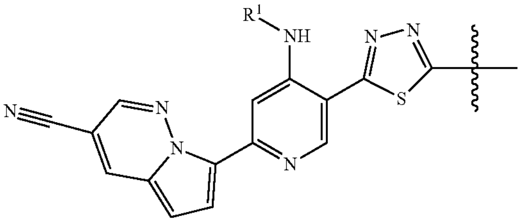
moiety has one of the following structures:
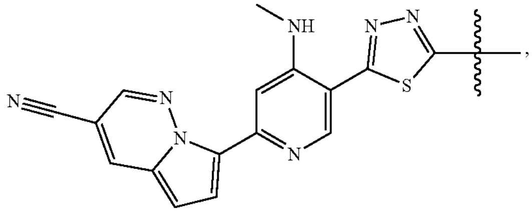
,
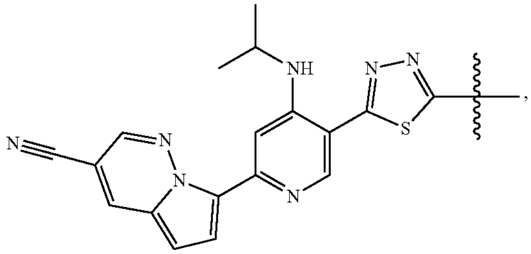
, or
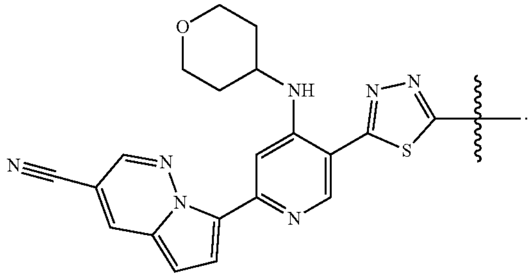
.
56. A compound which is:
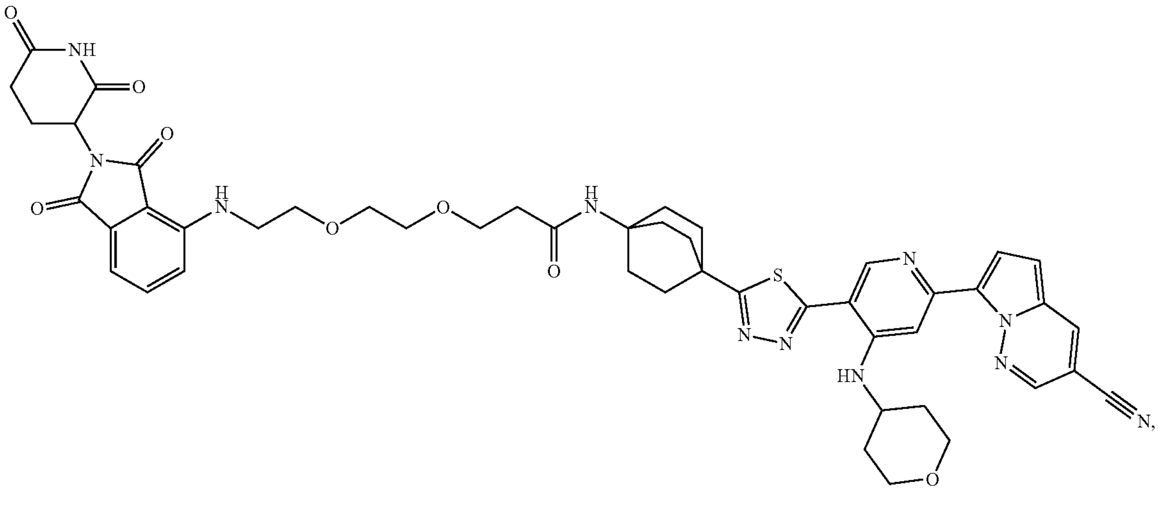

-continued
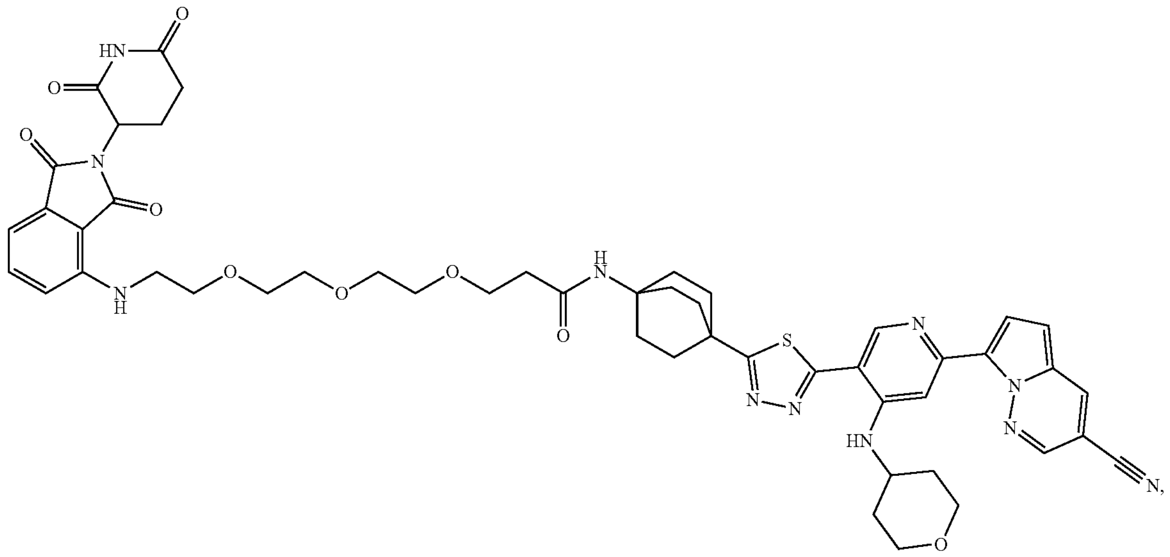
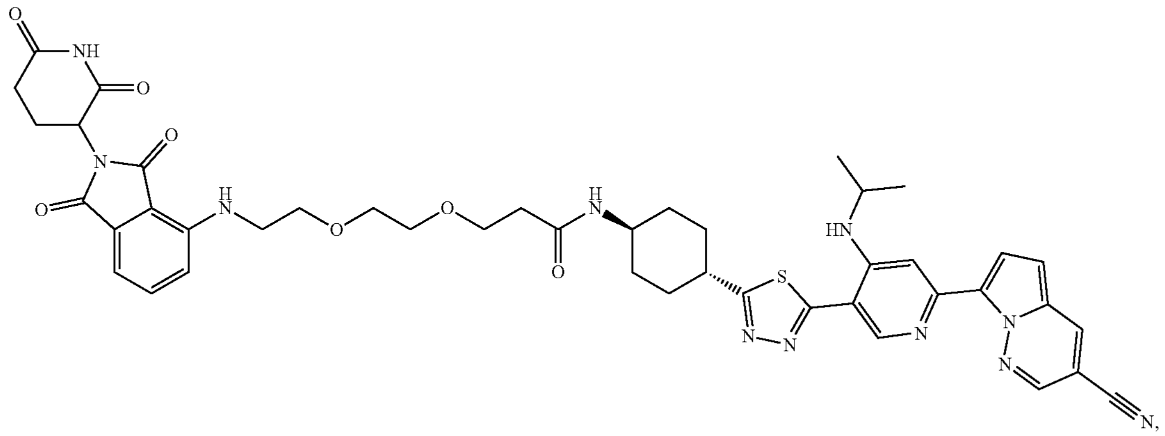
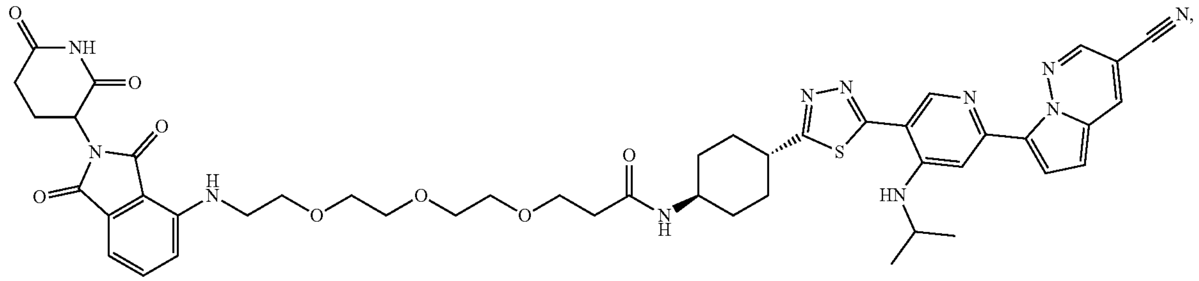
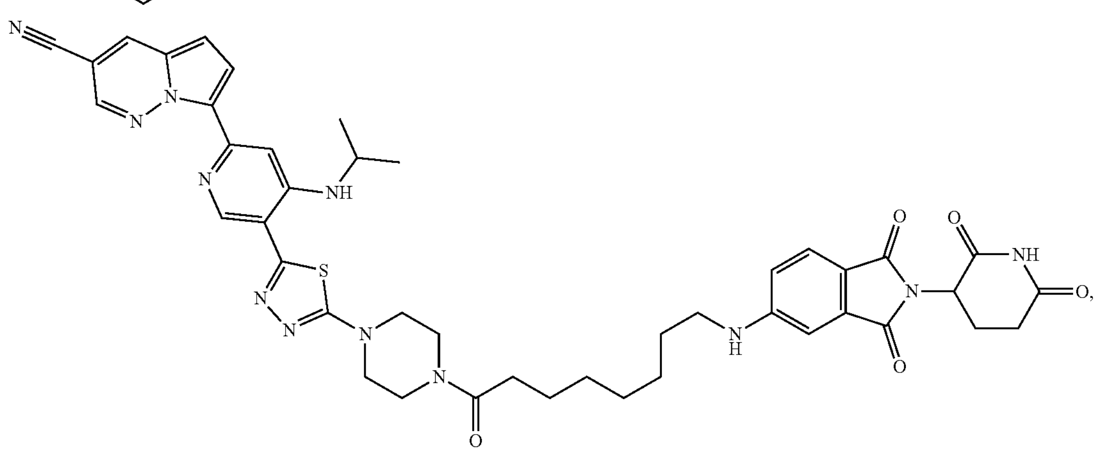

-continued
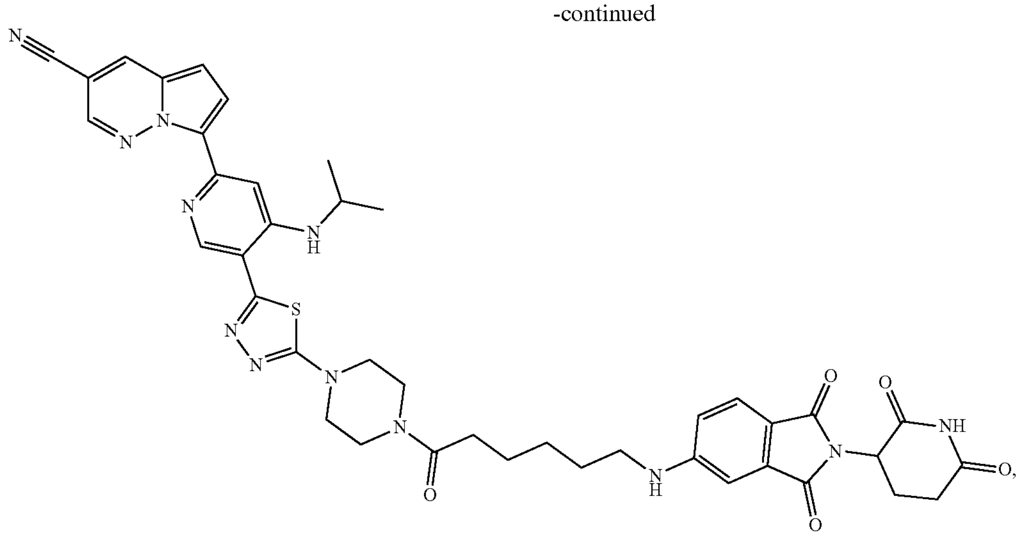
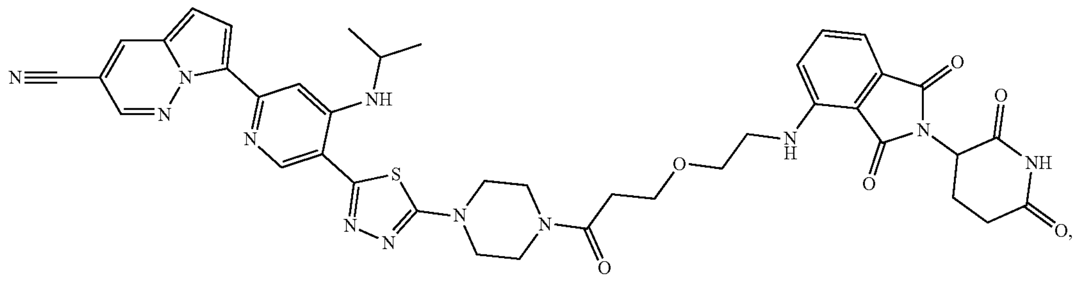
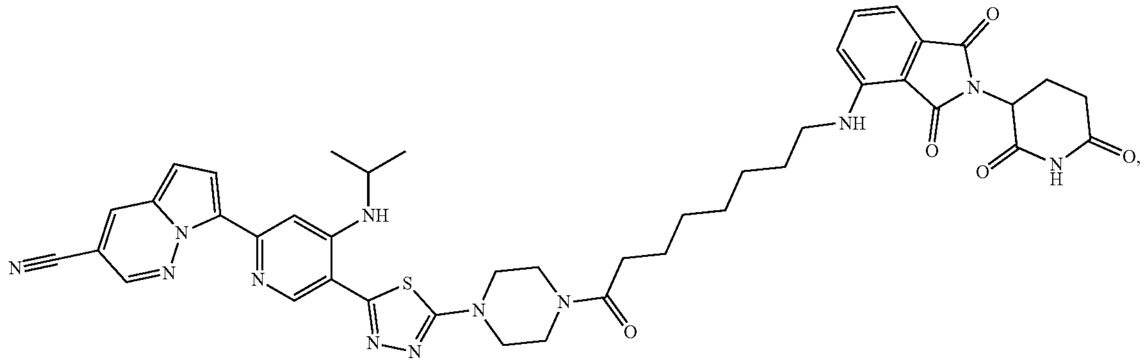
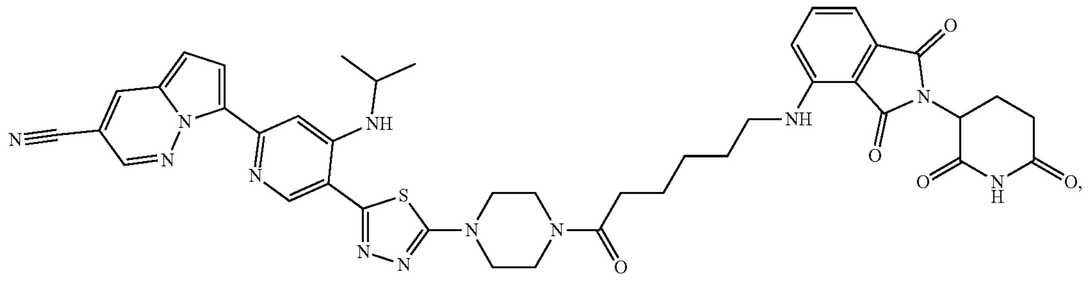

-continued
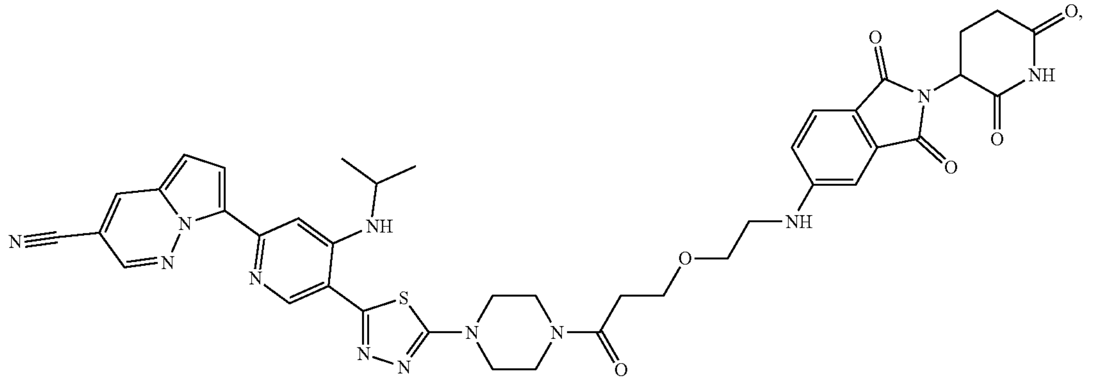
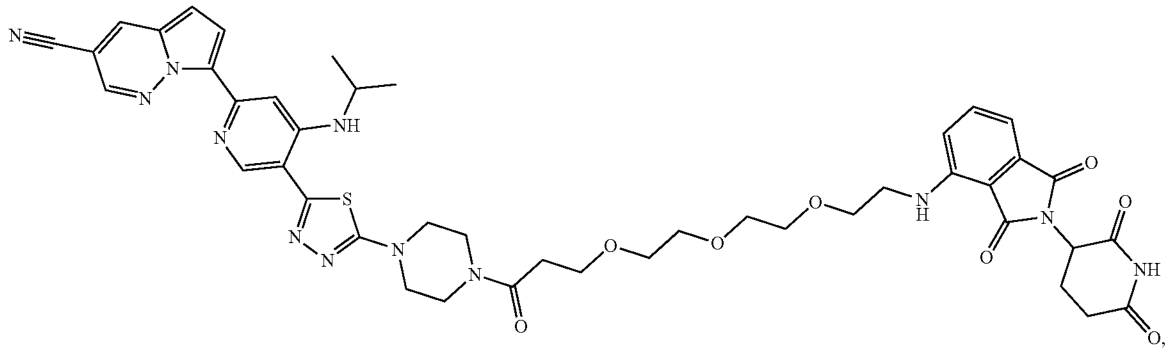
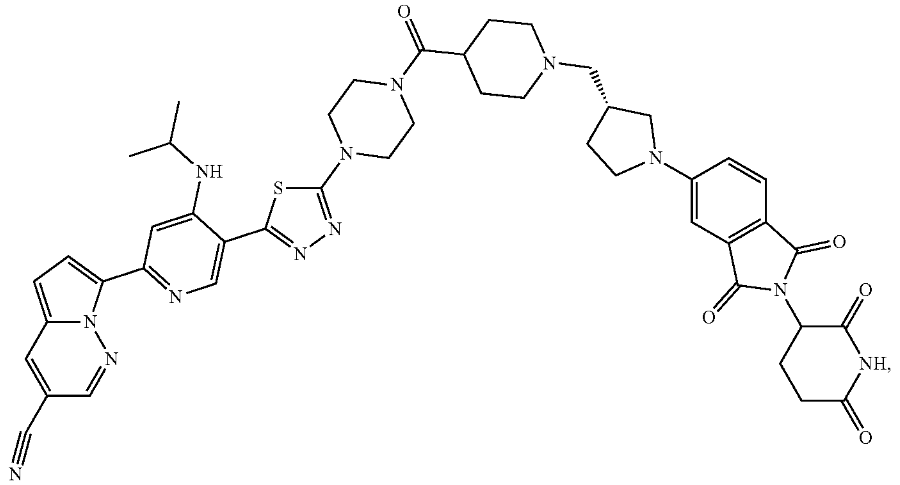
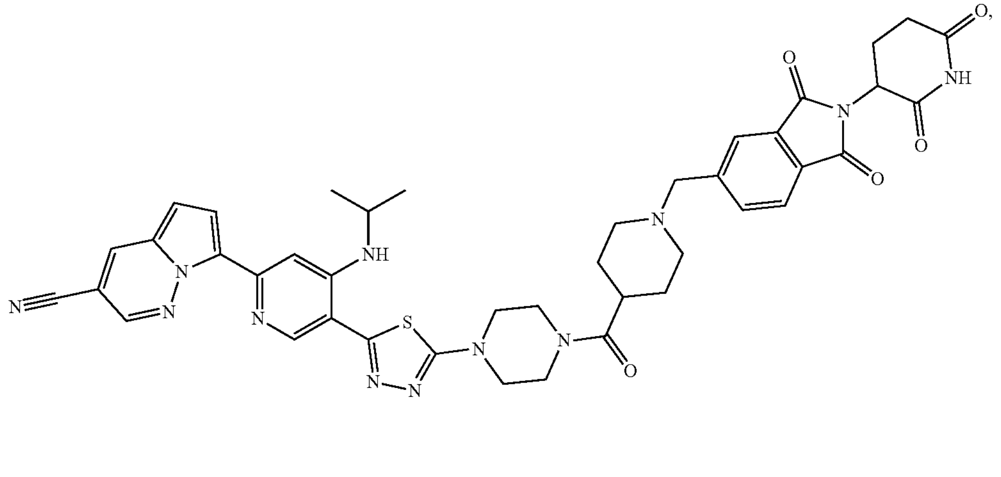

-continued
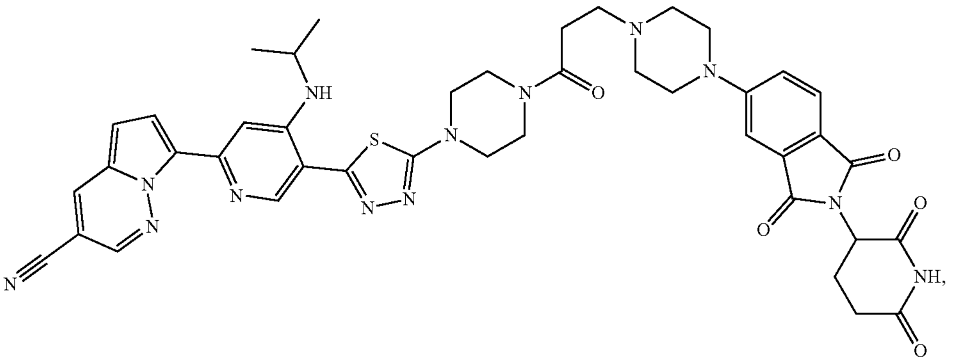
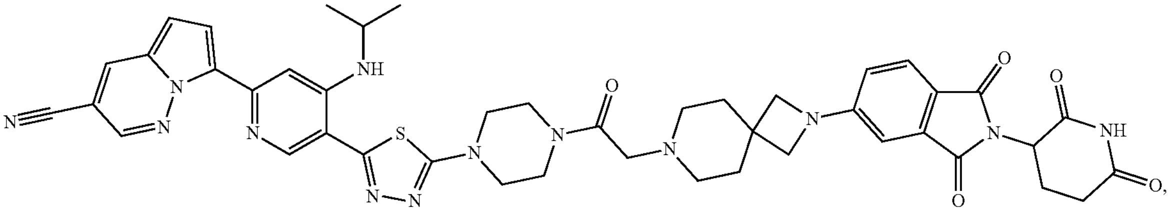
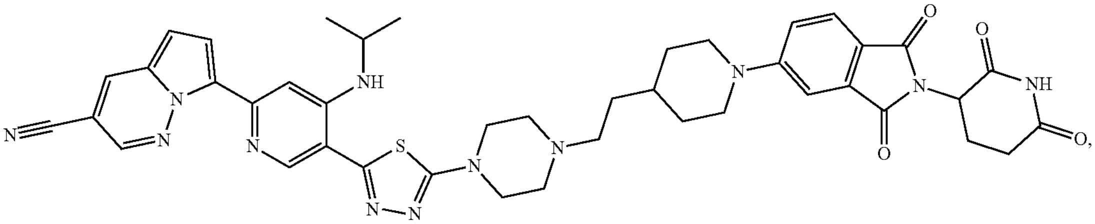
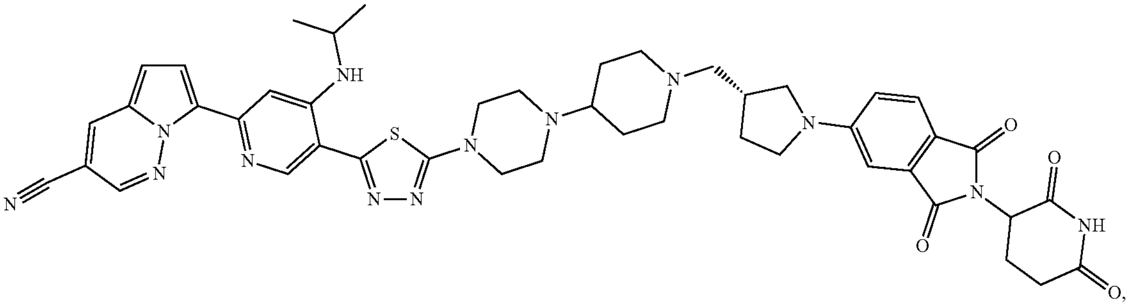
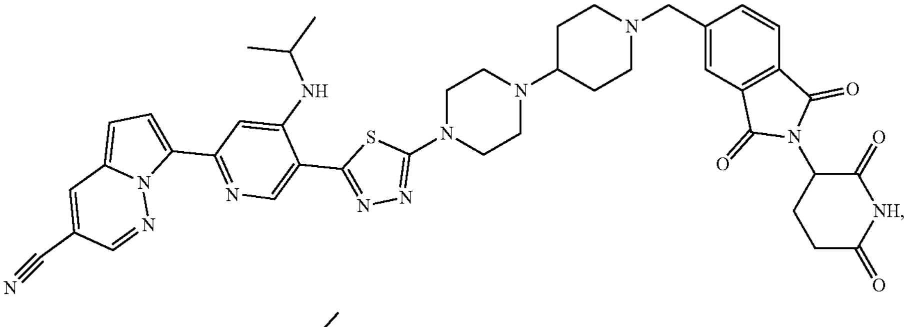
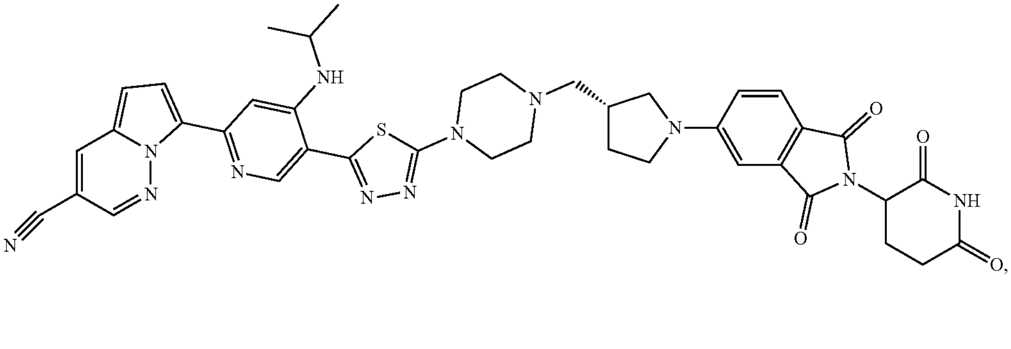

-continued
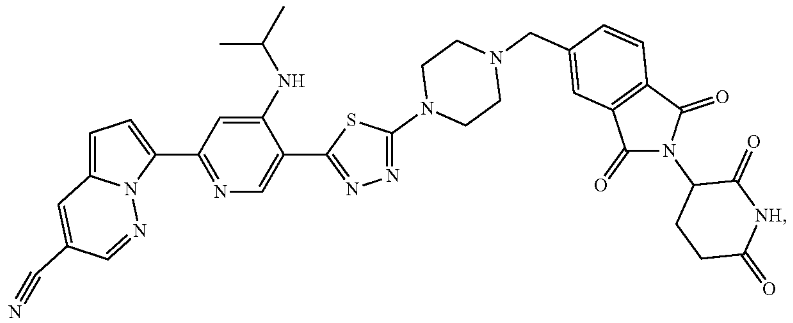
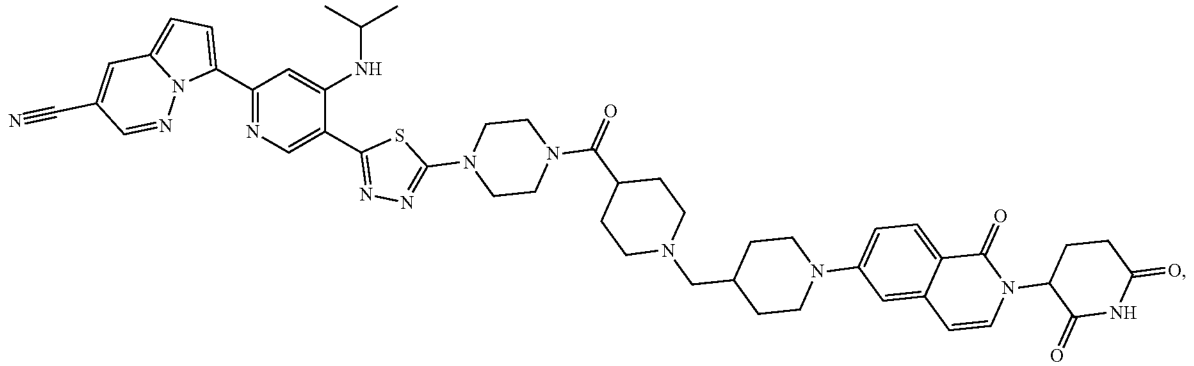
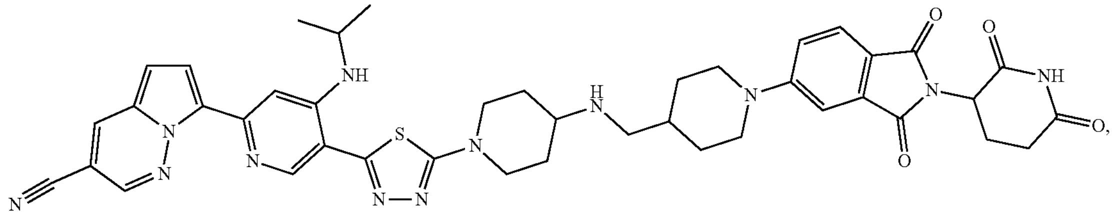
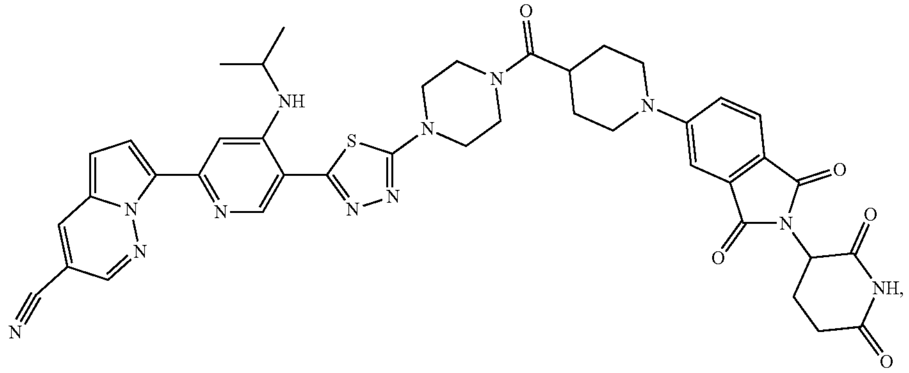
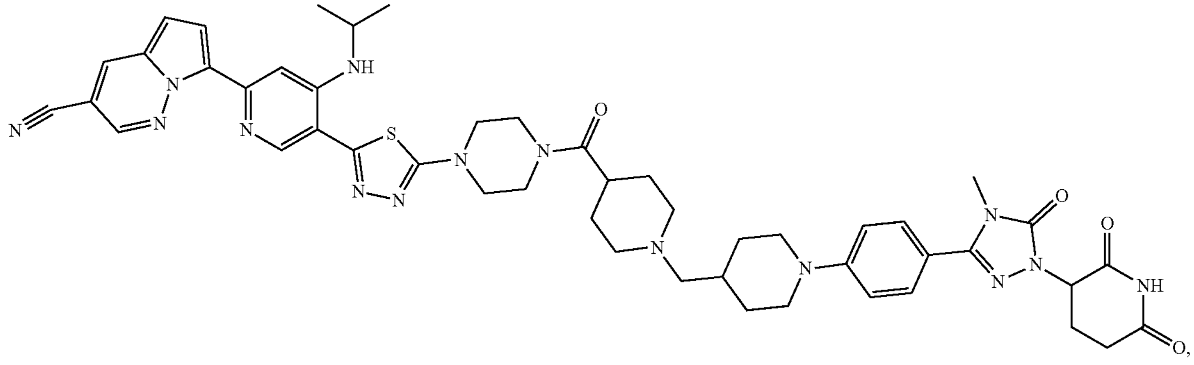

-continued
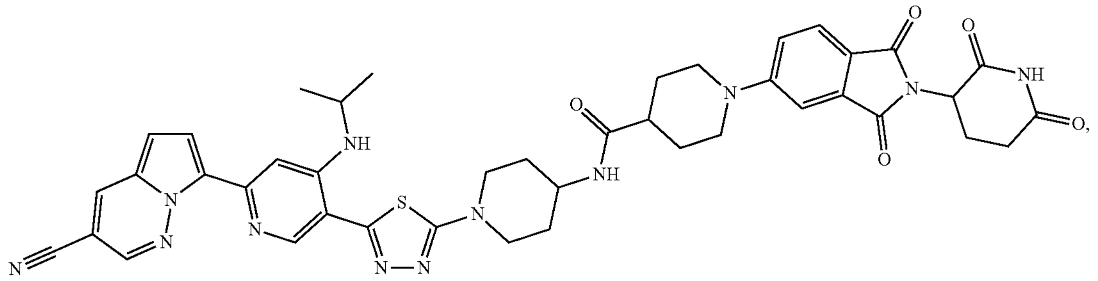
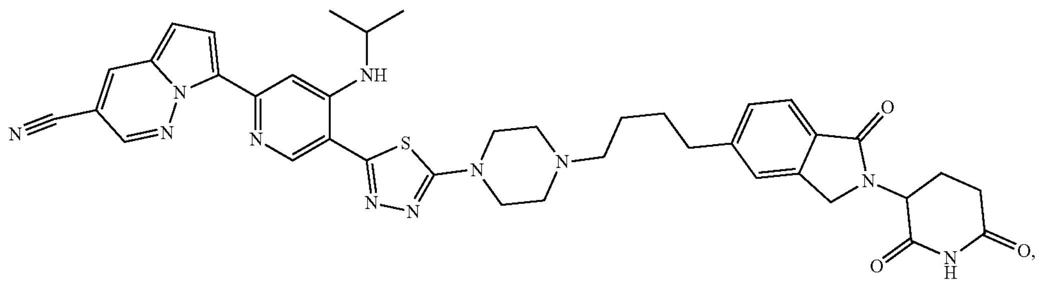
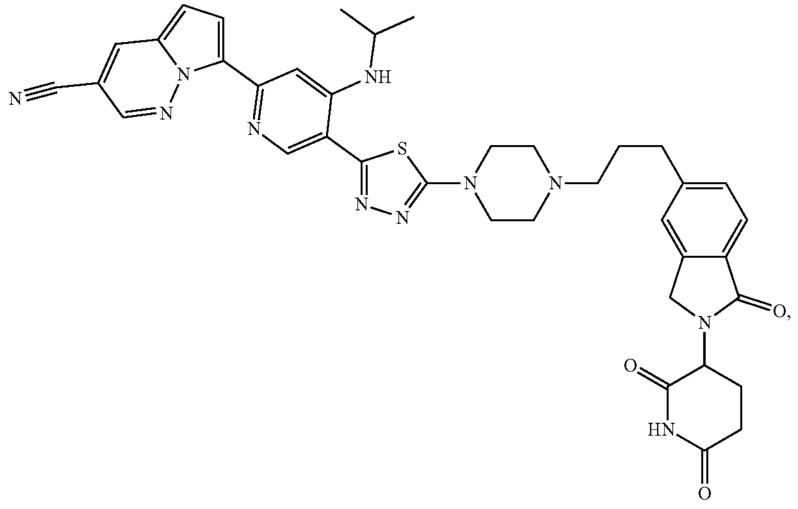
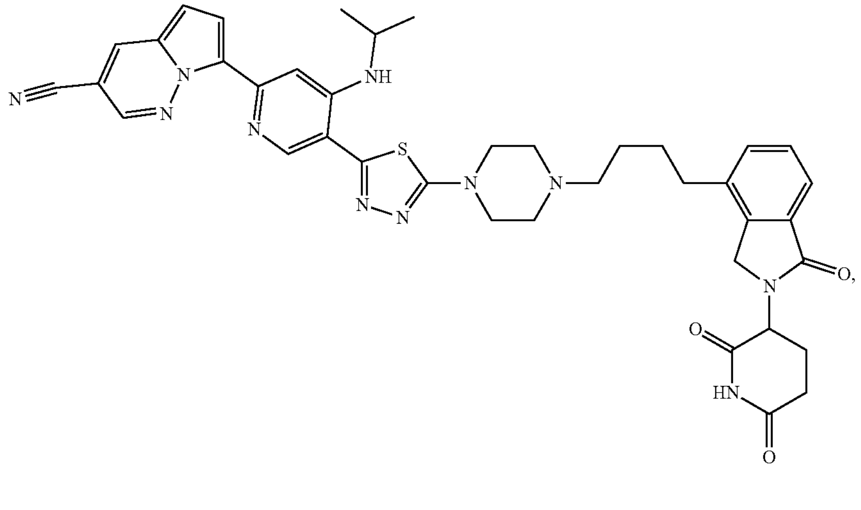

-continued
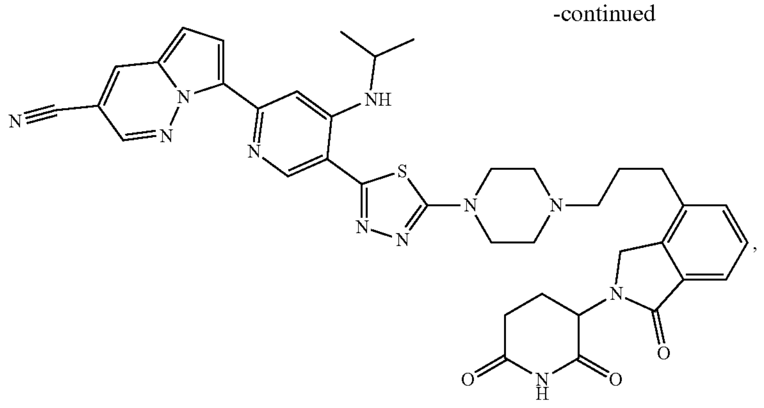
,
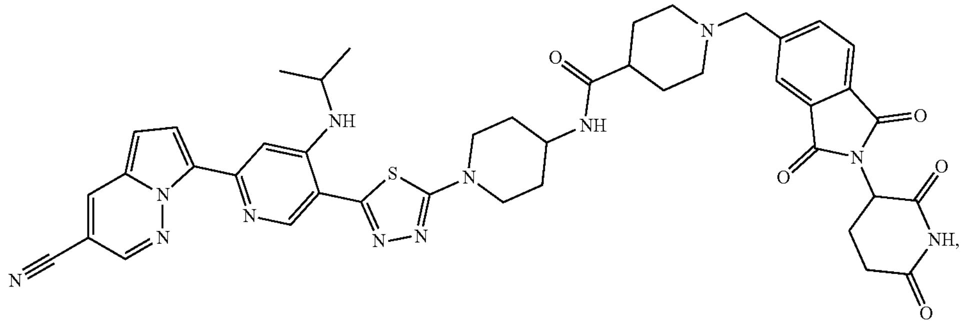
,
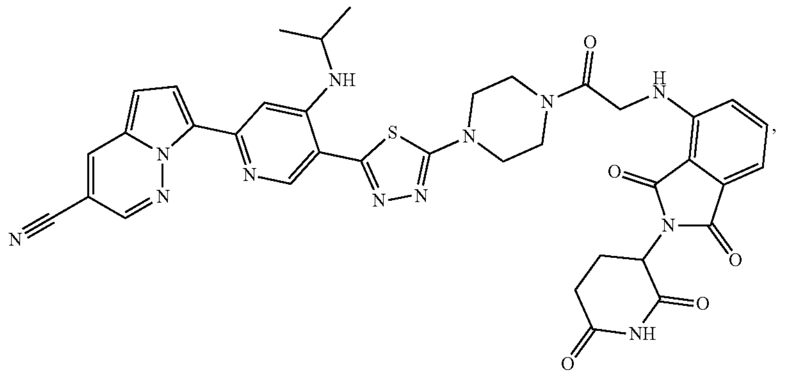
,
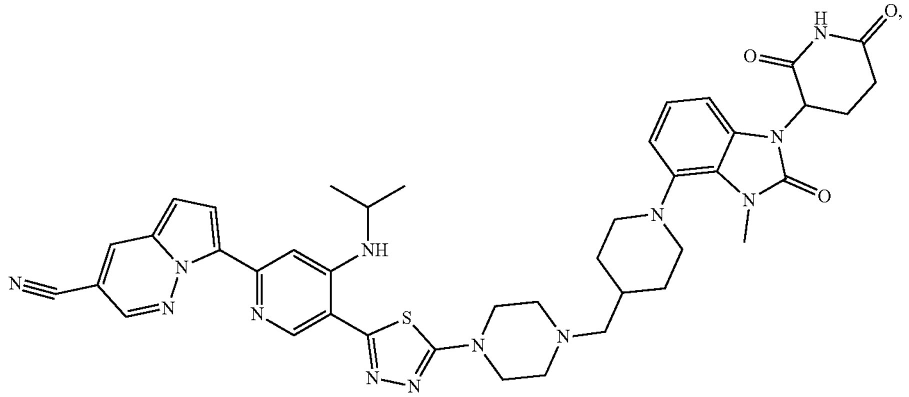
,

-continued
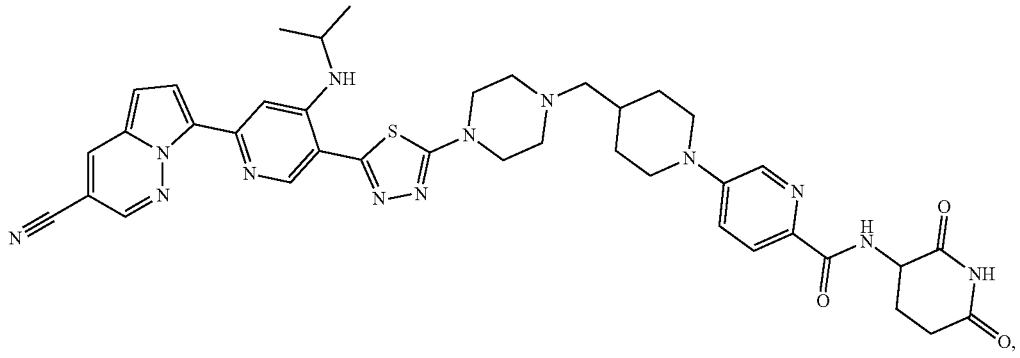
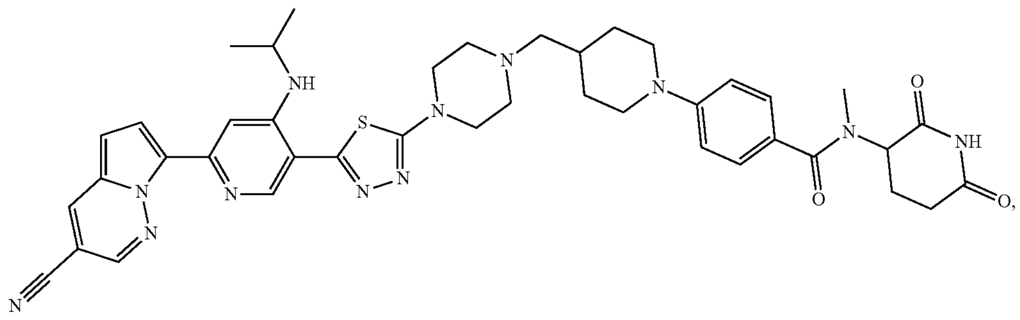
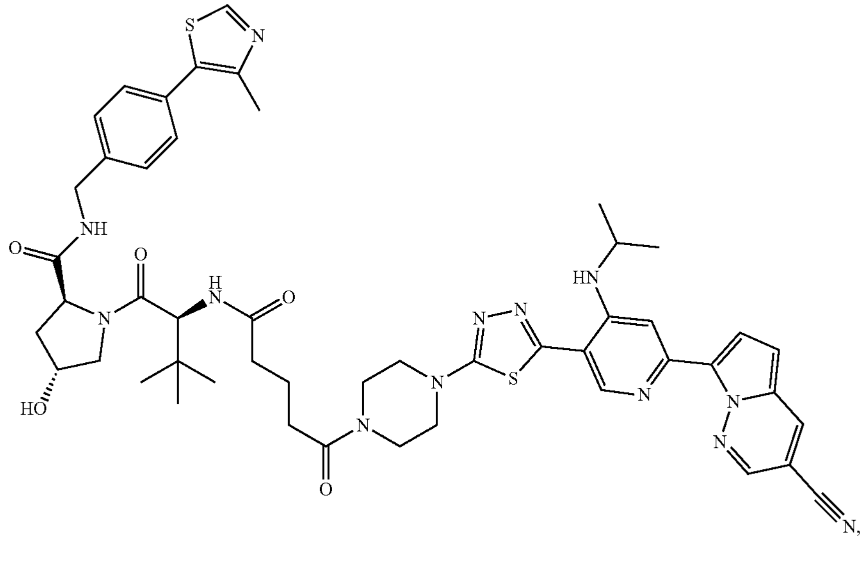

-continued
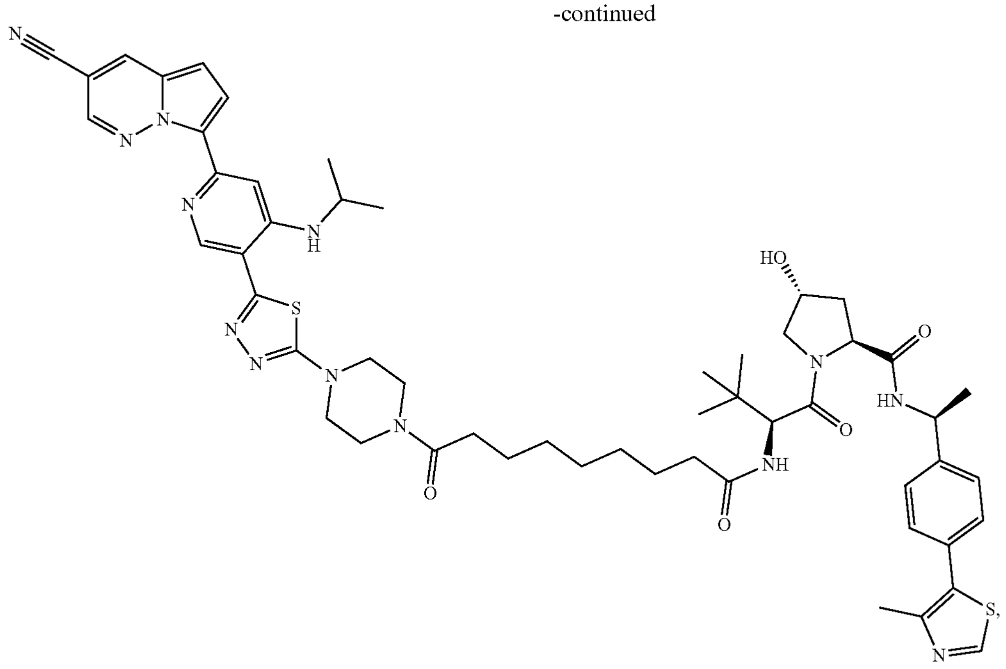
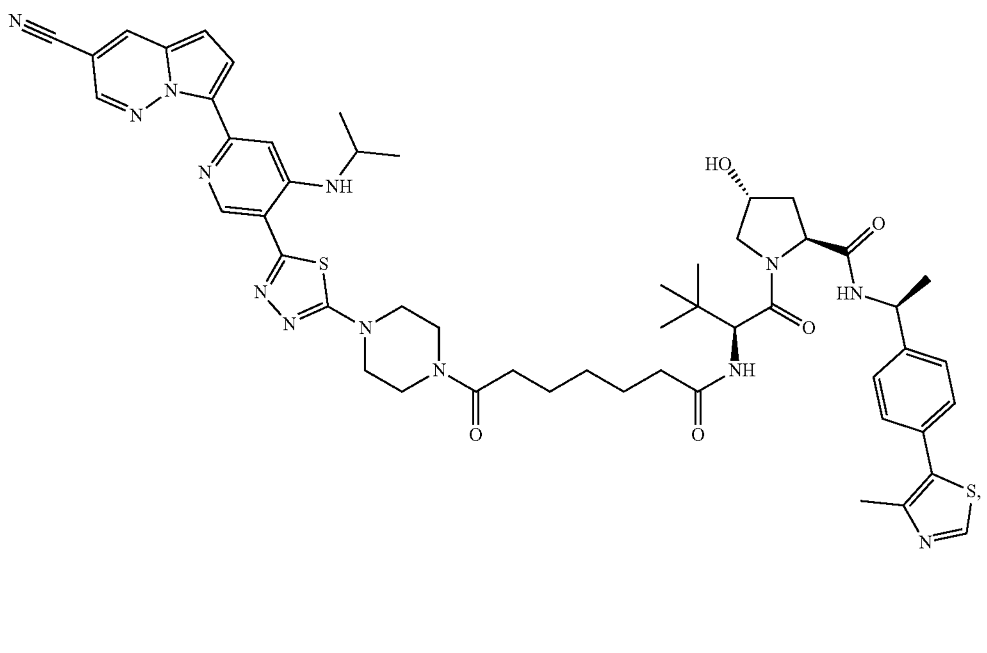

-continued
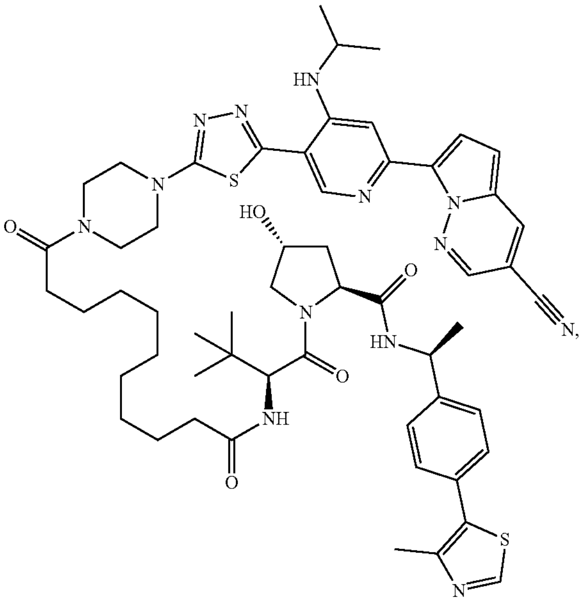
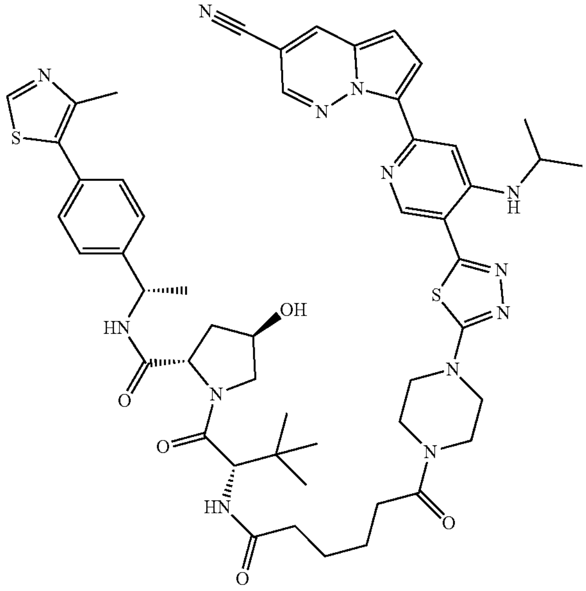
,
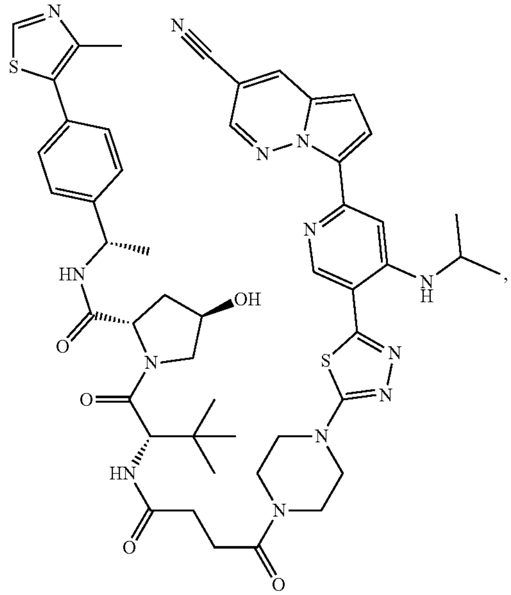
,
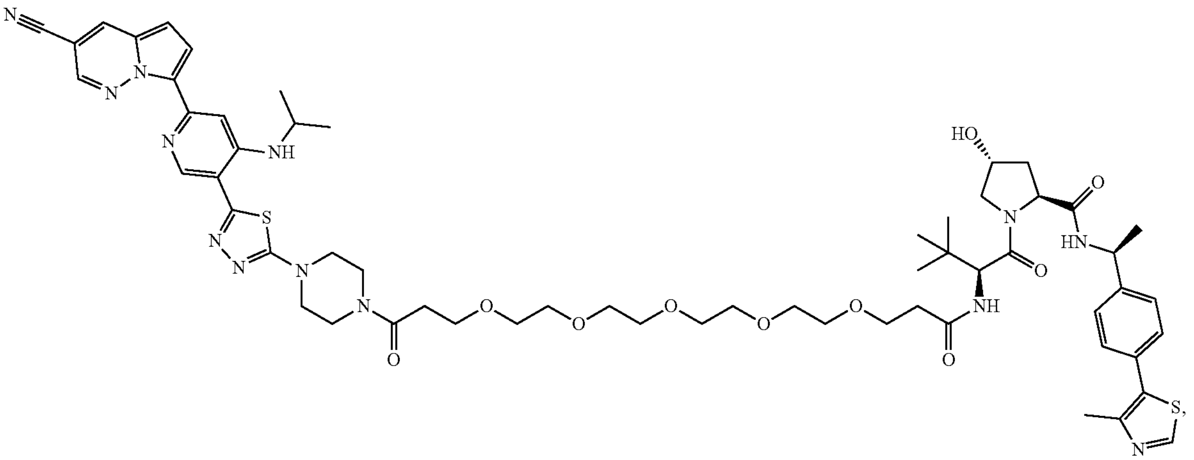

-continued
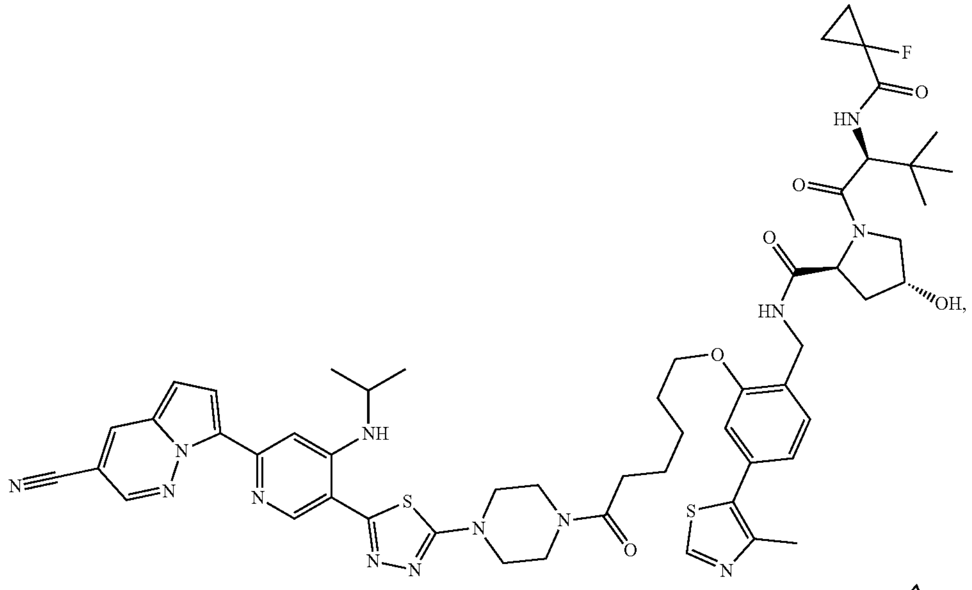
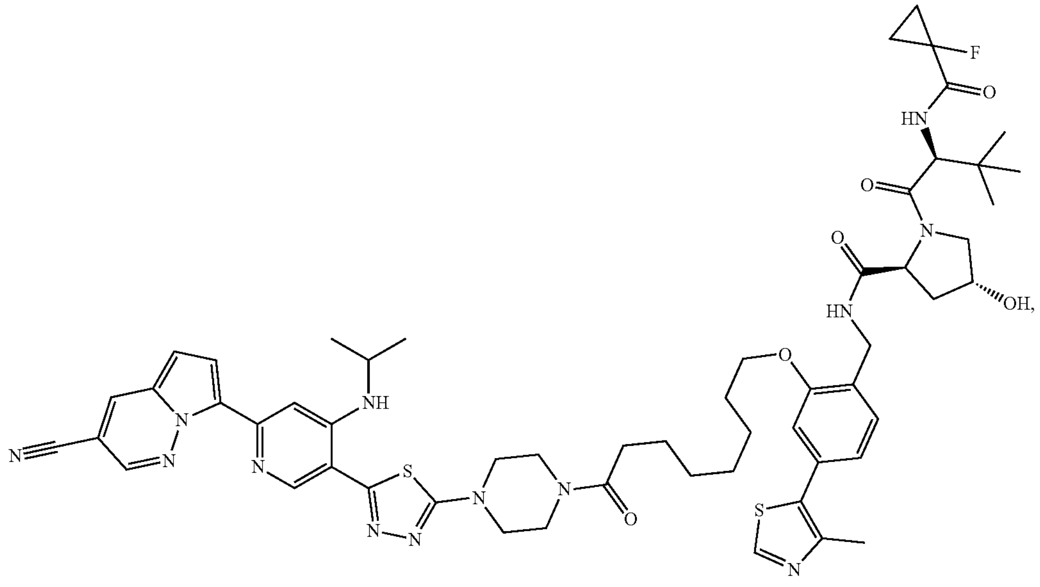
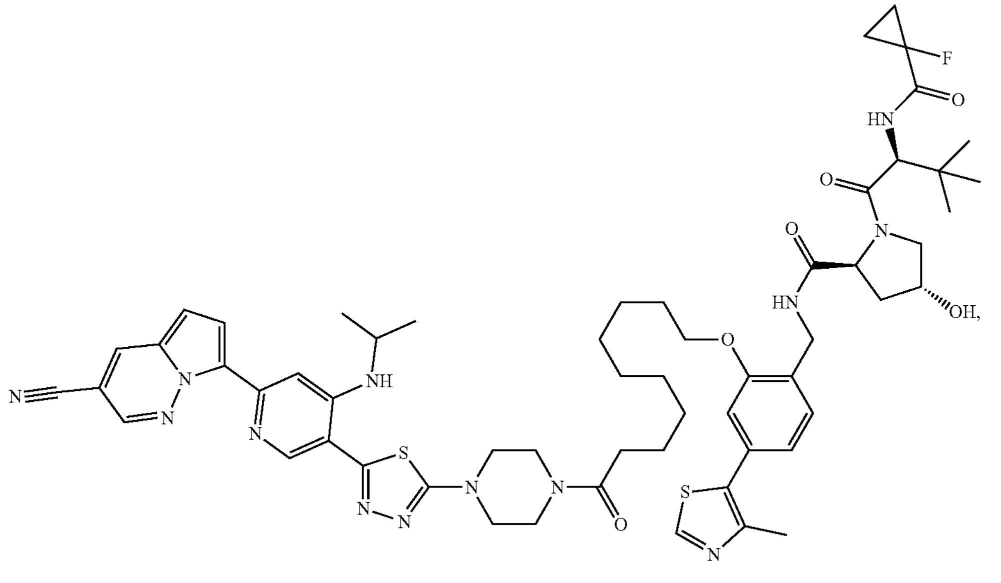

-continued
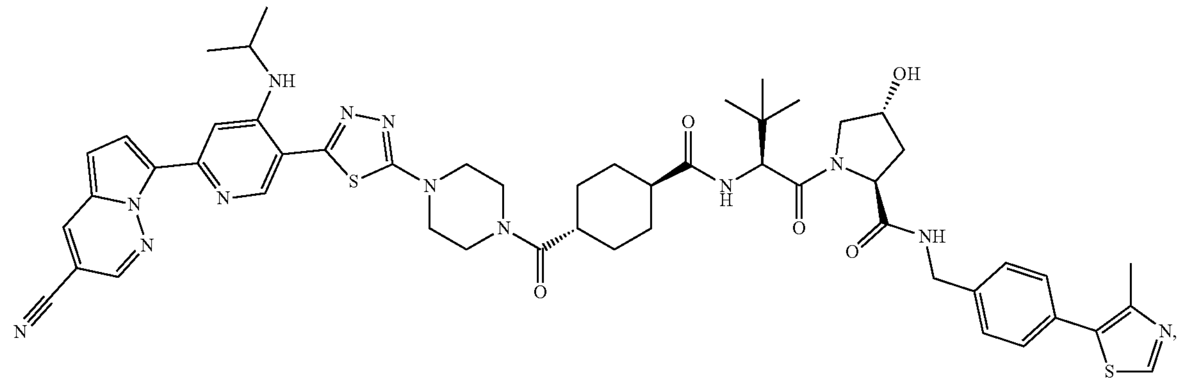
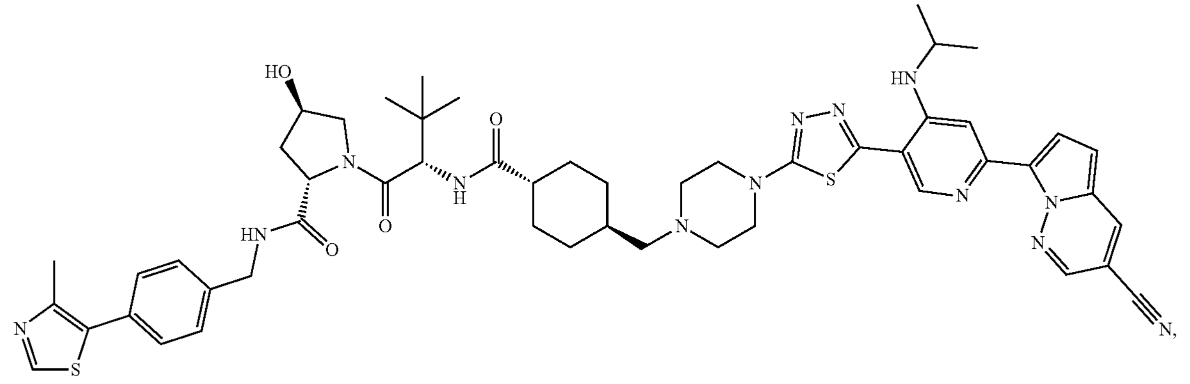
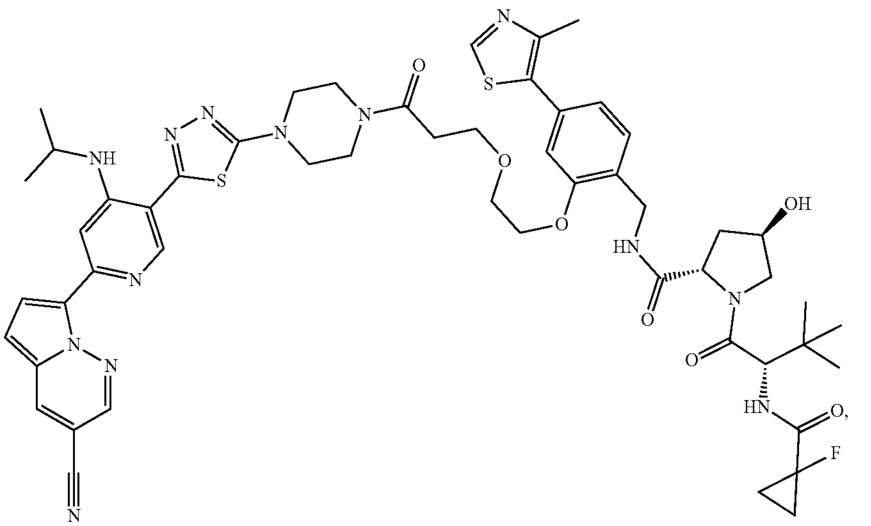

-continued
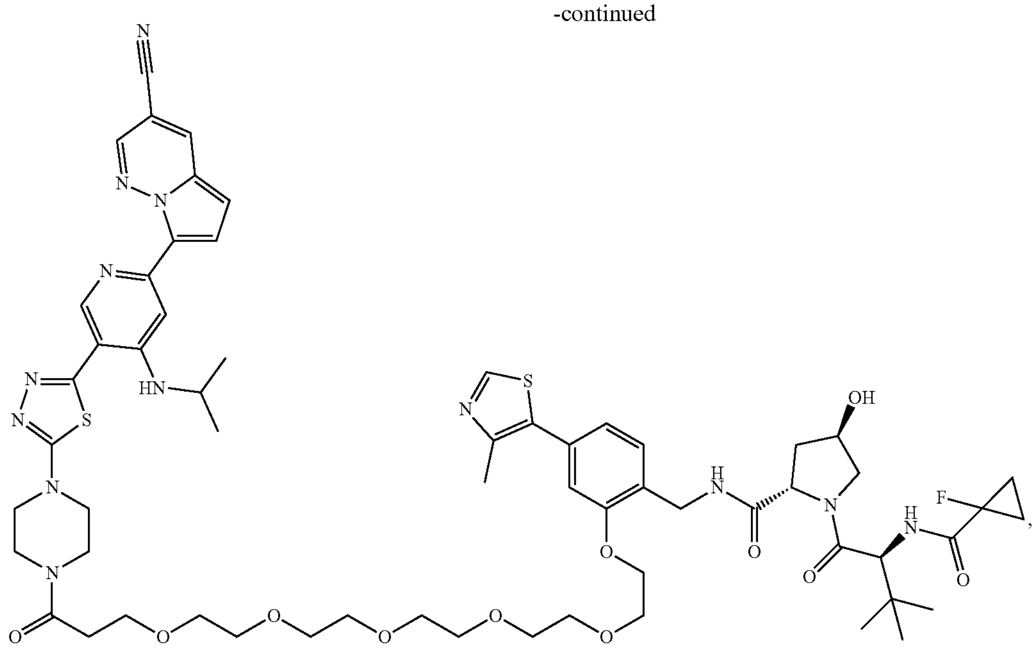
,
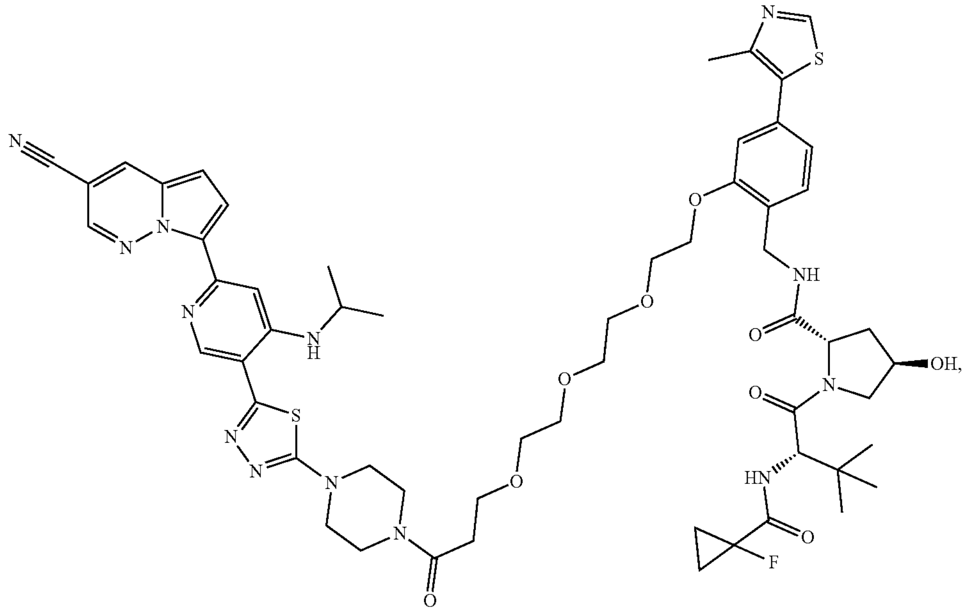
,
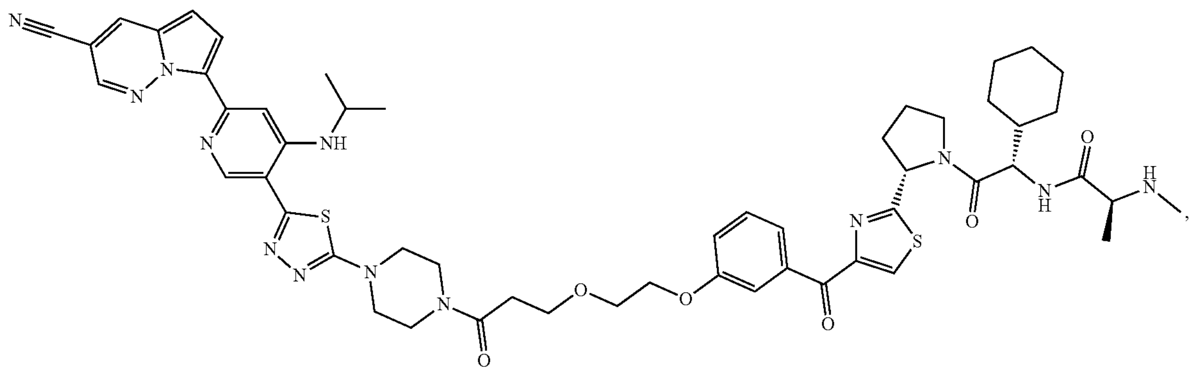
,

-continued
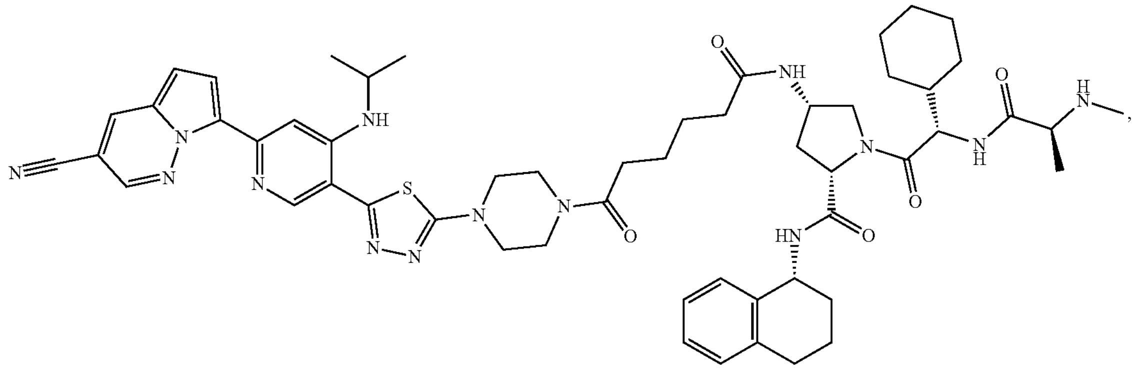
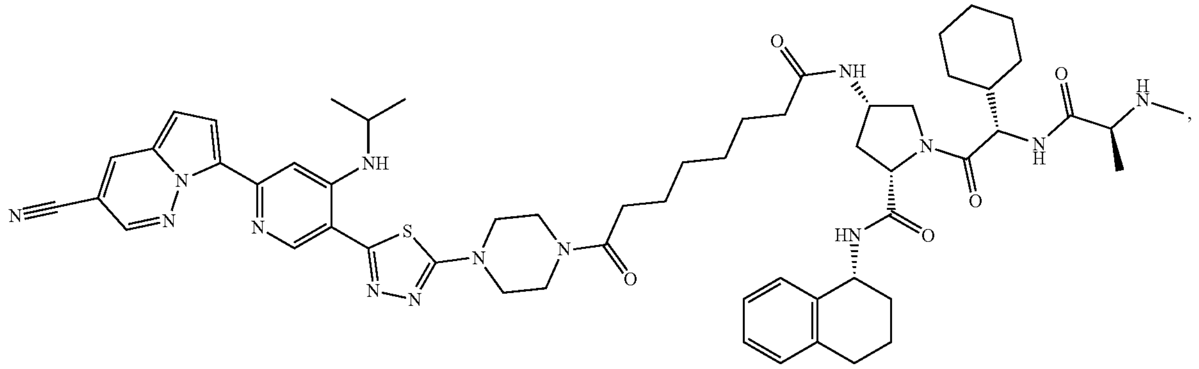
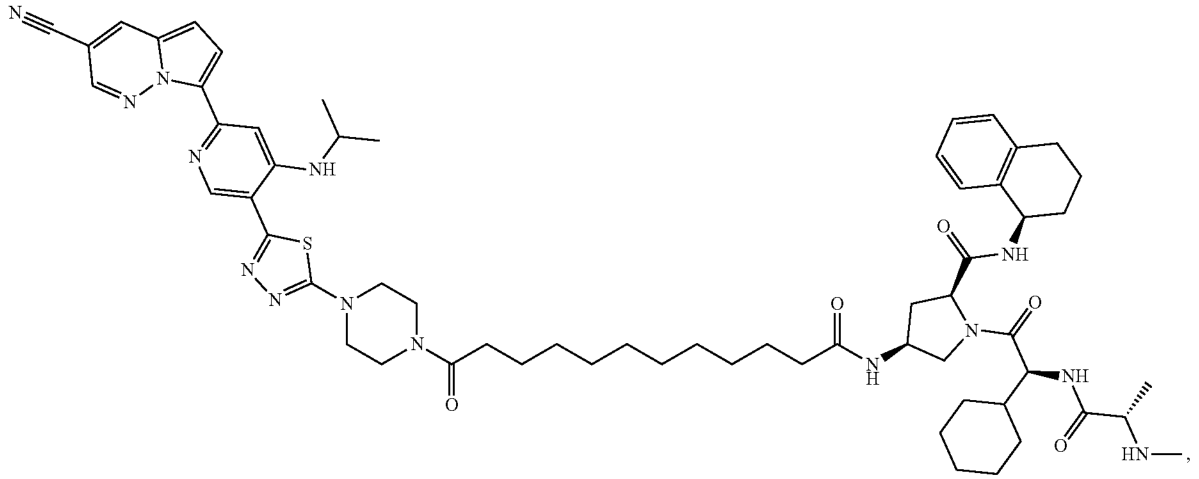
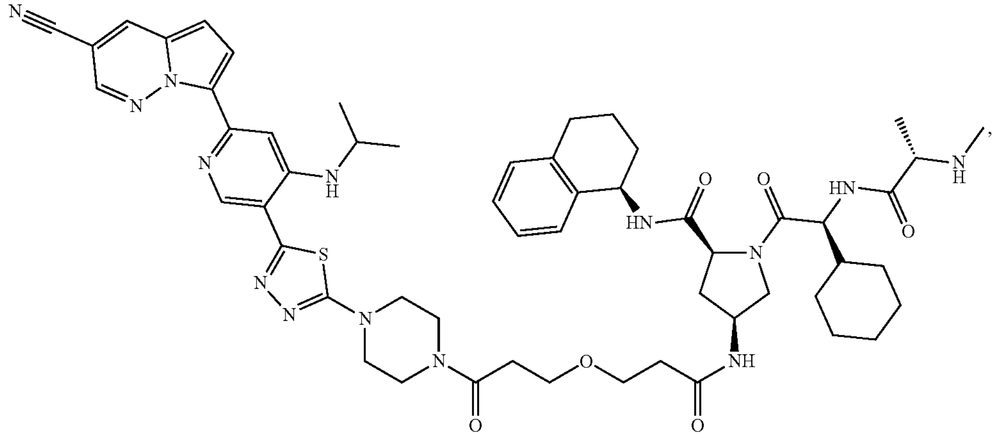

-continued
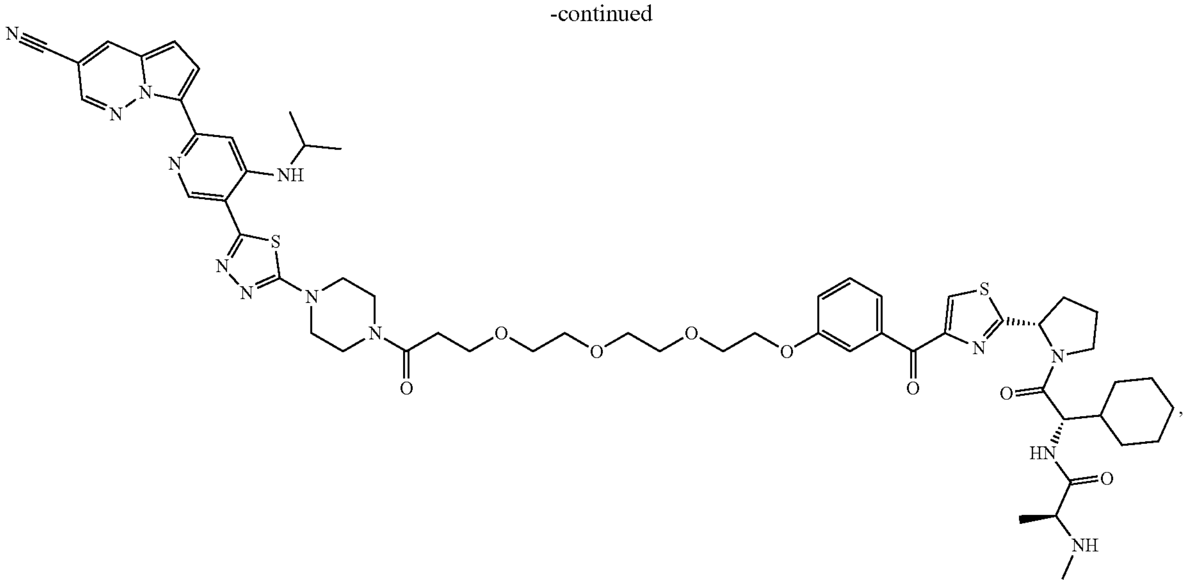
,
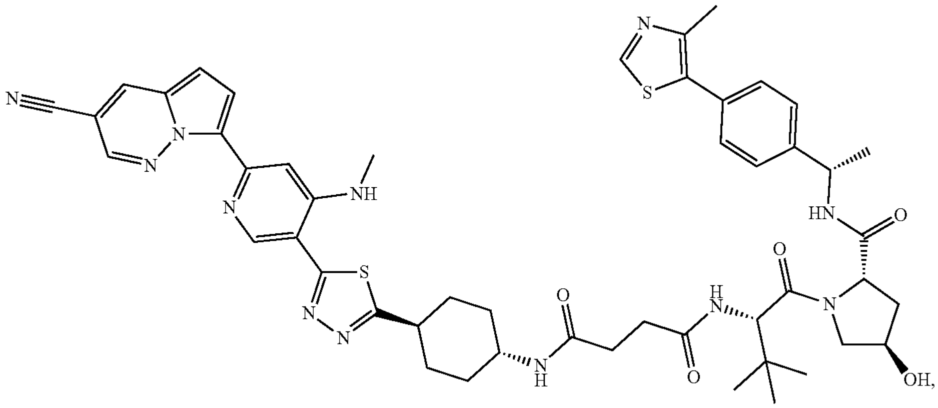
,
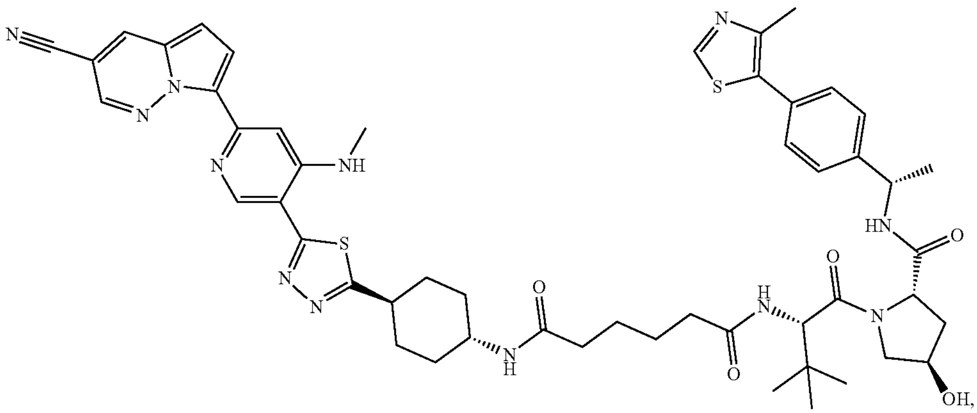
,

-continued
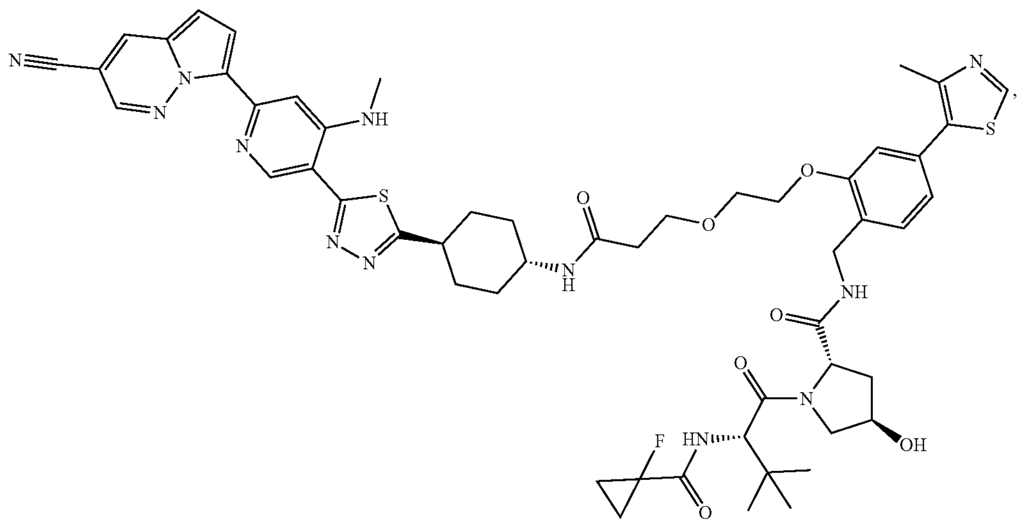
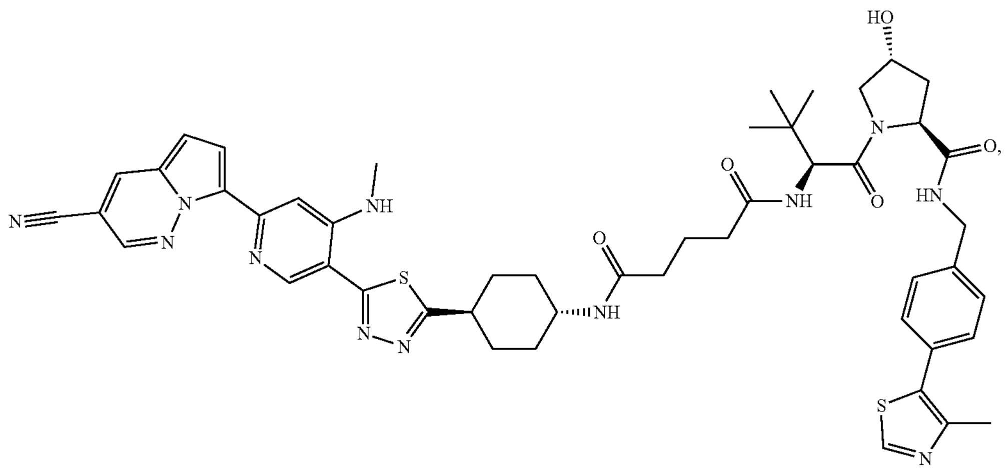
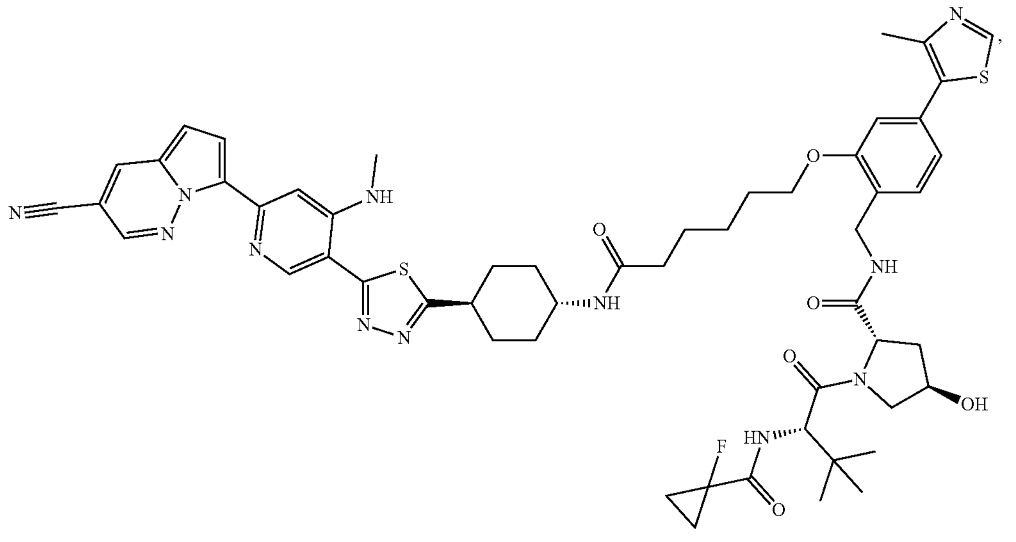

-continued
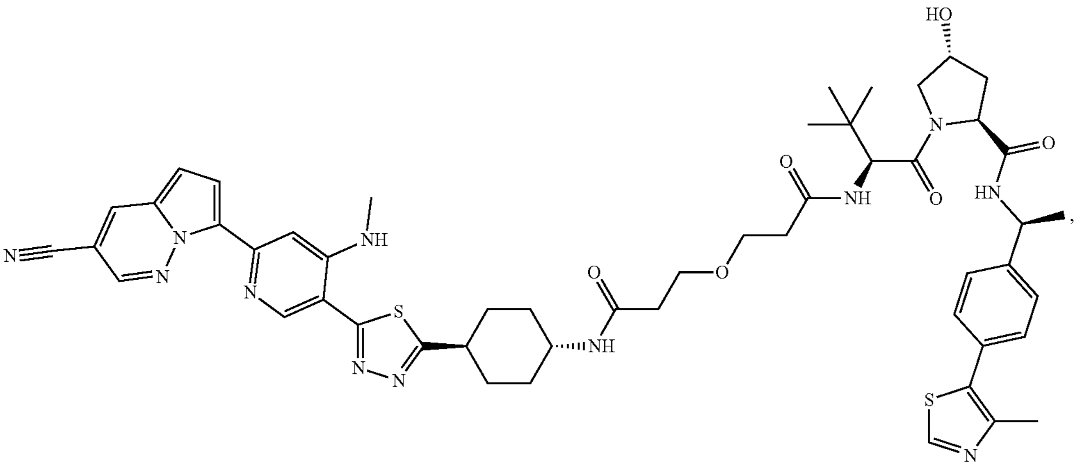
,
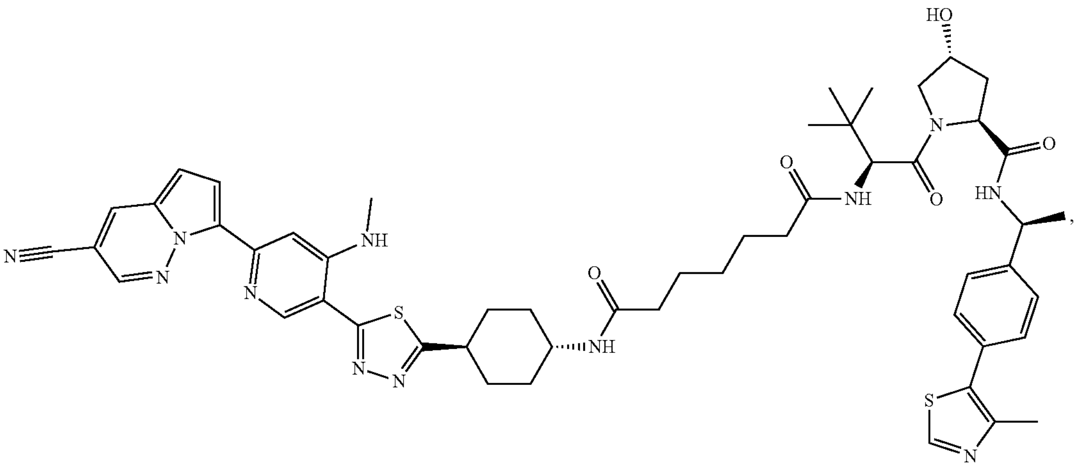
,
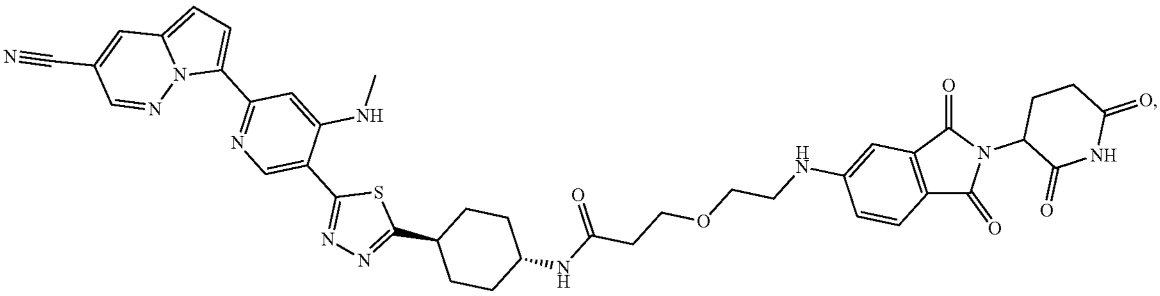
,
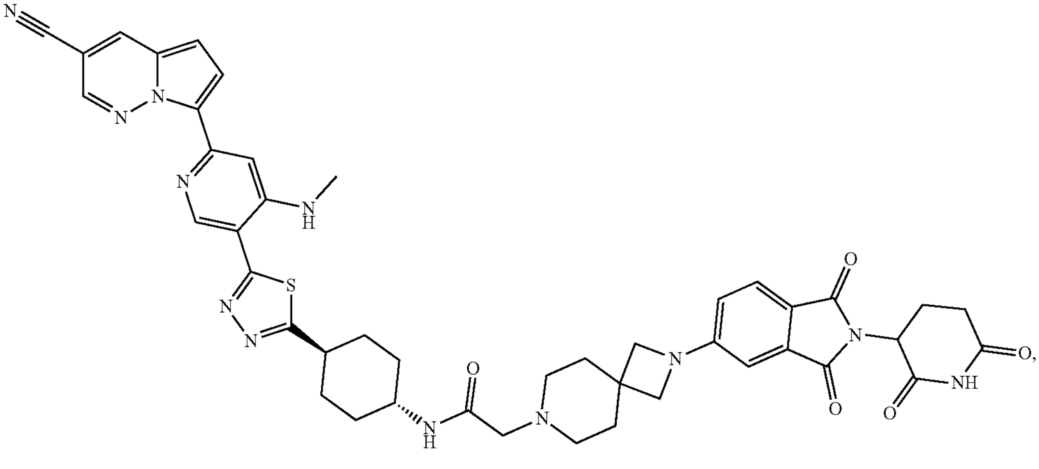
,

-continued
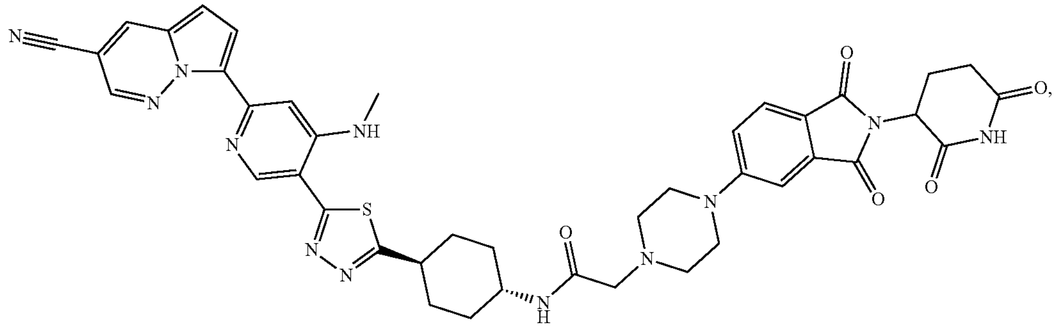
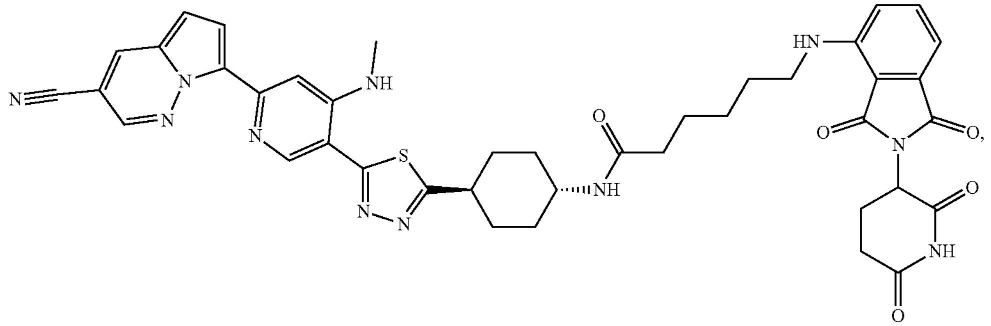
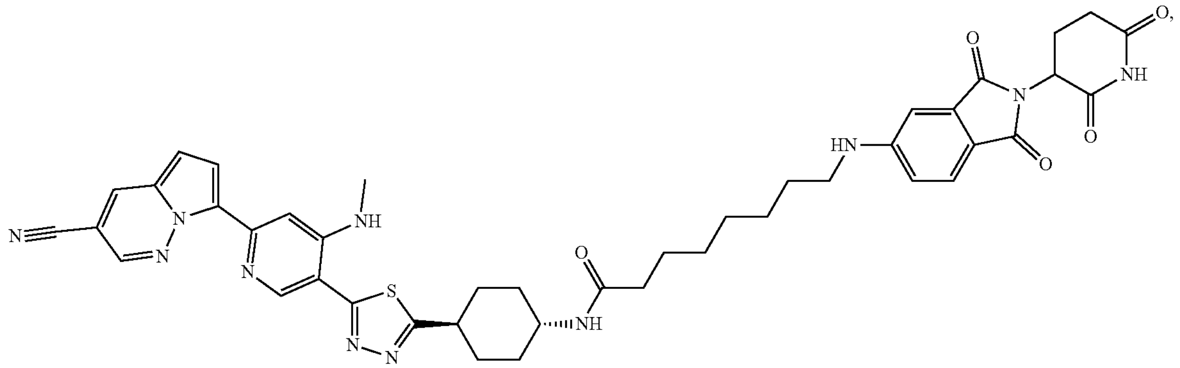
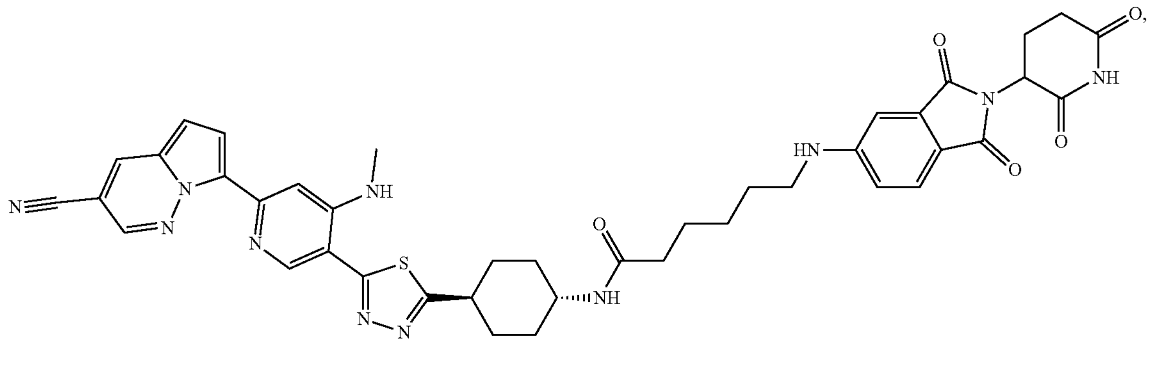

-continued
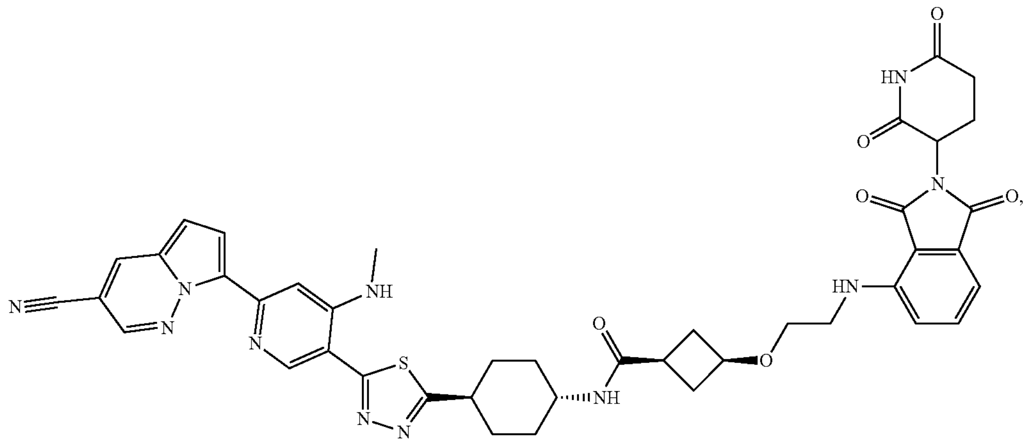
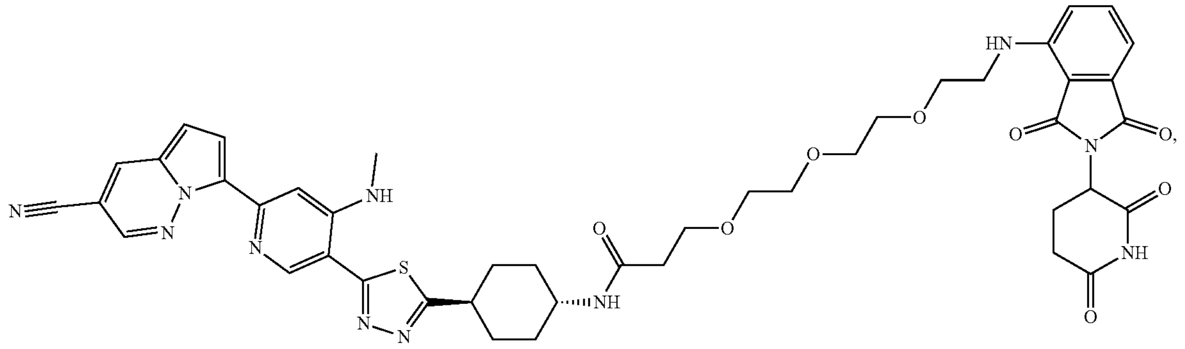
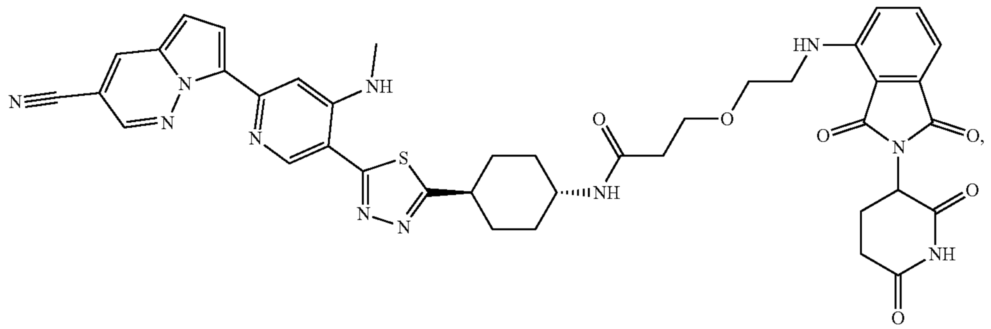
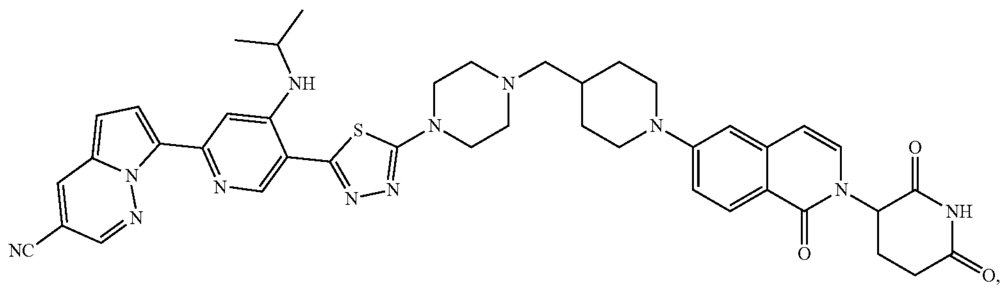

-continued
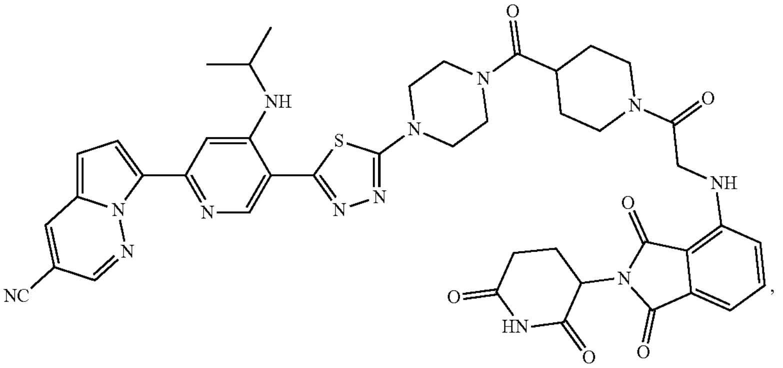
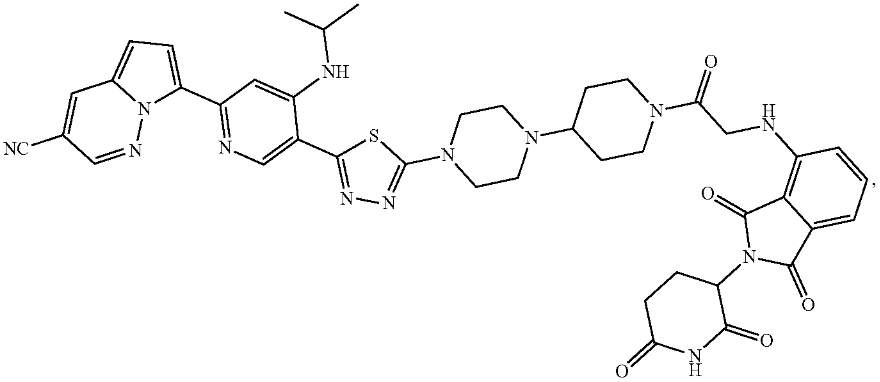
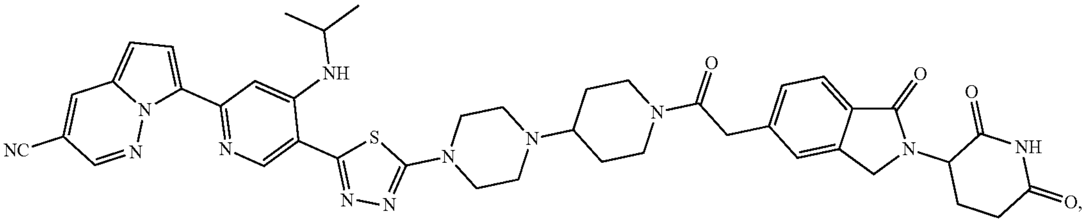
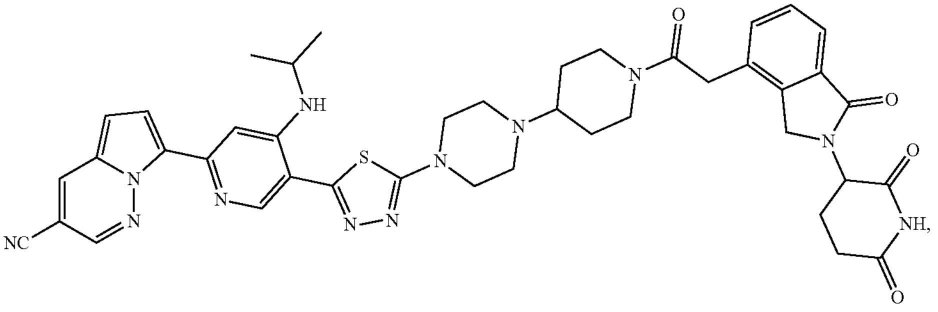
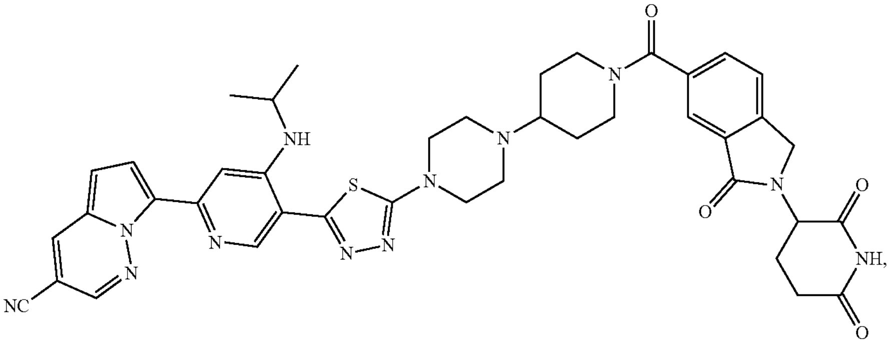

-continued
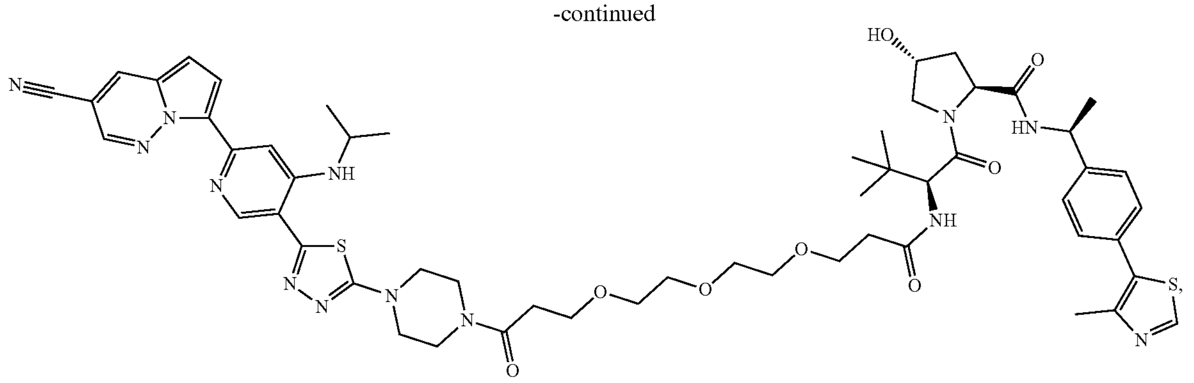
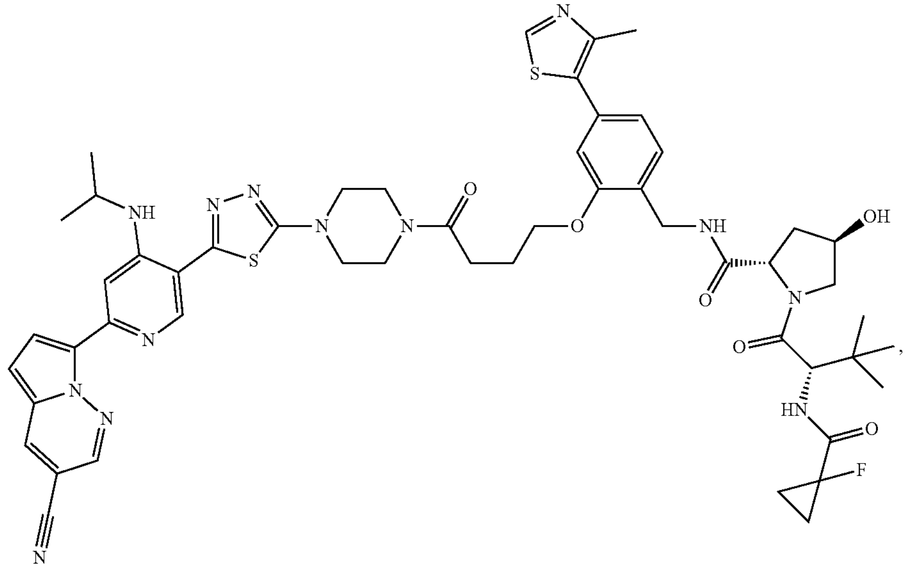
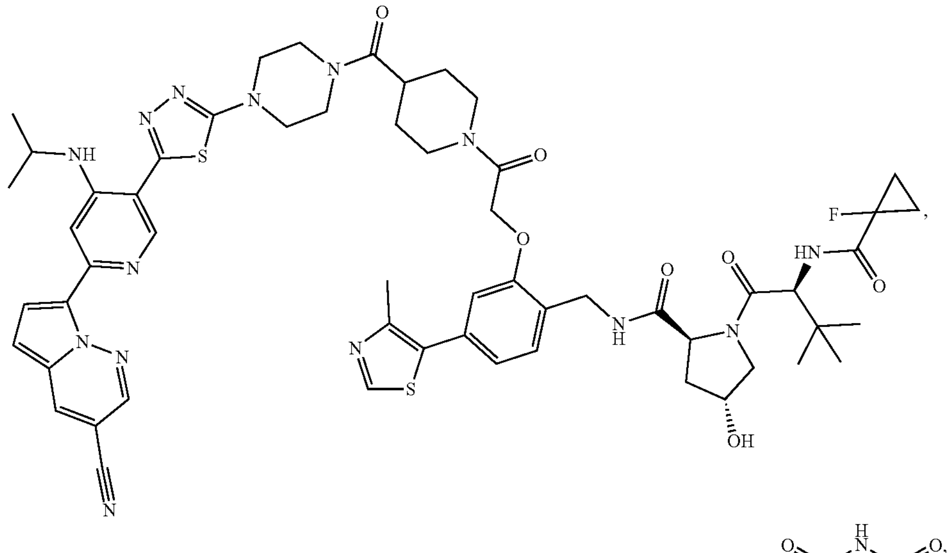
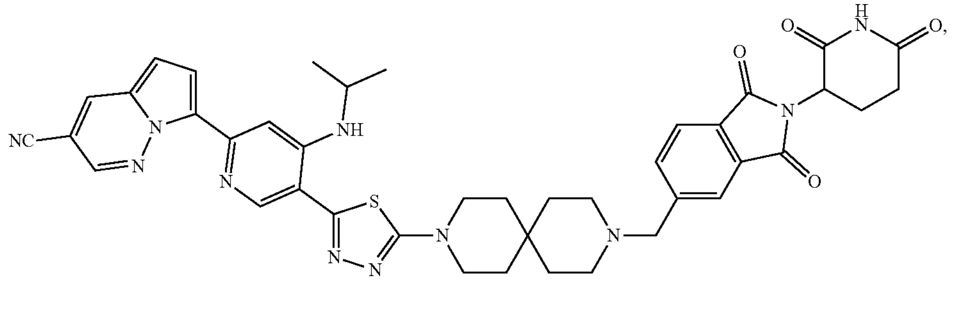

-continued
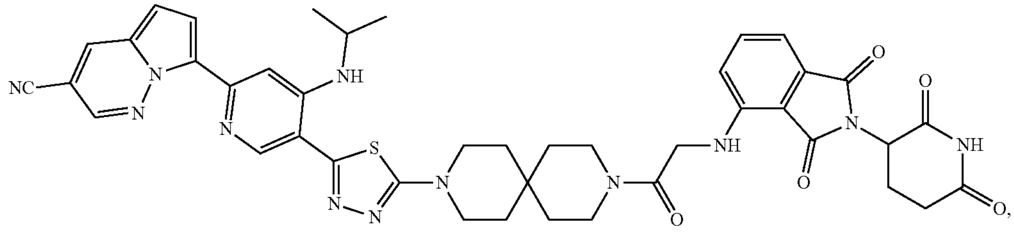
,
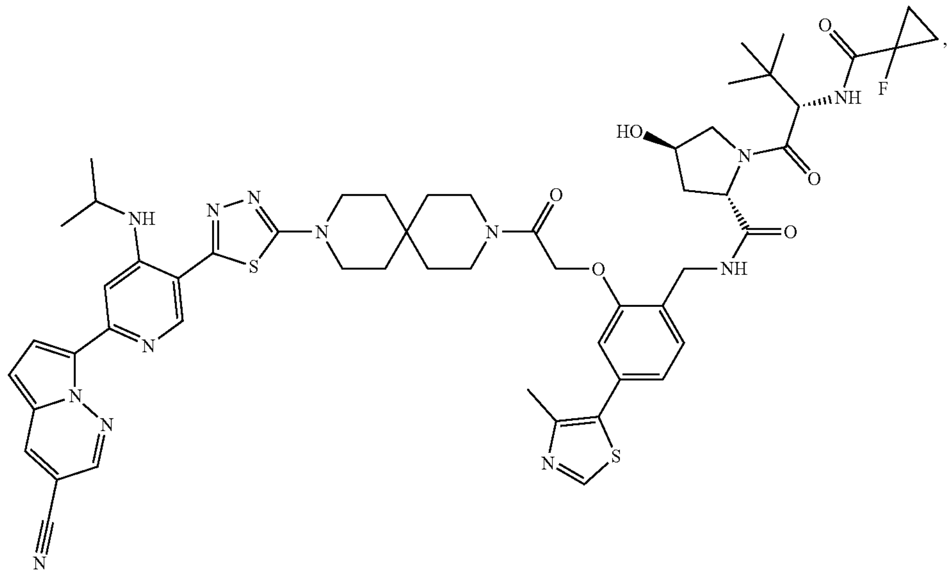
,
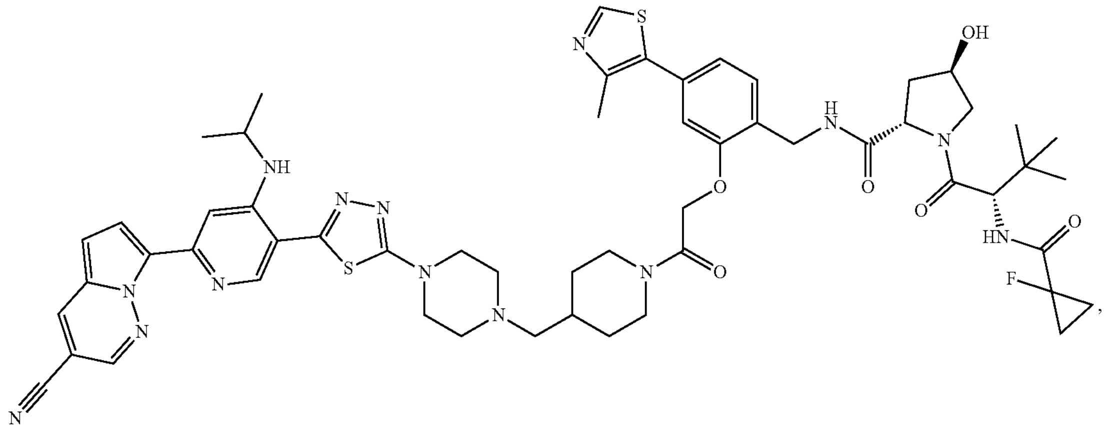
,
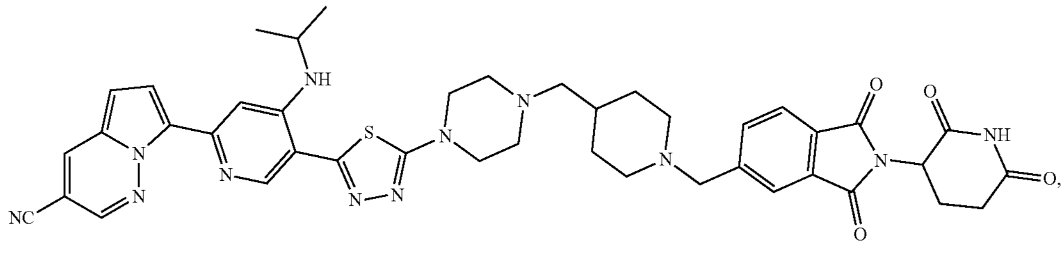
,

-continued
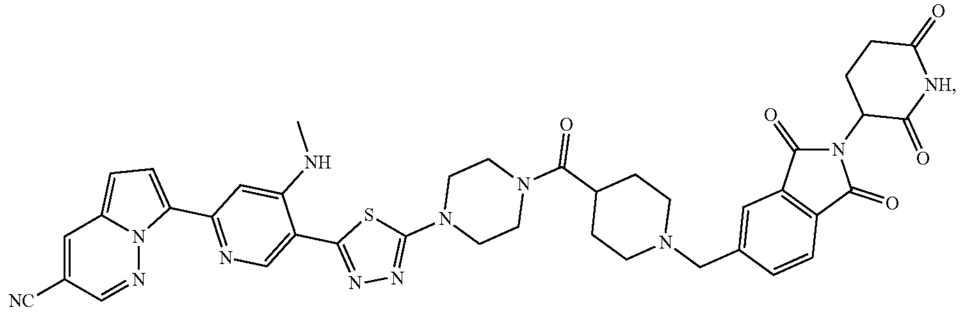
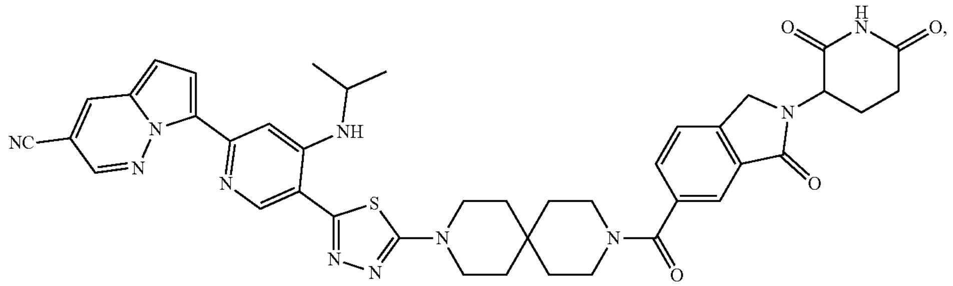
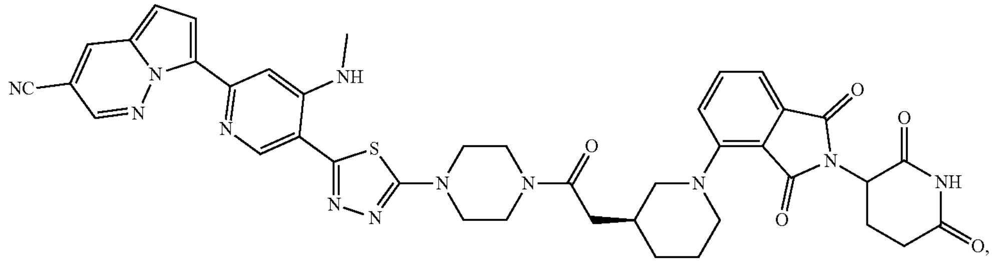
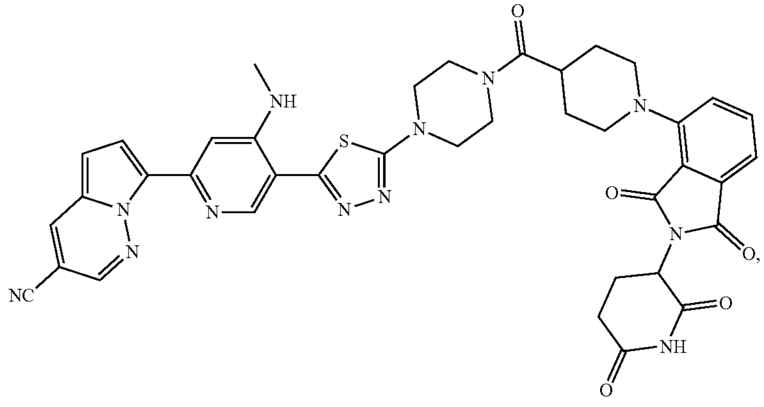
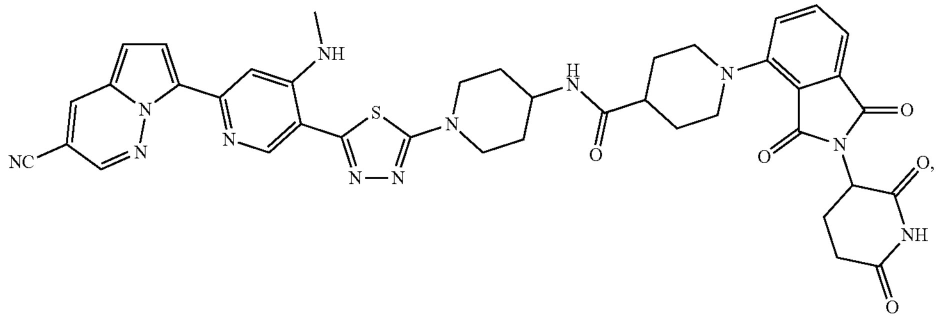

-continued
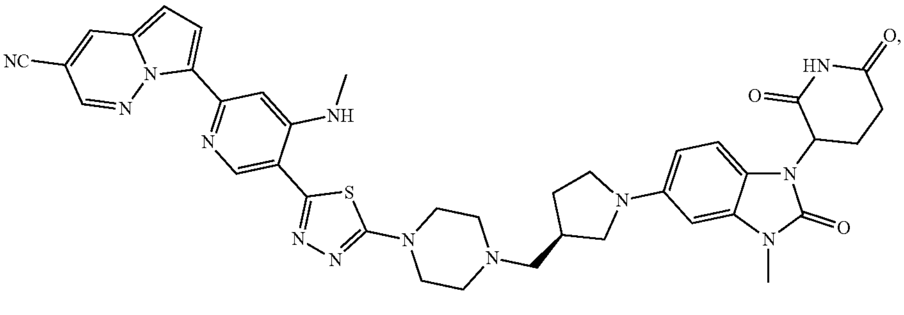
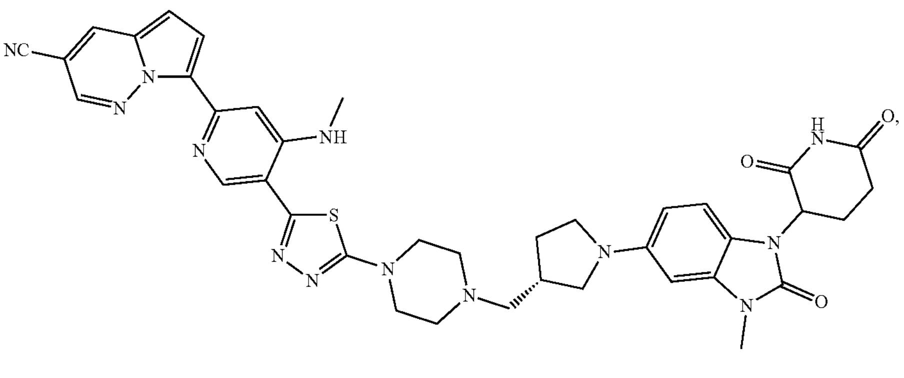
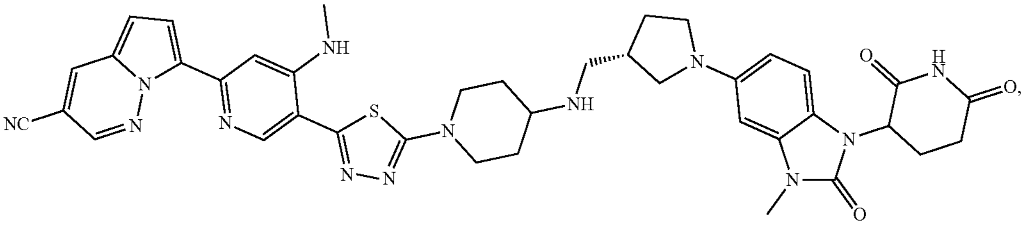
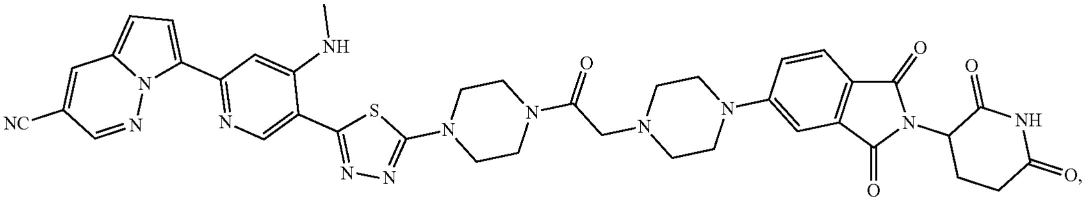
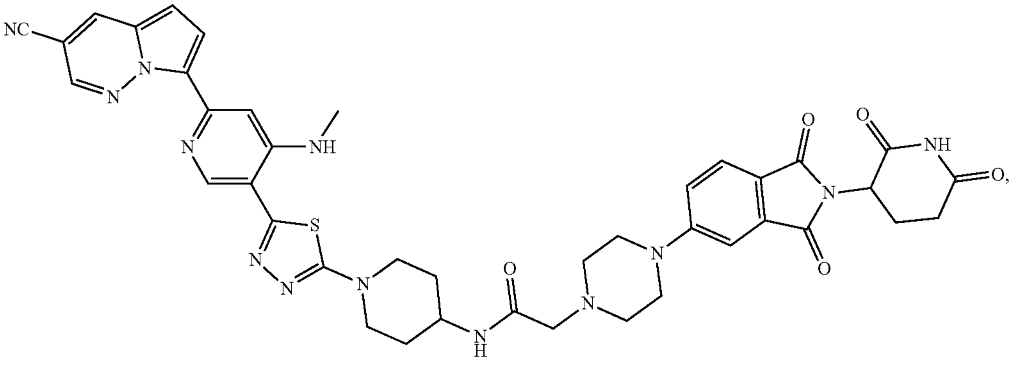

-continued
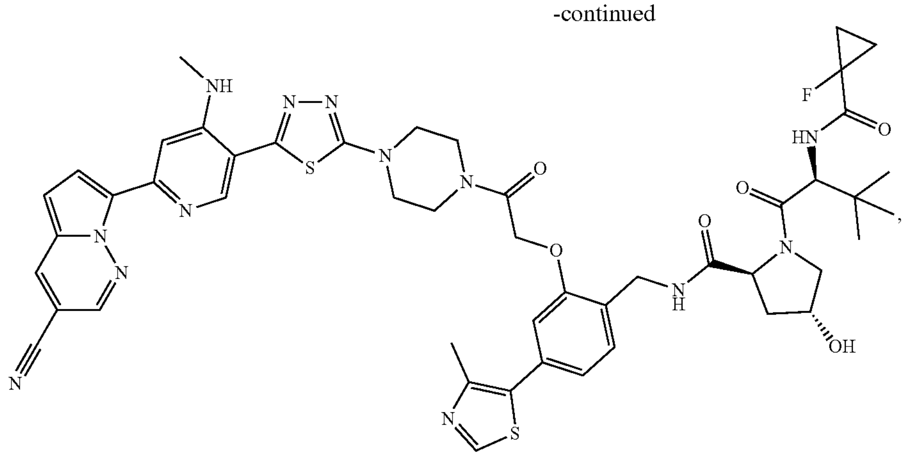
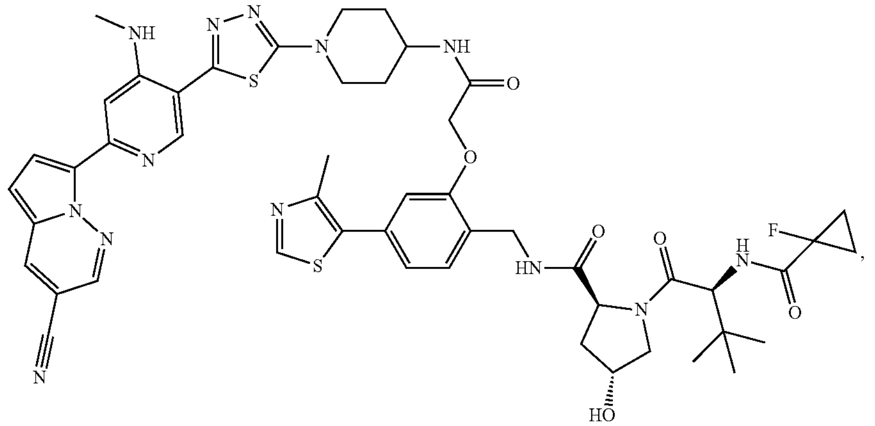
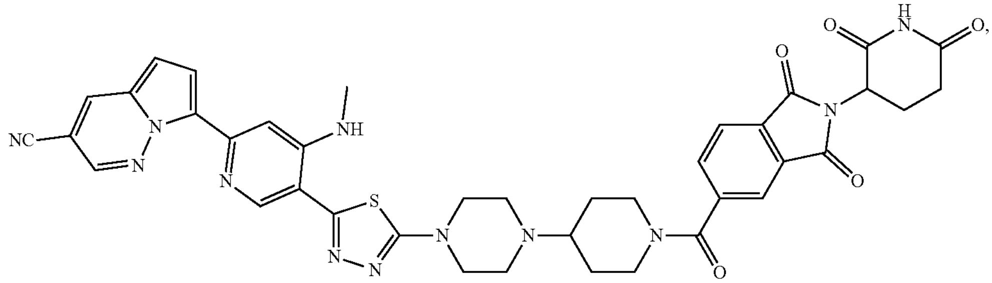
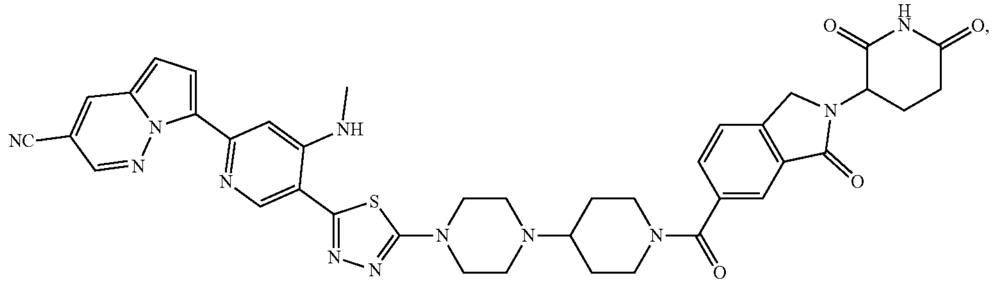
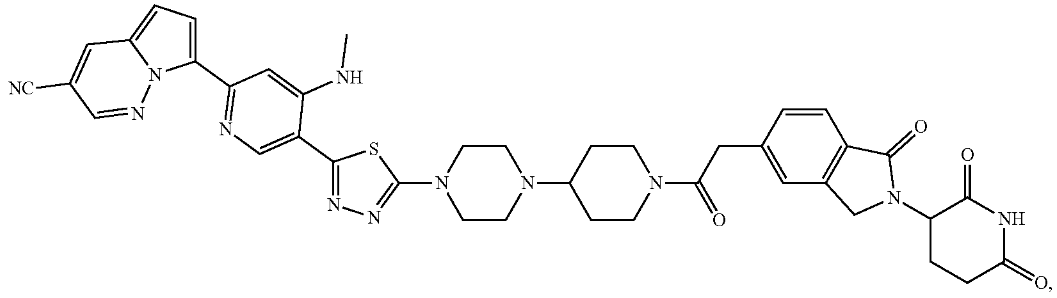

-continued
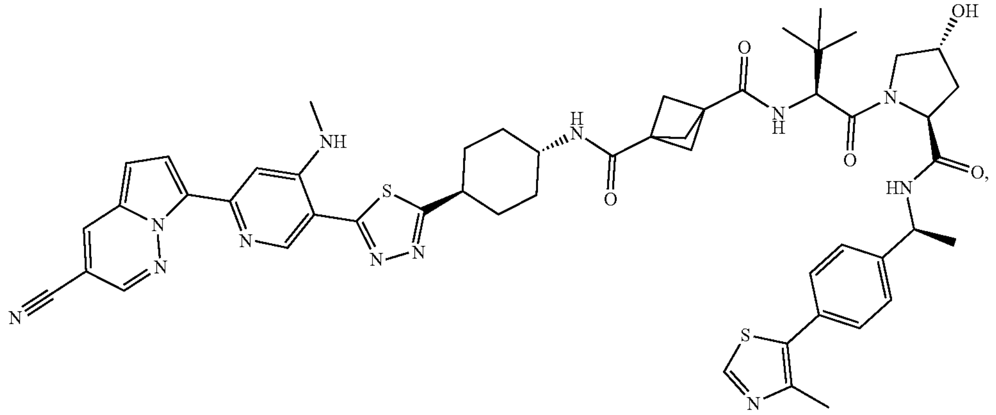
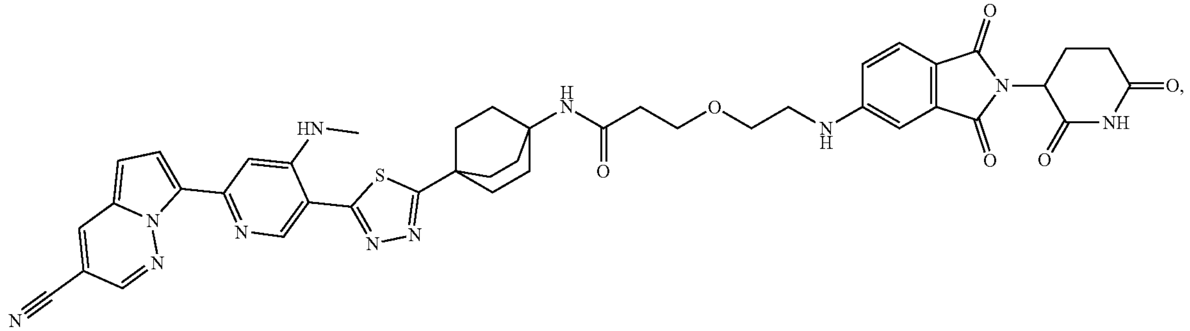
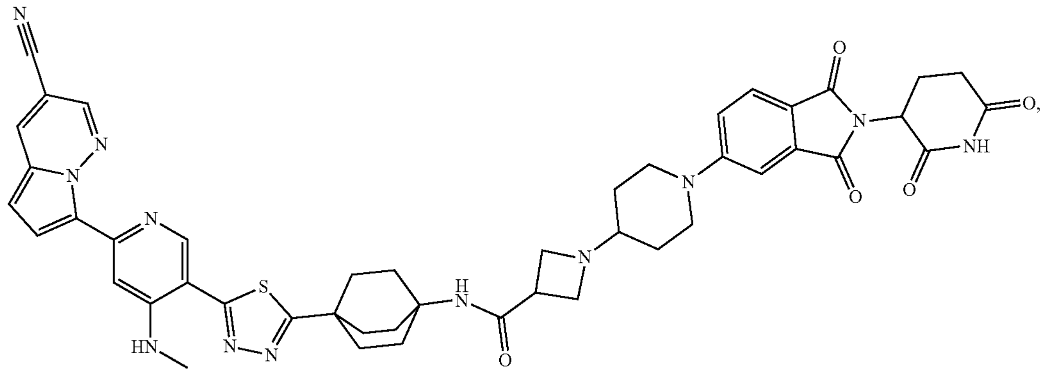
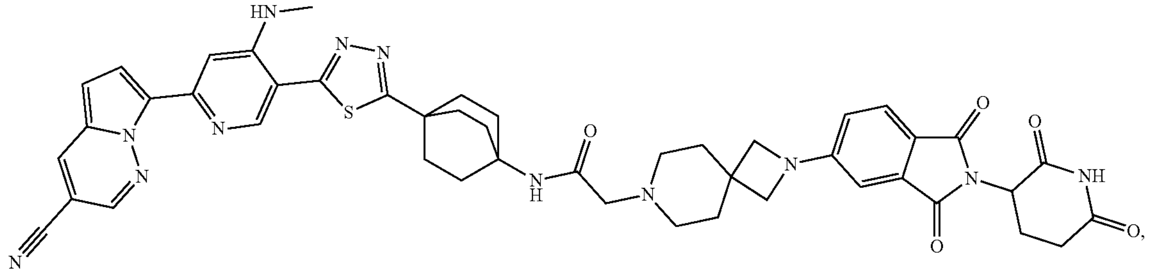
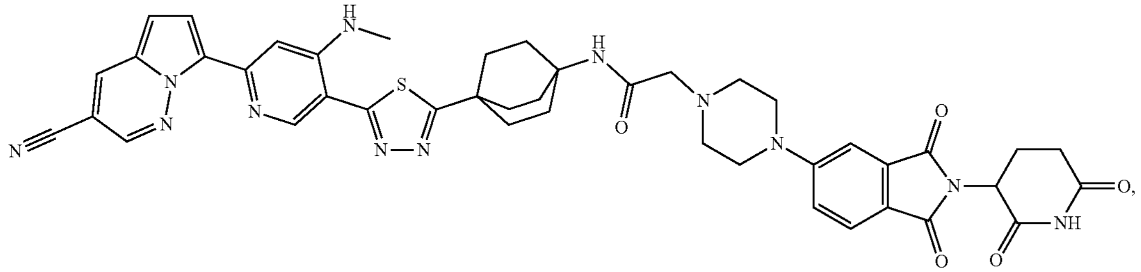

-continued
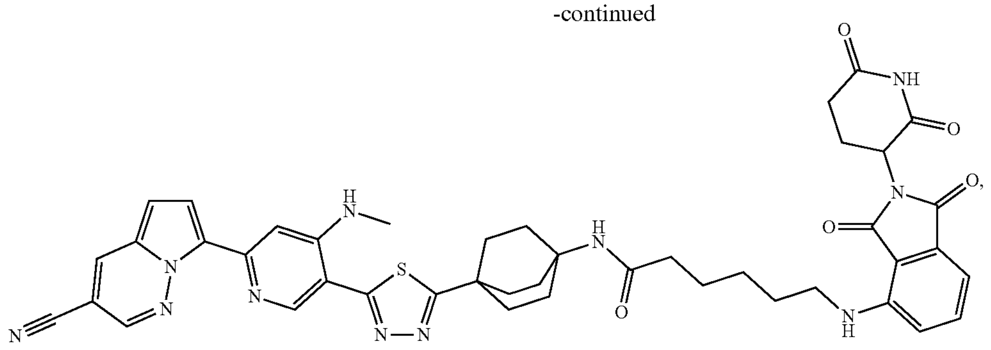
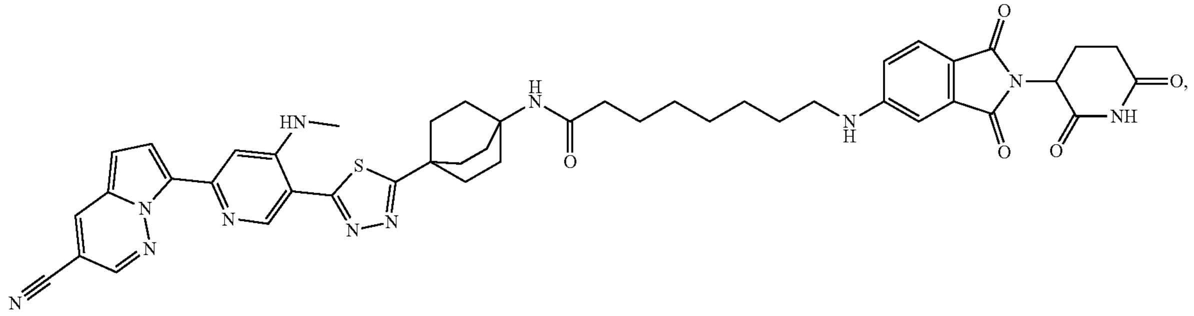
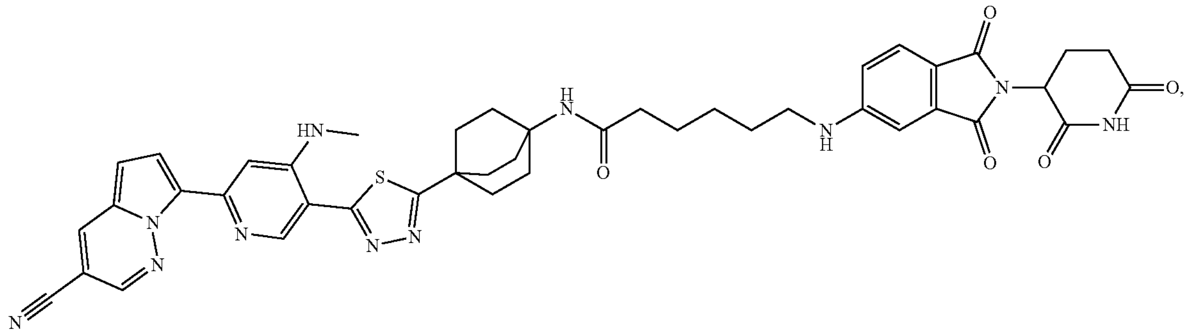
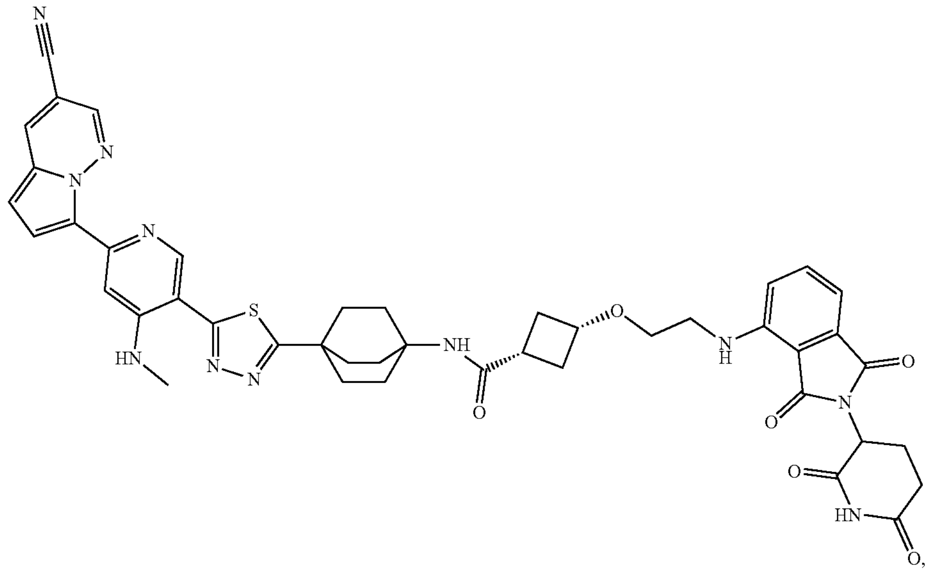

-continued
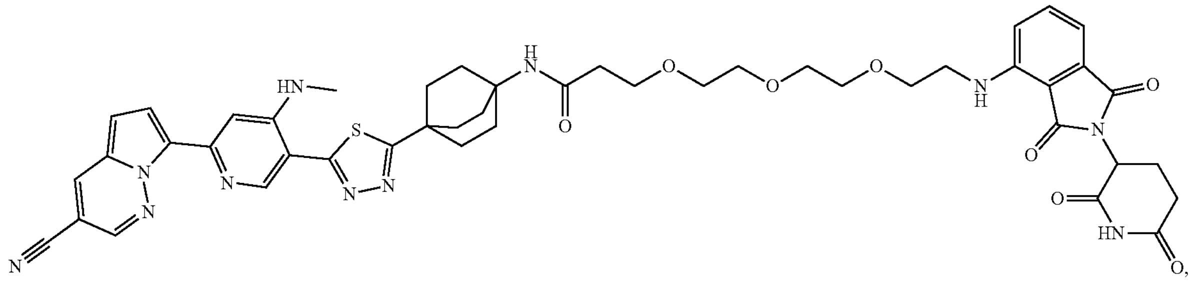
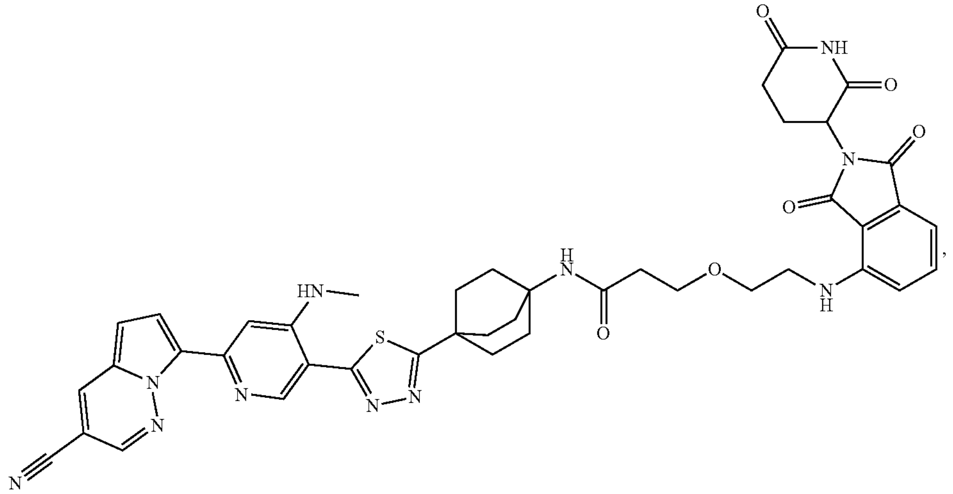
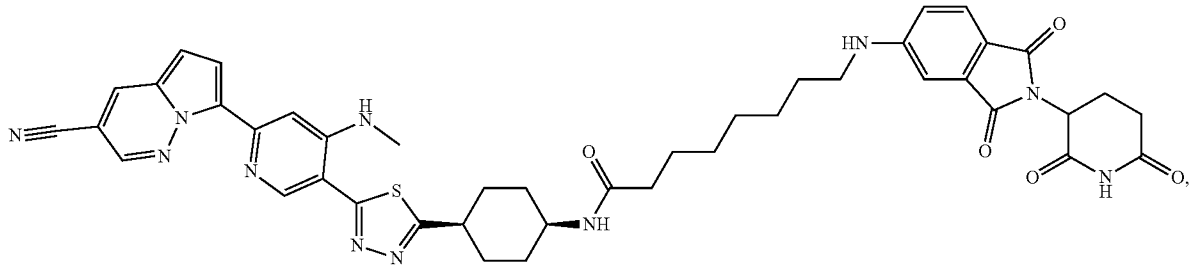
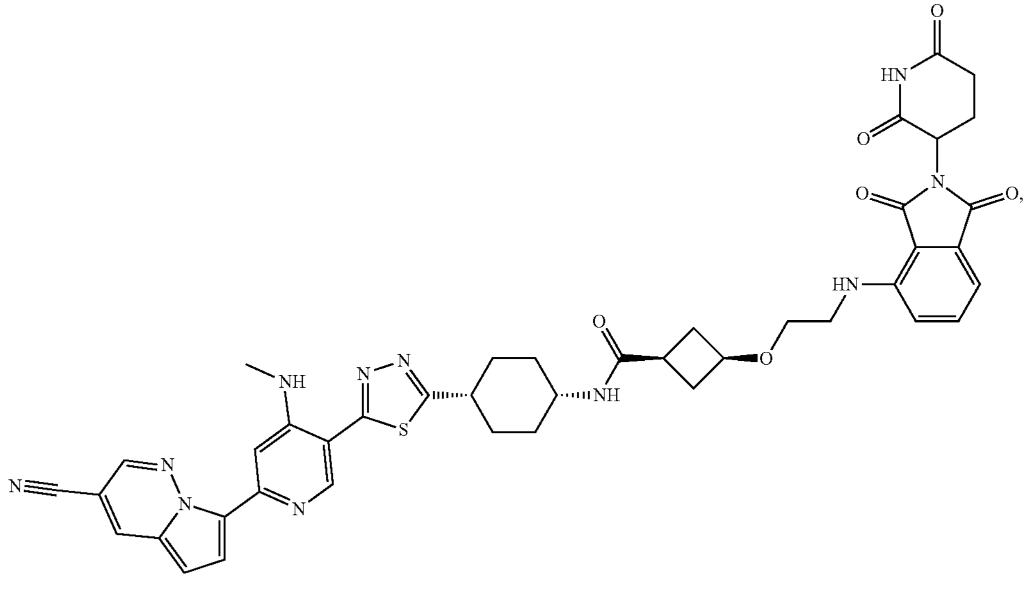

-continued
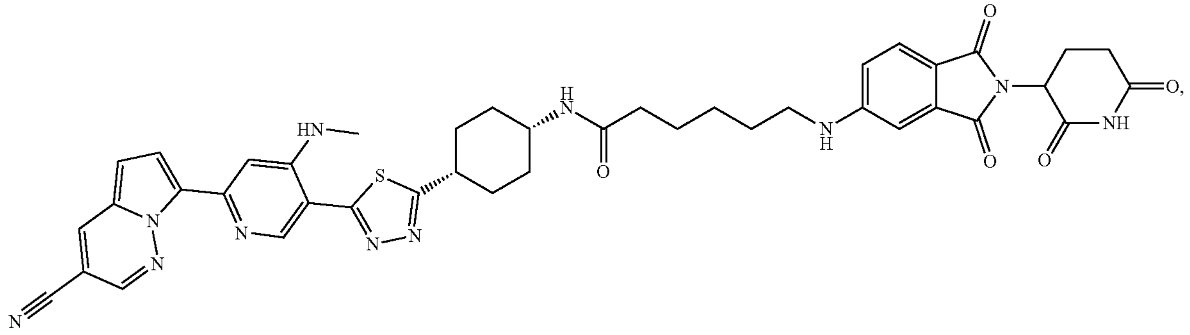
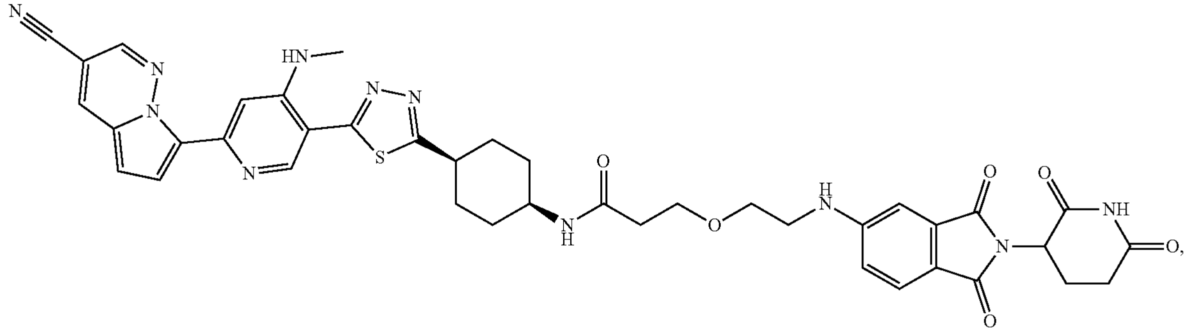
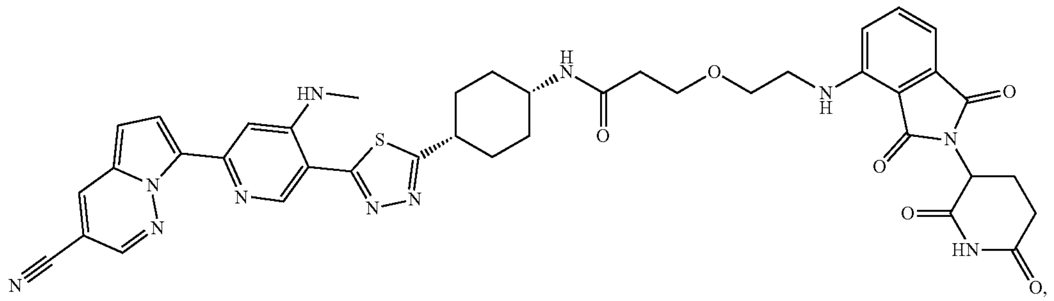
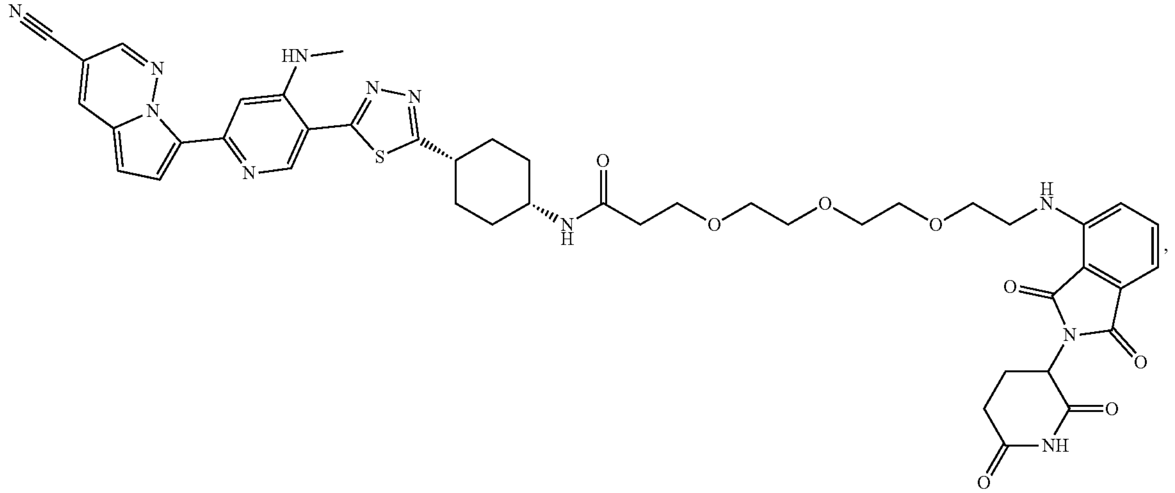

-continued
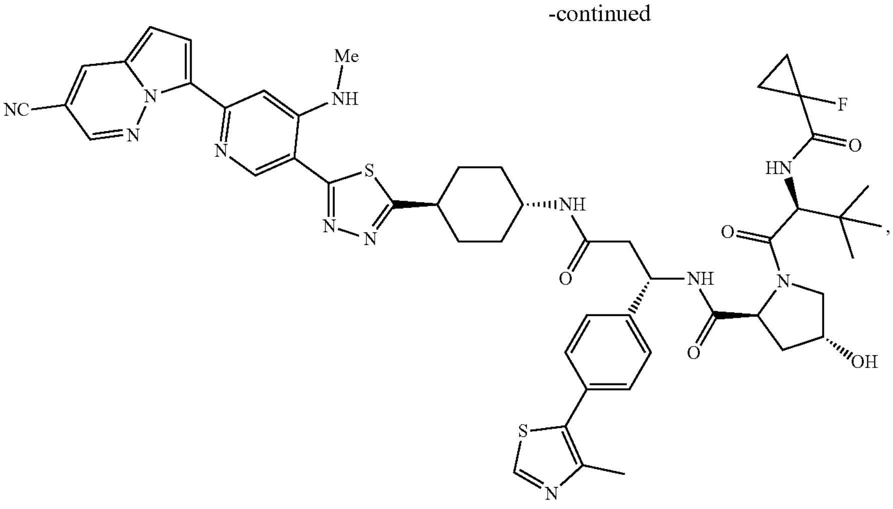
,
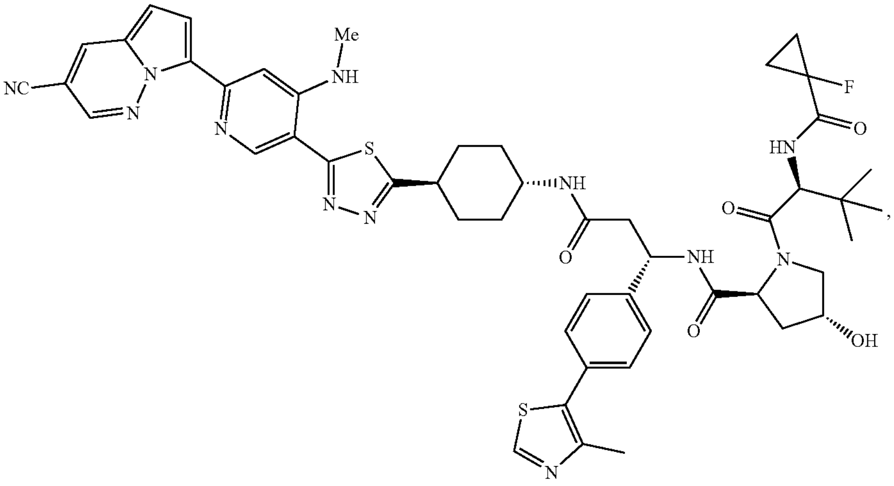
,
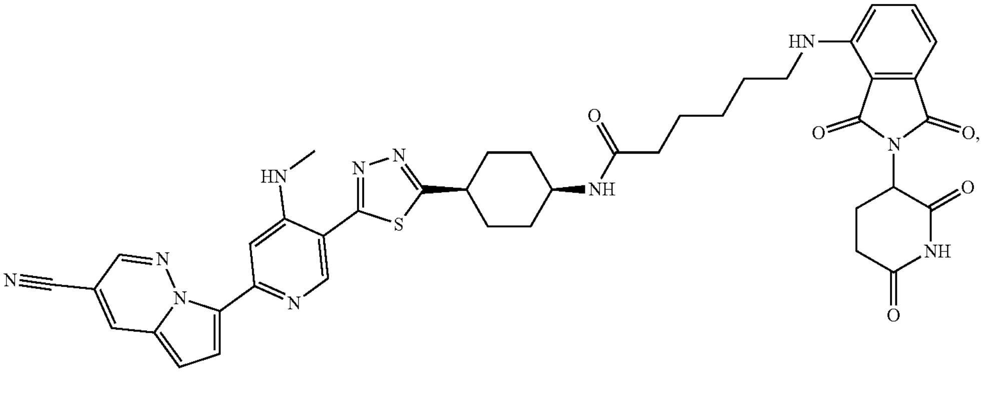
,

-continued
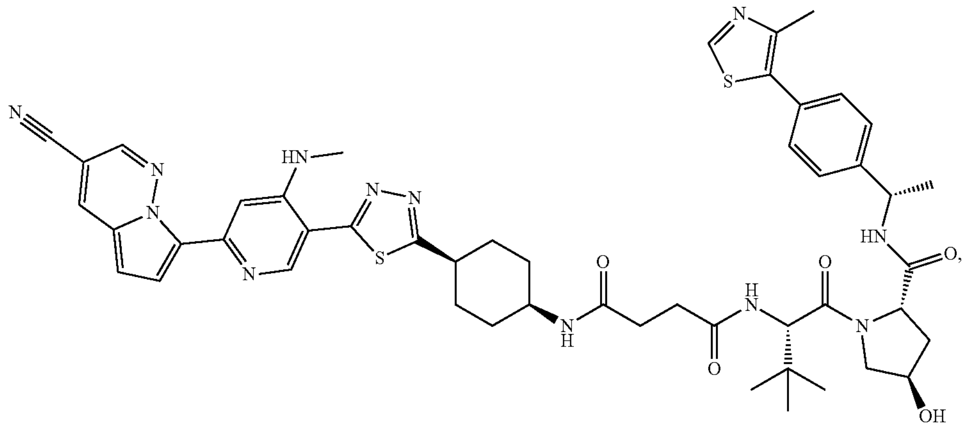
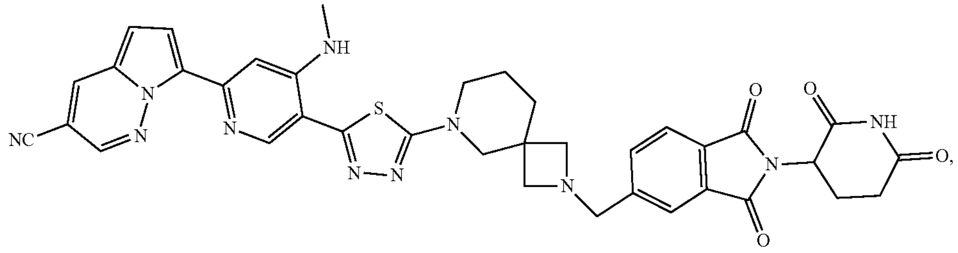
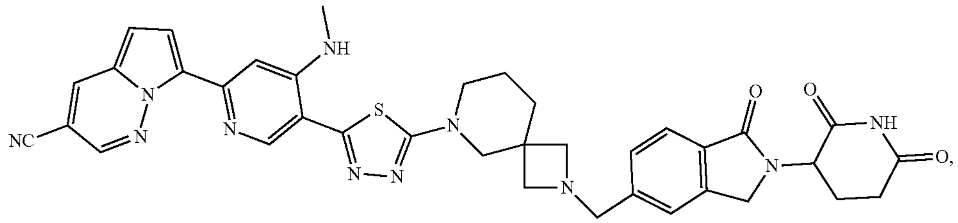
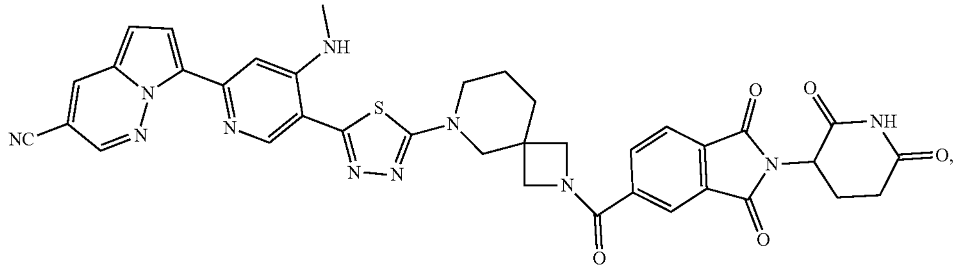
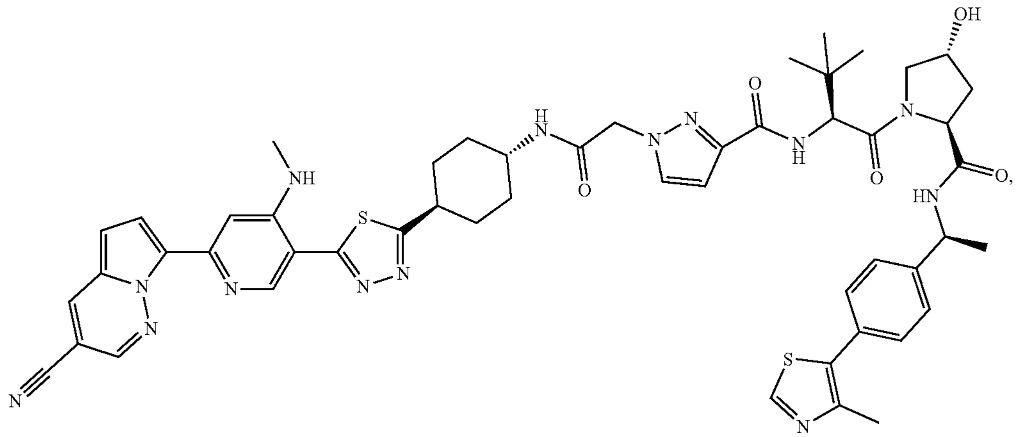

-continued
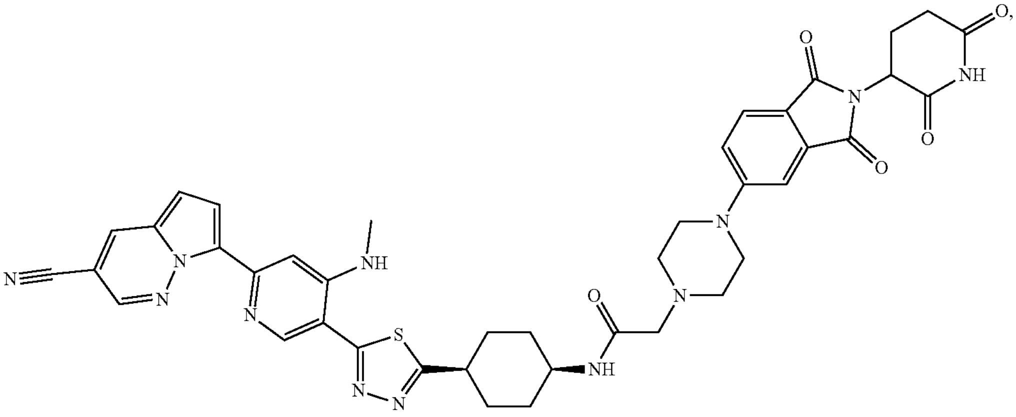
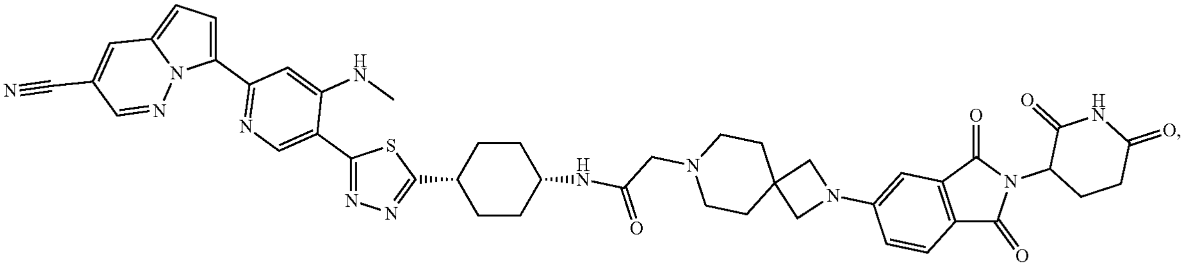
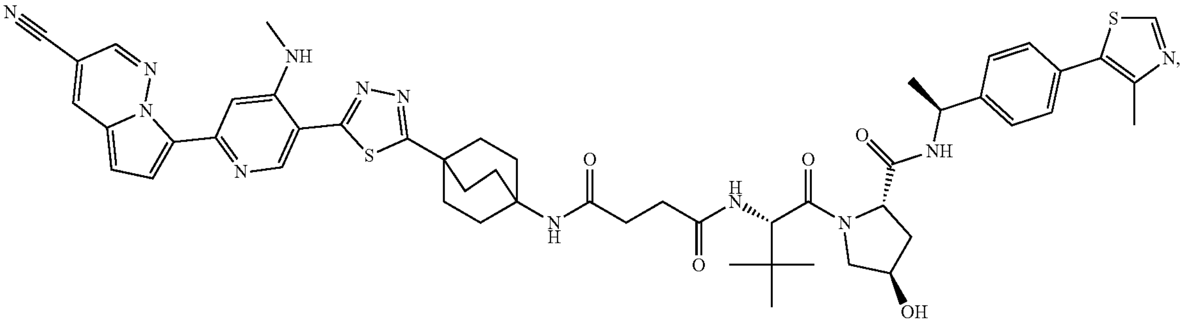
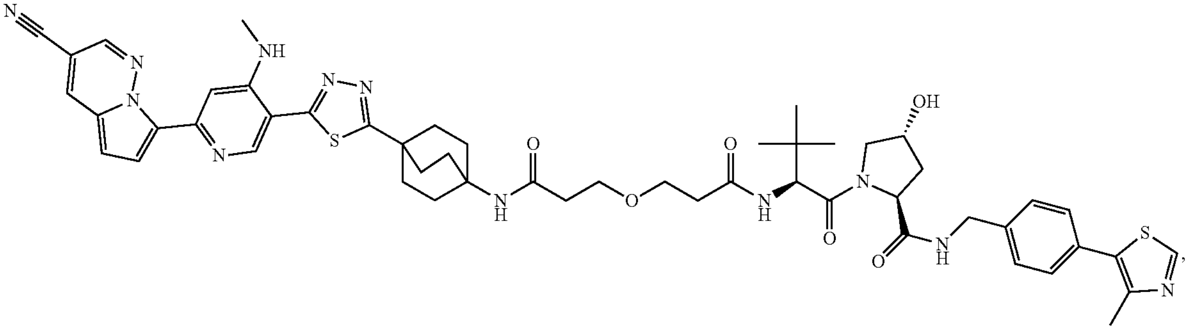
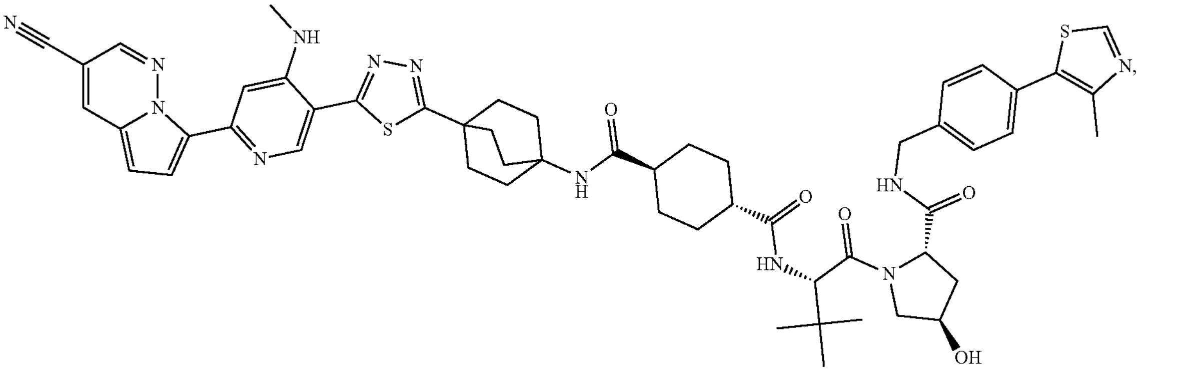

-continued
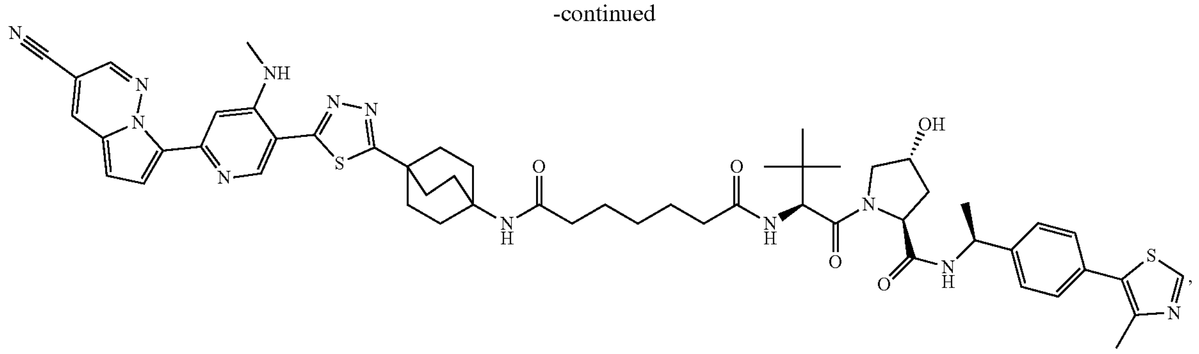
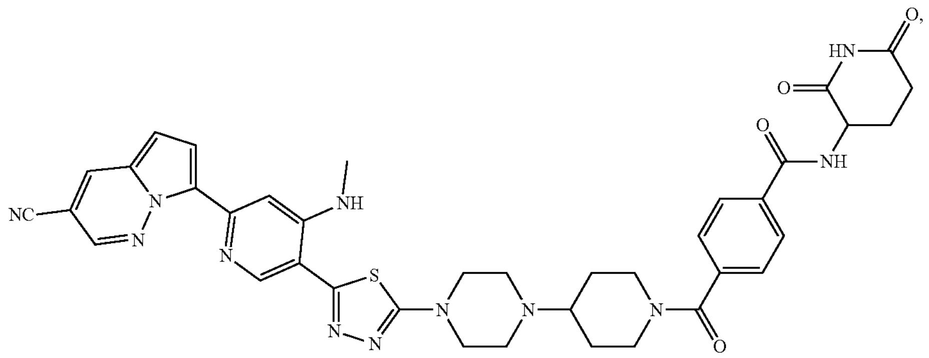
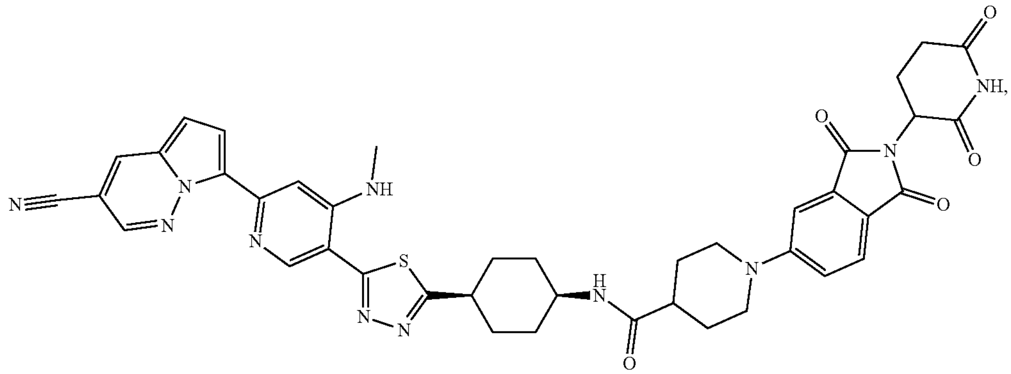
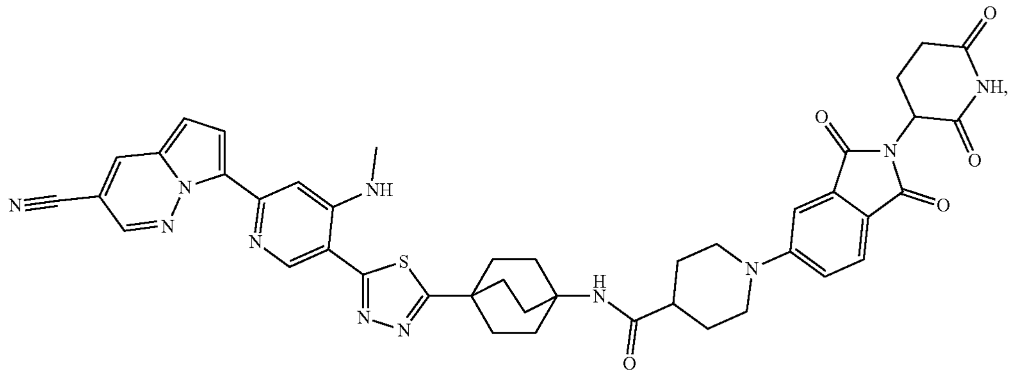

-continued
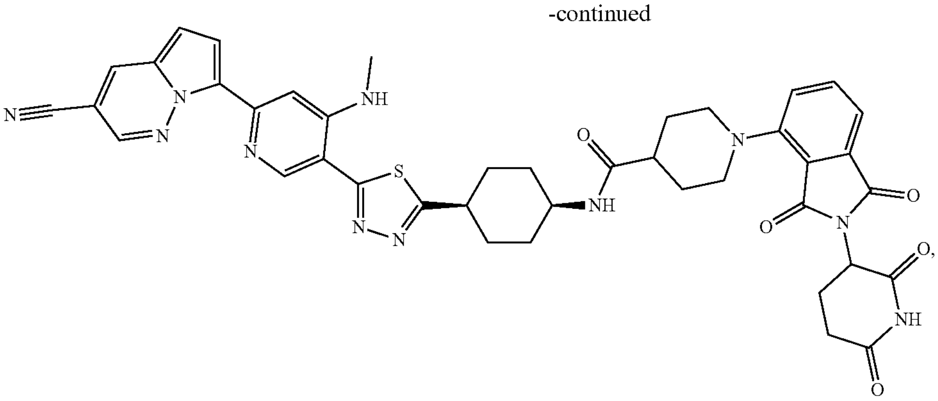
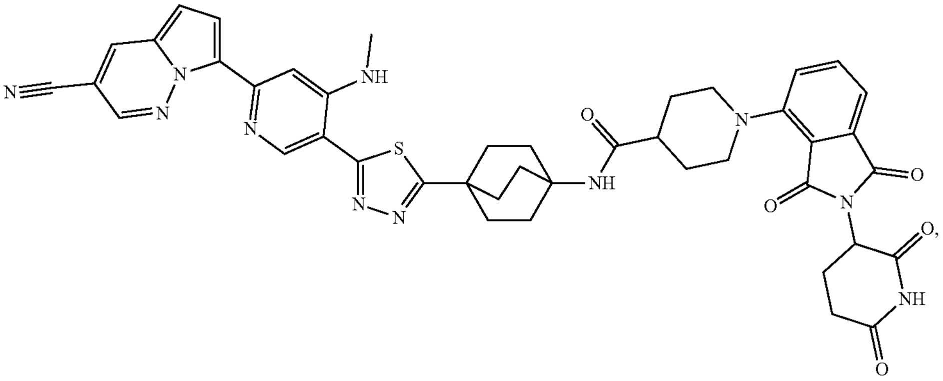
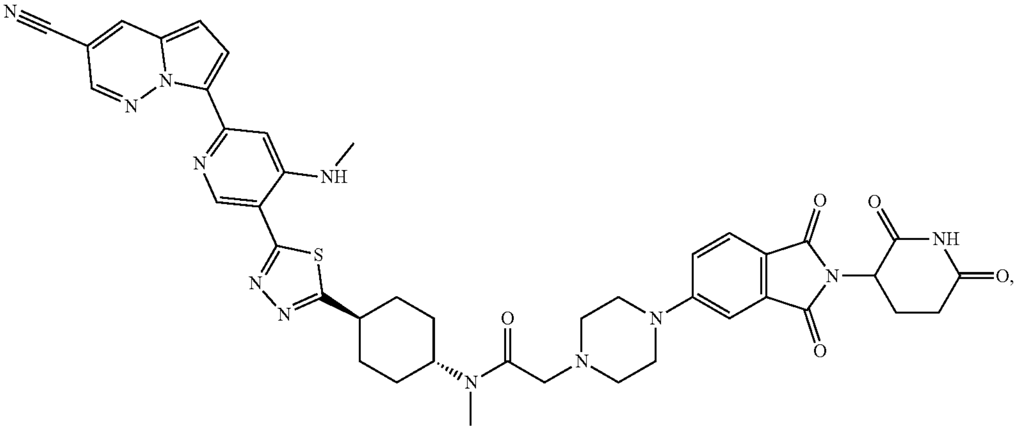
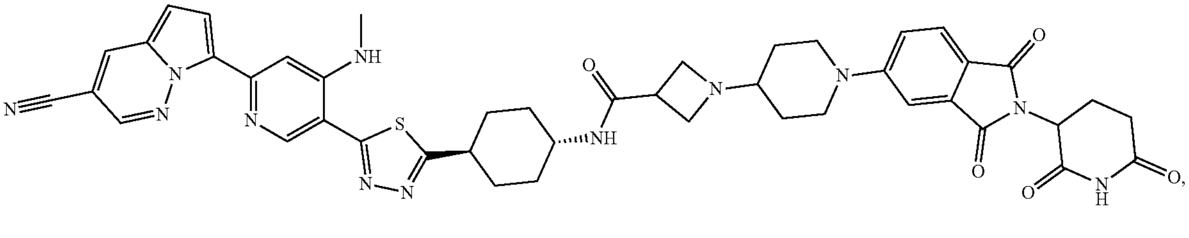

-continued
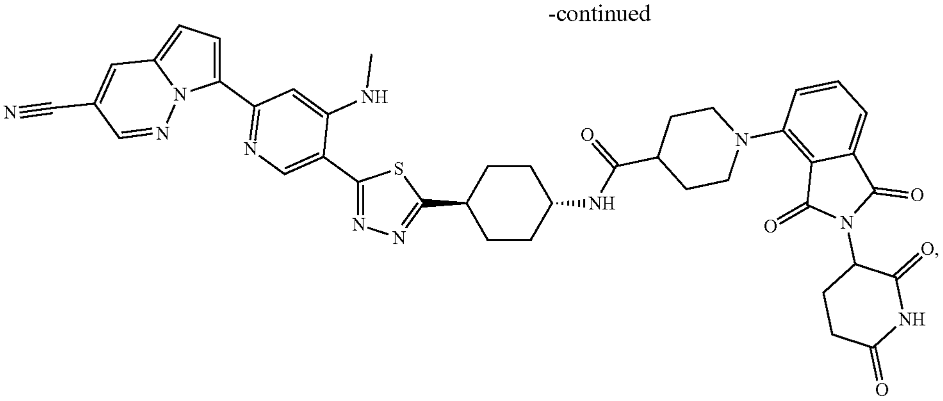
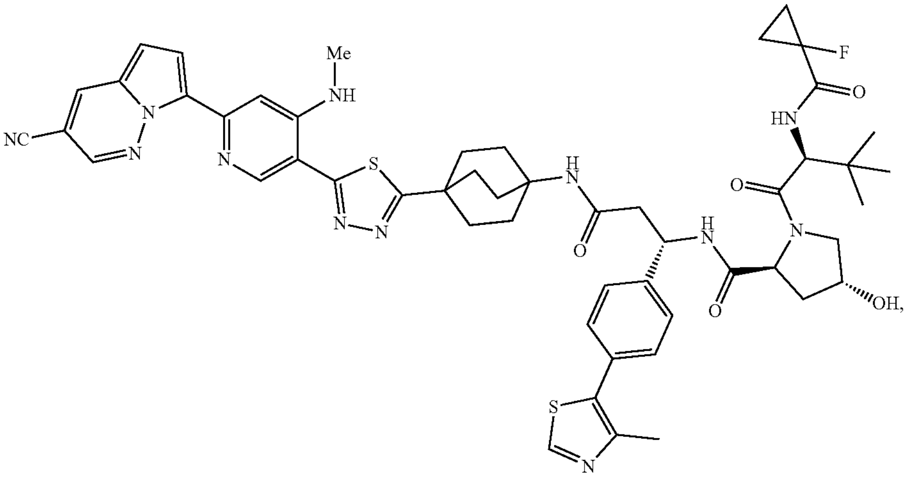
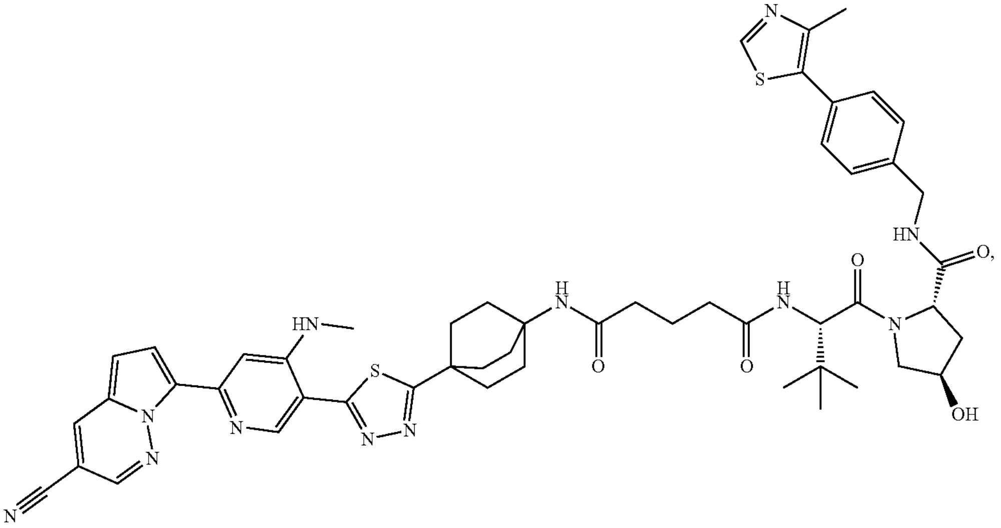

-continued
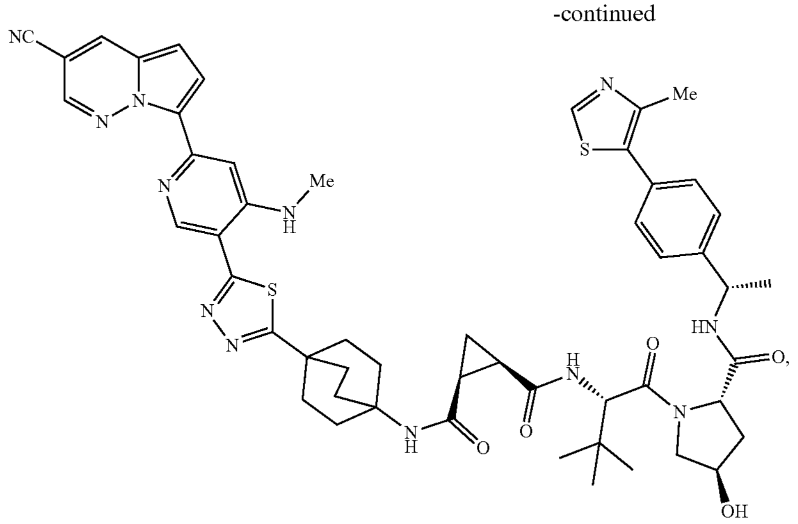
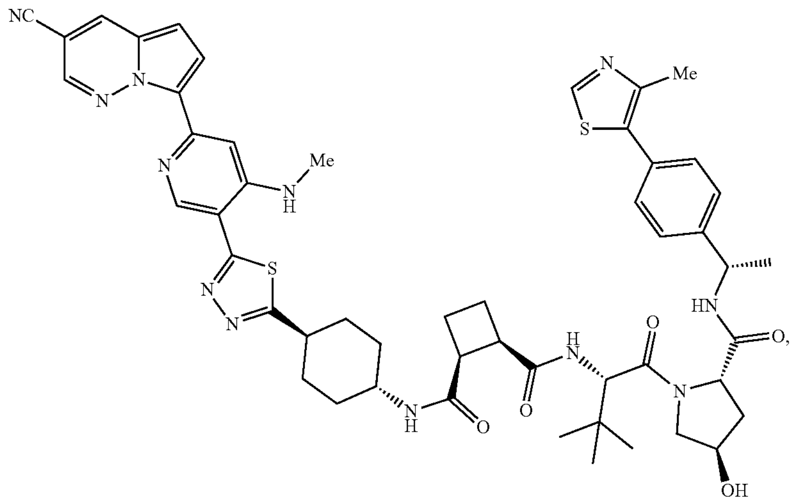
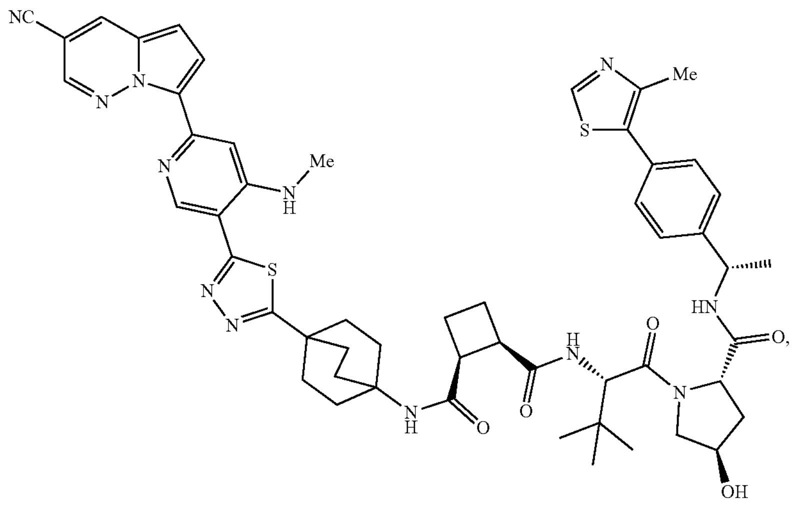

-continued
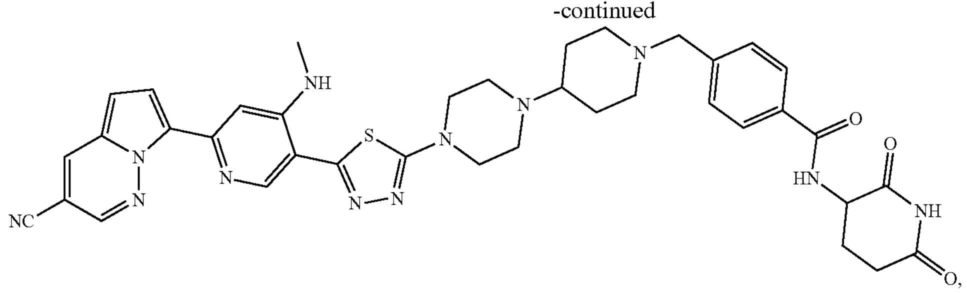
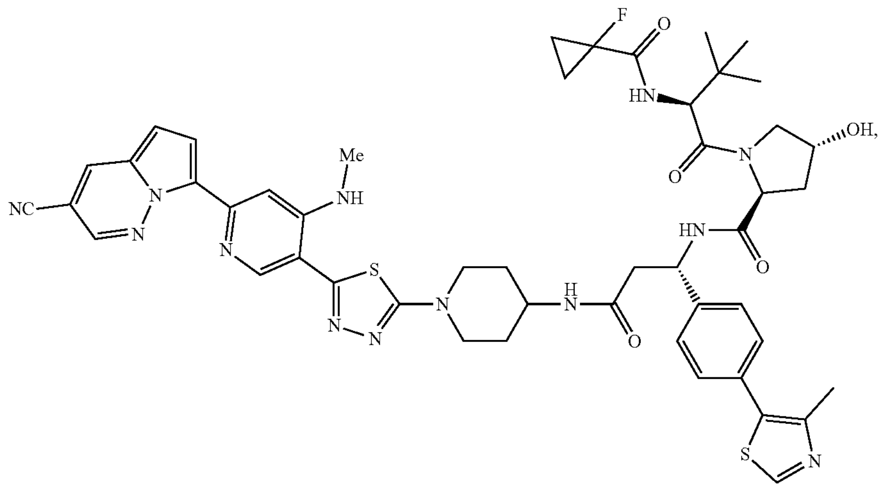
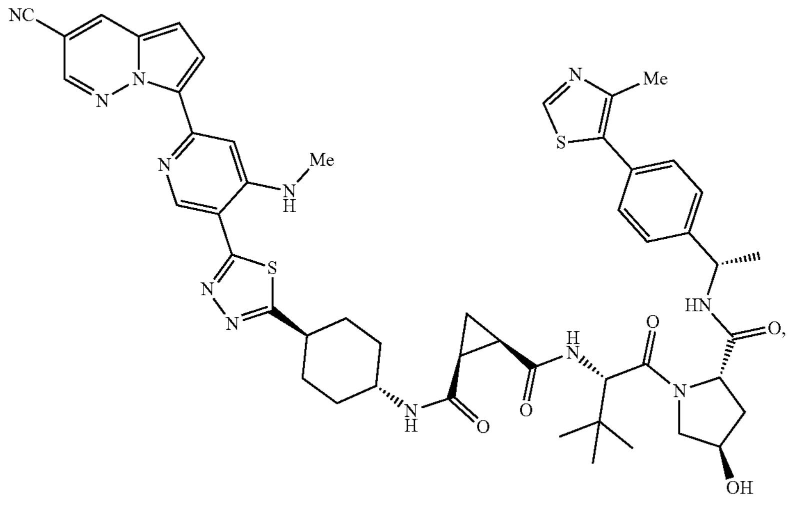
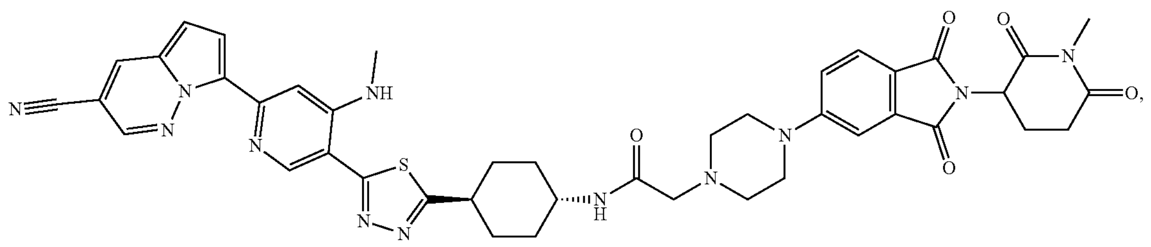

-continued
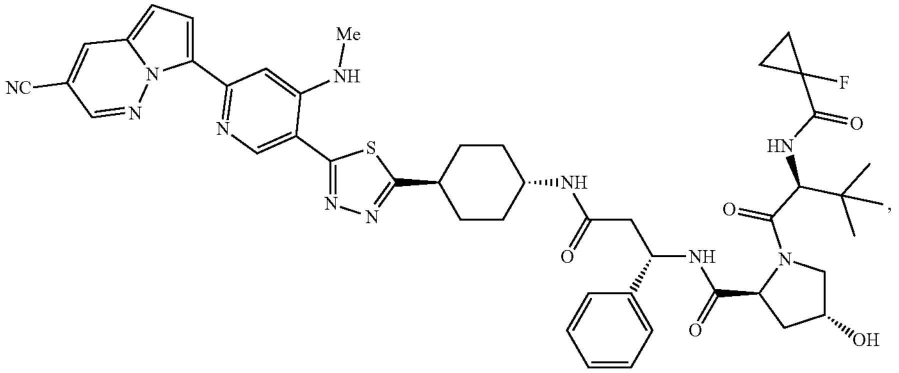
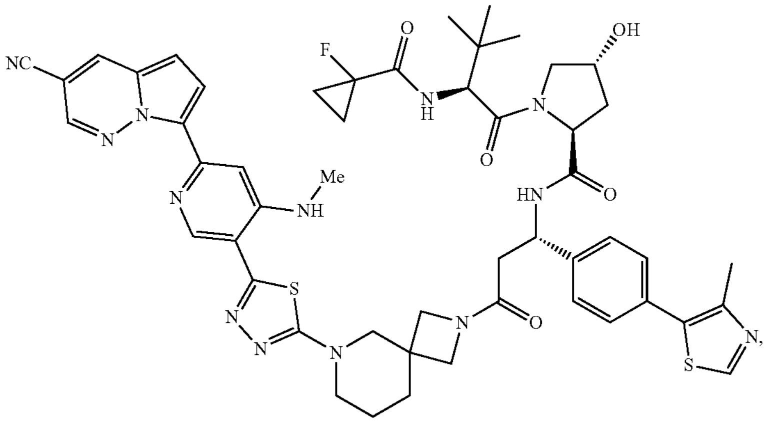
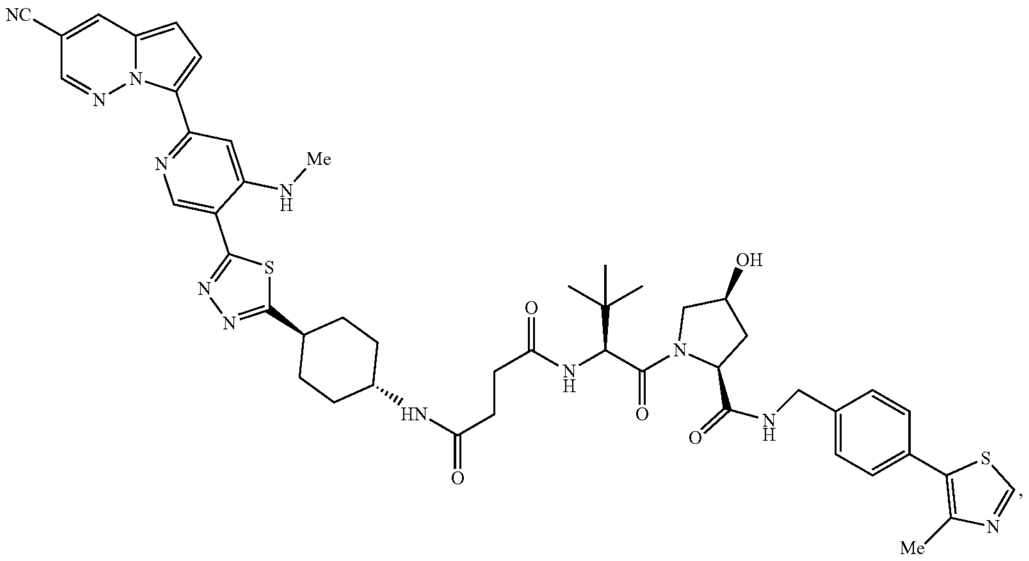
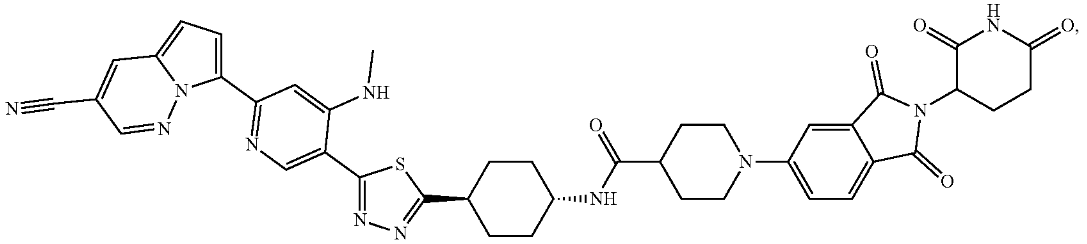

-continued
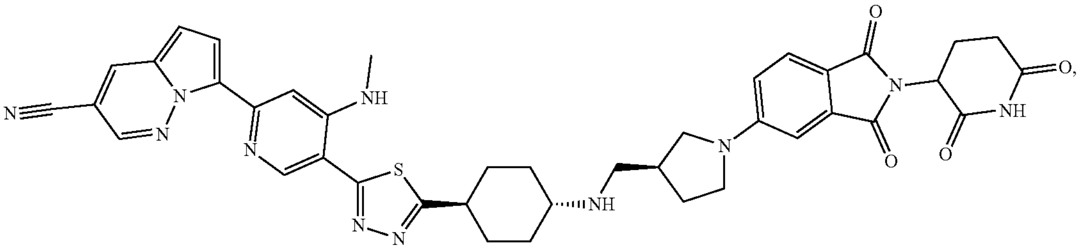
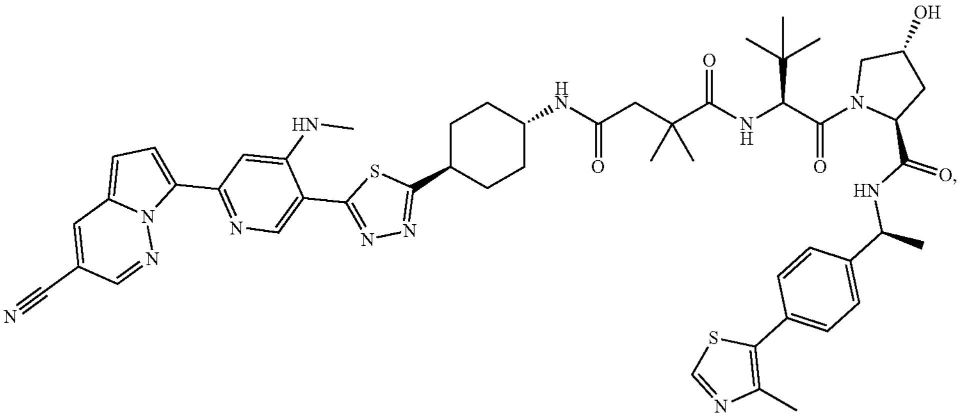
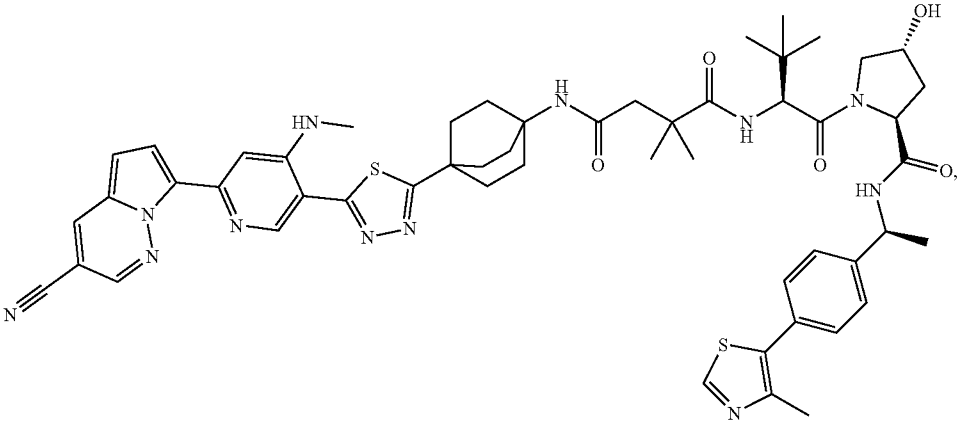
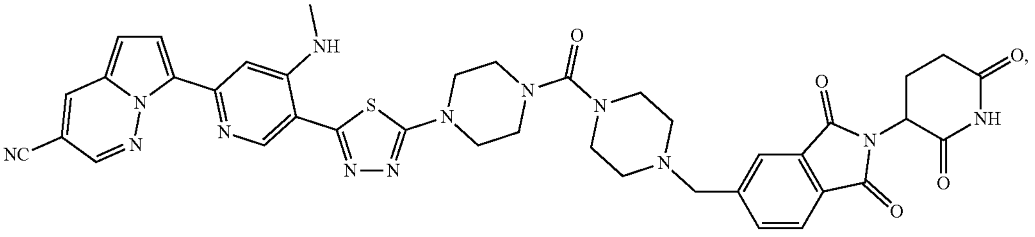
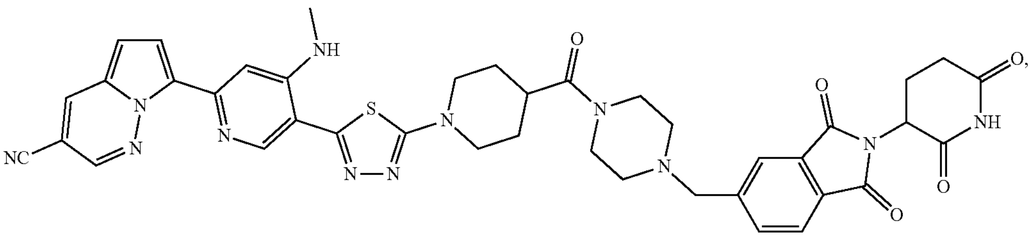

-continued
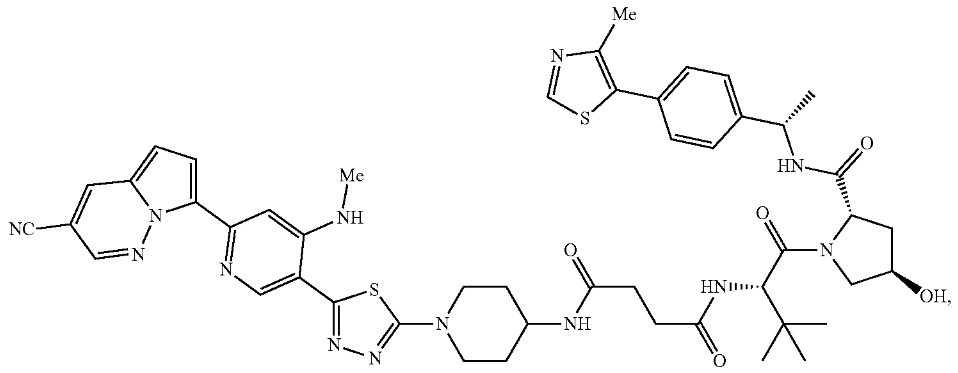
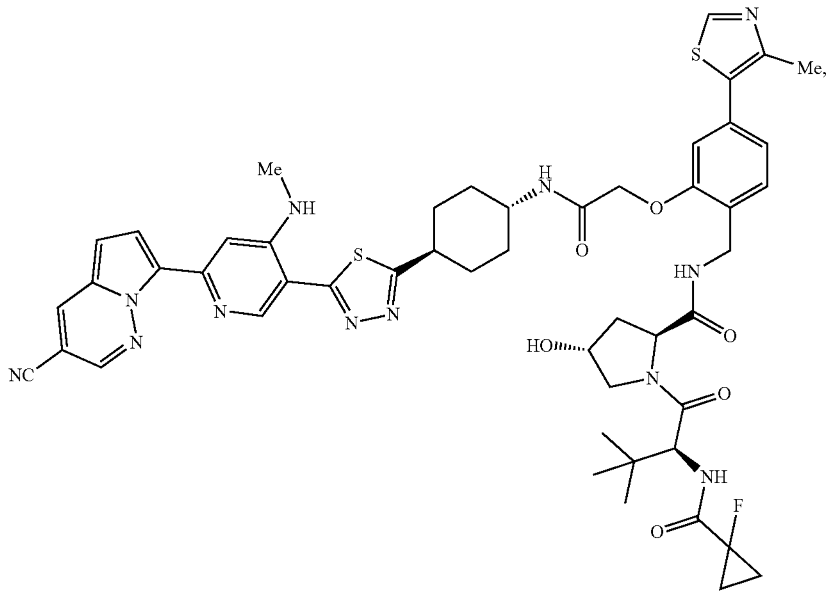
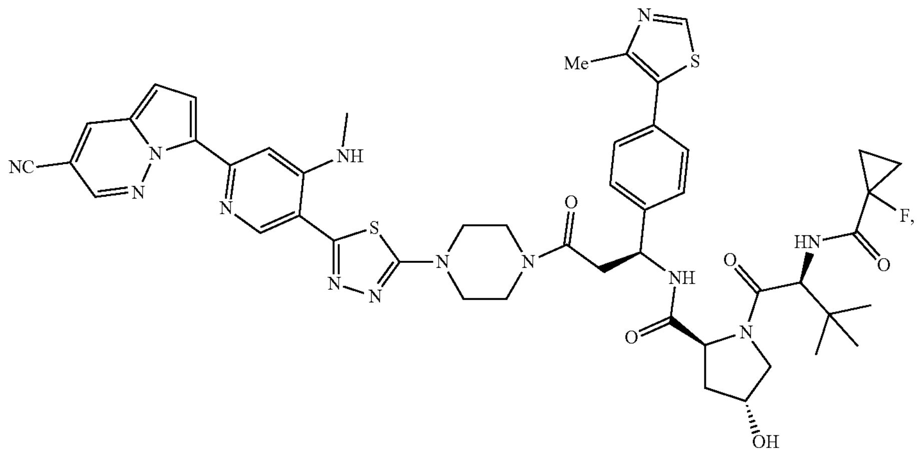

-continued
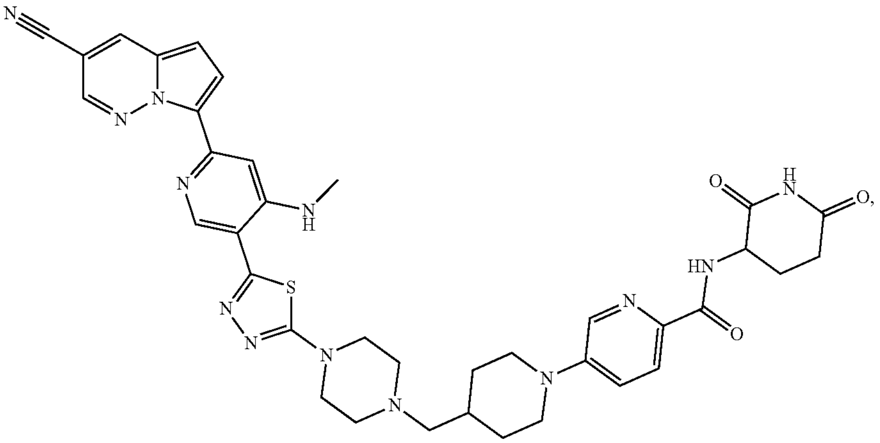
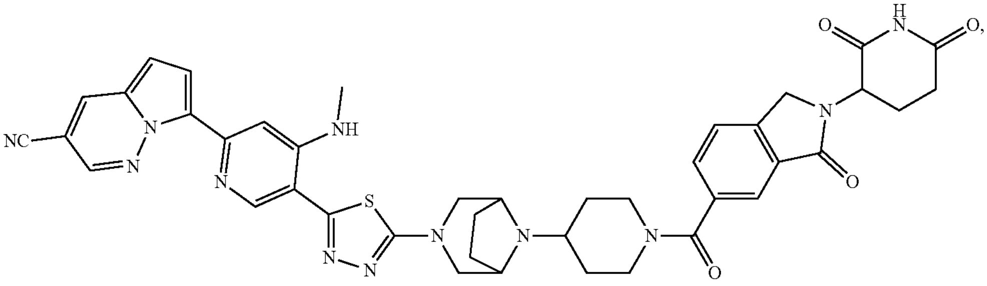
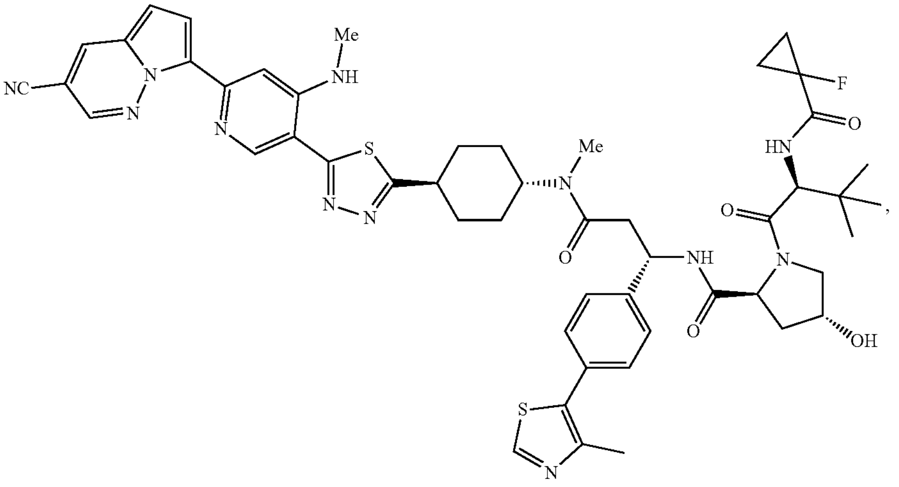
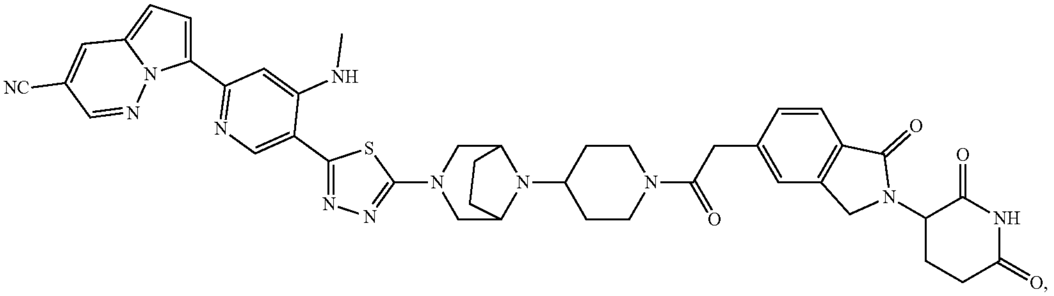

-continued
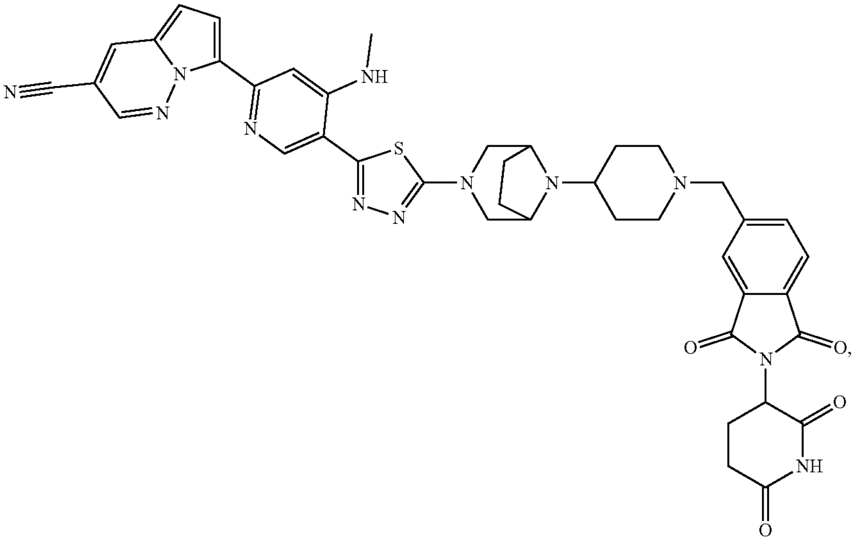
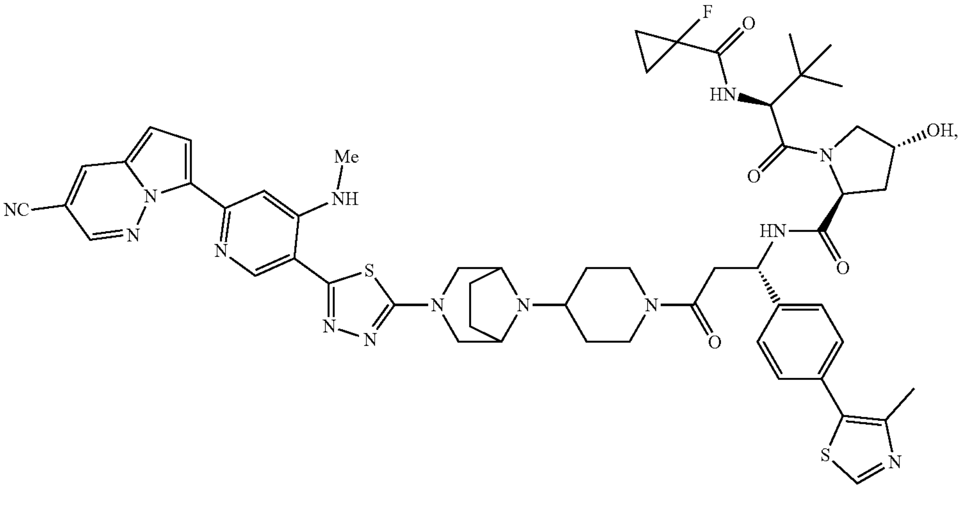
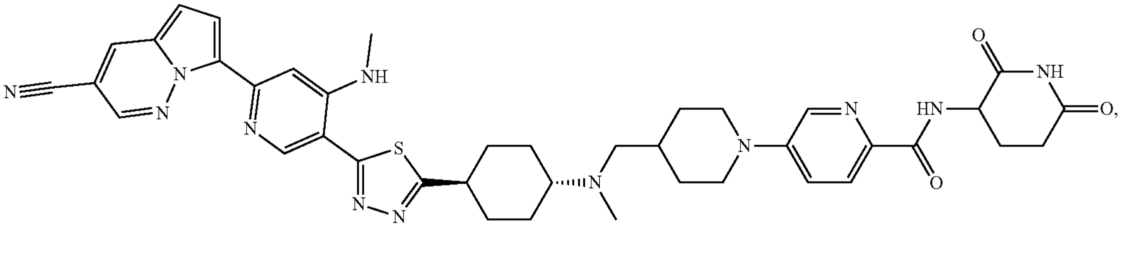
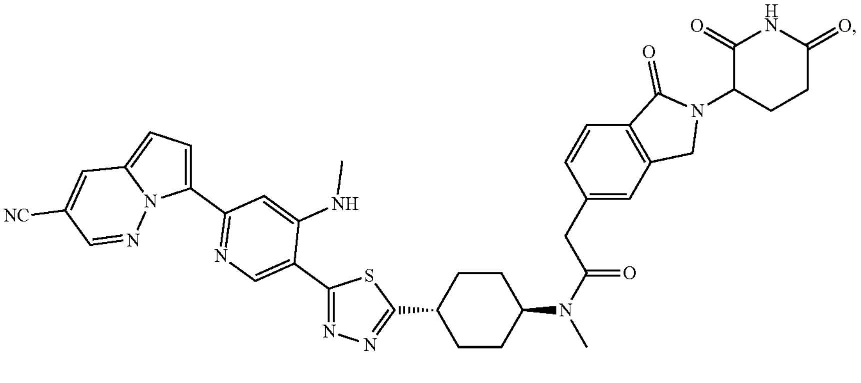

-continued
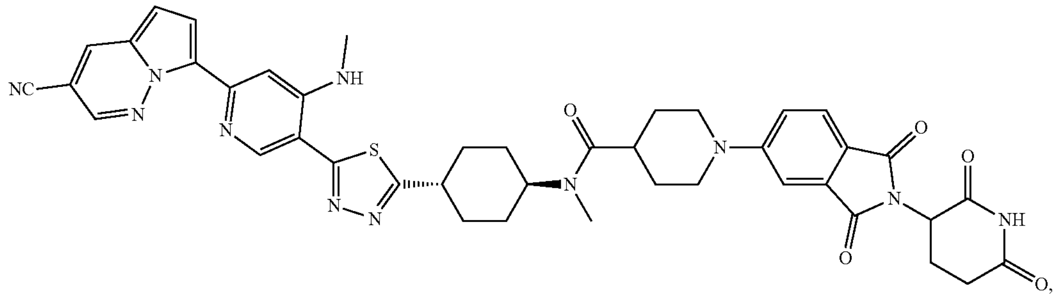
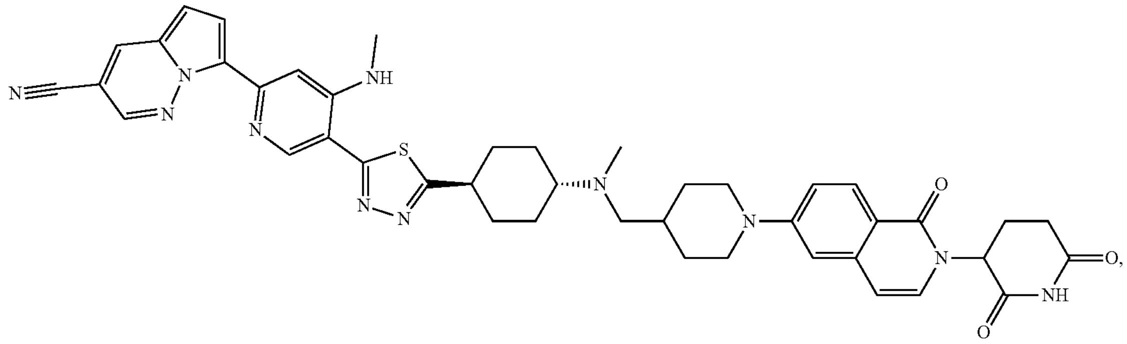
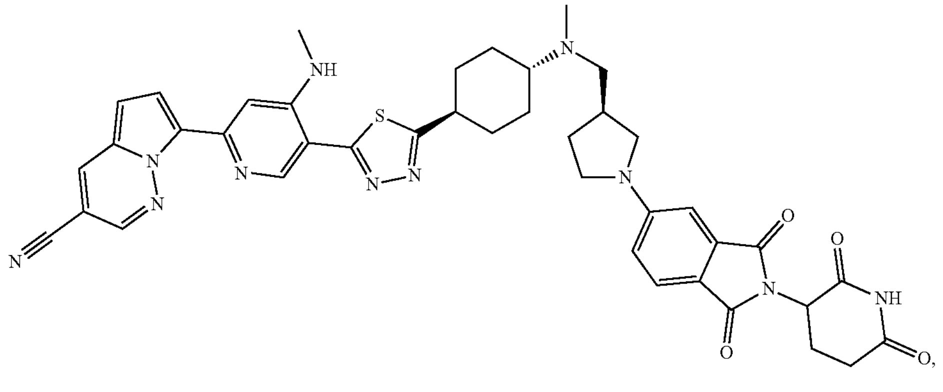
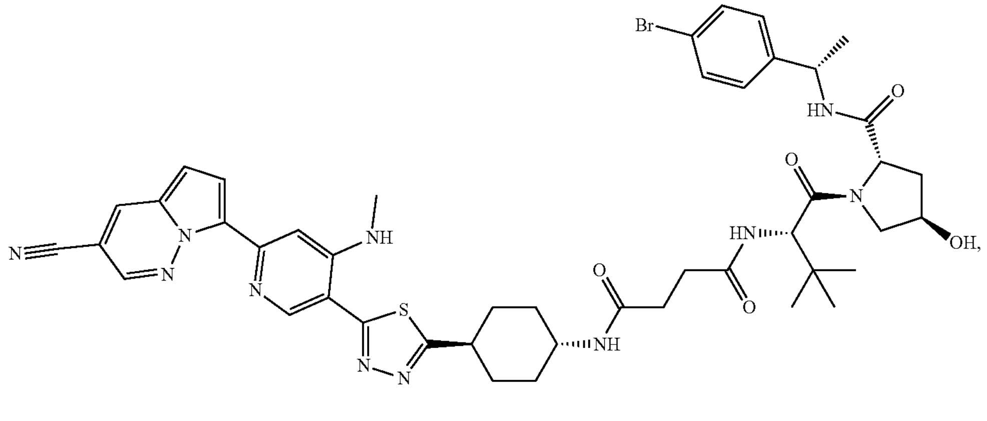

-continued
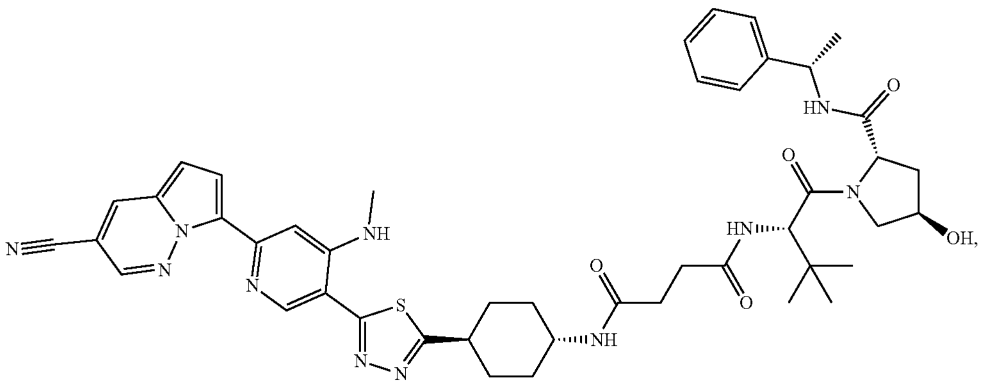
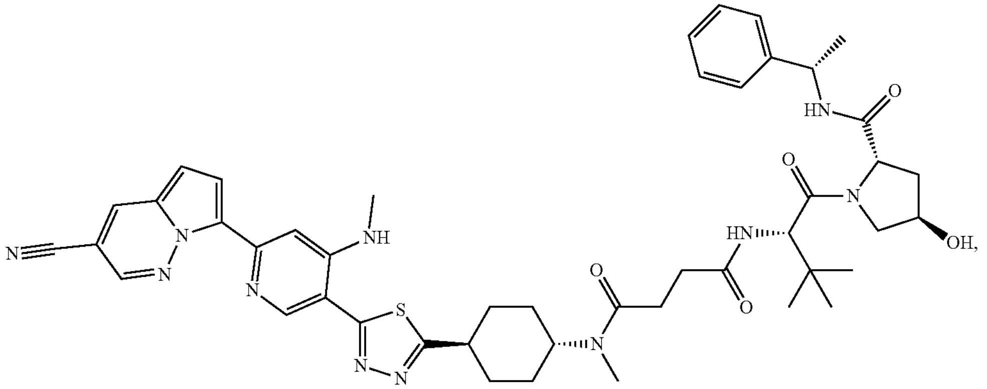
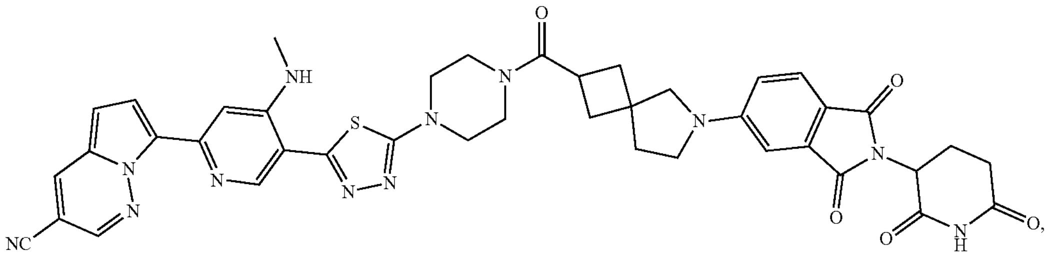
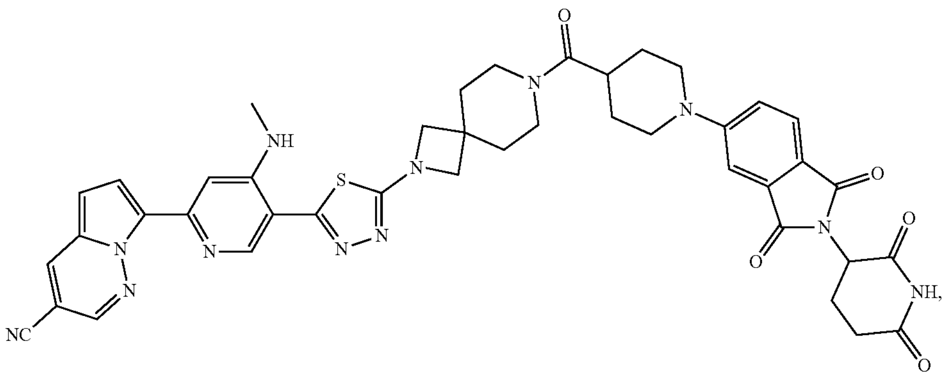
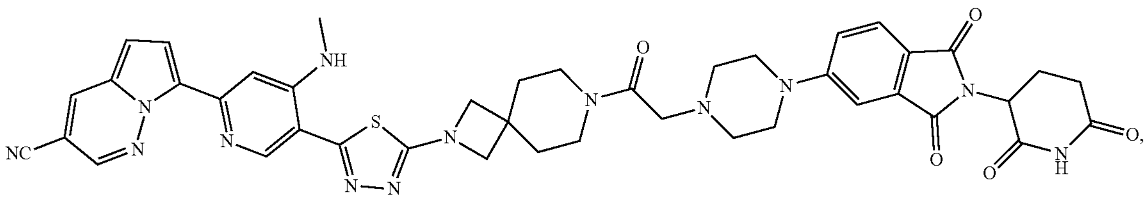

-continued
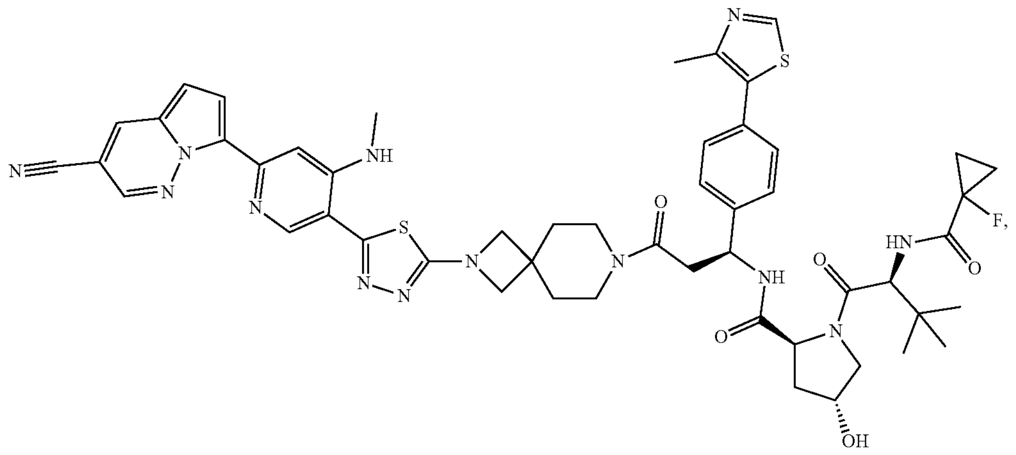
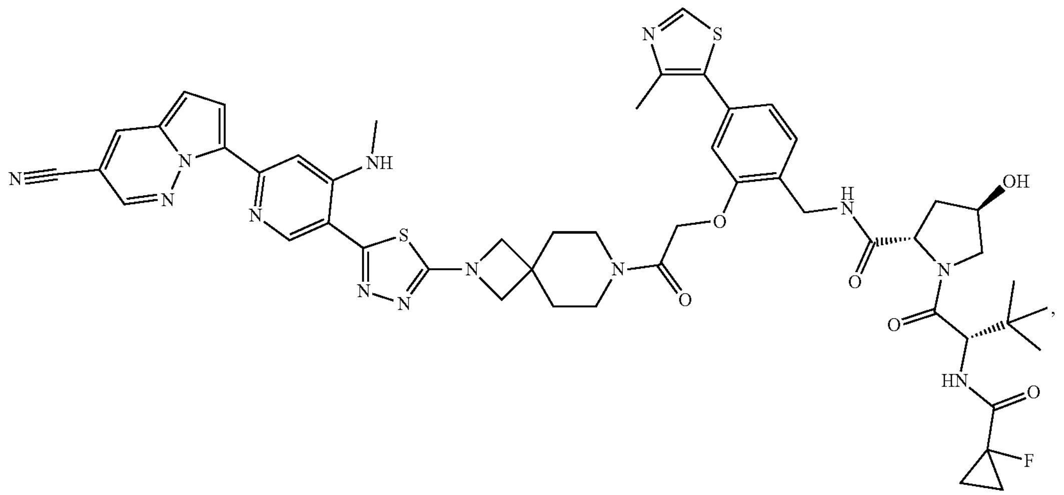
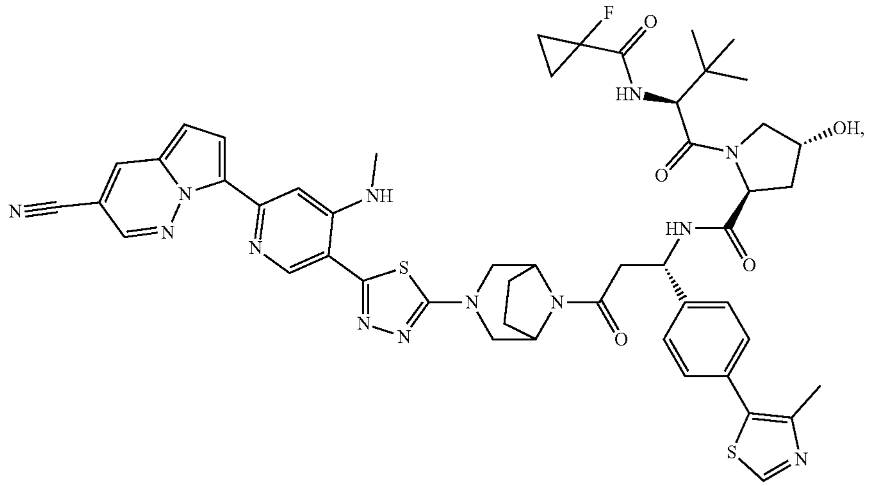

-continued
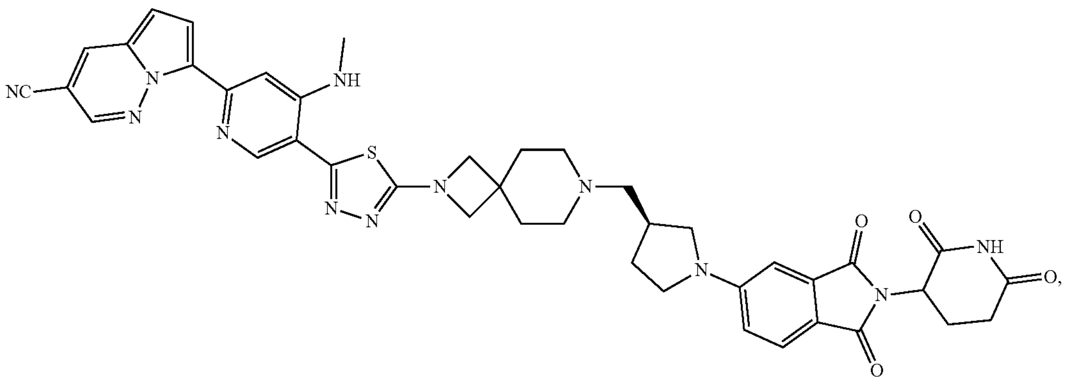
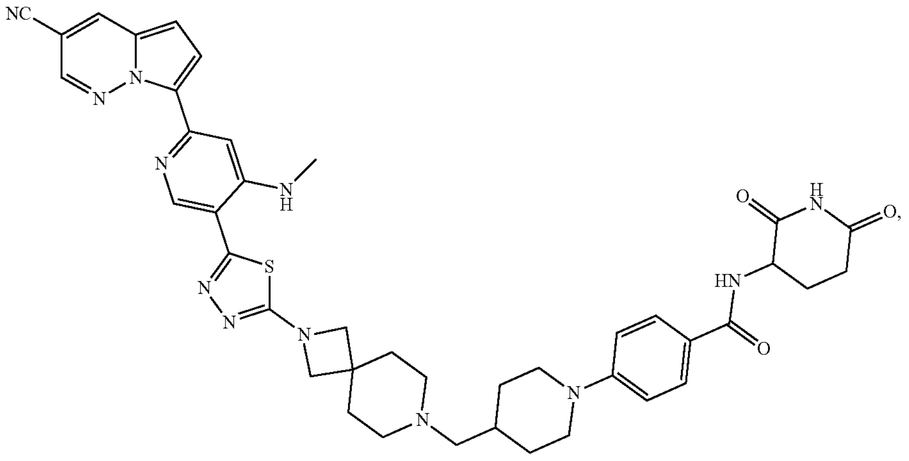
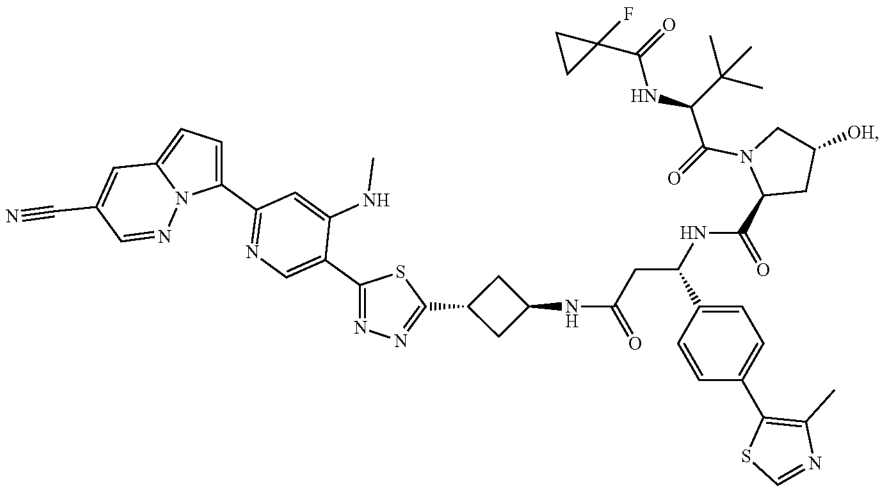
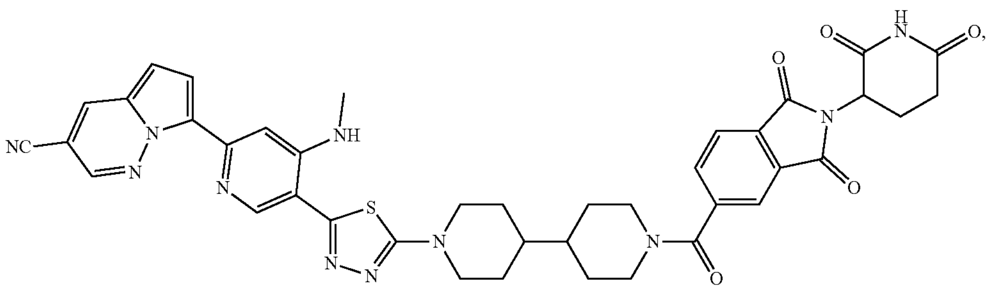

-continued
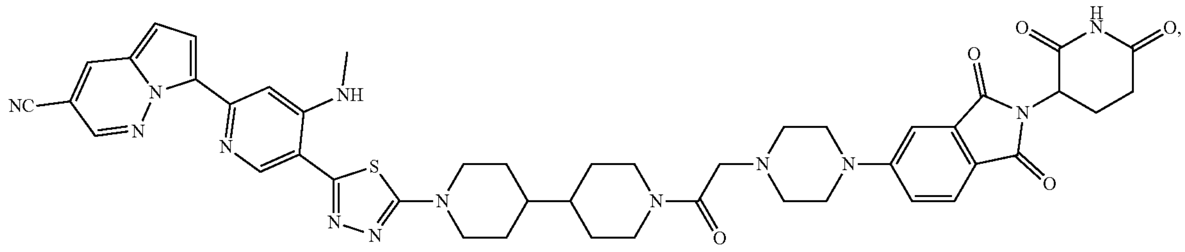
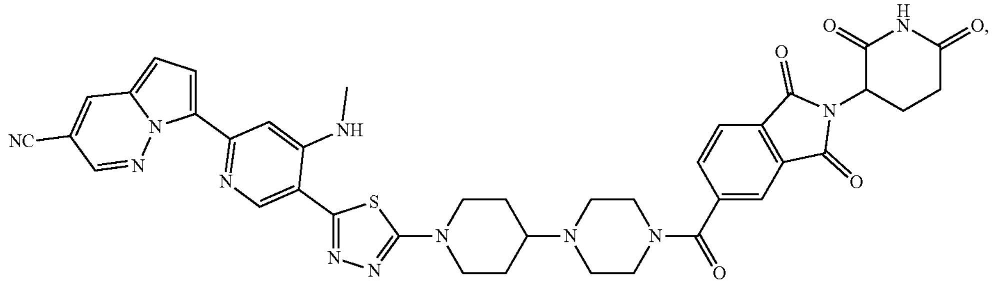
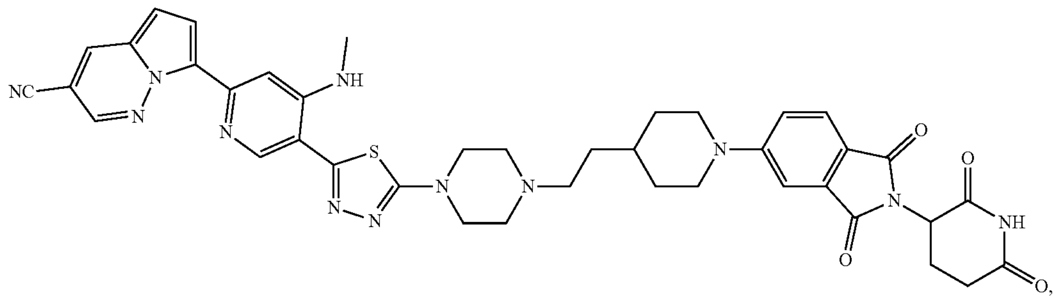
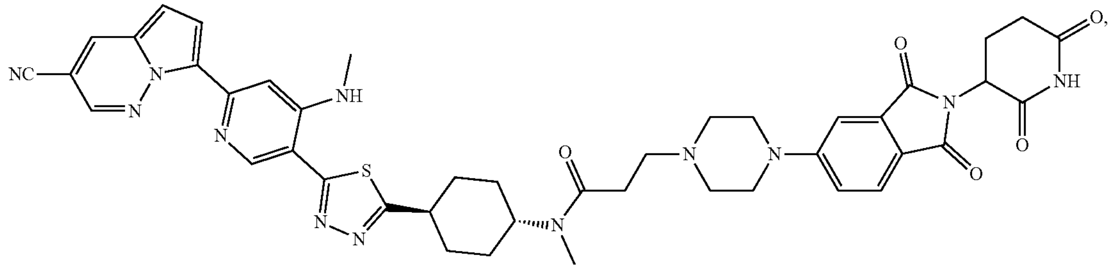
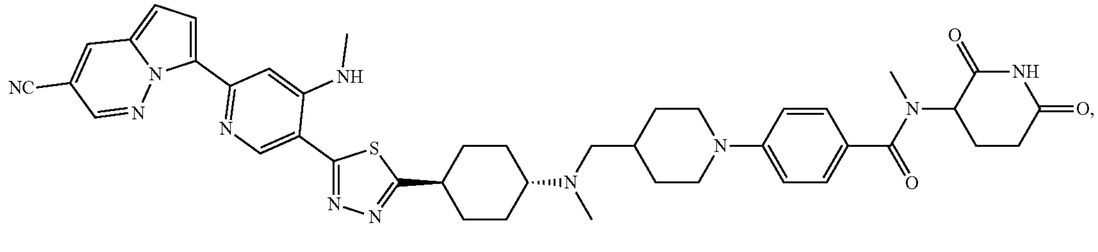

-continued
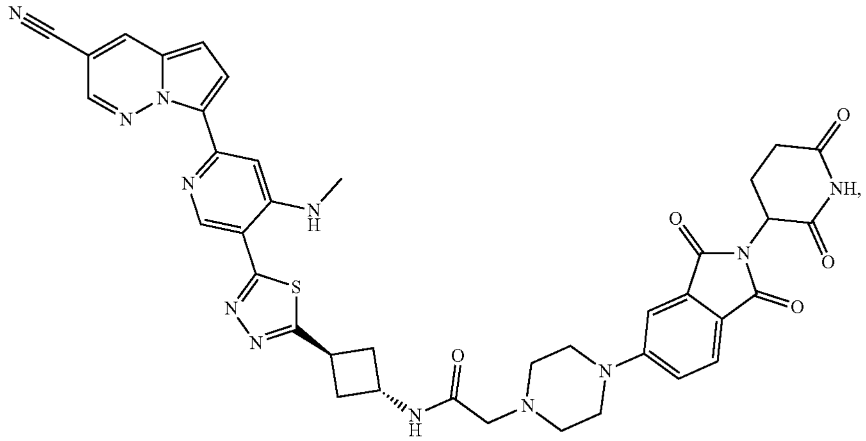
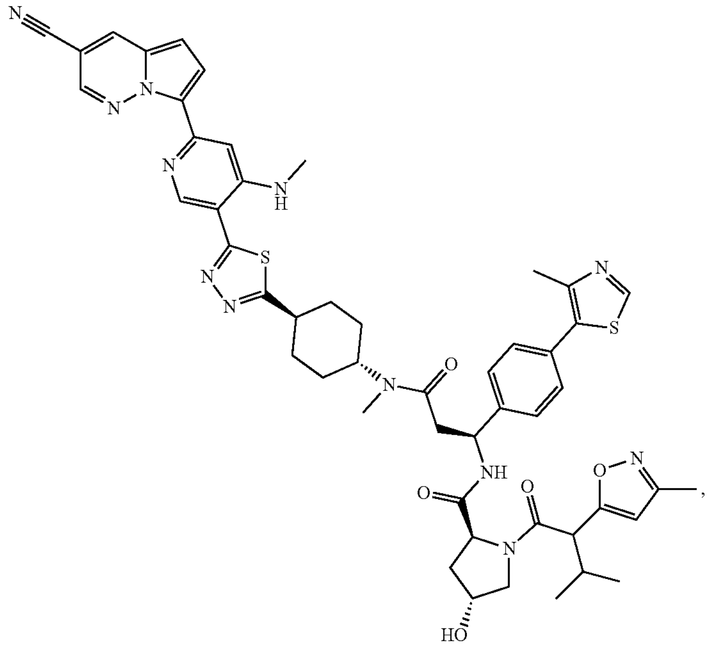 [SMILES: CCN(C(=O)C[C@H](NC(=O)[C@@H]1C[C@@H](O)CN1C(=O)C(c1cc(C)no1)C(C)C)c1ccc(-c2scnc2C)cc1)[C@H]1CC[C@H](c2nnc(-c3cnc(-c4ccc5cc(C#N)cnn45)cc3NC)s2)CC1]
, or

-continued
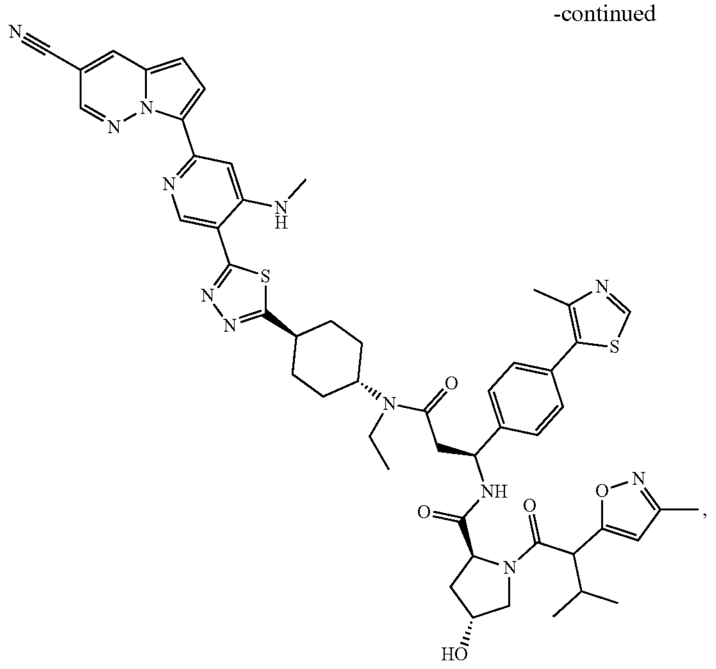
or a pharmaceutically acceptable salt thereof.
57. A pharmaceutical composition comprising a compound of claim 1 and a pharmaceutically acceptable carrier.
* * * * *